United States Patent
Chrzanowski et al.

(10) Patent No.: US 12,404,279 B2
(45) Date of Patent: Sep. 2, 2025

(54) DEUBIQUITINASE INHIBITORS AND METHODS OF USE THEREOF

(71) Applicant: Molecure S.A., Warsaw (PL)

(72) Inventors: Jacek Chrzanowski, Łódź (PL); Julita Nowicka, Wola Grzymkowa (PL); Łukasz Joachimiak, Lodz (PL); Robert Koralewski, Lodz (PL); Sylwia Olejniczak, Lodz (PL); Marzena Mazur, Lodz (PL); Bartlomiej Borek, Lodz (PL); Anna Gzik, Wartkowice (PL); Krzysztof Matyszewski, Lodz (PL); Sylwia Ciastek-Iskrzycka, Łódź (PL); Piotr Niedziejko, Warsaw (PL); Angelika Muchowicz, Warsaw (PL); Zbigniew Zasłona, Warsaw (PL); Roman Błaszczyk, Lodz (PL); Jacek Olczak, Łódź (PL); Adam Golebiowski, Madison, CT (US)

(73) Assignee: Molecure S.A., Warsaw (PL)

( * ) Notice: Subject to any disclaimer, the term of this patent is extended or adjusted under 35 U.S.C. 154(b) by 0 days.

(21) Appl. No.: 18/145,618

(22) Filed: Dec. 22, 2022

(65) Prior Publication Data
US 2023/0219973 A1     Jul. 13, 2023

Related U.S. Application Data

(60) Provisional application No. 63/296,570, filed on Jan. 5, 2022, provisional application No. 63/293,205, filed on Dec. 23, 2021.

(51) Int. Cl.
| | |
|---|---|
| *C07D 495/04* | (2006.01) |
| *A61P 35/00* | (2006.01) |
| *C07D 471/04* | (2006.01) |
| *C07D 491/048* | (2006.01) |
| *C07D 513/04* | (2006.01) |
| *C07D 519/00* | (2006.01) |

(52) U.S. Cl.
CPC ............ *C07D 495/04* (2013.01); *A61P 35/00* (2018.01); *C07D 471/04* (2013.01); *C07D 491/048* (2013.01); *C07D 513/04* (2013.01); *C07D 519/00* (2013.01); *C07B 2200/07* (2013.01)

(58) Field of Classification Search
CPC .. C07D 495/04; C07D 471/04; C07D 513/04; C07D 519/00; A61P 35/00; C07B 2200/07
See application file for complete search history.

(56) References Cited

U.S. PATENT DOCUMENTS 6,143,743 A * 11/2000 Wilde .................... A61P 25/22
                                                      544/266
10,722,514 B2 * 7/2020 Biannic ................ C07D 495/04

FOREIGN PATENT DOCUMENTS

WO      2020/068600      4/2020

OTHER PUBLICATIONS

Bucar et al. (Angew.Chem.Int. Ed.2015,54,6972-6993 (Year: 2015).*
Talaczynska et al. (Current Pharmaceutical Design, 2016, 22, 4975-4980 ) (Year: 2016).*
Patani Chemical Reviews, 1996, vol. 96, No. 8 (Year: 1996).*
Leger, Paul R. et al. "Discovery of Potent, Selective, and Orally Bioavailable Inhibitors of USP7 with In Vivo Antitumor Activity" Journal of Medicinal Chemistry (2020) vol. 63 (10), pp. 5398-5420.
International Search Report (ISR) with Written Opinion for PCT/IB2022062697 dated Feb. 20, 2023, pp. 1-16.

* cited by examiner

*Primary Examiner* — Clinton A Brooks
*Assistant Examiner* — Jerica Katlynn Wilson
(74) *Attorney, Agent, or Firm* — McDonnell Boehnen Hulbert & Berghoff LLP

(57) ABSTRACT

The inventive compounds are small molecule therapeutics that are potent inhibitors of USP7 activity. The invention also provides pharmaceutical compositions comprising the compounds, and methods for using the compounds for treating or preventing a disease, disorder, or condition associated with USP7 activity.

5 Claims, 24 Drawing Sheets

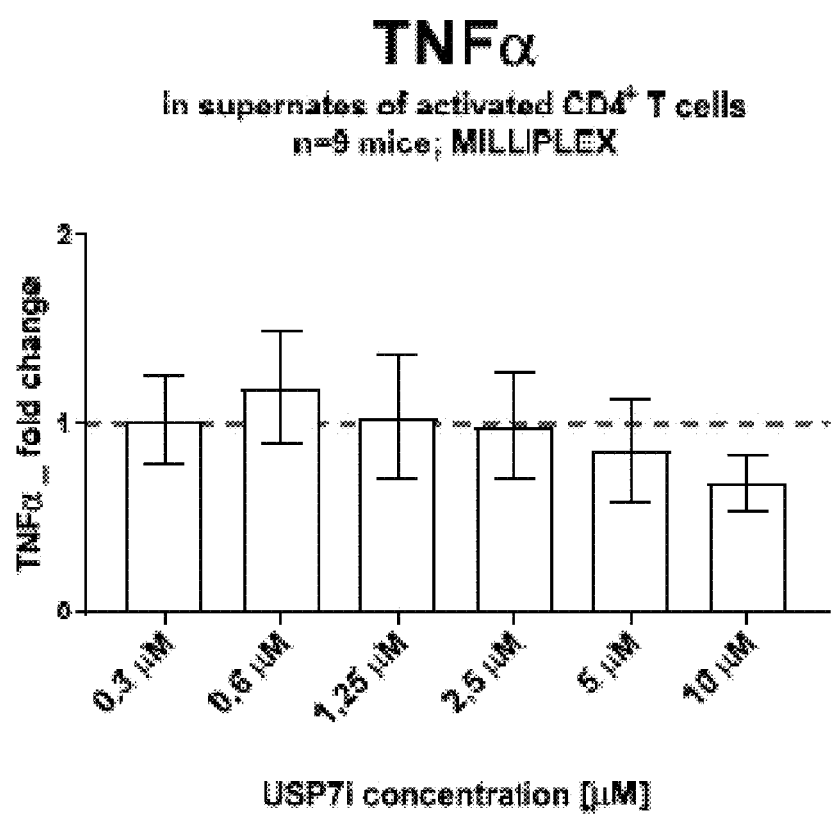

DEUBIQUITINASE INHIBITORS AND METHODS OF USE THEREOF

CROSS REFERENCE TO RELATED APPLICATIONS

This application claims the benefit of priority to Polish Patent Application number P.439979, filed Dec. 23, 2021, U.S. Provisional Patent Application Ser. No. 63/293,205, filed Dec. 23, 2021, Polish Patent Application number P.440083, filed Jan. 5, 2022, and U.S. Provisional Patent Application Ser. No. 63/296,570, filed Jan. 5, 2022, the disclosure of each of which is incorporated herein by reference in its entirety.

BACKGROUND OF THE INVENTION

Field of the Invention

This disclosure relates to small molecule therapeutic inhibitors of deubiquitinases.

Description of Related Art

Ubiquitin system is a major post-translational regulator of protein levels and regulates essential cellular processes in a cell. Ubiquitination is a covalent modification of a given protein that directs it towards proteasomal degradation. Ubiquitination as well as deubiquitination is tightly controlled by E1, E2 or E3 ligases and deubiquitinases (DUBs) respectively. Ubiquitination is usually done by formation of isopeptide bond on a protein's lysine side-chain. This process is further regulated by polyubiquitination during which a ubiquitin molecule's C-terminal Gly is conjugated with one of the seven Lys residues on another ubiquitin (Lys6, Lys11, Lys27, Lys29, Lys33, Lys48, or Lys63) or with the N-terminus to form linear chains. It is called "the ubiquitin code". The ubiquitination code is related to diverse aspects of cellular biology and therefore disruption of this balance contributes to many diseases.

The ubiquitination is a reversible process and the deubiquitination is catalyzed by enzymes called deubiquitinases (DUBs). There are approximately 100 DUBs known in human genome, any of which could be playing a key role in the ubiquitin proteasome system as well as other biological processes. The DUBs are subdivided into five families: UCHs, USPs, OTUs, Josephin, and JAM/MPN+. Except the last one (which is metalloprotease), all DUBs are cysteine proteases consisting catalytic triad with cysteine residue as nucleophile. It is prone to covalent modifications by electrophilic fragments in small molecules and this has interfered with screening methodology and lead to identification of many low quality DUBs inhibitors in the past. However, recent years brought increasing appreciation of this family of targets once more thorough characterization of small molecule inhibitors of DUBs was performed. Deubiquitinases generally prevent protein degradation by cleaving the ubiquitin molecule or editing the polyubiquitin chains. Inhibition of DUBs therefore increases the rate of degradation of DUB-targeted protein. Regulation of DUBs enzymes with their inhibitors allow to indirectly affect the levels of protein of interest. Moreover the protein degradation is getting increasing attention as it might be an alternative strategy to overcome protein mutations and resistance to direct inhibitors.

Among USPs, a ubiquitin specific protease 7—USP7 has been intensively studied in recent years and numerous inhibitors of USP7 have been identified. Widely known function of USP7 is genetically validated interaction with an E3 ligase MDM2, which ubiquitinates and thus directs for degradation the known oncosupressor p53. MDM2 is deubiquitinated by USP7 resulting in its stabilization. Inhibition of USP7 has proven to restore ubiquitinylation of MDM2 and subsequent proteasomal degradation. This results in accumulation of p53 and promotes cell cycle arrest and apoptosis. On the other hand USP7 can stabilize p53 itself. [U.S. Ser. No. 11/084,829B2 or WO2022170198A1] Highly potent, specific, reversible, orally bioavailable USP7 inhibitors demonstrate marked tumor growth inhibition in both p53-wild type and p53-mutant tumors, indicating that USP7 inhibition can suppress tumor growth in vivo through both p53 dependent and independent mechanisms [Leger, P. L. et al. *J. Med Chem.* 2020, 63, 5398-5420].

The further studies implicate numerous other partners for USP7 that are linked to DNA-damage response, cancer, immunotherapy, diabetes and viral infections [Nicholson B., Suresh Kumar K. G. The multifaceted roles of USP7; new therapeutic opportunities. *Cell Biochemistry and Biophysics* 2011, 60: 61-68.]. PTEN is thought to be a tumor suppressor in the nucleus. Its location is regulated by mono-ubiquitination. USP7 catalyzes the deubiquitylation nuclear PTEN which results in nuclear exclusion, blocking apoptosis in prostate cancer cells. That suggest that inhibition of USP7 triggers accumulation PTEN in nucleus and apoptosis. Other studies have uncovered a link between USP7 and Polycomb mediated silencing of genes. In particular, USP7 was shown to regulate the function of Ring1B and BMI1, which are essential core components of Polycomb Repressive Complex 1 and 2 [Gagarina, V. et al. *J. Mol. Biol.* 2020, 432, 4, 897-912.]. PRC 1 and 2 complexes catalyze the mono-, di- and trimethylation of lysine 27 of histone H3 (H3K27me1, H3K27me2 and H3K27me3) and is bound to CpG islands. H3K27me3 is a hallmark of PcG-associated transcriptional silencing and is thought to result in gene repression. The histone methyl transferase activity of PRC2 is mediated by one of the two catalytic subunits, enhancer of zeste homologue 1 (EZH1) or EZH2. Interaction between USP7 and PRC complexes, including EZH2 in particular but also other PRC components has been reported by several groups [De Bie, P. et al. *Biochemical and Biophysical Research Communications* 2010, 400, 3, 389-395; Lecona, E. et al. *Molecular and Cellular Biology* 2015, 35, 7, 1157-1168; Gagarina. V. et al. *J. Mol. Biol.* 2020, 432, 4, 897-912.]. Another epigenetic regulator—LSD1—was also reported to interact with USP7. Overexpression of LSD1 has been proved in numerous cancers, and high level of LSD1 aggressiveness and poor prognosis in lung, prostate, colon and breast cancers. The study shows that another oncogene—CARM1-dependendent methylation of LSD1 promotes deubiquitylation of LSD1 by USP7 [Liu. J. et al. *EMBO Rep.* 2020, 21(2), e48597.]. Wnt/beta-catenin/axin pathway plays important roles in many important biological processes and aberrant Wnt/β-catenin signaling has been associated with many human diseases, such as degenerative diseases and cancer. It was previously postulated that USP7 activates Wnt signaling and therefore inhibition of USP7 triggers Wnt attenuation. It was shown that USP7 stabilizes beta-catenin and once inhibited, beta-catenin is degraded and the canonical wnt pathway is inhibited [Novellasdemunt, L et al. *Cell Reports* 2017, 21(3), 612-627.]. However, recent study published by NIBR in Nat. Comm. shows that USP7 actually inhibits Wnt-induced beta-catenin accumulation [Ji, B. et al. *Nature Communications* 2019, 10, 4184.]. Both, genetic inhibition and pharmacological intervention on USP7 enhanced Wnt/B-catenin signaling with downstream effects on osteoblasts and adipocyte differentiation.

Importantly. USP7 plays a key role in determining half-life of crucial proteins involved in the regulation of immune response, namely FOXP3 and PD-L1 resulting in preservation of immunosuppressive functions of Tregs and causing escape of cancer cells from cytotoxic immune cells respectively. Evidence that USP7 by de-ubiquitylating of FOXP3 increases T Treg numbers and mediates suppression of tumor-infiltrating T effector cells has been elegantly demonstrated [Van Loosdregt, J. et al. *Immunity* 2013, 22, 39 (2), 259-271.]. This presented USP7 as an attractive immunoregulatory target. Indeed, USP7 deletion resulted in improved clinical outcome for many solid tumors. The observation that the accumulation of FOXP3+ Treg cells at the tumor or in draining lymph nodes signals poor prognosis highlights the significance of oncogenic mechanism of USP7.

As a part of immunotherapy, checkpoint blockades (PD-1/PD-L1) have acquired clinical success, antibody treatment has several limitations and need for small molecule is evident. Therefore the fact that USP7 has been demonstrated to be responsible for PD-L1 protein stabilization has serious therapeutic implications [Wang, Z. et al. *Acta Pharm. Sin. B.* 2021, 11, 3, 694-707.].

Overall it has been demonstrated that USP7 plays a critical role in affecting the tumor microenvironment. The effects of USP7 inhibition demonstrated promoting remodeling of the extracellular matrix (ECM), thereby promoting tumor invasion and metastasis. USP7 also affects angiogenesis and VEGF levels both systemically and in the tumor microenvironment (TME). Moreover, USP7 inhibition, particularly in the fibroblast compartment of the TME, leads to a significant decrease in both cell invasion and angiogenesis. USP7 inhibition also results in modulation of the tumor immune environment (e.g., by promoting infiltration of CD8 T cells). In vivo USP7 inhibition inhibits tumor growth in cell models that are not affected by direct inhibition by USP7 inhibitors in vitro. [WO2021161047A1]. Antitumor efficacy in the MC38 colon cancer syngeneic mouse model, through upregulating the tumor infiltration of CD8+ T, NK, and NKT cells and downregulating that of Tregs and MDSCs was recently published [Li X. et al. *J. Med. Chem.*, DOI: 10.1021/acs.jmedchem.2c01444].

Overall USP7 was found to be involved in many pathways that are aberrant in cancer and immune-oncology. Thus, inhibitors of USP7 can exert in vivo antitumor activity by: 1) directly inhibiting tumor cell proliferation via Hdm2 and other targets; 2) suppressing T regulatory cells via FOXP3, thereby facilitating the antitumor function of T effector cells; 3) inhibition of PD-L1 expression which sensitizes tumor cells towards cytotoxic effect of immune cells. First generation of USP7 inhibitors was often covalent (i.e., P5091 or HBX19818) or not selective. Next generation of allosteric and non-covalent inhibitors of USP7 was reported such as GNE-6640 and FT671 which exhibited in vivo efficacy.

Over the last years a potential of modulating immune system for the treatment of cancer has been described. A clinical success of immune checkpoint inhibitors, particularly those targeting the PD-1 axis, has set new trends in cancer therapy. Unfortunately, there is still unmet need and many patients do not improve after checkpoint blockade or other existing immunotherapies. T cell activation is crucial for the efficacy of immune checkpoint inhibitor therapies. Our experiments have been designed to highlight the effect of our compound T cell activation, particularly IFN-gamma production. IFN-gamma is known to have anti-cancer properties, such as antiproliferative effect and induction of necroptosis in apoptosis-resistant cancer cells, regression of the tumor vasculature, activation antigen-presenting cells, as well as enhancement Th1 differentiation and cytotoxic T lymphocyte function.

SUMMARY OF THE INVENTION

In one aspect, the invention provides a compound of structural Formula (I):

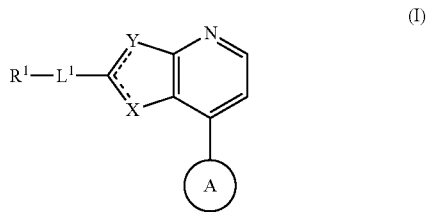

wherein:
the dotted line in the five-membered ring containing X and Y indicates a double bond in either of the possible positions between C and X or between C and Y, wherein the bond in the other one of these positions is a single bond;
either X is S and Y is $C(R^C)$; or
X is $C(R^C)$ and Y is S; or
X is N and Y is $N(R^N)$; or
X is $N(R^N)$ and Y is N; or
X is O and Y is $C(R^C)$; or
X is S and Y is N;

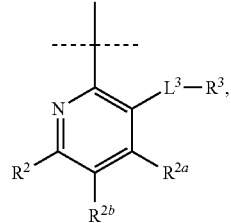

(A1)

A is (A1), (A2), (A3), (A4), (A5), (A6), (A7), or (A8):

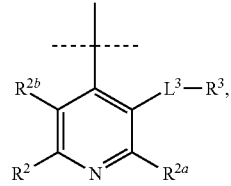

(A2)

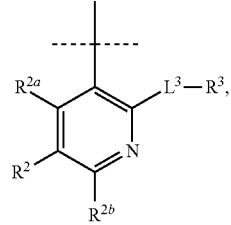

(A3)

-continued (A4)
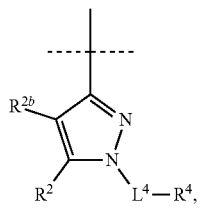

(A5)
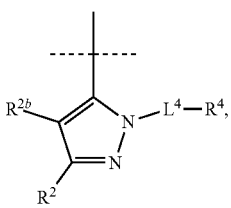

(A6)
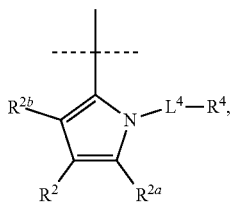

(A7)
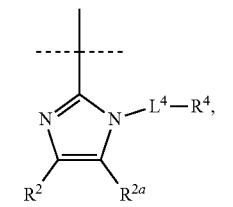

(A8)
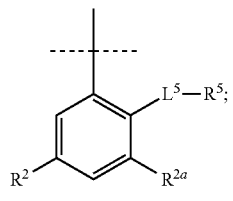

$L^1$ represents a single bond, —N($R^N$)—, —O—, —S—, —S(═O), —S(═O)$_2$—, or $C_1$-$C_3$ alkylene;

$R^1$ is selected from the group consisting of hydrogen, alkyl, and (4-6) membered heterocycloalkyl containing 1 to 3 nitrogen heteroatoms and optionally substituted with 1 or 2 substituents selected from the group consisting of hydroxy, oxo, methyl, and/or $C_1$-$C_3$ alkylene forming a $C_3$-$C_5$ cycloalkyl ring that shares one or two carbon ring atoms with said (4-6) membered heterocycloalkyl and is optionally substituted with 1 or 2 methyl groups;

$R^2$, $R^{2a}$, and $R^{2b}$ are each independently selected the group consisting of hydrogen, substituted or unsubstituted alkyl, —C≡N, —N$_3$, —NO$_2$, fluoro, chloro, bromo, iodo, —CF$_3$, —CCl$_3$, —CBr$_3$, —C$_{13}$, —CHF$_2$, —CHCl$_2$, —CHBr$_2$, —CHI$_2$, —CH$_2$F, —CH$_2$Cl, —CH$_2$Br, —CH$_2$I, —OH, —O-alkyl, —CO$_2$H, —CONH$_2$, —C(═O)-alkyl, —C(═O)—O-alkyl, —C(═O)—NH-alkyl, —C(═O)—N(alkyl)$_2$, —NH$_2$, —NH-alkyl, and —N(alkyl)$_2$;

$L^3$ represents a single bond, —O—, —S—, —S(═O)—, —S(═O)$_2$—, —C($R^C$)$_2$—, —C(═O)—, —NH—, —NH—C(═O)—CH$_2$—, —NH—C(═O)—, —C(═O)—NH—, or —CH(OH)—;

$R^3$ is selected from group consisting of $C_3$-$C_6$ cycloalkyl; (4-6) membered heterocycloalkyl containing 1 to 3 heteroatoms selected from N, O, and S; diazabicyclo[2.2.2]octanyl; (7-10) membered fused bicyclic heterocycloalkyl containing 2 nitrogen heteroatoms; and (7-9) membered spiro bicyclic heterocycloalkyl containing 1 nitrogen heteroatom; all the above members of the group representing $R^3$ being saturated or unsaturated, and optionally substituted with 1 or 2 or 3 substituents selected from fluoro, chloro, bromo, iodo, alkyl, —NH$_2$, —NH-alkyl, —N(alkyl)$_2$, —OH, oxo, -alkylene-NH$_2$, ureido, alanylamino, arginylamino, asparaginylamino, aspartylamino, cysteinylamino, glutaminylamino, glutamylamino, glycylamino, histidylamino, isoleucylamino, leucylamino, lysylamino, methionylamino, phenylalanylamino, prolylamino, serylamino, threonylamino, tryptophanylamino, tyrosylamino, valylamino, and 2,2,2-trifluoroacetyl;

or else $R^3$ is selected from the group consisting of —CF$_3$, —O-alkyl, —NH— alkyl, —N(alkyl)$_2$, and 2-(dimethylamino)ethyl(methyl)amino;

$L^4$ represents a single bond, —O—, —S—, —S(═O)—, —S(═O)$_2$—, —C($R^C$)$_2$—, —C(═O)—, —NH—, —NH—C(═O)—CH$_2$—, —NH—C(═O)—, —C(═O)—NH—, or —CH(OH)—;

$R^4$ is selected from hydrogen and (5-6) membered heterocycloalkyl containing 1 to 2 heteroatoms selected from N, O, and S;

$L^5$ represents a single bond, —NH—, —O—, —S—, —S(═O)—, —S(═O)$_2$—, —C(═O)—, —N($R^N$)—, —N($R^N$)—C(═O)—C($R^C$)$_2$—, —N($R^N$)—C(═O)—, —C(═O)—N($R^N$)—, or —CH(OH)—;

$R^5$ is selected from (5-6) membered heterocycloalkyl containing 1 to 2 heteroatoms selected from N, O, and S;

each occurrence of $R^C$ is independently selected from the group consisting of hydrogen, fluoro, chloro, bromo, iodo, alkyl, cycloalkyl, and aryl;

each occurrence of $R^N$ is independently selected from the group consisting of hydrogen, alkyl, cycloalkyl, and aryl;

provided that if X is S and Y is CH then $L^5$ is not —O—; and provided that the compound of Formula (I) is not 3-((7-(5-chloro-3-methyl-2-(piperidin-3-ylamino)phenyl)thieno[3,2-b]pyridin-2-yl)methyl)-6,6-dimethyl-3-azabicyclo[3.1.0]hexane-2,4-dione;

or a tautomer, stereoisomer, a racemic or scalemic mixture of stereoisomers, a pharmaceutically acceptable salt, ester, solvate, or polymorph thereof.

Also provided herein is a pharmaceutical composition comprising (i) a therapeutically effective amount of at least one compound of the invention, or a pharmaceutically acceptable salt, solvate, or polymorph thereof; and (ii) a pharmaceutically acceptable carrier, vehicle or excipient therefor.

In another aspect, the invention provides a method for inhibiting USP7 in a cell or a tissue, comprising contacting the cell or the tissue with at least one compound according to the invention, or a pharmaceutically acceptable salt, solvate, or polymorph thereof, or with a pharmaceutical composition according to the invention.

In another aspect, the invention provides a method for the treatment or prevention of a disease, disorder, or condition associated with aberrant expression or activity of USP7, comprising administering to the subject in need thereof a therapeutically effective amount of at least one compound according to the invention, or a pharmaceutically acceptable salt, solvate, or polymorph thereof, or a pharmaceutical composition according to the invention.

In another aspect, the invention provides a compound according to the invention, or a pharmaceutically acceptable salt, solvate, or polymorph thereof, for use in a method for inhibiting USP7 in a cell or a tissue, comprising contacting the cell or the tissue with at least one compound according to the invention, or a pharmaceutically acceptable salt, solvate, or polymorph thereof.

In another aspect, the invention provides use of at least one compound according to the invention, or a pharmaceutically acceptable salt, solvate, or polymorph thereof, in the manufacturing of a medicament for the treatment of a disease, disorder, or condition associated with expression of USP7.

In further aspect, the invention provides a compound according to the invention, or a pharmaceutically acceptable salt, solvate, or polymorph thereof, for use in a method for the treatment or prevention of a disease, disorder, or condition associated with aberrant expression or activity of USP7, comprising administering to the subject in need thereof a therapeutically effective amount of at least one compound according to the invention, or a pharmaceutically acceptable salt, solvate, or polymorph thereof, or a pharmaceutical composition according to the invention.

In another aspect, the invention provides at least one compound according to the invention, or a pharmaceutically acceptable salt, solvate, or polymorph thereof, for use in the treatment or prevention of a disease, disorder, or condition selected from the group consisting of cardiovascular disorders, pulmonary disorders, autoimmune disorders, immune disorders, immunoregulatory disorders, neurodegenerative disorders, metabolic disorders, hemolytic disorders, gastrointestinal disorders, sexual disorders, infections, wound healing disorders, and cancers.

In another aspect, the invention provides a method for activating cytokine release in T lymphocyte cell, comprising contacting the cell with at least one compound according to the invention, or a pharmaceutically acceptable salt, solvate, or polymorph thereof, or with a pharmaceutical composition according to the invention.

In further aspect, the invention provides a compound according to the invention for use in a method for activating cytokine release in T lymphocyte cell in vitro or ex vivo, comprising contacting the cell with at least one compound according to the invention, or a pharmaceutically acceptable salt, solvate, or polymorph thereof.

In another aspect, the invention provides use of a compound according to the invention, or a pharmaceutically acceptable salt, solvate, or polymorph thereof, for protecting an organ during transport.

BRIEF DESCRIPTION OF THE DRAWINGS

FIGS. 3A-3D show the effect of Example 77 on CD4⁺ T cell activation and pro-inflammatory cytokine release and, in particular, on levels of IFN, GM-CSF, TNF and IL-10.

DETAILED DESCRIPTION

Figure 1A:
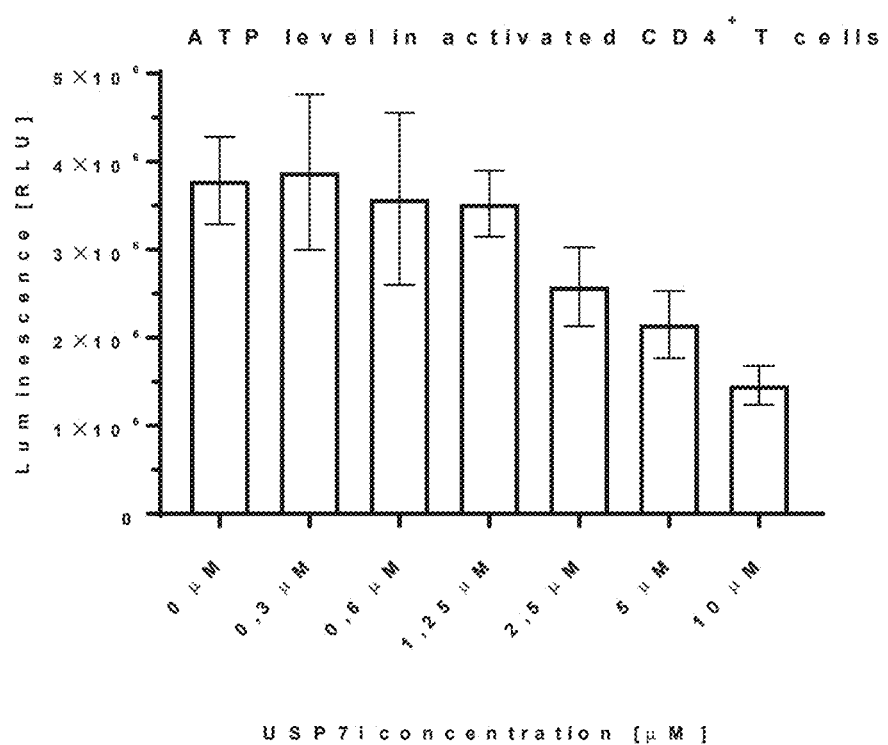
FIGS. 1A-1C are graphs showing results of assays comparing cell viability for compound Example 77 (denoted USP7i in the Figures) and a reference compound from RAPT Therapeutics.

The present invention is based on a surprising finding that some small molecule USP7 inhibitors possess very high activity accompanied by superior pharmacokinetics.

Definitions

The articles "a" and "an" are used herein to refer to one or to more than one (i.e., to at least one) of the grammatical object of the article. By way of example. "an element" means one element or more than one element.

The terms used herein may be preceded and/or followed by a single dash "—", or a double dash "=", to indicate the bond order of the bond between the named substituent and its parent moiety; a single dash indicates a single bond and a double dash indicates a double bond. In the absence of a single or double dash, it is understood that a single bond is formed between the substituent and its parent moiety; further, substituents are intended to be read "from left to right," unless a dash indicates otherwise. For example, $(C_1-C_6)$-alkoxycarbonyloxy and —OC(O)O($C_1$-$C_6$)alkyl indicate the same functionality; similarly arylalkyl and -alkylaryl indicate the same functionality.

The terms "hydrogen", "hydrogen atom", and symbol "H", as used herein in the context of substituents to Markush formulas, such as Formula (I), (Ia), (Ib), and (Ic), denote a hydrogen atom attached to the remaining part of the molecule or group in question. For the sake of simplicity, hydrogen atoms attached to carbon atoms are not shown in the structural formulas; each carbon atom is understood to be associated with enough hydrogen atoms to give the carbon atom four bonds.

The term "alkyl" as used herein is a term of art and refers to saturated aliphatic groups, including straight-chain alkyl groups, branched-chain alkyl groups, cycloalkyl (alicyclic)

groups, alkyl substituted cycloalkyl groups, and cycloalkyl substituted alkyl groups. In certain embodiments, a straight-chain or branched-chain alkyl has about 30 or fewer carbon atoms in its backbone (e.g., $C_1$-$C_{30}$ for straight chain, $C_3$-$C_{30}$ for branched chain), and alternatively, about 20 or fewer, 10 or fewer. Preferred alkyl groups have 1-6 carbons. Representative examples of alkyl include, but are not limited to, methyl, ethyl, n-propyl, isopropyl, n-butyl, sec-butyl, isobutyl, tert-butyl, n-pentyl, isopentyl, neopentyl, and n-hexyl. Alkyl groups are independently optionally substituted with at least one substituent independently selected from the group consisting of oxo, fluoro, chloro, bromo, iodo, —$CF_3$, —$CCl_3$, —$CBr_3$, —$C_{13}$, —$CHF_2$, —$CHCl_2$, —$CHBr_2$, —$CHI_2$, —$CH_2F$, —$CH_2Cl$, —$CH_2Br$, —$CH_2I$, —CN, —OH, —$NH_2$, —$CO_2H$, —$CONH_2$, —$NO_2$, —SH, —$SO_3H$, —$SO_4H$, —$SO_2NH_2$, —$NHNH_2$, —$ONH_2$, —NHC(=O)$NHNH_2$, —NHC(=O)$NH_2$, —$NHSO_2H$, —NHC(=O)H, —NHOH, —$OCF_3$, —$OCCl_3$, —$OCBr_3$, —$OC_{13}$, —$OCHF_2$, —$OCHCl_2$, —$OCHBr_2$, —$OCHI_2$, —$OCH_2F$, —$OCH_2Cl$, —$OCH_2Br$, —$OCH_2I$, ($C_1$-$C_6$) alkoxy, ($C_1$-$C_6$)haloalkoxy, ($C_3$-$C_8$)cycloalkyl, and ($C_6$-$C_{10}$) aryl.

The term "cycloalkyl" means monocyclic saturated or partially saturated carbocyclic rings, having from 3-6 carbon atoms in their ring structure. Examples of monocyclic cycloalkyls include cyclopropyl, cyclobutyl, cyclopentyl, cyclopentenyl, cyclohexyl, and cyclohexenyl. Cycloalkyl groups are independently optionally substituted by at least one substituent independently selected from the group consisting of oxo, fluoro, chloro, bromo, iodo, —$CF_3$, —$CCl_3$, —$CBr_3$, —$C_{13}$, —$CHF_2$, —$CHCl_2$, —$CHBr_2$, —$CHI_2$, —$CH_2F$, —$CH_2Cl$, —$CH_2Br$, —$CH_2I$, —CN, —OH, —$NH_2$, —$CO_2H$, —$CONH_2$, —$NO_2$, —SH, —$SO_3H$, —$SO_4H$, —$SO_2NH_2$, —$NHNH_2$, —$ONH_2$, —NHC(=O)$NHNH_2$, —NHC(=O)$NH_2$, —$NHSO_2H$, —NHC(=O)H, —NHOH, —$OCF_3$, —$OCCl_3$, —$OCBr_3$, —$OC_{13}$, —$OCHF_2$, —$OCHCl_2$, —$OCHBr_2$, —$OCHI_2$, —$OCH_2F$, —$OCH_2Cl$, —$OCH_2Br$, —$OCH_2I$, ($C_1$-$C_6$)alkyl, ($C_1$-$C_6$) alkoxy, ($C_1$-$C_6$)haloalkoxy, ($C_3$-$C_8$)cycloalkyl, and ($C_6$-$C_{10}$) aryl.

The term "heterocyclyl" as used herein refers to a radical of a non-aromatic ring system, including, monocyclic rings, which can be completely saturated or which can contain one or more units of unsaturation, for the avoidance of doubt, the degree of unsaturation does not result in an aromatic ring system, and having 3 to 7 atoms including at least one heteroatom, such as nitrogen, oxygen, or sulfur. More preferred heterocycloalkyl groups have from 5-7 ring members where from 1-4 of the ring members are hetero atoms selected from the group comprising O, N, and S, the remaining ring atoms being C. For purposes of exemplification, which should not be construed as limiting the scope of this invention, the following are examples of heterocyclic rings: aziridinyl, azirinyl, oxiranyl, thiiranyl, thiirenyl, dioxiranyl, diazirinyl, diazepanyl, 1,3-dioxanyl, 1,3-dioxolanyl, 1,3-dithiolanyl, 1,3-dithianyl, imidazolinyl, imidazolidinyl, isothiazolinyl, isothiazolidinyl, isoxazolinyl, isoxazolidinyl, azetyl, oxetanyl, oxetyl, thietanyl, thietyl, diazetidinyl, dioxetanyl, dioxetenyl, dithietanyl, dithietyl, furyl, dioxalanyl, pyrrolyl, oxazolyl, thiazolyl, imidazolyl, oxadiazolyl, thiadiazolyl, triazolyl, triazinyl, isothiazolyl, isoxazolyl, thiophenyl, pyrazolyl, tetrazolyl, pyridyl, pyridazinyl, pyrimidinyl, pyrazinyl, triazinyl, tetrazinyl, azepinyl, azepanyl, azetidinyl, morpholinyl, oxadiazolinyl, oxadiazolidinyl, oxazolinyl, oxazolidinyl, oxopiperidinyl, oxopyrrolidinyl, piperazinyl, piperidinyl, pyranyl, pyrazolinyl, pyrazolidinyl, pyrrolinyl, pyrrolidinyl, thiomorpholinyl, tetrahydropyranyl, tetrahydrofuranyl, tetrahydrothienyl, thiadiazolinyl, thiadiazolidinyl, thiazolinyl, thiazolidinyl, thiomorpholinyl, 1,1-dioxidothiomorpholinyl (thiomorpholine sulfone), thiopyranyl, and trithianyl.

A heterocyclyl group is optionally substituted by one or more substituents independently selected from the group consisting of oxo, fluoro, chloro, bromo, iodo, —$CF_3$, —$CCl_3$, —$CBr_3$, —$C_{13}$, —$CHF_2$, —$CHCl_2$, —$CHBr_2$, —$CHI_2$, —$CH_2F$, —$CH_2Cl$, —$CH_2Br$, —$CH_2I$, —CN, —OH, —$NH_2$, —$CO_2H$, —$CONH_2$, —$NO_2$, —SH, —$SO_3H$, —$SO_4H$, —$SO_2NH_2$, —$NHNH_2$, —$ONH_2$, —NHC(=O)$NHNH_2$, —NHC(=O)$NH_2$, —$NHSO_2H$, —NHC(=O)H, —NHC(=O)($C_1$-$C_6$)alkyl, —NH($C_1$-$C_6$)alkyl, —N($C_1$-$C_6$)alkyl($C_1$-$C_6$)alkyl, —NHOH, —$OCF_3$, —$OCCl_3$, —$OCBr_3$, —$OC_{13}$, —$OCHF_2$, —$OCHCl_2$, —$OCHBr_2$, —$OCHI_2$, —$OCH_2F$, —$OCH_2Cl$, —$OCH_2Br$, —$OCH_2I$, ($C_1$-$C_6$)alkyl, ($C_1$-$C_6$)alkoxy, ($C_1$-$C_6$)haloalkoxy, ($C_3$-$C_8$)cycloalkyl, and ($C_6$-$C_{10}$)aryl.

The term "heteroatom" is art-recognized, and includes an atom of any element other than carbon or hydrogen. Illustrative heteroatoms include oxygen, nitrogen and sulfur.

The term "cycloalkylalkyl" as used herein refers to an alkyl group substituted with one or more cycloalkyl groups.

The term "heterocycloalkylalkyl" as used herein refers to an alkyl group substituted with one or more heterocycloalkyl (i.e., heterocyclyl) groups.

The term "alkenyl" as used herein means a straight-chain or branched chain hydrocarbon radical containing from 2 to 6 carbons and containing at least one carbon-carbon double bond formed by the removal of two hydrogens. Representative examples of alkenyl include, but are not limited to, ethenyl, 2-propenyl, 2-methyl-2-propenyl, 3-butenyl, 4-pentenyl, and 5-hexenyl. The unsaturated bond(s) of the alkenyl group can be located anywhere in the moiety and can have either the (Z) or the (E) configuration about the double bond(s).

The term "amino" is a term of art and as used herein refers to both unsubstituted and substituted amines, e.g., a moiety that may be represented by the general formulas.

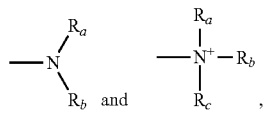

wherein $R_a$, $R_b$, and $R_c$ each independently represent a hydrogen, an alkyl, an alkenyl. —$(CH_2)_x$—$R_d$, or $R_a$ and $R_b$, taken together with the N atom to which they are attached complete a heterocycle having from 4 to 8 atoms in the ring structure; $R_d$ represents an aryl, a cycloalkyl, a cycloalkenyl, or a heterocyclyl; and x is zero or an integer in the range of 1 to 8. In certain embodiments, only one of $R_a$ or $R_b$ may be a carbonyl, e.g., $R_a$, $R_b$, and the nitrogen together do not form an imide. In other embodiments, $R_a$ and $R_b$ (and optionally $R_c$) each independently represent a hydrogen, an alkyl, an alkenyl, or —$(CH_2)_x$—$R_d$.

In certain embodiments, the term "amino" refers to —$NH_2$.

The term "alpha-amino acid" is a term of art, including, but not limited to, any one of 20 canonical alpha-amino acids, including their D- and L-isomers; and also glycine, as well as D- and L-proline (being, in fact, imino acids). The three-letter codes, trivial names, and systematic names of residues of these amino acids (L isomer series assumed) are as follows:

| Ala | alanyl | (S)-2-aminopropanoyl; |
|---|---|---|
| Arg | arginyl | (S)-2-amino-5-guanidinopentanoyl; |
| Asn | asparaginyl | (S)-2,4-diamino-4-oxobutanoyl; |
| Asp | aspartyl | (S)-2-amino-3-carboxypropanoyl; |
| Cys | cysteinyl | (R)-2-amino-3-mercaptopropanoyl; |
| Gln | glutaminyl | (S)-2,5-diamino-5-oxopentanoyl; |
| Glu | glutamyl | (S)-2-amino-4-carboxybutanoyl; |
| Gly | glycyl | 2-aminoacetyl; |
| His | histidyl | (S)-2-amino-3-(1H-imidazol-4-yl)propanoyl; |
| Ile | isoleucyl | (2S,3S)-2-amino-3-methylpentanoyl; |
| Leu | leucyl | (S)-2-amino-4-methylpentanoyl; |
| Lys | lysyl | (S)-2,6-diaminohexanoyl; |
| Met | methionyl | (S)-2-amino-4-(methylthio)butanoyl; |
| Phe | phenylalanyl | (S)-2-amino-3-phenylpropanoyl; |
| Pro | prolyl | (S)-pyrrolidine-2-carboxyl; |
| Ser | seryl | (S)-2-amino-3-hydroxypropanoyl; |
| Thr | threonyl | (2S,3R)-2-amino-3-hydroxybutanoyl; |
| Trp | tryptophanyl | (S)-2-amino-3-(1H-indol-3-yl)propanoyl; |
| Tyr | tyrosyl | (S)-2-amino-3-(4-hydroxyphenyl)propanoyl; |
| Val | valyl | (S)-2-amino-3-methylbutanoyl. |

Other alpha-amino acid residues mentioned in this disclosure are, for example,

| tert-Leu | tert-leucyl | (S)-2-amino-3,3-dimethylbutanoyl; |
|---|---|---|
| Nva | norvalyl | (S)-2-aminopentanoyl; |
| Orn | ornithyl | (S)-2,5-diaminopentanoyl; |
| Pyl | pyrrolysyl | (S)-2-amino-6-{[(2R,3R)-3-methyl-3,4-dihydro-2H-pyrrol-2-yl]carbonylamino}hexanoyl; |
| Sec | selenocysteinyl | (R)-2-amino-3-selanylpropanoyl; |
| SeMet | selenomethionyl | (S)-2-amino-4-(methylselanyl)butanoyl; |
| Cit | citrullinyl | (S)2-amino-5-(carbamoylamino)pentanoyl; (S)-2-amino-2-cyclopentylacetyl; (S)-2-amino-3-hydroxy-3-methylbutanoyl; and (S)-2-amino-2,3-dimethylbutanoyl. |

The term "amido", as used herein, means —NHC(=O)—, wherein the amido group is bound to the parent molecular moiety through the nitrogen. Examples of amido include alkylamido such as $CH_3C(=O)N(H)$— and $CH_3CH_2C(=O)N(H)$—.

The term "acyl" is a term of art and as used herein refers to any group or radical of the form RCO— where R is any organic group, e.g., alkyl, aryl, heteroaryl, aralkyl, and heteroaralkyl. Representative acyl groups include acetyl, benzoyl, and malonyl.

The term "aminoalkyl" as used herein refers to an alkyl group substituted with one or more one amino groups. In one embodiment, the term "aminoalkyl" refers to an aminomethyl group.

The term "aminoacyl" is a term of art and as used herein refers to an acyl group substituted with one or more amino groups.

The term "azide" or "azido", as used herein, means an —$N_3$ group.

The term "oxo" refers to the =O radical.

The term "carbonyl" as used herein refers to —C(=O)—.

The term "thiocarbonyl" as used herein refers to —C(=S)—.

The term "alkylthio" as used herein refers to alkyl-S—.

The term "carboxy", as used herein, means a —$CO_2H$ group.

The term "aryl" is a term of art and as used herein refers to includes monocyclic, bicyclic and polycyclic aromatic hydrocarbon groups, for example, benzene, naphthalene, anthracene, 1,2,3,4-tetrahydronaphthalene, indene, 2,3-dihydroindene, and pyrene. The aromatic ring may be substituted at one or more ring positions with one or more substituents, such as halogen, azide, alkyl, aralkyl, alkenyl, alkynyl, cycloalkyl, cycloalkylalkyl, (cycloalkyl)alkoxy, hydroxyl, alkoxyl, amino, nitro, sulfhydryl, imino, amido, phosphonate, phosphinate, carbonyl, carboxyl, silyl, ether, alkylthio, sulfonyl, aminosulfonyl, sulfonamido, ketone, aldehyde, ester, heterocyclyl, heterocyclylalkyl, aromatic or heteroaromatic moieties, aminoalkyl, haloalkyl, fluoroalkyl (such as trifluoromethyl), haloalkoxyl, cyano, or the like. The term "aryl" also includes polycyclic ring systems having two or more cyclic rings in which two or more carbons are common to two adjoining rings (the rings are "fused rings") wherein at least one of the rings is an aromatic hydrocarbon, e.g., the other cyclic rings may be cycloalkyls, cycloalkenyls, cycloalkynyls, aryls, heteroaryls, and/or heterocyclyls. Representative examples of the polycyclic aryl ring systems include, but are not limited to, azulenyl, naphthyl, dihydroinden-1-yl, dihydroinden-2-yl, dihydroinden-3-yl, dihydroinden-4-yl, 2,3-dihydroindol-4-yl, 2,3-dihydroindol-5-yl, 2,3-dihydroindol-6-yl, 2,3-dihydroindol-7-yl, inden-1-yl, inden-2-yl, inden-3-yl, inden-4-yl, dihydronaphthalen-2-yl, dihydronaphthalen-3-yl, dihydronaphthalen-4-yl, dihydronaphthalen-1-yl, 5,6,7,8-tetrahydronaphthalen-1-yl, 5,6,7,8-tetrahydronaphthalen-2-yl, 2,3-dihydrobenzofuran-4-yl, 2,3-dihydrobenzofuran-5-yl, 2,3-dihydrobenzofuran-6-yl, 2,3-dihydrobenzofuran-7-yl, benzo[d][1,3]dioxol-4-yl, benzo[d][1,3]dioxol-5-yl, 2H-chromen-2-on-5-yl, 2H-chromen-2-on-6-yl, 2H-chromen-2-on-7-yl, 2H-chromen-2-on-8-yl, isoindoline-1,3-dion-4-yl, isoindoline-1,3-dion-5-yl, inden-1-on-4-yl, inden-1-on-5-yl, inden-1-on-6-yl, inden-1-on-6-yl, 2,3-dihydrobenzo[b][1,4]dioxan-5-yl, 2,3-dihydrobenzo[b][1,4]dioxan-6-yl, 2H-benzo[b][1,4]oxazin3(4H)-on-5-yl, 2H-benzo[b][1,4]oxazin3(4H)-on-6-yl, 2H-benzo[b][1,4]oxazin3(4H)-on-7-yl, 2H-benzo[b][1,4]oxazin3(4H)-on-8-yl, benzo[d]oxazin-2(3H)-on-5-yl, benzo[d]oxazin-2(3H)-on-6-yl, benzo[d]oxazin-2(3H)-on-7-yl, benzo[d]oxazin-2(3H)-on-8-yl, quinazolin-4(3H)-on-5-yl, quinazolin-4(3H)-on-6-yl, quinazolin-4(3H)-on-7-yl, quinazolin-4(3H)-on-8-yl, quinoxalin-2(1H)-on-5-yl, quinoxalin-2(1H)-on-6-yl, quinoxalin-2(1H)-on-7-yl, quinoxalin-2(1H)-on-8-yl, benzo[d]thiazol-2(3H)-on-4-yl, benzo[d]thiazol-2(3H)-on-5-yl, benzo[d]thiazol-2(3H)-on-6-yl, and, benzo[d]thiazol-2(3H)-on-7-yl. In certain embodiments, the bicyclic aryl is (i) naphthyl, or (ii) a phenyl ring fused to either a 5 or 6 membered monocyclic cycloalkyl, a 5 or 6 membered monocyclic cycloalkenyl, or a 5 or 6 membered monocyclic heterocyclyl, wherein the fused cycloalkyl, cycloalkenyl, and heterocyclyl groups are optionally substituted. In certain embodiments, the term "aryl" refers to a phenyl group.

Aryl groups are optionally substituted by one or more substituents independently selected from the group consisting of fluoro, chloro, bromo, iodo, —$CF_3$, —$CCl_3$, —$CBr_3$, —$C_{I3}$, —$CHF_2$, —$CHCl_2$, —$CHBr_2$, —$CHI_2$, —$CH_2F$, —$CH_2Cl$, —$CH_2Br$, —$CH_2I$, —CN, —OH, —$NH_2$, —$CO_2H$, —$CONH_2$, —$NO_2$, —SH, —$SO_3H$, —$SO_4H$, —$SO_2NH_2$, —$NHNH_2$, —$ONH_2$, —$NHC(=O)NHNH_2$, —$NHC(=O)NH_2$, —$NHSO_2H$, —$NHC(=O)H$, —NHC(=O)($C_1$-$C_6$)alkyl, —NH($C_1$-$C_6$)alkyl, —N($C_1$-$C_6$)alkyl($C_1$-$C_6$)alkyl, —NHOH, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, ($C_1$-$C_6$)alkyl, ($C_1$-$C_6$)alkoxy, ($C_1$-$C_6$)haloalkoxy, ($C_3$-$C_8$)cycloalkyl, and ($C_6$-$C_{10}$)aryl.

The term "heteroaryl" is a term of art and as used herein refers to a monocyclic, bicyclic, and polycyclic aromatic group having 3 to 14, 5 to 14, or 3 to 12 total atoms including one or more heteroatoms such as nitrogen, oxygen, or sulfur in the ring structure. More preferred heteroaryl groups have from 5-10 ring members where from 1-4 of the ring members are hetero atoms selected from the group comprising O, N, and S. Exemplary heteroaryl groups include, for example, azaindolyl, benzo(b)thienyl, benzimidazolyl, benzofuranyl, benzoxazolyl, benzothiazolyl, benzothiadiazolyl, benzotriazolyl, benzoxadiazolyl, furanyl, imidazolyl, imidazopyridinyl, indolyl, indolinyl, indazolyl, isoindolinyl, isoxazolyl, isothiazolyl, isoquinolinyl, oxadiazolyl, oxazolyl, purinyl, pyranyl, pyrazinyl, pyrazolyl, pyridinyl, pyrimidinyl, pyrrolyl, pyrrolo[2,3-d]pyrimidinyl, pyrazolo[3,4-d]pyrimidinyl, quinolinyl, quinazolinyl, triazolyl, thiazolyl, thiophenyl, tetrahydroindolyl, tetrazolyl, thiadiazolyl, thienyl, thiomorpholinyl, triazolyl or tropanyl, and the like. The "heteroaryl" may be substituted at one or more ring positions with one or more substituents such as halogen, azido, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, fluoroalkyl (such as trifluromethyl), cyano, or the like. The term "heteroaryl" also includes polycyclic ring systems having two or more cyclic rings in which two or more carbons are common to two adjoining rings (the rings are "fused rings") wherein at least one of the rings is an aromatic group having one or more heteroatoms in the ring structure, e.g., the other cyclic rings may be cycloalkyls, cycloalkenyls, cycloalkynyls, aryls, heteroaryls, and/or heterocyclyls. Representative examples of bicyclic heteroaryl include, but are not limited to, benzimidazolyl, benzofuranyl, benzothienyl, benzoxadiazolyl, benzoxathiadiazolyl, benzothiazolyl, cinnolinyl, 5,6-dihydroquinolin-2-yl, 5,6-dihydroisoquinolin-1-yl, furopyridinyl, indazolyl, indolyl, isoquinolinyl, naphthyridinyl, quinolinyl, purinyl, 5,6,7,8-tetrahydroquinolin-2-yl, 5,6,7,8-tetrahydroquinolin-3-yl, 5,6,7,8-tetrahydroquinolin-4-yl, 5,6,7,8-tetrahydroisoquinolin-1-yl, thienopyridinyl, 4,5,6,7-tetrahydrobenzo[c][1,2,5]oxadiazolyl, and 6,7-dihydrobenzo[c][1,2,5]oxadiazol-4(5H)-onyl. Any bicyclic heteroaryl can be optionally substituted as detailed for "heteroaryl" above.

The term "aralkyl", "arylalkyl", or "aryl($C_1$-$C_6$)alkyl" is a term of art and as used herein refers to an alkyl group, for example a $C_1$-$C_6$ alkyl group, substituted with an aryl group, wherein the moiety is appended to the parent molecule through the alkyl group.

The term "heteroaralkyl", "heteroarylalkyl", or "heteroaryl($C_1$-$C_6$)alkyl" is a term of art and as used herein refers to an alkyl group, for example a $C_1$-$C_6$ alkyl group, substituted with a heteroaryl group, appended to the parent molecular moiety through the alkyl group.

The term "alkoxy" or "alkoxyl" as used herein means an alkyl group, as defined herein, appended to the parent molecular moiety through an oxygen atom. Representative examples of alkoxy include, but are not limited to, methoxy, ethoxy, propoxy, 2-propoxy, butoxy, tert-butoxy, pentyloxy, and hexyloxy.

The term "alkoxycarbonyl" means an alkoxy group, as defined herein, appended to the parent molecular moiety through a carbonyl group, represented by —C(=O)—, as defined herein. Representative examples of alkoxycarbonyl include, but are not limited to, methoxycarbonyl, ethoxycarbonyl, and tert-butoxycarbonyl.

The term "alkylcarbonyl", as used herein, means an alkyl group, as defined herein, appended to the parent molecular moiety through a carbonyl group, as defined herein. Representative examples of alkylcarbonyl include, but are not limited to, acetyl, 1-oxopropyl, 2,2-dimethyl-1-oxopropyl, 1-oxobutyl, and 1-oxopentyl.

The term "arylcarbonyl", as used herein, means an aryl group, as defined herein, appended to the parent molecular moiety through a carbonyl group, as defined herein. Representative examples of arylcarbonyl include, but are not limited to, benzoyl and (2-pyridinyl)carbonyl.

The term "alkylcarbonyloxy" and "arylcarbonyloxy", as used herein, means an alkylcarbonyl or arylcarbonyl group, as defined herein, appended to the parent molecular moiety through an oxygen atom. Representative examples of alkylcarbonyloxy include, but are not limited to, acetyloxy, ethylcarbonyloxy, and tert-butylcarbonyloxy. Representative examples of arylcarbonyloxy include, but are not limited to phenylcarbonyloxy.

The term "alkenoxy" or "alkenoxyl" means an alkenyl group, as defined herein, appended to the parent molecular moiety through an oxygen atom. Representative examples of alkenoxyl include, but are not limited to, 2-propen-1-oxyl (i.e., $CH_2$=CH—$CH_2$—O—) and vinyloxy (i.e., $CH_2$=CH—O—).

The term "aryloxy" as used herein means an aryl group, as defined herein, appended to the parent molecular moiety through an oxygen atom.

The term "heteroaryloxy" as used herein means a heteroaryl group, as defined herein, appended to the parent molecular moiety through an oxygen atom.

The terms "cyano" and "nitrile" are terms of art and as used herein refer to —CN.

The term "nitro", as used herein, means —$NO_2$.

The terms "halo" and "halogen" are terms of art and as used herein refer to —F, —Cl, —Br, or —I.

The term "haloalkyl" as used herein refers to an alkyl group, as defined herein, wherein some or all of the hydrogens are replaced with halogen atoms. The term "haloalkoxyl" refers to an alkoxy group, as defined herein, wherein some or all of the hydrogens are replaced with halogen atoms. An exemplary haloalkyl group is trifluoromethyl.

The terms "hydroxy" and "hydroxyl" are a term of art and as used herein refer to —OH.

The term "hydroxyalkyl", as used herein, means at least one hydroxy group, as defined herein, is appended to the parent molecular moiety through an alkyl group, as defined herein. Representative examples of hydroxyalkyl include, but are not limited to, hydroxymethyl, 2-hydroxyethyl, 3-hydroxypropyl, 2,3-dihydroxypentyl, and 2-ethyl-4-hydroxyheptyl.

The term "polyol", as used herein, denotes an organic compound containing more than one hydroxy group, an no other functional groups. Representative examples of polyols include, but are not limited to, glycerol, erythritol, xylitol, sorbitol, mannitol, and pinanediol.

Certain compounds contained in compositions of the present invention may exist in particular geometrical isomer or stereoisomeric forms. In addition, compounds of the present invention may also be optically active. The present invention contemplates all such compounds, including cis- and trans-isomers, (R)- and (S)-enantiomers, diastereoisomers, D-isomers, L-isomers, the racemic mixtures thereof, and other mixtures thereof, as falling within the scope of the invention. Additional asymmetric carbon atoms may be present in a substituent such as an alkyl group. All such isomers, as well as mixtures thereof, are intended to be included in this invention.

If, for instance, a particular enantiomer of compound of the present invention is desired, it may be prepared by asymmetric synthesis, or by derivation with a chiral auxiliary, where the resulting diastereomeric mixture is separated and the auxiliary group cleaved to provide the pure desired enantiomers. Alternatively, where the molecule contains a basic functional group, such as amino, or an acidic functional group, such as carboxyl, diastereomeric salts are formed with an appropriate optically-active acid or base, followed by resolution of the diastereomers thus formed by fractional crystallization or chromatographic means well known in the art, and subsequent recovery of the pure enantiomers.

"Optional" or "optionally" means that a subsequently described event or circumstance may or may not occur and that the description includes instances when the event or circumstance occurs and instances in which it does not. For example, "optionally substituted aryl" means that the aryl radical may or may not be substituted and that the description includes both substituted aryl radicals and aryl radicals having no substitution.

It will be understood that "substitution" or "substituted with" includes the implicit proviso that such substitution is in accordance with permitted valence of the substituted atom and the substituent, and that the substitution results in a stable compound. e.g., which does not spontaneously undergo transformation such as by rearrangement, fragmentation, decomposition, cyclization, elimination, or other reaction.

The term "substituted" is also contemplated to include all permissible substituents of organic compounds. In a broad aspect, the permissible substituents include acyclic and cyclic, branched and unbranched, carbocyclic and heterocyclic, aromatic and nonaromatic substituents of organic compounds. Illustrative substituents include, for example, halogen, azide, alkyl, aralkyl, alkenyl, alkynyl, cycloalkyl, cycloalkylalkyl, (cycloalkyl)alkoxyl, hydroxyl, alkoxyl, amino, nitro, sulfhydryl, imino, amido, phosphonate, phosphinate, carbonyl, carboxyl, silyl, ether, alkylthio, sulfonyl, aminosulfonyl, sulfonamido, ketone, aldehyde, ester, heterocyclyl, heterocyclylalkyl, aromatic or heteroaromatic moieties, aminoalkyl, haloalkyl, fluoroalkyl (such as trifluoromethyl), haloalkoxyl, cyano, or other substituents described above. The permissible substituents may be one or more and the same or different for appropriate organic compounds. For purposes of this invention, the heteroatoms such as nitrogen may have hydrogen substituents and/or any permissible substituents of organic compounds described herein which satisfy the valences of the heteroatoms. This invention is not intended to be limited in any manner by the permissible substituents of organic compounds.

The phrase "protecting group", as used herein, means temporary substituents which protect a potentially reactive functional group from undesired chemical transformations. Examples of such protecting groups include esters of carboxylic acids, silyl ethers of alcohols, and acetals and ketals of aldehydes and ketones, respectively. The field of protecting group chemistry has been reviewed (Greene, T. W.; Wuts, P. G. M. *Protective Groups in Organic Synthesis*, $2^{nd}$ ed.; Wiley: New York, 1991). Protected forms of the inventive compounds are included within the scope of this invention.

A "saturated" or "fully saturated" compound means that the referenced chemical structure does not contain any multiple carbon-carbon bonds. For example, a saturated cycloalkyl group as defined herein includes cyclohexyl, cyclopropyl, and the like.

An "unsaturated" or "partially saturated" compound means that the referenced chemical structure may contains on or more multiple carbon-carbon bonds, but is not aromatic. For example, an unsaturated cycloalkyl group as defined herein includes cyclohexenyl, cyclopentenyl, cyclohexadienyl, and the like.

For purposes of the invention, the chemical elements are identified in accordance with the Periodic Table of the Elements, CAS version, *Handbook of Chemistry and Physics*, 67th ed., 1986-87, inside cover.

It will be apparent to one skilled in the art that certain compounds of this disclosure may exist in tautomeric forms, all such tautomeric forms of the compounds being within the scope of the disclosure. A "tautomer" refers to a molecule wherein a proton shift from one atom of a molecule to another atom of the same molecule is possible. In certain embodiments, the compounds presented herein exist as tautomers. In circumstances where tautomerization is possible, a chemical equilibrium of tautomers will exist.

Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the disclosure. Both the R and the S stereochemical isomers, as well as all mixtures thereof, are included within the scope of the disclosure. A "racemic mixture" or "racemate" denotes equimolar mixture of two enantiomers, whereas a "scalemic mixture" denotes non-racemic mixture of two enantiomers.

The chemical structure of examples that are a mixture of diastereoisomers or a single diastereoisomer but with unknown relative configuration are drawn and named without defined stereochemical configuration.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The term "pharmaceutically acceptable salt" as used herein includes salts derived from inorganic or organic acids including, for example, hydrochloric, hydrobromic, sulfuric, nitric, perchloric, phosphoric, formic, acetic, lactic, maleic, fumaric, pamoic (embonic), succinic, tartaric, glycolic, salicylic, citric, methanesulfonic, benzenesulfonic, benzoic, malonic, trifluoroacetic, trichloroacetic, naphthalene-2-sulfonic, and other acids. Pharmaceutically acceptable salt forms can include forms wherein the ratio of molecules comprising the salt is not 1:1. For example, the salt may comprise more than one inorganic or organic acid molecule per molecule of base, such as two hydrochloric acid molecules per molecule of compound of Formula (I). As another example, the salt may comprise less than one inorganic or organic acid molecule per molecule of base, such as two molecules of compound of Formula (I) per molecule of tartaric acid.

The compounds according to the invention, e.g., the compounds of Formula (I), can form solvates with a stoichiometric or non-stoichiometric amount of one or more solvents, such as water, ethanol, diethyl ether, or ethyl acetate. The solvates formed with water ale called hydrates.

As used herein, a protic solvent is a solvent that has a hydrogen atom bound to an oxygen atom (as in a hydroxyl group) or a nitrogen atom (as in an amine group). In general terms, any solvent that contains labile H⁺ is called a protic solvent. The molecules of such solvents readily donate protons (H⁺) to reagents. In contrast, an aprotic solvent is a solvent that does not have a hydrogen atom bound to an oxygen (as in a hydroxyl group) or a nitrogen (as in an amine group), and it cannot donate hydrogen.

As used herein, a polar protic solvent is a protic solvent that will dissolve many salts. In general, these solvents have high dielectric constants and high polarity. Non-limiting examples of polar protic solvents include acetic acid, ammonia, ethanol, formic acid, isopropanol, methanol, n-butanol, nitromethane, n-propanol, tert-butanol, and water.

As used herein, a polar aprotic solvent is a solvent that will dissolve many salts, but lacks an acidic hydrogen; these solvents generally have intermediate to high dielectric constants and polarity. Non-limiting examples of polar aprotic solvents include acetone, acetonitrile, dichloromethane (DCM), dimethyl sulfoxide (DMSO), ethyl acetate, hexamethylphosphoric triamide (HMPT), N,N-dimethylformamide (DMF), and tetrahydrofuran (THF).

As used herein, a nonpolar aprotic solvent is a solvent that will dissolve many salts, but lacks an acidic hydrogen; these solvents generally have low dielectric constants and polarity. Non-limiting examples of nonpolar aprotic solvents include benzene, chloroform, cyclohexane, diethyl ether, hexane, pentane, and toluene.

A physician or veterinarian having ordinary skill in the art can readily determine and prescribe the therapeutically effective amount of the pharmaceutical composition required. For example, the physician or veterinarian could start doses of the pharmaceutical composition or compound at levels lower than that required in order to achieve the desired therapeutic effect and gradually increase the dosage until the desired effect is achieved. By "therapeutically effective amount" is meant the concentration of a compound that is sufficient to elicit the desired therapeutic effect. It is generally understood that the effective amount of the compound will vary according to the weight, sex, age, and medical history of the subject. Other factors which influence the effective amount may include, but are not limited to, the severity of the patient's condition, the disorder being treated, the stability of the compound, the mode of administration, the bioavailability of the particular compound, and, if desired, another type of therapeutic agent being administered with the compound of the invention. A larger total dose can be delivered by multiple administrations of the agent. Methods to determine efficacy and dosage are known to those skilled in the art (Isselbacher et al. (1996) *Harrison's Principles of Internal Medicine* 13 ed., 1814-1882, herein incorporated by reference).

"Modulating" or "modulate" refers to the treating, prevention, suppression, enhancement or induction of a function, condition or disorder.

The term "treating" includes prophylactic and/or therapeutic treatments. The term "prophylactic or therapeutic" treatment is art-recognized and includes administration to the host of one or more of the subject compositions. If it is administered prior to clinical manifestation of the unwanted condition (e.g., disease or other unwanted state of the host animal) then the treatment is prophylactic, in other words—preventive, (i.e., it protects the host against developing the unwanted condition), whereas if it is administered after manifestation of the unwanted condition, the treatment is therapeutic, (i.e., it is intended to diminish, ameliorate, or stabilize the existing unwanted condition or side effects thereof). Thus, in certain aspects, the disclosure encompasses non-prophylactic treatment, i.e., therapeutic treatment.

As used herein, "subject" refers to a warm blooded animal such as a mammal, preferably a human, or a human child, which is afflicted with, or has the potential to be afflicted with one or more diseases and disorders described herein.

"$EC_{50}$" refers to a dosage, concentration or amount of a particular test compound that elicits a dose-dependent response at 50% of maximal expression of a particular response that is induced, provoked or potentiated by the particular test compound.

"$IC_{50}$" refers to an amount, concentration or dosage of a particular test compound that achieves a 50% inhibition of a maximal response in an assay that measures such response.

Compounds of the Invention

In one aspect, the invention provides a compound of structural Formula (I):

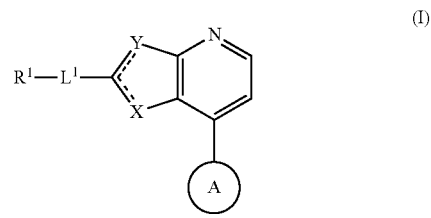

wherein:
the dotted line in the five-membered ring containing X and Y indicates a double bond in either of the possible positions between C and X or between C and Y, wherein the bond in the other one of these positions is a single bond;
either X is S and Y is C(R^C); or
X is C(R^C) and Y is S; or
X is N and Y is N(R^N); or
X is N(R^N) and Y is N; or
X is O and Y is C(R^C); or
X is S and Y is N;

Ⓐ is (A1), (A2), (A3), (A4),(A5), (A6), (A7), or (A8):

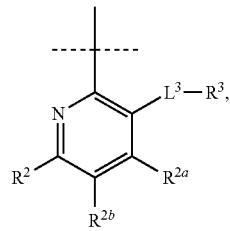

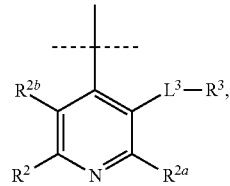

-continued

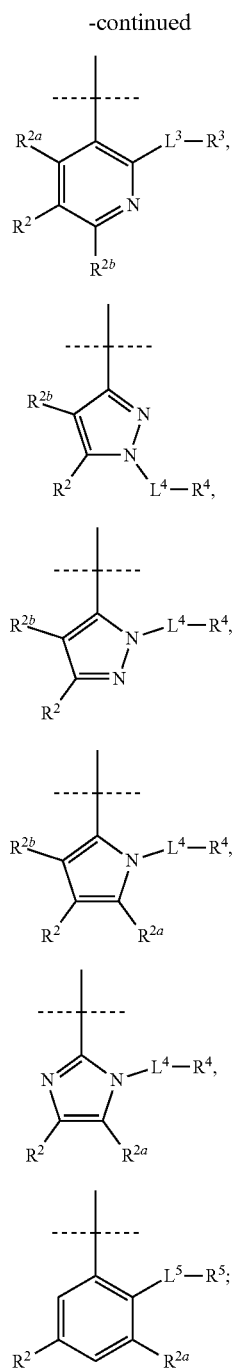

(A3)
(A4)
(A5)
(A6)
(A7)
(A8)

L¹ represents a single bond, —N(R^N)—, —O—, —S—, —S(=O)—, —S(=O)₂—, or C₁-C₃ alkylene;

R¹ is selected from the group consisting of hydrogen, alkyl, and (4-6) membered heterocycloalkyl containing 1 to 3 nitrogen heteroatoms and optionally substituted with 1 or 2 substituents selected from the group consisting of hydroxy, oxo, methyl, and/or C₁-C₃ alkylene forming a C₃-C₅ cycloalkyl ring that shares one or two carbon ring atoms with said (4-6) membered heterocycloalkyl and is optionally substituted with 1 or 2 methyl groups;

R², R²ᵃ, and R²ᵇ are each independently selected from the group consisting of hydrogen, substituted or unsubstituted alkyl, —C≡N, —N₃, —NO₂, fluoro, chloro, bromo, iodo, —CF₃, —CCl₃, —CBr₃, —C I₃, —CHF₂, —CHCl₂, —CHBr₂, —CHI₂, —CH₂F, —CH₂Cl, —CH₂Br, —CH₂I, —OH, —O-alkyl, —CO₂H, —CONH₂, —C(=O)-alkyl, —C(=O)—O-alkyl, —C(=O)—NH-alkyl, —C(=O)—N(alkyl)₂, —NH₂, —NH-alkyl, and —N(alkyl)₂;

L³ represents a single bond, —O—, —S—, —S(=O)—, —S(=O)₂—, —C(R^C)₂—, —C(=O)—, —NH—, —NH—C(=O)—CH₂—, —NH—C(=O)—, —C(=O)—NH—, or —CH(OH)—;

R³ is selected from group consisting of C₃-C₆ cycloalkyl; (4-6) membered heterocycloalkyl containing 1 to 3 heteroatoms selected from N, O, and S; diazabicyclo[2.2.2]octanyl; (7-10) membered fused bicyclic heterocycloalkyl containing 2 nitrogen heteroatoms; and (7-9) membered spiro bicyclic heterocycloalkyl containing 1 nitrogen heteroatom; all the above members of the group representing R³ being saturated or unsaturated, and optionally substituted with 1 or 2 or 3 substituents selected from fluoro, chloro, bromo, iodo, alkyl, —NH₂, —NH-alkyl, —N(alkyl)₂, —OH, oxo, -alkylene-NH₂, ureido, alanylamino, arginylamino, asparaginylamino, aspartylamino, cysteinylamino, glutaminylamino, glutamylamino, glycylamino, histidylamino, isoleucylamino, leucylamino, lysylamino, methionylamino, phenylalanylamino, prolylamino, serylamino, threonylamino, tryptophanylamino, tyrosylamino, valylamino, and 2,2,2-trifluoroacetyl;

or else R³ is selected from the group consisting of —CF₃, —O-alkyl, —NH— alkyl, —N(alkyl)₂, and 2-(dimethylamino)ethyl(methyl)amino;

L⁴ represents a single bond, —O—, —S—, —S(=O)—, —S(=O)₂—, —C(R^C)₂—, —C(=O)—, —NH—, —NH—C(=O)—CH₂—, —NH—C(=O)—, —C(=O)—NH—, or —CH(OH)—;

R⁴ is selected from hydrogen and (5-6) membered heterocycloalkyl containing 1 to 2 heteroatoms selected from N, O, and S;

L⁵ represents a single bond, —NH—, —O—, —S—, —S(=O)—, —S(=O)₂—, —C(=O)—, —N(R^N)—, —N(R^N)—C(=O)—C(R^C)₂—, —N(R^N)—C(=O)—, —C(=O)—N(R^N)—, or —CH(OH)—;

R⁵ is selected from (5-6) membered heterocycloalkyl containing 1 to 2 heteroatoms selected from N, O, and S;

each occurrence of R^C is independently selected from the group consisting of hydrogen, fluoro, chloro, bromo, iodo, alkyl, cycloalkyl, and aryl;

each occurrence of R^N is independently selected from the group consisting of hydrogen, alkyl, cycloalkyl, and aryl;

provided that if X is S and Y is CH then L⁵ is not —O—;

and provided that the compound of Formula (I) is not 3-((7-(5-chloro-3-methyl-2-(piperidin-3-ylamino)phenyl)thieno[3,2-b]pyridin-2-yl)methyl)-6,6-dimethyl-3-azabicyclo[3.1.0]hexane-2,4-dione;

or a tautomer, stereoisomer, a racemic or scalemic mixture of stereoisomers, a pharmaceutically acceptable salt, ester, solvate, or polymorph thereof.

To avoid any doubts, the structure of L³ is written from the heterocyclic ring at its left hand side to R³ at its right hand side, for example, (pyridin-3-yl)-NH—C(=O)—CH?-R³, as in the structure of Example 32. The same convention is used for notation of the structure of L$^5$.

The above-defined general Formula (I) covers certain compounds of the invention, which can be described in more detail as follows.

In some embodiments, the invention provides a compound of Formula (I), as defined above, or a tautomer, stereoisomer, a racemic or scalemic mixture of stereoisomers, a pharmaceutically acceptable salt, ester, solvate, or polymorph thereof, wherein:

the dotted line in the five-membered ring containing X and Y indicates a double bond in either of the possible positions between C and X or between C and Y, wherein the bond in the other one of these positions is a single bond;

either X is S and Y is CH; or
X is CH and Y is S; or
X is N and Y is NH; or
X is N and Y is NMe; or
X is NMe and Y is N; or
X is O and Y is CH; or
X is S and Y is N;

(A) is (A1), (A2), (A3), (A4), (A5), (A6), (A7), or (A8):

(A1)
(A2)
(A3)
(A4)
(A5)
(A6)
(A7)
(A8)

L$^1$ represents a single bond or —CH$_2$—;
R$^1$ is selected from the group consisting of hydrogen, methyl, R$^2$, R$^{2a}$, and R$^{2b}$ are each independently selected from the group consisting of hydrogen, methyl, ethyl, —C≡N, —NO$_2$, —NH$_2$, dimethylamino, chloro, fluoro, —CF$_3$, and ethoxycarbonyl;

L$^3$ represents a single bond, —O—, —CH$_2$—, —C(=O)—, —NH—, —NH—C(=O)—CH$_2$—, —NH—C(=O)—, —C(=O)—NH—, or —CH(OH)—;

R$^3$ is selected from the group consisting of C$_4$-cycloalkyl; (4-6) membered heterocycloalkyl containing 1 to 3 nitrogen heteroatoms or 1 nitrogen heteroatom and 1 oxygen heteroatom; 8-membered fused bicyclic heterocycloalkyl containing 2 nitrogen heteroatoms; diazabicyclo[2.2.2]octanyl; and (7-9) membered spiro bicyclic heterocycloalkyl containing 1 nitrogen heteroatom; all the above members of the group representing $R^3$ being saturated or unsaturated, and optionally substituted with 1 or 2 or 3 substituents selected from fluoro, methyl, ethyl, amino, methylamino, dimethylamino, ethylamino, isopropylamino, hydroxy, oxo, aminomethyl, 1-aminoethyl, (isopropylamino)methyl, ureido, alanylamino, valylamino, fluoromethyl, difluoromethyl, trifluoromethyl, and 2,2,2-trifluoroacetyl;

or else $R^3$ is selected from the group consisting of trifluoromethyl, methoxy, methylamino, and 2-(dimethylamino)ethyl(methyl)amino;

$L^4$ represents a single bond or —CH$_2$—;
$R^4$ is selected from hydrogen and morpholin-2-yl;
$L^5$ represents —NH—, —O— or —NH—C(=O)—; and
$R^5$ is selected from pyrrolidin-3-yl, piperidin-3-yl, and piperidin-4-yl;

provided that if X is S and Y is CH then $L^5$ is not —O—.

In some embodiments, the invention provides a compound of Formula (I), as defined above, or a tautomer, stereoisomer, a racemic or scalemic mixture of stereoisomers, a pharmaceutically acceptable salt, ester, solvate, or polymorph thereof, wherein:

the dotted line in the five-membered ring containing X and Y indicates a double bond in either of the possible positions between C and X or between C and Y, wherein the bond in the other one of these positions is a single bond;

either X is S and Y is CH; or
X is CH and Y is S; or
X is N and Y is NH; or
X is N and Y is NMe; or
X is NMe and Y is N; or
X is O and Y is CH; or
X is S and Y is N;

Ⓐ is (A1), (A2), (A3), (A4), (A5), (A6), (A7), or (A8):

(A1)

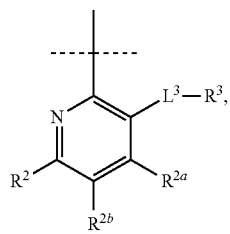

(A2)

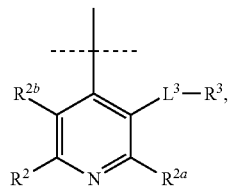

(A3)

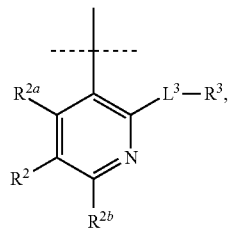

(A4)

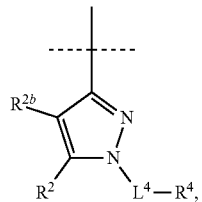

(A5)

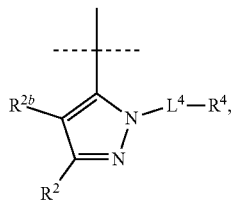

(A6)

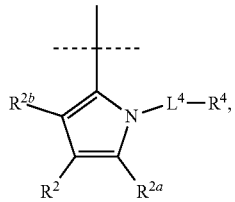

(A7)

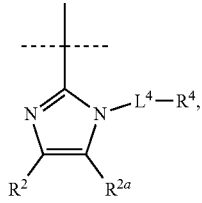

(A8)

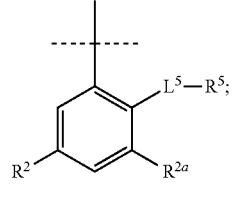

$L^1$ represents a single bond or —CH$_2$—;

$R^1$ is selected from the group consisting of hydrogen, methyl,

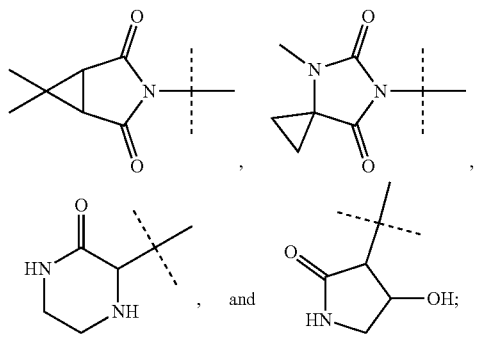

$R^2$, $R^{2a}$, and $R^{2b}$ are each independently selected from hydrogen, methyl, ethyl, —C≡N, —NO$_2$, —NH$_2$, dimethylamino, chloro, fluoro, —CF$_3$, and ethoxycarbonyl;

L³ represents a single bond, —O—, —CH₂—, —C(=O)—, —NH—, —NH—C(=O)—CH₂—, —NH—C(=O)—, —C(=O)—NH—, or —CH(OH)—;

R³ is selected from 3,3-difluorocyclobut-1-yl, 3,3-difluoroazetidin-1-yl, 3-(dimethyl-amino)azetidin-1-yl, azetidin-2-yl, azetidin-3-yl, 3-aminopyrrolidin-1-yl, 3-(methyl-amino)pyrrolidin-1-yl, 3-(dimethylamino)pyrrolidin-1-yl, 3-(dimethylamino)₄-methylpyrrolidin-1-yl, 3-(ethylamino)pyrrolidin-1-yl, 3-(isopropylamino)pyrrolidin-1-yl, 3-hydroxypyrrolidin-1-yl, 3-fluoropyrrolidin-1-yl, 3,3-difluoropyrrolidin-1-yl, 3,3-difluoro-4-(methylamino)pyrrolidin-1-yl, 2-oxopyrrolidin-1-yl, 3-(aminomethyl)pyrrolidin-1-yl, 3-amino-3-methylpyrrolidin-1-yl, 3-amino-4-methylpyrrolidin-1-yl, 3-methyl-4-(methylamino)pyrrolidin-1-yl, 3-(1-aminoethyl)-pyrrolidin-1-yl, 3-amino-4-fluoropyrrolidin-1-yl, 3-((isopropylamino)methyl)-pyrrolidin-1-yl, 3-(D-alanylamino)pyrrolidin-1-yl, 3-(D-valylamino)pyrrolidin-1-yl, 3-ureidopyrrolidin-1-yl, 3-(aminomethyl)pyrrolidin-1-yl, 3-(fluoromethyl)pyrrolidin-1-yl, 3-(difluoromethyl)pyrrolidin-1-yl, pyrrolidin-3-yl, 1-(2,2,2-trifluoroacetyl)-pyrrolidin-3-yl, 1H-1,2,4-triazol-1-yl, 3-(methylamino)piperidin-1-yl, 4-aminopiperidin-1-yl, 4,4-difluoropiperidin-1-yl, piperidin-3-yl, piperidin-4-yl, piperazin-1-yl, 2-methylpiperazin-1-yl, 4-methylpiperazin-1-yl, 2-oxopiperazin-1-yl, 4-methyl-2-oxopiperazin-1-yl, 2,4-dimethylpiperazin-1-yl, 2,6-dimethylpiperazin-1-yl, 3,3-dimethylpiperazin-1-yl, piperazin-2-yl, 4-ethylpiperazin-1-yl, 3-oxopiperazin-2-yl, 3,6-dioxopiperazin-2-yl, 2-oxotetrahydropyrimidin-1(2H)-yl, pyridin-3-yl, morpholino, 3-oxomorpholino, morpholin-2-yl, 4-methylmorpholin-2-yl, hexahydropyrrolo[3,4-b]pyrrol-1-yl, octahydropyrrolo[3,4-b]pyrrol-1-yl, octahydro-pyrrolo[3,4-b]pyrrol-5-yl, 2,5-diazabicyclo[2.2.2]octane-2-yl, 2-azaspiro[3.3]heptan-6-yl, 7-amino-5-azaspiro[2.4]heptan-5-yl, 1,7-diazaspiro[4.4]nonan-7-yl, trifluoromethyl, methoxy, methylamino, and 2-(dimethylamino)ethyl(methyl)amino;

L⁴ represents a single bond or —CH₂—;

R⁴ is selected from hydrogen and morpholin-2-yl;

L⁵ represents —NH—, —O—, or —NH—C(=O)—; and

R⁵ is selected from pyrrolidin-3-yl, piperidin-3-yl, and piperidin-4-yl;

provided that if X is S and Y is CH then L⁵ is not —O—.

In some embodiments, the invention provides a compound of Formula (I), as defined above, or a tautomer, stereoisomer, a racemic or scalemic mixture of stereoisomers, a pharmaceutically acceptable salt, ester, solvate, or polymorph thereof.

(I)

wherein:
the dotted line in the five-membered ring containing X and Y indicates a double bond in either of the possible positions between C and X or between C and Y, wherein the bond in the other one of these positions is a single bond;

either X is S and Y is C(R^C); or
X is C(R^C) and Y is S; or
X is N and Y is N(R^N); or
X is N(R^N) and Y is N; or
X is O and Y is C(R^C); or
X is S and Y is N;

$\text{A}$ is (A1), (A2), (A3), (A4), (A5), (A6), (A7), or (A8):

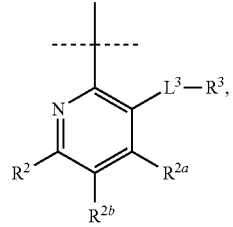

(A1)

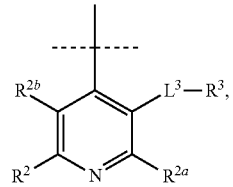

(A2)

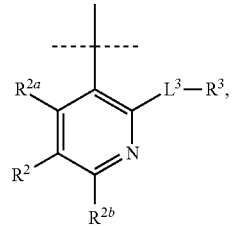

(A3)

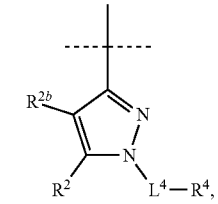

(A4)

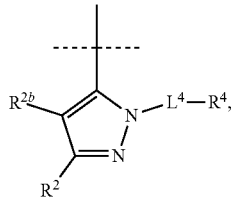

(A5)

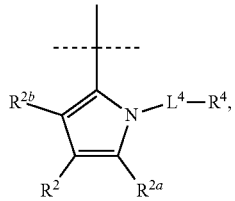

(A6)

-continued

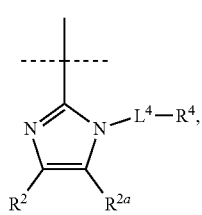
(A7)

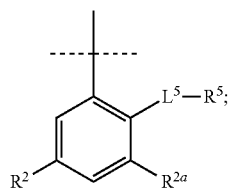
(A8)

L¹ represents a single bond, —N(R$^N$)—, —O—, —S—, —S(=O), —S(=O)$_2$—, or C$_1$-C$_3$ alkylene;

R¹ is selected from the group consisting of hydrogen, alkyl, and (4-6) membered heterocycloalkyl containing 1 to 3 nitrogen heteroatoms and optionally substituted with 1 or 2 substituents selected from the group consisting of oxo, methyl, and/or C$_1$-C$_3$ alkylene forming a C$_3$-C$_5$ cycloalkyl ring that shares one or two carbon ring atoms with said (4-6) membered heterocycloalkyl and is optionally substituted with 1 or 2 methyl groups;

R², R$^{2a}$, and R$^{2b}$ are each independently selected the group consisting of hydrogen, substituted or unsubstituted alkyl, —C≡N, —N$_3$, —NO$_2$, fluoro, chloro, bromo, iodo, —CF$_3$, —CCl$_3$, —CBr$_3$, —C$_{13}$, —CHF$_2$, —CHCl$_2$, —CHBr$_2$, —CHI$_2$, —CH$_2$F, —CH$_2$Cl, —CH$_2$Br, —CH$_2$I, —OH, —O-alkyl, —CO$_2$H, —CONH$_2$, —C(=O)-alkyl, —C(=O)—O-alkyl, —C(=O)—NH-alkyl, —C(=O)—N(alkyl)$_2$, —NH$_2$, —NH-alkyl, and —N(alkyl)$_2$;

L³ represents a single bond, —O—, —S—, —S(=O)—, —S(=O)$_2$—, —C(R$^C$)$_2$—, —C(=O)—, —NH—, —NH—C(=O)—CH$_2$—, —NH—C(=O)—, —C(=O)—NH—, or —CH(OH)—;

R³ is selected from group consisting of C$_3$-C$_6$ cycloalkyl; (4-6) membered heterocycloalkyl containing 1 to 3 heteroatoms selected from N, O, and S; (7-10) membered fused bicyclic heterocycloalkyl containing 2 nitrogen heteroatoms; and (7-9) membered spiro bicyclic heterocycloalkyl containing 1 nitrogen heteroatom; all the above members of the group representing R³ being saturated or unsaturated, and optionally substituted with 1 or 2 substituents selected from fluoro, chloro, bromo, iodo, alkyl, —NH$_2$, —NH-alkyl, —N(alkyl)$_2$, —OH, oxo, -alkylene-NH$_2$, ureido, alanylamino, arginylamino, asparaginylamino, aspartylamino, cysteinylamino, glutaminylamino, glutamylamino, glycylamino, histidylamino, isoleucylamino, leucylamino, lysylamino, methionylamino, phenylalanylamino, prolylamino, serylamino, threonylamino, tryptophanylamino, tyrosylamino, valylamino, and 2,2,2-trifluoroacetyl;

or else R³ is selected from the group consisting of —CF$_3$, —O-alkyl, —NH— alkyl, —N(alkyl)$_2$, and 2-(dimethylamino)ethyl(methyl)amino;

L⁴ represents a single bond, —O—, —S—, —S(=O)—, —S(=O)$_2$—, —C(R$^C$)$_2$—, —C(=O)—, —NH—, —NH—C(=O)—CH$_2$—, —NH—C(=O)—, —C(=O)—NH—, or —CH(OH)—;

R⁴ is selected from hydrogen and (5-6) membered heterocycloalkyl containing 1 to 2 heteroatoms selected from N, O, and S;

L⁵ represents a single bond, —O—, —S—, —S(=O)—, —S(=O)$_2$—, —C(=O)—, —N(R$^N$)—, —N(R$^N$)—C(=O)—C(R$^C$)$_2$—, —N(R$^N$)—C(=O)—, —C(=O)—N(R$^N$)—, or —CH(OH)—;

R⁵ is selected from (5-6) membered heterocycloalkyl containing 1 to 2 heteroatoms selected from N, O, and S;

each occurrence of R$^C$ is independently selected from the group consisting of hydrogen, fluoro, chloro, bromo, iodo, alkyl, cycloalkyl, and aryl;

each occurrence of R$^N$ is independently selected from the group consisting of hydrogen, alkyl, cycloalkyl, and aryl;

provided that if X is S and Y is CH then L⁵ is not —O—.

In some embodiments, the invention provides a compound of Formula (I), as defined above, or a tautomer, stereoisomer, a racemic or scalemic mixture of stereoisomers, a pharmaceutically acceptable salt, ester, solvate, or polymorph thereof, wherein:

the dotted line in the five-membered ring containing X and Y indicates a double bond in either of the possible positions between C and X or between C and Y, wherein the bond in the other one of these positions is a single bond;

either X is S and Y is CH; or
X is CH and Y is S; or
X is N and Y is NH; or
X is N and Y is NMe; or
X is NMe and Y is N; or
X is O and Y is CH; or
X is S and Y is N;

Ⓐ is (A1), (A2), (A3), (A4),(A5), (A6), (A7), or (A8):

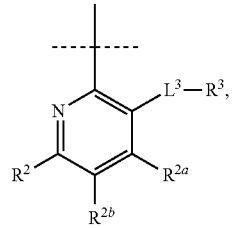
(A1)

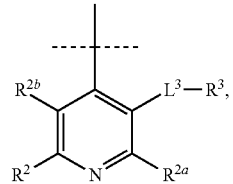
(A2)

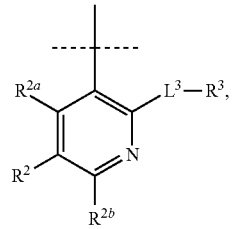
(A3)

-continued

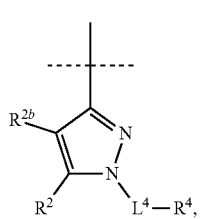
(A4)

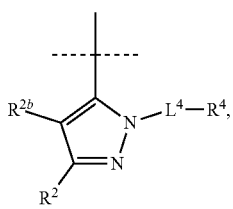
(A5)

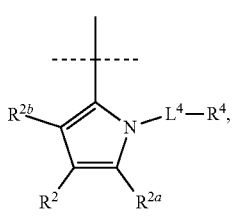
(A6)

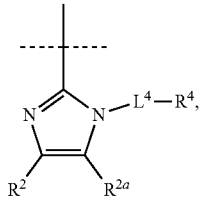
(A7)

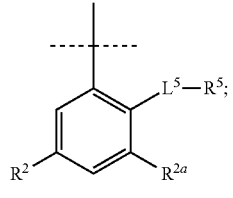
(A8)

$L^1$ represents a single bond or —CH$_2$—;
$R^1$ is selected from the group consisting of hydrogen, methyl,

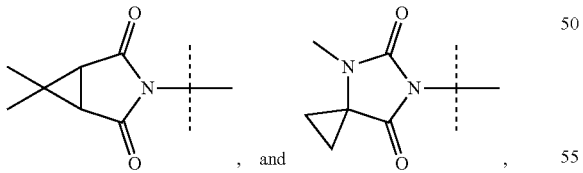
, and $R^2$, $R^{2a}$, and $R^{2b}$ are each independently selected from the group consisting of hydrogen, methyl, ethyl, —C≡N, chloro, —CF$_3$, and ethoxycarbonyl;
$L^3$ represents a single bond, —O—, —CH$_2$—, —C(=O)—, —NH—, —NH—C(=O)—CH$_2$—, —NH—C(=O)—, —C(=O)—NH—, or —CH(OH)—;
$R^3$ is selected from the group consisting of C$_4$-cycloalkyl; (4-6) membered heterocycloalkyl containing 1 to 3 nitrogen heteroatoms or 1 nitrogen heteroatom and 1 oxygen heteroatom; 8-membered fused bicyclic heterocycloalkyl containing 2 nitrogen heteroatoms; and (7-9) membered spiro bicyclic heterocycloalkyl containing 1 nitrogen heteroatom; all the above members of the group representing $R^3$ being saturated or unsaturated, and optionally substituted with 1 or 2 substituents selected from fluoro, methyl, ethyl, amino, methylamino, dimethylamino, ethylamino, isopropylamino, hydroxy, oxo, aminomethyl, 1-aminoethyl, (isopropylamino)methyl, ureido, alanylamino, valylamino, fluoromethyl, difluoromethyl, trifluoromethyl, and 2,2,2-trifluoroacetyl;

or else $R^3$ is selected from the group consisting of trifluoromethyl, methoxy, methylamino, and 2-(dimethylamino)ethyl(methyl)amino;

$L^4$ represents a single bond or —CH$_2$—;
$R^4$ is selected from hydrogen and morpholin-2-yl;
$L^5$ represents —O— or —NH—C(=O)—; and
$R^5$ is selected from pyrrolidin-3-yl, piperidin-3-yl, and piperidin-4-yl;

provided that if X is S and Y is CH then $L^5$ is not —O—.

In some embodiments, the invention provides a compound of Formula (I), as defined above, or a tautomer, stereoisomer, a racemic or scalemic mixture of stereoisomers, a pharmaceutically acceptable salt, ester, solvate, or polymorph thereof, wherein:

the dotted line in the five-membered ring containing X and Y indicates a double bond in either of the possible positions between C and X or between C and Y, wherein the bond in the other one of these positions is a single bond;

either X is S and Y is CH; or

X is CH and Y is S; or

X is N and Y is NH; or

X is N and Y is NMe; or

X is NMe and Y is N; or

X is O and Y is CH; or

X is S and Y is N;

Ⓐ is (A1), (A2), (A3), (A4), (A5), (A6), (A7), or (A8):

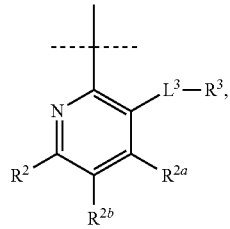
(A1)

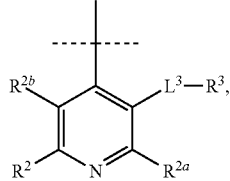
(A2)

(A3) 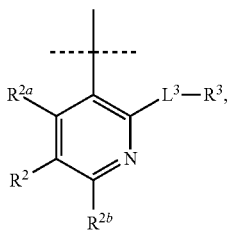

(A4) 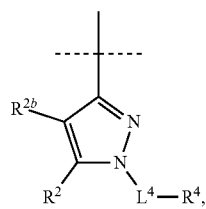

(A5) 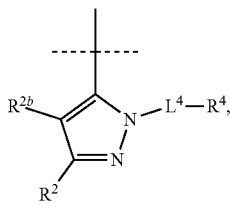

(A6) 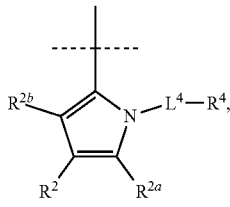

(A7) 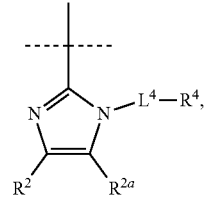

(A8) 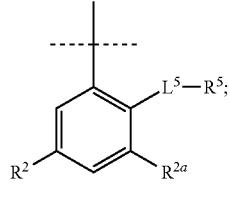

$L^1$ represents a single bond or —CH$_2$—;
$R^1$ is selected from the group consisting of hydrogen, methyl,

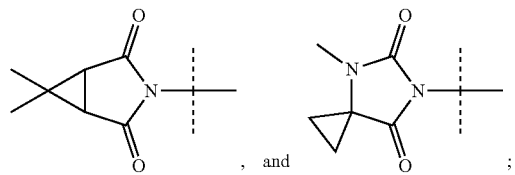

$R^2$, $R^{2a}$, and $R^{2b}$ are each independently selected from hydrogen, methyl, ethyl, —C≡N, chloro, —CF$_3$, and ethoxycarbonyl;

$L^3$ represents a single bond, —O—, —CH$_2$—, —C(=O)—, —NH—, —NH—C(=O)—CH$_2$—, —NH—C(=O)—, —C(=O)—NH—, or —CH(OH)—;

$R^3$ is selected from 3,3-difluorocyclobut-1-yl, 3,3-difluoroazetidin-1-yl, 3-(dimethyl-amino)azetidin-1-yl, azetidin-2-yl, azetidin-3-yl, 3-aminopyrrolidin-1-yl, 3-(methyl-amino)pyrrolidin-1-yl, 3-(dimethylamino)pyrrolidin-1-yl, 3-(ethylamino)pyrrolidin-1-yl, 3-(isopropylamino)pyrrolidin-1-yl, 3-hydroxypyrrolidin-1-yl, 3-fluoropyrrolidin-1-yl, 3,3-difluoropyrrolidin-1-yl, 2-oxopyrrolidin-1-yl, 3-(aminomethyl)pyrrolidin-1-yl, 3-amino-3-methylpyrrolidin-1-yl, 3-amino-4-methylpyrrolidin-1-yl, 3-(1-aminoethyl)pyrrolidin-1-yl, 3-amino-4-fluoropyrrolidin-1-yl, 3-((isopropylamino)methyl)pyrrolidin-1-yl, 3-(D-alanylamino)pyrrolidin-1-yl, 3-(D-valylamino)pyrrolidin-1-yl, 3-ureidopyrrolidin-1-yl, 3-(aminomethyl)pyrrolidin-1-yl, 3-(fluoromethyl)pyrrolidin-1-yl, 3-(difluoromethyl)pyrrolidin-1-yl, pyrrolidin-3-yl, 1-(2,2,2-trifluoroacetyl)pyrrolidin-3-yl, 1H-1,2,4-triazol-1-yl, 3-(methylamino)piperidin-1-yl; 4-aminopiperidin-1-yl, 4,4-difluoropiperidin-1-yl, piperidin-3-yl, piperidin-4-yl, piperazin-1-yl, 2-methyl-piperazin-1-yl, 4-methylpiperazin-1-yl, 2-oxopiperazin-1-yl, 4-methyl-2-oxo-piperazin-1-yl, 2,4-dimethylpiperazin-1-yl, 2,6-dimethylpiperazin-1-yl, 3,3-dimethylpiperazin-1-yl, piperazin-2-yl, 4-ethylpiperazin-1-yl, 3,6-dioxopiperazin-2-yl, 2-oxotetrahydropyrimidin-1(2H)-yl, pyridin-3-yl, morpholino, 3-oxomorpholino, morpholin-2-yl, 4-methylmorpholin-2-yl, octahydropyrrolo[3,4-b]pyrrol-1-yl, octa-hydropyrrolo[3,4-b]pyrrol-5-yl, 2-azaspiro[3.3]heptan-6-yl, 1,7-diazaspiro[4.4]-nonan-7-yl, trifluoromethyl, methoxy, methylamino, and 2-(dimethylamino)-ethyl(methyl)amino;

$L^4$ represents a single bond or —CH$_2$—;
$R^4$ is selected from hydrogen and morpholin-2-yl;
$L^5$ represents —O— or —NH—C(=O)—; and
$R^5$ is selected from pyrrolidin-3-yl, piperidin-3-yl, and piperidin-4-yl;
provided that if X is S and Y is CH then $L^5$ is not —O—.

In some embodiments, the invention provides a compound of Formula (I), as defined above, or a tautomer, stereoisomer, a racemic or scalemic mixture of stereoisomers, a pharmaceutically acceptable salt, ester, solvate, or polymorph thereof, wherein

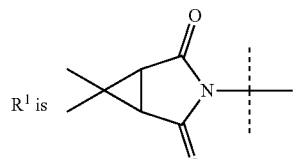

$R^1$ is and $L^1$ is —CH$_2$—.

In some embodiments, the invention provides a compound of Formula (I), as defined above, or a tautomer, stereoisomer, a racemic or scalemic mixture of stereoisomers, a pharmaceutically acceptable salt, ester, solvate, or polymorph thereof, wherein X is S and Y is CH.

In some embodiments, the invention provides a compound of Formula (I), as defined above, having the structural Formula (Ia):

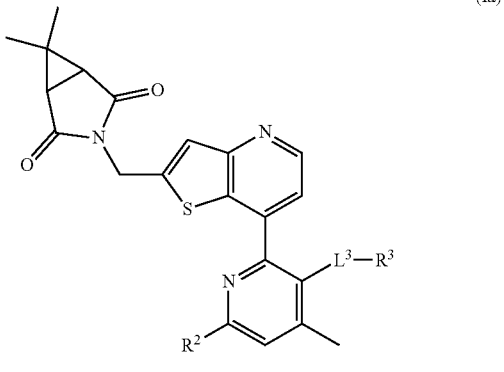

(Ia)

wherein:
R² is selected from hydrogen, methyl, ethyl, chloro, —C≡N, and —CF₃;
L³ represents a single bond, —O—, —CH₂—, —C(=O)—, —NH—, or —NH—C(=O)—; and
R³ is selected from (4-6) membered heterocycloalkyl containing 1 to 2 nitrogen heteroatoms or 1 nitrogen heteroatom and 1 oxygen heteroatom, and optionally substituted with 1 or 2 substituents selected from fluoro, methyl, ethyl, amino, methylamino, dimethylamino, ethylamino, isopropylamino, hydroxy, oxo, aminomethyl, 1-aminoethyl, (isopropylamino)methyl, ureido, alanylamino, valylamino, fluoromethyl, difluoromethyl, trifluoromethyl, and 2,2,2-trifluoroacetyl;
or a tautomer, stereoisomer, a racemic or scalemic mixture of stereoisomers, a pharmaceutically acceptable salt, ester, solvate, or polymorph thereof.

In some embodiments, the invention provides a compound of Formula (I), as defined above, having the structural Formula (Ib):

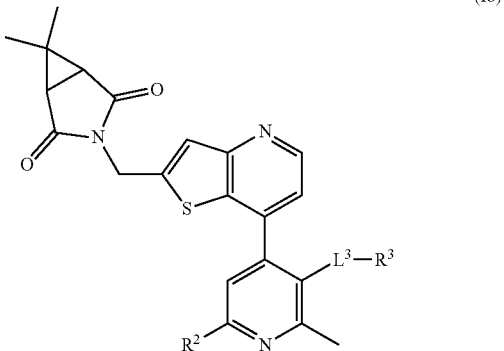

(Ib)

wherein:
R² is selected from methyl, ethyl, chloro, —C≡N, and —CF₃;
L³ represents —O—, —CH₂—, —C(=O)—, or —NH—; and
R³ is selected from (4-6) membered heterocycloalkyl containing 1 to 2 nitrogen heteroatoms or 6-membered heterocycloalkyl containing 1 nitrogen heteroatom and 1 oxygen heteroatom.
or a tautomer, stereoisomer, a racemic or scalemic mixture of stereoisomers, a pharmaceutically acceptable salt, ester, solvate, or polymorph thereof.

In some embodiments, the invention provides a compound of Formula (I), as defined above, having the structural Formula (Ic):

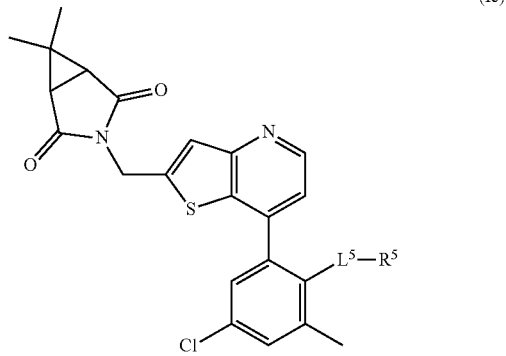

(Ic)

wherein:
L⁵ represents —NH—C(=O)—; and
R⁵ is selected from pyrrolidin-3-yl, piperidin-3-yl, and piperidin-4-yl;
or a tautomer, stereoisomer, a racemic or scalemic mixture of stereoisomers, a pharmaceutically acceptable salt, ester, solvate, or polymorph thereof.

In certain embodiments, the compound according to the invention is:
6-(2-((6,6-dimethyl-2,4-dioxo-3-azabicyclo[3.1.0]hexan-3-yl)methyl)thieno[3,2-b]pyridin-7-yl)-4-methyl-5-(piperidin-3-yloxy)picolinonitrile;
3-((7-(6-chloro-4-methyl-3-(pyrrolidin-3-yloxy)pyridin-2-yl)thieno[3,2-b]pyridin-2-yl)methyl)-6,6-dimethyl-3-azabicyclo[3.1.0]hexane-2,4-dione;
3-((7-(6-chloro-4-methyl-3-(piperidin-3-yloxy)pyridin-2-yl)thieno[3,2-b]pyridin-2-yl)methyl)-6,6-dimethyl-3-azabicyclo[3.1.0]hexane-2,4-dione;
3-((7-(6-chloro-4-methyl-3-(((S)-piperidin-3-yl)oxy)pyridin-2-yl)thieno[3,2-b]pyridin-2-yl)methyl)-6,6-dimethyl-3-azabicyclo[3.1.0]hexane-2,4-dione;
4-(2-((6,6-dimethyl-2,4-dioxo-3-azabicyclo[3.1.0]hexan-3-yl)methyl)thieno[3,2-b]pyridin-7-yl)-6-methyl-5-((S)-2-methylpiperazine-1-carbonyl)picolinonitrile;
6,6-dimethyl-3-((7-(1-(morpholin-2-ylmethyl)-5-(trifluoromethyl)-1H-pyrazol-3-yl)thieno[3,2-b]pyridin-2-yl)methyl)-3-azabicyclo[3.1.0]hexane-2,4-dione;
6,6-dimethyl-3-((7-(1-(morpholin-2-ylmethyl)-3-(trifluoromethyl)-1H-pyrazol-5-yl)thieno[3,2-b]pyridin-2-yl)methyl)-3-azabicyclo[3.1.0]hexane-2,4-dione;
5-((R)-3-aminopyrrolidine-1-carbonyl)-4-(2-((6,6-dimethyl-2,4-dioxo-3-azabicyclo[3.1.0]hexan-3-yl)methyl)thieno[3,2-b]pyridin-7-yl)-6-methylpicolinonitrile;
6,6-dimethyl-3-((7-(1-(morpholin-2-ylmethyl)-1H-pyrrol-2-yl)thieno[3,2-b]pyridin-2-yl)methyl)-3-azabicyclo[3.1.0]hexane-2,4-dione;
5-(3,3-difluoropyrrolidine-1-carbonyl)-4-(2-((6,6-dimethyl-2,4-dioxo-3-azabicyclo[3.1.0]hexan-3-yl)methyl)thieno[3,2-b]pyridin-7-yl)-6-methylpicolinonitrile;
4-(2-((6,6-dimethyl-2,4-dioxo-3-azabicyclo[3.1.0]hexan-3-yl)methyl)thieno[3,2-b]pyridin-7-yl)-5-((S)-3-hydroxypyrrolidine-1-carbonyl)-6-methylpicolinonitrile;

4-(2-((6,6-dimethyl-2,4-dioxo-3-azabicyclo[3.1.0]hexan-3-yl)methyl)thieno[3,2-b]pyridin-7-yl)-5-((R)-3-hydroxypyrrolidine-1-carbonyl)-6-methylpicolinonitrile;

5-(4,4-difluoropiperidine-1-carbonyl)-4-(2-((6,6-dimethyl-2,4-dioxo-3-azabicyclo[3.1.0]hexan-3-yl)methyl)thieno[3,2-b]pyridin-7-yl)-6-methylpicolinonitrile;

6-cyano-N-(3,3-difluorocyclobutyl)-4-(2-((6,6-dimethyl-2,4-dioxo-3-azabicyclo[3.1.0]hexan-3-yl)methyl)thieno[3,2-b]pyridin-7-yl)-2-methylnicotinamide;

5-((S)-3-aminopyrrolidine-1-carbonyl)-4-(2-((6,6-dimethyl-2,4-dioxo-3-azabicyclo[3.1.0]hexan-3-yl)methyl)thieno[3,2-b]pyridin-7-yl)-6-methylpicolinonitrile;

N-(azetidin-3-yl)-6-cyano-4-(2-((6,6-dimethyl-2,4-dioxo-3-azabicyclo[3.1.0]hexan-3-yl)methyl)thieno[3,2-b]pyridin-7-yl)-2-methylnicotinamide;

4-(2-((6,6-dimethyl-2,4-dioxo-3-azabicyclo[3.1.0]hexan-3-yl)methyl)thieno[3,2-b]pyridin-7-yl)-6-methyl-5-(piperazine-1-carbonyl)picolinonitrile;

6,6-dimethyl-3-((7-(4-methyl-3-(pyrrolidin-3-ylamino)-6-(trifluoromethyl)pyridin-2-yl)thieno[3,2-b]pyridin-2-yl)methyl)-3-azabicyclo[3.1.0]hexane-2,4-dione;

5-(3,3-difluoroazetidine-1-carbonyl)-4-(2-((6,6-dimethyl-2,4-dioxo-3-azabicyclo[3.1.0]hexan-3-yl)methyl)thieno[3,2-b]pyridin-7-yl)-6-methylpicolinonitrile;

6-(2-((6,6-dimethyl-2,4-dioxo-3-azabicyclo[3.1.0]hexan-3-yl)methyl)thieno[3,2-b]pyridin-7-yl)-4-methyl-5-(pyrrolidin-3-ylamino)picolinonitrile;

6,6-dimethyl-3-((7-(2-methyl-3-(pyrrolidin-3-yloxy)-6-(trifluoromethyl)pyridin-4-yl)thieno[3,2-b]pyridin-2-yl)methyl)-3-azabicyclo[3.1.0]hexane-2,4-dione;

6,6-dimethyl-3-((7-(2-methyl-3-(((S)-pyrrolidin-3-yl)oxy)-6-(trifluoromethyl)pyridin-4-yl)thieno[3,2-b]pyridin-2-yl)methyl)-3-azabicyclo[3.1.0]hexane-2,4-dione;

6,6-dimethyl-3-((7-(2-methyl-3-(((S)-piperidin-3-yl)oxy)-6-(trifluoromethyl)pyridin-4-yl)thieno[3,2-b]pyridin-2-yl)methyl)-3-azabicyclo[3.1.0]hexane-2,4-dione;

5-(azetidin-3-ylamino)-6-(2-((6,6-dimethyl-2,4-dioxo-3-azabicyclo[3.1.0]hexan-3-yl)methyl)thieno[3,2-b]pyridin-7-yl)-4-methylpicolinonitrile;

6,6-dimethyl-3-((7-(2-methyl-3-(pyrrolidin-3-ylamino)-6-(trifluoromethyl)pyridin-4-yl)thieno[3,2-b]pyridin-2-yl)methyl)-3-azabicyclo[3.1.0]hexane-2,4-dione;

4-(2-((6,6-dimethyl-2,4-dioxo-3-azabicyclo[3.1.0]hexan-3-yl)methyl)thieno[3,2-b]pyridin-7-yl)-6-methyl-5-(pyrrolidin-3-ylamino)picolinonitrile;

N-(6-cyano-4-(2-((6,6-dimethyl-2,4-dioxo-3-azabicyclo[3.1.0]hexan-3-yl)methyl)thieno[3,2-b]pyridin-7-yl)-2-methylpyridin-3-yl)azetidine-2-carboxamide;

N-(2-(2-((6,6-dimethyl-2,4-dioxo-3-azabicyclo[3.1.0]hexan-3-yl)methyl)thieno[3,2-b]pyridin-7-yl)-4-methyl-6-(trifluoromethyl)pyridin-3-yl)azetidine-3-carboxamide;

N-(6-chloro-4-(2-((6,6-dimethyl-2,4-dioxo-3-azabicyclo[3.1.0]hexan-3-yl)methyl)thieno[3,2-b]pyridin-7-yl)-2-methylpyridin-3-yl)azetidine-3-carboxamide;

N-(6-cyano-4-(2-((6,6-dimethyl-2,4-dioxo-3-azabicyclo[3.1.0]hexan-3-yl)methyl)thieno[3,2-b]pyridin-7-yl)-2-methylpyridin-3-yl)azetidine-3-carboxamide;

(S)-4-(5-chloro-3-methyl-2-(piperidin-3-yloxy)phenyl)thieno[2,3-b]pyridine;

2-(3,3-difluoroazetidin-1-yl)-N-(4-(2-((6,6-dimethyl-2,4-dioxo-3-azabicyclo[3.1.0]hexan-3-yl)methyl)thieno[3,2-b]pyridin-7-yl)-2-methyl-6-(trifluoromethyl)pyridin-3-yl)acetamide;

N-(4-(2-((6,6-dimethyl-2,4-dioxo-3-azabicyclo[3.1.0]hexan-3-yl)methyl)thieno[3,2-b]pyridin-7-yl)-2-ethyl-6-(trifluoromethyl)pyridin-3-yl)piperidine-4-carboxamide;

(3S)—N-(4-chloro-2-(2-((6,6-dimethyl-2,4-dioxo-3-azabicyclo[3.1.0]hexan-3-yl)methyl)thieno[3,2-b]pyridin-7-yl)-6-methylphenyl)pyrrolidine-3-carboxamide;

6,6-dimethyl-3-((7-(4-methyl-3-(piperazin-2-ylmethyl)-6-(trifluoromethyl)pyridin-2-yl)thieno[3,2-b]pyridin-2-yl)methyl)-3-azabicyclo[3.1.0]hexane-2,4-dione;

3-((7-(3-((1H-1,2,4-triazol-1-yl)methyl)-4-methyl-6-(trifluoromethyl)pyridin-2-yl)thieno[3,2-b]pyridin-2-yl)methyl)-6,6-dimethyl-3-azabicyclo[3.1.0]hexane-2,4-dione;

3-((7-(3-((3,6-dioxopiperazin-2-yl)methyl)-4-methyl-6-(trifluoromethyl)pyridin-2-yl)thieno[3,2-b]pyridin-2-yl)methyl)-6,6-dimethyl-3-azabicyclo[3.1.0]hexane-2,4-dione;

6,6-dimethyl-3-((7-(4-methyl-3-((3-oxomorpholino)methyl)-6-(trifluoromethyl)pyridin-2-yl)thieno[3,2-b]pyridin-2-yl)methyl)-3-azabicyclo[3.1.0]hexane-2,4-dione;

6,6-dimethyl-3-((7-(4-methyl-3-((2-oxopyrrolidin-1-yl)methyl)-6-(trifluoromethyl)pyridin-2-yl)thieno[3,2-h]pyridin-2-yl)methyl)-3-azabicyclo[3.1.0]hexane-2,4-dione;

6,6-dimethyl-3-((7-(4-methyl-3-((2-oxopiperazin-1-yl)methyl)-6-(trifluoromethyl)pyridin-2-yl)thieno[3,2-b]pyridin-2-yl)methyl)-3-azabicyclo[3.1.0]hexane-2,4-dione;

6,6-dimethyl-3-((7-(4-methyl-3-((4-methyl-2-oxopiperazin-1-yl)methyl)-6-(trifluoromethyl)pyridin-2-yl)thieno[3,2-b]pyridin-2-yl)methyl)-3-azabicyclo[3.1.0]hexane-2,4-dione;

6-cyano-2-(2-((6,6-dimethyl-2,4-dioxo-3-azabicyclo[3.1.0]hexan-3-yl)methyl)thieno[3,2-b]pyridin-7-yl)-N-(2-(dimethylamino)ethyl)-N,4-dimethylnicotinamide;

6-(2-((6,6-dimethyl-2,4-dioxo-3-azabicyclo[3.1.0]hexan-3-yl)methyl)thieno[3,2-b]pyridin-7-yl)-5-(3-(dimethylamino)azetidine-1-carbonyl)-4-methylpicolinonitrile;

6-(2-((6,6-dimethyl-2,4-dioxo-3-azabicyclo[3.1.1]hexan-3-yl)methyl)thieno[3,2-b]pyridin-7-yl)-5-((S)-3-(dimethylamino)pyrrolidine-1-carbonyl)-4-methylpicolinonitrile;

6,6-dimethyl-3-((7-(4-methyl-3-(piperazine-1-carbonyl)pyridin-2-yl)thieno[3,2-b]pyridin-2-yl)methyl)-3-azabicyclo[3.1.0]hexane-2,4-dione;

6,6-dimethyl-3-((7-(4-methyl-3-(piperazin-1-ylmethyl)pyridin-2-yl)thieno[3,2-b]pyridin-2-yl)methyl)-3-azabicyclo[3.1.0]hexane-2,4-dione;

6-(2-((6,6-dimethyl-2,4-dioxo-3-azabicyclo[3.1.0]hexan-3-yl)methyl)thieno[3,2-b]pyridin-7-yl)-4-methyl-5-((S)-2-methylpiperazine-1-carbonyl)picolinonitrile;

6,6-dimethyl-3-((7-(4-methyl-3-(morpholine-4-carbonyl)pyridin-2-yl)thieno[3,2-b]pyridin-2-yl)methyl)-3-azabicyclo[3.1.0]hexane-2,4-dione;

3-((7-(3-(3,3-difluoropyrrolidine-1-carbonyl)-4-methylpyridin-2-yl)thieno[3,2-b]pyridin-2-yl)methyl)-6,6-dimethyl-3-azabicyclo[3.1.0]hexane-2,4-dione;

3-((7-(3-(3,3-difluoroazetidine-1-carbonyl)-4-methylpyridin-2-yl)thieno[3,2-b]pyridin-2-yl)methyl)-6,6-dimethyl-3-azabicyclo[3.1.0]hexane-2,4-dione;

5-(3,3-difluoroazetidine-1-carbonyl)-6-(2-((6,6-dimethyl-2,4-dioxo-3-azabicyclo[3.1.0]hexan-3-yl)methyl)thieno[3,2-b]pyridin-7-yl)-4-methylpicolinonitrile;

6-(2-((6,6-dimethyl-2,4-dioxo-3-azabicyclo[3.1.0]hexan-3-yl)methyl)thieno[3,2-b]pyridin-7-yl)-5-((S)-2,4-dimethylpiperazine-1-carbonyl)-4-methylpicolinonitrile;

6-(2-((6,6-dimethyl-2,4-dioxo-3-azabicyclo[3.1.0]hexan-3-yl)methyl)thieno[3,2-b]pyridin-7-yl)-5-(3,3-dimethylpiperazine-1-carbonyl)-4-methylpicolinonitrile;

6-(2-((6,6-dimethyl-2,4-dioxo-3-azabicyclo[3.1.0]hexan-3-yl)methyl)thieno[3,2-b]pyridin-7-yl)-4-methyl-5-((R)-2-methylpiperazine-1-carbonyl)picolinonitrile;

6-(2-((6,6-dimethyl-2,4-dioxo-3-azabicyclo[3.1.0]hexan-3-yl)methyl)thieno[3,2-b]pyridin-7-yl)-4-methyl-5-(piperazine-1-carbonyl)picolinonitrile;

N-(azetidin-3-yl)-6-cyano-2-(2-((6,6-dimethyl-2,4-dioxo-3-azabicyclo[3.1.0]hexan-3-yl)methyl)thieno[3,2-b]pyridin-7-yl)-4-methylnicotinamide;

6-cyano-N-(3,3-difluorocyclobutyl)-2-(2-((6,6-dimethyl-2,4-dioxo-3-azabicyclo[3.1.0]hexan-3-yl)methyl)thieno[3,2-b]pyridin-7-yl)-4-methylnicotinamide;

6-(2-((6,6-dimethyl-2,4-dioxo-3-azabicyclo[3.1.0]hexan-3-yl)methyl)thieno[3,2-b]pyridin-7-yl)-4-methyl-5-(morpholine-4-carbonyl)picolinonitrile;

5-(3,3-difluoropyrrolidine-1-carbonyl)-6-(2-((6,6-dimethyl-2,4-dioxo-3-azabicyclo[3.1.0]hexan-3-yl)methyl)thieno[3,2-b]pyridin-7-yl)-4-methylpicolinonitrile;

N-(4-(2-((6,6-dimethyl-2,4-dioxo-3-azabicyclo[3.1.0]hexan-3-yl)methyl)thieno[3,2-b]pyridin-7-yl)-2-methyl-6-(trifluoromethyl)pyridin-3-yl)-2-(methylamino)acetamide;

N-(4-(2-((6,6-dimethyl-2,4-dioxo-3-azabicyclo[3.1.0]hexan-3-yl)methyl)thieno[3,2-b]pyridin-7-yl)-2-methyl-6-(trifluoromethyl)pyridin-3-yl)-2-methoxyacetamide;

N-(4-(2-((6,6-dimethyl-2,4-dioxo-3-azabicyclo[3.1.0]hexan-3-yl)methyl)thieno[3,2-b]pyridin-7-yl)-2-methyl-6-(trifluoromethyl)pyridin-3-yl)-2,2,2-trifluoroacetamide;

N-(4-(2-((6,6-dimethyl-2,4-dioxo-3-azabicyclo[3.1.0]hexan-3-yl)methyl)thieno[3,2-b]pyridin-7-yl)-2-methyl-6-(trifluoromethyl)pyridin-3-yl)nicotinamide;

N-(4-(2-((6,6-dimethyl-2,4-dioxo-3-azabicyclo[3.1.0]hexan-3-yl)methyl)thieno[3,2-b]pyridin-7-yl)-2-methyl-6-(trifluoromethyl)pyridin-3-yl)pyrrolidine-3-carboxamide;

N-(4-(2-((6,6-dimethyl-2,4-dioxo-3-azabicyclo[3.1.0]hexan-3-yl)methyl)thieno[3,2-b]pyridin-7-yl)-2-methyl-6-(trifluoromethyl)pyridin-3-yl)-1-(2,2,2-trifluoroacetyl)pyrrolidine-3-carboxamide;

N-(4-(2-((6,6-dimethyl-2,4-dioxo-3-azabicyclo[3.1.0]hexan-3-yl)methyl)thieno[3,2-b]pyridin-7-yl)-2-methyl-6-(trifluoromethyl)pyridin-3-yl)azetidine-3-carboxamide;

(S)-7-(5-chloro-3-methyl-2-(piperidin-3-yloxy)phenyl)-2-methyl-3H-imidazo[4,5-b]pyridine;

(S)-7-(5-chloro-3-methyl-2-(piperidin-3-yloxy)phenyl)-2,3-dimethyl-3H-imidazo[4,5-b]pyridine;

(S)-7-(5-chloro-3-methyl-2-(piperidin-3-yloxy)phenyl)-1,2-dimethyl-1H-imidazo[4,5-b]pyridine;

N-(azetidin-3-yl)-2-(2-((6,6-dimethyl-2,4-dioxo-3-azabicyclo[3.1.0]hexan-3-yl)methyl)thieno[3,2-b]pyridin-7-yl)-4-methyl-6-(trifluoromethyl)nicotinamide;

6,6-dimethyl-3-((7-(4-methyl-3-(1,7-diazaspiro[4.4]nonane-7-carbonyl)-6-(trifluoromethyl)pyridin-2-yl)thieno[3,2-b]pyridin-2-yl)methyl)-3-azabicyclo[3.1.0]hexane-2,4-dione;

6,6-dimethyl-3-((7-(4-methyl-3-(octahydropyrrolo[3,4-b]pyrrole-1-carbonyl)-6-(trifluoromethyl)pyridin-2-yl)thieno[3,2-b]pyridin-2-yl)methyl)-3-azabicyclo[3.1.0]hexane-2,4-dione;

3-((7-(3-((S)-3-(ethylamino)pyrrolidine-1-carbonyl)-4-methyl-6-(trifluoromethyl)pyridin-2-yl)thieno[3,2-b]pyridin-2-yl)methyl)-6,6-dimethyl-3-azabicyclo[3.1.0]hexane-2,4-dione;

3-((7-(3-((S)-3-(isopropylamino)pyrrolidine-1-carbonyl)-4-methyl-6-(trifluoromethyl)pyridin-2-yl)thieno[3,2-b]pyridin-2-yl)methyl)-6,6-dimethyl-3-azabicyclo[3.1.0]hexane-2,4-dione;

2-(2-((6,6-dimethyl-2,4-dioxo-3-azabicyclo[3.1.0]hexan-3-yl)methyl)thieno[3,2-b]pyridin-7-yl)-4-methyl-N—((S)-pyrrolidin-3-yl)-6-(trifluoromethyl)nicotinamide;

6,6-dimethyl-3-((7-(4-methyl-3-(piperazine-1-carbonyl)-6-(trifluoromethyl)pyridin-2-yl)thieno[3,2-b]pyridin-2-yl)methyl)-3-azabicyclo[3.1.0]hexane-2,4-dione;

6,6-dimethyl-3-((7-(4-methyl-3-((S)-3-(methylamino)pyrrolidine-1-carbonyl)-6-(trifluoromethyl)pyridin-2-yl)thieno[3,2-b]pyridin-2-yl)methyl)-3-azabicyclo[3.1.0]hexane-2,4-dione;

6,6-dimethyl-3-((7-(4-methyl-3-((S)-2-methylpiperazine-1-carbonyl)-6-(trifluoromethyl)pyridin-2-yl)thieno[3,2-b]pyridin-2-yl)methyl)-3-azabicyclo[3.1.0]hexane-2,4-dione;

3-((7-(3-((S)-2,4-dimethylpiperazine-1-carbonyl)-4-methyl-6-(trifluoromethyl)pyridin-2-yl)thieno[3,2-b]pyridin-2-yl)methyl)-6,6-dimethyl-3-azabicyclo[3.1.0]hexane-2,4-dione;

6,6-dimethyl-3-((7-(4-methyl-3-(4-methylpiperazine-1-carbonyl)-6-(trifluoromethyl)pyridin-2-yl)thieno[3,2-b]pyridin-2-yl)methyl)-3-azabicyclo[3.1.0]hexane-2,4-dione;

3-((7-(3-((S)-3-aminopyrrolidine-1-carbonyl)-4-methyl-6-(trifluoromethyl)pyridin-2-yl)thieno[3,2-b]pyridin-2-yl)methyl)-6,6-dimethyl-3-azabicyclo[3.1.0]hexane-2,4-dione;

3-((7-(3-((S)-3-(dimethylamino)pyrrolidine-1-carbonyl)-4-methyl-6-(trifluoromethyl)pyridin-2-yl)thieno[3,2-b]pyridin-2-yl)methyl)-6,6-dimethyl-3-azabicyclo[3.1.0]hexane-2,4-dione;

3-((7-(3-(3,3-difluoropyrrolidine-1-carbonyl)-4-methyl-6-(trifluoromethyl)pyridin-2-yl)thieno[3,2-b]pyridin-2-yl)methyl)-6,6-dimethyl-3-azabicyclo[3.1.0]hexane-2,4-dione;

6,6-dimethyl-3-((7-(4-methyl-3-(morpholine-4-carbonyl)-6-(trifluoromethyl)pyridin-2-yl)thieno[3,2-b]pyridin-2-yl)methyl)-3-azabicyclo[3.1.0]hexane-2,4-dione;

3-((7-(3-(3,3-difluoroazetidine-1-carbonyl)-4,6-dimethylpyridin-2-yl)thieno[3,2-b]pyridin-2-yl)methyl)-6,6-dimethyl-3-azabicyclo[3.1.0]hexane-2,4-dione;

N-(4-(2-((6,6-dimethyl-2,4-dioxo-3-azabicyclo[3.1.0]hexan-3-yl)methyl)thieno[3,2-b]pyridin-7-yl)-2-methyl-6-(trifluoromethyl)pyridin-3-yl)-3,3-difluorocyclobutane-1-carboxamide;

N-(4-(2-((6,6-dimethyl-2,4-dioxo-3-azabicyclo[3.1.0]hexan-3-yl)methyl)thieno[3,2-b]pyridin-7-yl)-2-methyl-6-(trifluoromethyl)pyridin-3-yl)piperidine-4-carboxamide;

6,6-dimethyl-3-((7-(2-methyl-3-(pyrrolidin-3-ylmethyl)-6-(trifluoromethyl)pyridin-4-yl)thieno[3,2-b]pyridin-2-yl)methyl)-3-azabicyclo[3.1.0]hexane-2,4-dione;

6,6-dimethyl-3(7-(2-methyl-3-(((R)-pyrrolidin-3-yl)methyl)-6-(trifluoromethyl)pyridin-4-yl)thieno[3,2-b]pyridin-2-yl)methyl)-3-azabicyclo[3.1.0]hexane-2,4-dione;

6,6-dimethyl-3-((7-(2-methyl-3-(((S)-pyrrolidin-3-yl)methyl)-6-(trifluoromethyl)pyridin-4-yl)thieno[3,2-b]pyridin-2-yl)methyl)-3-azabicyclo[3.1.0]hexane-2,4-dione;

6,6-dimethyl-3-((7-(2-methyl-3-(morpholin-2-ylmethyl)-6-(trifluoromethyl)pyridin-4-yl)thieno[3,2-b]pyridin-2-yl)methyl)-3-azabicyclo[3.1.0]hexane-2,4-dione;

6,6-di methyl-3-((7-(4-methyl-3-(morpholin-2-yl methyl)-6-(trifluoromethyl)pyridin-2-yl)thieno[3,2-b]pyridin-2-yl)methyl)-3-azabicyclo[3.1.0]hexane-2,4-dione;

6,6-dimethyl-3-((7-(4-methyl-2-(morpholin-2-ylmethyl)pyridin-3-yl)thieno[3,2-b]pyridin-2-yl)methyl)-3-azabicyclo[3.1.0]hexane-2,4-dione;

6-(2-((6,6-dimethyl-2,4-dioxo-3-azabicyclo[3.1.0]hexan-3-yl)methyl)thieno[3,2-b]pyridin-7-yl)-4-methyl-5-(morpholin-2-ylmethyl)picolinonitrile;

6,6-dimethyl-3-((7-(4-methyl-3-(((S)-morpholin-2-yl)methyl)-6-(trifluoromethyl)pyridin-2-yl)thieno[3,2-b]pyridin-2-yl)methyl)-3-azabicyclo[3.1.0]hexane-2,4-dione;

6,6-dimethyl-3-((7-(4-methyl-3-(((R)-morpholin-2-yl)methyl)-6-(trifluoromethyl)pyridin-2-yl)thieno[3,2-b]pyridin-2-yl)methyl)-3-azabicyclo[3.1.0]hexane-2,4-dione;

6,6-dimethyl-3-((7-(4-methyl-3-(((S)-4-methylmorpholin-2-yl)methyl)-6-(trifluoromethyl)pyridin-2-yl)thieno[3,2-b]pyridin-2-yl)methyl)-3-azabicyclo[3.1.0]hexane-2,4-dione;

6,6-dimethyl-3-((7-(4-methyl-3-(((R)-4-methylmorpholin-2-yl)methyl)-6-(trifluoromethyl)pyridin-2-yl)thieno[3,2-b]pyridin-2-yl)methyl)-3-azabicyclo[3.1.0]hexane-2,4-dione;

6,6-dimethyl-3-((7-(2-(((R)-morpholin-2-yl)methyl)-5-(trifluoromethyl)pyridin-3-yl)thieno[3,2-b]pyridin-2-yl)methyl)-3-azabicyclo[3.1.0]hexane-2,4-dione;

3-((7-(3-(hydroxy((S)-morpholin-2-yl)methyl)-4-methylpyridin-2-yl)thieno[3,2-b]pyridin-2-yl)methyl)-6,6-dimethyl-3-azabicyclo[3.1.0]hexane-2,4-dione;

3-((7-(3-(hydroxy((S)-morpholin-2-yl)methyl)-4-methylpyridin-2-yl)thieno[3,2-b]pyridin-2-yl)methyl)-6,6-dimethyl-3-azabicyclo[3.1.0]hexane-2,4-dione;

6,6-dimethyl-3-((7-(2-methyl-3-(piperazin-1-ylmethyl)-6-(trifluoromethyl)pyridin-4-yl)thieno[3,2-b]pyridin-2-yl)methyl)-3-azabicyclo[3.1.0]hexane-2,4-dione;

3-((7-(3-((3,3-difluoroazetidin-1-yl)methyl)-2-methyl-6-(trifluoromethyl)pyridin-4-yl)thieno[3,2-b]pyridin-2-yl)methyl)-6,6-dimethyl-3-azabicyclo[3.1.0]hexane-2,4-dione;

3-((7-(3-((S)-3-(difluoromethyl)pyrrolidine-1-carbonyl)-4-methyl-6-(trifluoromethyl)pyridin-2-yl)thieno[3,2-b]pyridin-2-yl)methyl)-6,6-dimethyl-3-azabicyclo[3.1.0]hexane-2,4-dione;

3-((7-(3-((S)-3-(fluoromethyl)pyrrolidine-1-carbonyl)-4-methyl-6-(trifluoromethyl)pyridin-2-yl)thieno[3,2-b]pyridin-2-yl)methyl)-6,6-dimethyl-3-azabicyclo[3.1.0]hexane-2,4-dione;

3-((7-(3-((3S,4S)-3-amino-4-methylpyrrolidine-1-carbonyl)-4-methyl-6-(trifluoromethyl)pyridin-2-yl)thieno[3,2-b]pyridin-2-yl)methyl)-6,6-dimethyl-3-azabicyclo[3.1.0]hexane-2,4-dione;

3-((7-(3-((3S,4R)-3-amino-4-methylpyrrolidine-1-carbonyl)-4-methyl-6-(trifluoromethyl)pyridin-2-yl)thieno[3,2-b]pyridin-2-yl)methyl)-6,6-dimethyl-3-azabicyclo[3.1.0]hexane-2,4-dione;

6,6-dimethyl-3-((7-(4-methyl-3-((3aR,6aR)-octahydropyrrolo[3,4-b]pyrrole-5-carbonyl)-6-(trifluoromethyl)pyridin-2-yl)thieno[3,2-b]pyridin-2-yl)methyl)-3-azabicyclo[3.1.0]hexane-2,4-dione;

(2S)-2-amino-N-((3S)-1-(2-(2-((6,6-dimethyl-2,4-dioxo-3-azabicyclo[3.1.0]hexan-3-yl)methyl)thieno[3,2-b]pyridin-7-yl)-4-methyl-6-(trifluoromethyl)nicotinoyl)pyrrolidin-3-yl)-3-methylbutanamide;

(2S)-2-amino-N-((3S)-1-(2-(2-((6,6-dimethyl-2,4-dioxo-3-azabicyclo[3.1.0]hexan-3-yl)methyl)thieno[3,2-b]pyridin-7-yl)-4-methyl-6-(trifluoromethyl)nicotinoyl)pyrrolidin-3-yl)propanamide;

2-(2-((6,6-dimethyl-2,4-dioxo-3-azabicyclo[3.1.0]hexan-3-yl)methyl)thieno[3,2-b]pyridin-7-yl)-4-methyl-N-(piperidin-4-yl)-6-(trifluoromethyl)nicotinamide;

3-((7-(3-(4-aminopiperidine-1-carbonyl)-4-methyl-6-(trifluoromethyl)pyridin-2-yl)thieno[3,2-b]pyridin-2-yl)methyl)-6,6-dimethyl-3-azabicyclo[3.1.0]hexane-2,4-dione;

3-((7-(3-((S)-3-hydroxypyrrolidine-1-carbonyl)-4-methyl-6-(trifluoromethyl)pyridin-2-yl)thieno[3,2-b]pyridin-2-yl)methyl)-6,6-dimethyl-3-azabicyclo[3.1.0]hexane-2,4-dione;

3-((7-(3-((S)-3-fluoropyrrolidine-1-carbonyl)-4-methyl-6-(trifluoromethyl)pyridin-2-yl)thieno[3,2-b]pyridin-2-yl)methyl)-6,6-dimethyl-3-azabicyclo[3.1.0]hexane-2,4-dione;

3-((7-(3-((R)-3-(aminomethyl)pyrrolidine-1-carbonyl)-4-methyl-6-(trifluoromethyl)pyridin-2-yl)thieno[3,2-b]pyridin-2-yl)methyl)-6,6-dimethyl-3-azabicyclo[3.1.0]hexane-2,4-dione;

6,6-dimethyl-3-((7-(4-methyl-3-((3aR,6aR)-octahydropyrrolo[3,4-b]pyrrole-1-carbonyl)-6-(trifluoromethyl)pyridin-2-yl)thieno[3,2-b]pyridin-2-yl)methyl)-3-azabicyclo[3.1.0]hexane-2,4-dione;

3-((7-(3-((3R,4R)-3-amino-4-fluoropyrrolidine-1-carbonyl)-4-methyl-6-(trifluoromethyl)pyridin-2-yl)thieno[3,2-b]pyridin-2-yl)methyl)-6,6-dimethyl-3-azabicyclo[3.1.0]hexane-2,4-dione;

N-(4-chloro-2-(2-((6,6-dimethyl-2,4-dioxo-3-azabicyclo[3.1.0]hexan-3-yl)methyl)thieno[3,2-b]pyridin-7-yl)-6-methylphenyl)piperidine-4-carboxamide;

6,6-dimethyl-3-((7-(2-methyl-5-(((S)-piperidin-3-yl)oxy)pyridin-4-yl)thieno[3,2-b]pyridin-2-yl)methyl)-3-azabicyclo[3.1.0]hexane-2,4-dione;

(3R)—N-(6-chloro-4-(2-((6,6-dimethyl-2,4-dioxo-3-azabicyclo[3.1.0]hexan-3-yl)methyl)thieno[3,2-b]pyridin-7-yl)-2-methylpyridin-3-yl)pyrrolidine-3-carboxamide;

3-((7-(6-chloro-4-methyl-3-(2-oxotetrahydropyrimidin-1(2H)-yl)pyridin-2-yl)thieno[3,2-b]pyridin-2-yl)methyl)-6,6-dimethyl-3-azabicyclo[3.1.0]hexane-2,4-dione;

3-((7-(3-(azetidin-3-ylamino)-6-chloro-4-methylpyridin-2-yl)thieno[3,2-b]pyridin-2-yl)methyl)-6,6-dimethyl-3-azabicyclo[3.1.0]hexane-2,4-dione;

3-((7-(6-chloro-3-((3,3-difluorocyclobutyl)amino)-4-methylpyridin-2-yl)thieno[3,2-b]pyridin-2-yl)methyl)-6,6-dimethyl-3-azabicyclo[3.1.0]hexane-2,4-dione;

3-((7-(4,6-dimethyl-3-(pyrrolidin-3-ylamino)pyridin-2-yl)thieno[3,2-b]pyridin-2-yl)methyl)-6,6-dimethyl-3-azabicyclo[3.1.0]hexane-2,4-dione;

3-((7-(6-chloro-2-methyl-3-(pyrrolidin-3-ylamino)pyridin-4-yl)thieno[3,2-b]pyridin-2-yl)methyl)-6,6-dimethyl-3-azabicyclo[3.1.0]hexane-2,4-dione;

3-((7-(6-chloro-4-methyl-3-(pyrrolidin-3-ylamino)pyridin-2-yl)thieno[3,2-b]pyridin-2-yl)methyl)-6,6-dimethyl-3-azabicyclo[3.1.0]hexane-2,4-dione;

3-((7-(6-chloro-4-methyl-3-(piperidin-4-ylamino)pyridin-2-yl)thieno[3,2-b]pyridin-2-yl)methyl)-6,6-dimethyl-3-azabicyclo[3.1.0]hexane-2,4-dione;

6,6-dimethyl-3-((7-(4-methyl-3-(piperidin-4-ylamino)-6-(trifluoromethyl)pyridin-2-yl)thieno[3,2-b]pyridin-2-yl)methyl)-3-azabicyclo[3.1.0]hexane-2,4-dione;

3-((7-(6-chloro-4-methyl-3-(piperidin-3-ylamino)pyridin-2-yl)thieno[3,2-b]pyridin-2-yl)methyl)-6,6-dimethyl-3-azabicyclo[3.1.0]hexane-2,4-dione;

6,6-dimethyl-3-((7-(4-methyl-3-(piperidin-3-ylamino)-6-(trifluoromethyl)pyridin-2-yl)thieno[3,2-b]pyridin-2-yl)methyl)-3-azabicyclo[3.1.0]hexane-2,4-dione;

3-((7-(3-((2-azaspiro[3.3]heptan-6-yl)amino)-6-chloro-4-methylpyridin-2-yl)thieno[3,2-b]pyridin-2-yl)methyl)-6,6-dimethyl-3-azabicyclo[3.1.0]hexane-2,4-dione;

3-((7-(3-((2-azaspiro[3.3]heptan-6-yl)amino)-4-methyl-6-(trifluoromethyl)pyridin-2-yl)thieno[3,2-b]pyridin-2-yl)methyl)-6,6-dimethyl-3-azabicyclo[3.1.0]hexane-2,4-dione;

N-(2-(2-((6,6-dimethyl-2,4-dioxo-3-azabicyclo[3.1.0]hexan-3-yl)methyl)thieno[3,2-b]pyridin-7-yl)-4,6-dimethylpyridin-3-yl)azetidine-3-carboxamide;

N-(2-(2-((6,6-dimethyl-2,4-dioxo-3-azabicyclo[3.1.0]hexan-3-yl)methyl)thieno[3,2-b]pyridin-7-yl)-4,6-dimethylpyridin-3-yl)piperidine-4-carboxamide;

3-((7-(6-chloro-4-methyl-3-(piperadine-1-carbonyl)pyridin-2-yl)thieno[3,2-b]pyridin-2-yl)methyl)-6,6-dimethyl-3-azabicyclo[3.1.0]hexane-2,4-dione;

1-((3S)-1-(2-(2-((6,6-dimethyl-2,4-dioxo-3-azabicyclo[3.1.0]hexan-3-yl)methyl)thieno[3,2-b]pyridin-7-yl)-4-methyl-6-(trifluoromethyl)nicotinoyl)pyrrolidin-3-yl)urea;

3-((7-(3-(3-amino-3-methylpyrrolidine-1-carbonyl)-4-methyl-6-(trifluoromethyl)pyridin-2-yl)thieno[3,2-b]pyridin-2-yl)methyl)-6,6-dimethyl-3-azabicyclo[3.1.0]hexane-2,4-dione;

3-((7-(3-((3S)-3-(1-aminoethyl)pyrrolidine-1-carbonyl)-4-methyl-6-(trifluoromethyl)pyridin-2-yl)thieno[3,2-b]pyridin-2-yl)methyl)-6,6-dimethyl-3-azabicyclo[3.1.0]hexane-2,4-dione;

3-((7-(3-(3-(aminomethyl)pyrrolidine-1-carbonyl)-4-methyl-6-(trifluoromethyl)pyridin-2-yl)thieno[3,2-b]pyridin-2-yl)methyl)-6,6-dimethyl-3-azabicyclo[3.1.0]hexane-2,4-dione;

3-((7-(3-(3-((isopropylamino)methyl)pyrrolidine-1-carbonyl)-4-methyl-6-(trifluoromethyl)pyridin-2-yl)thieno[3,2-b]pyridin-2-yl)methyl)-6,6-dimethyl-3-azabicyclo[3.1.0]hexane-2,4-dione;

3-((7-(3-((2S,6S)-2,6-dimethylpiperazine-1-carbonyl)-4-methyl-6-(trifluoromethyl)pyridin-2-yl)thieno[3,2-b]pyridin-2-yl)methyl)-6,6-dimethyl-3-azabicyclo[3.1.0]hexane-2,4-dione;

3-((7-(3-((2R,6R)-2,6-dimethylpiperazine-1-carbonyl)-4-methyl-6-(trifluoromethyl)pyridin-2-yl)thieno[3,2-b]pyridin-2-yl)methyl)-6,6-dimethyl-3-azabicyclo[3.1.0]hexane-2,4-dione;

3-((7-(3-(4-ethylpiperazine-1-carbonyl)-4-methyl-6-(trifluoromethyl)pyridin-2-yl)thieno[3,2-b]pyridin-2-yl)methyl)-6,6-dimethyl-3-azabicyclo[3.1.0]hexane-2,4-dione;

6,6-dimethyl-3-((7-(4-methyl-3-((S)-3-(methylamino)piperidine-1-carbonyl)-6-(trifluoromethyl)pyridin-2-yl)thieno[3,2-b]pyridin-2-yl)methyl)-3-azabicyclo[3.1.0]hexane-2,4-dione;

4-methyl-6-((7-(4-methyl-3-(pyrrolidin-3-ylamino)-6-(trifluoromethyl)pyridin-2-yl)thieno[3,2-b]pyridin-2-yl)methyl)-4,6-diazaspiro[2.4]heptane-5,7-dione;

3-((7-(1H-imidazol-2-yl)thieno[3,2-b]pyridin-2-yl)methyl)-6,6-dimethyl-3-azabicyclo[3.1.0]hexane-2,4-dione;

6,6-dimethyl-3-((7-(1-(morpholin-2-ylmethyl)-1H-imidazol-2-yl)thieno[3,2-b]pyridin-2-yl)methyl)-3-azabicyclo[3.1.0]hexane-2,4-dione;

ethyl 5-(2-((6,6-dimethyl-2,4-dioxo-3-azabicyclo[3.1.0]hexan-3-yl)methyl)thieno[3,2-b]pyridin-7-yl)-2-methyl-1-(((S)-morpholin-2-yl)methyl)-1H-pyrrole-3-carboxylate;

6,6-dimethyl-3-((7-(1-(((S)-morpholin-2-yl)methyl)-4-(trifluoromethyl)-1H-imidazol-2-yl)thieno[3,2-b]pyridin-2-yl)methyl)-3-azabicyclo[3.1.0]hexane-2,4-dione;

(S)-7-(5-chloro-3-methyl-2-(piperidin-3-yloxy)phenyl)furo[3,2-b]pyridine; or 3-((7-(5-chloro-3-methyl-2-(((S)-piperidin-3-yl)oxy)phenyl)thiazolo[4,5-b]pyridin-2-yl)methyl)-6,6-dimethyl-3-azabicyclo[3.1.0]hexane-2,4-dione;

or a tautomer, stereoisomer, a racemic or scalemic mixture of stereoisomers, a pharmaceutically acceptable salt, ester, solvate, or polymorph thereof.

In certain embodiments, the compound according to the invention is;

6-(2-((6,6-dimethyl-2,4-dioxo-3-azabicyclo[3.1.0]hexan-3-yl)methyl)thieno[3,2-b]pyridin-7-yl)-4-methyl-5-(piperidin-3-yloxy)picolinonitrile;

3-((7-(6-chloro-4-methyl-3-(pyrrolidin-3-yloxy)pyridin-2-yl)thieno[3,2-b]pyridin-2-yl)methyl)-6,6-dimethyl-3-azabicyclo[3.1.0]hexane-2,4-dione;

3-((7-(6-chloro-4-methyl-3-(piperidin-3-yloxy)pyridin-2-yl)thieno[3,2-b]pyridin-2-yl)methyl)-6,6-dimethyl-3-azabicyclo[3.1.0]hexane-2,4-dione;

3-((7-(6-chloro-4-methyl-3-(((S)-piperidin-3-yl)oxy)pyridin-2-yl)thieno[3,2-b]pyridin-2-yl)methyl)-6,6-dimethyl-3-azabicyclo[3.1.0]hexane-2,4-dione;

4-(2-((6,6-dimethyl-2,4-dioxo-3-azabicyclo[3.1.0]hexan-3-yl)methyl)thieno[3,2-b]pyridin-7-yl)-6-methyl-5-((S)-2-methylpiperazine-1-carbonyl)picolinonitrile;

4-(2-((6,6-dimethyl-2,4-dioxo-3-azabicyclo[3.1.0]hexan-3-yl)methyl)thieno[3,2-b]pyridin-7-yl)-5-((S)-3-hydroxypyrrolidine-1-carbonyl)-6-methylpicolinonitrile;

5-((S)-3-aminopyrrolidine-1-carbonyl)-4-(2-((6,6-dimethyl-2,4-dioxo-3-azabicyclo[3.1.0]hexan-3-yl)methyl)thieno[3,2-b]pyridin-7-yl)-6-methylpicolinonitrile;

6,6-dimethyl-3-((7-(4-methyl-3-(pyrrolidin-3-ylamino)-6-(trifluoromethyl)pyridin-2-yl)thieno[3,2-b]pyridin-2-yl)methyl)-3-azabicyclo[3.1.0]hexane-2,4-dione;

6-(2-((6,6-dimethyl-2,4-dioxo-3-azabicyclo[3.1.0]hexan-3-yl)methyl)thieno[3,2-b]pyridin-7-yl)-4-methyl-5-(pyrrolidin-3-ylamino)picolinonitrile;

6,6-dimethyl-3-((7-(2-methyl-3-(pyrrolidin-3-yloxy)-6-(trifluoromethyl)pyridin-4-yl)thieno[3,2-b]pyridin-2-yl)methyl)-3-azabicyclo[3.1.0]hexane-2,4-dione;

6,6-dimethyl-3-((7-(2-methyl-3-(((S)-piperidin-3-yl)oxy)-6-(trifluoromethyl)pyridin-4-yl)thieno[3,2-b]pyridin-2-yl)methyl)-3-azabicyclo[3.1.0]hexane-2,4-dione;

5-(azetidin-3-ylamino)-6-(2-((6,6-dimethyl-2,4-dioxo-3-azabicyclo[3.1.0]hexan-3-yl)methyl)thieno[3,2-b]pyridin-7-yl)-4-methylpicolinonitrile;

6,6-dimethyl-3-((7-(2-methyl-3-(pyrrolidin-3-ylamino)-6-(trifluoromethyl)pyridin-4-yl)thieno[3,2-b]pyridin-2-yl)methyl)-3-azabicyclo[3.1.0]hexane-2,4-dione;

4-(2-((6,6-dimethyl-2,4-dioxo-3-azabicyclo[3.1.0]hexan-3-yl)methyl)thieno[3,2-b]pyridin-7-yl)-6-methyl-5-(pyrrolidin-3-ylamino)picolinonitrile;

N-(2-(2-((6,6-dimethyl-2,4-dioxo-3-azabicyclo[3.1.0]hexan-3-yl)methyl)thieno[3,2-b]pyridin-7-yl)-4-methyl-6-(trifluoromethyl)pyridin-3-yl)azetidine-3-carboxamide;

N-(6-chloro-4-(2-((6,6-dimethyl-2,4-dioxo-3-azabicyclo[3.1.0]hexan-3-yl)methyl)thieno[3,2-b]pyridin-7-yl)-2-methylpyridin-3-yl)azetidine-3-carboxamide;

N-(6-cyano-4-(2-((6,6-dimethyl-2,4-dioxo-3-azabicyclo[3.1.0]hexan-3-yl)methyl)thieno[3,2-b]pyridin-7-yl)-2-methylpyridin-3-yl)azetidine-3-carboxamide;

(3S)—N-(4-chloro-2-(2-((6,6-dimethyl-2,4-dioxo-3-azabicyclo[3.1.0]hexan-3-yl)methyl)thieno[3,2-b]pyridin-7-yl)-6-methylphenyl)pyrrolidine-3-carboxamide;

6,6-dimethyl-3-((7-(4-methyl-3-(piperazin-2-ylmethyl)-6-(trifluoromethyl)pyridin-2-yl)thieno[3,2-b]pyridin-2-yl)methyl)-3-azabicyclo[3.1.0]hexane-2,4-dione;

6-(2-((6,6-dimethyl-2,4-dioxo-3-azabicyclo[3.1.0]hexan-3-yl)methyl)thieno[3,2-b]pyridin-7-yl)-4-methyl-5-((S)-2-methylpiperazine-1-carbonyl)picolinonitrile;

5-(3,3-difluoroazetidine-1-carbonyl)-6-(2-((6,6-dimethyl-2,4-dioxo-3-azabicyclo[3.1.0]hexan-3-yl)methyl)thieno[3,2-b]pyridin-7-yl)-4-methylpicolinonitrile;

6-(2-((6,6-dimethyl-2,4-dioxo-3-azabicyclo[3.1.0]hexan-3-yl)methyl)thieno[3,2-b]pyridin-7-yl)-5-((S)-2,4-dimethylpiperazine-1-carbonyl)-4-methylpicolinonitrile;

6-(2-((6,6-dimethyl-2,4-dioxo-3-azabicyclo[3.1.0]hexan-3-yl)methyl)thieno[3,2-b]pyridin-7-yl)-4-methyl-5-(piperazine-1-carbonyl)picolinonitrile;

5-(3,3-difluoropyrrolidine-1-carbonyl)-6-(2-((6,6-dimethyl-2,4-dioxo-3-azabicyclo[3.1.0]hexan-3-yl)methyl)thieno[3,2-b]pyridin-7-yl)-4-methylpicolinonitrile;

6,6-dimethyl-3-((7-(4-methyl-3-(1,7-diazaspiro[4.4]nonane-7-carbonyl)-6-(trifluoromethyl)pyridin-2-yl)thieno[3,2-b]pyridin-2-yl)methyl)-3-azabicyclo[3.1.0]hexane-2,4-dione;

6,6-dimethyl-3-((7-(4-methyl-3-(octahydropyrrolo[3,4-b]pyrrole-1-carbonyl)-6-(trifluoromethyl)pyridin-2-yl)thieno[3,2-b]pyridin-2-yl)methyl)-3-azabicyclo[3.1.0]hexane-2,4-dione;

3-((7-(3-((S)-3-(ethylamino)pyrrolidine-1-carbonyl)-4-methyl-6-(trifluoromethyl)pyridin-2-yl)thieno[3,2-b]pyridin-2-yl)methyl)-6,6-dimethyl-3-azabicyclo[3.1.0]hexane-2,4-dione;

3-((7-(3-((S)-3-(isopropylamino)pyrrolidine-1-carbonyl)-4-methyl-6-(trifluoromethyl)pyridin-2-yl)thieno[3,2-b]pyridin-2-yl)methyl)-6,6-dimethyl-3-azabicyclo[3.1.0]hexane-2,4-dione;

6,6-dimethyl-3-((7-(4-methyl-3-(piperazine-1-carbonyl)-6-(trifluoromethyl)pyridin-2-yl)thieno[3,2-b]pyridin-2-yl)methyl)-3-azabicyclo[3.1.0]hexane-2,4-dione;

6,6-dimethyl-3-((7-(4-methyl-3-((S)-3-(methylamino)pyrrolidine-1-carbonyl)-6-(trifluoromethyl)pyridin-2-yl)thieno[3,2-b]pyridin-2-yl)methyl)-3-azabicyclo[3.1.0]hexane-2,4-dione;

6,6-dimethyl-3-((7-(4-methyl-3-((S)-2-methylpiperazine-1-carbonyl)-6-(trifluoromethyl)pyridin-2-yl)thieno[3,2-b]pyridin-2-yl)methyl)-3-azabicyclo[3.1.0]hexane-2,4-dione;

3-((7-(3-((S)-2,4-dimethylpiperazine-1-carbonyl)-4-methyl-6-(trifluoromethyl)pyridin-2-yl)thieno[3,2-b]pyridin-2-yl)methyl)-6,6-dimethyl-3-azabicyclo[3.1.0]hexane-2,4-dione;

6,6-dimethyl-3-((7-(4-methyl-3-(4-methylpiperazine-1-carbonyl)-6-(trifluoromethyl)pyridin-2-yl)thieno[3,2-b]pyridin-2-yl)methyl)-3-azabicyclo[3.1.0]hexane-2,4-dione;

3-((7-(3-((S)-3-aminopyrrolidine-1-carbonyl)-4-methyl-6-(trifluoromethyl)pyridin-2-yl)thieno[3,2-b]pyridin-2-yl)methyl)-6,6-dimethyl-3-azabicyclo[3.1.0]hexane-2,4-dione;

3-((7-(3-((S)-3-(dimethylamino)pyrrolidine-1-carbonyl)-4-methyl-6-(trifluoromethyl)pyridin-2-yl)thieno[3,2-b]pyridin-2-yl)methyl)-6,6-dimethyl-3-azabicyclo[3.1.0]hexane-2,4-dione;

3-((7-(3-(3,3-difluoropyrrolidine-1-carbonyl)-4-methyl-6-(trifluoromethyl)pyridin-2-yl)thieno[3,2-b]pyridin-2-yl)methyl)-6,6-dimethyl-3-azabicyclo[3.1.0]hexane-2,4-dione;

6,6-dimethyl-3-((7-(2-methyl-3-(pyrrolidin-3-ylmethyl)-6-(trifluoromethyl)pyridin-4-yl)thieno[3,2-b]pyridin-2-yl)methyl)-3-azabicyclo[3.1.0]hexane-2,4-dione;

6,6-dimethyl-3-((7-(2-methyl-3-(((R)-pyrrolidin-3-yl)methyl)-6-(trifluoromethyl)pyridin-4-yl)thieno[3,2-b]pyridin-2-yl)methyl)-3-azabicyclo[3.1.0]hexane-2,4-dione;

6,6-dimethyl-3-((7-(2-methyl-3-(((S)-pyrrolidin-3-yl)methyl)-6-(trifluoromethyl)pyridin-4-yl)thieno[3,2-b]pyridin-2-yl)methyl)-3-azabicyclo[3.1.0]hexane-2,4-dione;

6,6-dimethyl-3-((7-(2-methyl-3-(morpholin-2-ylmethyl)-6-(trifluoromethyl)pyridin-4-yl)thieno[3,2-b]pyridin-2-yl)methyl)-3-azabicyclo[3.1.0]hexane-2,4-dione;

6,6-dimethyl-3-((7-(4-methyl-3-(morpholin-2-ylmethyl)-6-(trifluoromethyl)pyridin-2-yl)thieno[3,2-b]pyridin-2-yl)methyl)-3-azabicyclo[3.1.0]hexane-2,4-dione;

6-(2-((6,6-dimethyl-2,4-dioxo-3-azabicyclo[3.1.0]hexan-3-yl)methyl)thieno[3,2-b]pyridin-7-yl)-4-methyl-5-(morpholin-2-ylmethyl)picolinonitrile;

6,6-dimethyl-3-((7-(4-methyl-3-(((S)-morpholin-2-yl)methyl)-6-(trifluoromethyl)pyridin-2-yl)thieno[3,2-b]pyridin-2-yl)methyl)-3-azabicyclo[3.1.0]hexane-2,4-dione;

6,6-dimethyl-3-((7-(4-methyl-3-(((R)-morpholin-2-yl)methyl)-6-(trifluoromethyl)pyridin-2-yl)thieno[3,2-b]pyridin-2-yl)methyl)-3-azabicyclo[3.1.0]hexane-2,4-dione;

6,6-dimethyl-3-((7-(4-methyl-3-(((R)-4-methylmorpholin-2-yl)methyl)-6-(trifluoromethyl)pyridin-2-yl)thieno[3,2-b]pyridin-2-yl)methyl)-3-azabicyclo[3.1.0]hexane-2,4-dione;

6,6-dimethyl-3-((7-(2-(((R)-morpholin-2-yl)methyl)-5-(trifluoromethyl)pyridin-3-yl)thieno[3,2-b]pyridin-2-yl)methyl)-3-azabicyclo[3.1.0]hexane-2,4-dione;

3-((7-(3-((S)-3-(difluoromethyl)pyrrolidine-1-carbonyl)-4-methyl-6-(trifluoromethyl)pyridin-2-yl)thieno[3,2-b]pyridin-2-yl)methyl)-6,6-dimethyl-3-azabicyclo[3.1.0]hexane-2,4-dione;

3-((7-(3-((S)-3-(fluoromethyl)pyrrolidine-1-carbonyl)-4-methyl-6-(trifluoromethyl)pyridin-2-yl)thieno[3,2-b]pyridin-2-yl)methyl)-6,6-dimethyl-3-azabicyclo[3.1.0]hexane-2,4-dione;

3-((7-(3-((3S,4S)-3-amino-4-methylpyrrolidine-1-carbonyl)-4-methyl-6-(trifluoromethyl)pyridin-2-yl)thieno[3,2-b]pyridin-2-yl)methyl)-6,6-dimethyl-3-azabicyclo[3.1.0]hexane-2,4-dione;

3-((7-(3-((3S,4R)-3-amino-4-methylpyrrolidine-1-carbonyl)-4-methyl-6-(trifluoromethyl)pyridin-2-yl)thieno[3,2-b]pyridin-2-yl)methyl)-6,6-dimethyl-3-azabicyclo[3.1.0]hexane-2,4-dione;

6,6-dimethyl-3-((7-(4-methyl-3-((3aR,6aR)-octahydropyrrolo[3,4-b]pyrrole-5-carbonyl)-6-(trifluoromethyl)pyridin-2-yl)thieno[3,2-b]pyridin-2-yl)methyl)-3-azabicyclo[3.1.0]hexane-2,4-dione;

(2S)-2-amino-N-((3S)-1-(2-(2-((6,6-dimethyl-2,4-dioxo-3-azabicyclo[3.1.0]hexan-3-yl)methyl)thieno[3,2-b]pyridin-7-yl)-4-methyl-6-(trifluoromethyl)nicotinoyl)pyrrolidin-3-yl)-3-methylbutanamide;

3-((7-(3-(4-aminopiperidine-1-carbonyl)-4-methyl-6-(trifluoromethyl)pyridin-2-yl)thieno[3,2-b]pyridin-2-yl)methyl)-6,6-dimethyl-3-azabicyclo[3.1.0]hexane-2,4-dione;

3-((7-(3-((S)-3-hydroxypyrrolidine-1-carbonyl)-4-methyl-6-(trifluoromethyl)pyridin-2-yl)thieno[3,2-b]pyridin-2-yl)methyl)-6,6-dimethyl-3-azabicyclo[3.1.0]hexane-2,4-dione;

3-((7-(3-((S)-3-fluoropyrrolidine-1-carbonyl)-4-methyl-6-(trifluoromethyl)pyridin-2-yl)thieno[3,2-b]pyridin-2-yl)methyl)-6,6-dimethyl-3-azabicyclo[3.1.0]hexane-2,4-dione;

6,6-dimethyl-3-((7-(4-methyl-3-((3aR,6aR)-octahydropyrrolo[3,4-h]pyrrole-1-carbonyl)-6-(trifluoromethyl)pyridin-2-yl)thieno[3,2-b]pyridin-2-yl)methyl)-3-azabicyclo[3.1.0]hexane-2,4-dione;

3-((7-(3-((3R,4R)-3-amino-4-fluoropyrrolidine-1-carbonyl)-4-methyl-6-(trifluoromethyl)pyridin-2-yl)thieno[3,2-b]pyridin-2-yl)methyl)-6,6-dimethyl-3-azabicyclo[3.1.0]hexane-2,4-dione;

N-(4-chloro-2-(2-((6,6-dimethyl-2,4-dioxo-3-azabicyclo[3.1.0]hexan-3-yl)methyl)thieno[3,2-b]pyridin-7-yl)-6-methylphenyl)piperidine-4-carboxamide;

3-((7-(3-(azetidin-3-ylamino)-6-chloro-4-methylpyridin-2-yl)thieno[3,2-b]pyridin-2-yl)methyl)-6,6-dimethyl-3-azabicyclo[3.1.0]hexane-2,4-dione;

3-((7-(4,6-dimethyl-3-(pyrrolidin-3-ylamino)pyridin-2-yl)thieno[3,2-b]pyridin-2-yl)methyl)-6,6-dimethyl-3-azabicyclo[3.1.0]hexane-2,4-dione;

3-((7-(6-chloro-2-methyl-3-(pyrrolidin-3-ylamino)pyridin-4-yl)thieno[3,2-b]pyridin-2-yl)methyl)-6,6-dimethyl-3-azabicyclo[3.1.0]hexane-2,4-dione;

3-((7-(6-chloro-4-methyl-3-(pyrrolidin-3-ylamino)pyridin-2-yl)thieno[3,2-b]pyridin-2-yl)methyl)-6,6-dimethyl-3-azabicyclo[3.1.0]hexane-2,4-dione;

3-((7-(6-chloro-4-methyl-3-(piperidin-4-ylamino)pyridin-2-yl)thieno[3,2-b]pyridin-2-yl)methyl)-6,6-dimethyl-3-azabicyclo[3.1.0]hexane-2,4-dione;

6,6-dimethyl-3-((7-(4-methyl-3-(piperidin-4-ylamino)-6-(trifluoromethyl)pyridin-2-yl)thieno[3,2-b]pyridin-2-yl)methyl)-3-azabicyclo[3.1.0]hexane-2,4-dione;

3-((7-(6-chloro-4-methyl-3-(piperidin-3-ylamino)pyridin-2-yl)thieno[3,2-b]pyridin-2-yl)methyl)-6,6-dimethyl-3-azabicyclo[3.1.0]hexane-2,4-dione;

6,6-dimethyl-3-((7-(4-methyl-3-(piperidin-3-ylamino)-6-(trifluoromethyl)pyridin-2-yl)thieno[3,2-b]pyridin-2-yl)methyl)-3-azabicyclo[3.1.0]hexane-2,4-dione;

3-((7-(3-((2-azaspiro[3.3]heptan-6-yl)amino)-6-chloro-4-methylpyridin-2-yl)thieno[3,2-b]pyridin-2-yl)methyl)-6,6-dimethyl-3-azabicyclo[3.1.0]hexane-2,4-dione;

3-((7-(3-((2-azaspiro[3.3]heptan-6-yl)amino)-4-methyl-6-(trifluoromethyl)pyridin-2-yl)thieno[3,2-b]pyridin-2-yl)methyl)-6,6-dimethyl-3-azabicyclo[3.1.0]hexane-2,4-dione;

3-((7-(3-(3-(aminomethyl)pyrrolidine-1-carbonyl)-4-methyl-6-(trifluoromethyl)pyridin-2-yl)thieno[3,2-b]pyridin-2-yl)methyl)-6,6-dimethyl-3-azabicyclo[3.1.0]hexane-2,4-dione;

3-((7-(3-(3-((isopropylamino)methyl)pyrrolidine-1-carbonyl)-4-methyl-6-(trifluoromethyl)pyridin-2-yl)thieno[3,2-b]pyridin-2-yl)methyl)-6,6-dimethyl-3-azabicyclo[3.1.0]hexane-2,4-dione;

3-((7-(3-((2S,6S)-2,6-dimethylpiperazine-1-carbonyl)-4-methyl-6-(trifluoromethyl)pyridin-2-yl)thieno[3,2-b]pyridin-2-yl)methyl)-6,6-dimethyl-3-azabicyclo[3.1.0]hexane-2,4-dione;

3-((7-(3-(4-ethylpiperazine-1-carbonyl)-4-methyl-6-(trifluoromethyl)pyridin-2-yl)thieno[3,2-b]pyridin-2-yl)methyl)-6,6-dimethyl-3-azabicyclo[3.1.0]hexane-2,4-dione; or 4-methyl-6-((7-(4-methyl-3-(pyrrolidin-3-ylamino)-6-(trifluoromethyl)pyridin-2-yl)thieno[3,2-b]pyridin-2-yl)methyl)-4,6-diazaspiro[2.4]heptane-5,7-dione;

or a tautomer, stereoisomer, a racemic or scalemic mixture of stereoisomers, a pharmaceutically acceptable salt, ester, solvate, or polymorph thereof.

In certain embodiments, the compound according to the invention is;

3-((7-(5-fluoro-2-(((S)-piperidin-3-yl)oxy)pyridin-3-yl)thieno[3,2-b]pyridin-2-yl)methyl)-6,6-dimethyl-3-azabicyclo[3.1.0]hexane-2,4-dione;

3-((7-(3-(((3aR,6aR)-hexahydropyrrolo[3,4-b]pyrrol-1(2H)-yl)methyl)-4-methyl-6-(trifluoromethyl)pyridin-2-yl)thieno[3,2-b]pyridin-2-yl)methyl)-6,6-dimethyl-3-azabicyclo[3.1.0]hexane-2,4-dione;

6,6-dimethyl-3-((7-(5-methyl-1-(((S)-morpholin-2-yl)methyl)-4-nitro-1H-pyrrol-2-yl)thieno[3,2-b]pyridin-2-yl)methyl)-3-azabicyclo[3.1.0]hexane-2,4-dione;

ethyl 2-(2-((6,6-dimethyl-2,4-dioxo-3-azabicyclo[3.1.0]hexan-3-yl)methyl)thieno[3,2-b]pyridin-7-yl)-5-methyl-1-(((S)-morpholin-2-yl)methyl)-4-(trifluoromethyl)-1H-pyrrole-3-carboxylate;

3-((7-(3-(2,5-diazabicyclo[2.2.2]octane-2-carbonyl)-4-methyl-6-(trifluoromethyl)pyridin-2-yl)thieno[3,2-b]pyridin-2-yl)methyl)-6,6-dimethyl-3-azabicyclo[3.1.0]hexane-2,4-dione;

3-((7-(5-fluoro-2-(((S)-pyrrolidin-3-yl)oxy)pyridin-3-yl)thieno[3,2-b]pyridin-2-yl)methyl)-6,6-dimethyl-3-azabicyclo[3.1.0]hexane-2,4-dione;

3-((7-(5-fluoro-2-(((R)-pyrrolidin-3-yl)oxy)pyridin-3-yl)thieno[3,2-b]pyridin-2-yl)methyl)-6,6-dimethyl-3-azabicyclo[3.1.0]hexane-2,4-dione;

6,6-dimethyl-3-((7-(4-methyl-3-(((S)-3-(methylamino)pyrrolidin-1-yl)methyl)-6-(trifluoromethyl)pyridin-2-yl)thieno[3,2-b]pyridin-2-yl)methyl)-3-azabicyclo[3.1.0]hexane-2,4-dione;

3-((7-(5-chloro-2-(((S)-piperidin-3-yl)oxy)pyridin-3-yl)thieno[3,2-b]pyridin-2-yl)methyl)-6,6-dimethyl-3-azabicyclo[3.1.0]hexane-2,4-dione;

3-((7-(4-chloro-5-methyl-1-(((S)morpholin-2-yl)methyl)-1H-pyrrol-2-yl)thieno[3,2-b]pyridin-2-yl)methyl)-6,6-dimethyl-3-azabicyclo[3.1.0]hexane-2,4-dione;

6,6-dimethyl-3-((7-(4-methyl-3-((3aS,6aS)-octahydropyrrolo[3,4-b]pyrrole-5-carbonyl)-6-(trifluoromethyl)pyridin-2-yl)thieno[3,2-b]pyridin-2-yl)methyl)-3-azabicyclo[3.1.0]hexane-2,4-dione;

3-((7-(5-chloro-2-(((S)-pyrrolidin-3-yl)oxy)pyridin-3-yl)thieno[3,2-b]pyridin-2-yl)methyl)-6,6-dimethyl-3-azabicyclo[3.1.0]hexane-2,4-dione;

6,6-dimethyl-3-((7-(4-methyl-3-((3-oxopiperazin-2-yl)methyl)-6-(trifluoromethyl)pyridin-2-yl)thieno[3,2-b]pyridin-2-yl)methyl)-3-azabicyclo[3.1.0]hexane-2,4-dione;

6,6-dimethyl-3-((7-(2-((3-oxopiperazin-2-yl)methyl)-5-(trifluoromethyl)pyridin-3-yl)thieno[3,2-b]pyridin-2-yl)methyl)-3-azabicyclo[3.1.0]hexane-2,4-dione;

6,6-dimethyl-3-((7-(5-methyl-1-(((R)-morpholin-2-yl)methyl)-4-nitro-1H-pyrrol-2-yl)thieno[3,2-b]pyridin-2-yl)methyl)-3-azabicyclo[3.1.0]hexane-2,4-dione;

6,6-dimethyl-3-((7-(4-methyl-3-((3R,4S)-3-methyl-4-(methylamino)pyrrolidine-1-carbonyl)-6-(trifluoromethyl)pyridin-2-yl)thieno[3,2-b]pyridin-2-yl)methyl)-3-azabicyclo[3.1.0]hexane-2,4-dione;

3-((7-(3-((3R,4S)-3-amino-4-fluoropyrrolidine-1-carbonyl)-4-methyl-6-(trifluoromethyl)pyridin-2-yl)thieno[3,2-b]pyridin-2-yl)methyl)-6,6-dimethyl-3-azabicyclo[3.1.0]hexane-2,4-dione;

3-((7-(3-(((3S,4S)-3-amino-4-fluoropyrrolidine-1-carbonyl)-4-methyl-6-(trifluoromethyl)pyridin-2-yl)thieno[3,2-b]pyridin-2-yl)methyl)-6,6-dimethyl-3-azabicyclo[3.1.0]hexane-2,4-dione;

3-((7-(3-(((3S,4R)-3-amino-4-fluoropyrrolidine-1-carbonyl)-4-methyl-6-(trifluoromethyl)pyridin-2-yl)thieno[3,2-b]pyridin-2-yl)methyl)-6,6-dimethyl-3-azabicyclo[3.1.0]hexane-2,4-dione;

3-((7-(3-(((3S,4R)-3-(dimethylamino)-4-methylpyrrolidine-1-carbonyl)-4-methyl-6-(trifluoromethyl)pyridin-2-yl)thieno[3,2-b]pyridin-2-yl)methyl)-6,6-dimethyl-3-azabicyclo[3.1.0]hexane-2,4-dione;

3-((7-(3-((S)-7-amino-5-azaspiro[2.4]heptane-5-carbonyl)-4-methyl-6-(trifluoromethyl)pyridin-2-yl)thieno[3,2-b]pyridin-2-yl)methyl)-6,6-dimethyl-3-azabicyclo[3.1.0]hexane-2,4-dione;

3-((3-fluoro-7-(4-methyl-3-((S)-3-(methylamino)pyrrolidine-1-carbonyl)-6-(trifluoromethyl)pyridin-2-yl)thieno[3,2-b]pyridin-2-yl)methyl)-6,6-dimethyl-3-azabicyclo[3.1.0]hexane-2,4-dione;

3-((7-(5-chloro-3-methyl-2-(pyrrolidin-3-ylamino)phenyl)thieno[3,2-b]pyridin-2-yl)methyl)-6,6-dimethyl-3-azabicyclo[3.1.0]hexane-2,4-dione;

3-((7-(4-amino-5-methyl-1-(((S)-morpholin-2-yl)methyl)-1H-pyrrol-2-yl)thieno[3,2-b]pyridin-2-yl)methyl)-6,6-dimethyl-3-azabicyclo[3.1.0]hexane-2,4-dione;

3-((7-(4-(dimethylamino)-5-methyl-1-(((S)-morpholin-2-yl)methyl)-1H-pyrrol-2-yl)thieno[3,2-b]pyridin-2-yl)methyl)-6,6-dimethyl-3-azabicyclo[3.1.0]hexane-2,4-dione;

3-((7-(5-chloro-3-methyl-2-(((S)-piperidin-3-yl)oxy)phenyl)thieno[3,2-b]pyridin-2-yl)methyl)piperazin-2-one;

3-((7-(5-chloro-3-methyl-2-(((S)-piperidin-3-yl)oxy)phenyl)thieno[3,2-b]pyridin-2-yl)methyl)-4-hydroxypyrrolidin-2-one; or 3-((7-(3-(3,3-difluoro-4-(methylamino)pyrrolidine-1-carbonyl)-4-methyl-6-(trifluoromethyl)pyridin-2-yl)thieno[3,2-b]pyridin-2-yl)methyl)-6,6-dimethyl-3-azabicyclo[3.1.0]hexane-2,4-dione;

or a tautomer, stereoisomer, a racemic or scalemic mixture of stereoisomers, a pharmaceutically acceptable salt, ester, solvate, or polymorph thereof.

The following representative structures of compounds of Formula (I), (Ia), (Ib), or (Ic), mainly in the form of salts thereof, are disclosed herein:

| Ex. No. | Structure | IUPAC Name |
|---|---|---|
| 1. | 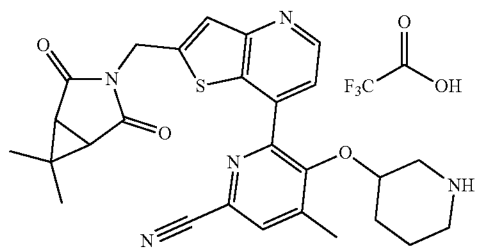 | 6-(2-((6,6-dimethyl-2,4-dioxo-3-azabicyclo[3.1.0]hexan-3-yl)methyl)thieno[3,2-b]pyridin-7-yl)-4-methyl-5-(piperidin-3-yloxy)picolinonitrile 2,2,2-trifluoroacetate |
| 2. | 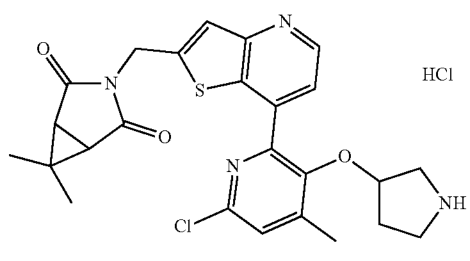 [SMILES: Cc1cc(Cl)nc(-c2ccnc3cc(CN4C(=O)C5C(C4=O)C5(C)C)sc23)c1OC1CCNC1 ; Cl] | 3-((7-(6-chloro-4-methyl-3-(pyrrolidin-3-yloxy)pyridin-2-yl)thieno[3,2-b]pyridin-2-yl)methyl)-6,6-dimethyl-3-azabicyclo[3.1.0]hexane-2,4-dione hydrochloride |
| 3. | 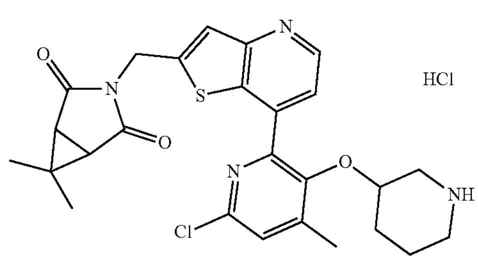 [SMILES: Cc1cc(Cl)nc(-c2ccnc3cc(CN4C(=O)C5C(C4=O)C5(C)C)sc23)c1OC1CCCNC1 ; Cl] | 3-((7-(6-chloro-4-methyl-3-(piperidin-3-yloxy)pyridin-2-yl)thieno[3,2-b]pyridin-2-yl)methyl)-6,6-dimethyl-3-azabicyclo[3.1.0]hexane-2,4-dione hydrochloride |

-continued

| Ex. No. | Structure | IUPAC Name |
|---|---|---|
| 4. | 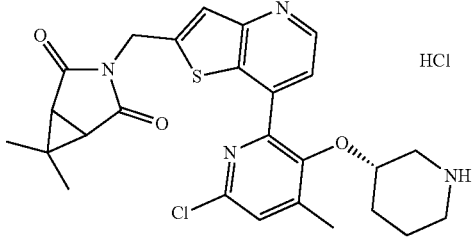 [SMILES: Cc1cc(Cl)nc(-c2ccnc3cc(CN4C(=O)C5C(C4=O)C5(C)C)sc23)c1O[C@H]1CCCNC1 ; Cl] Single enantiomer of Ex. 3 | 3-((7-(6-chloro-4-methyl-3-(((S)-piperidin-3-yl)oxy)pyridin-2-yl)thieno[3,2-b]pyridin-2-yl)methyl)-6,6-dimethyl-3-azabicyclo[3.1.0]hexane-2,4-dione hydrochloride |
| 5. | 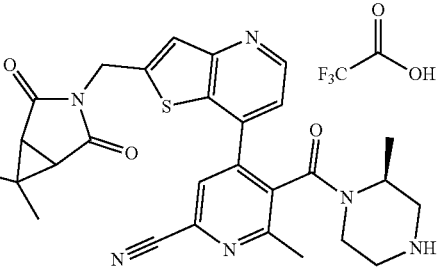 | 4-(2-((6,6-dimethyl-2,4-dioxo-3-azabicyclo[3.1.0]hexan-3-yl)methyl)thieno[3,2-b]pyridin-7-yl)-6-methyl-5-((S)-2-methylpiperazine-1-carbonyl)picolinonitrile 2,2,2-trifluoroacetate |
| 6. | 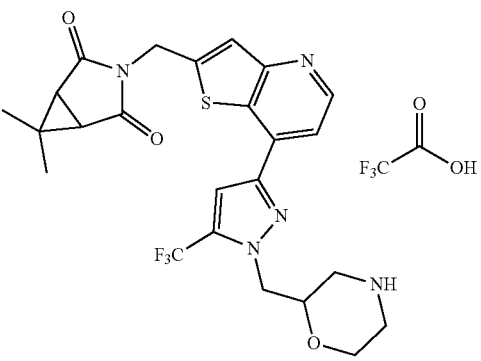 [SMILES: CC1(C)C2C(=O)N(Cc3cc4nccc(-c5cc(C(F)(F)F)n(CC6CNCCO6)n5)c4s3)C(=O)C21 ; O=C(O)C(F)(F)F] Uncertain position of morpholine substituent | 6,6-dimethyl-3-((7-(1-(morpholin-2-ylmethyl)-5-(trifluoromethyl)-1H-pyrazol-3-yl)thieno[3,2-b]pyridin-2-yl)methyl)-3-azabicyclo[3.1.0]hexane-2,4-dione 2,2,2-trifluoroacetate |
| 7. | 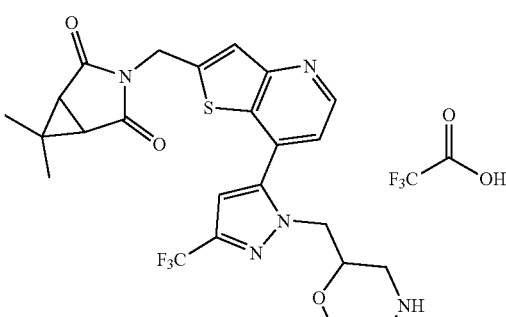 Uncertain position of morpholine substituent | 6,6-dimethyl-3-((7-(1-(morpholin-2-ylmethyl)-3-(trifluoromethyl)-1H-pyrazol-5-yl)thieno[3,2-b]pyridin-2-yl)methyl)-3-azabicyclo[3.1.0]hexane-2,4-dione 2,2,2-trifluoroacetate |

| Ex. No. | Structure | IUPAC Name |
|---|---|---|
| 8. | 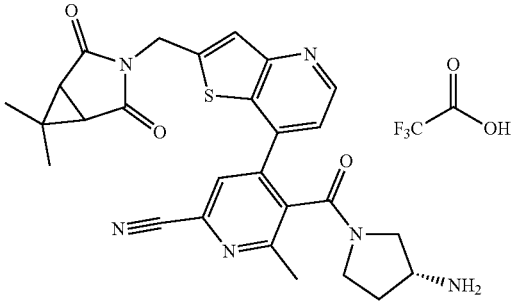 [SMILES: Cc1nc(C#N)cc(-c2ccnc3cc(CN4C(=O)C5C(C4=O)C5(C)C)sc23)c1C(=O)N1CC[C@@H](N)C1 ; O=C(O)C(F)(F)F] | 5-((R)-3-aminopyrrolidine-1-carbonyl)-4-(2-((6,6-dimethyl-2,4-dioxo-3-azabicyclo[3.1.0]hexan-3-yl)methyl)thieno[3,2-b]pyridin-7-yl)-6-methylpicolinonitrile 2,2,2-trifluoroacetate |
| 9. | 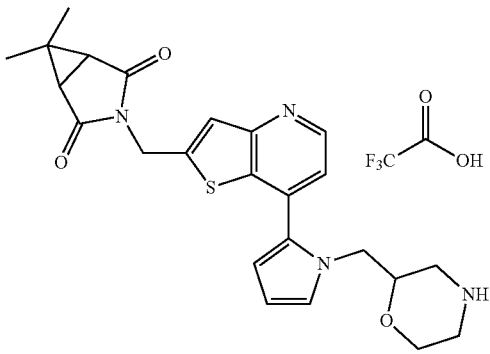 [SMILES: CC1(C)C2C(=O)N(Cc3cc4nccc(-c5cccn5CC5CNCCO5)c4s3)C(=O)C21 ; O=C(O)C(F)(F)F] | 6,6-dimethyl-3-((7-(1-(morpholin-2-ylmethyl)-1H-pyrrol-2-yl)thieno[3,2-b]pyridin-2-yl)methyl)-3-azabicyclo[3.1.0]hexane-2,4-dione 2,2,2-trifluoroacetate |
| 10. | 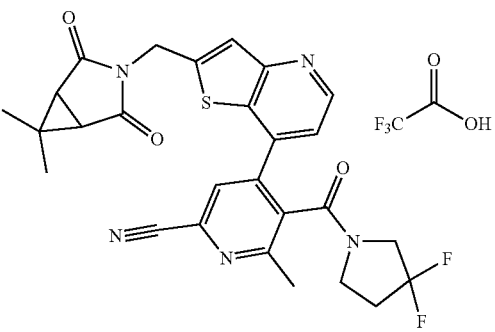 [SMILES: Cc1nc(C#N)cc(-c2ccnc3cc(CN4C(=O)C5C(C4=O)C5(C)C)sc23)c1C(=O)N1CCC(F)(F)C1 ; O=C(O)C(F)(F)F] | 5-(3,3-difluoropyrrolidine-1-carbonyl)-4-(2-((6,6-dimethyl-2,4-dioxo-3-azabicyclo[3.1.0]hexan-3-yl)methyl)thieno[3,2-b]pyridin-7-yl)-6-methylpicolinonitrile 2,2,2-trifluoroacetate |
| 11. | 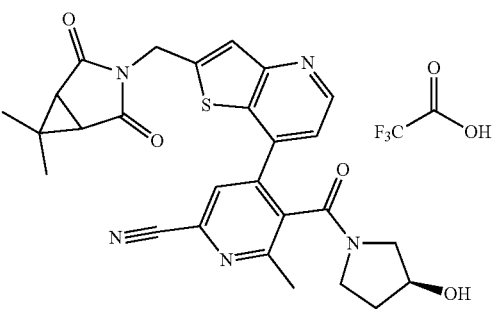 [SMILES: Cc1nc(C#N)cc(-c2ccnc3cc(CN4C(=O)C5C(C4=O)C5(C)C)sc23)c1C(=O)N1CC[C@H](O)C1 ; O=C(O)C(F)(F)F] | 4-(2-((6,6-dimethyl-2,4-dioxo-3-azabicyclo[3.1.0]hexan-3-yl)methyl)thieno[3,2-6]pyridin-7-yl)-5-((S)-3-hydroxypyrrolidine-1-carbonyl)-6-methylpicolinonitrile 2,2,2-trifluoroacetate |

| Ex. No. | Structure | IUPAC Name |
|---|---|---|
| 12. | 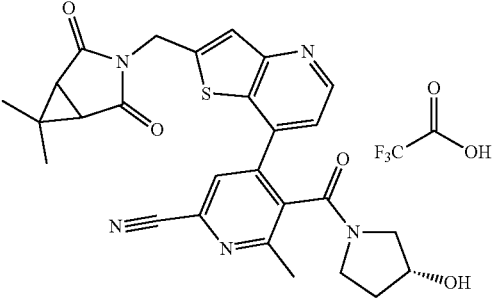 | 4-(2-((6,6-dimethyl-2,4-dioxo-3-azabicyclo[3.1.0]hexan-3-yl)methyl)thieno[3,2-b]pyridin-7-yl)-5-((R)-3-hydroxypyrrolidine-1-carbonyl)-6-methylpicolinonitrile 2,2,2-trifluoroacetate |
| 13. | 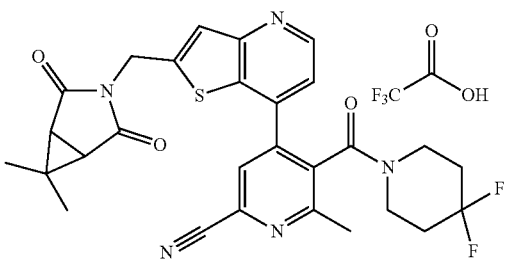 | 5-(4,4-difluoropiperidine-1-carbonyl)-4-(2-((6,6-dimethyl-2,4-dioxo-3-azabicyclo[3.1.0]hexan-3-yl)methyl)thieno[3,2-b]pyridin-7-yl)-6-methylpicolinonitrile 2,2,2-trifluoroacetate |
| 14. | 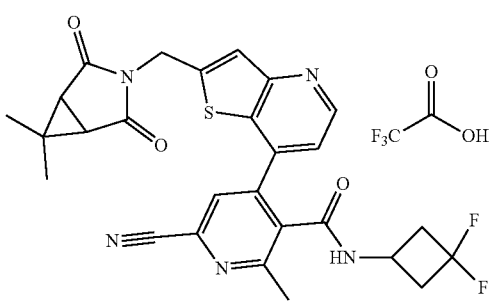 [SMILES: Cc1nc(C#N)cc(-c2ccnc3cc(CN4C(=O)C5C(C4=O)C5(C)C)sc23)c1C(=O)NC1CC(F)(F)C1 ; O=C(O)C(F)(F)F] | 6-cyano-N-(3,3-difluorocyclobutyl)-4-(2-((6,6-dimethyl-2,4-dioxo-3-azabicyclo[3.1.0]hexan-3-yl)methyl)thieno[3,2-b]pyridin-7-yl)-2-methylnicotinamide 2,2,2-trifluoroacetate |
| 15. | 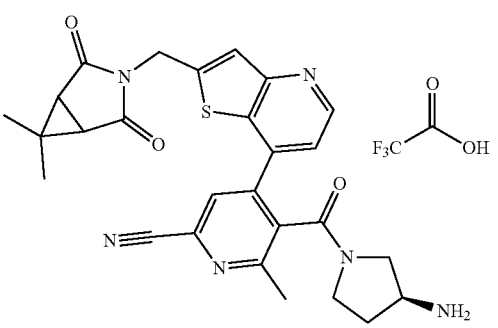 [SMILES: Cc1nc(C#N)cc(-c2ccnc3cc(CN4C(=O)C5C(C4=O)C5(C)C)sc23)c1C(=O)N1CC[C@H](N)C1 ; O=C(O)C(F)(F)F] | 5-((S)-3-aminopyrrolidine-1-carbonyl)-4-(2-((6,6-dimethyl-2,4-dioxo-3-azabicyclo[3.1.0]hexan-3-yl)methyl)thieno[3,2-b]pyridin-7-yl)-6-methylpicolinonitrile 2,2,2-trifluoroacetate |
| 16. | 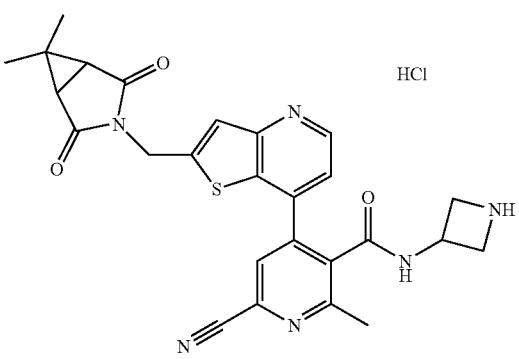 [SMILES: Cc1nc(C#N)cc(-c2ccnc3cc(CN4C(=O)C5C(C4=O)C5(C)C)sc23)c1C(=O)NC1CNC1 ; Cl] | N-(azetidin-3-yl)-6-cyano-4-(2-((6,6-dimethyl-2,4-dioxo-3-azabicyclo[3.1.0]hexan-3-yl)methyl)thieno[3,2-b]pyridin-7-yl)-2-methylnicotinamide hydrochloride |

| Ex. No. | Structure | IUPAC Name |
|---|---|---|
| 17. | 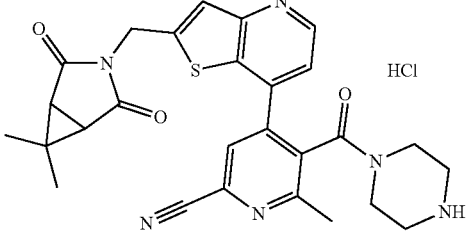 | 4-(2-((6,6-dimethyl-2,4-dioxo-3-azabicyclo[3.1.0]hexan-3-yl)methyl)thieno[3,2-b]pyridin-7-yl)-6-methyl-5-(piperazine-1-carbonyl)picolinonitrile hydrochloride |
| 18. | 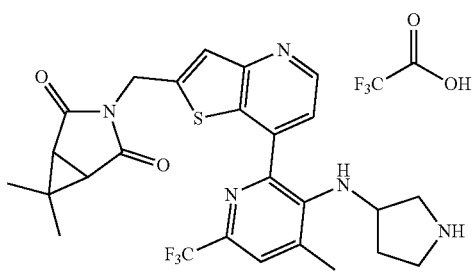 | 6,6-dimethyl-3-((7-(4-methyl-3-(pyrrolidin-3-ylamino)-6-(trifluoromethyl)pyridin-2-yl)thieno[3,2-b]pyridin-2-yl)methyl)-3-azabicyclo[3.1.0]hexane-2,4-dione 2,2,2-trifluoroacetate |
| 19. | 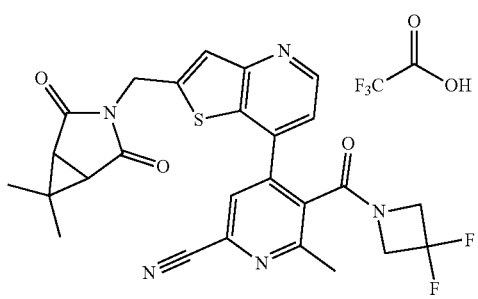 | 5-(3,3-difluoroazetidine-1-carbonyl)-4-(2-((6,6-dimethyl-2,4-dioxo-3-azabicyclo[3.1.0]hexan-3-yl)methyl)thieno[3,2-b]pyridin-7-yl)-6-methylpicolinonitrile 2,2,2-trifluoroacetate |
| 20. | 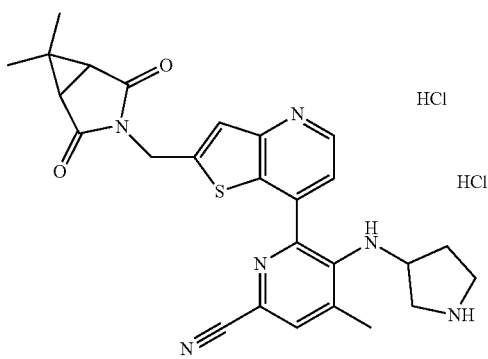 [SMILES: Cc1cc(C#N)nc(-c2ccnc3cc(CN4C(=O)C5C(C4=O)C5(C)C)sc23)c1NC1CCNC1 ; Cl ; Cl] | 6-(2-((6,6-dimethyl-2,4-dioxo-3-azabicyclo[3.1.0]hexan-3-yl)methyl)thieno[3,2-b]pyridin-7-yl)-4-methyl-5-(pyrrolidin-3-ylamino)picolinonitrile dihydrochloride |
| 21. | 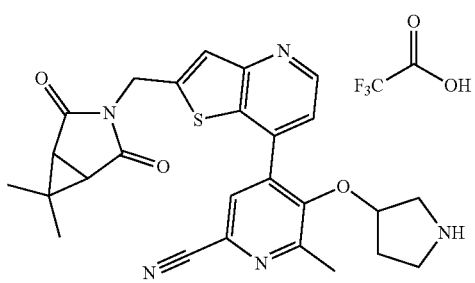 | 6,6-dimethyl-3-((7-(2-methyl-3-(pyrrolidin-3-yloxy)-6-(trifluoromethyl)pyridin-4-yl)thieno[3,2-b]pyridin-2-yl)methyl)-3-azabicyclo[3.1.0]hexane-2,4-dione 2,2,2-trifluoroacetate |

| Ex. No. | Structure | IUPAC Name |
|---|---|---|
| 22. | 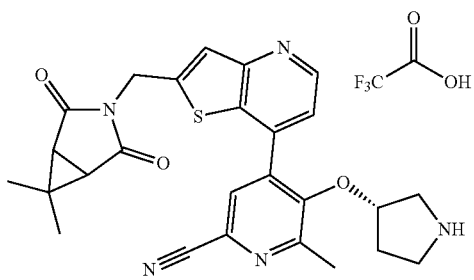<br>Single enantiomer of Ex. 21 | 6,6-dimethyl-3-((7-(2-methyl-3-(((S)-pyrrolidin-3-yl)oxy)-6-(trifluoromethyl)pyridin-4-yl)thieno[3,2-b]pyridin-2-yl)methyl)-3-azabicyclo[3.1.0]hexane-2,4-dione 2,2,2-trifluoroacetate |
| 23. | 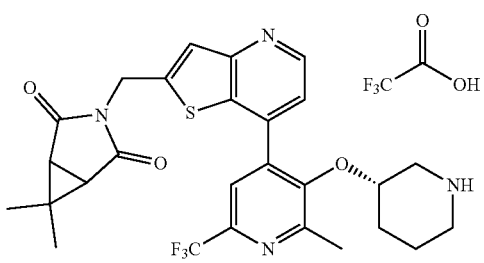 [SMILES: Cc1nc(C(F)(F)F)cc(-c2ccnc3cc(CN4C(=O)C5C(C4=O)C5(C)C)sc23)c1O[C@H]1CCCNC1 ; O=C(O)C(F)(F)F] | 6,6-dimethyl-3-((7-(2-methyl-3-(((S)-piperidin-3-yl)oxy)-6-(trifluoromethyl)pyridin-4-yl)thieno[3,2-b]pyridin-2-yl)methyl)-3-azabicyclo[3.1.0]hexane-2,4-dione 2,2,2-trifluoroacetate |
| 24. | 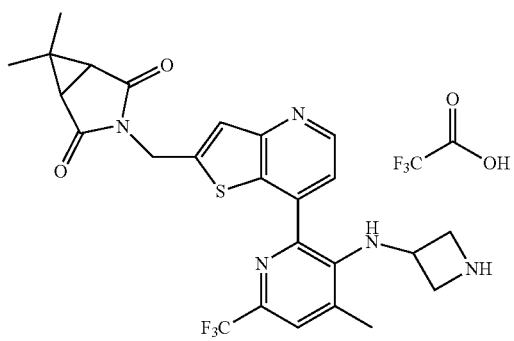 [SMILES: Cc1cc(C(F)(F)F)nc(-c2ccnc3cc(CN4C(=O)C5C(C4=O)C5(C)C)sc23)c1NC1CNC1 ; O=C(O)C(F)(F)F] | 5-(azetidin-3-ylamino)-6-(2-((6,6-dimethyl-2,4-dioxo-3-azabicyclo[3.1.0]hexan-3-yl)methyl)thieno[3,2-b]pyridin-7-yl)-4-methylpicolinonitrile 2,2,2-trifluoroacetate |
| 25. | 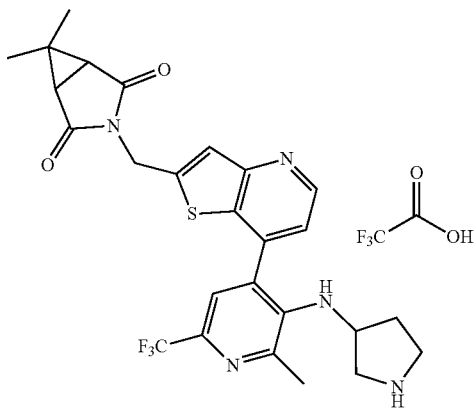 [SMILES: Cc1nc(C(F)(F)F)cc(-c2ccnc3cc(CN4C(=O)C5C(C4=O)C5(C)C)sc23)c1NC1CCNC1 ; O=C(O)C(F)(F)F]<br>Racemate | 6,6-dimethyl-3-((7-(2-methyl-3-(pyrrolidin-3-ylamino)-6-(trifluoromethyl)pyridin-4-yl)thieno[3,2-b]pyridin-2-yl)methyl)-3-azabicyclo[3.1.0]hexane-2,4-dione 2,2,2-trifluoroacetate |

| Ex. No. | Structure | IUPAC Name |
|---|---|---|
| 26. | 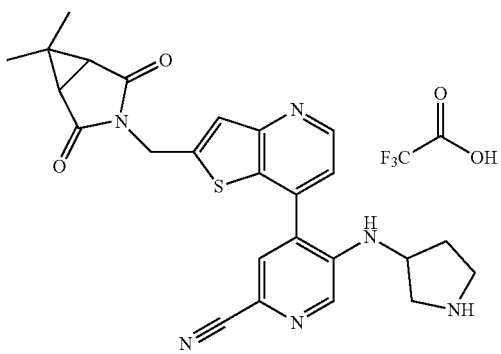 [SMILES: CC1(C)C2C(=O)N(Cc3cc4nccc(-c5cc(C#N)ncc5NC5CCNC5)c4s3)C(=O)C21 ; O=C(O)C(F)(F)F] | 4-(2-((6,6-dimethyl-2,4-dioxo-3-azabicyclo[3.1.0]hexan-3-yl)methyl)thieno[3,2-b]pyridin-7-yl)-6-methyl-5-(pyrrolidin-3-ylamino)picolinonitrile 2,2,2-trifluoroacetate |
| 27. | 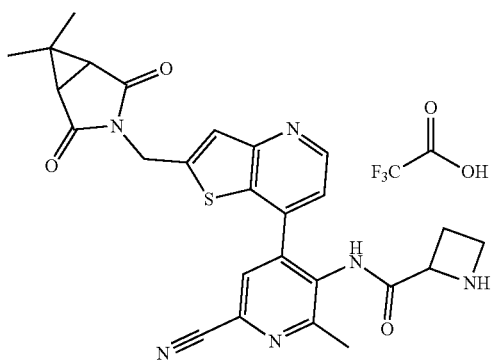 [SMILES: Cc1nc(C#N)cc(-c2ccnc3cc(CN4C(=O)C5C(C4=O)C5(C)C)sc23)c1NC(=O)C1CCN1 ; O=C(O)C(F)(F)F] | N-(6-cyano-4-(2-((6,6-dimethyl-2,4-dioxo-3-azabicyclo[3.1.0]hexan-3-yl)methyl)thieno[3,2-b]pyridin-7-yl)-2-methylpyridin-3-yl)azetidine-2-carboxamide 2,2,2-trifluoroacetate |
| 28. | 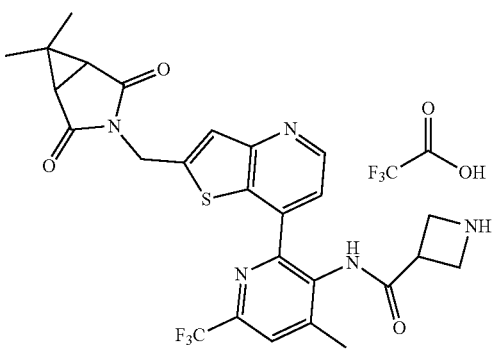 | N-(2-(2-((6,6-dimethyl-2,4-dioxo-3-azabicyclo[3.1.0]hexan-3-yl)methyl)thieno[3,2-b]pyridin-7-yl)-4-methyl-6-(trifluoromethyl)pyridin-3-yl)azetidine-3-carboxamide 2,2,2-trifluoroacetate |
| 29. | 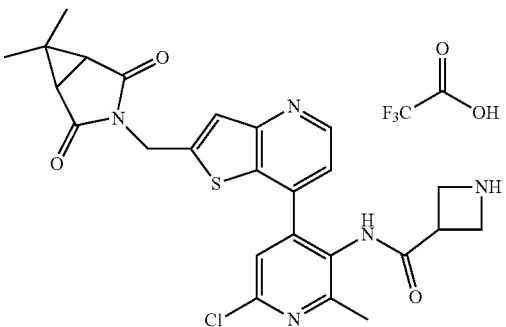 [SMILES: Cc1nc(Cl)cc(-c2ccnc3cc(CN4C(=O)C5C(C4=O)C5(C)C)sc23)c1NC(=O)C1CNC1 ; O=C(O)C(F)(F)F] | N-(6-chloro-4-(2-((6,6-dimethyl-2,4-dioxo-3-azabicyclo[3.1.0]hexan-3-yl)methyl)thieno[3,2-b]pyridin-7-yl)-2-methylpyridin-3-yl)azetidine-3-carboxamide 2,2,2-trifluoroacetate |

| Ex. No. | Structure | IUPAC Name |
|---|---|---|
| 30. | 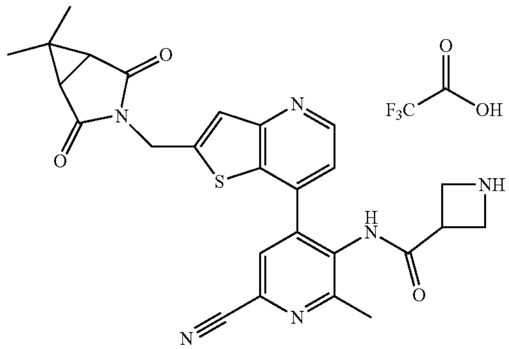 [SMILES: Cc1nc(C#N)cc(-c2ccnc3cc(CN4C(=O)C5C(C4=O)C5(C)C)sc23)c1NC(=O)C1CNC1 ; O=C(O)C(F)(F)F] | N-(6-cyano-4-(2-((6,6-dimethyl-2,4-dioxo-3-azabicyclo[3.1.0]hexan-3-yl)methyl)thieno[3,2-b]pyridin-7-yl)-2-methylpyridin-3-yl)azetidine-3-carboxamide 2,2,2-trifluoroacetate |
| 31. | 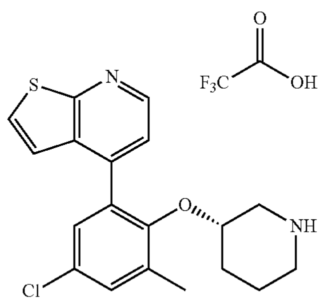 [SMILES: Cc1cc(Cl)cc(-c2ccnc3sccc23)c1O[C@H]1CCCNC1 ; O=C(O)C(F)(F)F] | (S)-4-(5-chloro-3-methyl-2-(piperidin-3-yloxy)phenyl)thieno[2,3-b]pyridine 2,2,2-trifluoroacetate |
| 32. | 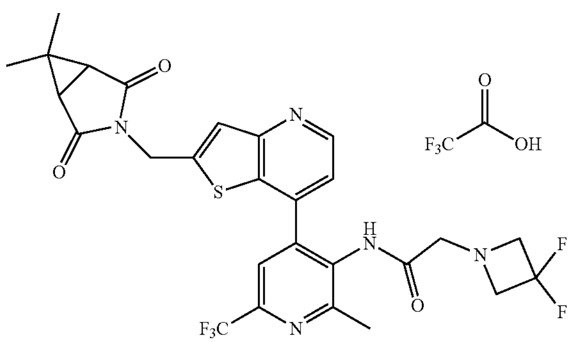 [SMILES: Cc1nc(C(F)(F)F)cc(-c2ccnc3cc(CN4C(=O)C5C(C4=O)C5(C)C)sc23)c1NC(=O)CN1CC(F)(F)C1 ; O=C(O)C(F)(F)F] | 2-(3,3-difluoroazetidin-1-yl)-N-(4-(2-((6,6-dimethyl-2,4-dioxo-3-azabicyclo[3.1.0]hexan-3-yl)methyl)thieno[3,2-b]pyridin-7-yl)-2-methyl-6-(trifluoromethyl)pyridin-3-yl)acetamide 2,2,2-trifluoroacetate |
| 33. | 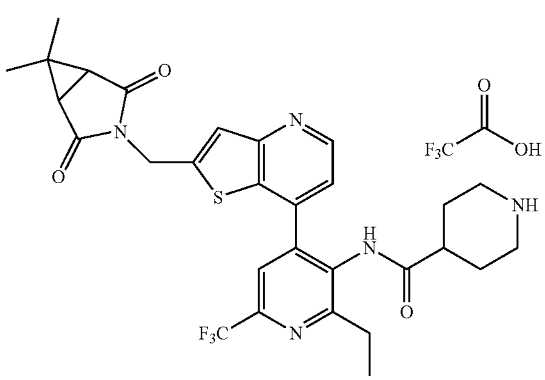 | N-(4-(2-((6,6-dimethyl-2,4-dioxo-3-azabicyclo[3.1.0]hexan-3-yl)methyl)thieno[3,2-b]pyridin-7-yl)-2-ethyl-6-(trifluoromethyl)pyridin-3-yl)piperidine-4-carboxamide 2,2,2-trifluoroacetate |

| Ex. No. | Structure | IUPAC Name |
|---|---|---|
| 34. | 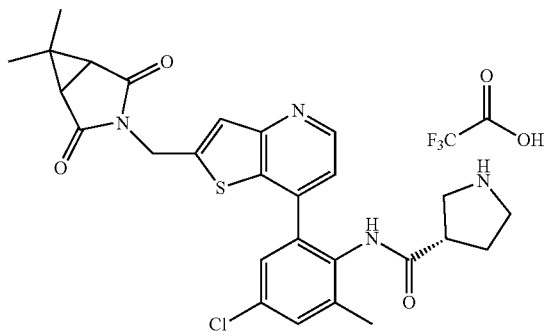 | (3S)-N-(4-chloro-2-(2-((6,6-dimethyl-2,4-dioxo-3-azabicyclo[3.1.0]hexan-3-yl)methyl)thieno[3,2-b]pyridin-7-yl)-6-methylphenyl)pyrrolidine-3-carboxamide 2,2,2-trifluoroacetate |
| 35. | 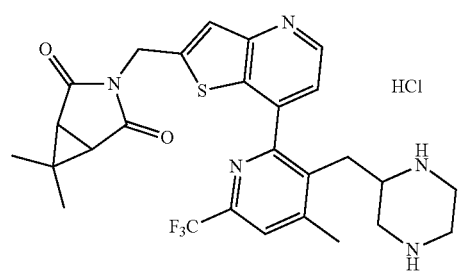<br>Racemate | 6,6-dimethyl-3-((7-(4-methyl-3-(piperazin-2-ylmethyl)-6-(trifluoromethyl)pyridin-2-yl)thieno[3,2-b]pyridin-2-yl)methyl)-3-azabicyclo[3.1.0]hexane-2,4-dione hydrochloride |
| 36. | 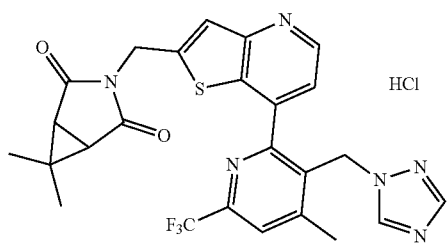 [SMILES: Cc1cc(C(F)(F)F)nc(-c2ccnc3cc(CN4C(=O)C5C(C4=O)C5(C)C)sc23)c1Cn1cncn1 ; Cl] | 3-((7-(3-((1H-1,2,4-triazol-1-yl)methyl)-4-methyl-6-(trifluoromethyl)pyridin-2-yl)thieno[3,2-b]pyridin-2-yl)methyl)-6,6-dimethyl-3-azabicyclo[3.1.0]hexane-2,4-dione hydrochloride |
| 37. | 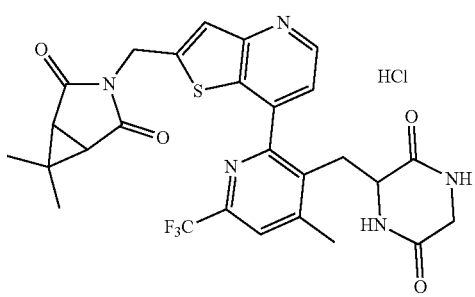 [SMILES: Cc1cc(C(F)(F)F)nc(-c2ccnc3cc(CN4C(=O)C5C(C4=O)C5(C)C)sc23)c1CC1NC(=O)CNC1=O ; Cl] | 3-((7-(3-((3,6-dioxopiperazin-2-yl)methyl)-4-methyl-6-(trifluoromethyl)pyridin-2-yl)thieno[3,2-b]pyridin-2-yl)methyl)-6,6-dimethyl-3-azabicyclo[3.1.0]hexane-2,4-dione hydrochloride |
| 38. | 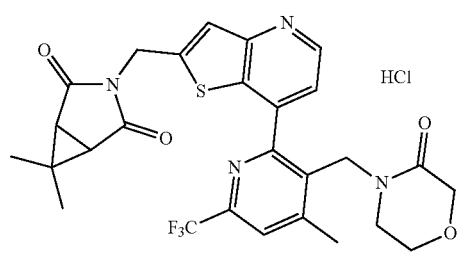 [SMILES: Cc1cc(C(F)(F)F)nc(-c2ccnc3cc(CN4C(=O)C5C(C4=O)C5(C)C)sc23)c1CN1CCOCC1=O ; Cl] | 6,6-dimethyl-3-((7-(4-methyl-3-((3-oxomorpholino)methyl)-6-(trifluoromethyl)pyridin-2-yl)thieno[3,2-b]pyridin-2-yl)methyl)-3-azabicyclo[3.1.0]hexane-2,4-dione hydrochloride |

-continued

| Ex. No. | Structure | IUPAC Name |
|---|---|---|
| 39 | 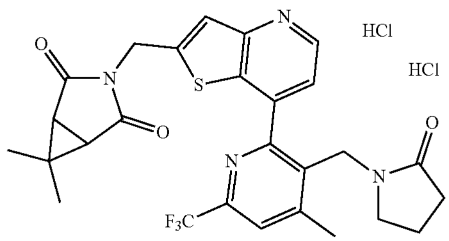 [SMILES: Cc1cc(C(F)(F)F)nc(-c2ccnc3cc(CN4C(=O)C5C(C4=O)C5(C)C)sc23)c1CN1CCCC1=O ; Cl ; Cl] | 6,6-dimethyl-3-((7-(4-methyl-3-((2-oxopyrrolidin-1-yl)methyl)-6-(trifluoromethyl)pyridin-2-yl)thieno[3,2-b]pyridin-2-yl)methyl)-3-azabicyclo[3.1.0]hexane-2,4-dione dihydrochloride |
| 40. | 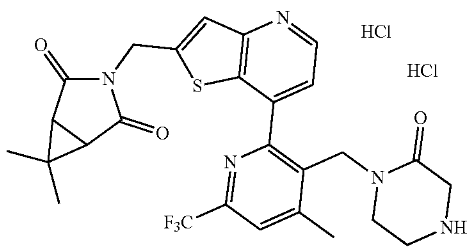 [SMILES: Cc1cc(C(F)(F)F)nc(-c2ccnc3cc(CN4C(=O)C5C(C4=O)C5(C)C)sc23)c1CN1CCNCC1=O ; Cl ; Cl] | 6,6-dimethyl-3-((7-(4-methyl-3-((2-oxopiperazin-1-yl)methyl)-6-(trifluoromethyl)pyridin-2-yl)thieno[3,2-b]pyridin-2-yl)methyl)-3-azabicyclo[3.1.0]hexane-2,4-dione dihydrochloride |
| 41. | 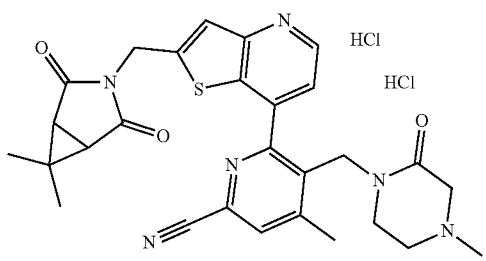 | 6,6-dimethyl-3-((7-(4-methyl-3-((4-methyl-2-oxopiperazin-1-yl)methyl)-6-(trifluoromethyl)pyridin-2-yl)thieno[3,2-b]pyridin-2-yl)methyl)-3-azabicyclo[3.1.0]hexane-2,4-dione dihydrochloride |
| 42. | 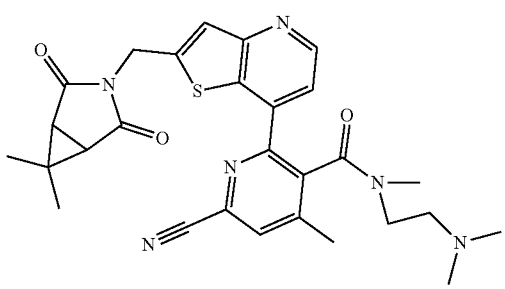 | 6-cyano-2-(2-(((6,6-dimethyl-2,4-dioxo-3-azabicyclo[3.1.0]hexan-3-yl)methyl)thieno[3,2-b]pyridin-7-yl)-N-(2-(dimethylamino)ethyl)-N,4-dimethylnicotinamide |
| 43. | 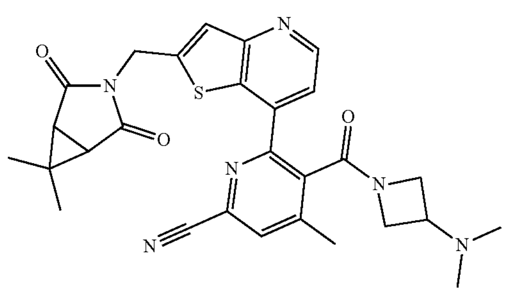 | 6-(2-((6,6-dimethyl-2,4-dioxo-3-azabicyclo[3.1.0]hexan-3-yl)methyl)thieno[3,2-b]pyridin-7-yl)-5-(3-(dimethylamino)azetidine-1-carbonyl)-4-methylpicolinonitrile |

| Ex. No. | Structure | IUPAC Name |
|---|---|---|
| 44. | 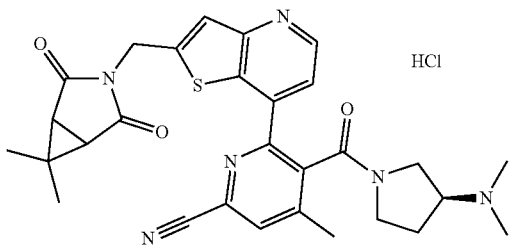 | 6-(2-((6,6-dimethyl-2,4-dioxo-3-azabicyclo[3.1.0]hexan-3-yl)methyl)thieno[3,2-b]pyridin-7-yl)-5-((S)-3-(dimethylamino)pyrrolidine-1-carbonyl)-4-methylpicolinonitrile hydrochloride |

| Ex. No. | Structure | IUPAC Name |
|---|---|---|
| 45. | 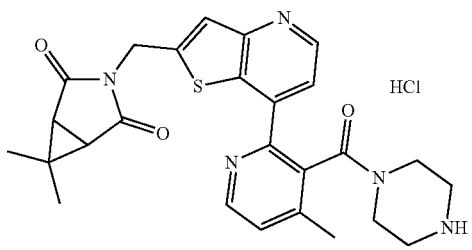 [SMILES: Cc1ccnc(-c2ccnc3cc(CN4C(=O)C5C(C4=O)C5(C)C)sc23)c1C(=O)N1CCNCC1 ; Cl] | 6,6-dimethyl-3-((7-(4-methyl-3-(piperazine-1-carbonyl)pyridin-2-yl)thieno[3,2-6]pyridin-2-yl)methyl)-3-azabicyclo[3.1.0]hexane-2,4-dione hydrochloride |
| 46. | 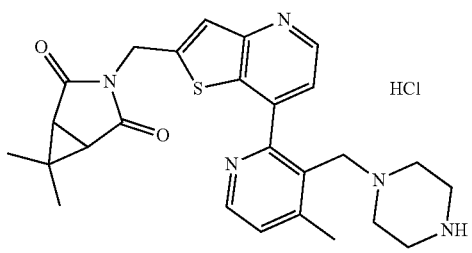 [SMILES: Cc1ccnc(-c2ccnc3cc(CN4C(=O)C5C(C4=O)C5(C)C)sc23)c1CN1CCNCC1 ; Cl] | 6,6-dimethyl-3-((7-(4-methyl-3-(piperazin-1-ylmethyl)pyridin-2-yl)thieno[3,2-6]pyridin-2-yl)methyl)-3-azabicyclo[3.1.0]hexane-2,4-dione hydrochloride |
| 47. | 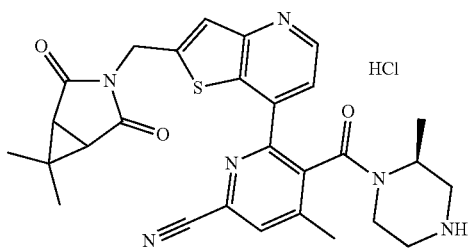 [SMILES: Cc1cc(C#N)nc(-c2ccnc3cc(CN4C(=O)C5C(C4=O)C5(C)C)sc23)c1C(=O)N1CCNC[C@@H]1C ; Cl] | 6-(2-((6,6-dimethyl-2,4-dioxo-3-azabicyclo[3.1.0]hexan-3-yl)methyl)thieno[3,2-b]pyridin-7-yl)-4-methyl-5-((S)-2-methylpiperazine-1-carbonyl)picolinonitrile hydrochloride |
| 48. | 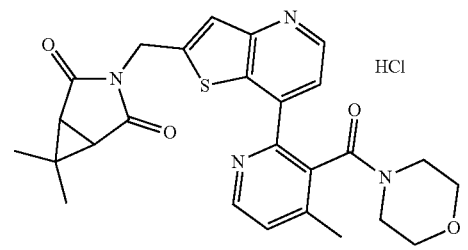 [SMILES: Cc1ccnc(-c2ccnc3cc(CN4C(=O)C5C(C4=O)C5(C)C)sc23)c1C(=O)N1CCOCC1 ; Cl] | 6,6-dimethyl-3-((7-(4-methyl-3-(morpholine-4-carbonyl)pyridin-2-yl)thieno[3,2-b]pyridin-2-yl)methyl)-3-azabicyclo[3.1.0]hexane-2,4-dione hydrochloride |

| Ex. No. | Structure | IUPAC Name |
|---|---|---|
| 49. | 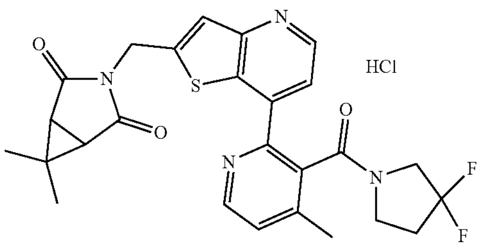 [SMILES: Cc1ccnc(-c2ccnc3cc(CN4C(=O)C5C(C4=O)C5(C)C)sc23)c1C(=O)N1CCC(F)(F)C1 ; Cl] | 3-((7-(3-(3,3-difluoropyrrolidine-1-carbonyl)-4-methylpyridin-2-yl)thieno[3,2-b]pyridin-2-yl)methyl)-6,6-dimethyl-3-azabicyclo[3.1.0]hexane-2,4-dione hydrochloride |
| 50. | 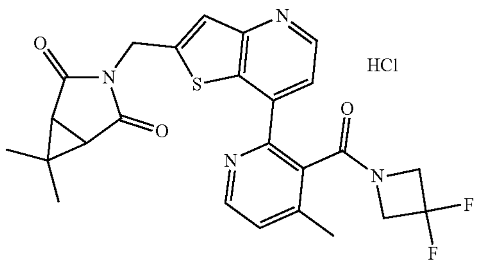 [SMILES: Cc1ccnc(-c2ccnc3cc(CN4C(=O)C5C(C4=O)C5(C)C)sc23)c1C(=O)N1CC(F)(F)C1 ; Cl] | 3-((7-(3-(3,3-difluoroazetidine-1-carbonyl)-4-methylpyridin-2-yl)thieno[3,2-b]pyridin-2-yl)methyl)-6,6-dimethyl-3-azabicyclo[3.1.0]hexane-2,4-dione hydrochloride |
| 51. | 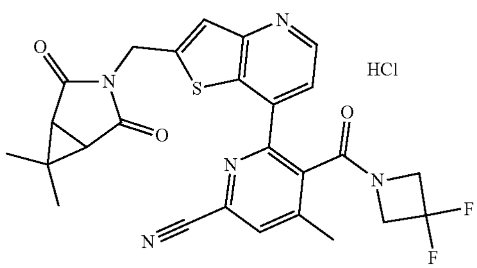 [SMILES: Cc1cc(C#N)nc(-c2ccnc3cc(CN4C(=O)C5C(C4=O)C5(C)C)sc23)c1C(=O)N1CC(F)(F)C1 ; Cl] | 5-(3,3-difluoroazetidine-1-carbonyl)-6-(2-((6,6-dimethyl-2,4-dioxo-3-azabicyclo[3.1.0]hexan-3-yl)methyl)thieno[3,2-b]pyridin-7-yl)-4-methylpicolinonitrile hydrochloride |
| 52. | 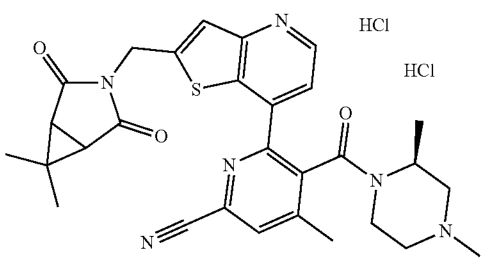 | 6-(2-((6,6-dimethyl-2,4-dioxo-3-azabicyclo[3.1.0]hexan-3-yl)methyl)thieno[3,2-b]pyridin-7-yl)-5-((S)-2,4-dimethylpiperazine-1-carbonyl)-4-methylpicolinonitrile dihydrochloride |
| 53. | 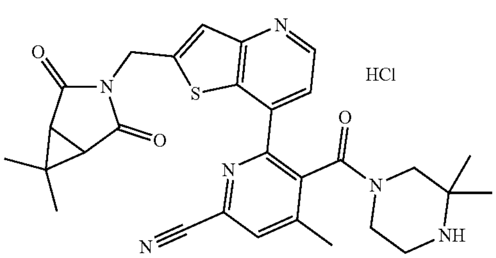 | 6-(2-((6,6-dimethyl-2,4-dioxo-3-azabicyclo[3.1.0]hexan-3-yl)methyl)thieno[3,2-b]pyridin-7-yl)-5-(3,3-dimethylpiperazine-1-carbonyl)-4-methylpicolinonitrile hydrochloride |
| 54. | 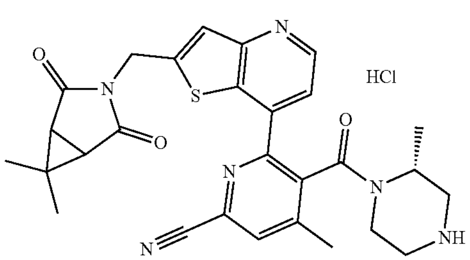 [SMILES: Cc1cc(C#N)nc(-c2ccnc3cc(CN4C(=O)C5C(C4=O)C5(C)C)sc23)c1C(=O)N1CCNC[C@H]1C ; Cl] | 6-(2-((6,6-dimethyl-2,4-dioxo-3-azabicyclo[3.1.0]hexan-3-yl)methyl)thieno[3,2-b]pyridin-7-yl)-4-methyl-5-((R)-2-methylpiperazine-1-carbonyl)picolinonitrile hydrochloride |

| Ex. No. | Structure | IUPAC Name |
|---|---|---|
| 55. | 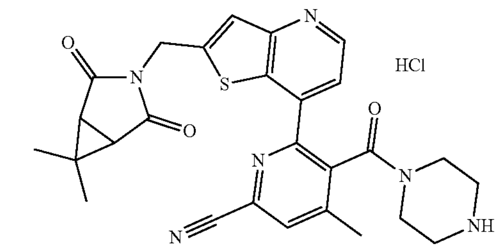 [SMILES: Cc1cc(C#N)nc(-c2ccnc3cc(CN4C(=O)C5C(C4=O)C5(C)C)sc23)c1C(=O)N1CCNCC1 ; Cl] | 6-(2-(((6,6-dimethyl-2,4-dioxo-3-azabicyclo[3.1.0]hexan-3-yl)methyl)thieno[3,2-b]pyridin-7-yl)-4-methyl-5-(piperazine-1-carbonyl)picolinonitrile hydrochloride |
| 56. | 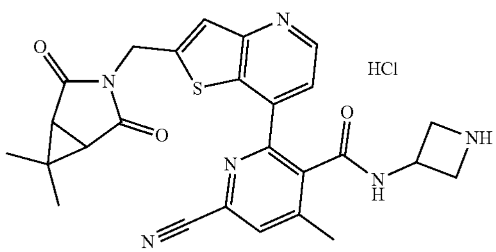 [SMILES: Cc1cc(C#N)nc(-c2ccnc3cc(CN4C(=O)C5C(C4=O)C5(C)C)sc23)c1C(=O)NC1CNC1 ; Cl] | N-(azetidin-3-yl)-6-cyano-2-(2-((6,6-dimethyl-2,4-dioxo-3-azabicyclo[3.1.0]hexan-3-yl)methyl)thieno[3,2-b]pyridin-7-yl)-4-methylnicotinamide hydrochloride |
| 57. | 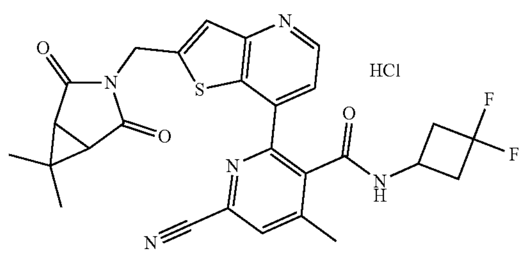 [SMILES: Cc1cc(C#N)nc(-c2ccnc3cc(CN4C(=O)C5C(C4=O)C5(C)C)sc23)c1C(=O)NC1CC(F)(F)C1 ; Cl] | 6-cyano-N-(3,3-difluorocyclobutyl)-2-(2-((6,6-dimethyl-2,4-dioxo-3-azabicyclo[3.1.0]hexan-3-yl)methyl)thieno[3,2-b]pyridin-7-yl)-4-methylnicotinamide hydrochloride |
| 58. | 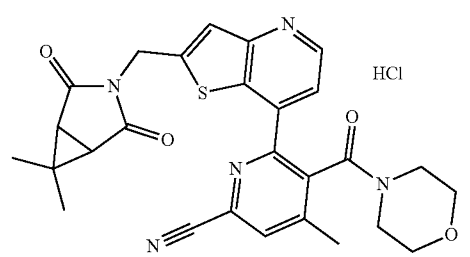 [SMILES: Cc1cc(C#N)nc(-c2ccnc3cc(CN4C(=O)C5C(C4=O)C5(C)C)sc23)c1C(=O)N1CCOCC1 ; Cl] | 6-(2-((6,6-dimethyl-2,4-dioxo-3-azabicyclo[3.1.0]hexan-3-yl)methyl)thieno[3,2-b]pyridin-7-yl)-4-methyl-5-(morpholine-4-carbonyl)picolinonitrile hydrochloride |
| 59. | 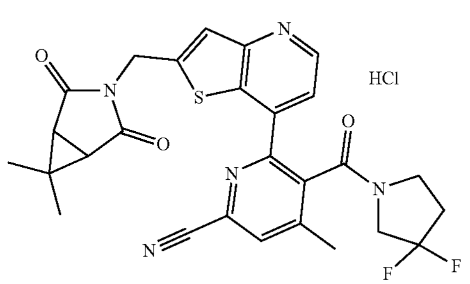 [SMILES: Cc1cc(C#N)nc(-c2ccnc3cc(CN4C(=O)C5C(C4=O)C5(C)C)sc23)c1C(=O)N1CCC(F)(F)C1 ; Cl] | 5-(3,3-difluoropyrrolidine-1-carbonyl)-6-(2-((6,6-dimethyl-2,4-dioxo-3-azabicyclo[3.1.0]hexan-3-yl)methyl)thieno[3,2-b]pyridin-7-yl)-4-methylpicolinonitrile hydrochloride |

-continued

| Ex. No. | Structure | IUPAC Name |
|---|---|---|
| 60. | 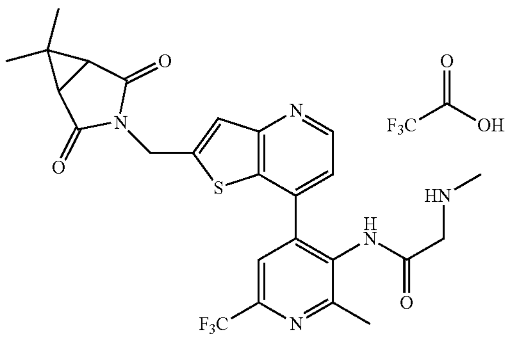 | N-(4-(2-((6,6-dimethyl-2,4-dioxo-3-azabicyclo[3.1.0]hexan-3-yl)methyl)thieno[3,2-b]pyridin-7-yl)-2-methyl-6-(trifluoromethyl)pyridin-3-yl)-2-(methylamino)acetamide 2,2,2-trifluoroacetate |
| 61. | 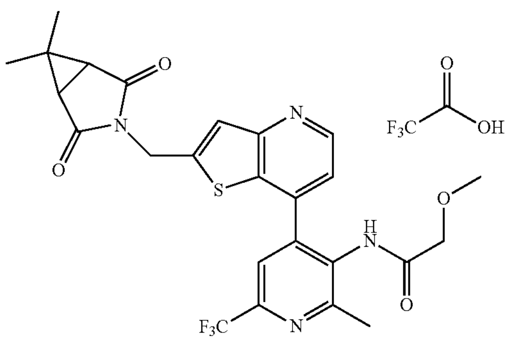 | N-(4-(2-((6,6-dimethyl-2,4-dioxo-3-azabicyclo[3.1.0]hexan-3-yl)methyl)thieno[3,2-b]pyridin-7-yl)-2-methyl-6-(trifluoromethyl)pyridin-3-yl)-2-methoxyacetamide 2,2,2-trifluoroacetate |
| 62. | 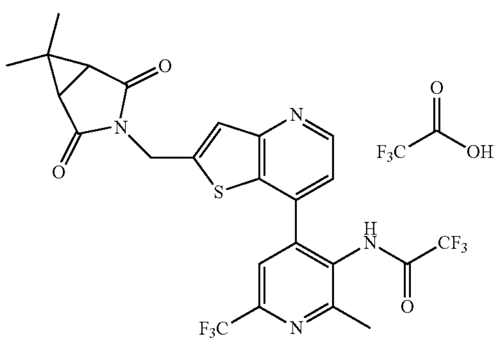 [SMILES: Cc1nc(C(F)(F)F)cc(-c2ccnc3cc(CN4C(=O)C5C(C4=O)C5(C)C)sc23)c1NC(=O)C(F)(F)F ; O=C(O)C(F)(F)F] | N-(4-(2-((6,6-dimethyl-2,4-dioxo-3-azabicyclo[3.1.0]hexan-3-yl)methyl)thieno[3,2-b]pyridin-7-yl)-2-methyl-6-(trifluoromethyl)pyridin-3-yl)-2,2,2-trifluoroacetamide 2,2,2-trifluoroacetate |
| 63. | 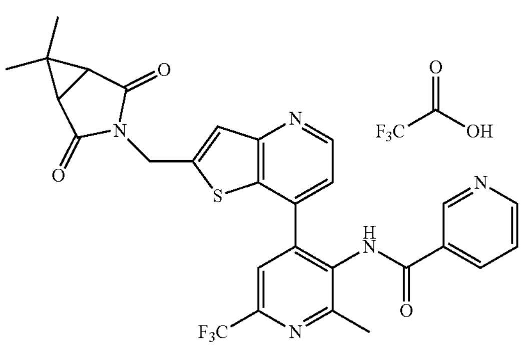 | N-(4-(2-((6,6-dimethyl-2,4-dioxo-3-azabicyclo[3.1.0]hexan-3-yl)methyl)thieno[3,2-b]pyridin-7-yl)-2-methyl-6-(trifluoromethyl)pyridin-3-yl)nicotinamide 2,2,2-trifluoroacetate |

-continued

| Ex. No. | Structure | IUPAC Name |
|---|---|---|
| 64. | 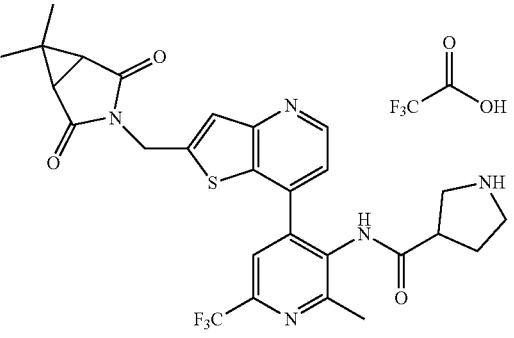 [SMILES: Cc1nc(C(F)(F)F)cc(-c2ccnc3cc(CN4C(=O)C5C(C4=O)C5(C)C)sc23)c1NC(=O)C1CCNC1 ; O=C(O)C(F)(F)F] Racemate | N-(4-(2-((6,6-dimethyl-2,4-dioxo-3-azabicyclo[3.1.0]hexan-3-yl)methyl)thieno[3,2-b]pyridin-7-yl)-2-methyl-6-(trifluoromethyl)pyridin-3-yl)pyrrolidine-3-carboxamide 2,2,2-trifluoroacetate |
| 65. | 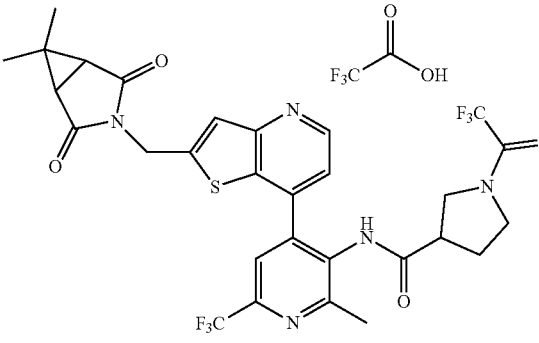 Racemate | N-(4-(2-((6,6-dimethyl-2,4-dioxo-3-azabicyclo[3.1.0]hexan-3-yl)methyl)thieno[3,2-b]pyridin-7-yl)-2-methyl-6-(trifluoromethyl)pyridin-3-yl)-1-(2,2,2-trifluoroacetyl)pyrrolidine-3-carboxamide 2,2,2-trifluoroacetate |
| 66. | 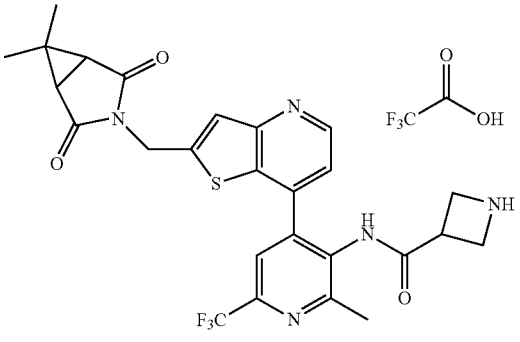 [SMILES: Cc1nc(C(F)(F)F)cc(-c2ccnc3cc(CN4C(=O)C5C(C4=O)C5(C)C)sc23)c1NC(=O)C1CNC1 ; O=C(O)C(F)(F)F] | N-(4-(2-((6,6-dimethyl-2,4-dioxo-3-azabicyclo[3.1.0]hexan-3-yl)methyl)thieno[3,2-6]pyridin-7-yl)-2-methyl-6-(trifluoromethyl)pyridin-3-yl)azetidine-3-carboxamide 2,2,2-trifluoroacetate |
| 67. | 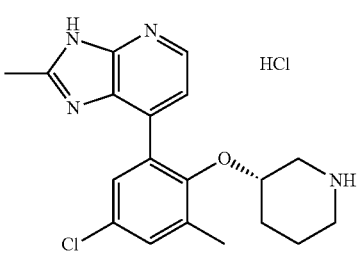 [SMILES: Cc1nc2c(-c3cc(Cl)cc(C)c3O[C@H]3CCCNC3)ccnc2[nH]1 ; Cl] | (S)-7-(5-chloro-3-methyl-2-(piperidin-3-yloxy)phenyl)-2-methyl-3H-imidazo[4,5-b]pyridine hydrochloride |
| 68. | 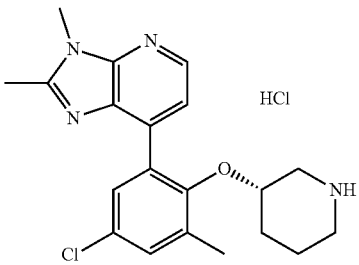 [SMILES: Cc1cc(Cl)cc(-c2ccnc3c2nc(C)n3C)c1O[C@H]1CCCNC1 ; Cl] | (S)-7-(5-chloro-3-methyl-2-(piperidin-3-yloxy)phenyl)-2,3-dimethyl-3H-imidazo[4,5-b]pyridine hydrochloride |

| Ex. No. | Structure | IUPAC Name |
| --- | --- | --- |
| 69. | 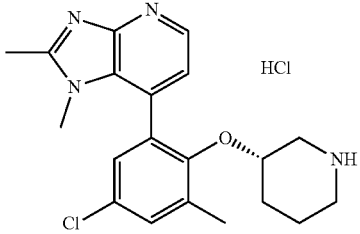 [SMILES: Cc1cc(Cl)cc(-c2ccnc3nc(C)n(C)c23)c1O[C@H]1CCCNC1 ; Cl] | (S)-7-(5-chloro-3-methyl-2-(piperidin-3-yloxy)phenyl)-1,2-dimethyl-1H-imidazo[4,5-b]pyridine hydrochloride |
| 70. | 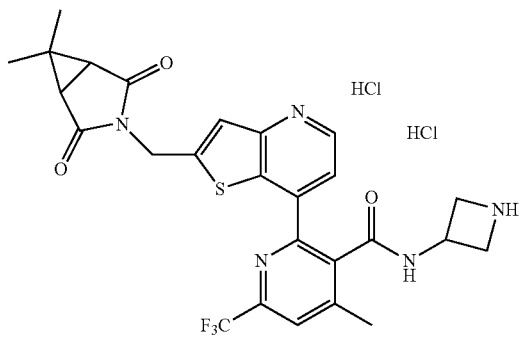 [SMILES: Cc1cc(C(F)(F)F)nc(-c2ccnc3cc(CN4C(=O)C5C(C4=O)C5(C)C)sc23)c1C(=O)NC1CNC1 ; Cl ; Cl] | N-(azetidin-3-yl)-2-(2-((6,6-dimethyl-2,4-dioxo-3-azabicyclo[3.1.0]hexan-3-yl)methyl)thieno[3,2-b]pyridin-7-yl)-4-methyl-6-(trifluoromethyl)nicotinamide dihydrochloride |
| 71. | 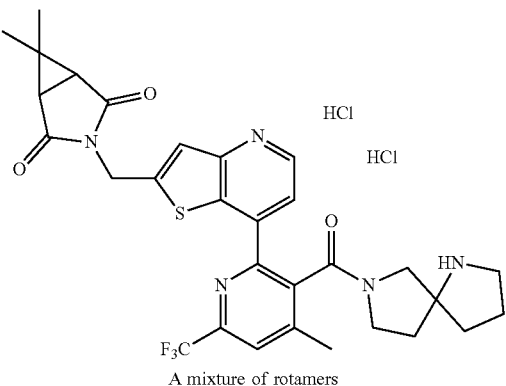  A mixture of rotamers | 6,6-dimethyl-3-((7-(4-methyl-3-(1,7-diazaspiro[4.4]nonane-7-carbonyl)-6-(trifluoromethyl)pyridin-2-yl)thieno[3,2-b]pyridin-2-yl)methyl)-3-azabicyclo[3.1.0]hexane-2,4-dione dihydrochloride |
| 72. | 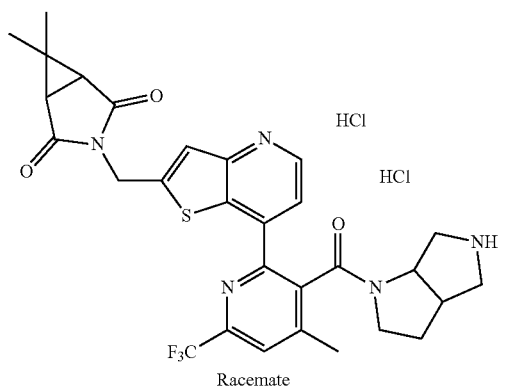  Racemate | 6,6-dimethyl-3-((7-(4-methyl-3-(octahydropyrrolo[3,4-b]pyrrole-1-carbonyl)-6-(trifluoromethyl)pyridin-2-yl)thieno[3,2-b]pyridin-2-yl)methyl)-3-azabicyclo[3.1.0]hexane-2,4-dione dihydrochloride |

| Ex. No. | Structure | IUPAC Name |
|---|---|---|
| 73. | 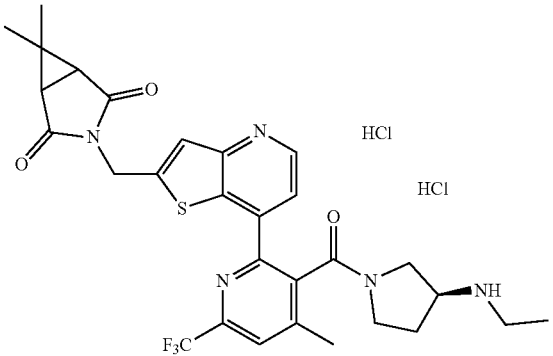 [SMILES: CCN[C@H]1CCN(C(=O)c2c(C)cc(C(F)(F)F)nc2-c2ccnc3cc(CN4C(=O)C5C(C4=O)C5(C)C)sc23)C1 ; Cl ; Cl] | 3-((7-(3-((S)-3-(ethylamino)pyrrolidine-1-carbonyl)-4-methyl-6-(trifluoromethyl)pyridin-2-yl)thieno[3,2-b]pyridin-2-yl)methyl)-6,6-dimethyl-3-azabicyclo[3.1.0]hexane-2,4-dione dihydrochloride |
| 74. | 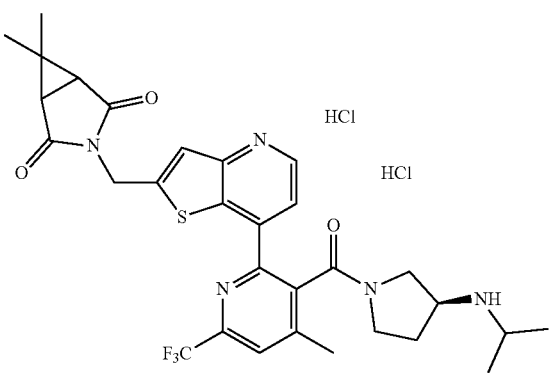 [SMILES: Cc1cc(C(F)(F)F)nc(-c2ccnc3cc(CN4C(=O)C5C(C4=O)C5(C)C)sc23)c1C(=O)N1CC[C@H](NC(C)C)C1 ; Cl ; Cl] | 3-((7-(3-((S)-3-(isopropylamino)pyrrolidine-1-carbonyl)-4-methyl-6-(trifluoromethyl)pyridin-2-yl)thieno[3,2-b]pyridin-2-yl)methyl)-6,6-dimethyl-3-azabicyclo[3.1.0]hexane-2,4-dione dihydrochloride |
| 75. | 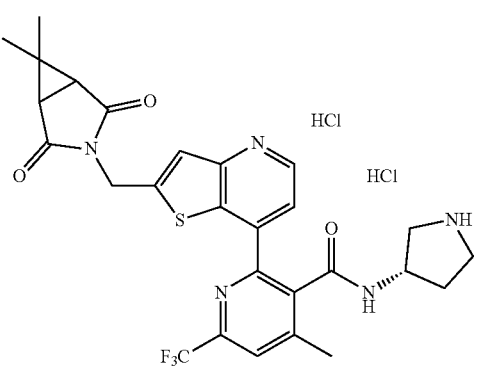 [SMILES: Cc1cc(C(F)(F)F)nc(-c2ccnc3cc(CN4C(=O)C5C(C4=O)C5(C)C)sc23)c1C(=O)N[C@H]1CCNC1 ; Cl ; Cl] | 2-(2-((6,6-dimethyl-2,4-dioxo-3-azabicyclo[3.1.0]hexan-3-yl)methyl)thieno[3,2-b]pyridin-7-yl)-4-methyl-N-((S)-pyrrolidin-3-yl)-6-(trifluoromethyl)nicotinamide dihydrochloride |
| 76. | 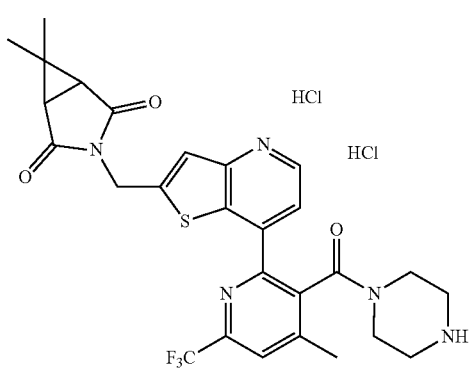 [SMILES: Cc1cc(C(F)(F)F)nc(-c2ccnc3cc(CN4C(=O)C5C(C4=O)C5(C)C)sc23)c1C(=O)N1CCNCC1 ; Cl ; Cl] | 6,6-dimethyl-3-((7-(4-methyl-3-(piperazine-1-carbonyl)-6-(trifluoromethyl)pyridin-2-yl)thieno[3,2-b]pyridin-2-yl)methyl)-3-azabicyclo[3.1.0]hexane-2,4-dione dihydrochloride |

| Ex. No. | Structure | IUPAC Name |
|---|---|---|
| 77. | 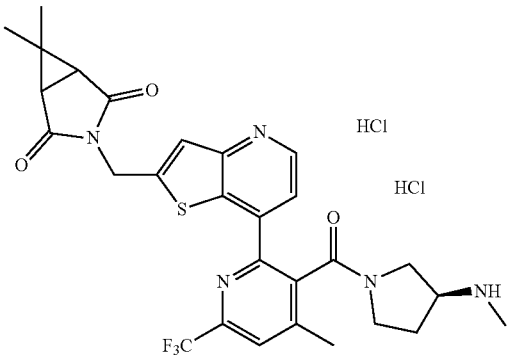 | 6,6-dimethyl-3-((7-(4-methyl-3-((S)-3-(methylamino)pyrrolidine-1-carbonyl)-6-(trifluoromethyl)pyridin-2-yl)thieno[3,2-b]pyridin-2-yl)methyl)-3-azabicyclo[3.1.0]hexane-2,4-dione dihydrochloride |
| 78. | 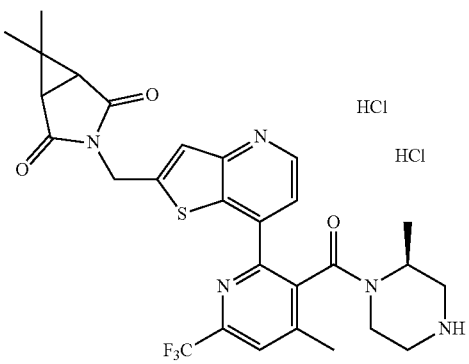 [SMILES: Cc1cc(C(F)(F)F)nc(-c2ccnc3cc(CN4C(=O)C5C(C4=O)C5(C)C)sc23)c1C(=O)N1CCNC[C@@H]1C ; Cl ; Cl] | 6,6-dimethyl-3-((7-(4-methyl-3-((S)-2-methylpiperazine-1-carbonyl)-6-(trifluoromethyl)pyridin-2-yl)thieno[3,2-b]pyridin-2-yl)methyl)-3-azabicyclo[3.1.0]hexane-2,4-dione dihydrochloride |
| 79. | 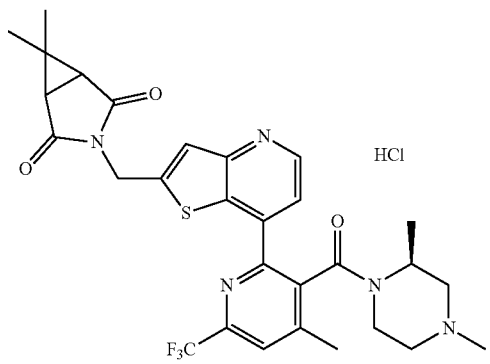 | 3-((7-(3-((S)-2,4-dimethylpiperazine-1-carbonyl)-4-methyl-6-(trifluoromethyl)pyridin-2-yl)thieno[3,2-b]pyridin-2-yl)methyl)-6,6-dimethyl-3-azabicyclo[3.1.0]hexane-2,4-dione hydrochloride |
| 80. | 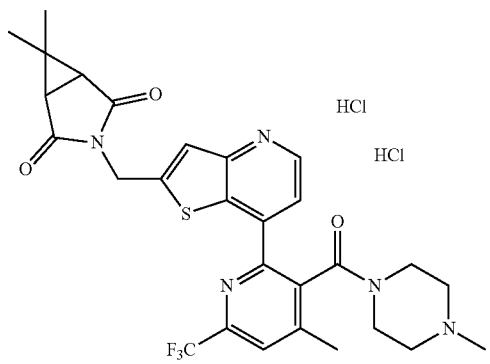 | 6,6-dimethyl-3-((7-(4-methyl-3-(4-methylpiperazine-1-carbonyl)-6-(trifluoromethyl)pyridin-2-yl)thieno[3,2-b]pyridin-2-yl)methyl)-3-azabicyclo[3.1.0]hexane-2,4-dione dihydrochloride |

| Ex. No. | Structure | IUPAC Name |
|---|---|---|
| 81. | 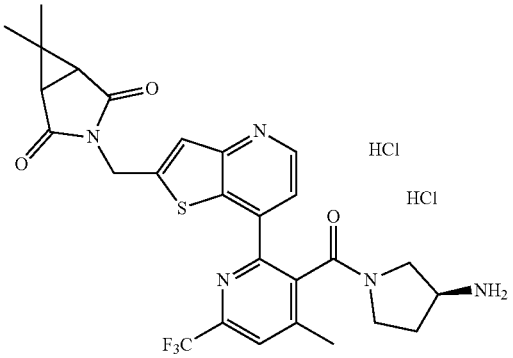 [SMILES: Cc1cc(C(F)(F)F)nc(-c2ccnc3cc(CN4C(=O)C5C(C4=O)C5(C)C)sc23)c1C(=O)N1CC[C@H](N)C1 ; Cl ; Cl] | 3-((7-(3-((S)-3-aminopyrrolidine-1-carbonyl)-4-methyl-6-(trifluoromethyl)pyridin-2-yl)thieno[3,2-b]pyridin-2-yl)methyl)-6,6-dimethyl-3-azabicyclo[3.1.0]hexane-2,4-dione dihydrochloride |
| 82. | 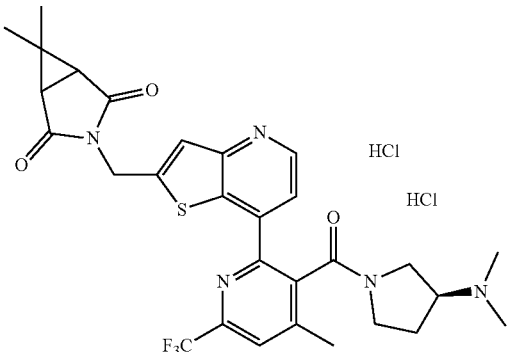 | 3-((7-(3-((S)-3-(dimethylamino)pyrrolidine-1-carbonyl)-4-methyl-6-(trifluoromethyl)pyridin-2-yl)thieno[3,2-b]pyridin-2-yl)methyl)-6,6-dimethyl-3-azabicyclo[3.1.0]hexane-2,4-dione dihydrochloride |
| 83. | 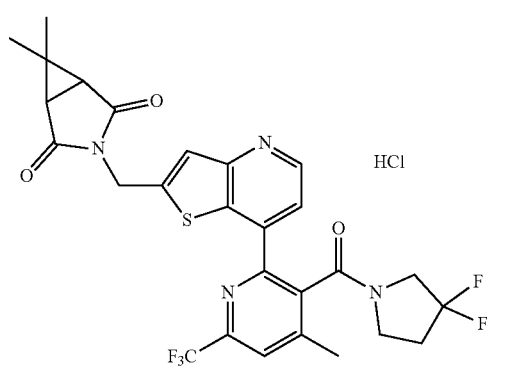 [SMILES: Cc1cc(C(F)(F)F)nc(-c2ccnc3cc(CN4C(=O)C5C(C4=O)C5(C)C)sc23)c1C(=O)N1CCC(F)(F)C1 ; Cl] | 3-((7-(3-(3,3-difluoropyrrolidine-1-carbonyl)-4-methyl-6-(trifluoromethyl)pyridin-2-yl)thieno[3,2-b]pyridin-2-yl)methyl)-6,6-dimethyl-3-azabicyclo[3.1.0]hexane-2,4-dione hydrochloride |
| 84. | 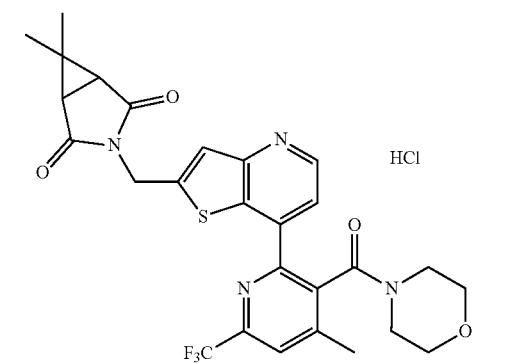 [SMILES: Cc1cc(C(F)(F)F)nc(-c2ccnc3cc(CN4C(=O)C5C(C4=O)C5(C)C)sc23)c1C(=O)N1CCOCC1 ; Cl] | 6,6-dimethyl-3-((7-(4-methyl-3-(morpholine-4-carbonyl)-6-(trifluoromethyl)pyridin-2-yl)thieno[3,2-b]pyridin-2-yl)methyl)-3-azabicyclo[3.1.0]hexane-2,4-dione hydrochloride |

| Ex. No. | Structure | IUPAC Name |
| --- | --- | --- |
| 85. | 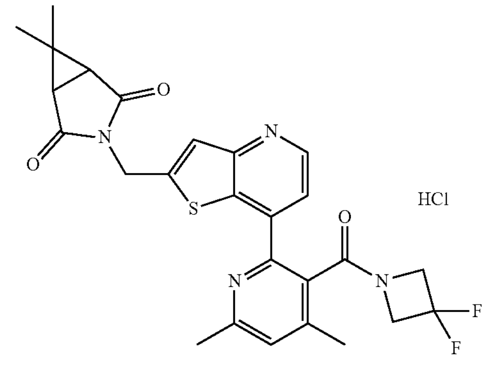 [SMILES: Cc1cc(C)c(C(=O)N2CC(F)(F)C2)c(-c2ccnc3cc(CN4C(=O)C5C(C4=O)C5(C)C)sc23)n1 ; Cl] | 3-((7-(3-(3,3-difluoroazetidine-1-carbonyl)-4,6-dimethylpyridin-2-yl)thieno[3,2-b]pyridin-2-yl)methyl)-6,6-dimethyl-3-azabicyclo[3.1.0]hexane-2,4-dione hydrochloride |
| 86. | 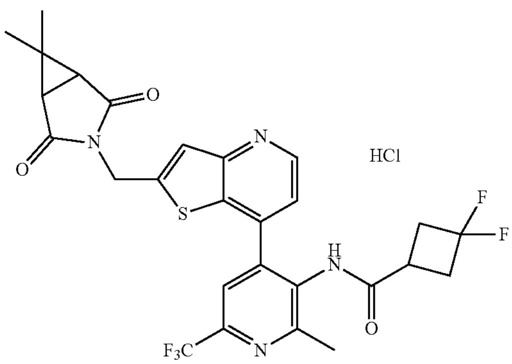 [SMILES: Cc1nc(C(F)(F)F)cc(-c2ccnc3cc(CN4C(=O)C5C(C4=O)C5(C)C)sc23)c1NC(=O)C1CC(F)(F)C1 ; Cl] | N-(4-(2-((6,6-dimethyl-2,4-dioxo-3-azabicyclo[3.1.0]hexan-3-yl)methyl)thieno[3,2-b]pyridin-7-yl)-2-methyl-6-(trifluoromethyl)pyridin-3-yl)-3,3-difluorocyclobutane-1-carboxamide hydrochloride |
| 87. | 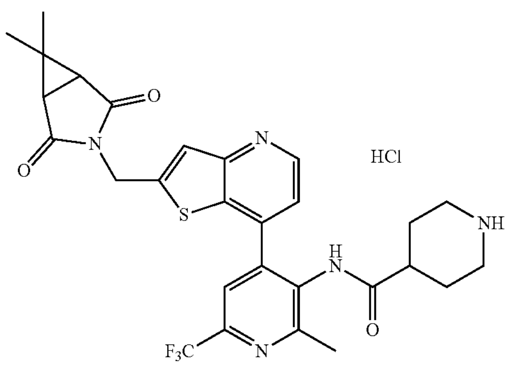 [SMILES: Cc1nc(C(F)(F)F)cc(-c2ccnc3cc(CN4C(=O)C5C(C4=O)C5(C)C)sc23)c1NC(=O)C1CCNCC1 ; Cl] | N-(4-(2-((6,6-dimethyl-2,4-dioxo-3-azabicyclo[3.1.0]hexan-3-yl)methyl)thieno[3,2-6]pyridin-7-yl)-2-methyl-6-(trifluoromethyl)pyridin-3-yl)piperidine-4-carboxamide hydrochloride |
| 88. | 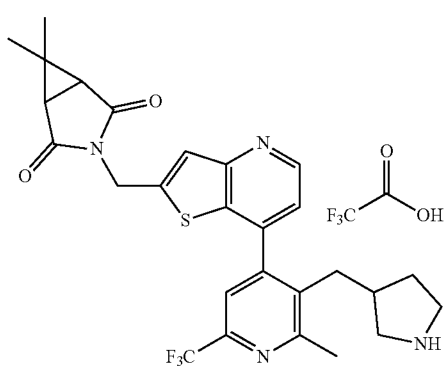 | 6,6-dimethyl-3-((7-(2-methyl-3-(pyrrolidin-3-ylmethyl)-6-(trifluoromethyl)pyridin-4-yl)thieno[3,2-b]pyridin-2-yl)methyl)-3-azabicyclo[3.1.0]hexane-2,4-dione 2,2,2-trifluoroacetate |

| Ex. No. | Structure | IUPAC Name |
|---|---|---|
| 89. | 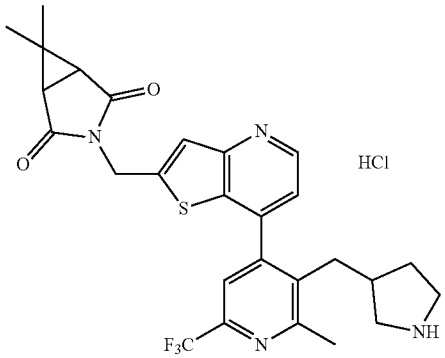 [SMILES: Cc1nc(C(F)(F)F)cc(-c2ccnc3cc(CN4C(=O)C5C(C4=O)C5(C)C)sc23)c1CC1CCNC1 ; Cl]<br>Single enantiomer of Ex. 88 | 6,6-dimethyl-3-((7-(2-methyl-3-(pyrrolidin-3-ylmethyl)-6-(trifluoromethyl)pyridin-4-yl)thieno[3,2-b]pyridin-2-yl)methyl)-3-azabicyclo[3.1.0]hexane-2,4-dione hydrochloride |

| Ex. No. | Structure | IUPAC Name |
|---|---|---|
| 90. | 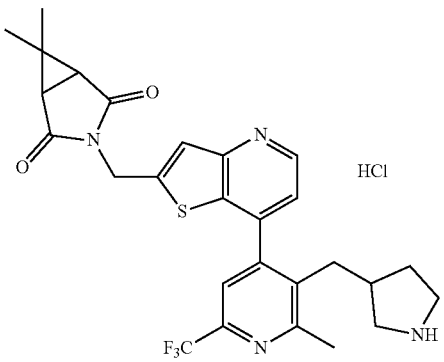 [SMILES: Cc1nc(C(F)(F)F)cc(-c2ccnc3cc(CN4C(=O)C5C(C4=O)C5(C)C)sc23)c1CC1CCNC1 ; Cl]<br>Single enantiomer of Ex. 88 | 6,6-dimethyl-3-((7-(2-methyl-3-(pyrrolidin-3-ylmethyl)-6-(trifluoromethyl)pyridin-4-yl)thieno[3,2-b]pyridin-2-yl)methyl)-3-azabicyclo[3.1.0]hexane-2,4-dione hydrochloride |
| 91. | 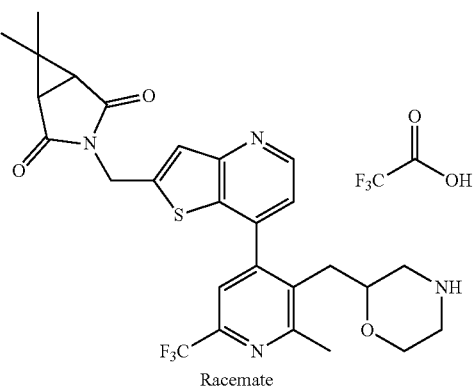<br>Racemate | 6,6-dimethyl-3-((7-(2-methyl-3-(morpholin-2-ylmethyl)-6-(trifluoromethyl)pyridin-4-yl)thieno[3,2-b]pyridin-2-yl)methyl)-3-azabicyclo[3.1.0]hexane-2,4-dione 2,2,2-trifluoroacetate |

| Ex. No. | Structure | IUPAC Name |
|---|---|---|
| 92. | 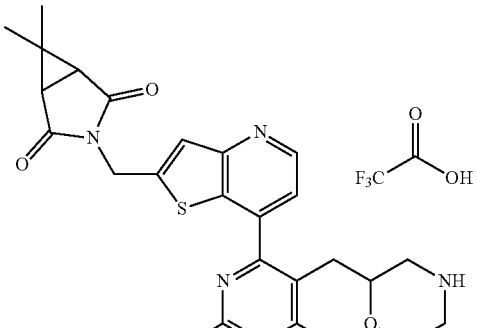<br>Racemate | 6,6-dimethyl-3-((7-(4-methyl-3-(morpholin-2-ylmethyl)-6-(trifluoromethyl)pyridin-2-yl)thieno[3,2-b]pyridin-2-yl)methyl)-3-azabicyclo[3.1.0]hexane-2,4-dione 2,2,2-trifluoroacetate |
| 93. | 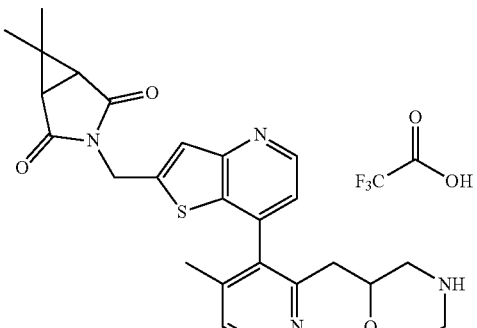<br>Racemate | 6,6-dimethyl-3-((7-(4-methyl-2-(morpholin-2-ylmethyl)pyridin-3-yl)thieno[3,2-b]pyridin-2-yl)methyl)-3-azabicyclo[3.1.0]hexane-2,4-dione 2,2,2-trifluoroacetate |
| 94. | 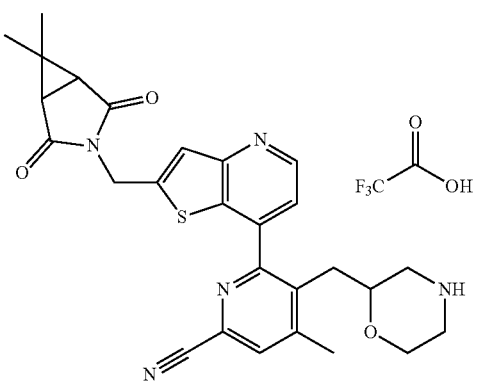<br>Racemate | 6-(2-(((6,6-dimethyl-2,4-dioxo-3-azabicyclo[3.1.0]hexan-3-yl)methyl)thieno[3,2-b]pyridin-7-yl])-4-methyl-5-(morpholin-2-ylmethyl)picolinonitrile 2,2,2-trifluoroacetate |
| 95. | 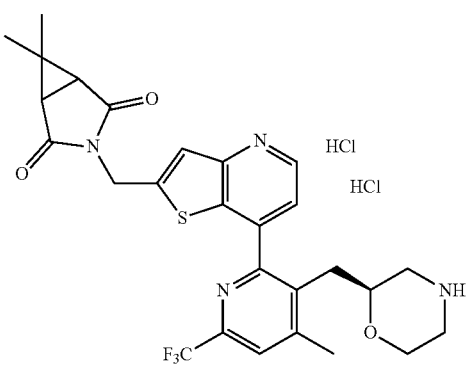 [SMILES: Cc1cc(C(F)(F)F)nc(-c2ccnc3cc(CN4C(=O)C5C(C4=O)C5(C)C)sc23)c1C[C@H]1CNCCO1 ; Cl ; Cl] | 6,6-dimethyl-3-((7-(4-methyl-3-(((S)-morpholin-2-ylmethyl)-6-(trifluoromethyl)pyridin-2-yl)thieno[3,2-b]pyridin-2-yl)methyl)-3-azabicyclo[3.1.0]hexane-2,4-dione dihydrochloride |

| Ex. No. | Structure | IUPAC Name |
|---|---|---|
| 96. | 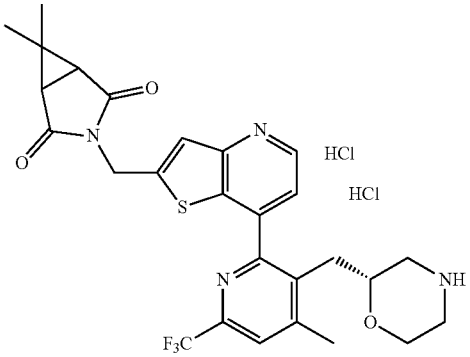 [SMILES: Cc1cc(C(F)(F)F)nc(-c2ccnc3cc(CN4C(=O)C5C(C4=O)C5(C)C)sc23)c1C[C@@H]1CNCCO1 ; Cl ; Cl] | 6,6-dimethyl-3-((7-(4-methyl-3-(((R)-morpholin-2-yl)methyl)-6-(trifluoromethyl)pyridin-2-yl)thieno[3,2-b]pyridin-2-yl)methyl)-3-azabicyclo[3.1.0]hexane-2,4-dione dihydrochloride |
| 97 | 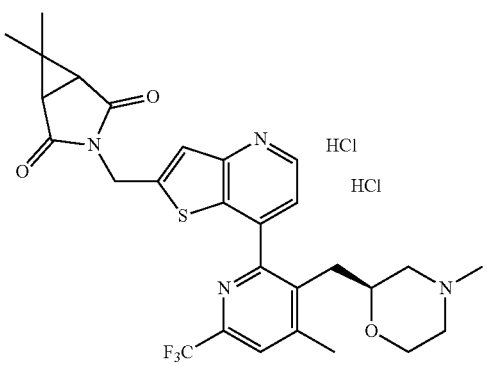 | 6,6-dimethyl-3-((7-(4-methyl-3-(((S)-4-methylmorpholin-2-yl)methyl)-6-(trifluoromethyl)pyridin-2-yl)thieno[3,2-b]pyridin-2-yl)methyl)-3-azabicyclo[3.1.0]hexane-2,4-dione dihydrochloride |
| 98. | 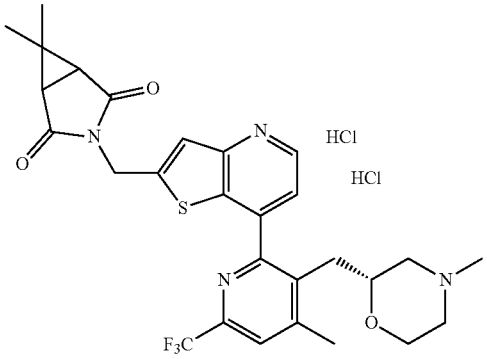 | 6,6-dimethyl-3-((7-(4-methyl-3-(((R)-4-methylmorpholin-2-yl)methyl)-6-(trifluoromethyl)pyridin-2-yl)thieno[3,2-b]pyridin-2-yl)methyl)-3-azabicyclo[3.1.0]hexane-2,4-dione dihydrochloride |
| 99. | 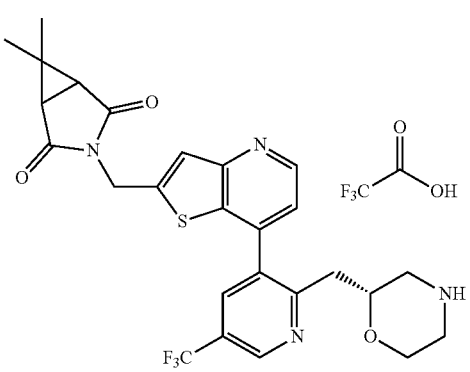 [SMILES: CC1(C)C2C(=O)N(Cc3cc4nccc(-c5cc(C(F)(F)F)cnc5C[C@@H]5CNCCO5)c4s3)C(=O)C21 ; O=C(O)C(F)(F)F] | 6,6-dimethyl-3-((7-(2-(((R)-morpholin-2-yl)methyl)-5-(trifluoromethyl)pyridin-3-yl)thieno[3,2-b]pyridin-2-yl)methyl)-3-azabicyclo[3.1.0]hexane-2,4-dione 2,2,2-trifluoroacetate |

| Ex. No. | Structure | IUPAC Name |
|---|---|---|
| 100. | 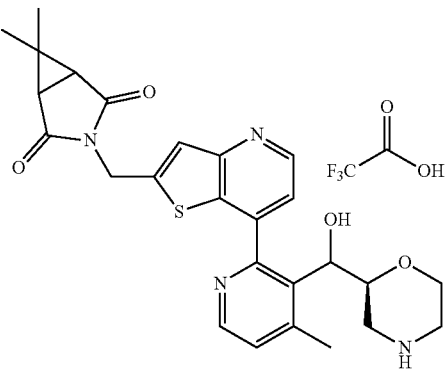 | 3-((7-(3-(hydroxy((S)-morpholin-2-yl)methyl)-4-methylpyridin-2-yl)thieno[3,2-b]pyridin-2-yl)methyl)-6,6-dimethyl-3-azabicyclo[3.1.0]hexane-2,4-dione 2,2,2-trifluoroacetate |
| 101. | 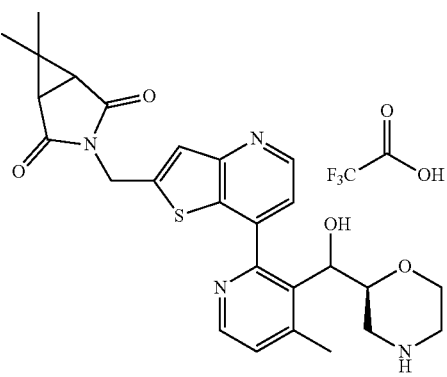 | 3-((7-(3-(hydroxy((S)-morpholin-2-yl)methyl)-4-methylpyridin-2-yl)thieno[3,2-b]pyridin-2-yl)methyl)-6,6-dimethyl-3-azabicyclo[3.1.0]hexane-2,4-dione 2,2,2-trifluoroacetate |
| 102. | 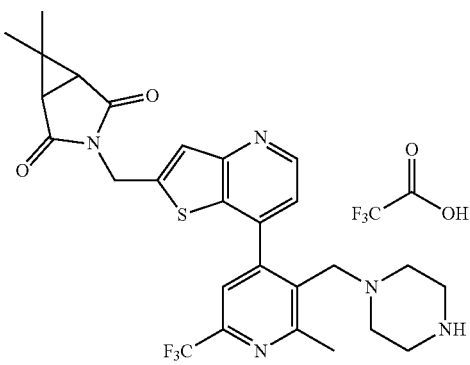 [SMILES: Cc1nc(C(F)(F)F)cc(-c2ccnc3cc(CN4C(=O)C5C(C4=O)C5(C)C)sc23)c1CN1CCNCC1 ; O=C(O)C(F)(F)F] | 6,6-dimethyl-3-((7-(2-methyl-3-(piperazin-1-ylmethyl)-6-(trifluoromethyl)pyridin-4-yl)thieno[3,2-b]pyridin-2-yl)methyl)-3-azabicyclo[3.1.0]hexane-2,4-dione 2,2,2-trifluoroacetate |
| 103. | 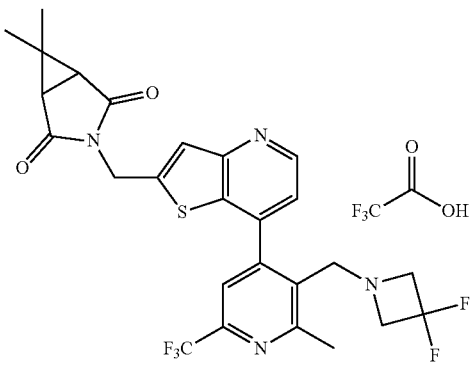 [SMILES: Cc1nc(C(F)(F)F)cc(-c2ccnc3cc(CN4C(=O)C5C(C4=O)C5(C)C)sc23)c1CN1CC(F)(F)C1 ; O=C(O)C(F)(F)F] | 3-((7-(3-((3,3-difluoroazetidin-1-yl)methyl)-2-methyl-6-(trifluoromethyl)pyridin-4-yl)thieno[3,2-b]pyridin-2-yl)methyl)-6,6-dimethyl-3-azabicyclo[3.1.0]hexane-2,4-dione 2,2,2-trifluoroacetate |

| Ex. No. | Structure | IUPAC Name |
|---|---|---|
| 104. | 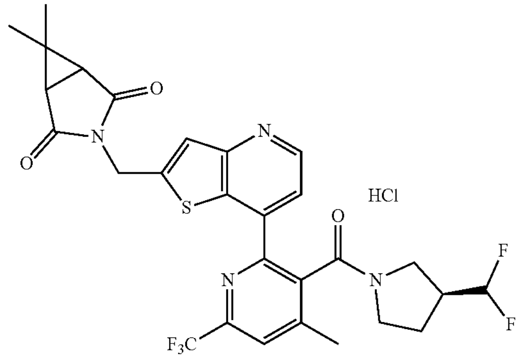 [SMILES: Cc1cc(C(F)(F)F)nc(-c2ccnc3cc(CN4C(=O)C5C(C4=O)C5(C)C)sc23)c1C(=O)N1CC[C@H](C(F)F)C1 ; Cl] | 3-((7-(3-((S)-3-(difluoromethyl)pyrrolidine-1-carbonyl)-4-methyl-6-(trifluoromethyl)pyridin-2-yl)thieno[3,2-b]pyridin-2-yl)methyl)-6,6-dimethyl-3-azabicyclo[3.1.0]hexane-2,4-dione hydrochloride |
| 105. | 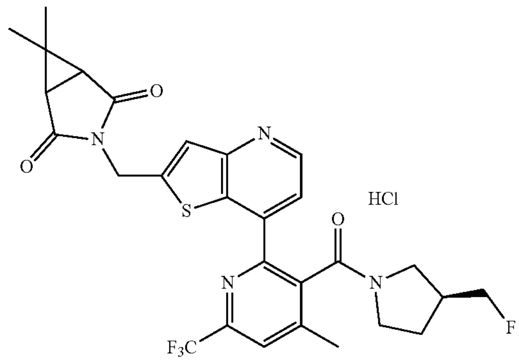 [SMILES: Cc1cc(C(F)(F)F)nc(-c2ccnc3cc(CN4C(=O)C5C(C4=O)C5(C)C)sc23)c1C(=O)N1CC[C@H](CF)C1 ; Cl] | 3-((7-(3-((S)-3-(fluoromethyl)pyrrolidine-1-carbonyl)-4-methyl-6-(trifluoromethyl)pyridin-2-yl)thieno[3,2-b]pyridin-2-yl)methyl)-6,6-dimethyl-3-azabicyclo[3.1.0]hexane-2,4-dione hydrochloride |
| 106. | 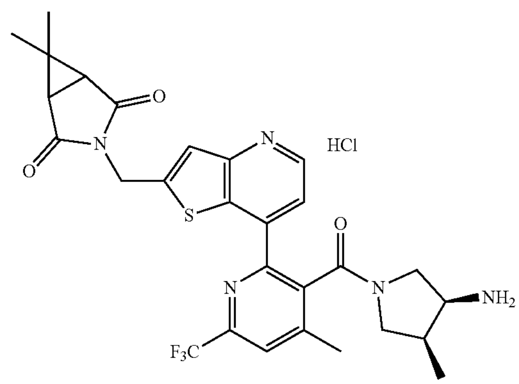 [SMILES: Cc1cc(C(F)(F)F)nc(-c2ccnc3cc(CN4C(=O)C5C(C4=O)C5(C)C)sc23)c1C(=O)N1C[C@@H](N)[C@@H](C)C1 ; Cl] | 3-((7-(3-((3S,4S)-3-amino-4-methylpyrrolidine-1-carbonyl)-4-methyl-6-(trifluoromethyl)pyridin-2-yl)thieno[3,2-b]pyridin-2-yl)methyl)-6,6-dimethyl-3-azabicyclo[3.1.0]hexane-2,4-dione hydrochloride |
| 107. | 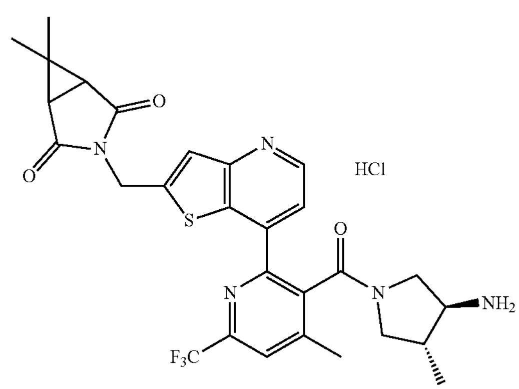 [SMILES: Cc1cc(C(F)(F)F)nc(-c2ccnc3cc(CN4C(=O)C5C(C4=O)C5(C)C)sc23)c1C(=O)N1C[C@@H](C)[C@H](N)C1 ; Cl] | 3-((7-(3-((3S,4R)-3-amino-4-methylpyrrolidine-1-carbonyl)-4-methyl-6-(trifluoromethyl)pyridin-2-yl)thieno[3,2-b]pyridin-2-yl)methyl)-6,6-dimethyl-3-azabicyclo[3.1.0]hexane-2,4-dione hydrochloride |

| Ex. No. | Structure | IUPAC Name |
|---|---|---|
| 108. | 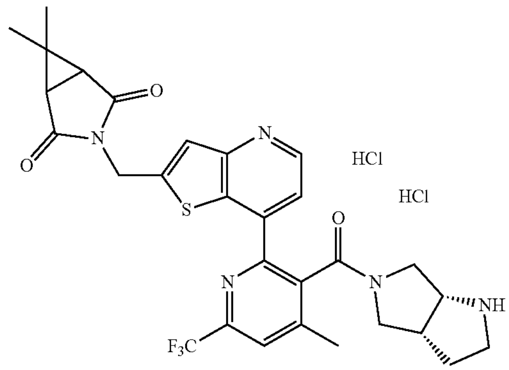 [SMILES: Cc1cc(C(F)(F)F)nc(-c2ccnc3cc(CN4C(=O)C5C(C4=O)C5(C)C)sc23)c1C(=O)N1C[C@H]2CCN[C@H]2C1 ; Cl ; Cl] | 6,6-dimethyl-3-((7-(4-methyl-3-((3aR,6aR)-octahydropyrrolo[3,4-b]pyrrole-5-carbonyl)-6-(trifluoromethyl)pyridin-2-yl)thieno[3,2-b]pyridin-2-yl)methyl)-3-azabicyclo[3.1.0]hexane-2,4-dione dihydrochloride |
| 109. | 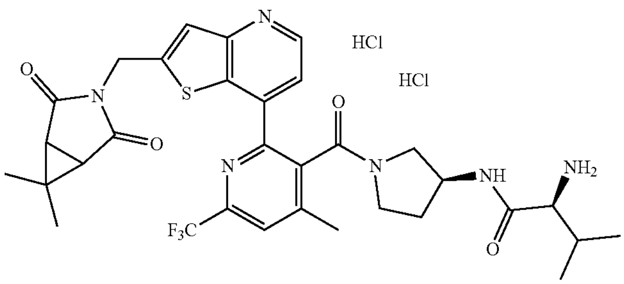 [SMILES: Cc1cc(C(F)(F)F)nc(-c2ccnc3cc(CN4C(=O)C5C(C4=O)C5(C)C)sc23)c1C(=O)N1CC[C@H](NC(=O)[C@@H](N)C(C)C)C1 ; Cl ; Cl] | (2S)-2-amino-N-((3S)-1-(2-(2-((6,6-dimethyl-2,4-dioxo-3-azabicyclo[3.1.0]hexan-3-yl)methyl)thieno[3,2-b]pyridin-7-yl)-4-methyl-6-(trifluoromethyl)nicotinoyl)pyrrolidin-3-yl)-3-methylbutanamide dihydrochloride |
| 110. | 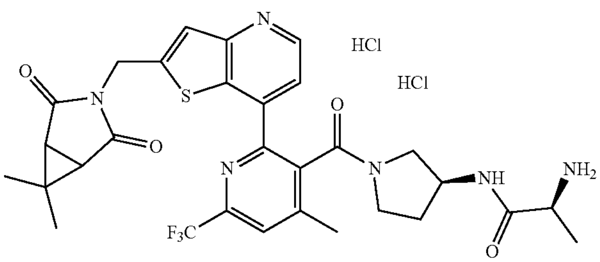 [SMILES: Cc1cc(C(F)(F)F)nc(-c2ccnc3cc(CN4C(=O)C5C(C4=O)C5(C)C)sc23)c1C(=O)N1CC[C@H](NC(=O)[C@H](C)N)C1 ; Cl ; Cl] | (2S)-2-amino-N-((3S)-1-(2-(2-((6,6-dimethyl-2,4-dioxo-3-azabicyclo[3.1.0]hexan-3-yl)methyl)thieno[3,2-b]pyridin-7-yl)-4-methyl-6-(trifluoromethyl)nicotinoyl)pyrrolidin-3-yl)propanamide dihydrochloride |
| 111. | 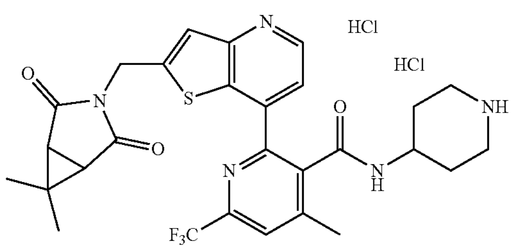 [SMILES: Cc1cc(C(F)(F)F)nc(-c2ccnc3cc(CN4C(=O)C5C(C4=O)C5(C)C)sc23)c1C(=O)NC1CCNCC1 ; Cl ; Cl] | 2-(2-((6,6-dimethyl-2,4-dioxo-3-azabicyclo[3.1.0]hexan-3-yl)methyl)thieno[3,2-b]pyridin-7-yl)-4-methyl-N-(piperidin-4-yl)-6-(trifluoromethyl)nicotinamide dihydrochloride |
| 112. | 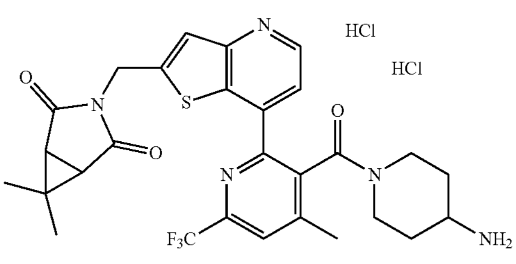 [SMILES: Cc1cc(C(F)(F)F)nc(-c2ccnc3cc(CN4C(=O)C5C(C4=O)C5(C)C)sc23)c1C(=O)N1CCC(N)CC1 ; Cl ; Cl] | 3-((7-(3-(4-aminopiperidine-1-carbonyl)-4-methyl-6-(trifluoromethyl)pyridin-2-yl)thieno[3,2-b]pyridin-2-yl)methyl)-6,6-dimethyl-3-azabicyclo[3.1,0]hexane-2,4-dione dihydrochloride |

| Ex. No. | Structure | IUPAC Name |
|---|---|---|
| 113. | 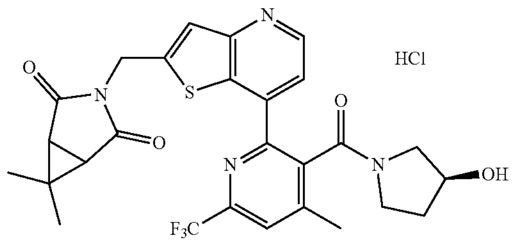 [SMILES: Cc1cc(C(F)(F)F)nc(-c2ccnc3cc(CN4C(=O)C5C(C4=O)C5(C)C)sc23)c1C(=O)N1CC[C@H](O)C1 ; Cl] | 3-((7-(3-((S)-3-hydroxypyrrolidine-1-carbonyl)-4-methyl-6-(trifluoromethyl)pyridin-2-yl)thieno[3,2-b]pyridin-2-yl)methyl)-6,6-dimethyl-3-azabicyclo[3.1.0]hexane-2,4-dione hydrochloride |
| 114. | 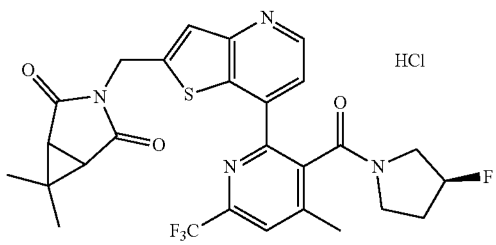 [SMILES: Cc1cc(C(F)(F)F)nc(-c2ccnc3cc(CN4C(=O)C5C(C4=O)C5(C)C)sc23)c1C(=O)N1CC[C@H](F)C1 ; Cl] | 3-((7-(3-((S)-3-fluoropyrrolidine-1-carbonyl)-4-methyl-6-(trifluoromethyl)pyridin-2-yl)thieno[3,2-b]pyridin-2-yl)methyl)-6,6-dimethyl-3-azabicyclo[3.1.0]hexane-2,4-dione hydrochloride |
| 115. | 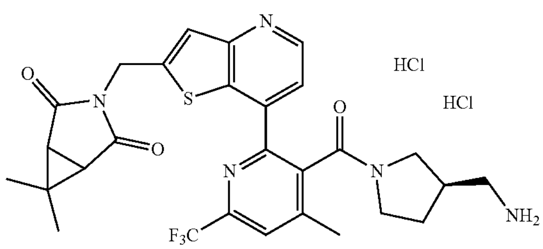 [SMILES: Cc1cc(C(F)(F)F)nc(-c2ccnc3cc(CN4C(=O)C5C(C4=O)C5(C)C)sc23)c1C(=O)N1CC[C@H](CN)C1 ; Cl ; Cl] | 3-((7-(3-((R)-3-(aminomethyl)pyrrolidine-1-carbonyl)-4-methyl-6-(trifluoromethyl)pyridin-2-yl)thieno[3,2-b]pyridin-2-yl)methyl)-6,6-dimethyl-3-azabicyclo[3.1.0]hexane-2,4-dione dihydrochloride |
| 116. | 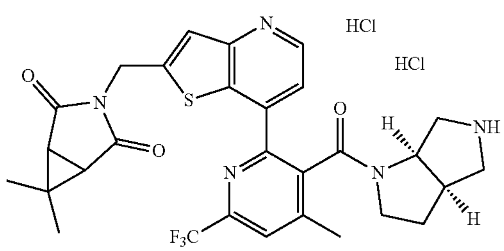 [SMILES: Cc1cc(C(F)(F)F)nc(-c2ccnc3cc(CN4C(=O)C5C(C4=O)C5(C)C)sc23)c1C(=O)N1CC[C@@H]2CNC[C@@H]21 ; Cl ; Cl] | 6,6-dimethyl-3-((7-(4-methyl-3-((3aR,6aR)-octahydropyrrolo[3,4-b]pyrrole-1-carbonyl)-6-(trifluoromethyl)pyridin-2-yl)thieno[3,2-b]pyridin-2-yl)methyl)-3-azabicyclo[3.1.0]hexane-2,4-dione dihydrochloride |
| 117. | 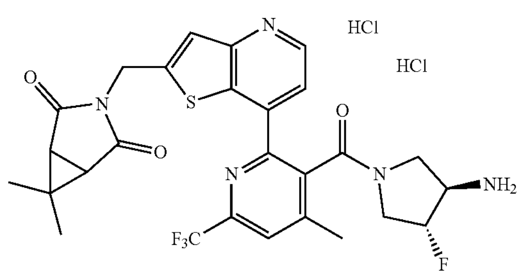 [SMILES: Cc1cc(C(F)(F)F)nc(-c2ccnc3cc(CN4C(=O)C5C(C4=O)C5(C)C)sc23)c1C(=O)N1C[C@@H](N)[C@H](F)C1 ; Cl ; Cl] | 3-((7-(3-((3R,4R)-3-amino-4-fluoropyrrolidine-1-carbonyl)-4-methyl-6-(trifluoromethyl)pyridin-2-yl)thieno[3,2-b]pyridin-2-yl)methyl)-6,6-dimethyl-3-azabicyclo[3.1.0]hexane-2,4-dione dihydrochloride |
| 118. | 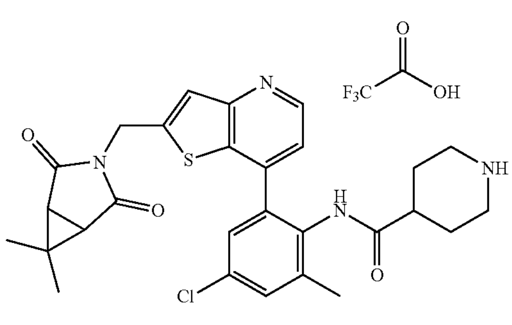 | N-(4-chloro-2-(2-((6,6-dimethyl-2,4-dioxo-3-azabicyclo[3.1.0]hexan-3-yl)methyl)thieno[3,2-b]pyridin-7-yl)-6-methylphenyl)piperidine-4-carboxamide 2,2,2-trifluoroacetate |

| Ex. No. | Structure | IUPAC Name |
|---|---|---|
| 119. | 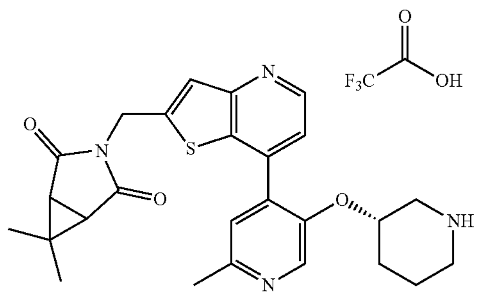 [SMILES: Cc1cc(-c2ccnc3cc(CN4C(=O)C5C(C4=O)C5(C)C)sc23)c(O[C@H]2CCCNC2)cn1 ; O=C(O)C(F)(F)F] | 6,6-dimethyl-3-((7-(2-methyl-5-(((S)-piperidin-3-yl)oxy)pyridin-4-yl)thieno[3,2-b]pyridin-2-yl)methyl)-3-azabicyclo[3.1.0]hexane-2,4-dione 2,2,2-trifluoroacetate |
| 120. | 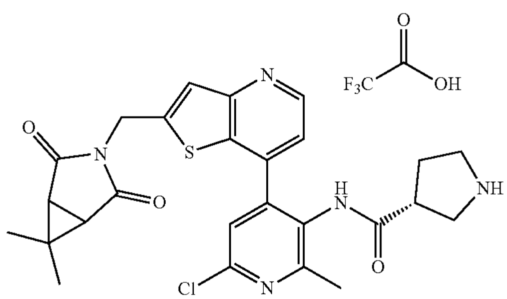 [SMILES: Cc1nc(Cl)cc(-c2ccnc3cc(CN4C(=O)C5C(C4=O)C5(C)C)sc23)c1NC(=O)[C@@H]1CCNC1 ; O=C(O)C(F)(F)F] | (3R)-N-(6-chloro-4-(2-((6,6-dimethyl-2,4-dioxo-3-azabicyclo[3.1.0]hexan-3-yl)methyl)thieno[3,2-b]pyridin-7-yl)-2-methylpyridin-3-yl)pyrrolidine-3-carboxamide 2,2,2-trifluoroacetate |
| 121. | 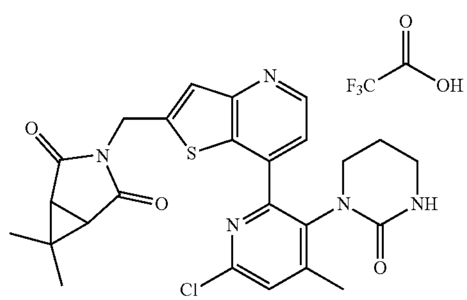 | 3-((7-(6-chloro-4-methyl-3-(2-oxotetrahydropyrimidin-1(2H)-yl)pyridin-2-yl)thieno[3,2-b]pyridin-2-yl)methyl)-6,6-dimethyl-3-azabicyclo[3.1.0]hexane-2,4-dione 2,2,2-trifluoroacetate |
| 122. | 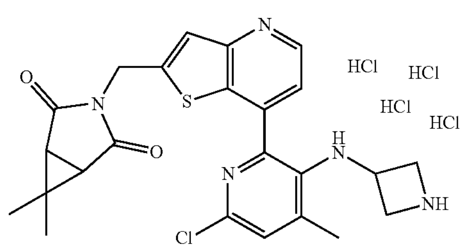 [SMILES: Cc1cc(Cl)nc(-c2ccnc3cc(CN4C(=O)C5C(C4=O)C5(C)C)sc23)c1NC1CNC1 ; Cl ; Cl ; Cl ; Cl] | 3-((7-(3-(azetidin-3-ylamino)-6-chloro-4-methylpyridin-2-yl)thieno[3,2-b]pyridin-2-yl)methyl)-6,6-dimethyl-3-azabicyclo[3.1.0]hexane-2,4-dione tetrahydrochloride |
| 123. | 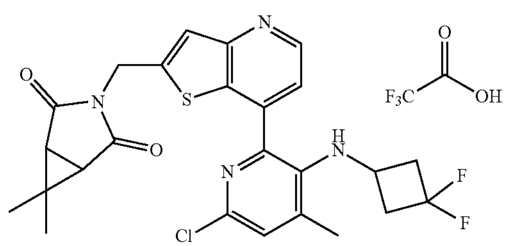 [SMILES: Cc1cc(Cl)nc(-c2ccnc3cc(CN4C(=O)C5C(C4=O)C5(C)C)sc23)c1NC1CC(F)(F)C1 ; O=C(O)C(F)(F)F] | 3-((7-(6-chloro-3-((3,3-difluorocyclobutyl)amino)-4-methylpyridin-2-yl)thieno[3,2-b]pyridin-2-yl)methyl)-6,6-dimethyl-3-azabicyclo[3.1.0]hexane-2,4-dione 2,2,2-trifluoroacetate |

| Ex. No. | Structure | IUPAC Name |
|---|---|---|
| 124. | 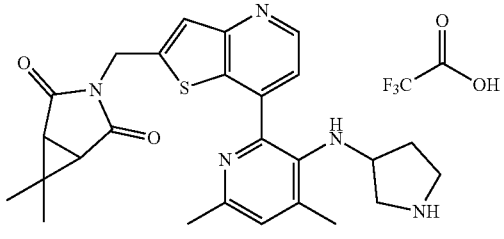 Racemate | 3-((7-(4,6-dimethyl-3-(pyrrolidin-3-ylamino)pyridin-2-yl)thieno[3,2-b]pyridin-2-yl)methyl)-6,6-dimethyl-3-azabicyclo[3.1.0]hexane-2,4-dione 2,2,2-trifluoroacetate |
| 125. | 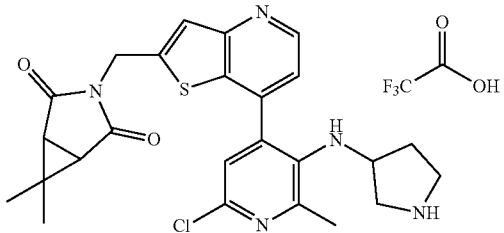 Racemate | 3-((7-(6-chloro-2-methyl-3-(pyrrolidin-3-ylamino)pyridin-4-yl)thieno[3,2-b]pyridin-2-yl)methyl)-6,6-dimethyl-3-azabicyclo[3.1.0]hexane-2,4-dione 2,2,2-trifluoroacetate |
| 126. | 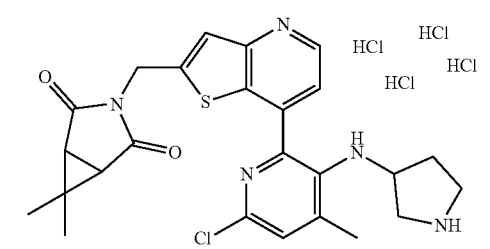 Racemate | 3-((7-(6-chloro-4-methyl-3-(pyrrolidin-3-ylamino)pyridin-2-yl)thieno[3,2-b]pyridin-2-yl)methyl)-6,6-dimethyl-3-azabicyclo[3.1.0]hexane-2,4-dione tetrahydrochloride |
| 127. | 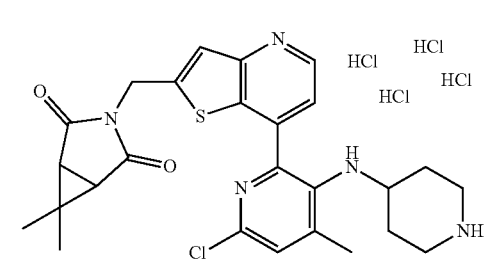 [SMILES: Cc1cc(Cl)nc(-c2ccnc3cc(CN4C(=O)C5C(C4=O)C5(C)C)sc23)c1NC1CCNCC1 ; Cl ; Cl ; Cl ; Cl] | 3-((7-(6-chloro-4-methyl-3-(piperidin-4-ylamino)pyridin-2-yl)thieno[3,2-b]pyridin-2-yl)methyl)-6,6-dimethyl-3-azabicyclo[3.1.0]hexane-2,4-dione tetrahydrochloride |
| 128. | 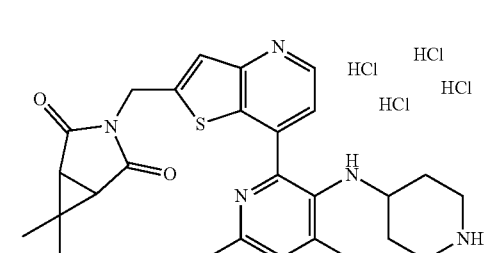 | 6,6-dimethyl-3-((7-(4-methyl-3-(piperidin-4-ylamino)-6-(trifluoromethyl)pyridin-2-yl)thieno[3,2-b]pyridin-2-yl)methyl)-3-azabicyclo[3.1.0]hexane-2,4-dione tetrahydrochloride |

| Ex. No. | Structure | IUPAC Name |
|---|---|---|
| 129. | 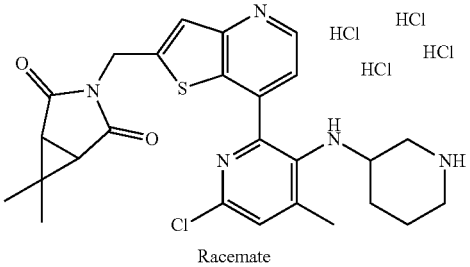 [SMILES: Cc1cc(Cl)nc(-c2ccnc3cc(CN4C(=O)C5C(C4=O)C5(C)C)sc23)c1NC1CCCNC1 ; Cl ; Cl ; Cl ; Cl] Racemate | 3-((7-(6-chloro-4-methyl-3-(piperidin-3-ylamino)pyridin-2-yl)thieno[3,2-b]pyridin-2-yl)methyl)-6,6-dimethyl-3-azabicyclo[3.1.0]hexane-2,4-dione tetrahydrochloride |
| 130. | 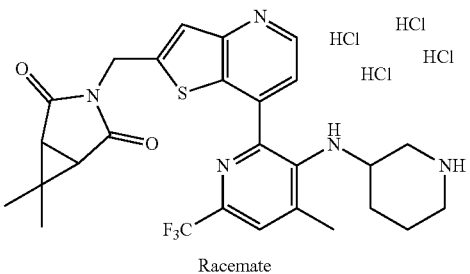 [SMILES: Cc1cc(C(F)(F)F)nc(-c2ccnc3cc(CN4C(=O)C5C(C4=O)C5(C)C)sc23)c1NC1CCCNC1 ; Cl ; Cl ; Cl ; Cl] Racemate | 6,6-dimethyl-3-((7-(4-methyl-3-(piperidin-3-ylamino)-6-(trifluoromethyl)pyridin-2-yl)thieno[3,2-b]pyridin-2-yl)methyl)-3-azabicyclo[3.1.0]hexane-2,4-dione tetrahydrochloride |
| 131. | 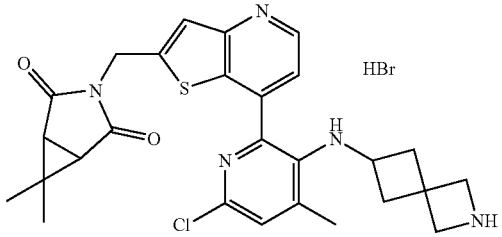 [SMILES: Cc1cc(Cl)nc(-c2ccnc3cc(CN4C(=O)C5C(C4=O)C5(C)C)sc23)c1NC1CC2(CNC2)C1 ; Br] | 3-((7-(3-((2-azaspiro[3.3]heptan-6-yl)amino)-6-chloro-4-methylpyridin-2-yl)thieno[3,2-b]pyridin-2-yl)methyl)-6,6-dimethyl-3-azabicyclo[3.1.0]hexane-2,4-dione hydrobromide |
| 132. | 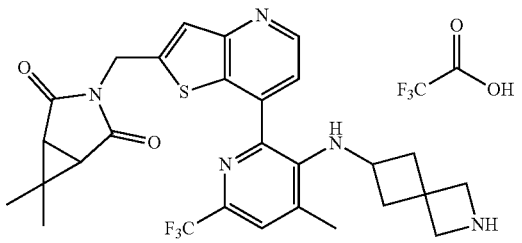 [SMILES: Cc1cc(C(F)(F)F)nc(-c2ccnc3cc(CN4C(=O)C5C(C4=O)C5(C)C)sc23)c1NC1CC2(CNC2)C1 ; O=C(O)C(F)(F)F] | 3-((7-(3-((2-azaspiro[3.3]heptan-6-yl)amino)-4-methyl-6-(trifluoromethyl)pyridin-2-yl)thieno[3,2-b]pyridin-2-yl)methyl)-6,6-dimethyl-3-azabicyclo[3.1.0]hexane-2,4-dione 2,2,2-trifluoroacetate |
| 133. | 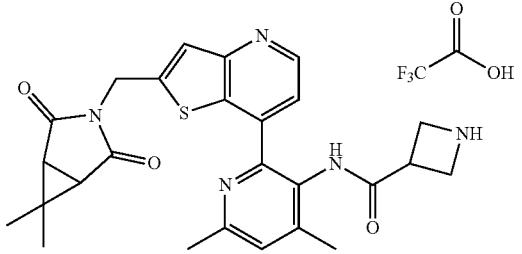 | N-(2-(2-((6,6-dimethyl-2,4-dioxo-3-azabicyclo[3.1.0]hexan-3-yl)methyl)thieno[3,2-b]pyridin-7-yl)-4,6-dimethylpyridin-3-yl)azetidine-3-carboxamide 2,2,2-trifluoroacetate |

| Ex. No. | Structure | IUPAC Name |
|---|---|---|
| 134. | 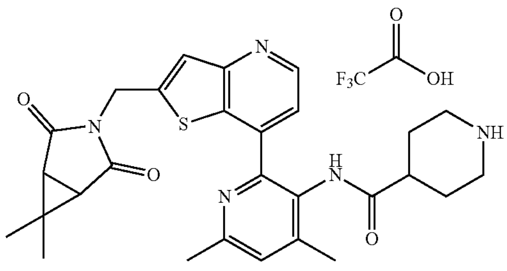 | N-(2-(2-((6,6-dimethyl-2,4-dioxo-3-azabicyclo[3.1.0]hexan-3-yl)methyl)thieno[3,2-b]pyridin-7-yl)-4,6-dimethylpyridin-3-yl)piperidine-4-carboxamide 2,2,2-trifluoroacetate |
| 135. | 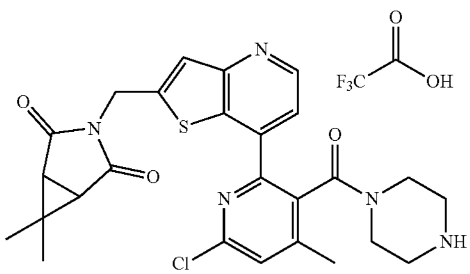 | 3-((7-(6-chloro-4-methyl-3-(piperazine-1-carbonyl)pyridin-2-yl)thieno[3,2-b]pyridin-2-yl)methyl)-6,6-dimethyl-3-azabicyclo[3.1.0]hexane-2,4-dione 2,2,2-trifluoroacetate |
| 136. | 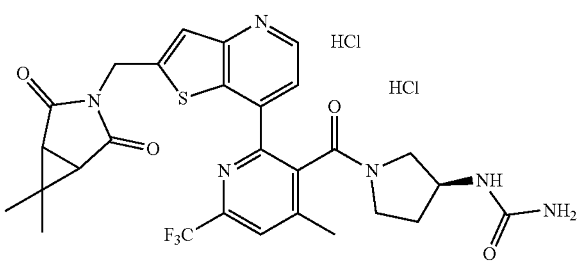 [SMILES: Cc1cc(C(F)(F)F)nc(-c2ccnc3cc(CN4C(=O)C5C(C4=O)C5(C)C)sc23)c1C(=O)N1CC[C@H](NC(N)=O)C1 ; Cl ; Cl] | 1-((3S)-1-(2-(2-((6,6-dimethyl-2,4-dioxo-3-azabicyclo[3.1.0]hexan-3-yl)methyl)thieno[3,2-b]pyridin-7-yl)-4-methyl-6-(trifluoromethyl)nicotinoyl)pyrrolidin-3-yl)urea dihydrochloride |

| Ex. No. | Structure | IUPAC Name |
|---|---|---|
| 137. | Racemate | 3-((7-(3-(3-amino-3-methylpyrrolidine-1-carbonyl)-4-methyl-6-(trifluoromethyl)pyridin-2-yl)thieno[3,2-b]pyridin-2-yl)methyl)-6,6-dimethyl-3-azabicyclo[3.1.0]hexane-2,4-dione trihydrochloride |
| 138. | One diastereoisomer | 3-((7-(3-((3S)-3-(1-aminoethyl)pyrrolidine-1-carbonyl)-4-methyl-6-(trifluoromethyl)pyridin-2-yl)thieno[3,2-b]pyridin-2-yl)methyl)-6,6-dimethyl-3-azabicyclo[3.1.0]hexane-2,4-dione trihydrochloride |

| Ex. No. | Structure | IUPAC Name |
|---|---|---|
| 139. | 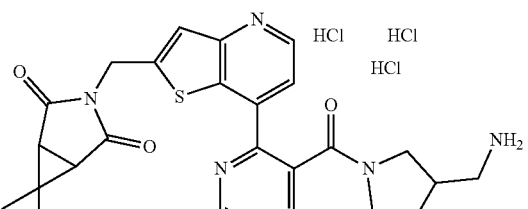 Racemate | 3-((7-(3-(3-(aminomethyl)pyrrolidine-1-carbonyl)-4-methyl-6-(trifluoromethyl)pyridin-2-yl)thieno[3,2-b]pyridin-2-yl)methyl)-6,6-dimethyl-3-azabicyclo[3.1.0]hexane-2,4-dione trihydrochloride |
| 140. | 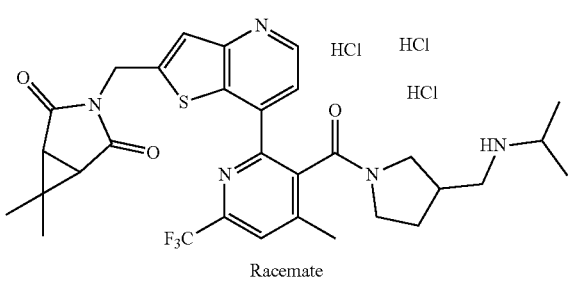 [SMILES: Cc1cc(C(F)(F)F)nc(-c2ccnc3cc(CN4C(=O)C5C(C4=O)C5(C)C)sc23)c1C(=O)N1CCC(CNC(C)C)C1 ; Cl ; Cl ; Cl] Racemate | 3-((7-(3-(3-((isopropylamino)methyl)pyrrolidine-1-carbonyl)-4-methyl-6-(trifluoromethyl)pyridin-2-yl)thieno[3,2-b]pyridin-2-yl)methyl)-6,6-dimethyl-3-azabicyclo[3.1.0]hexane-2,4-dione trihydrochloride |
| 141. | 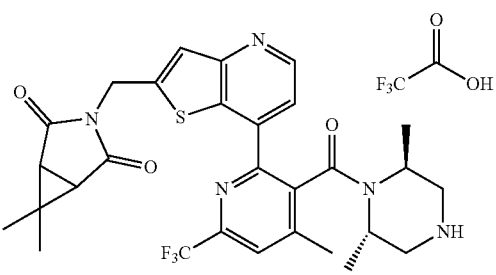 | 3-((7-(3-((2S,6S)-2,6-dimethylpiperazine-1-carbonyl)-4-methyl-6-(trifluoromethyl)pyridin-2-yl)thieno[3,2-b]pyridin-2-yl)methyl)-6,6-dimethyl-3-azabicyclo[3.1.0]hexane-2,4-dione 2,2,2-trifluoroacetate |
| 142. | 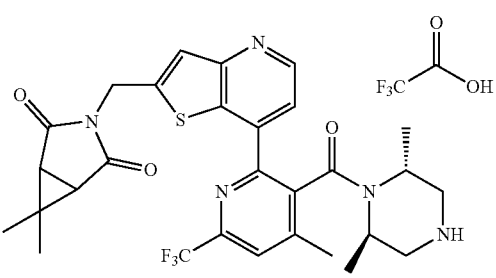 | 3-((7-(3-((2R,6R)-2,6-dimethylpiperazine-1-carbonyl)-4-methyl-6-(trifluoromethyl)pyridin-2-yl)thieno[3,2-b]pyridin-2-yl)methyl)-6,6-dimethyl-3-azabicyclo[3.1.0]hexane-2,4-dione 2,2,2-trifluoroacetate |
| 143. | 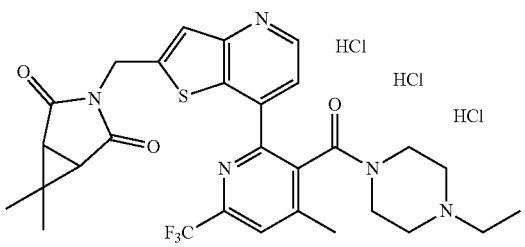 [SMILES: CCN1CCN(C(=O)c2c(C)cc(C(F)(F)F)nc2-c2ccnc3cc(CN4C(=O)C5C(C4=O)C5(C)C)sc23)CC1 ; Cl ; Cl ; Cl] | 3-((7-(3-(4-ethylpiperazine-1-carbonyl)-4-methyl-6-(trifluoromethyl)pyridin-2-yl)thieno[3,2-b]pyridin-2-yl)methyl)-6,6-dimethyl-3-azabicyclo[3.1.0]hexane-2,4-dione trihydrochloride |

| Ex. No. | Structure | IUPAC Name |
|---|---|---|
| 144. | 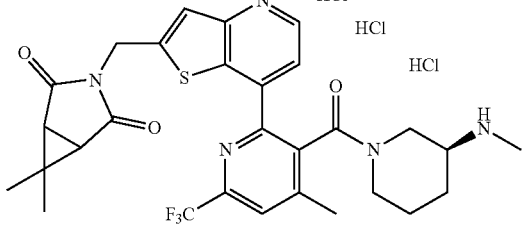 | 6,6-dimethyl-3-((7-(4-methyl-3-((S)-3-(methylamino)piperidine-1-carbonyl)-6-(trifluoromethyl)pyridin-2-yl)thieno[3,2-b]pyridin-2-yl)methyl)-3-azabicyclo[3.1.0]hexane-2,4-dione trihydrochloride |
| 145. | 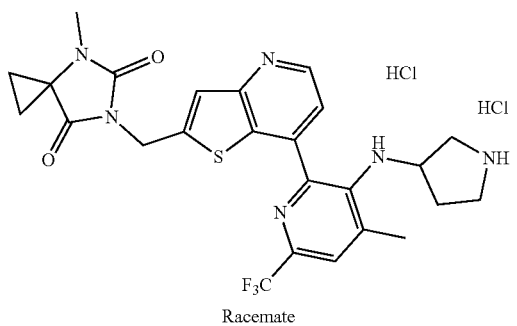 [SMILES: Cc1cc(C(F)(F)F)nc(-c2ccnc3cc(CN4C(=O)N(C)C5(CC5)C4=O)sc23)c1NC1CCNC1 ; Cl ; Cl] | 4-methyl-6-((7-(4-methyl-3-(pyrrolidin-3-ylamino)-6-(trifluoromethyl)pyridin-2-yl)thieno[3,2-b]pyridin-2-yl)methyl)-4,6-diazaspiro[2.4]heptane-5,7-dione dihydrochloride |
| 146. | 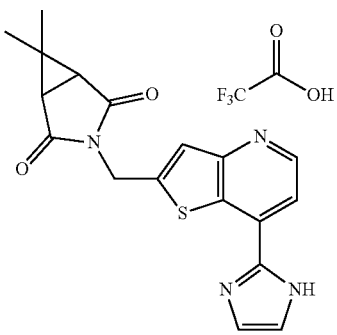 | 3-((7-(1H-imidazol-2-yl)thieno[3,2-b]pyridin-2-yl)methyl)-6,6-dimethyl-3-azabicyclo[3.1.0]hexane-2,4-dione 2,2,2-trifluoroacetate |
| 147. | 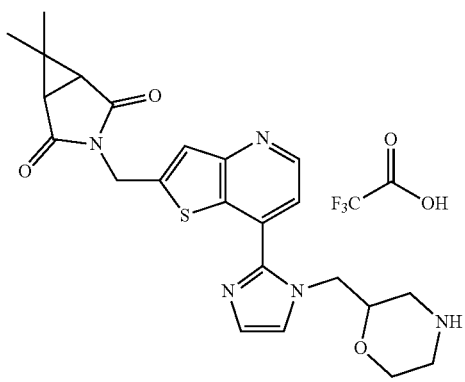 | 6,6-dimethyl-3-((7-(1-(morpholin-2-ylmethyl)-1H-imidazol-2-yl)thieno[3,2-b]pyridin-2-yl)methyl)-3-azabicyclo[3.1.0]hexane-2,4-dione 2,2,2-trifluoroacetate |

| Ex. No. | Structure | IUPAC Name |
|---|---|---|
| 148. | 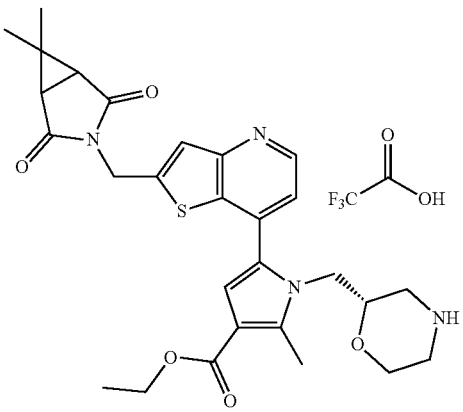 | ethyl 5-(2-(((6,6-dimethyl-2,4-dioxo-3-azabicyclo[3.1.0]hexan-3-yl)methyl)thieno[3,2-b]pyridin-7-yl)-2-methyl-1-(((S)-morpholin-2-yl)methyl)-1H-pyrrole-3-carboxylate 2,2,2-trifluoroacetate |
| 149. | 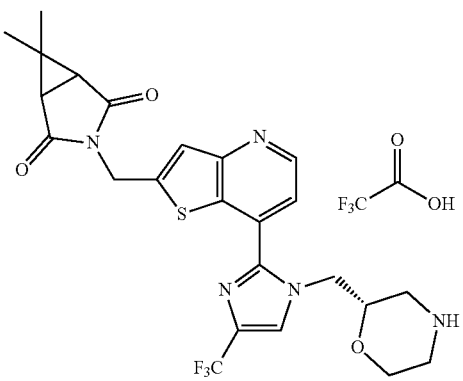 [SMILES: CC1(C)C2C(=O)N(Cc3cc4nccc(-c5nc(C(F)(F)F)cn5C[C@@H]5CNCCO5)c4s3)C(=O)C21 ; O=C(O)C(F)(F)F] | 6,6-dimethyl-3-((7-(1-(((S)-morpholin-2-yl)methyl)-4-(trifluoromethyl)-1H-imidazol-2-yl)thino[3,2-b]pyridin-2-yl)methyl)-3-azabicyclo[3.1.0]hexane-2,4-dione 2,2,2-trifluoroacetate |
| 150. | 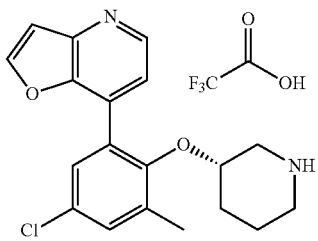 [SMILES: Cc1cc(Cl)cc(-c2ccnc3ccoc23)c1O[C@H]1CCCNC1 ; O=C(O)C(F)(F)F] | (S)-7-(5-chloro-3-methyl-2-(piperidin-3-yloxy)phenyl)furo[3,2-b]pyridine 2,2,2-trifluoroacetate |
| 151. | 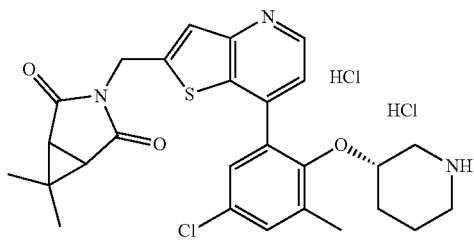 [SMILES: Cc1cc(Cl)cc(-c2ccnc3cc(CN4C(=O)C5C(C4=O)C5(C)C)sc23)c1O[C@H]1CCCNC1 ; Cl ; Cl] | 3-((7-(5-chloro-3-methyl-2-(((S)-piperidin-3-yl)oxy)phenyl)thiazolo[4,5-b]pyridin-2-yl)methyl)-6,6-dimethyl-3-azabicyclo[3.1.0]hexane-2,4-dione dihydrochloride |
| 152. | 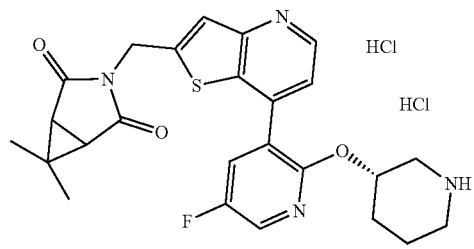 [SMILES: CC1(C)C2C(=O)N(Cc3cc4nccc(-c5cc(F)cnc5O[C@H]5CCCNC5)c4s3)C(=O)C21 ; Cl ; Cl] | 3-((7-(5-fluoro-2-(((S)-piperidin-3-yl)oxy)pyridin-3-yl)thieno[3,2-b]pyridin-2-yl)methyl)-6,6-dimethyl-3-azabicyclo[3.1.0]hexane-2,4-dione dihydrochloride |

-continued

| Ex. No. | Structure | IUPAC Name |
|---|---|---|
| 153. | 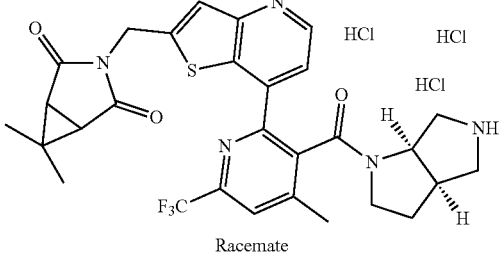<br>Racemate | 3-((7-(3-(((3aR,6aR)-hexahydropyrrolo[3,4-b]pyrrol-1(2H)-yl)methyl)-4-methyl-6-(trifluoromethyl)pyridin-2-yl)thieno[3,2-b]pyridin-2-yl)methyl)-6,6-dimethyl-3-azabicyclo[3.1.0]hexane-2,4-dione trihydrochloride |
| 154. | 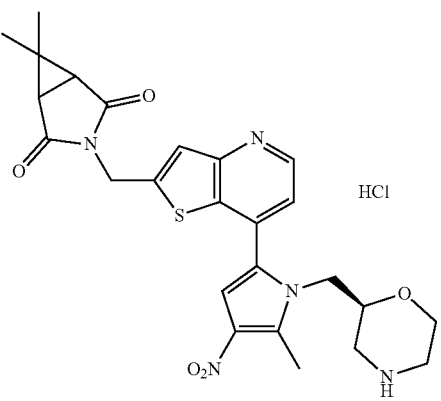 [SMILES: Cc1c([N+](=O)[O-])cc(-c2ccnc3cc(CN4C(=O)C5C(C4=O)C5(C)C)sc23)n1C[C@@H]1CNCCO1 ; Cl] | 6,6-dimethyl-3-((7-(5-methyl-1-(((S)-morpholin-2-yl)methyl)-4-nitro-1H-pyrrol-2-yl)thieno[3,2-6]pyridin-2-yl)methyl)-3-azabicyclo[3.1.0]hexane-2,4-dione hydrochloride |
| 155. | 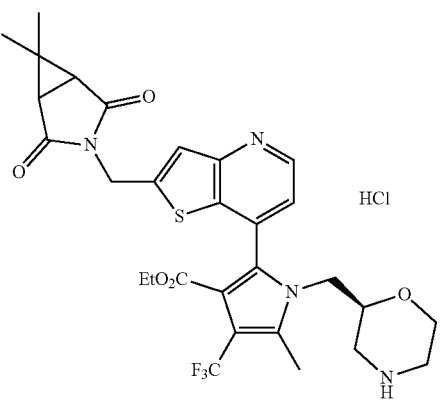 [SMILES: CCOC(=O)c1c(C(F)(F)F)c(C)n(C[C@@H]2CNCCO2)c1-c1ccnc2cc(CN3C(=O)C4C(C3=O)C4(C)C)sc12 ; Cl] | ethyl 2-(2-(((6,6-dimethyl-2,4-dioxo-3-azabicyclo[3.1.0]hexan-3-yl)methyl)thieno[3,2-b]pyridin-7-yl)-5-methyl-1-(((S)-morpholin-2-yl)methyl)-4-(trifluoromethyl)-1H-pyrrole-3-carboxylate hydrochloride |
| 156. | 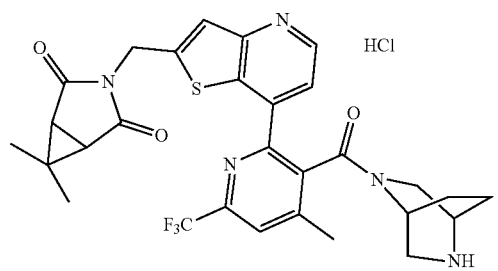 [SMILES: Cc1cc(C(F)(F)F)nc(-c2ccnc3cc(CN4C(=O)C5C(C4=O)C5(C)C)sc23)c1C(=O)N1CC2CCC1CN2 ; Cl] | 3-((7-(3-(2,5-diazabicyclo[2.2.2]octane-2-carbonyl)-4-methyl-6-(trifluoromethyl)pyridin-2-yl)thieno[3,2-b]pyridin-2-yl)methyl)-6,6-dimethyl-3-azabicyclo[3.1.0]hexane-2,4-dione hydrochloride |
| 157. | 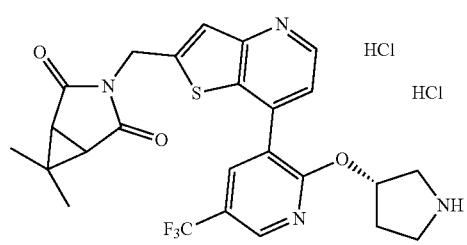 [SMILES: CC1(C)C2C(=O)N(Cc3cc4nccc(-c5cc(C(F)(F)F)cnc5O[C@H]5CCNC5)c4s3)C(=O)C21 ; Cl ; Cl] | 3-((7-(5-fluoro-2-(((S)-pyrrolidin-3-yl)oxy)pyridin-3-yl)thieno[3,2-b]pyridin-2-yl)methyl)-6,6-dimethyl-3-azabicyclo[3.1.0]hexane-2,4-dione dihydrochloride |

| Ex. No. | Structure | IUPAC Name |
|---|---|---|
| 158. | 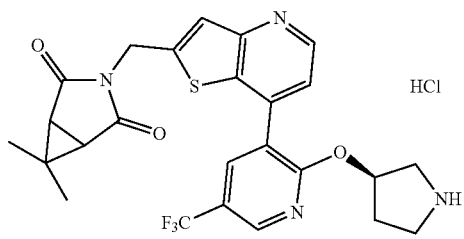 [SMILES: CC1(C)C2C(=O)N(Cc3cc4nccc(-c5cc(C(F)(F)F)cnc5O[C@@H]5CCNC5)c4s3)C(=O)C21 ; Cl] | 3-((7-(5-fluoro-2-(((R)-pyrrolidin-3-yl)oxy)pyridin-3-yl)thieno[3,2-b]pyridin-2-yl)methyl)-6,6-dimethyl-3-azabicyclo[3.1.0]hexane-2,4-dione hydrochloride |
| 159. | 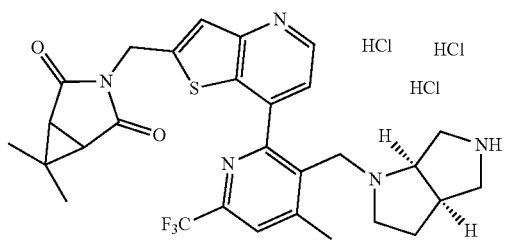<br>Single Enantiomer of Ex. 153 | 3-((7-(3-(((3aR,6aR)-hexahydropyrrolo[3,4-b]pyrrol-1(2H)-yl)methyl)-4-methyl-6-(trifluoromethyl)pyridin-2-yl)thieno[3,2-b]pyridin-2-yl)methyl)-6,6-dimethyl-3-azabicyclo[3.1.0]hexane-2,4-dione trihydrochloride |
| 160. | 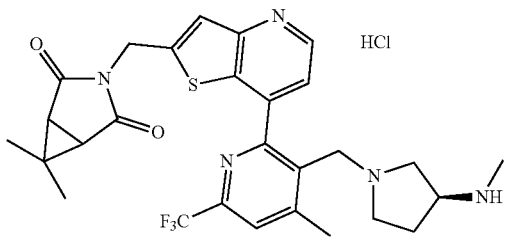 | 6,6-dimethyl-3-((7-(4-methyl-3-(((S)-3-(methylamino)pyrrolidin-1-yl)methyl)-6-(trifluoromethyl)pyridin-2-yl)thieno[3,2-b]pyridin-2-yl)methyl)-3-azabicyclo[3.1.0]hexane-2,4-dione hydrochloride |
| 161. | 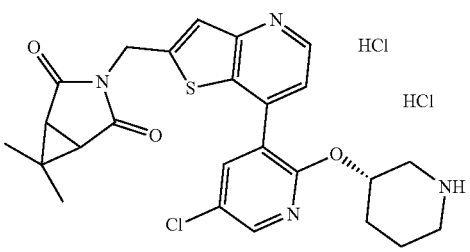 [SMILES: CC1(C)C2C(=O)N(Cc3cc4nccc(-c5cc(Cl)cnc5O[C@H]5CCCNC5)c4s3)C(=O)C21 ; Cl ; Cl] | 3-((7-(5-chloro-2-(((S)-piperidin-3-yl)oxy)pyridin-3-yl)thieno[3,2-b]pyridin-2-yl)methyl)-6,6-dimethyl-3-azabicyclo[3.1.0]hexane-2,4-dione dihydrochloride |
| 162. | 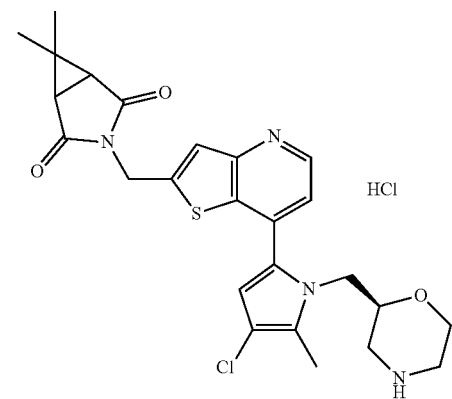 [SMILES: Cc1c(Cl)cc(-c2ccnc3cc(CN4C(=O)C5C(C4=O)C5(C)C)sc23)n1C[C@@H]1CNCCO1 ; Cl] | 3-((7-(4-chloro-5-methyl-1-(((S)-morpholin-2-yl)methyl)-1H-pyrrol-2-yl)thieno[3,2-b]pyridin-2-yl)methyl)-6,6-dimethyl-3-azabicyclo[3.1.0]hexane-2,4-dione hydrochloride |

| Ex. No. | Structure | IUPAC Name |
|---|---|---|
| 163. | 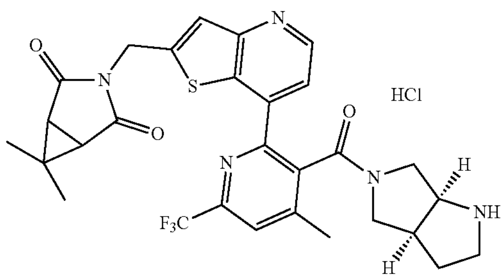 [SMILES: Cc1cc(C(F)(F)F)nc(-c2ccnc3cc(CN4C(=O)C5C(C4=O)C5(C)C)sc23)c1C(=O)N1C[C@@H]2CCN[C@@H]2C1 ; Cl] | 6,6-dimethyl-3-((7-(4-methyl-3-(((3aS,6aS)-octahydropyrrolo[3,4-b]pyrrole-5-carbonyl)-6-(trifluoromethyl)pyridin-2-yl)thieno[3,2-b]pyridin-2-yl)methyl)-3-azabicyclo[3.1.0]hexane-2,4-dione hydrochloride |
| 164. | 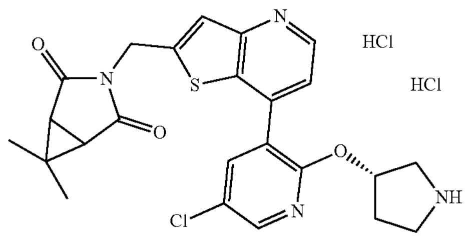 [SMILES: CC1(C)C2C(=O)N(Cc3cc4nccc(-c5cc(Cl)cnc5O[C@H]5CCNC5)c4s3)C(=O)C21 ; Cl ; Cl] | 3-((7-(5-chloro-2-(((S)-pyrrolidin-3-yl)oxy)pyridin-3-yl)thieno[3,2-b]pyridin-2-yl)methyl)-6,6-dimethyl-3-azabicyclo[3.1.0]hexane-2,4-dione dihydrochloride |
| 165. | 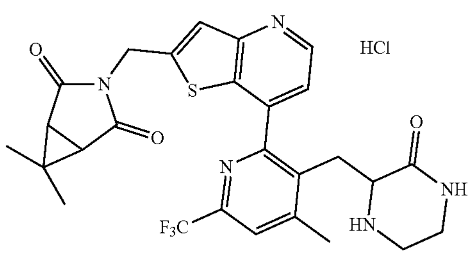 [SMILES: Cc1cc(C(F)(F)F)nc(-c2ccnc3cc(CN4C(=O)C5C(C4=O)C5(C)C)sc23)c1CC1NCCNC1=O ; Cl] | 6,6-dimethyl-3-((7-(4-methyl-3-((3-oxopiperazin-2-yl)methyl)-6-(trifluoromethyl)pyridin-2-yl)thieno[3,2-b]pyridin-2-yl)methyl)-3-azabicyclo[3.1.0]hexane-2,4-dione hydrochloride |
| 166. | 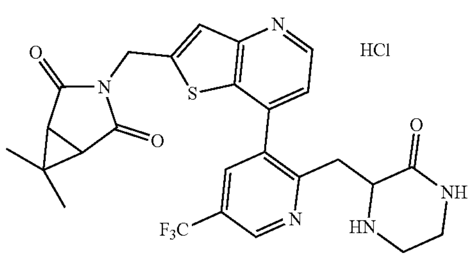 [SMILES: CC1(C)C2C(=O)N(Cc3cc4nccc(-c5cc(C(F)(F)F)cnc5CC5NCCNC5=O)c4s3)C(=O)C21 ; Cl] | 6,6-dimethyl-3-((7-(2-((3-oxopiperazin-2-yl)methyl)-5-(trifluoromethyl)pyridin-3-yl)thieno[3,2-b]pyridin-2-yl)methyl)-3-azabicyclo[3.1.0]hexane-2,4-dione hydrochloride |
| 167. | 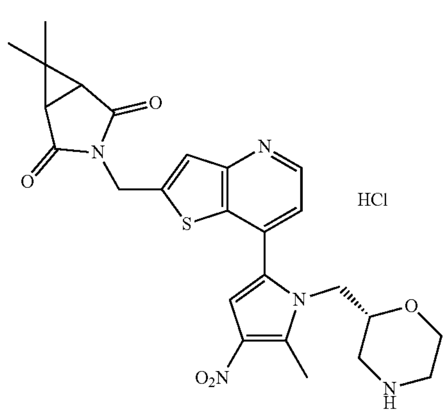 [SMILES: Cc1c([N+](=O)[O-])cc(-c2ccnc3cc(CN4C(=O)C5C(C4=O)C5(C)C)sc23)n1C[C@H]1CNCCO1 ; Cl] | 6,6-dimethyl-3-((7-(5-methyl-1-(((R)-morpholin-2-yl)methyl)-4-nitro-1H-pyrrol-2-yl)thieno[3,2-b]pyridin-2-yl)methyl)-3-azabicyclo[3.1.0]hexane-2,4-dione hydrochloride |

| Ex. No. | Structure | IUPAC Name |
|---|---|---|
| 168. | 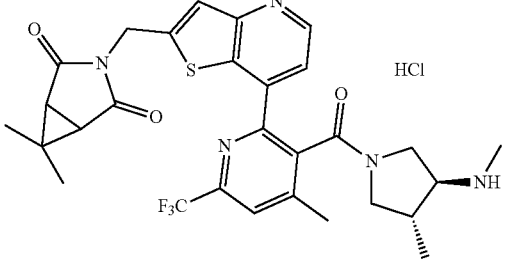 | 6,6-dimethyl-3-((7-(4-methyl-3-((3R,4S)-3-methyl-4-(methylamino)pyrrolidine-1-carbonyl)-6-(trifluoromethyl)pyridin-2-yl)thieno[3,2-b]pyridin-2-yl)methyl)-3-azabicyclo[3.1.0]hexane-2,4-dione hydrochloride |
| 169. | 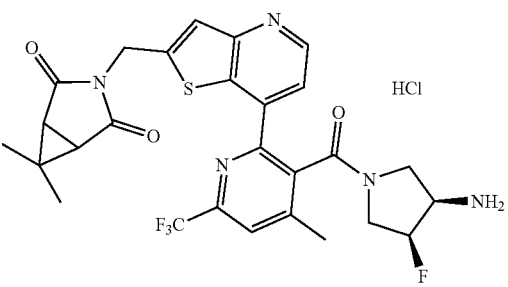 [SMILES: Cc1cc(C(F)(F)F)nc(-c2ccnc3cc(CN4C(=O)C5C(C4=O)C5(C)C)sc23)c1C(=O)N1C[C@@H](N)[C@@H](F)C1 ; Cl] | 3-((7-(3-((3R,4S)-3-amino-4-fluoropyrrolidine-1-carbonyl)-4-methyl-6-(trifluoromethyl)pyridin-2-yl)thieno[3,2-b]pyridin-2-yl)methyl)-6,6-dimethyl-3-azabicyclo[3.1.0]hexane-2,4-dione hydrochloride |
| 170. | 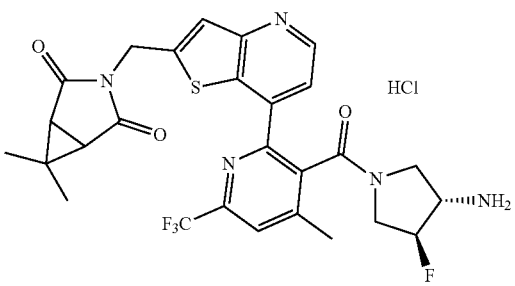 [SMILES: Cc1cc(C(F)(F)F)nc(-c2ccnc3cc(CN4C(=O)C5C(C4=O)C5(C)C)sc23)c1C(=O)N1C[C@H](N)[C@@H](F)C1 ; Cl] | 3-((7-(3-((3S,4S)-3-amino-4-fluoropyrrolidine-1-carbonyl)-4-methyl-6-(trifluoromethyl)pyridin-2-yl)thieno[3,2-b]pyridin-2-yl)methyl)-6,6-dimethyl-3-azabicyclo[3.1.0]hexane-2,4-dione hydrochloride |
| 171. | 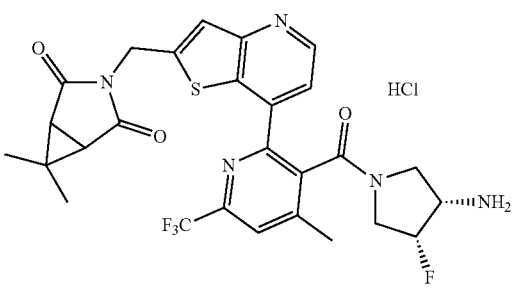 [SMILES: Cc1cc(C(F)(F)F)nc(-c2ccnc3cc(CN4C(=O)C5C(C4=O)C5(C)C)sc23)c1C(=O)N1C[C@@H](F)[C@@H](N)C1 ; Cl] | 3-((7-(3-((3S,4R)-3-amino-4-fluoropyrrolidine-1-carbonyl)-4-methyl-6-(trifluoromethyl)pyridin-2-yl)thieno[3,2-b]pyridin-2-yl)methyl)-6,6-dimethyl-3-azabicyclo[3.1.0]hexane-2,4-dione hydrochloride |
| 172. | 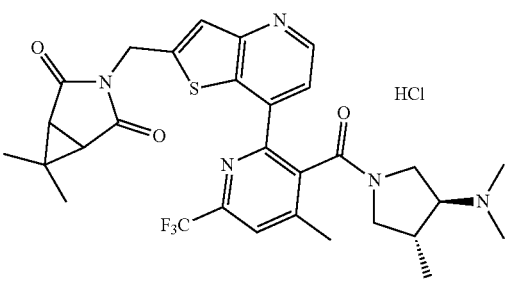 | 3-((7-(3-((3S,4R)-3-(dimethylamino)-4-methylpyrrolidine-1-carbonyl)-4-methyl-6-(trifluoromethyl)pyridin-2-yl)thieno[3,2-b]pyridin-2-yl)methyl)-6,6-dimethyl-3-azabicyclo[3.1.0]hexane-2,4-dione hydrochloride |

| Ex. No. | Structure | IUPAC Name |
|---|---|---|
| 173. | 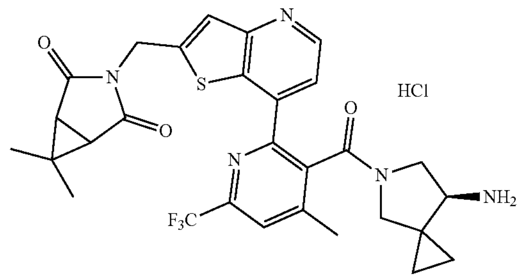 [SMILES: Cc1cc(C(F)(F)F)nc(-c2ccnc3cc(CN4C(=O)C5C(C4=O)C5(C)C)sc23)c1C(=O)N1C[C@@H](N)C2(CC2)C1 ; Cl] | 3-((7-(3-((S)-7-amino-5-azaspiro[2.4]heptane-5-carbonyl)-4-methyl-6-(trifluoromethyl)pyridin-2-yl)thieno[3,2-b]pyridin-2-yl)methyl)-6,6-dimethyl-3-azabicyclo[3.1.0]hexane-2,4-dione hydrochloride |
| 174. | 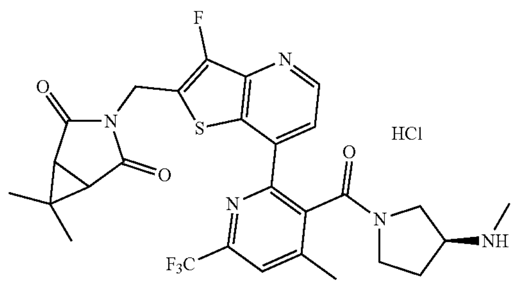 | 3-((3-fluoro-7-(4-methyl-3-((S)-3-(methylamino)pyrrolidine-1-carbonyl)-6-(trifluoromethyl)pyridin-2-yl)thieno[3,2-b]pyridin-2-yl)methyl)-6,6-dimethyl-3-azabicyclo[3.1.0]hexane-2,4-dione hydrochloride |
| 175. | 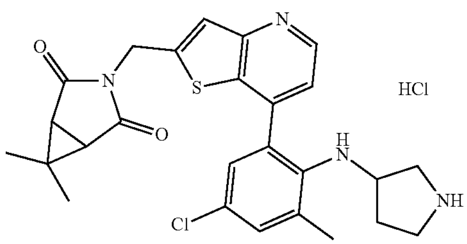 [SMILES: Cc1cc(Cl)cc(-c2ccnc3cc(CN4C(=O)C5C(C4=O)C5(C)C)sc23)c1NC1CCNC1 ; Cl] | 3-((7-(5-chloro-3-methyl-2-(pyrrolidin-3-ylamino)phenyl)thieno[3,2-b]pyridin-2-yl)methyl)-6,6-dimethyl-3-azabicyclo[3.1.0]hexane-2,4-dione hydrochloride |
| 176. | 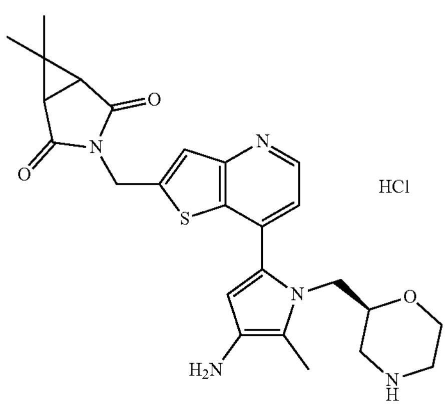 [SMILES: Cc1c(N)cc(-c2ccnc3cc(CN4C(=O)C5C(C4=O)C5(C)C)sc23)n1C[C@@H]1CNCCO1 ; Cl] | 3-((7-(4-amino-5-methyl-1-(((S)-morpholin-2-yl)methyl)-1H-pyrrol-2-yl)thieno[3,2-b]pyridin-2-yl)methyl)-6,6-dimethyl-3-azabicyclo[3.1.0]hexane-2,4-dione hydrochloride |

| Ex. No. | Structure | IUPAC Name |
|---|---|---|
| 177. | 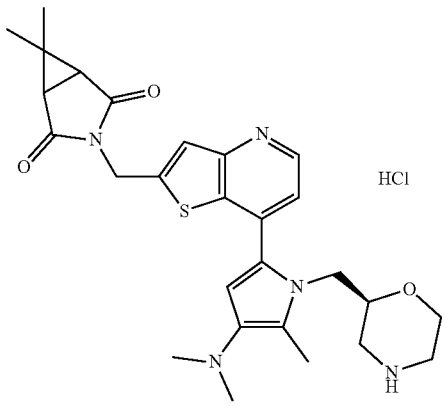 [SMILES: Cc1c(N(C)C)cc(-c2ccnc3cc(CN4C(=O)C5C(C4=O)C5(C)C)sc23)n1C[C@@H]1CNCCO1 ; Cl] | 3-((7-(4-(dimethylamino)-5-methyl-1-(((S)-morpholin-2-yl)methyl)-1H-pyrrol-2-yl)thieno[3,2-b]pyridin-2-yl)methyl)-6,6-dimethyl-3-azabicyclo[3.1.0]hexane-2,4-dione hydrochloride |
| 178. | 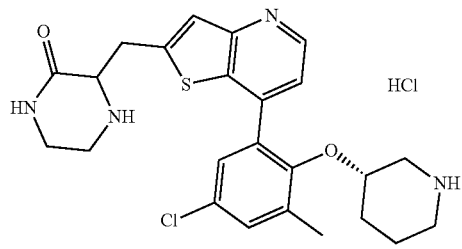 [SMILES: Cc1cc(Cl)cc(-c2ccnc3cc(CC4NCCNC4=O)sc23)c1O[C@H]1CCCNC1 ; Cl] | 3-((7-(5-chloro-3-methyl-2-(((S)-piperidin-3-yl)oxy)phenyl)thieno[3,2-b]pyridin-2-yl)methyl)piperazin-2-one hydrochloride |
| 179. | 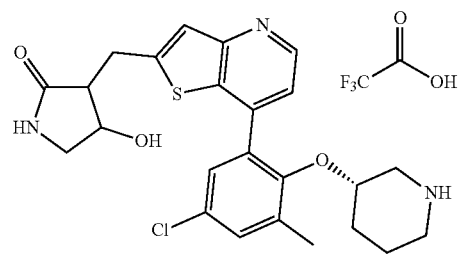 A single diastereoisomer | 3-((7-(5-chloro-3-methyl-2-(((S)-piperidin-3-yl)oxy)phenyl)thieno[3,2-b]pyridin-2-yl)methyl)-4-hydroxypyrrolidin-2-one 2,2,2-trifluoroacetate |
| 180. | 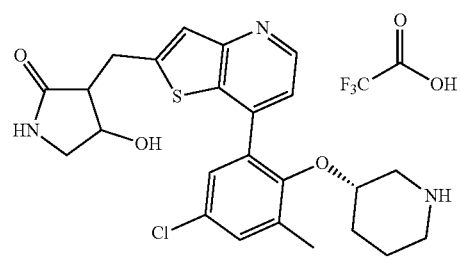 A single diastereoisomer | 3-((7-(5-chloro-3-methyl-2-(((S)-piperidin-3-yl)oxy)phenyl)thieno[3,2-b]pyridin-2-yl)methyl)-4-hydroxypyrrolidin-2-one 2,2,2-trifluoroacetate |
| 181. | 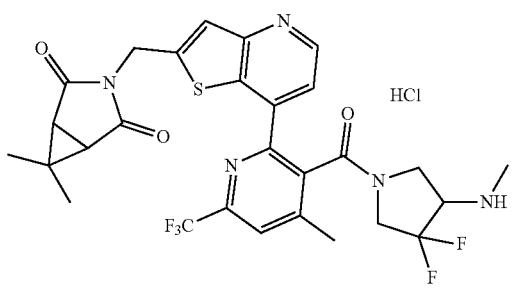 | 3-((7-(3-(3,3-difluoro-4-(methylamino)pyrrolidine-1-carbonyl)-4-methyl-6-(trifluoromethyl)pyridin-2-yl)thieno[3,2-b]pyridin-2-yl)methyl)-6,6-dimethyl-3-azabicyclo[3.1.0]hexane-2,4-dione hydrochloride |

Pharmaceutical Compositions of the Invention

In another aspect, the invention provides a pharmaceutical composition comprising (i) a therapeutically effective amount of at least one compound according to the invention, or a pharmaceutically acceptable salt, solvate, or polymorph thereof; and (ii) a pharmaceutically acceptable carrier, vehicle or excipient therefor. In general, pharmaceutical compositions comprise (i) a therapeutically effective amount of at least one compound of the invention, or a tautomer, stereoisomer, pharmaceutically acceptable salt, and/or a solvate thereof; and (ii) a pharmaceutically acceptable carrier, vehicle or excipient therefor, including, but not limited to, bioavailability enhancers, penetration enhancers, biopolymers, PLGA-based nanoparticles, sugar-based nanoparticles, coating to avoid the deleterious effects of the stomach environment, either by protection of the compound of the invention or derivative thereof, or by release of the biologically active material beyond the stomach environment, such as in the intestine.

The exact nature of the carrier, or, for example excipient or diluent, will depend upon the desired use for the composition, and may be suitable or acceptable for veterinary use and/or suitable or acceptable for human use. The composition may optionally include one or more additional compounds, including one or more additional therapeutic agents.

Compounds of the invention can be combined with other therapeutic agents. The compound of the invention and other therapeutic agent may be administered simultaneously or sequentially. When the other therapeutic agents are administered simultaneously, they can be administered in the same or separate formulations, but they are administered substantially at the same time. The other therapeutic agents are administered sequentially with one another and with compound of the invention, when the administration of the other therapeutic agents and the compound of the invention is temporally separated. The separation in time between the administration of these compounds may be a matter of minutes or it may be longer.

Examples of other therapeutic agents that may be administered with the compounds of the invention include steroids, membrane stabilizers, 5LO inhibitors, leukotriene synthesis and receptor inhibitors, inhibitors of IgE isotype switching or IgE synthesis, IgG isotype switching or IgG synthesis, β-agonists, tryptase inhibitors, aspirin, COX inhibitors, methotrexate, anti-TNF drugs, rituximab, p38 inhibitors, PDE4 inhibitors, and antihistamines, immunotherapeutic agents, including checkpoint inhibitors such as PD-1, PD-L1, CTLA-4, LAG-3, TIM-3, TIGIT, VISTA inhibitors, IDO/TDO inhibitors, Arg1 and Arg2 inhibitors, adenosine A2A receptor antagonists, ectonucleotidase (CD73 and CD39) inhibitors, immunosuppressants, agents affecting interleukins, cytokines and chemokines, kinase inhibitors, chemotherapeutic agents including alkylating antineoplastic agents, antimetabolites, anti-microtubule agents, topoisomerase inhibitors, cytotoxic antibiotics or targeted therapies such as antibodies, antibodies drug conjugates, cell-based immunotherapies, nanoparticles, anticancer vaccines and radiotherapy.

In some embodiments, the one or more additional chemotherapeutic agents includes aminoglutethimide, amsacrine, anastrozole, asparaginase, AZD5363, *Bacillus* Calmette-Guerin vaccine (BCG), bicalutamide, bleomycin, bortezomib, buserelin, busulfan, camptothecin, capecitabine, carboplatin, carfilzomib, carmustine, chlorambucil, chloroquine, cisplatin, cladribine, clodronate, cobimetinib, colchicine, cyclophosphamide, cyproterone, cytarabine, dacarbazine, dactinomycin, daunorubicin, demethoxyviridin, dexamethasone, dichloroacetate, dienestrol, diethylstilbestrol, docetaxel, doxorubicin, epirubicin, erlotinib, estradiol, estramustine, etoposide, everolimus, exemestane, filgrastim, fludarabine, fludrocortisone, fluorouracil, fluoxymesterone, flutamide, gemcitabine, genistein, goserelin, hydroxyurea, idarubicin, ifosfamide, imatinib, interferon, irinotecan, lenalidomide, letrozole, leucovorin, leuprolide, levamisole, lomustine, lonidamine, mechlorethamine, medroxyprogesterone, megestrol, melphalan, mercaptopurine, mesna, metformin, methotrexate, miltefosine, mitomycin, mitotane, mitoxantrone, MK-2206, nilutamide, nocodazole, octreotide, olaparib, oxaliplatin, paclitaxel, pamidronate, pazopanib, pentostatin, perifosine, plicamycin, pomalidomide, porfimer, procarbazine, raltitrexed, rituximab, rucaparib, selumetinib, sorafenib, streptozocin, sunitinib, suramin, talazoparib, tamoxifen, temozolomide, temsirolimus, teniposide, testosterone, thalidomide, thioguanine, thiotepa, titanocene dichloride, topotecan, trametinib, trastuzumab, tretinoin, veliparib, vinblastine, vincristine, vindesine, or vinorelbine.

In some embodiments, the one or more additional chemotherapeutic agents include abagovomab, adecatumumab, afutuzumab, anatumomab mafenatox, apolizumab, avelumab, blinatumomab, catumaxomab, durvalumab, epratuzumab, inotuzumab ozogamicin, intelumumab, ipilimumab, isatuximab, lambrolizumab, nivolumab, ocaratuzumab, olatatumab, pembrolizumab, pidilizumab, ticilimumab, samalizumab, tremelimumab, and BMS-936559.

In other embodiments, the method further comprises administering one or more non-chemical methods of cancer treatment, such as radiation therapy, surgery, thermoablation, focused ultrasound therapy, cryotherapy, or a combination thereof.

As stated above, an "effective amount" refers to any amount that is sufficient to achieve a desired biological effect. Combined with the teachings provided herein, by choosing among the various active compounds and weighing factors such as potency, relative bioavailability, patient body weight, severity of adverse side-effects and preferred mode of administration, an effective prophylactic or therapeutic treatment regimen can be planned which does not cause substantial unwanted toxicity and yet is effective to treat the particular subject. The effective amount for any particular application can vary depending on such factors as the disease or condition being treated, the particular compound of the invention being administered, the size of the subject, or the severity of the disease or condition. One of ordinary skill in the art can empirically determine the effective amount of a particular compound of the invention and/or other therapeutic agent without necessitating undue experimentation. It is preferred generally that a maximum dose be used, that is, the highest safe dose according to some medical judgment. Multiple doses per day may be contemplated to achieve appropriate systemic levels of compounds. Appropriate systemic levels can be determined by, for example, measurement of the patient's peak or sustained plasma level of the drug. "Dose" and "dosage" are used interchangeably herein.

Generally, daily oral doses of active compounds will be, for human subjects, from about 0.0001 milligrams/kg per day, 0.001 milligrams/kg per day, or 0.01 milligrams/kg per day to about 100 milligrams/kg per day or 1000 milligrams/kg per day. It is expected that oral doses in the range of 0.5 to 50 milligrams/kg, in one or several administrations per day, will yield the desired results. Dosage may be adjusted appropriately to achieve desired drug levels sufficient to achieve or maintain a desired therapeutic effect, local or systemic, depending upon the mode of administration. For example, it is expected that intravenous administration would be from one order to several orders of magnitude lower dose per day. In the event that the response in a subject is insufficient at such doses, even higher doses (or effective higher doses by a different, more localized delivery route) may be employed to the extent that patient tolerance permits. Multiple doses per day are contemplated to achieve appropriate systemic levels of compounds. The compounds may be administered once per week, several times per week (e.g., every other day), once per day or multiple times per day, depending upon, among other things, the mode of administration, the specific indication being treated and the judgment of the prescribing physician.

In one embodiment, intravenous administration of a compound of the invention may typically be from 0.1 mg/kg/day to 20 mg/kg/day.

Determination of an effective dosage of a compound for a particular use and mode of administration is well within the capabilities of those skilled in the art. Effective dosages may be estimated initially from in vitro activity and metabolism assays. For example, an initial dosage of compound for use in animals may be formulated to achieve a circulating blood or serum concentration of the metabolite active compound that is at or above an $IC_{50}$ of the particular compound as measured in as in vitro assay. Calculating dosages to achieve such circulating blood or serum concentrations taking into account the bioavailability of the particular compound via the desired route of administration is well within the capabilities of skilled artisans. Initial dosages of compound can also be estimated from in vivo data, such as animal models. For any compound described herein the therapeutically effective amount can be initially determined from animal models. A therapeutically effective dose can also be determined from human data for compounds of the invention which have been tested in humans and for compounds which are known to exhibit similar pharmacological activities, such as other related active agents. Higher doses may be required for parenteral administration. The applied dose can be adjusted based on the relative bioavailability and potency of the administered compound. Adjusting the dose to achieve maximal efficacy based on the methods described above and other methods as are well-known in the art is well within the capabilities of the ordinarily skilled artisan.

The formulations of the invention can be administered in pharmaceutically acceptable solutions, which may routinely contain pharmaceutically acceptable concentrations of salt, buffering agents, preservatives, compatible carriers, adjuvants, and optionally other therapeutic ingredients.

Pharmaceutical compositions comprising the compound of the invention may be manufactured by means of conventional mixing, dissolving, granulating, dragée-making levigating, emulsifying, encapsulating, entrapping or lyophilization processes. The compositions may be formulated in conventional manner using one or more physiologically acceptable carriers, diluents, excipients or auxiliaries which facilitate processing of the compounds into preparations which can be used pharmaceutically.

For use in therapy, an effective amount of the compound of the invention can be administered to a subject by any mode that delivers the compound of the invention to the desired surface. Administering the pharmaceutical composition of the present invention may be accomplished by any means known to the skilled artisan. Routes of administration include but are not limited to oral, buccal, nasal, rectal, vaginal, ocular, topical, intravenous, intramuscular, intraperitoneal, subcutaneous, transdermal, direct injection (for example, into an abscess), mucosal, inhalation, and insufflation.

For oral administration, the compounds (i.e., compounds of the invention, and other therapeutic agents) can be formulated readily by combining the active compound(s) with pharmaceutically acceptable carriers well known in the art. Such carriers enable the compounds of the invention to be formulated as tablets, pills, dragées, lozenges, capsules, liquids, gels, syrups, slurries, suspensions and the like, for oral ingestion by a subject to be treated. Pharmaceutical preparations for oral use can be obtained as solid excipient, optionally grinding a resulting mixture, and processing the mixture of granules, after adding suitable auxiliaries, if desired, to obtain tablets or dragée cores. Suitable excipients are, in particular, binding agents, fillers, lubricants, disintegrants, and wetting agents. Suitable fillers include sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate. Optionally the oral formulations may also be formulated in saline or buffers, e.g., EDTA for neutralizing internal acid conditions or may be administered without any carriers.

Also specifically contemplated are oral dosage forms of the above component or components. The component or components may be chemically modified so that oral delivery of the derivative is efficacious. Generally, the chemical modification contemplated is the attachment of at least one moiety to the component molecule itself, where said moiety permits (a) inhibition of acid hydrolysis; and (b) uptake into the blood stream from the stomach or intestine. Also desired is the increase in overall stability of the component or components and increase in circulation time in the body. Examples of such moieties include: polyethylene glycol, copolymers of ethylene glycol and propylene glycol, carboxymethyl cellulose, dextran, polyvinyl alcohol, polyvinyl pyrrolidone and polyproline. Abuchowski and Davis, "*Soluble Polymer-Enzyme Adducts*", In: Enzymes as Drugs, Hocenberg and Roberts, eds., Wiley-Interscience, New York, N.Y., pp. 367-383 (1981); Newmark et al., *J Appl Biochem* 4:185-9 (1982). Other polymers that could be used are poly-1,3-dioxolane and poly-1,3,6-tioxocane. Preferred for pharmaceutical usage, as indicated above, are polyethylene glycol moieties.

For the component (or derivative) the location of release may be the stomach, the small intestine (the duodenum, the jejunum, or the ileum), or the large intestine. One skilled in the art has available formulations which will not dissolve in the stomach, yet will release the material in the duodenum or elsewhere in the intestine. Preferably, the release will avoid the deleterious effects of the stomach environment, either by protection of the compound of the invention (or derivative) or by release of the biologically active material beyond the stomach environment, such as in the intestine.

To ensure full gastric resistance a coating impermeable to at least pH 5.0 is essential. Examples of the more common inert ingredients that are used as enteric coatings are cellulose acetate trimellitate (CAT), hydroxypropylmethylcellulose phthalate (HPMCP), HPMCP 50, HPMCP 55, polyvinyl acetate phthalate (PVAP), Eudragit L30D, Aquateric, cellulose acetate phthalate (CAP), Eudragit L, Eudragit S, and shellac. These coatings may be used as mixed films.

A coating or mixture of coatings can also be used on tablets, which are not intended for protection against the stomach. This can include sugar coatings, or coatings which make the tablet easier to swallow. Capsules may consist of a hard shell (such as gelatin) for delivery of dry therapeutic (e.g., powder), for liquid forms, a soft gelatin shell may be used. The shell material of cachets could be thick starch or other edible paper. For pills, lozenges, molded tablets or tablet triturates, moist massing techniques can be used.

The therapeutic can be included in the formulation as fine multi-particulates in the form of granules or pellets of particle size about 1 mm. The formulation of the material for capsule administration could also be as a powder, lightly compressed plugs or even as tablets. The therapeutic could be prepared by compression.

Colorants and flavoring agents may all be included. For example, the compound of the invention (or derivative) may be formulated (such as by liposome or microsphere encapsulation) and then further contained within an edible product, such as a refrigerated beverage containing colorants and flavoring agents.

One may dilute or increase the volume of the therapeutic with an inert material. These diluents could include carbohydrates, especially mannitol, α-lactose, anhydrous lactose, cellulose, sucrose, modified dextrans and starch. Certain inorganic salts may be also be used as fillers including calcium triphosphate, magnesium carbonate and sodium chloride. Some commercially available diluents are Fast-Flo, Emdex, STA-Rx 1500, Emcompress and Avicell.

Disintegrants may be included in the formulation of the therapeutic into a solid dosage form. Materials used as disintegrates include but are not limited to starch, including the commercial disintegrant based on starch, Explotab. Sodium starch glycolate. Amberlite, sodium carboxymethylcellulose, ultramylopectin, sodium alginate, gelatin, orange peel, acid carboxymethyl cellulose, natural sponge and bentonite may all be used. Another form of the disintegrants are the insoluble cationic exchange resins. Powdered gums may be used as disintegrants and as binders and these can include powdered gums such as agar, Karaya or tragacanth. Alginic acid and its sodium salt are also useful as disintegrants.

Binders may be used to hold the therapeutic agent together to form a hard tablet and include materials from natural products such as acacia, tragacanth, starch and gelatin. Others include methyl cellulose (MC), ethyl cellulose (EC) and carboxymethyl cellulose (CMC). Polyvinyl pyrrolidone (PVP) and hydroxypropylmethyl cellulose (HPMC) could both be used in alcoholic solutions to granulate the therapeutic.

An anti-frictional agent may be included in the formulation of the therapeutic to prevent sticking during the formulation process. Lubricants may be used as a layer between the therapeutic and the die wall, and these can include but are not limited to; stearic acid including its magnesium and calcium salts, polytetrafluoroethylene (PTFE), liquid paraffin, vegetable oils and waxes. Soluble lubricants may also be used such as sodium lauryl sulfate, magnesium lauryl sulfate, polyethylene glycol of various molecular weights, Carbowax 4000 and 6000.

Glidants that might improve the flow properties of the drug during formulation and to aid rearrangement during compression might be added. The glidants may include starch, talc, pyrogenic silica and hydrated silicoaluminate.

To aid dissolution of the therapeutic into the aqueous environment a surfactant might be added as a wetting agent. Surfactants may include anionic detergents such as sodium lauryl sulfate, dioctyl sodium sulfosuccinate and dioctyl sodium sulfonate. Cationic detergents which can be used and can include benzalkonium chloride and benzethonium chloride. Potential non-ionic detergents that could be included in the formulation as surfactants include lauromacrogol 400, polyoxyl 40 stearate, polyoxyethylene hydrogenated castor oil 10, 50 and 60, glycerol monostearate, polysorbate 40, 60, 65 and 80, sucrose fatty acid ester, methyl cellulose and carboxymethyl cellulose. These surfactants could be present in the formulation of the compound of the invention or derivative either alone or as a mixture in different ratios.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. Microspheres formulated for oral administration may also be used. Such microspheres have been well defined in the art. All formulations for oral administration should be in dosages suitable for such administration.

Liquid preparations for oral administration may take the form of, for example, elixirs, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol, or fractionated vegetable oils); and preservatives (e.g., methyl or propyl-p-hydroxybenzoates or sorbic acid). The preparations may also contain buffer salts, preservatives, flavoring, coloring and sweetening agents as appropriate.

The pharmaceutical compositions may, if desired, be presented in a pack or dispenser device which may contain one or more unit dosage forms containing the compound(s). The pack may, for example, comprise metal or plastic foil, such as a blister pack. The pack or dispenser device may be accompanied by instructions for administration.

For buccal administration, the compositions may take the form of tablets or lozenges formulated in conventional manner.

For topical administration, the compound may be formulated as solutions, gels, ointments, creams, suspensions, etc. as are well-known in the art. Systemic formulations include those designed for administration by injection, e.g., subcutaneous, intravenous, intramuscular, intrathecal or intraperitoneal injection, as well as those designed for transdermal, transmucosal, oral or pulmonary administration.

For administration by inhalation, the compounds for use according to the present invention may be conveniently delivered in the form of an aerosol spray presentation from pressurized packs or a nebulizer, with the use of a suitable propellant, e.g., dichlorodifluoro-methane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g., gelatin for use in an inhaler or insufflator may be formulated containing a powder mix of the compound and a suitable powder base such as lactose or starch.

Also contemplated herein is pulmonary delivery of the compounds of the invention (or derivatives thereof). The compound of the invention (or derivative) is delivered to the lungs of a mammal while inhaling and traverses across the lung epithelial lining to the blood stream. Other reports of inhaled molecules include Adjei et al., *Pharm Res* 7:565-569 (1990); Adjei et al., *Int J Pharmaceutics* 63:135-144 (1990) (leuprolide acetate); Braquet et al., *J Cardiovasc Pharmacol* 13(suppl. 5):143-146 (1989) (endothelin-1); Hubbard et al., *Annal Int Med* 3:206-212 (1989) (α1-antitrypsin); Smith et al., 1989, *J Clin Invest* 84:1145-1146 (a-1-proteinase); Oswein et al., 1990, "Aerosolization of Proteins", Proceedings of Symposium on Respiratory Drug Delivery II, Keystone, Colorado, March, (recombinant human growth hormone); Debs et al., 1988, *J Immunol* 140:3482-3488 (interferon-gamma and tumor necrosis factor alpha) and Platz et al., U.S. Pat. No. 5,284,656 (granulocyte colony stimulating factor). A method and composition for pulmonary delivery of drugs for systemic effect is described in U.S. Pat. No. 5,451,569, issued Sep. 19, 1995 to Wong et al.

Contemplated for use in the practice of this invention are a wide range of mechanical devices designed for pulmonary delivery of therapeutic products, including but not limited to nebulizers, metered dose inhalers, and powder inhalers, all of which are familiar to those skilled in the art.

Some specific examples of commercially available devices suitable for the practice of this invention are the Ultravent nebulizer, manufactured by Mallinckrodt, Inc., St. Louis, Mo.; the Acorn II nebulizer, manufactured by Marquest Medical Products, Englewood, Colo.; the Ventolin metered dose inhaler, manufactured by Glaxo Inc., Research Triangle Park, North Carolina; and the Spinhaler powder inhaler, manufactured by Fisons Corp., Bedford, Mass.

All such devices require the use of formulations suitable for the dispensing of compound of the invention (or derivative). Typically, each formulation is specific to the type of device employed and may involve the use of an appropriate propellant material, in addition to the usual diluents, adjuvants and/or carriers useful in therapy. Also, the use of liposomes, microcapsules or microspheres, inclusion complexes, or other types of carriers is contemplated. Chemically modified compound of the invention may also be prepared in different formulations depending on the type of chemical modification or the type of device employed.

Formulations suitable for use with a nebulizer, either jet or ultrasonic, will typically comprise compound of the invention (or derivative) dissolved in water at a concentration of about 0.1 to 25 mg of biologically active compound of the invention per mL of solution. The formulation may also include a buffer and a simple sugar (e.g., for compound of the invention stabilization and regulation of osmotic pressure). The nebulizer formulation may also contain a surfactant, to reduce or prevent surface induced aggregation of the compound of the invention caused by atomization of the solution in forming the aerosol.

Formulations for use with a metered-dose inhaler device will generally comprise a finely divided powder containing the compound of the invention (or derivative) suspended in a propellant with the aid of a surfactant. The propellant may be any conventional material employed for this purpose, such as a chlorofluorocarbon, a hydrochlorofluorocarbon, a hydrofluorocarbon, or a hydrocarbon, including trichlorofluoromethane, dichlorodifluoromethane, dichlorotetrafluoroethanol, and 1,1,2-tetrafluoroethane, or combinations thereof. Suitable surfactants include sorbitan trioleate and soya lecithin. Oleic acid may also be useful as a surfactant.

Formulations for dispensing from a powder inhaler device will comprise a finely divided dry powder containing compound of the invention (or derivative) and may also include a bulking agent, such as lactose, sorbitol, sucrose, or mannitol in amounts which facilitate dispersal of the powder from the device, e.g., 50 to 90% by weight of the formulation. The compound of the invention (or derivative) should advantageously be prepared in particulate form with an average particle size of less than 10 micrometers (μm), most preferably 0.5 to 5 μm, for most effective delivery to the deep lung.

Nasal delivery of a pharmaceutical composition of the present invention is also contemplated. Nasal delivery allows the passage of a pharmaceutical composition of the present invention to the blood stream directly after administering the therapeutic product to the nose, without the necessity for deposition of the product in the lung. Formulations for nasal delivery include those with dextran or cyclodextran.

For nasal administration, a useful device is a small, hard bottle to which a metered dose sprayer is attached. In one embodiment, the metered dose is delivered by drawing the pharmaceutical composition of the present invention solution into a chamber of defined volume, which chamber has an aperture dimensioned to aerosolize and aerosol formulation by forming a spray when a liquid in the chamber is compressed. The chamber is compressed to administer the pharmaceutical composition of the present invention. In a specific embodiment, the chamber is a piston arrangement. Such devices are commercially available.

Alternatively, a plastic squeeze bottle with an aperture or opening dimensioned to aerosolize an aerosol formulation by forming a spray when squeezed is used. The opening is usually found in the top of the bottle, and the top is generally tapered to partially fit in the nasal passages for efficient administration of the aerosol formulation. Preferably, the nasal inhaler will provide a metered amount of the aerosol formulation, for administration of a measured dose of the drug.

The compounds, when it is desirable to deliver them systemically, may be formulated for parenteral administration by injection, e.g., by bolus injection or continuous infusion. Formulations for injection may be presented in unit dosage form, e.g., in ampoules or in multi-dose containers, with an added preservative. The compositions may take such forms as sterile suspensions, solutions, or emulsions in oily or aqueous vehicles, and may contain formulatory agents such as suspending, stabilizing and/or dispersing agents.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethylcellulose, sorbitol, or dextran. Optionally, the suspension may also contain suitable stabilizers or agents which increase the solubility of the compounds to allow for the preparation of highly concentrated solutions.

Alternatively, the active compounds may be in powder form for constitution with a suitable vehicle, e.g., sterile pyrogen-free water, buffer, dextrose solution, before use. To this end, the active compound may be dried by any art-known technique, such as lyophilization, and reconstituted prior to use.

The compounds may also be formulated in rectal or vaginal compositions such as suppositories or retention enemas. e.g., containing conventional suppository bases such as cocoa butter or other glycerides.

For transmucosal administration, penetrants appropriate to the barrier to be permeated are used in the formulation. Such penetrants are known in the art.

For ocular administration, the compound(s) may be formulated as a solution, emulsion, suspension, etc. suitable for administration to the eye. A variety of vehicles suitable for administering compounds to the eye are known in the art.

In addition to the formulations described above, for prolonged delivery, the compounds may also be formulated as a depot preparation for administration by, for example, implantation or intramuscular injection. Such long acting formulations may be formulated with suitable polymeric or hydrophobic materials (for example as an emulsion in an acceptable oil) or ion exchange resins, or as sparingly soluble derivatives, for example, as a sparingly soluble salt. Alternatively, transdermal delivery systems manufactured as an adhesive disc or patch which slowly releases the compound for percutaneous absorption may be used. To this end, permeation enhancers may be used to facilitate transdermal penetration of the compound.

The pharmaceutical compositions also may comprise suitable solid or gel phase carriers or excipients. Examples of such carriers or excipients include but are not limited to calcium carbonate, calcium phosphate, various sugars, starches, cellulose derivatives, gelatin, and polymers such as polyethylene glycols.

Suitable liquid or solid pharmaceutical preparation forms are, for example, aqueous or saline solutions for inhalation, microencapsulated, encochleated, coated onto microscopic gold particles, contained in liposomes, nebulized, aerosols, pellets for implantation into the skin, or dried onto a sharp object to be scratched into the skin. The pharmaceutical compositions also include granules, powders, tablets, coated tablets, (micro)capsules, suppositories, syrups, emulsions, suspensions, creams, drops or preparations with protracted release of active compounds, in whose preparation excipients and additives and/or auxiliaries such as disintegrants, binders, coating agents, swelling agents, lubricants, flavorings, sweeteners or solubilizers are customarily used as described above. The pharmaceutical compositions are suitable for use in a variety of drug delivery systems. For a brief review of methods for drug delivery, see Langer R, *Science* 249:1527-33 (1990), which is incorporated herein by reference.

The compounds of the invention and optionally other therapeutics may be administered per se (neat) or in the form of a pharmaceutically acceptable salt. When used in medicine the salts should be pharmaceutically acceptable, but non-pharmaceutically acceptable salts may conveniently be used to prepare pharmaceutically acceptable salts thereof. Such salts include, but are not limited to, those prepared from the following acids: hydrochloric, hydrobromic, sulfuric, nitric, phosphoric, maleic, acetic, salicylic, p-toluenesulfonic, tartaric, citric, methane sulfonic, formic, malonic, succinic, naphthalene-2-sulfonic, and benzenesulfonic. Also, such salts can be prepared as alkaline metal or alkaline earth salts, such as sodium, potassium or calcium salts of the carboxylic acid group. Typically, such salts are more soluble in aqueous solutions than the corresponding free acids and bases, but salts having lower solubility than the corresponding free acids and bases may also be formed.

The compounds may alternatively be formulated in the pharmaceutical composition per se, or in the form of a hydrate, solvate, or N-oxide.

Suitable buffering agents include: acetic acid and a salt (1-2% w/v); citric acid and a salt (1-3% w/v); boric acid and a salt (0.5-2.5% w/v); and phosphoric acid and a salt (0.8-2% w/v). Suitable preservatives include benzalkonium chloride (0.003-0.03% w/v); chlorobutanol (0.3-0.9% w/v); parabens (0.01-0.25% w/v) and thimerosal (0.004-0.02% w/v).

Pharmaceutical compositions of the invention contain an effective amount of a compound of the invention and optionally therapeutic agents included in a pharmaceutically acceptable carrier. The term "pharmaceutically acceptable carrier" means one or more compatible solid or liquid filler, diluents or encapsulating substances which are suitable for administration to a human or other vertebrate animal. The term "carrier" denotes an organic or inorganic ingredient, natural or synthetic, with which the active ingredient is combined to facilitate the application. The components of the pharmaceutical compositions also are capable of being commingled with the compounds of the present invention, and with each other, in a manner such that there is no interaction which would substantially impair the desired pharmaceutical efficiency.

The therapeutic agent(s), including specifically but not limited to the compound of the invention, may be provided in particles. Particles as used herein means nanoparticles or microparticles (or in some instances larger particles) which can consist in whole or in part of the compound of the invention or the other therapeutic agent(s) as described herein. The particles may contain the therapeutic agent(s) in a core surrounded by a coating, including, but not limited to, an enteric coating. The therapeutic agent(s) also may be dispersed throughout the particles. The therapeutic agent(s) also may be adsorbed into the particles. The particles may be of any order release kinetics, including zero-order release, first-order release, second-order release, delayed release, sustained release, immediate release, and any combination thereof, etc. The particle may include, in addition to the therapeutic agent(s), any of those materials routinely used in the art of pharmacy and medicine, including, but not limited to, erodible, non-erodible, biodegradable, or non-biodegradable material or combinations thereof. The particles may be microcapsules which contain the compound of the invention in a solution or in a semi-solid state. The particles may be of virtually any shape.

Both non-biodegradable and biodegradable polymeric materials can be used in the manufacture of particles for delivering the therapeutic agent(s). Such polymers may be natural or synthetic polymers. The polymer is selected based on the period of time over which release is desired. Bioadhesive polymers of particular interest include bio-erodible hydrogels described in Sawhney H S et al. (1993) *Macromolecules* 26:581-7, the teachings of which are incorporated herein. These include polyhyaluronic acids, casein, gelatin, glutin, polyanhydrides, polyacrylic acid, alginate, chitosan, poly(methyl methacrylates), poly(ethyl methacrylates), poly (butylmethacrylate), poly(isobutyl methacrylate), poly (hexyl methacrylate), poly(isodecyl methacrylate), poly(lauryl methacrylate), poly(phenyl methacrylate), poly(methyl acrylate), poly(isopropyl acrylate), poly(isobutyl acrylate), and poly(octadecyl acrylate).

The therapeutic agent(s) may be contained in controlled release systems. The term "controlled release" is intended to refer to any drug-containing formulation in which the manner and profile of drug release from the formulation are controlled. This refers to immediate as well as non-immediate release formulations, with non-immediate release formulations including but not limited to sustained release and delayed release formulations. The term "sustained release" (also referred to as "extended release") is used in its conventional sense to refer to a drug formulation that provides for gradual release of a drug over an extended period of time, and that preferably, although not necessarily, results in substantially constant blood levels of a drug over an extended time period. The term "delayed release" is used in its conventional sense to refer to a drug formulation in which there is a time delay between administration of the formulation and the release of the drug there from. "Delayed release" may or may not involve gradual release of drug over an extended period of time, and thus may or may not be "sustained release."

Use of a long-term sustained release implant may be particularly suitable for treatment of chronic conditions. "Long-term" release, as used herein, means that the implant is constructed and arranged to deliver therapeutic levels of the active ingredient for at least 7 days, and preferably 30-60 days. Long-term sustained release implants are well-known to those of ordinary skill in the art and include some of the release systems described above.

It will be understood by one of ordinary skill in the relevant arts that other suitable modifications and adaptations to the compositions, methods, and uses described herein are readily apparent from the description of the invention contained herein in view of information known to the ordinarily skilled artisan, and may be made without departing from the scope of the invention or any embodiment thereof.

Methods and Uses

As shown herein, the compounds of the invention are useful for inhibiting the enzymatic and biological activity of ubiquitin specific protease 7.

Another aspect of the invention is a method for inhibiting USP7 in a cell or a tissue, comprising contacting the cell or the tissue with at least one compound according to the invention, or a pharmaceutically acceptable salt, solvate, or polymorph thereof, or with a pharmaceutical composition according to the invention.

In another aspect, the invention provides a method for the treatment or prevention of a disease, disorder, or condition associated with aberrant expression or activity of USP7, comprising administering to the subject in need thereof a therapeutically effective amount of at least one compound according to the invention, or a pharmaceutically acceptable salt, solvate, or polymorph thereof, or a pharmaceutical composition according to the invention.

In certain embodiments, the disease, disorder, or condition is selected from the group consisting of cardiovascular disorders, pulmonary disorders, autoimmune disorders, immune disorders, immunoregulatory disorders, neurodegenerative disorders, metabolic disorders, hemolytic disorders, gastrointestinal disorders, sexual disorders, infections, wound healing disorders, and cancers.

In certain embodiments, the invention provides a compound of Formula (I), (Ia), (Ib), or (Ic) for use in a method for inhibiting USP7 in a cell or a tissue, comprising contacting the cell or the tissue with at least one such compound, or a pharmaceutically acceptable salt, solvate, or polymorph thereof.

In some aspects, the invention provides use of a compound according to the invention, or a pharmaceutically acceptable salt, solvate, or polymorph thereof, in the manufacturing of a medicament for the treatment of a disease, disorder, or condition associated with expression of USP7.

Additionally, the invention provides a compound according to the invention, or a pharmaceutically acceptable salt, solvate, or polymorph thereof, for use in a method for the treatment or prevention of a disease, disorder, or condition associated with aberrant expression or activity of USP7, comprising administering to the subject in need thereof a therapeutically effective amount of at least one compound according to the invention, or a pharmaceutically acceptable salt, solvate, or polymorph thereof, or a pharmaceutical composition according to the invention.

In certain embodiments, the disease, disorder, or condition is selected from the group consisting of cardiovascular disorders, pulmonary disorders, autoimmune disorders, immune disorders, immunoregulatory disorders, neurodegenerative disorders, metabolic disorders, hemolytic disorders, gastrointestinal disorders, sexual disorders, infections, wound healing disorders, and cancers.

In certain embodiments, the disease, disorder, or condition is a cardiovascular disorder selected from the group consisting of systemic hypertension, pulmonary arterial hypertension (PAH), pulmonary arterial hypertension in high altitude, ischemia reperfusion (IR) injury, myocardial infarction, and atherosclerosis.

In certain embodiments, the cardiovascular disorder is pulmonary arterial hypertension (PAH).

In certain embodiments, the cardiovascular disorder is ischemia reperfusion (IR) injury selected from the group consisting of liver IR, kidney IR, and myocardial IR.

In certain embodiments, the cardiovascular disorder is myocardial infarction or atherosclerosis.

In certain embodiments, the disease, disorder, or condition is a pulmonary disorder selected from the group consisting of chemically-induced lung fibrosis, idiopathic pulmonary fibrosis, cystic fibrosis, chronic obstructive pulmonary disease (COPD), and asthma.

In certain embodiments, the disease, disorder, or condition is an autoimmune disorder selected from the group consisting of encephalomyelitis, multiple sclerosis, antiphospholipid syndrome 1, autoimmune hemolytic anemia, chronic inflammatory demyelinating polyradiculoneuropathy, psoriasis, dermatitis herpetiformis, dermatomyositis, myasthenia gravis, pemphigus, rheumatoid arthritis, stiff-person syndrome, type 1 diabetes, ankylosing spondylitis, paroxysmal nocturnal hemoglobinuria (PNH), paroxysmal cold hemoglobinuria, severe idiopathic autoimmune hemolytic anemia, and Goodpasture's syndrome.

In certain embodiments, the disease, disorder, or condition is an immune disorder selected from the group consisting of T-cell dysfunction mediated by myeloid-derived suppressor cells (MDSC), human immunodeficiency virus (HIV) infection, autoimmune encephalomyelitis, and ABO mismatch transfusion reaction.

In certain embodiments, the immune disorder is T-cell dysfunction mediated by myeloid-derived suppressor cells (MDSC).

In certain embodiments, the disease, disorder, or condition is a disease resulting from an immunoregulatory disorder selected from the group consisting of renal disease inflammation, hepatic fibrosis, leishmaniosis, neurodegenerative diseases, wound healing, human immunodeficiency virus (HIV) infection, hepatitis B virus (HBV) infection, *Helicobacter pylori* infection, fibrotic disorders, arthritis, candidiasis, periodontal disease, keloids, adenotonsilar disease, African sleeping sickness, Chagas' disease, and transplant rejection.

In certain embodiments, the disease, disorder, or condition is a neurodegenerative disorder selected from the group consisting of Alzheimer's disease, Parkinson's disease, Huntington's disease, extrapyramidal syndrome, dystonia, akathisia, epilepsy, periodic limb movement, and dementia.

In certain embodiments, the disease, disorder, or condition is a metabolic disorder selected from the group consisting of diabetes, non-alcoholic steatohepatitis (NASH), and non-alcoholic fatty liver disease (NAFLD).

In certain embodiments, the disease, disorder, or condition is a hemolytic disorder selected from the group consisting of sickle-cell disease, thalassemias, hereditary spherocytosis, stomatocytosis, microangiopathic hemolytic anemias, pyruvate kinase deficiency, infection-induced anemia, cardiopulmonary bypass, mechanical heart valve-induced anemia, and chemical-induced anemia.

In certain embodiments, the hemolytic disorder is sickle-cell disease.

In certain embodiments, the disease, disorder, or condition is a gastrointestinal disorder selected from the group consisting of gastrointestinal motility disorders, gastric cancers, inflammatory bowel disease, Crohn's disease, ulcerative colitis, and gastric ulcers.

In certain embodiments, the disease, disorder, or condition is a sexual disorder selected from the group consisting of Peyronie's disease, and erectile dysfunction.

In certain embodiments, the disease, disorder, or condition is a wound healing disorder selected from the group consisting of infected and uninfected wound healing.

In certain embodiments, the disease, disorder, or condition is a cancer selected from the group consisting of oesophagic, gastric, colon, ovary, breast, pancreatic, head-and-neck, bladder, and lung cancers (including squamous and non-small cell lung carcinoma), renal cell carcinoma, prostate carcinoma, multiple myeloma, neuroblastoma, glioblastoma, astrocytoma, mesothelioma and melanoma, B cells, T cells and NK cells lymphomas, acute and chronic, myeloid leukemia, and lymphoid leukemia.

In certain embodiments, the disease, disorder, or condition is a cancer selected from the group consisting of gastric cancer (including, but not limited to, gastric or gastroesophageal junction cancer), colorectal cancer, pancreatic cancer, liver cancer, breast cancer, lung cancers (including, but not limited to, non-small cell lung carcinoma), renal cell carcinoma, prostate carcinoma, multiple myeloma, acute and chronic leukemias, T cell, B cell and NK cell lymphomas, brain tumors (including, but not limited to, neuroblastoma, glioblastoma, astrocytoma), squamous-cell carcinomas of the head and neck, and melanoma.

In certain embodiments, the disease, disorder, or condition is a cancer selected from the group consisting of chronic lymphocytic leukemia, acute lymphoblastic leukemia, chronic myelogenous leukemia, acute myeloid leukemia, adrenocortical carcinoma, anal cancer, appendix cancer, atypical teratoid/rhabdoid tumor, basal cell carcinoma, bile duct cancer, bladder cancer, bone cancer, brain tumor, brain and spinal cord tumor, brain stem glioma, central nervous system atypical teratoid/rhabdoid tumor, central nervous system embryonal tumors, breast cancer, bronchial tumors, Burkitt lymphoma, carcinoid tumor, carcinoma of unknown primary, central nervous system cancer, cervical cancer, childhood cancers, chordoma, chronic myeloproliferative disorders, colon cancer, craniopharyngioma, cutaneous T-cell lymphoma, ductal carcinoma in situ, embryonal tumors, endometrial cancer, ependymoblastoma, ependymoma, esophageal cancer, esthesioneuroblastoma, Ewing sarcoma, extracranial germ cell tumor, extrahepatic bile duct cancer, eye cancer, fibrous histiocytoma of bone, gallbladder cancer, gastric cancer, gastrointestinal carcinoid tumor, gastrointestinal stromal tumors, germ cell tumor, extracranial germ cell tumor, extragonadal germ cell tumor, ovarian germ cell tumor, gestational trophoblastic tumor, glioma, hairy cell leukemia, head and neck cancer, heart cancer, hepatocellular cancer, histiocytosis, Langerhans cell cancer, Hodgkin's lymphoma, hypopharyngeal cancer, intraocular melanoma, islet cell tumors, Kaposi sarcoma, kidney cancer, Langerhans cell histiocytosis, laryngeal cancer, lip and oral cavity cancer, lobular carcinoma in situ, lymphoma, AIDS-related lymphoma, macroglobulinemia, male breast cancer, medulloblastoma, medulloepithelioma, Merkel cell carcinoma, malignant mesothelioma, metastatic squamous neck cancer, midline tract carcinoma involving NUT gene, mouth cancer, multiple endocrine neoplasia syndrome, plasma cell neoplasm, mycosis fungoides, myeloma, chronic myeloproliferative disorder, nasal cavity cancer, paranasal sinus cancer, nasopharyngeal cancer, non-Hodgkin's lymphoma, oral cancer, oral cavity cancer, lip cancer, oropharyngeal cancer, osteosarcoma, ovarian cancer, papillomatosis, paraganglioma, paranasal sinus cancer, nasal cavity cancer, parathyroid cancer, penile cancer, pharyngeal cancer, pheochromocytoma, pineal parenchymal tumors of intermediate differentiation, pineoblastoma, pituitary tumor, plasma cell neoplasm, pleuropulmonary blastoma, primary central nervous system lymphoma, rectal cancer, renal cell cancer, renal pelvis cancer, ureter cancer, transitional cell cancer, retinoblastoma, rhabdomyosarcoma, salivary gland cancer, sarcoma, Sézary syndrome, skin cancer, small cell lung cancer, small intestine cancer, soft tissue sarcoma, squamous cell carcinoma, squamous neck cancer with occult primary, supratentorial primitive neuroectodermal tumors, testicular cancer, throat cancer, thymoma, thymic carcinoma, thyroid cancer, transitional cell cancer of the renal pelvis and ureter, gestational trophoblastic tumor, unknown primary, unusual cancer of childhood, urethral cancer, uterine cancer, uterine sarcoma, Waldenstroms macroglobulinemia, or Wilms' tumor.

In certain embodiments, the at least one compound according to the invention is administered simultaneously or sequentially with a therapeutically effective amount of one or more other therapeutic agent(s) selected from the group consisting of anti-viral agents, chemotherapeutic agents (including alkylating antineoplastic agents, antimetabolites, anti-microtubule agents), immunosuppressants, anti-tumor vaccines, antiviral vaccines, cytokine therapy, tyrosine kinase inhibitors, immunotherapeutic agents, including checkpoint inhibitors such as PD-1, PD-L1 or CTLA-4 inhibitors and IDO/TDO inhibitors, adenosine A2A receptor antagonists, ectonucleotidase (CD73 and CD39) inhibitors, agent affecting interleukins, cytokines and chemokines, topoisomerase inhibitors, and cytotoxic antibiotics, or targeted therapies comprising antibodies, antibody drug conjugates, cell-based immunotherapy, nanoparticles, and radiotherapy.

In certain embodiments, the antibodies comprise a therapeutically effective amount of anti-PD-1, anti-PD-L1 or anti-CTLA4 antibodies.

In another aspect, the invention provides use of a compound according to the invention, or a pharmaceutically acceptable salt, solvate, or polymorph thereof, for protecting an organ during transport.

In certain embodiments, the subject is a mammal selected from the group consisting of human, dog, cat, horse, cow, pig, sheep, goat, and ape.

EXAMPLES

The present invention is further illustrated by the following examples, which in no way should be construed as limiting the scope of the claimed invention.

Methods of Preparation and Characterization

The compounds of the present disclosure may be prepared by use of known chemical reactions and procedures. Representative methods for synthesizing compounds of the disclosure are presented below. It is understood that the nature of the substituents required for the desired target compound often determines the preferred method of synthesis. All variable groups of these methods are as described in the generic description if they are not specifically defined below. The meaning of the symbols is limited to a particular reaction scheme and is not necessarily the same for all the structural formulas.

Those having skill in the art will recognize that the starting materials and reaction conditions may be varied, the sequence of the reactions altered, and additional steps employed to produce compounds encompassed by the present disclosure, as demonstrated by the following examples. Many general references providing commonly known chemical synthetic schemes and conditions useful for synthesizing the disclosed compounds are available (see, e.g., Smith and March, *March's Advanced Organic Chemistry: Reactions, Mechanisms, and Structure*, Fifth Edition, Wiley-Interscience, 2001; or Vogel, *A Textbook of Practical Organic Chemistry. Including Qualitative Organic Analysis*, Fourth Edition, New York: Longman, 1978).

The reactions are performed in a solvent appropriate to the reagents and materials employed and suitable for the transformations being effected. It will be understood by those skilled in the art of organic synthesis that the functionality present on the molecule should be consistent with the transformations proposed. This will sometimes require a judgment to modify the order of the synthetic steps or to select one particular process scheme over another in order to obtain a desired compound of the disclosure.

In some cases, protection of certain reactive functionalities may be necessary to achieve some of the above transformations. In general, the need for such protecting groups as well as the conditions necessary to attach and remove such groups will be apparent to those skilled in the art of organic synthesis. An authoritative account describing the many alternatives to the trained practitioner are in J. F. W. McOmie, "*Protective Groups in Organic Chemistry*," Plenum Press, London and New York 1973, in T. W. Greene and P. G. M. Wuts, "*Protective Groups in Organic Synthesis*," Third edition, Wiley, New York 1999, in "*The Peptides*;" Volume 3 (editors: E. Gross and J. Meienhofer), Academic Press, London and New York 1981, in "*Methoden der organmschen Chemie*," Houben-Weyl, 4th edition. Vol. 15/1, Georg Thieme Verlag, Stuttgart 1974, in H.-D. Jakubke and H. Jescheit, "*Aminosauren, Peptide, Proteine*," Verlag Chemie, Weinheim, Deerfield Beach, and Basel 1982, and/or in Jochen Lehmann, "*Chemie der Kohlenhydrate: Monosaccharide und Derivate*," Georg Thieme Verlag, Stuttgart 1974. The protecting groups may be removed at a convenient subsequent stage using methods known from the art. The disclosures of all articles and references mentioned in this application, including patents, are incorporated herein by reference in their entirety.

Starting materials can be obtained from commercial sources or prepared by literature methods.

All solvents, substrates and reagents that were commercially available were used without further purification. TLC analysis was performed using pre-coated glass plates (TLC silica gel 60 $F_{254}$) from Merck. Column chromatography was performed using high-purity grade silica gel (pore size 60 Å, 230-400 mesh particle size, 40-63 μm particle size) from Merck.

Preparative HPLC were performed on LC-20AP Shimadzu with ELSD-LTII detector equipped with Luna 21.2/250 mm, 5 μm C18(2) 100 Å LC column. The target compounds, when subjected to reversed-phase chromatographic purification in the presence of TFA, were usually obtained in the form of TFA salts.

$^1$H and $^{19}$F NMR spectra were recorded on Bruker AVANCE II PLUS (Ultra Shield) NMR spectrometer at 700 MHz and 250 MHz.

All spectra were recorded in appropriate deuterated solvents ($CDCl_3$, DMSO-$d_6$, $D_2O$, $CD_3OD$, etc.) that were commercially available.

Resonances are given in parts per million relative to tetramethylsilane. Data are reported as follows: chemical shift, multiplicity (s=singlet, d=doublet, t=triplet, m=multiplet, bs=broad singlet), coupling constants (Hz) and integration.

ESI-MS spectra were obtained on a Shimadzu LC-20AD LPG separation module with a SPD-M20A UV detector and LCMS-2020 mass detector equipped with Kinetex 2.1/30 mm, 1.7 μm XB—C18 100 Å LC column eluted with 1 mL/min flow of 10-90% gradient (over 3 min) of acetonitrile in water.

Microwave-assisted reactions were performed using CEM MARS 6™ Synthesis system (240/50, Model no. 911105).

Abbreviations used are those conventional in the art or the following: Ac=acetyl, aq=aqueous, Bn=benzyl, Boc=tert-butoxycarbonyl, t-Bu=tert-butyl, ° C.=degree Celsius, Cod=1,5-cyclooctadiene, DCE=1,2-dichloroethane, DCM=dichloromethane, DMF=N,N-dimethylformamide, DMSO=dimethyl sulfoxide, dppe=1,2-bis(diphenylphosphino)ethane, dppf=1,1'-ferrocenediyl-bis(diphenylphosphine). ELSD=evaporative light scattering detector, EtOAc or AcOEt=ethyl acetate, EtOH=ethanol, ESI+ MS=electrospray ionization mass spectrometry (in the positive ion mode), ESI-MS=electrospray ionization mass spectrometry (in the negative ion mode), g=gram, h=hour(s), HMPA=hexamethylphosphoramide, HPLC=high pressure liquid chromatography, K=kelvin. L=liter, LCMS=liquid chromatography and mass spectrometry, MeCN=acetonitrile, MeOH=methanol, min=minutes, mL=milliliter(s), M=molar, MW=microwave irradiation, m/z=mass to charge ratio, nM=nanomolar, NMR=nuclear magnetic resonance. N=normal. RT or rt=room temperature, TEA=triethylamine, TFA=trifluoroacetic acid, THF=tetrahydrofuran, TMSCl=chlorotrimethylsilane, Z—OSu=N-(benzyloxycarbonyloxy)succinimide.

If not otherwise defined, purity of a solid substance is expressed as a ratio of the weight of the component in question to the total weight, multiplied by 100 (weight %); purity of a liquid is expressed as a ratio of the volume of the component in question to the total volume, multiplied by 100 (volume %); concentration of a solution is expressed as a ratio of the weight of the solute (in grams) to the total volume (in mL) of the solution, multiplied by 100 (w/v %). Yield of a reaction is expressed as a ratio of the weight of the product in question to the theoretical yield of this product, multiplied by 100(%). Composition of a mixed solvent is expressed as a proportion of volume parts of the component solvents (e.g., 3:1).

Biological Assays
Enzymatic Assay to Determine IC50 of USP7 Inhibitors

The IC50 is the concentration of an inhibitor where the measured enzyme activity is reduced by half. In the case of USP7 deubiquitinase, the IC50 of an USP7 inhibitor is the molar concentration of the compound that inhibits 50% of the activity observed in a USP7-mediated-ubiquitin-rhodamine cleavage assay. For the inhibitors disclosed herein, their potency was measured using the following method.

A 45 µl reaction volume containing full-length USP7 (0.5 nM) in 50 mM HEPES pH 7.5, 150 mM NaCl, 1 mM DTT, 1 mg/ml BSA and 0.05% Tween20 was assembled in wells of 96 well half area black flat bottom plates. Test compounds were first dissolved to 25 mM stocks in DMSO and subsequently introduced to enzyme 15 min after USP7 incubation with DTT at room temperature. The enzymatic reaction was started by adding 0.5 µM Ubiquitin-Rhodamine 110 (final concentration) and allowed to proceed for 45 min at 37° C., 250 RPM shaking before Rhodamine fluorescence (485 nm excitation/520 nm emission) was measured using Tecan Spark M10 plate reader. The IC50 values were determined by data fitting to variable slope model four-parameter dose-response curve using GraphPad 7.05.

B-Catenin Reporter Assay
Cellular Assay to Determine EC50 of USP7 Inhibitors

The $EC_{50}$ refers to the concentration of the inhibitor that in a cellular context inhibits activation of a target protein-dependent pathway by half. For the described here compounds, $EC_{50}$ was measured as the potency to inhibit the activation of the β-catenin-dependent WNT signaling pathway measured using TOPFlash and FOPFlash wnt/b-catenin activity assays (Sigma Aldrich, #17-285).

Briefly, colon adenocarcinoma derived SW480 cells were seeded at the density of 15 000 cells/well in a full medium containing DMEM-029, 10% FBS, 1% penicillin-streptomycin in a 96-well transparent plate, 48 hours later cells were transfected either with TOPFlash (Cat. #21-170, Sigma Aldrich) firefly luciferase plasmid or FOPFlash (Cat. #21-169, Sigma Aldrich) firefly luciferase plasmid. Additionally, cells at each well were transfected with *Renilla* luciferase plasmid (pGL4.75, Promega. #E693A) as the internal control. 24 h after transfection cells were treated with DMSO (0.3%) or described compounds at 10 different concentrations performed at 3-fold serial dilutions starting from 33.3 µM concentration. After 24 h luminescence signal of firefly (from TOP and FOP) and *Renilla* luciferase were evaluated using DualGlo® Luciferase Assay System (E2920). Luminescence signal was measured using Tecan Spark M10 plate reader. The $EC_{50}$ values were determined by data fitting to variable slope model (four parameters) inhibitor-response curve using GraphPad 7.05.

Immunomodulatory Effect of Example 77 on Isolated CD4+ T-Cells from C56BL/6 Mice Splenocytes from three C57BL/6 mice donors were isolated separately. Next, specific CD4+ cells were extracted from all splenocytes with EasySep™ Mouse CD4+ T cell Isolation Kit by negative selection (StemCell; Cat. #19852). The purity of splenic CD4+ T cells exceeded 95%, as confirmed by flow cytometric analysis following staining with anti-mouse CD3 and CD4 antibodies. Pure CD4+ cells were subsequently seeded in RPMI full medium (50 000 cells/well) on 96-well U-bottom plate covered with 1 µg/mL antiCD3 and 1 µg/mL antiCD28 (for stimulation and activation). Then. OAT compounds were added in 6 concentrations (0.3, 0.6, 1.25, 2.5, 5 and 10 µM) in three technical replicates. The final concentration of DMSO in wells was 0.03%. After 72 h, lymphocyte activation was evaluated by counting, testing viability (LDH Assay, CellTiter Glo Assay) and cytokine. Statistical significance of observed effects was determined based on mean values calculated from technical replicates for each mouse (n=9; experiment was performed three times).

Readouts:
1. ATP level in cell lysates (CellTiterGlo Viability Assay. Promega;)
2. LDH level in cell culture medium
3. Cell counting (Orange-Acridine staining, Luna automated cell counter, Logos Biosystems)
4. mTNF-α in supernatants (ELISA)
5. mIFN-γ in supernatants (ELISA)
6. Magpix Luminex (T-Cells Panel: GM-CSF, IFN-γ, IL-10 TNF-α)

Figure 1B:
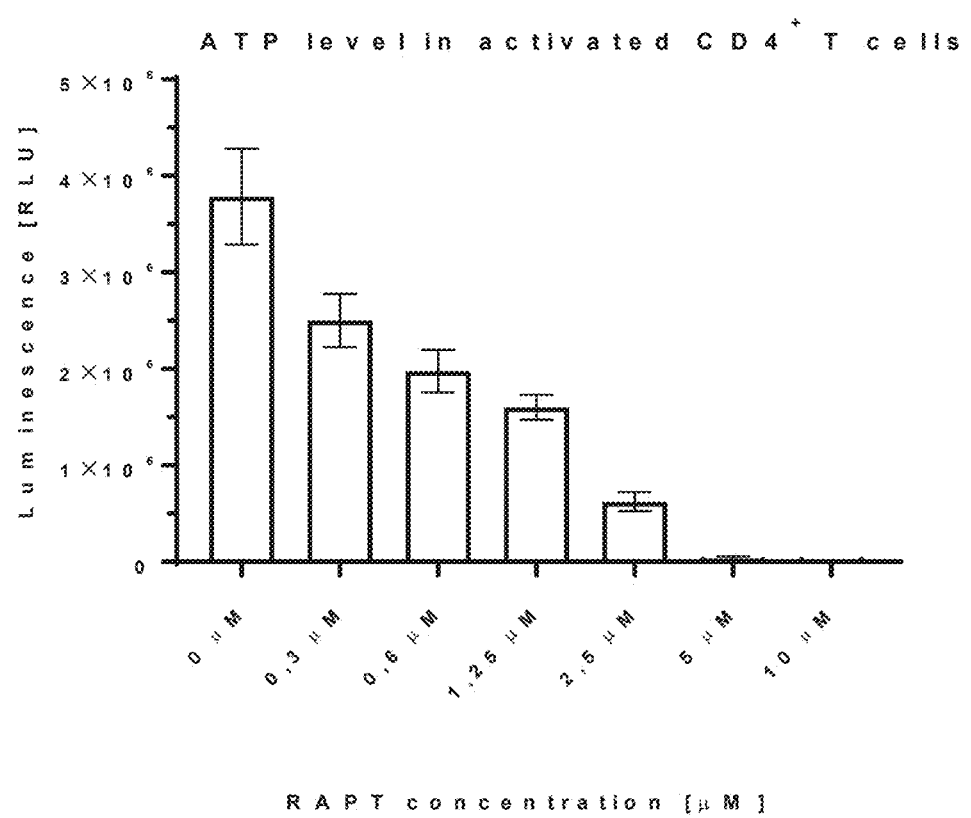
Figure 1C:
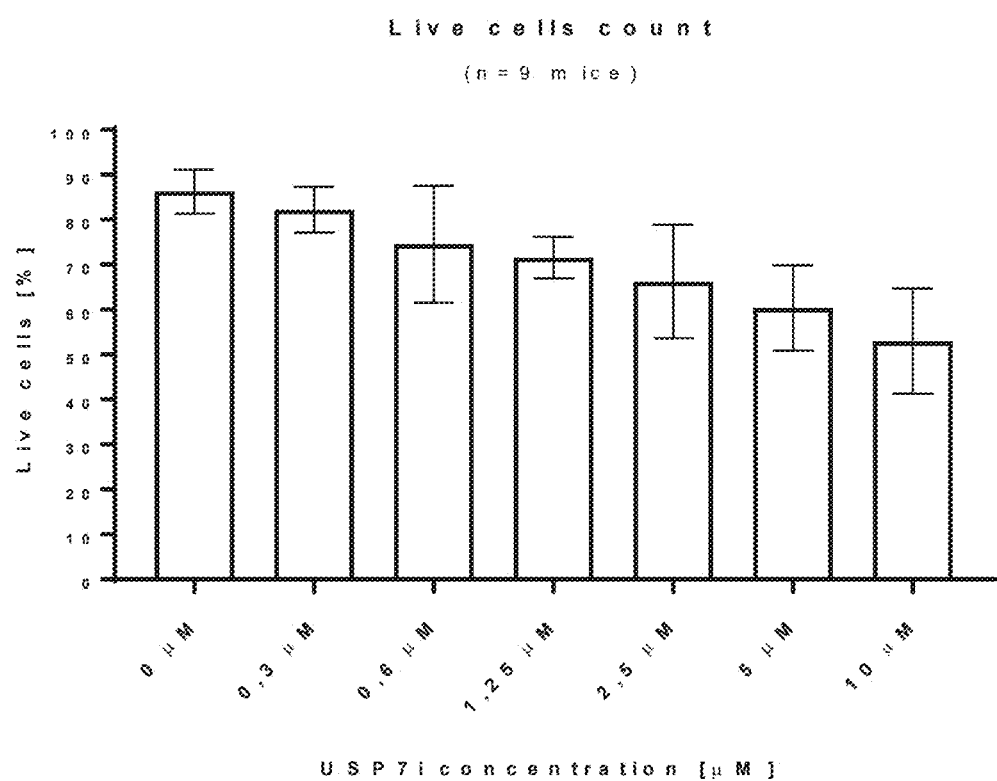

The cell viability was measured "head to head" for the compound Example 77 (denoted also USP7i in the Figures) and reference compound RAPT Therapeutics with CellTiter Glo Assay (Promega). Example 77 was 10-time less cytotoxic (1C50~9 uM) than the reference RAPT compound. Cells were also counted after 72 h of incubation with Example 77 with the Luna cell counter, after trypan blue staining (1:1). The viability was comparable to that obtained with CellTiter Glo. The assay results are presented in FIGS. 1A-1C.

Figure 2A:
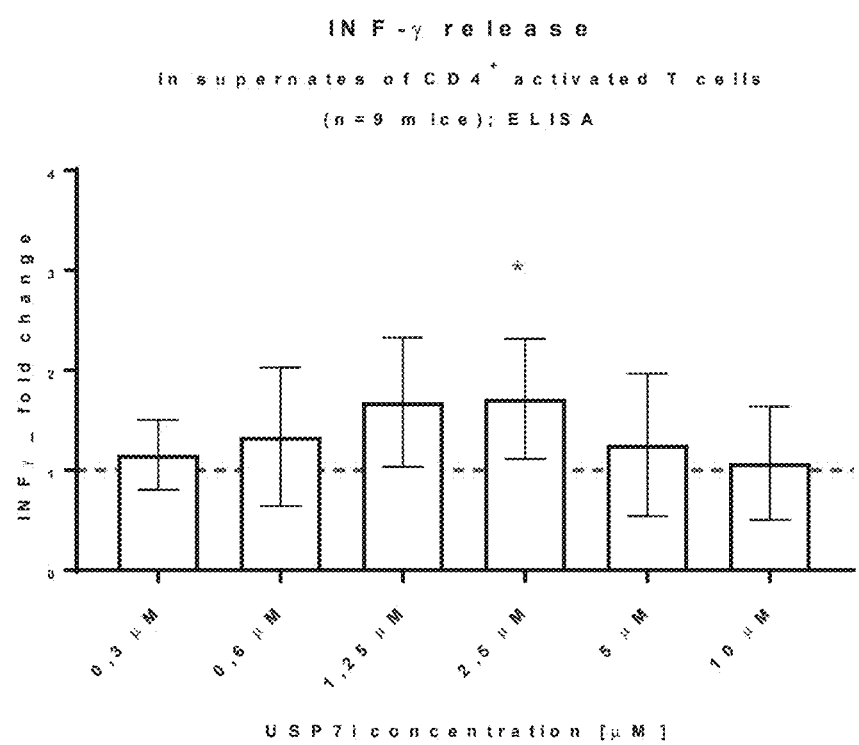
FIGS. 2A and 2B show TNF-α and IFN-γ levels in supernatants obtained from three independent ELISA experiments.
Figure 2B:
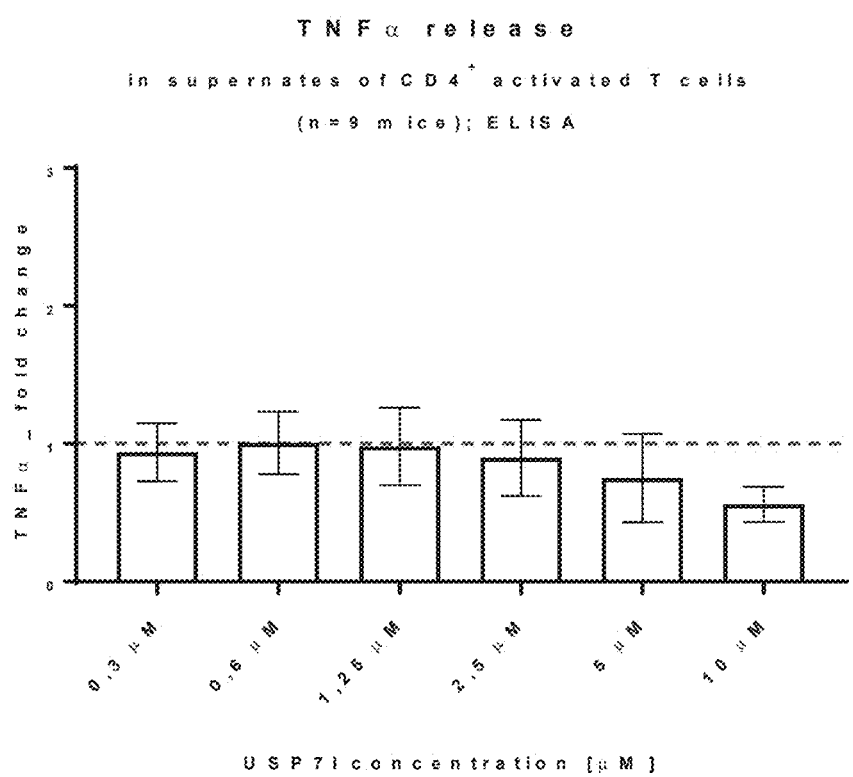
Figure 3A:
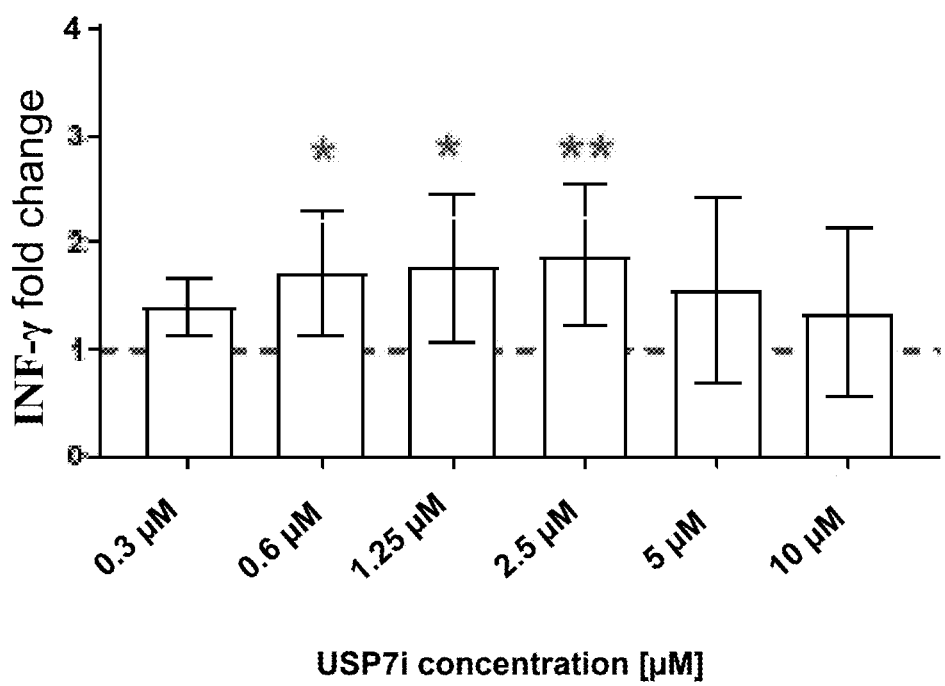
Figure 3B:
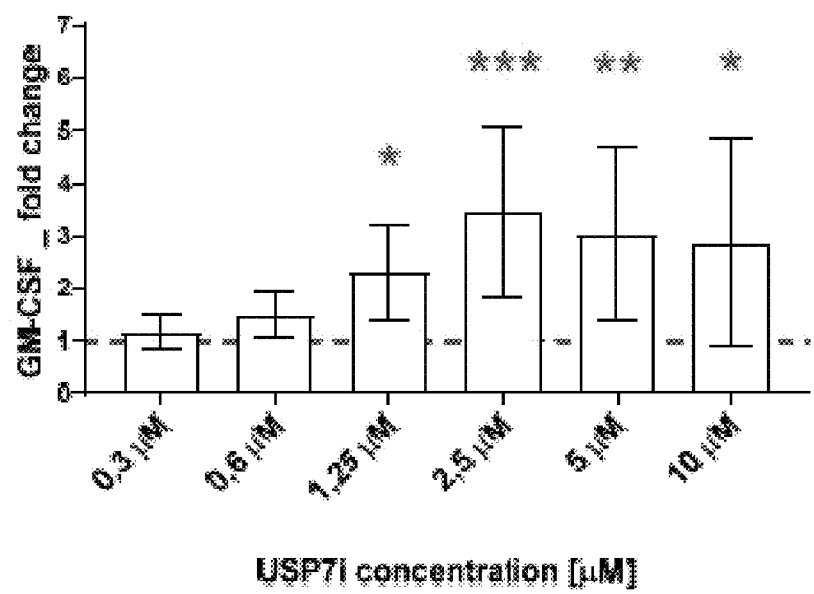
Figure 3D:
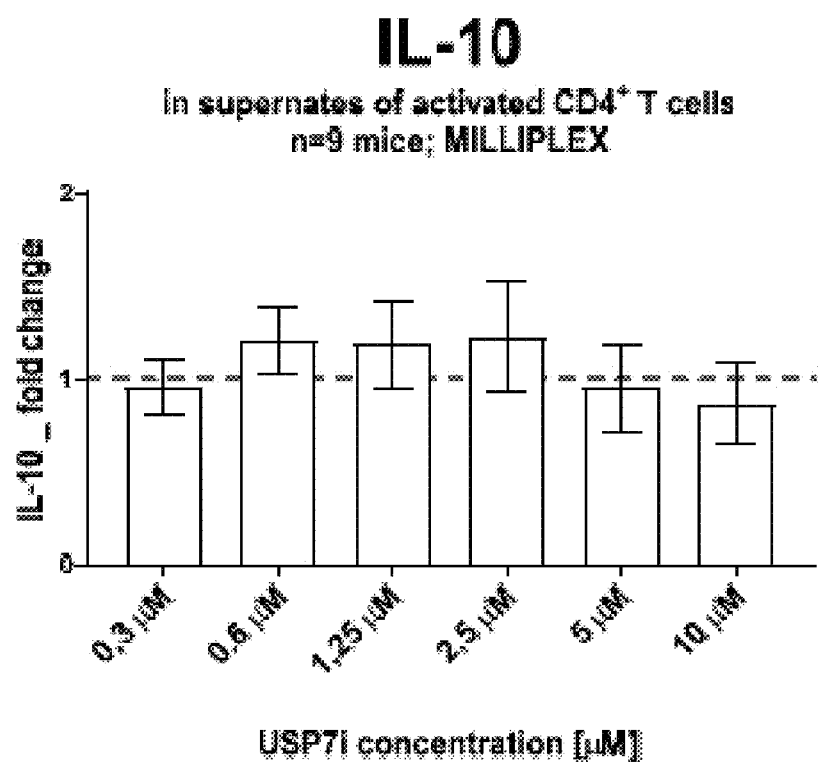
Figure 4A:
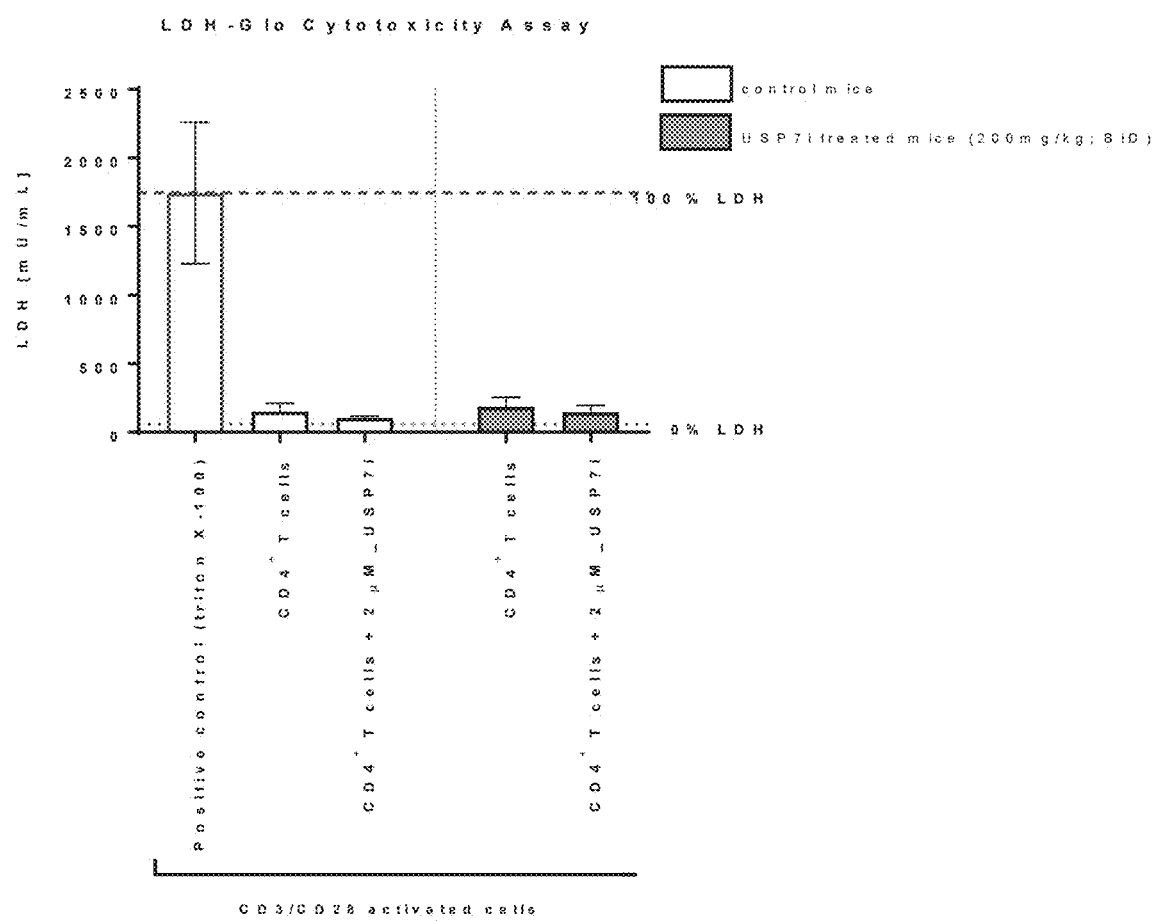
FIGS. 4A-4D show the in vivo and ex vivo immunomodulatory effects of Example 77 in BALB/c mice.
Figure 4B:
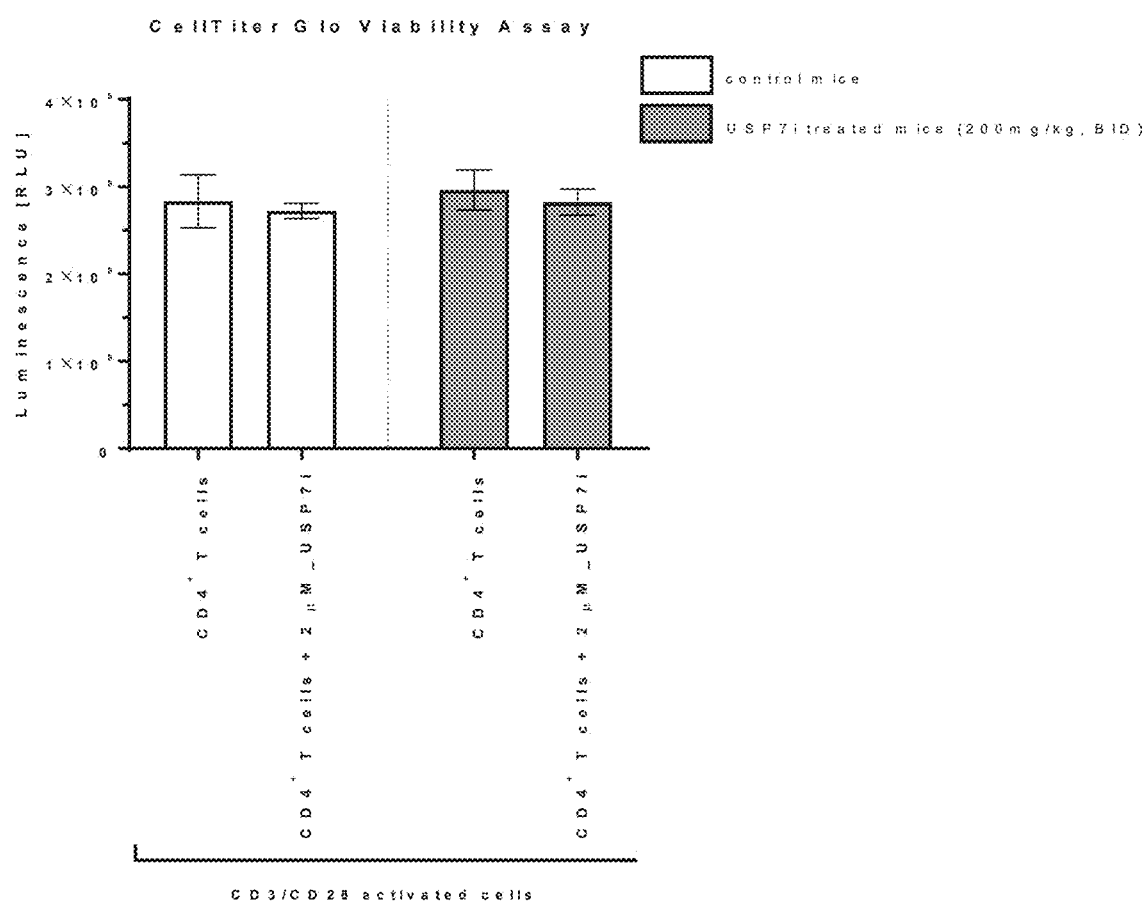
Figure 4C:
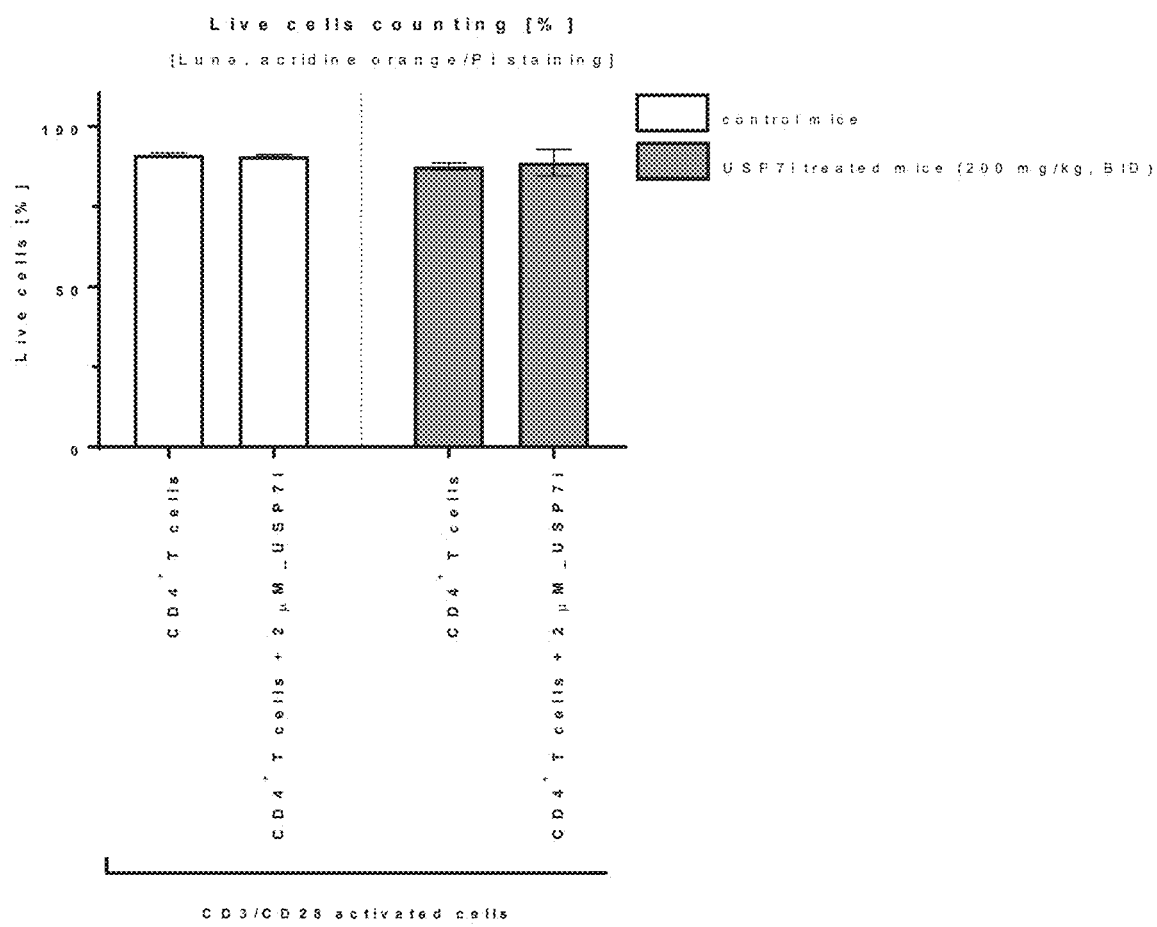
Figure 4D:
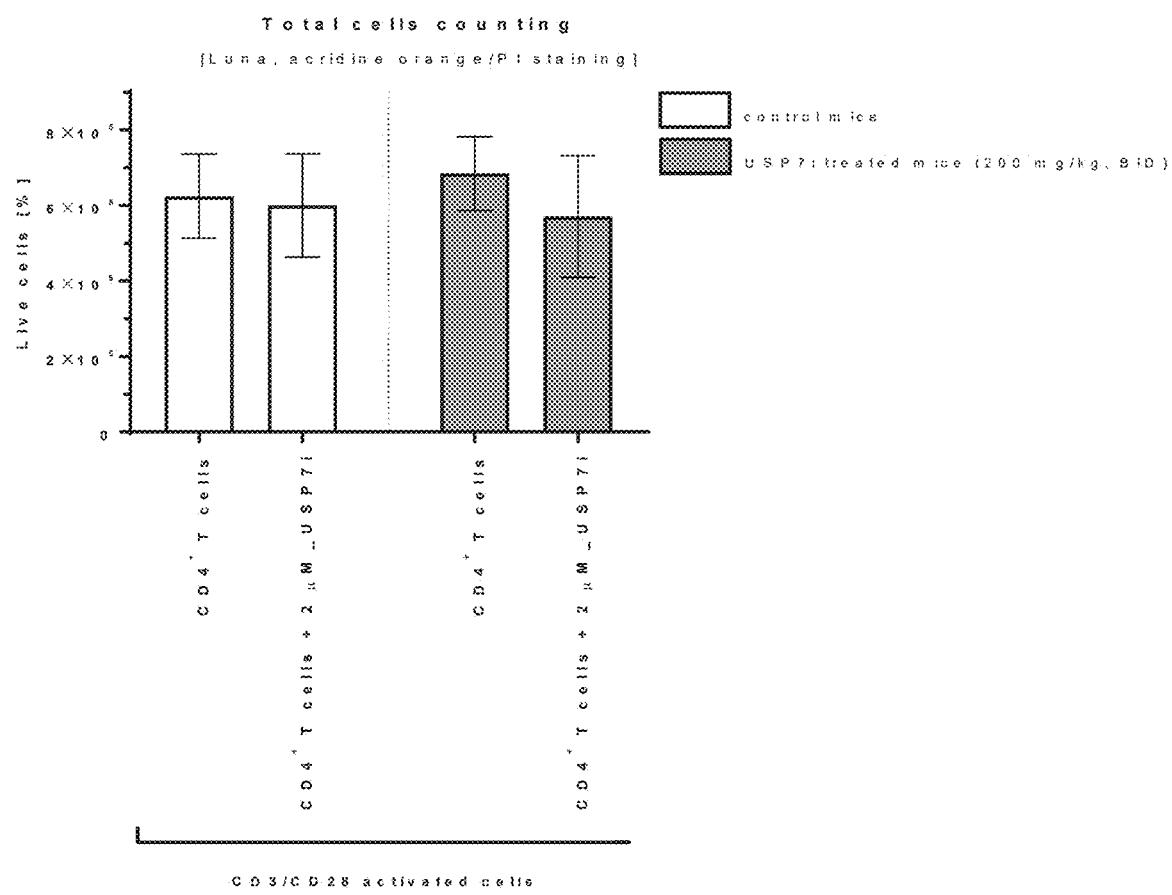

Results for TNF-α and IFN-γ level in supernatants obtained from three independent sets of experiments by ELISA are combined on bar graphs below (n=9 mice). Data were confirmed and complemented with Magpix Luminex instrument where 6 different cytokines (IFN-γ, TNF-α, GM-CSF, IL-10) were measured in supernatants from activated CD4+ T cells treated with Example 77 (samples from 3 independent experiments, n=9 mice). See, FIGS. 2A and 2B.

Example 77 added at low concentration (0.5-2.5 µM) does not disturb CD4+ T cells activation and pro-inflammatory cytokine release. Statistically significant increase of IFNg and GM-CSF was observed. The level of TNFa and IL-10 was not affected. See, FIGS. 3A-3D.

In Vivo and Ex Vivo Immunomodulatory Effect of Example 77 in BALB/c Mice

BALB/c mice (10-week-old females, n=3) were administered with Example 77 at 200 mg/kg (BID) by oral gavage for 3 consecutive days. Untreated mice were used as the control group (n=3). Animals were sacrificed 16 hours following the last dosing. The spleens were collected and total CD4+ lymphocytes were isolated by bead-based negative separation according to the manufacturers manual (EasySep™ Mouse CD4+ T cell Isolation Kit, StemCell; Cat. #19852). The purity of splenic CD4+ T cells exceeded 95%, as confirmed by flow cytometric analysis following staining with anti-mouse CD3 and CD4 antibodies. Isolated CD4+ T cells were seeded in triplicates (50 000 cells/well in RPMI full medium) on 96-well U-bottom plate covered with 1 µg/mL anti-CD3 and 1 µg/mL anti-CD28 antibodies (for stimulation and activation of cells). Following one hour preincubation in 37° C. degree, CD4+ T cells were treated with 2 µM of Example 77, the final concentration of DMSO in wells was 0.03%. After 72 h lymphocytes activation was evaluated by testing viability, cytotoxicity and cytokine release: mTNF-α and mIFN-γ.

Readouts:
1. ATP level in cell lysates (CellTiterGlo Viability Assay, Promega)
2. Lactate dehydrogenase (LDH) level in cell culture medium (LDH-Glo Cytotoxicity Assay, Promega)
3. Cell counting (Fluorescence staining, Luna automated cell counter, Logos Biosystems)

4. mTNF-α in supernatants by ELISA
5. mIFN-γ in supernatants by ELISA

Results of the assay are presented in FIGS. 4A-4D.

Figure 5A:
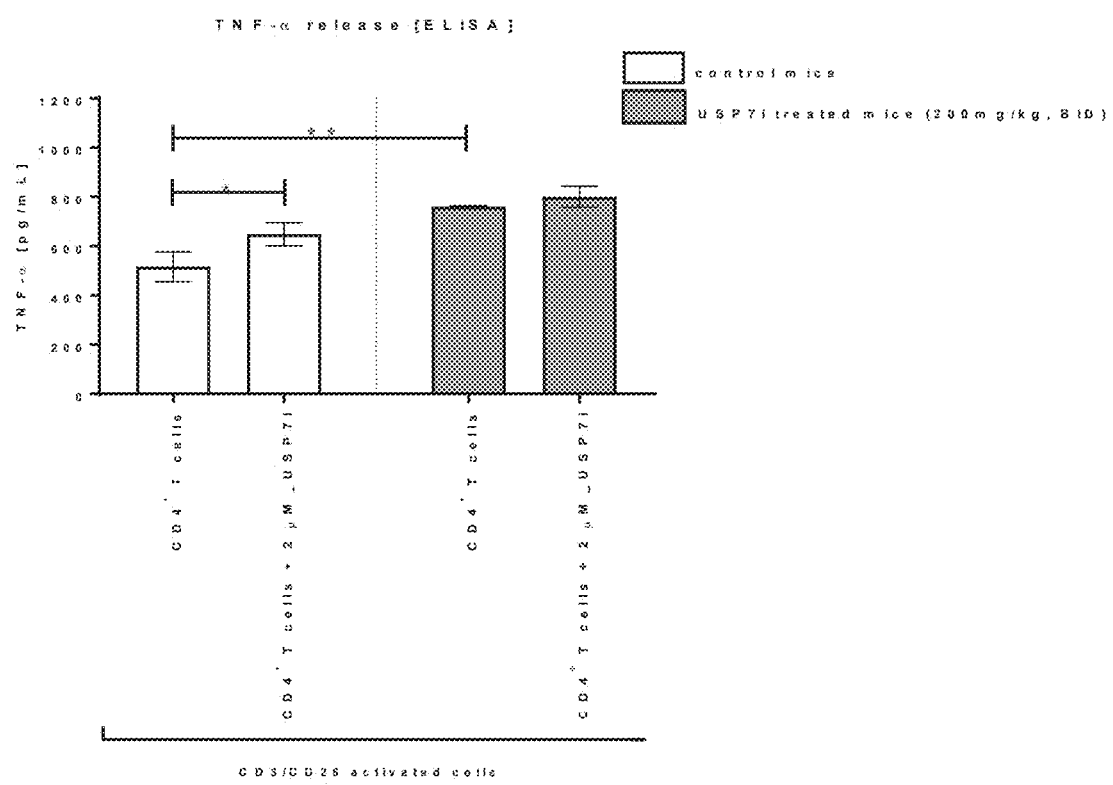
FIGS. 5A and 5B shows the effect of 2 μM Example 77 on CD4⁺ T cell viability as determined in a LDH-Glo and a CellTiter Glo Assay.
Figure 5B:
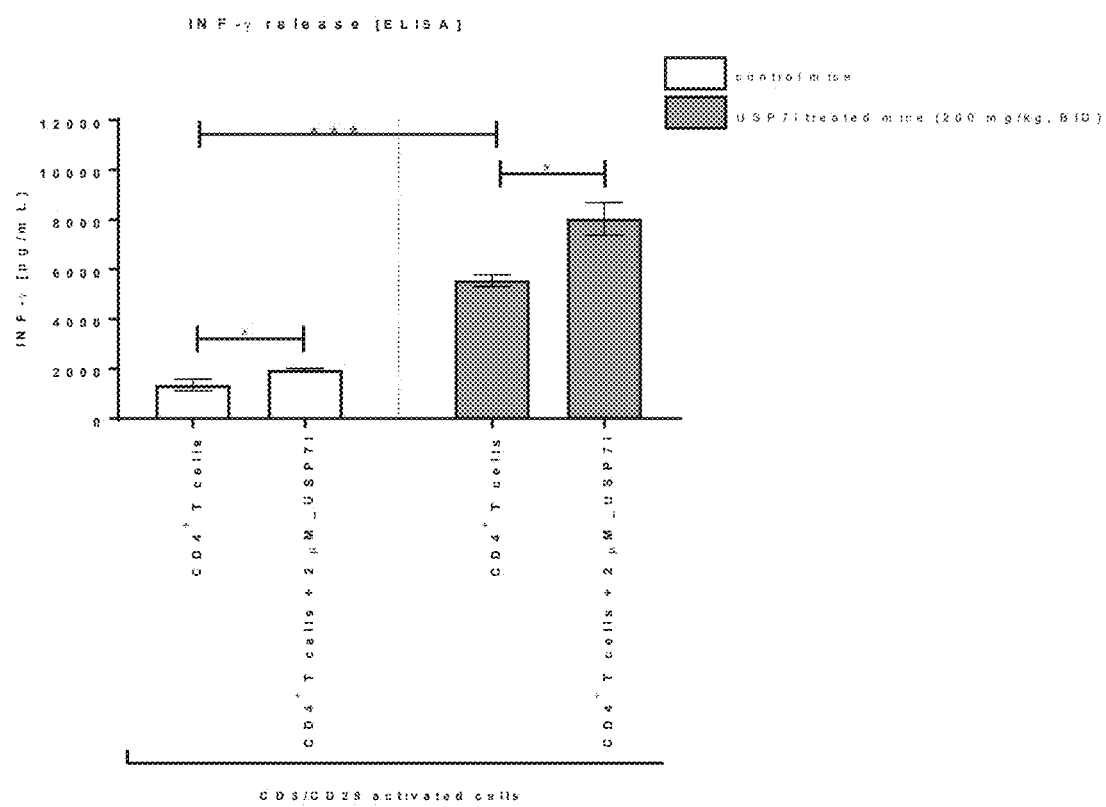

Example 77 does not affect T cells viability. At tested 2 µM concentration, Example 77 was not cytotoxic for CD4+ T-cells, what was confirmed by LDH-Glo cytotoxicity assay, where LDH concentration in the culture medium didn't exceed 5% vs. positive control. Viability of cells was additionally conformed by CellTiter Glo Assay where compound didn't affect total ATP level. Results of the assay are presented in FIGS. 5A and 5B.

Example 77 does not affect CD4+ T cells activation and pro-inflammatory cytokines release: TNF-α and IFN-γ. Activated CD4+ T cells isolated from Example 77 treated mice release ex vivo much more pro-inflammatory cytokines than CD4+ T cells from control mice. Furthermore, ex vivo treatment of isolated T-cells with Example 77 additionally increases pro-inflammatory cytokines release.

To evaluate the antitumor efficacy of Example 77 the syngeneic mouse model of colon cancer was used. The 7-8-week old BALB/c females (BALB/cAnNCrl, Charles River Laboratories) were injected subcutaneously in the right flank with 5×10$^5$ CT26 cells. USP7 inhibitors were dosed by oral gavage twice per day at indicated doses starting from 2-5 days after the tumor implantation. Anti-PD-1 antibody (InVivoPlus anti-mouse PD-1, clone RMP1-14. BioXCell) or isotype antibody (GoInVivo Purified rat IgG2b anti-KLH, clone LTF-2) were injected intraperitoneally at dose 2.5 mg/kg (Example 77) or 5 mg/kg (Example 124, U.S. Ser. No. 11/084,829B2). In the T cell depletion experiments, an anti-CD8 antibody (InVivoPlus anti-mouse CD8, clone YTS169.4, BioXCell) was injected intraperitoneally at dose of 100 µg on days: 1, 7, and 14. Tumor volume was estimated by a formula: width×length×depth×π/6. Differences at a p-value less than 0.05 were considered statistically significant. TGI (tumor growth inhibition) index was calculated by the formula: (1−A/B)×100%, where A is the tumor volume in the treated group and B is the tumor volume in the control group.

To investigate the killing capability of T cells the splenocytes were isolated from tumor-bearing mice treated and untreated with different concentrations of Example 77. CT26 cells were seeded and stained with Green Cell Tracker. Stained CT26 cells were co-cultured with splenocytes from experimental animals in two ratios 1:10 and 1:50. After 36 h cells were harvested and analyzed on the flow cytometer.

Figure 6A:
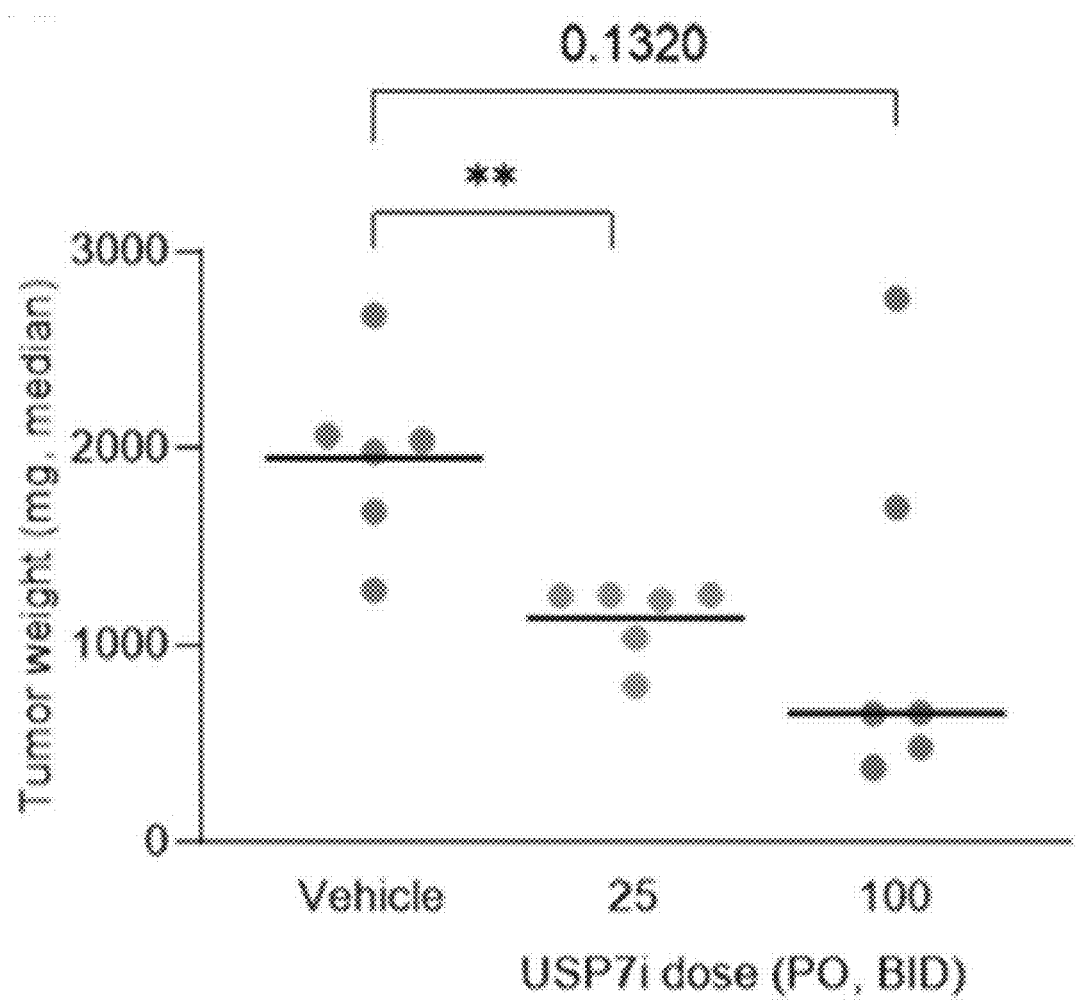
FIG. 6A shows the antitumor efficacy effect of Example 77 in the subcutaneous CT26 model of colon carcinoma.
Figure 6B:
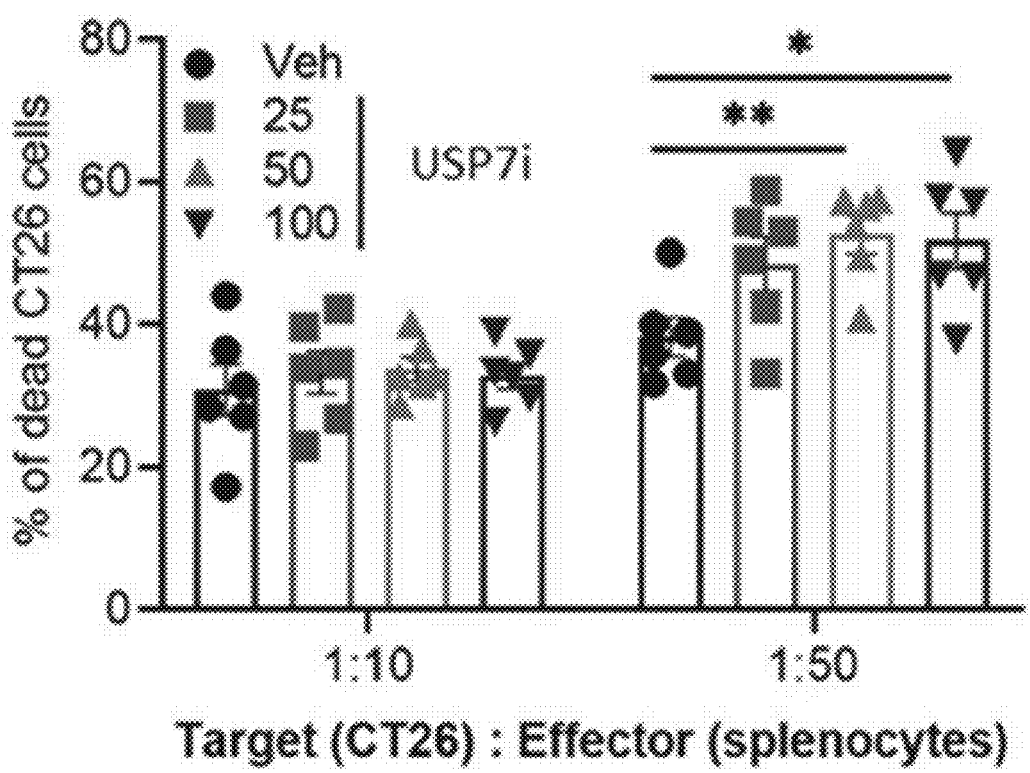
FIG. 6B shows the effect of Example 77 in a and killing assay measuring splenocyte cytotoxicity to tumor cells.
Figure 6C:
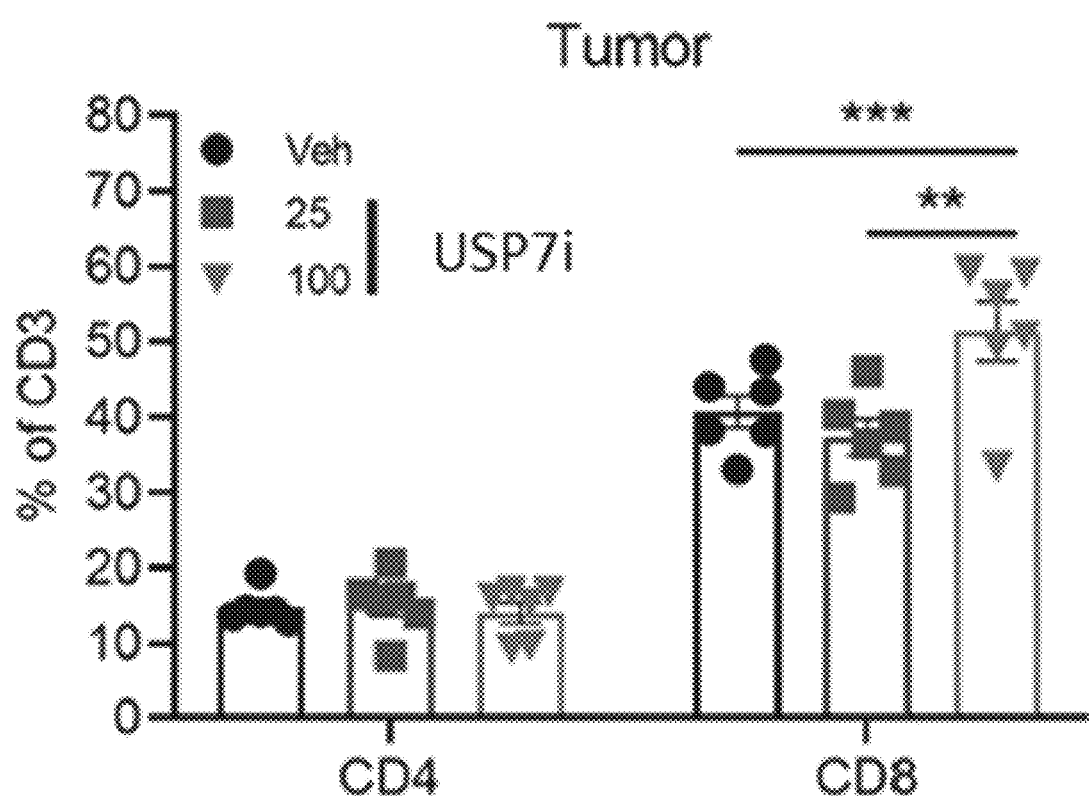
FIG. 6C shows the effect of Example 77 on % of CD4 and CD8 T lymphocytes in tumor by cytometric analysis.
Figure 6D:
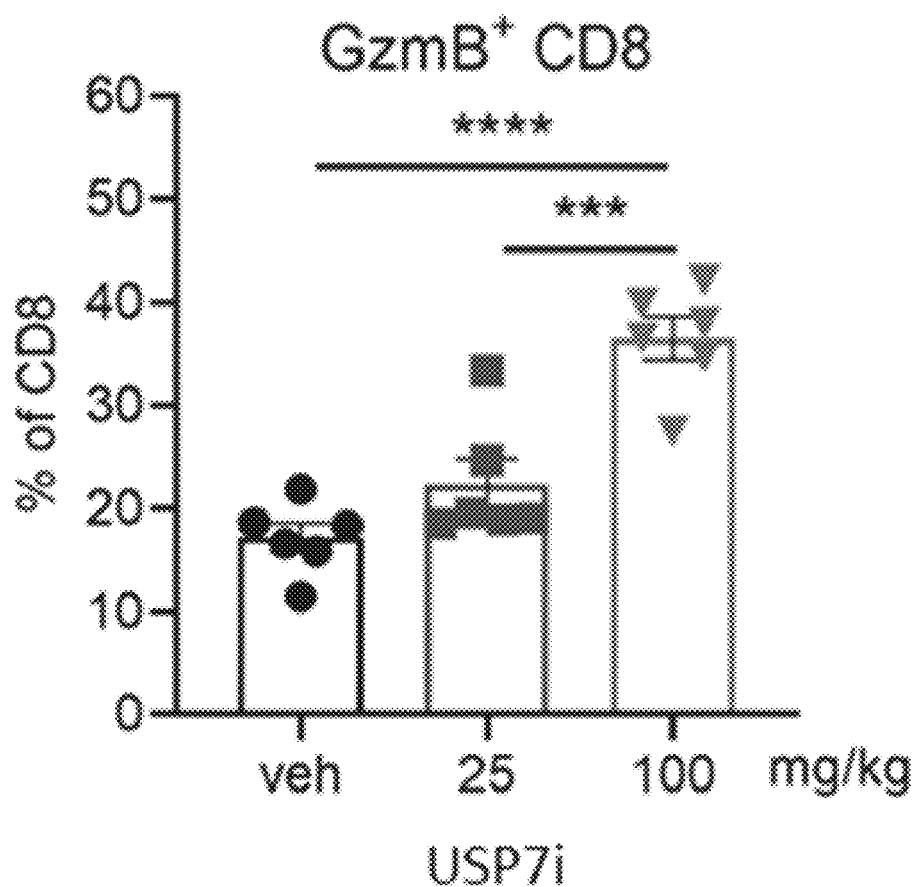
FIG. 6D shows the effect of Example 77 on granzyme B production in CD8+ T cells at varying concentrations against vehicle.

Example 77 exerted a dose-dependent antitumor effect of up to 67% tumor growth inhibition (TGI, p=0.048, FIG. 6A) at day 20 post-inoculation. Notably, splenocytes isolated from CT26-bearing mice treated with different concentrations of Example 77 showed enhanced killing capability in comparison to splenocytes isolated from control mice (FIG. 6B). Additionally, the obtained results indicated an increase in the percent of CD8+ T cells (FIG. 6C) that produce enhanced amounts of both interferon-γ (data not shown) and granzyme B in mice treated with 100 mg/kg of Example 77 (FIG. 6D).

FIGS. 6A-6D show the results of an evaluation of the antitumor efficacy in the subcutaneous CT26 model of colon carcinoma (6A) and killing assay presenting splenocytes cytotoxicity to tumor cells (6B), cytometric analysis of % of CD4 and CD8 T lymphocytes in tumor (6C) and granzyme B production in CD8+ T cells also measured via flow cytometry. Mann-Whitney test was used for statistical analysis.

Figure 7A:
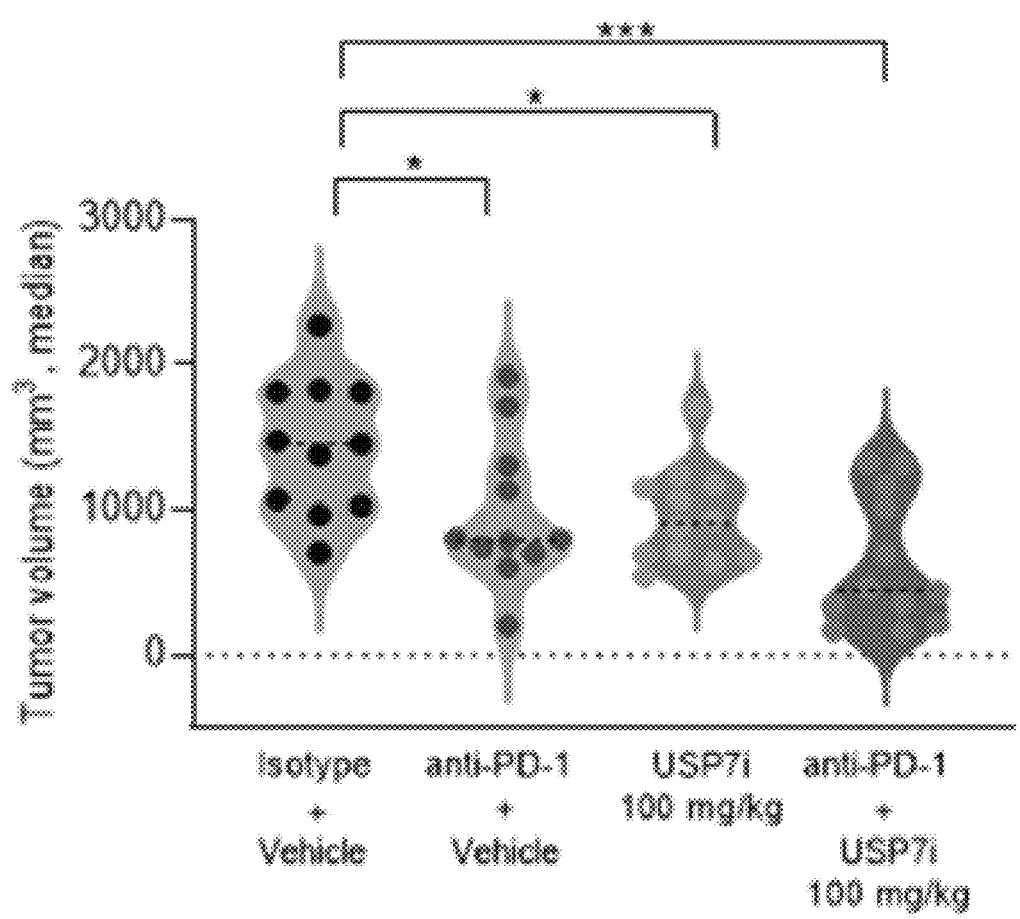
FIG. 7A shows result of evaluating the antitumor efficacy of Example 77 in combination with anti-PD-1 antibodies in the subcutaneous CT26 model of colon carcinoma in a Man-Whitney test.

Moreover, Example 77 potentiated the therapeutic effect of anti-PD-1 antibody (immune checkpoint inhibitor), (FIG. 7A). Treatment with 100 mg/kg (PO, BID) of Example 77 resulted in the TGI of 69%, while monotherapy with anti-PD-1 antibody reached the TGI of 45%. Survival analysis, performed for the experiment, proved a statistically significant increase in survival time (by 26%, 29 days vs. 25 days) upon the treatment with Example 77 (100 mg/kg, PO, BID) vs. anti-PD-1 monotherapy group (FIG. 7B).

Figure 7B:
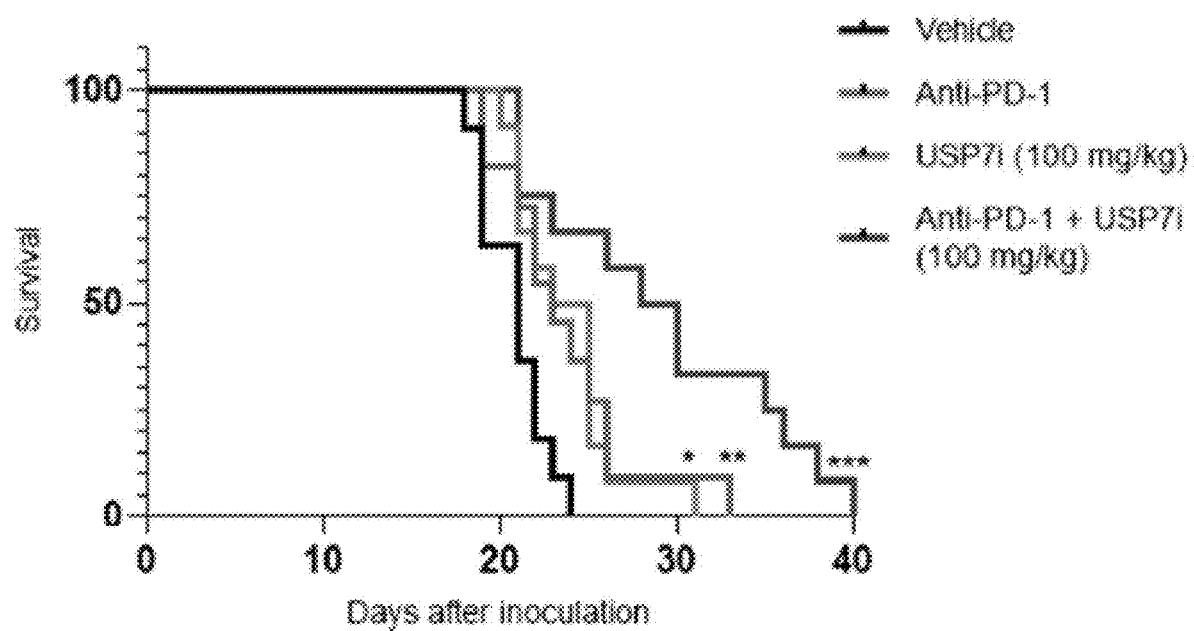
FIG. 7B shows result of evaluating the antitumor efficacy of Example 77 in combination with anti-PD-1 antibodies in the subcutaneous CT26 model of colon carcinoma in a log-rank test.

FIGS. 7A and 7B show the results of an evaluation of the antitumor efficacy of Example 77 in combination with anti-PD-1 antibodies in the subcutaneous CT26 model of colon carcinoma. Man-Whitney test (7A), and log-rank test (7B) were used for statistical significance analysis.

Figure 8:
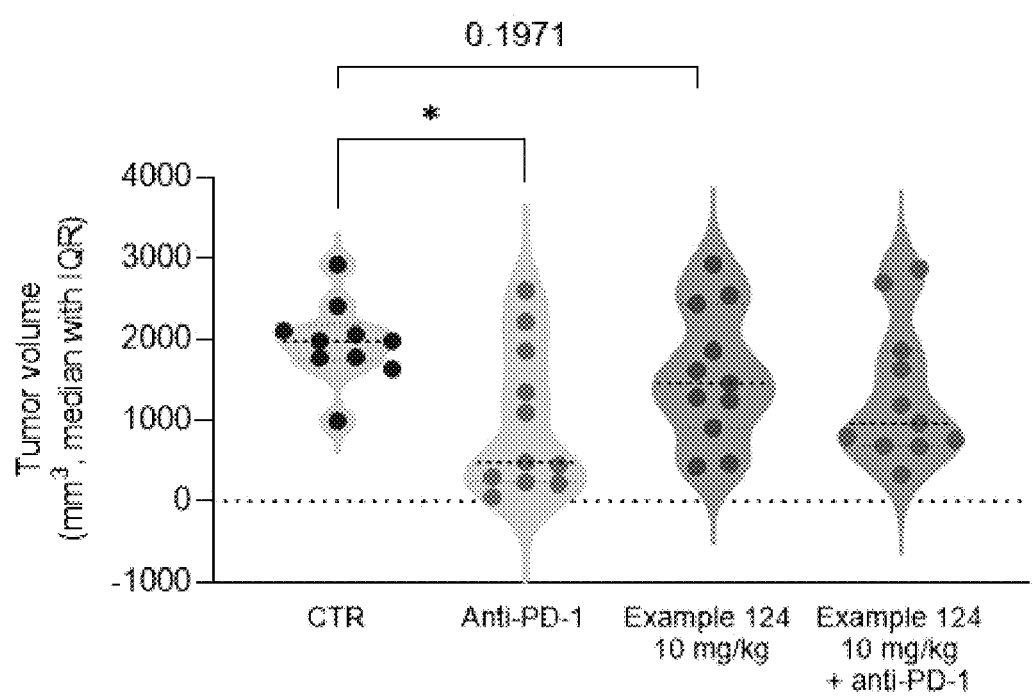
FIG. 8 shows the effect of Example 124 of U.S. Pat. No. 11,084,829 on antitumor activity in a CT26 model alone and in combination with anti-PD-1 therapy.

Importantly, the compound described as a USP7 inhibitor in U.S. Pat. No. 11,084,829B2 patent (Example 124) did not exert significant antitumor activity as well as diminished the efficacy of anti-PD-1 therapy in the CT26 model. FIG. 8 shows the antitumor activity of Example 124 from U.S. Pat. No. 11,084,829B2) as assessed in the CT26 model. Example 124 was administered at a dose of 10 mg/kg. The dose was selected based on pharmacokinetic data and potential toxicity.

Figure 9:
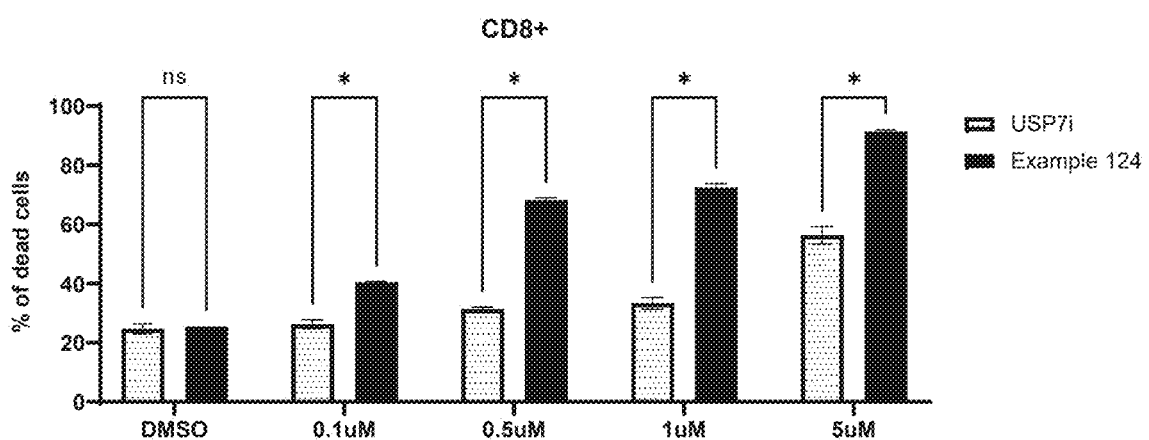
FIG. 9 compares the cytotoxic effect of Example 77 against the effect of Example 124 of U.S. Pat. No. 11,084,829 in mouse CD8+ T cells.

Example 124 of U.S. Ser. No. 11/084,829B2 exerted significant cytotoxicity to CD8 T cells while the toxicity of Example 77 was shown to be limited. In these experiments, the mouse splenocytes were seeded into in 24-well plate and after 24 hours of incubation with USP7 inhibitors the T cells viability was analyzed with flow cytometry. FIG. 9 compares the cytotoxic effect of Example 77 and Example 124 (U.S. Pat. No. 11,084,829B2) to mouse CD8+ T cells. Mann-Whitney test.

Figure 10:
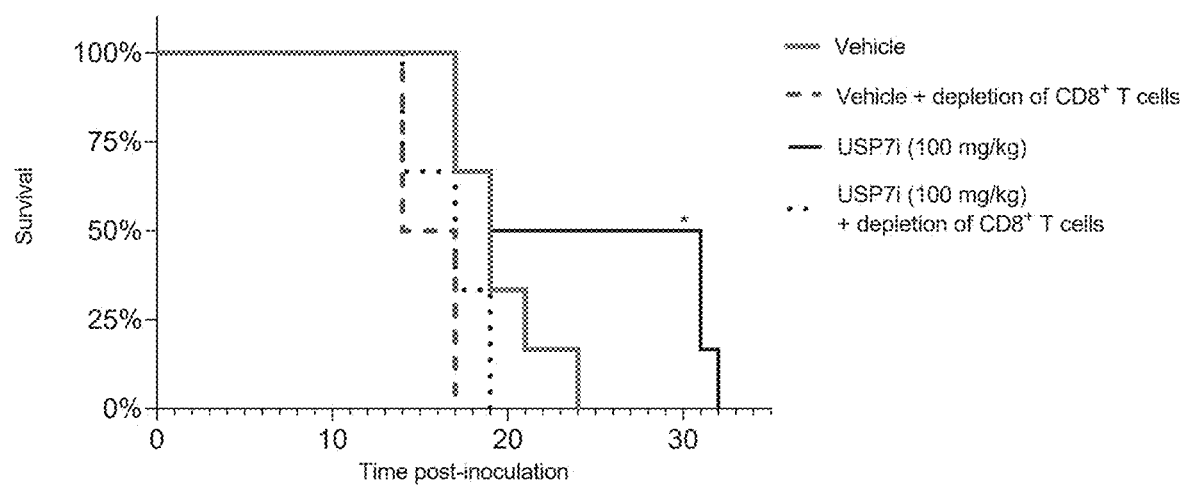
FIG. 10 shows the rate of survival after treatment with Example 77 and CD8-depleting antibodies.

Next, the role of CD8+ T cells in the antitumor activity of Example 77 was evaluated. Tumor-bearing mice were injected with anti-CD8 antibodies that completely abrogated the antitumor effect of Example 77. FIG. 10 shows the rate of survival after treatment with Example 77 and CD8-depleting antibodies.

The results indicate that Example 77 requires CD8+ T cells for its antitumor activity, which is exerted in the syngeneic model and increases the efficiency of other immunotherapy-anti-PD-1 antibodies. Notably, the reference compound Example 124 of U.S. Ser. No. 11/084,829B2 is not efficient in the CT26 model, it does not potentiate the anti-PD-1 treatment as well as presents toxicity to CD8 T cells.

The compounds disclosed in Table I below for which IC$_{50}$ values towards USP7 have been calculated as described above are characterized as falling into the following groups:

A: <0.5 µM;

B: 0.5-1 µM;

C: 1-10 µM;

D: >10 µM.

If the IC$_{50}$ value has not been determined yet, a percent value of inhibition of USP7 activity at 1 µM of the test compound is specified. The following percentage ranges correspond to the corresponding letters with an asterisk; the compounds that lack IC$_{50}$ values are characterized as falling into the following groups:

A*; >70% inhibition;

B*; 50-70% inhibition;

C*; 20-49% inhibition;

D*; <20% inhibition.

TABLE 1

| Ex. No. | Structure | USP7 IC$_{50}$ |
|---|---|---|
| 1. | [structure with trifluoroacetic acid salt] | A |
| 2. | [structure with HCl salt] | A |
| 3. | [structure with HCl salt] Racemate | A |
| 4. | [structure with HCl salt] Single enantiomer of Ex. 3 | A |
| 5. | [structure with trifluoroacetic acid salt] | A |

TABLE 1-continued
| Ex. No. | Structure | USP7 IC$_{50}$ |
|---|---|---|
| 6. | 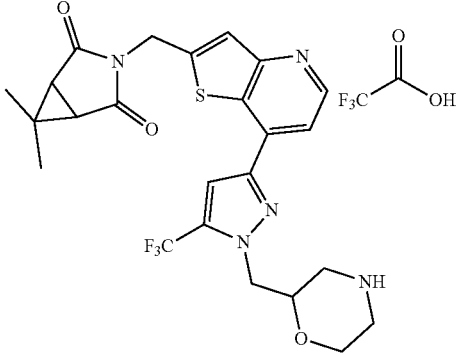 Uncertain position of morpholine substituent | D* |
| 7. | 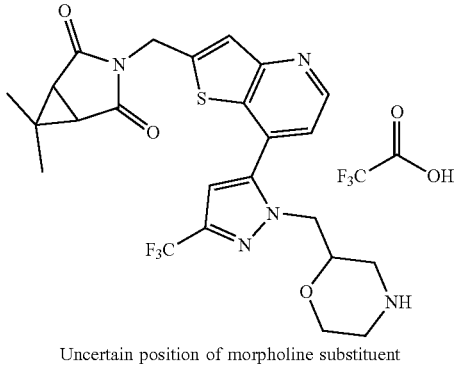 Uncertain position of morpholine substituent | D* |
| 8. | 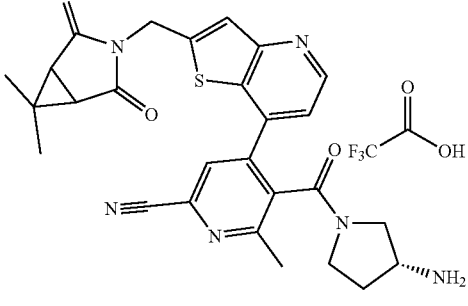 | B |
| 9. | 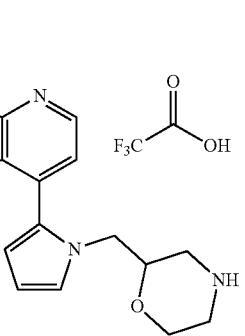 | D* |

TABLE 1-continued

| Ex. No. | Structure | USP7 IC$_{50}$ |
|---|---|---|
| 10. | 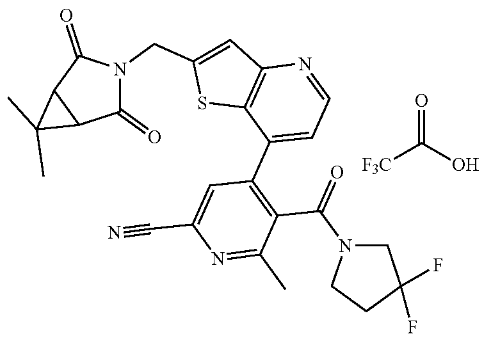 | C |
| 11. | 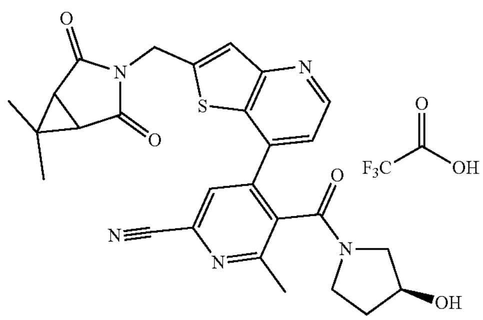 | A |
| 12. | 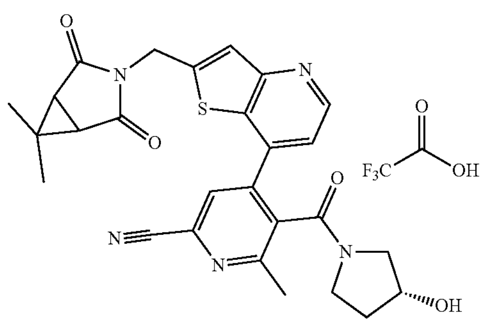 | B |
| 13. | 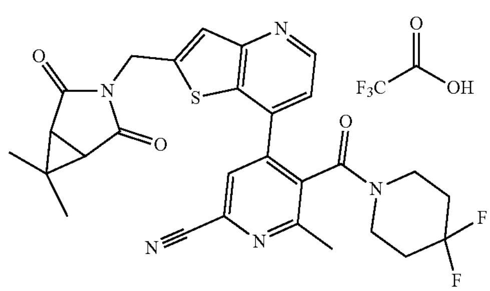 | C* |
| 14. | 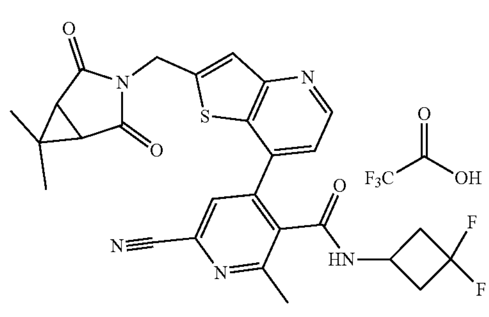 | D* |

TABLE 1-continued
| Ex. No. | Structure | USP7 IC$_{50}$ |
|---|---|---|
| 15. | 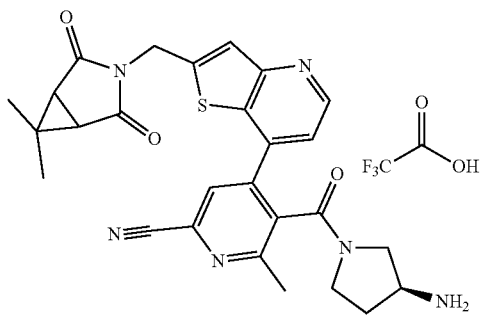 | A |
| 16. | 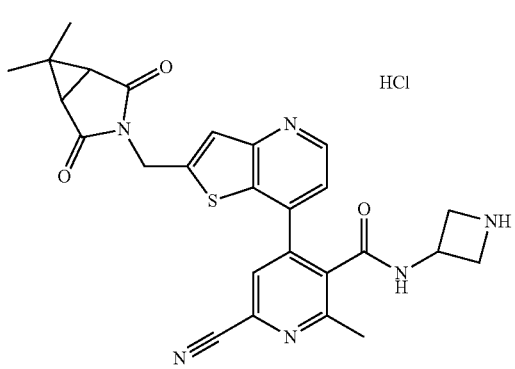 [SMILES: Cc1nc(C#N)cc(-c2ccnc3cc(CN4C(=O)C5C(C4=O)C5(C)C)sc23)c1C(=O)NC1CNC1 ; Cl] | C* |
| 17. | 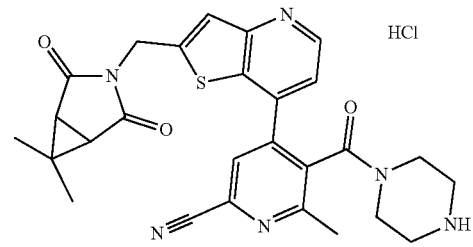 [SMILES: Cc1nc(C#N)cc(-c2ccnc3cc(CN4C(=O)C5C(C4=O)C5(C)C)sc23)c1C(=O)N1CCNCC1 ; Cl] | B |
| 18. | 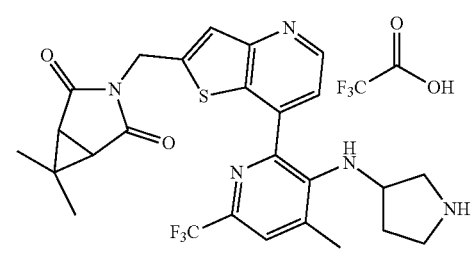 | A |
| 19. | 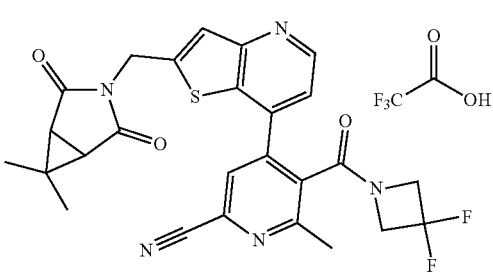 | B |

TABLE 1-continued
| Ex. No. | Structure | USP7 IC$_{50}$ |
|---|---|---|
| 20. | 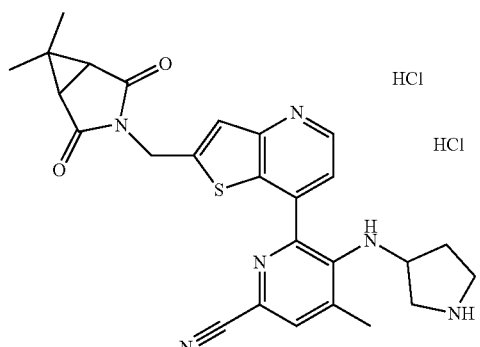 HCl HCl | A |
| 21. | 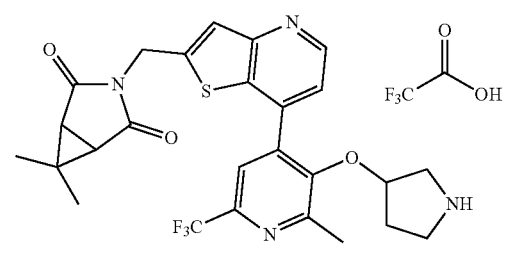 [SMILES: Cc1nc(C(F)(F)F)cc(-c2ccnc3cc(CN4C(=O)C5C(C4=O)C5(C)C)sc23)c1OC1CCNC1 ; O=C(O)C(F)(F)F] Racemate | A |
| 22. | 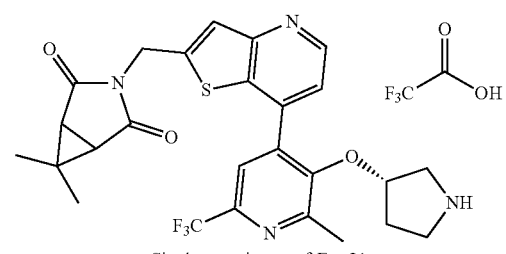 Single enantiomer of Ex. 21 | B |
| 23. | 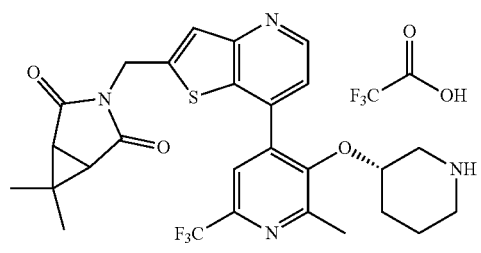 | A |
| 24. | 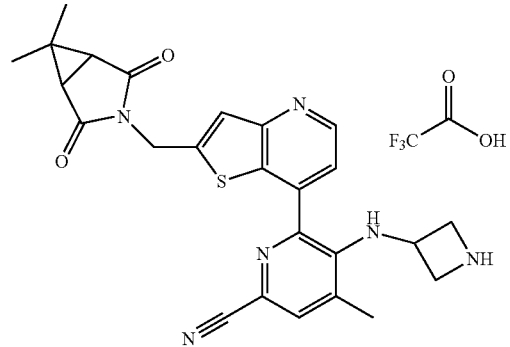 [SMILES: Cc1cc(C#N)nc(-c2ccnc3cc(CN4C(=O)C5C(C4=O)C5(C)C)sc23)c1NC1CNC1 ; O=C(O)C(F)(F)F] | A |

TABLE 1-continued
| Ex. No. | Structure | USP7 IC$_{50}$ |
|---|---|---|
| 25. | 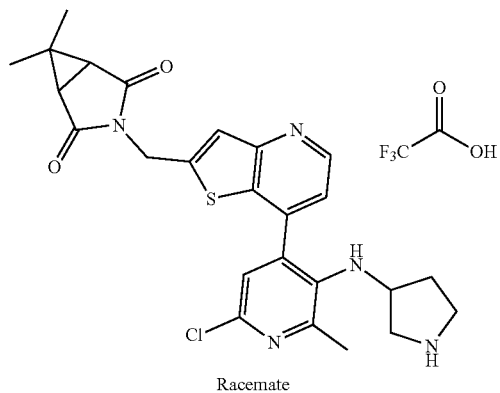 Racemate | A |
| 26. | 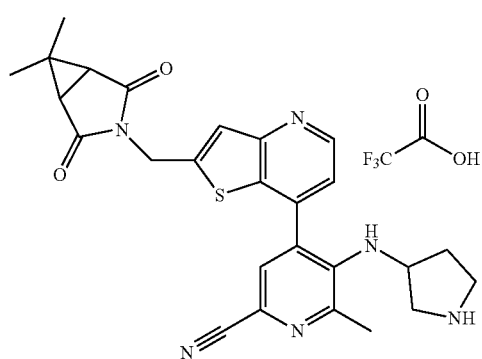 | A |
| 27. | 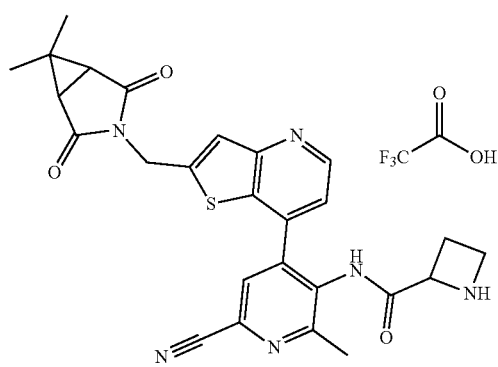 [SMILES: Cc1nc(C#N)cc(-c2ccnc3cc(CN4C(=O)C5C(C4=O)C5(C)C)sc23)c1NC(=O)C1CCN1 ; O=C(O)C(F)(F)F] | D* |
| 28 | 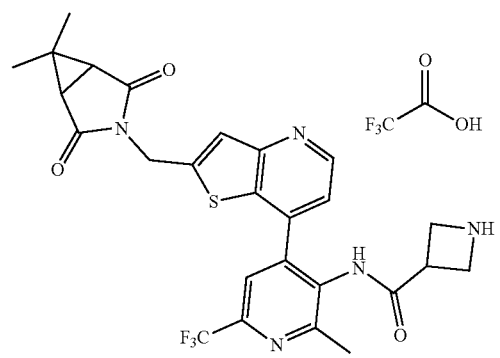 [SMILES: Cc1nc(C(F)(F)F)cc(-c2ccnc3cc(CN4C(=O)C5C(C4=O)C5(C)C)sc23)c1NC(=O)C1CNC1 ; O=C(O)C(F)(F)F] | A |

TABLE 1-continued
| Ex. No. | Structure | USP7 IC$_{50}$ |
|---|---|---|
| 29. | 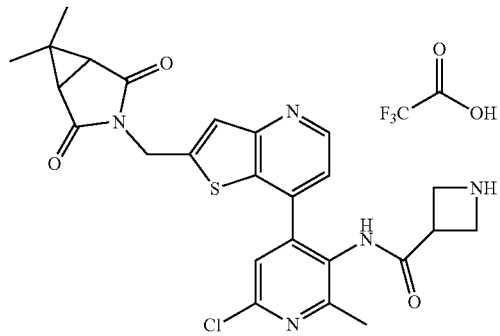 [SMILES: Cc1nc(Cl)cc(-c2ccnc3cc(CN4C(=O)C5C(C4=O)C5(C)C)sc23)c1NC(=O)C1CNC1 ; O=C(O)C(F)(F)F] | A |
| 30. | 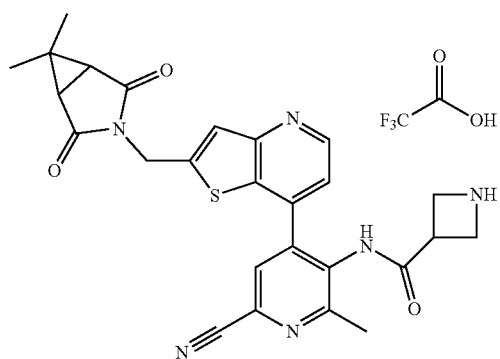 [SMILES: Cc1nc(C#N)cc(-c2ccnc3cc(CN4C(=O)C5C(C4=O)C5(C)C)sc23)c1NC(=O)C1CNC1 ; O=C(O)C(F)(F)F] | A |
| 31. | 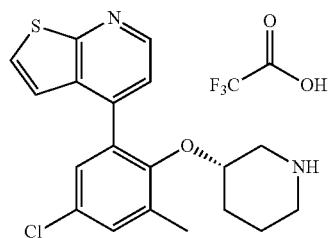 [SMILES: Cc1cc(Cl)cc(-c2ccnc3sccc23)c1O[C@H]1CCCNC1 ; O=C(O)C(F)(F)F] | C |
| 32. | 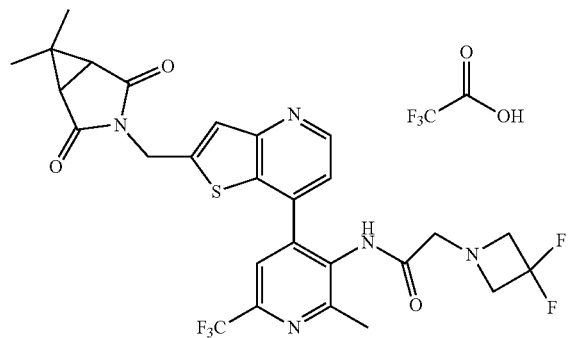 [SMILES: Cc1nc(C(F)(F)F)cc(-c2ccnc3cc(CN4C(=O)C5C(C4=O)C5(C)C)sc23)c1NC(=O)CN1CC(F)(F)C1 ; O=C(O)C(F)(F)F] | D* |

TABLE 1-continued

| Ex. No. | Structure | USP7 IC$_{50}$ |
| --- | --- | --- |
| 33. | 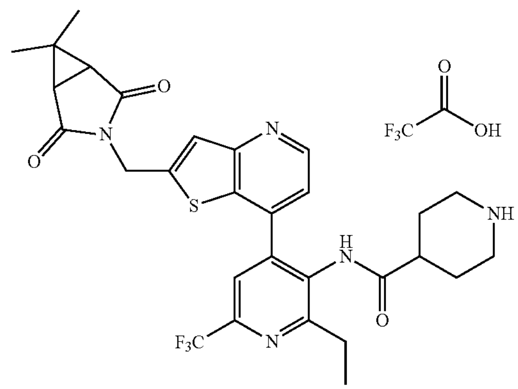 [SMILES: CCc1nc(C(F)(F)F)cc(-c2ccnc3cc(CN4C(=O)C5C(C4=O)C5(C)C)sc23)c1NC(=O)C1CCNCC1 ; O=C(O)C(F)(F)F] | D* |
| 34. | 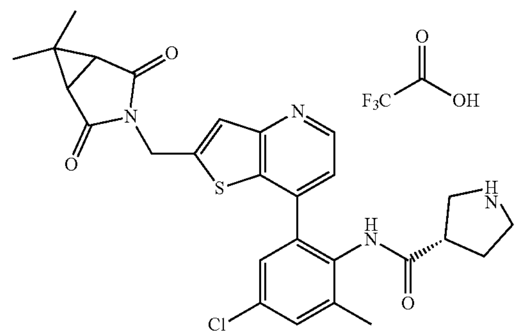 [SMILES: Cc1cc(Cl)cc(-c2ccnc3cc(CN4C(=O)C5C(C4=O)C5(C)C)sc23)c1NC(=O)[C@H]1CCNC1 ; O=C(O)C(F)(F)F] | A |
| 35. | (Racemate) | A |
| 36. | 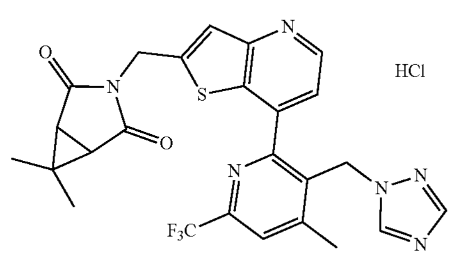 [SMILES: Cc1cc(C(F)(F)F)nc(-c2ccnc3cc(CN4C(=O)C5C(C4=O)C5(C)C)sc23)c1Cn1cncn1 ; Cl] | D* |
| 37. | 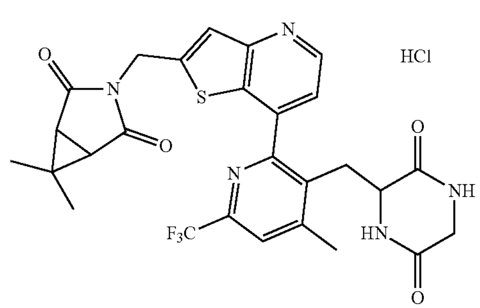 [SMILES: Cc1cc(C(F)(F)F)nc(-c2ccnc3cc(CN4C(=O)C5C(C4=O)C5(C)C)sc23)c1CC1NC(=O)CNC1=O ; Cl] | D* |

TABLE 1-continued

| Ex. No. | Structure | USP7 IC$_{50}$ |
|---|---|---|
| 38. | (structure) HCl | D* |
| 39. | (structure) HCl, HCl | C* |
| 40. | (structure) HCl, HCl | C* |
| 41. | (structure) HCl, HCl | D* |
| 42. | (structure) | D* |
| 43. | (structure) | B* |

TABLE 1-continued

| Ex. No. | Structure | USP7 IC$_{50}$ |
|---|---|---|
| 44. | (structure) HCl | C |
| 45. | (structure) HCl | D* |
| 46. | (structure) HCl | D* |
| 47. | (structure) HCl | A |
| 48. | (structure) HCl | D* |
| 49. | (structure) HCl | D* |

TABLE 1-continued

| Ex. No. | Structure | USP7 IC$_{50}$ |
|---|---|---|
| 50. | HCl | D* |
| 51. | HCl | A |
| 52. | HCl, HCl | A |
| 53. | HCl | C |
| 54. | HCl | B |
| 55. | HCl | A |

TABLE 1-continued
| Ex. No. | Structure | USP7 IC$_{50}$ |
|---|---|---|
| 56. | 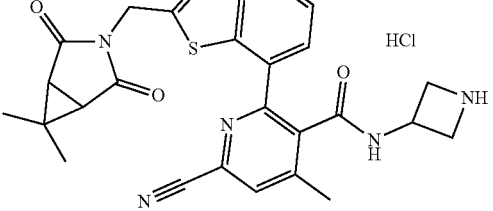 HCl | C |
| 57. | 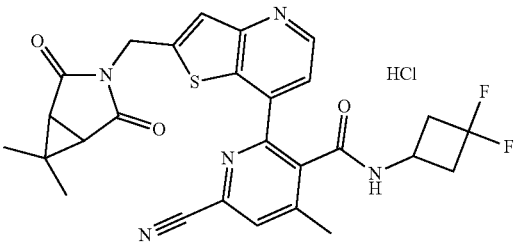 [SMILES: Cc1cc(C#N)nc(-c2ccnc3cc(CN4C(=O)C5C(C4=O)C5(C)C)sc23)c1C(=O)NC1CC(F)(F)C1 ; Cl] HCl | D* |
| 58. | 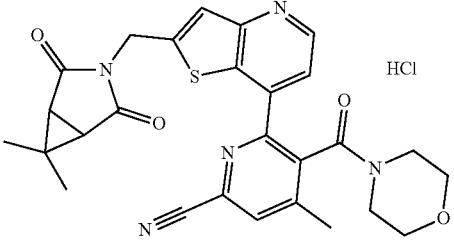 [SMILES: Cc1cc(C#N)nc(-c2ccnc3cc(CN4C(=O)C5C(C4=O)C5(C)C)sc23)c1C(=O)N1CCOCC1 ; Cl] HCl | B |
| 59 | 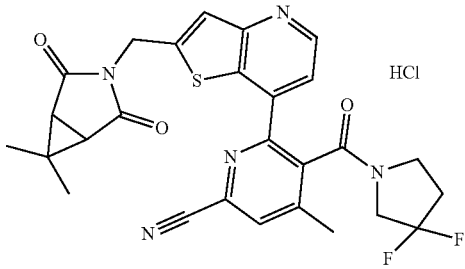 [SMILES: Cc1cc(C#N)nc(-c2ccnc3cc(CN4C(=O)C5C(C4=O)C5(C)C)sc23)c1C(=O)N1CCC(F)(F)C1 ; Cl] HCl | A |
| 60. | 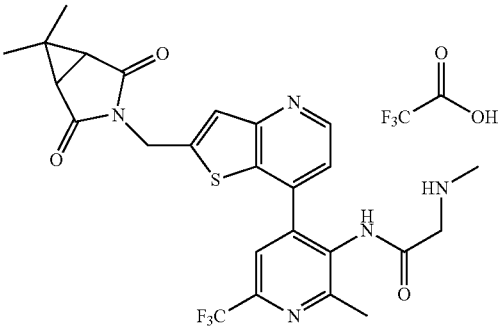 | D |

TABLE 1-continued

| Ex. No. | Structure | USP7 IC$_{50}$ |
|---|---|---|
| 61 | 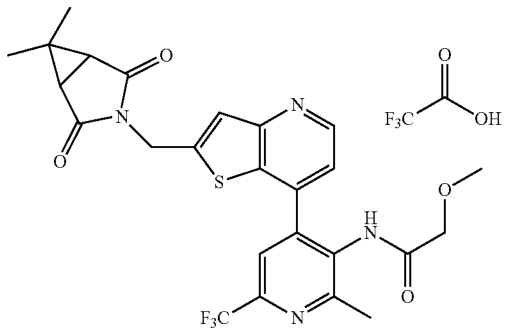 | D |
| 62. | 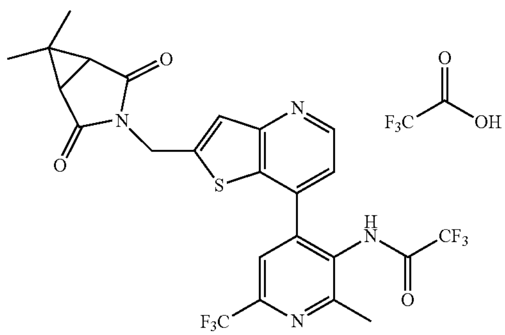 [SMILES: Cc1nc(C(F)(F)F)cc(-c2ccnc3cc(CN4C(=O)C5C(C4=O)C5(C)C)sc23)c1NC(=O)C(F)(F)F ; O=C(O)C(F)(F)F] | C |
| 63. | 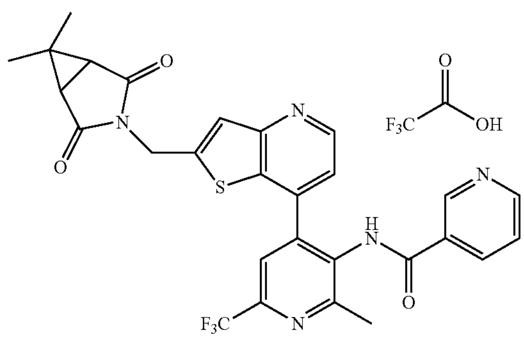 | D |
| 64. | Racemate | C |

-continued
| | | |
|---|---|---|
| 65. | 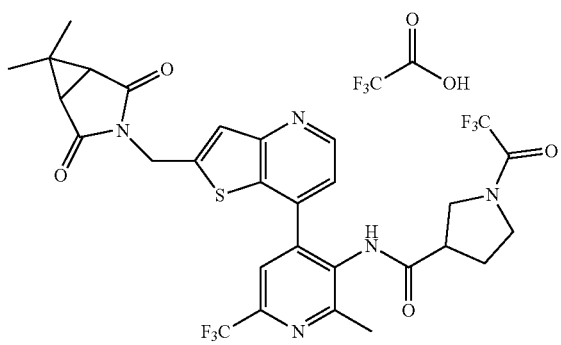 Racemate | D |
| 66. | 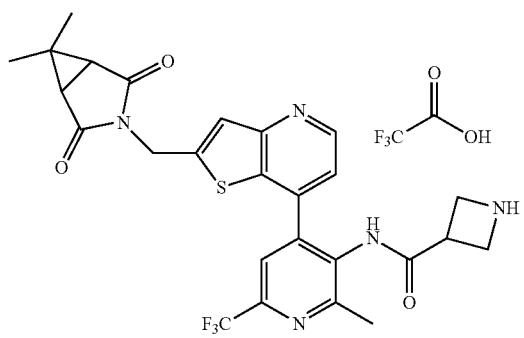 [SMILES: Cc1nc(C(F)(F)F)cc(-c2ccnc3cc(CN4C(=O)C5C(C4=O)C5(C)C)sc23)c1NC(=O)C1CNC1 ; O=C(O)C(F)(F)F] | C |
| 67. | 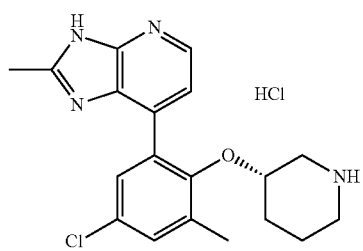 [SMILES: Cc1nc2c(-c3cc(Cl)cc(C)c3O[C@H]3CCCNC3)ccnc2[nH]1 ; Cl] | D* |
| 68. | 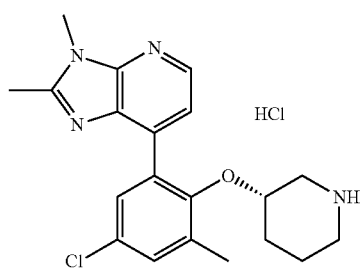 [SMILES: Cc1cc(Cl)cc(-c2ccnc3c2nc(C)n3C)c1O[C@H]1CCCNC1 ; Cl] | D* |
| 69. | 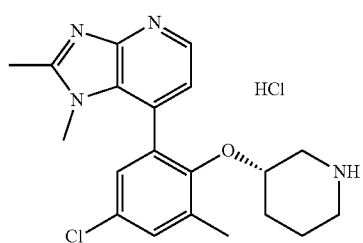 [SMILES: Cc1cc(Cl)cc(-c2ccnc3nc(C)n(C)c23)c1O[C@H]1CCCNC1 ; Cl] | D* |

-continued
70. 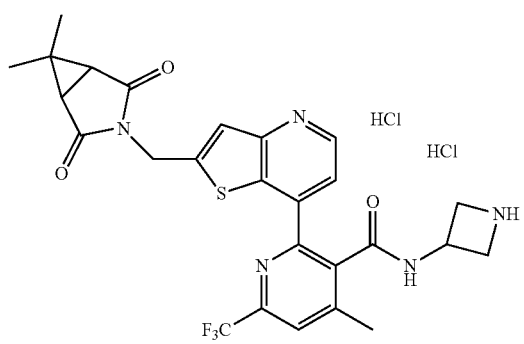 [SMILES: Cc1cc(C(F)(F)F)nc(-c2ccnc3cc(CN4C(=O)C5C(C4=O)C5(C)C)sc23)c1C(=O)NC1CNC1 ; Cl ; Cl] B
71. 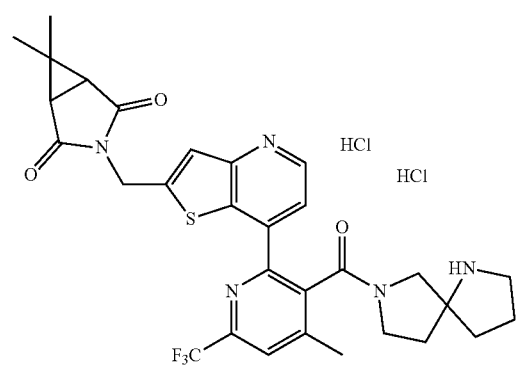 [SMILES: Cc1cc(C(F)(F)F)nc(-c2ccnc3cc(CN4C(=O)C5C(C4=O)C5(C)C)sc23)c1C(=O)N1CCC2(CCCN2)C1 ; Cl ; Cl] A
A mixture of rotamers
72. 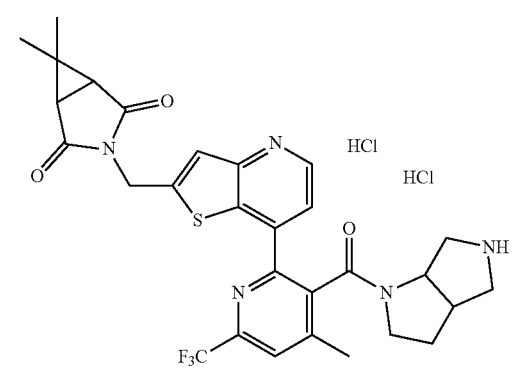 [SMILES: Cc1cc(C(F)(F)F)nc(-c2ccnc3cc(CN4C(=O)C5C(C4=O)C5(C)C)sc23)c1C(=O)N1CCC2CNCC21 ; Cl ; Cl] A
Racemate
73. 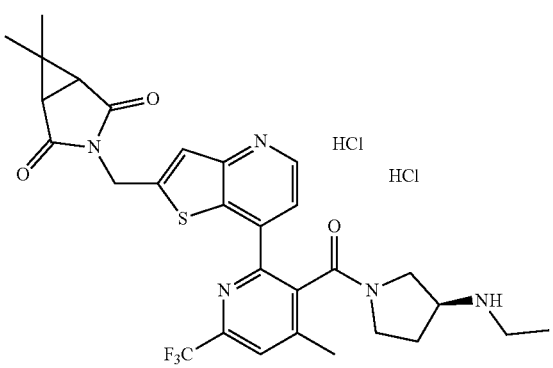 [SMILES: CCN[C@H]1CCN(C(=O)c2c(C)cc(C(F)(F)F)nc2-c2ccnc3cc(CN4C(=O)C5C(C4=O)C5(C)C)sc23)C1 ; Cl ; Cl] A 74. 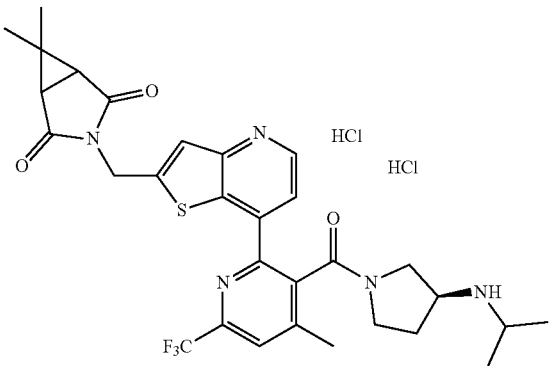 [SMILES: Cc1cc(C(F)(F)F)nc(-c2ccnc3cc(CN4C(=O)C5C(C4=O)C5(C)C)sc23)c1C(=O)N1CC[C@H](NC(C)C)C1 ; Cl ; Cl] A
75. 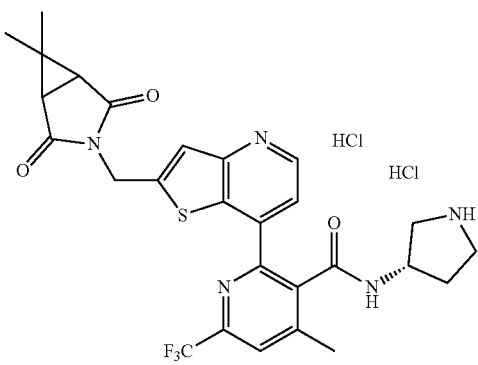 [SMILES: Cc1cc(C(F)(F)F)nc(-c2ccnc3cc(CN4C(=O)C5C(C4=O)C5(C)C)sc23)c1C(=O)N[C@H]1CCNC1 ; Cl ; Cl] C
76. 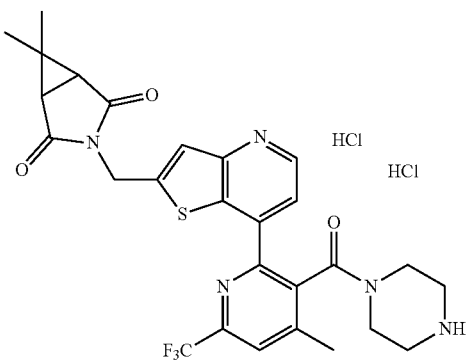 [SMILES: Cc1cc(C(F)(F)F)nc(-c2ccnc3cc(CN4C(=O)C5C(C4=O)C5(C)C)sc23)c1C(=O)N1CCNCC1 ; Cl ; Cl] A
77. 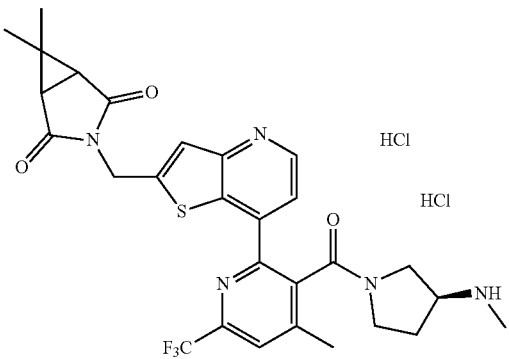 A -continued
| | | |
|---|---|---|
| 78. | 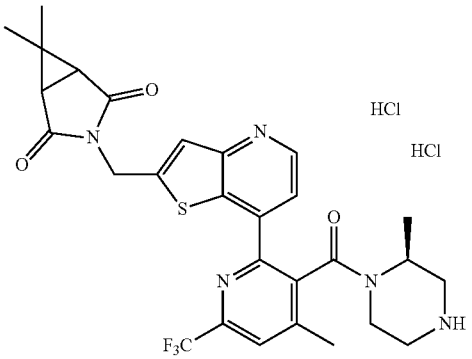 [SMILES: Cc1cc(C(F)(F)F)nc(-c2ccnc3cc(CN4C(=O)C5C(C4=O)C5(C)C)sc23)c1C(=O)N1CCNC[C@@H]1C ; Cl ; Cl] | A<br>HCl<br>HCl |
| 79. | 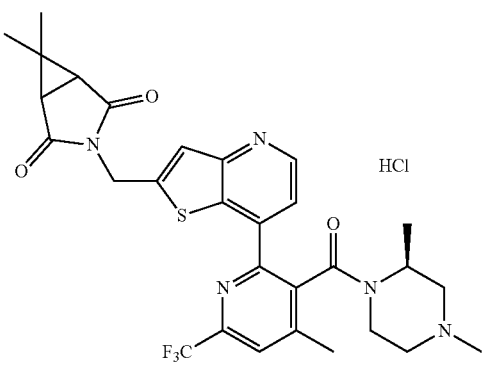 | A<br>HCl |
| 80. | 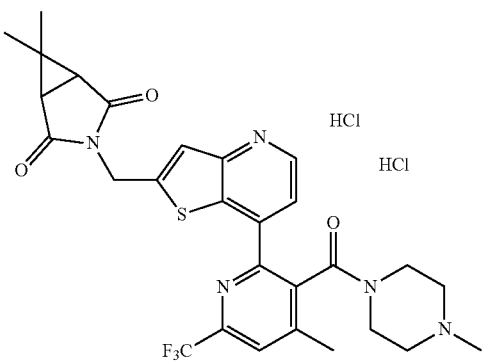 | A<br>HCl<br>HCl |
| 81. | 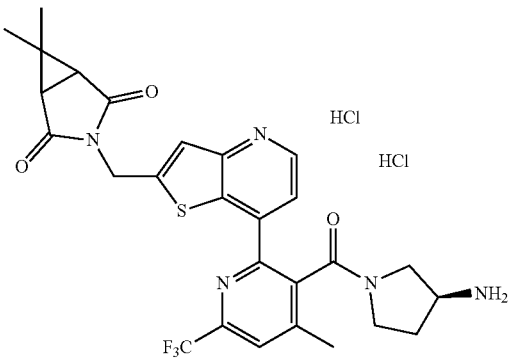 [SMILES: Cc1cc(C(F)(F)F)nc(-c2ccnc3cc(CN4C(=O)C5C(C4=O)C5(C)C)sc23)c1C(=O)N1CC[C@H](N)C1 ; Cl ; Cl] | A<br>HCl<br>HCl |

-continued
| | | |
|---|---|---|
| 82. | 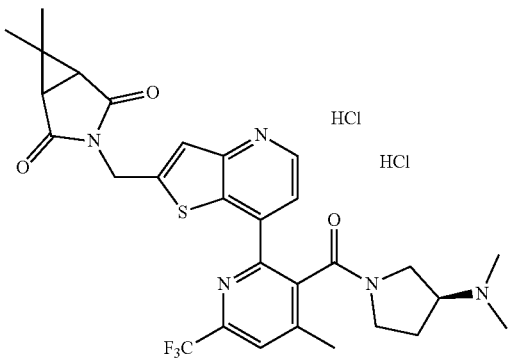 | A |
| 83. | 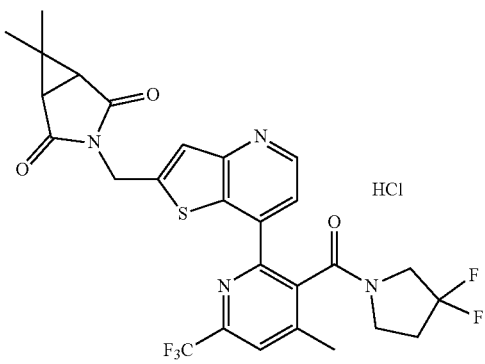 [SMILES: Cc1cc(C(F)(F)F)nc(-c2ccnc3cc(CN4C(=O)C5C(C4=O)C5(C)C)sc23)c1C(=O)N1CCC(F)(F)C1 ; Cl] | A |
| 84. | 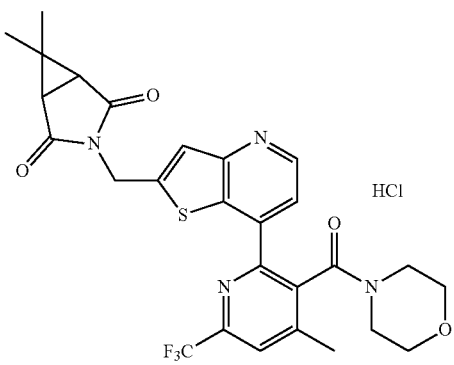 [SMILES: Cc1cc(C(F)(F)F)nc(-c2ccnc3cc(CN4C(=O)C5C(C4=O)C5(C)C)sc23)c1C(=O)N1CCOCC1 ; Cl] | B |
| 85. | 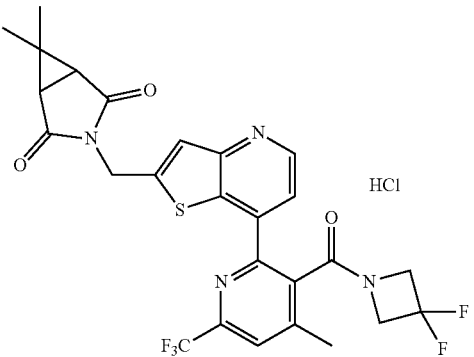 [SMILES: Cc1cc(C(F)(F)F)nc(-c2ccnc3cc(CN4C(=O)C5C(C4=O)C5(C)C)sc23)c1C(=O)N1CC(F)(F)C1 ; Cl] | C |

| 86. | 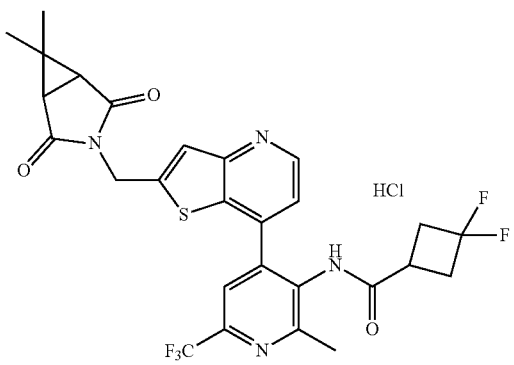 [SMILES: Cc1nc(C(F)(F)F)cc(-c2ccnc3cc(CN4C(=O)C5C(C4=O)C5(C)C)sc23)c1NC(=O)C1CC(F)(F)C1 ; Cl] | D |
|---|---|---|
| 87. | 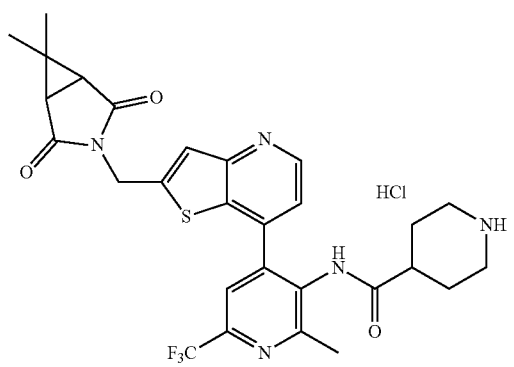 [SMILES: Cc1nc(C(F)(F)F)cc(-c2ccnc3cc(CN4C(=O)C5C(C4=O)C5(C)C)sc23)c1NC(=O)C1CCNCC1 ; Cl] | C |
| 88. | 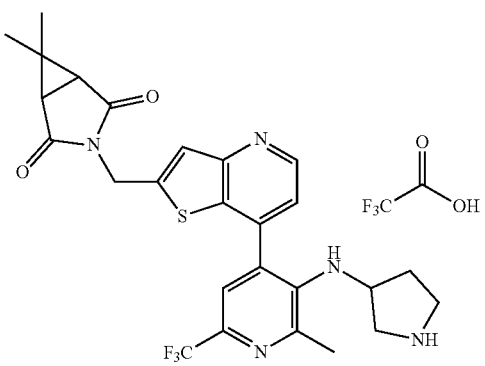 [SMILES: Cc1nc(C(F)(F)F)cc(-c2ccnc3cc(CN4C(=O)C5C(C4=O)C5(C)C)sc23)c1NC1CCNC1 ; O=C(O)C(F)(F)F]<br>Racemate | A |
| 89. | 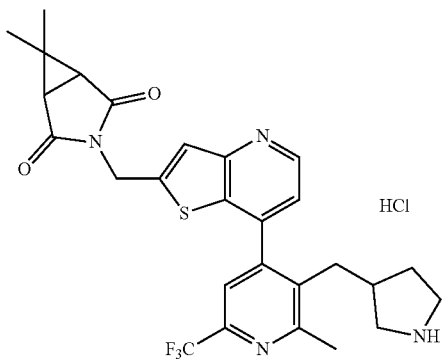 [SMILES: Cc1nc(C(F)(F)F)cc(-c2ccnc3cc(CN4C(=O)C5C(C4=O)C5(C)C)sc23)c1CC1CCNC1 ; Cl]<br>Single enantiomer of Ex. 88 | A |

90.
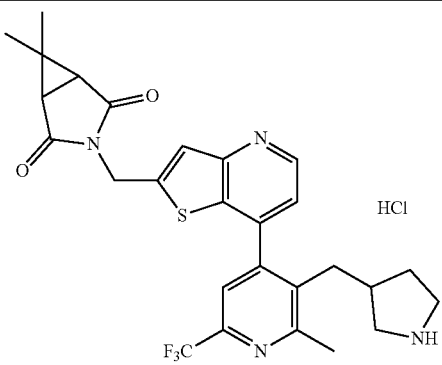
Single enantiomer of Ex. 88
A
91.
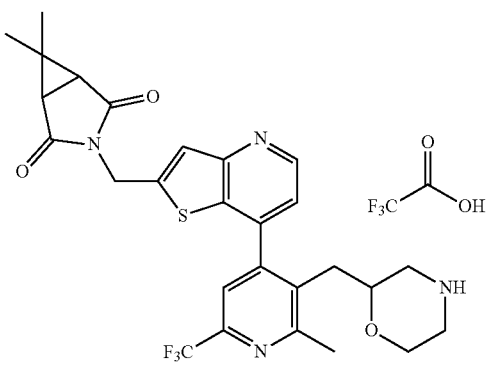 [SMILES: Cc1nc(C(F)(F)F)cc(-c2ccnc3cc(CN4C(=O)C5C(C4=O)C5(C)C)sc23)c1CC1CNCCO1 ; O=C(O)C(F)(F)F]
Racemate
A
92.
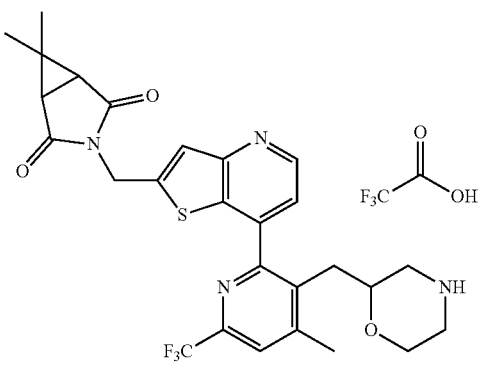 [SMILES: Cc1cc(C(F)(F)F)nc(-c2ccnc3cc(CN4C(=O)C5C(C4=O)C5(C)C)sc23)c1CC1CNCCO1 ; O=C(O)C(F)(F)F]
Racemate
A
93.
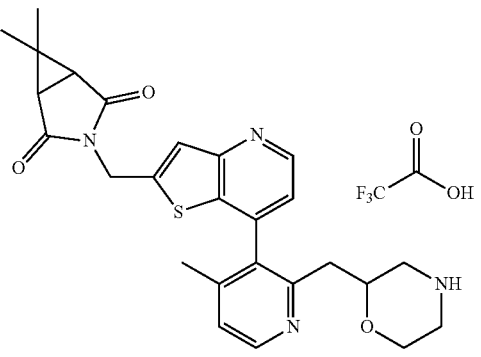 [SMILES: Cc1ccnc(CC2CNCCO2)c1-c1ccnc2cc(CN3C(=O)C4C(C3=O)C4(C)C)sc12 ; O=C(O)C(F)(F)F]
Racemate
D*

94.
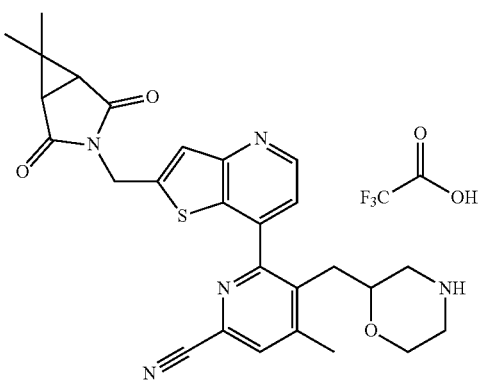 [SMILES: Cc1cc(C#N)nc(-c2ccnc3cc(CN4C(=O)C5C(C4=O)C5(C)C)sc23)c1CC1CNCCO1 ; O=C(O)C(F)(F)F]
Racemate
95. 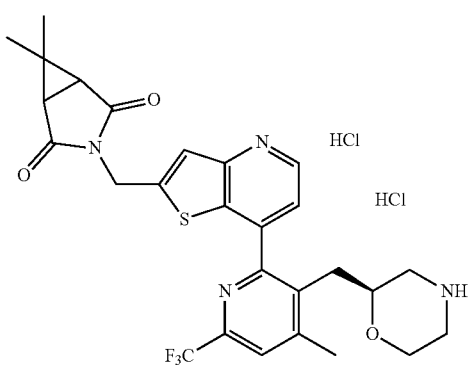 [SMILES: Cc1cc(C(F)(F)F)nc(-c2ccnc3cc(CN4C(=O)C5C(C4=O)C5(C)C)sc23)c1C[C@H]1CNCCO1 ; Cl ; Cl] A
96. 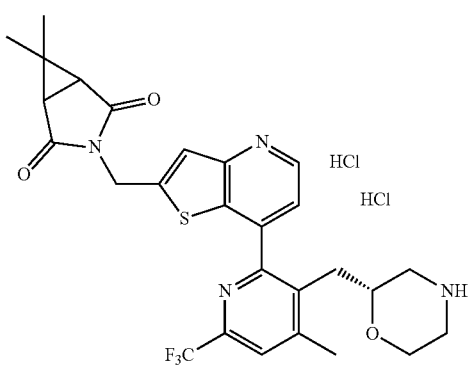 [SMILES: Cc1cc(C(F)(F)F)nc(-c2ccnc3cc(CN4C(=O)C5C(C4=O)C5(C)C)sc23)c1C[C@@H]1CNCCO1 ; Cl ; Cl] A
97. 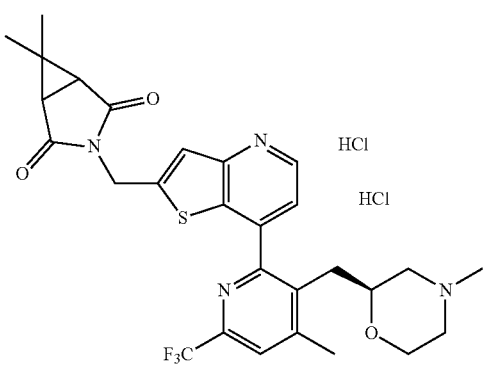 C

| | | |
|---|---|---|
| 98. | 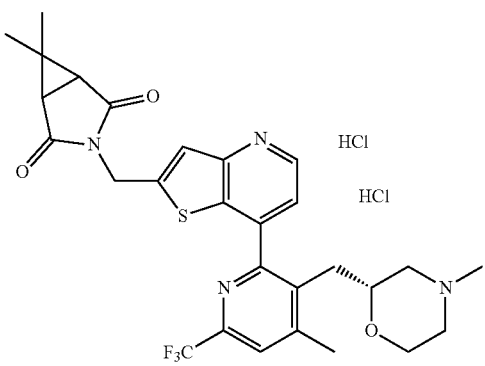 | A |
| 99. | 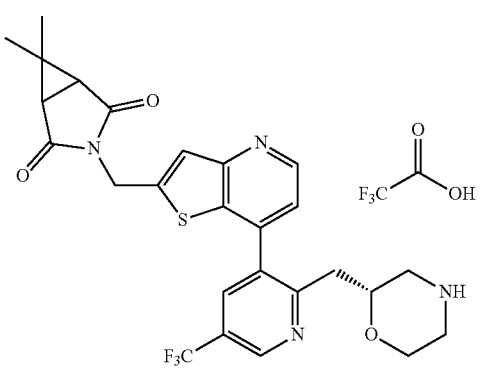 [SMILES: CC1(C)C2C(=O)N(Cc3cc4nccc(-c5cc(C(F)(F)F)cnc5C[C@@H]5CNCCO5)c4s3)C(=O)C21 ; O=C(O)C(F)(F)F] | A |
| 100. | 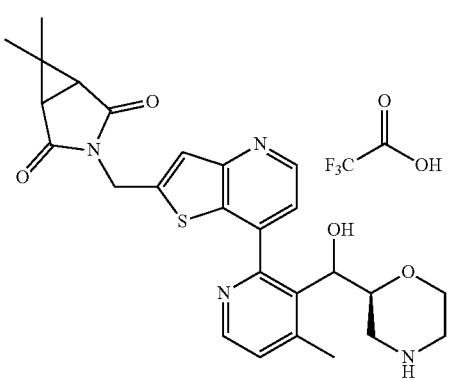 | C |
| 101. | 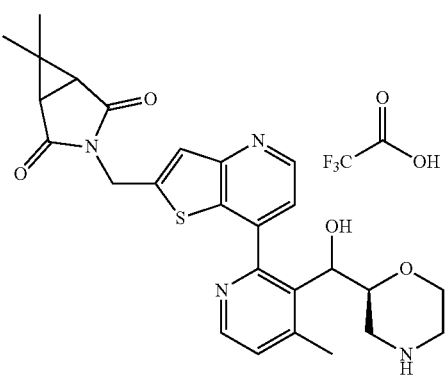 | D* |

-continued
| | | |
|---|---|---|
| 102. | 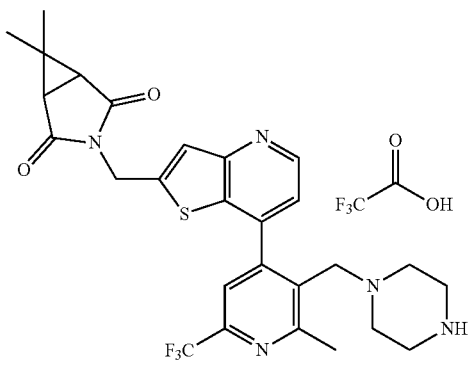 [SMILES: Cc1nc(C(F)(F)F)cc(-c2ccnc3cc(CN4C(=O)C5C(C4=O)C5(C)C)sc23)c1CN1CCNCC1 ; O=C(O)C(F)(F)F] | C |
| 103. | 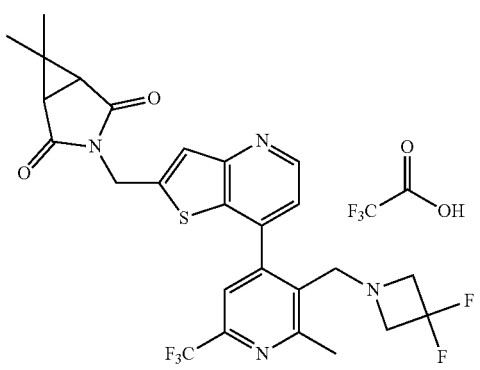 [SMILES: Cc1nc(C(F)(F)F)cc(-c2ccnc3cc(CN4C(=O)C5C(C4=O)C5(C)C)sc23)c1CN1CC(F)(F)C1 ; O=C(O)C(F)(F)F] | C |
| 104. | 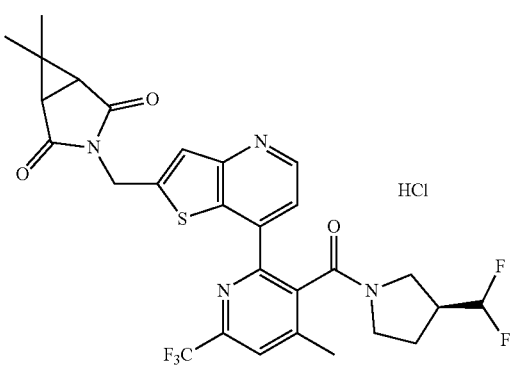 [SMILES: Cc1cc(C(F)(F)F)nc(-c2ccnc3cc(CN4C(=O)C5C(C4=O)C5(C)C)sc23)c1C(=O)N1CC[C@H](C(F)F)C1 ; Cl] | A |
| 105. | 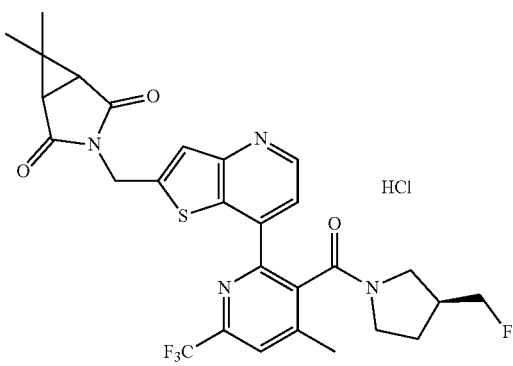 [SMILES: Cc1cc(C(F)(F)F)nc(-c2ccnc3cc(CN4C(=O)C5C(C4=O)C5(C)C)sc23)c1C(=O)N1CC[C@H](CF)C1 ; Cl] | A |

| | | |
|---|---|---|
| 106. | 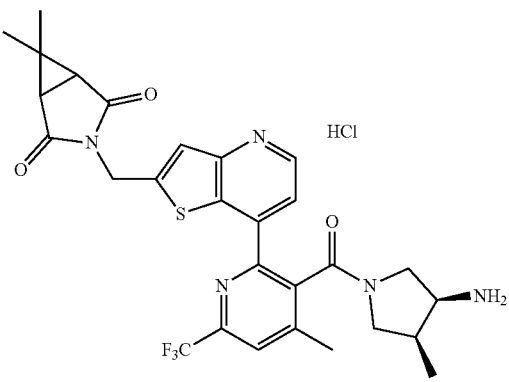 [SMILES: Cc1cc(C(F)(F)F)nc(-c2ccnc3cc(CN4C(=O)C5C(C4=O)C5(C)C)sc23)c1C(=O)N1C[C@@H](N)[C@@H](C)C1 ; Cl] | A |
| 107. | 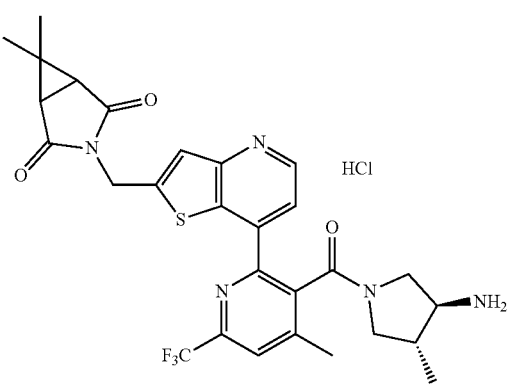 [SMILES: Cc1cc(C(F)(F)F)nc(-c2ccnc3cc(CN4C(=O)C5C(C4=O)C5(C)C)sc23)c1C(=O)N1C[C@@H](C)[C@H](N)C1 ; Cl] | A |
| 108. | 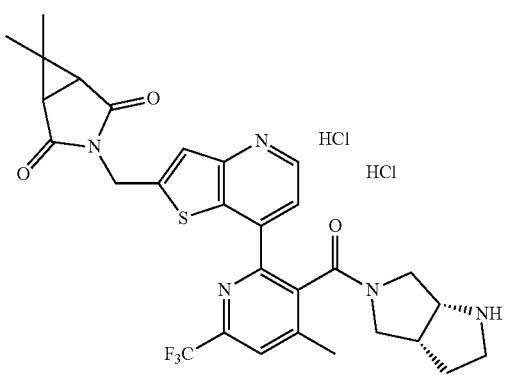 [SMILES: Cc1cc(C(F)(F)F)nc(-c2ccnc3cc(CN4C(=O)C5C(C4=O)C5(C)C)sc23)c1C(=O)N1C[C@H]2CCN[C@H]2C1 ; Cl ; Cl] | A |
| 109. | 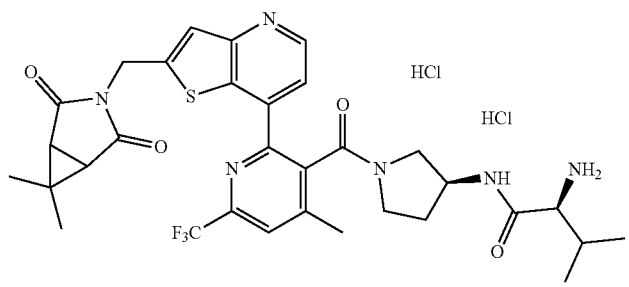 [SMILES: Cc1cc(C(F)(F)F)nc(-c2ccnc3cc(CN4C(=O)C5C(C4=O)C5(C)C)sc23)c1C(=O)N1CC[C@H](NC(=O)[C@@H](N)C(C)C)C1 ; Cl ; Cl] | A |

-continued
| | | | |
|---|---|---|---|
| 110. | 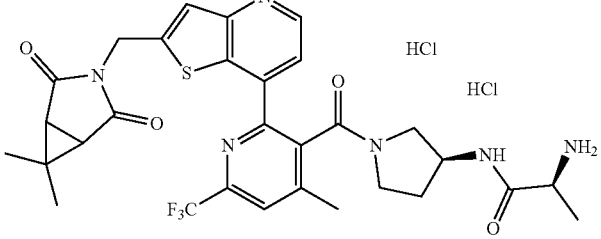 | HCl HCl | B |
| 111. | 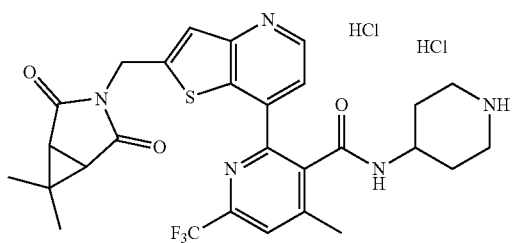 [SMILES: Cc1cc(C(F)(F)F)nc(-c2ccnc3cc(CN4C(=O)C5C(C4=O)C5(C)C)sc23)c1C(=O)NC1CCNCC1 ; Cl ; Cl] | HCl HCl | D* |
| 112. | 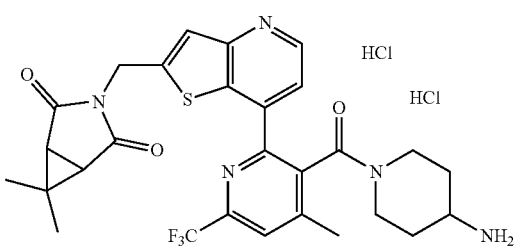 [SMILES: Cc1cc(C(F)(F)F)nc(-c2ccnc3cc(CN4C(=O)C5C(C4=O)C5(C)C)sc23)c1C(=O)N1CCC(N)CC1 ; Cl ; Cl] | HCl HCl | A |
| 113. | 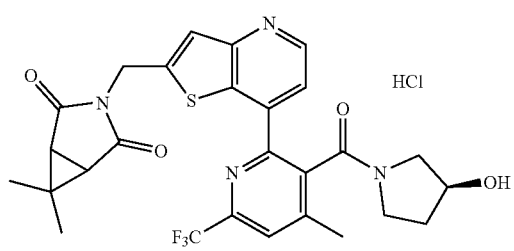 [SMILES: Cc1cc(C(F)(F)F)nc(-c2ccnc3cc(CN4C(=O)C5C(C4=O)C5(C)C)sc23)c1C(=O)N1CC[C@H](O)C1 ; Cl] | HCl | A |
| 114. | 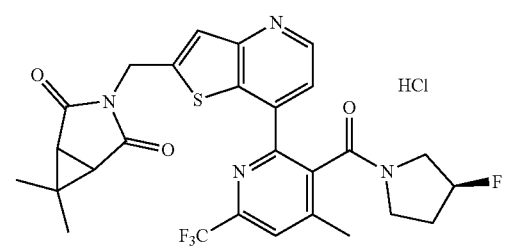 [SMILES: Cc1cc(C(F)(F)F)nc(-c2ccnc3cc(CN4C(=O)C5C(C4=O)C5(C)C)sc23)c1C(=O)N1CC[C@H](F)C1 ; Cl] | HCl | A |
| 115. | 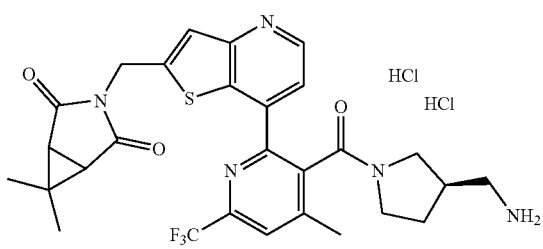 [SMILES: Cc1cc(C(F)(F)F)nc(-c2ccnc3cc(CN4C(=O)C5C(C4=O)C5(C)C)sc23)c1C(=O)N1CC[C@H](CN)C1 ; Cl ; Cl] | HCl HCl | B |

-continued
| | | |
|---|---|---|
| 116. | 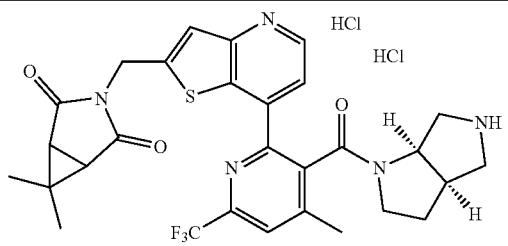 | A |
| 117. | 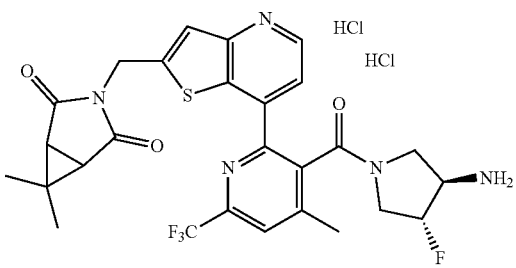 [SMILES: Cc1cc(C(F)(F)F)nc(-c2ccnc3cc(CN4C(=O)C5C(C4=O)C5(C)C)sc23)c1C(=O)N1C[C@@H](N)[C@H](F)C1 ; Cl ; Cl] | A |
| 118. | 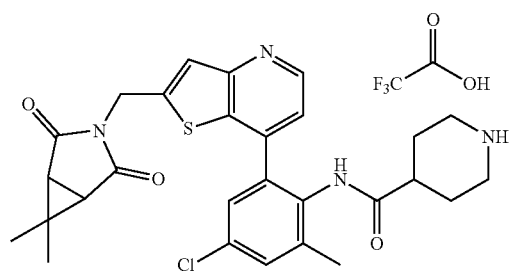 | A |
| 119. | 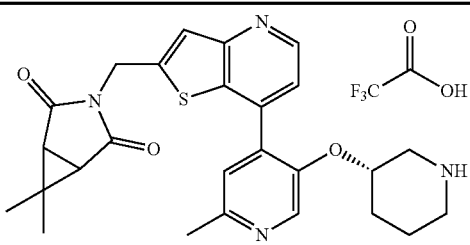 | D* |
| 120. | 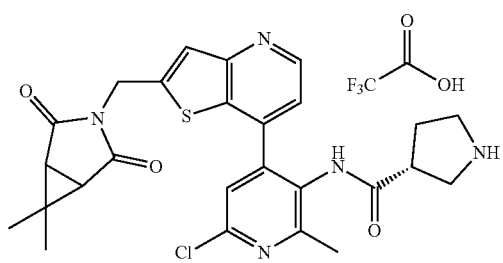 | C |
| 121. | 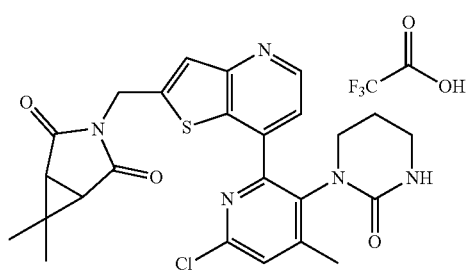 | B |

-continued
| | | | |
|---|---|---|---|
| 122. | 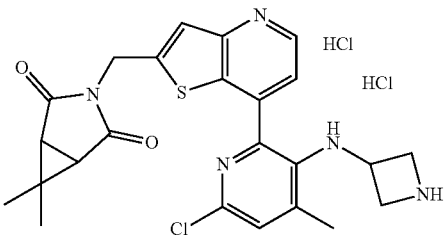 [SMILES: Cc1cc(Cl)nc(-c2ccnc3cc(CN4C(=O)C5C(C4=O)C5(C)C)sc23)c1NC1CNC1 ; Cl ; Cl] HCl HCl | | A |
| 123. | 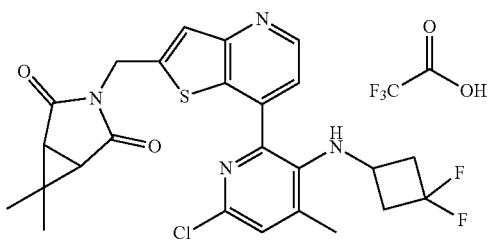 [SMILES: Cc1cc(Cl)nc(-c2ccnc3cc(CN4C(=O)C5C(C4=O)C5(C)C)sc23)c1NC1CC(F)(F)C1 ; O=C(O)C(F)(F)F] F₃C⟶OH | | B |
| 124. | 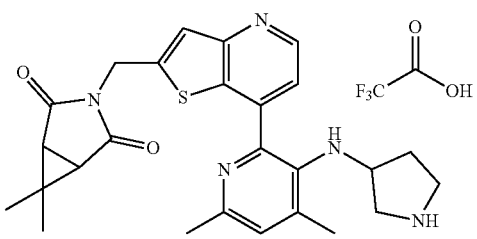 [SMILES: Cc1cc(C)c(NC2CCNC2)c(-c2ccnc3cc(CN4C(=O)C5C(C4=O)C5(C)C)sc23)n1 ; O=C(O)C(F)(F)F] F₃C⟶OH Racemate | | A |
| 125. | 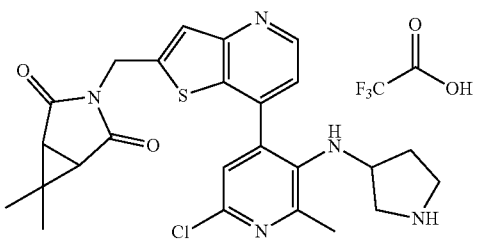 [SMILES: Cc1nc(Cl)cc(-c2ccnc3cc(CN4C(=O)C5C(C4=O)C5(C)C)sc23)c1NC1CCNC1 ; O=C(O)C(F)(F)F] F₃C⟶OH Racemate | | A |
| 126. | 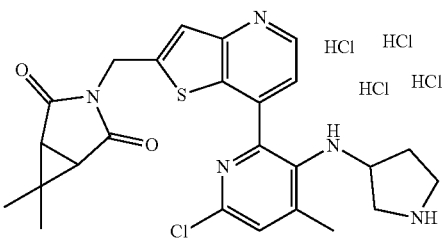 [SMILES: Cc1cc(Cl)nc(-c2ccnc3cc(CN4C(=O)C5C(C4=O)C5(C)C)sc23)c1NC1CCNC1 ; Cl ; Cl ; Cl ; Cl] HCl HCl HCl HCl Racemate | | A |
| 127. | 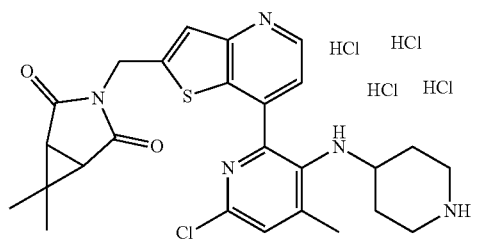 [SMILES: Cc1cc(Cl)nc(-c2ccnc3cc(CN4C(=O)C5C(C4=O)C5(C)C)sc23)c1NC1CCNCC1 ; Cl ; Cl ; Cl ; Cl] HCl HCl HCl HCl | | A |

-continued
| | | |
|---|---|---|
| 128. | 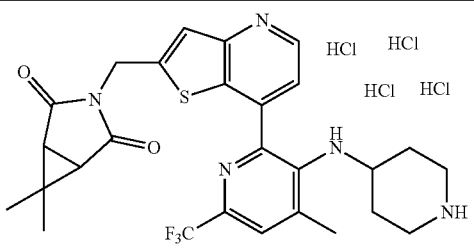 | A |
| 129. | 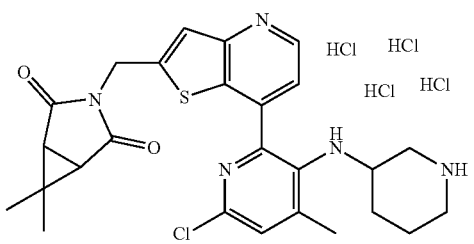 [SMILES: Cc1cc(Cl)nc(-c2ccnc3cc(CN4C(=O)C5C(C4=O)C5(C)C)sc23)c1NC1CCCNC1 ; Cl ; Cl ; Cl ; Cl]<br>Racemate | A |
| 130. | 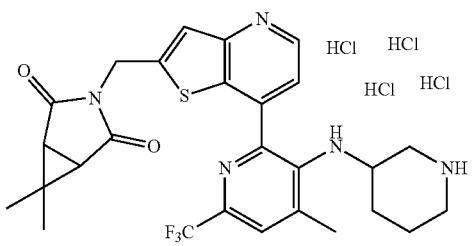 [SMILES: Cc1cc(C(F)(F)F)nc(-c2ccnc3cc(CN4C(=O)C5C(C4=O)C5(C)C)sc23)c1NC1CCCNC1 ; Cl ; Cl ; Cl ; Cl]<br>Racemate | A |
| 131. | 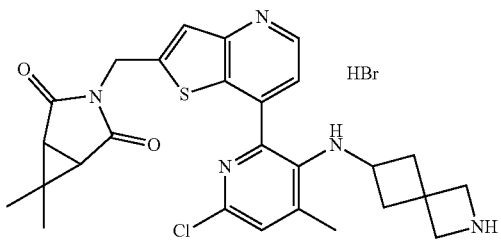 [SMILES: Cc1cc(Cl)nc(-c2ccnc3cc(CN4C(=O)C5C(C4=O)C5(C)C)sc23)c1NC1CC2(CNC2)C1 ; Br] | A |
| 132. | 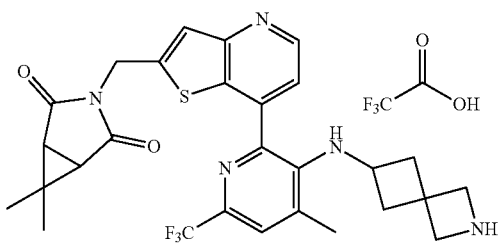 [SMILES: Cc1cc(C(F)(F)F)nc(-c2ccnc3cc(CN4C(=O)C5C(C4=O)C5(C)C)sc23)c1NC1CC2(CNC2)C1 ; O=C(O)C(F)(F)F] | A |
| 133. | 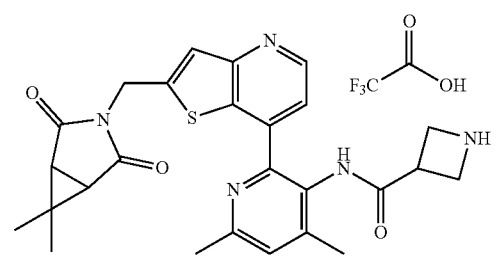 | C |

-continued
| | | |
|---|---|---|
| 134. | 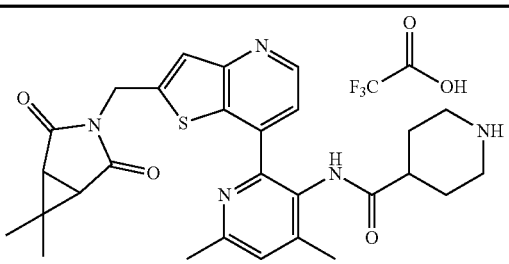 | D* |
| 135. | 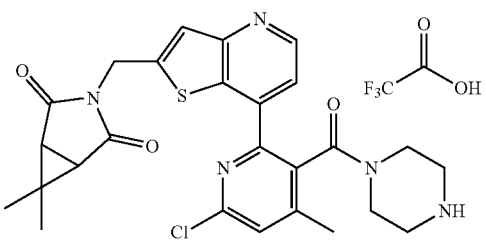 | D* |
| 136. | 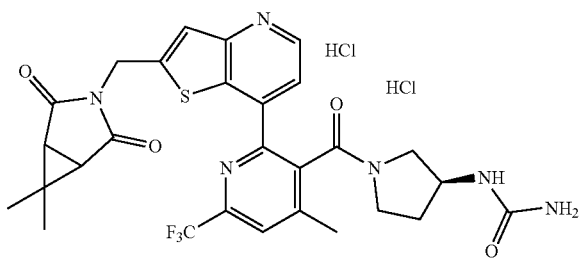 [SMILES: Cc1cc(C(F)(F)F)nc(-c2ccnc3cc(CN4C(=O)C5C(C4=O)C5(C)C)sc23)c1C(=O)N1CC[C@H](NC(N)=O)C1 ; Cl ; Cl] | B |
| 137. | 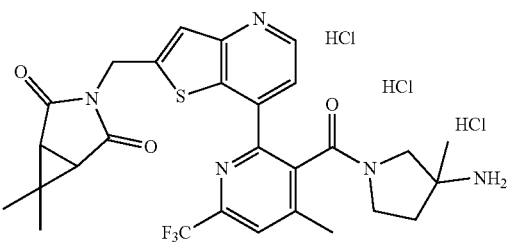 [SMILES: Cc1cc(C(F)(F)F)nc(-c2ccnc3cc(CN4C(=O)C5C(C4=O)C5(C)C)sc23)c1C(=O)N1CCC(C)(N)C1 ; Cl ; Cl ; Cl]
Racemate | B |
| 138. | 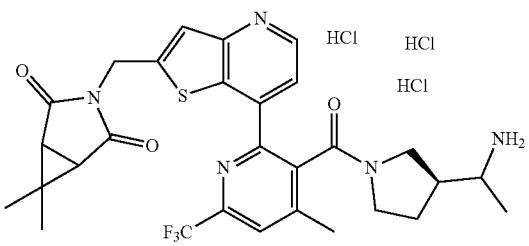 [SMILES: Cc1cc(C(F)(F)F)nc(-c2ccnc3cc(CN4C(=O)C5C(C4=O)C5(C)C)sc23)c1C(=O)N1CC[C@H](C(C)N)C1 ; Cl ; Cl ; Cl]
One diastereoisomer | B* |
| 139. | 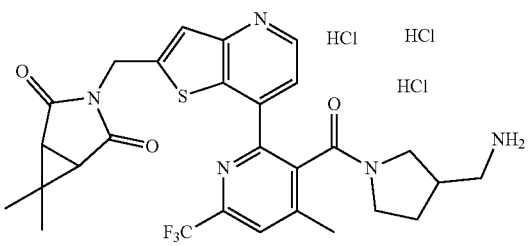 [SMILES: Cc1cc(C(F)(F)F)nc(-c2ccnc3cc(CN4C(=O)C5C(C4=O)C5(C)C)sc23)c1C(=O)N1CCC(CN)C1 ; Cl ; Cl ; Cl]
Racemate | A |

140. 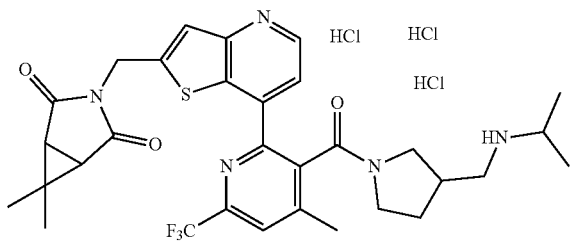 [SMILES: Cc1cc(C(F)(F)F)nc(-c2ccnc3cc(CN4C(=O)C5C(C4=O)C5(C)C)sc23)c1C(=O)N1CCC(CNC(C)C)C1 ; Cl ; Cl ; Cl] A
Racemate
141. 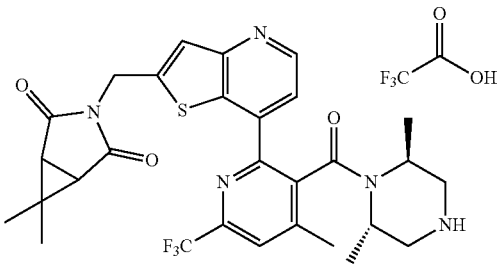 A
142. 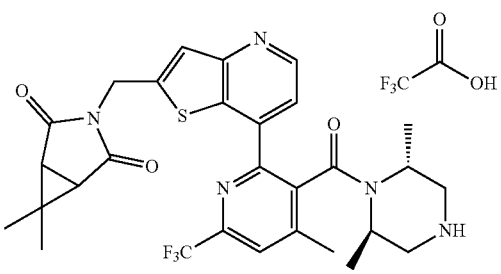 C
143. 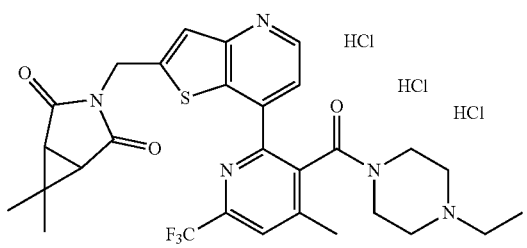 [SMILES: CCN1CCN(C(=O)c2c(C)cc(C(F)(F)F)nc2-c2ccnc3cc(CN4C(=O)C5C(C4=O)C5(C)C)sc23)CC1 ; Cl ; Cl ; Cl] A
144. 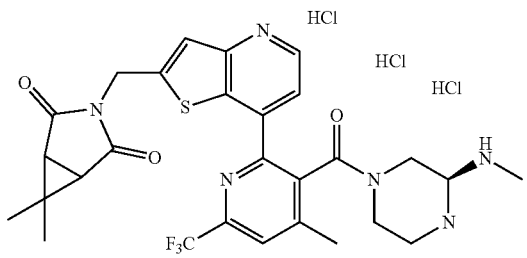 C

| | | |
|---|---|---|
| 145. | 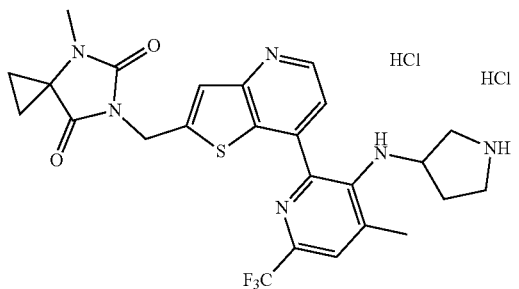 [SMILES: Cc1cc(C(F)(F)F)nc(-c2ccnc3cc(CN4C(=O)N(C)C5(CC5)C4=O)sc23)c1NC1CCNC1 ; Cl ; Cl] Racemate | A |
| 146. | 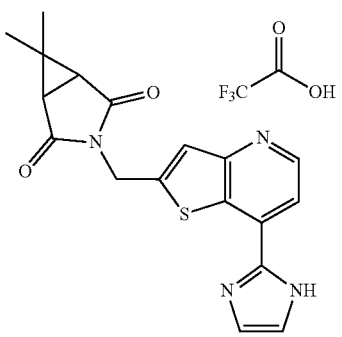 | D* |
| 147. | 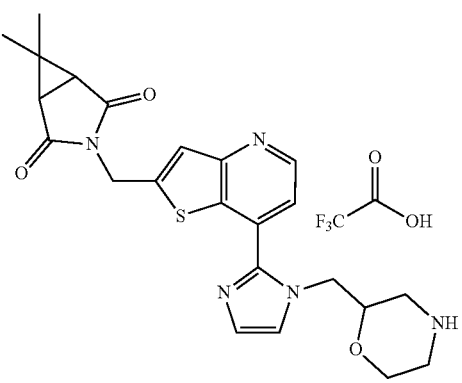 | D* |
| 148. | 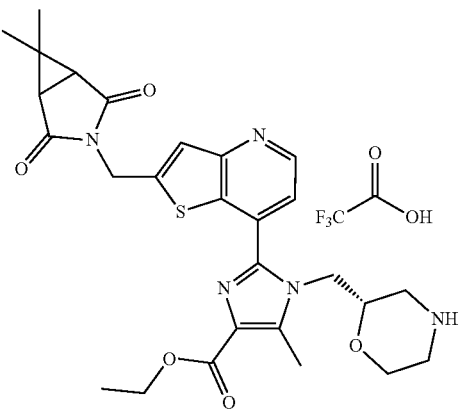 | C |

-continued
| 149. | 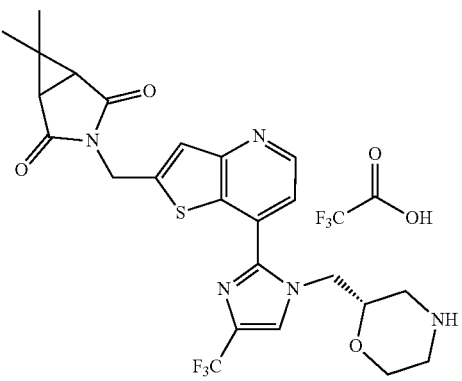 | D* |
| 150. | 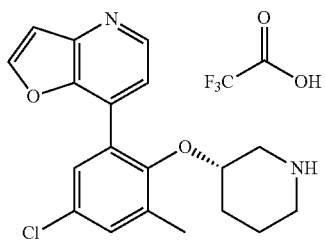 [SMILES: Cc1cc(Cl)cc(-c2ccnc3ccoc23)c1O[C@H]1CCCNC1 ; O=C(O)C(F)(F)F] | C |
| 151. | 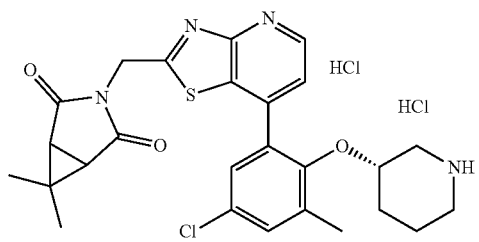 [SMILES: Cc1cc(Cl)cc(-c2ccnc3nc(CN4C(=O)C5C(C4=O)C5(C)C)sc23)c1O[C@H]1CCCNC1 ; Cl ; Cl] | D* |
| 152. | 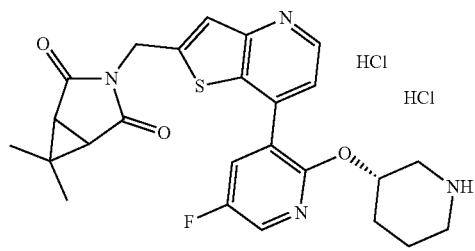 [SMILES: CC1(C)C2C(=O)N(Cc3cc4nccc(-c5cc(F)cnc5O[C@H]5CCCNC5)c4s3)C(=O)C21 ; Cl ; Cl] | D* |
| 153. | 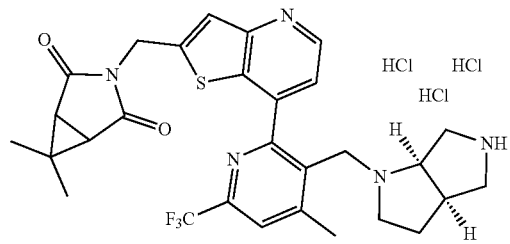 [SMILES: Cc1cc(C(F)(F)F)nc(-c2ccnc3cc(CN4C(=O)C5C(C4=O)C5(C)C)sc23)c1CN1CC[C@@H]2CNC[C@@H]21 ; Cl ; Cl ; Cl]<br>A racemate | A |

-continued
154. 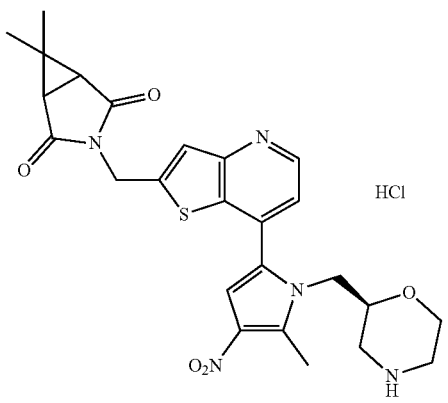 [SMILES: Cc1c([N+](=O)[O-])cc(-c2ccnc3cc(CN4C(=O)C5C(C4=O)C5(C)C)sc23)n1C[C@@H]1CNCCO1 ; Cl] A
155. 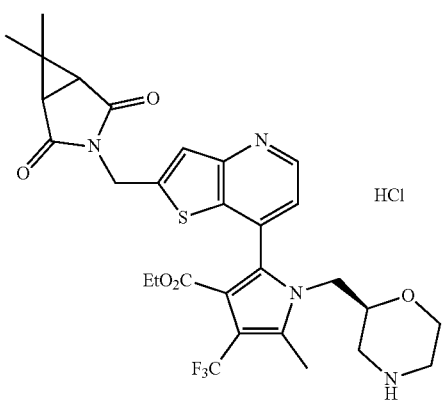 [SMILES: CCOC(=O)c1c(C(F)(F)F)c(C)n(C[C@@H]2CNCCO2)c1-c1ccnc2cc(CN3C(=O)C4C(C3=O)C4(C)C)sc12 ; Cl] D*
156. 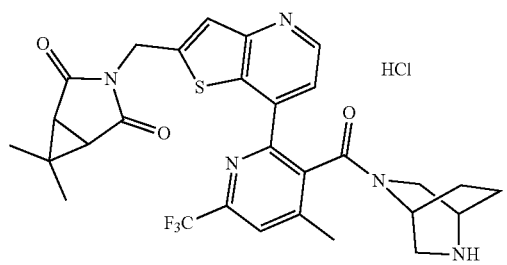 [SMILES: Cc1cc(C(F)(F)F)nc(-c2ccnc3cc(CN4C(=O)C5C(C4=O)C5(C)C)sc23)c1C(=O)N1CC2CCC1CN2 ; Cl] A
157. 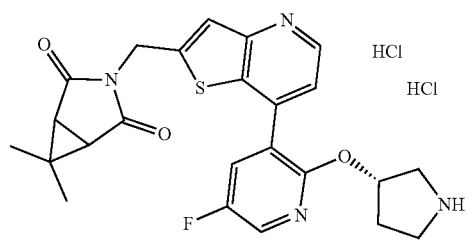 [SMILES: CC1(C)C2C(=O)N(Cc3cc4nccc(-c5cc(F)cnc5O[C@H]5CCNC5)c4s3)C(=O)C21 ; Cl ; Cl] D*
158. 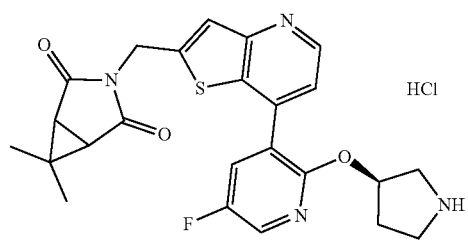 [SMILES: CC1(C)C2C(=O)N(Cc3cc4nccc(-c5cc(F)cnc5O[C@@H]5CCNC5)c4s3)C(=O)C21 ; Cl] D*

| | | |
|---|---|---|
| 159. | 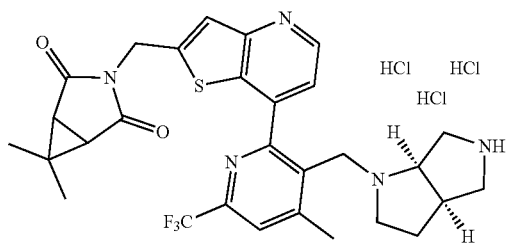 [SMILES: Cc1cc(C(F)(F)F)nc(-c2ccnc3cc(CN4C(=O)C5C(C4=O)C5(C)C)sc23)c1CN1CC[C@@H]2CNC[C@@H]21 ; Cl ; Cl ; Cl] A single enantiomer of the compound 153 | A |
| 160. | 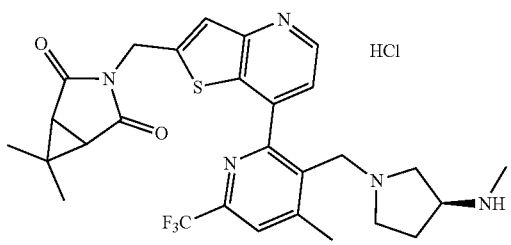 | A |
| 161. | 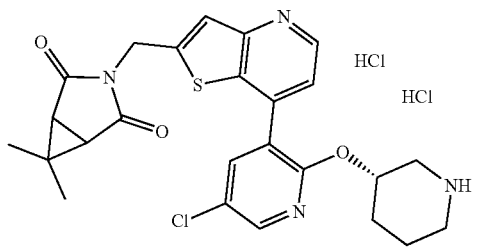 [SMILES: CC1(C)C2C(=O)N(Cc3cc4nccc(-c5cc(Cl)cnc5O[C@H]5CCCNC5)c4s3)C(=O)C21 ; Cl ; Cl] | B* |
| 162. | 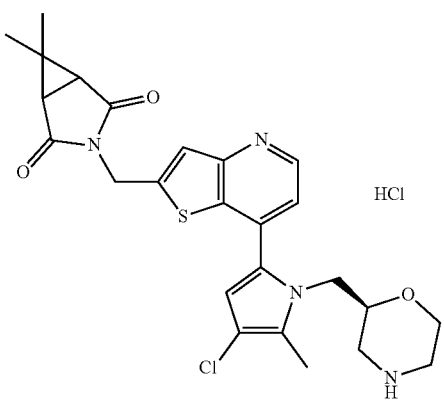 [SMILES: Cc1c(Cl)cc(-c2ccnc3cc(CN4C(=O)C5C(C4=O)C5(C)C)sc23)n1C[C@@H]1CNCCO1 ; Cl] | A |
| 163. | 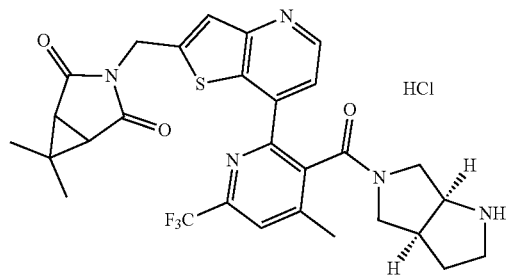 [SMILES: Cc1cc(C(F)(F)F)nc(-c2ccnc3cc(CN4C(=O)C5C(C4=O)C5(C)C)sc23)c1C(=O)N1C[C@@H]2CCN[C@@H]2C1 ; Cl] | B |

-continued
| | | |
|---|---|---|
| 164. | 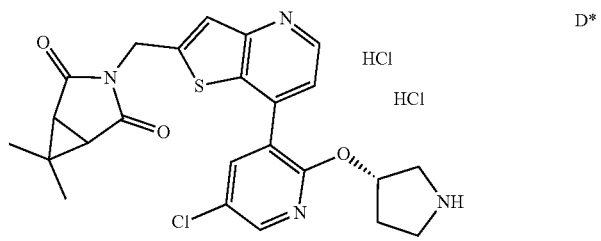 | D* |
| 165. | 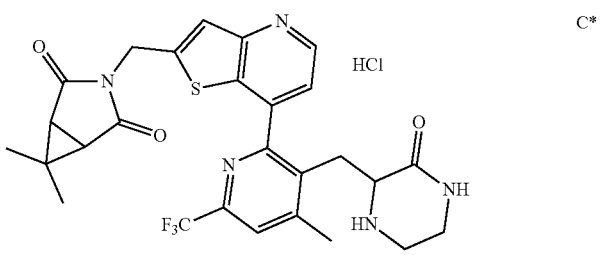 | C* |
| 166. | 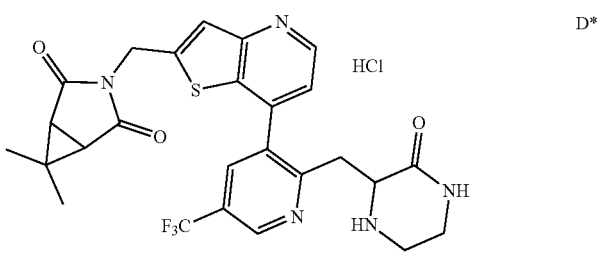 | D* |
| 167. | 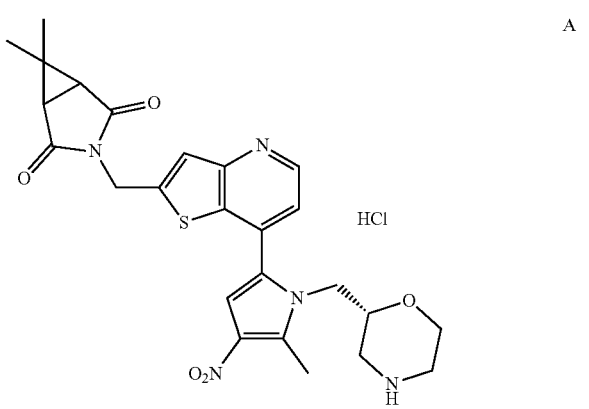 | A |
| 168. | 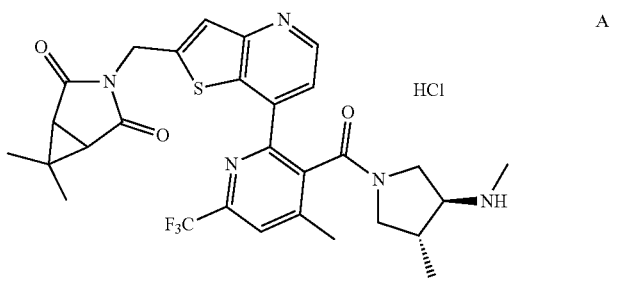 | A |

-continued
| | | |
|---|---|---|
| 169. | 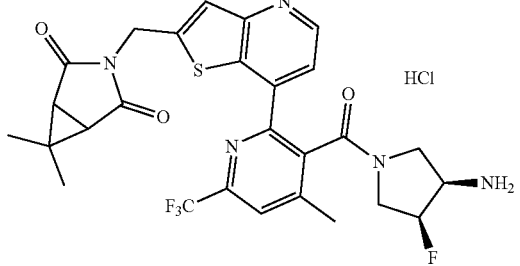 | A |
| 170. | 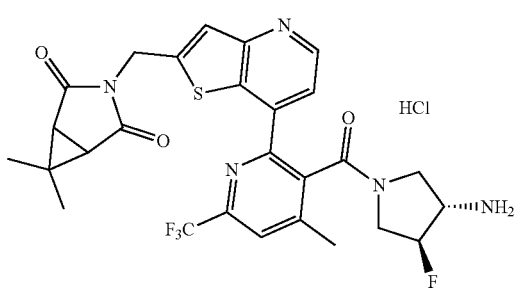 [SMILES: Cc1cc(C(F)(F)F)nc(-c2ccnc3cc(CN4C(=O)C5C(C4=O)C5(C)C)sc23)c1C(=O)N1C[C@H](N)[C@@H](F)C1 ; Cl] | A |
| 171. | 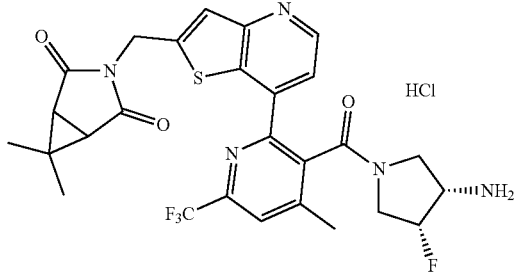 [SMILES: Cc1cc(C(F)(F)F)nc(-c2ccnc3cc(CN4C(=O)C5C(C4=O)C5(C)C)sc23)c1C(=O)N1C[C@@H](F)[C@@H](N)C1 ; Cl] | B* |
| 172. | 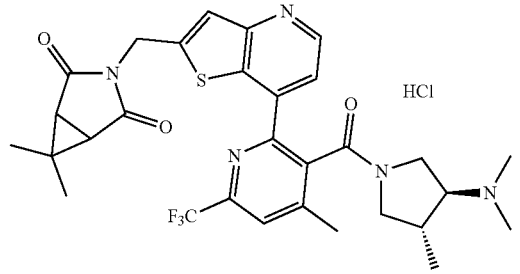 | A* |
| 173. | 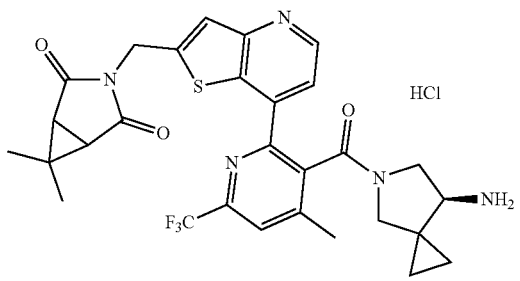 [SMILES: Cc1cc(C(F)(F)F)nc(-c2ccnc3cc(CN4C(=O)C5C(C4=O)C5(C)C)sc23)c1C(=O)N1C[C@@H](N)C2(CC2)C1 ; Cl] | A |

-continued
| | | |
|---|---|---|
| 174. | 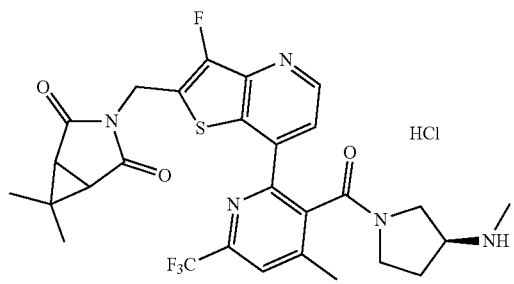 | B*<br>HCl |
| 175. | 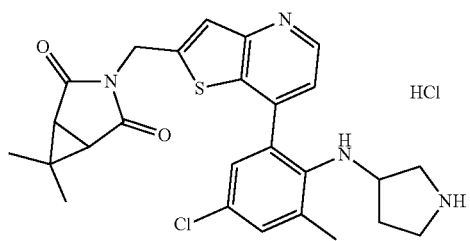 [SMILES: Cc1cc(Cl)cc(-c2ccnc3cc(CN4C(=O)C5C(C4=O)C5(C)C)sc23)c1NC1CCNC1 ; Cl] | A<br>HCl |
| 176. | 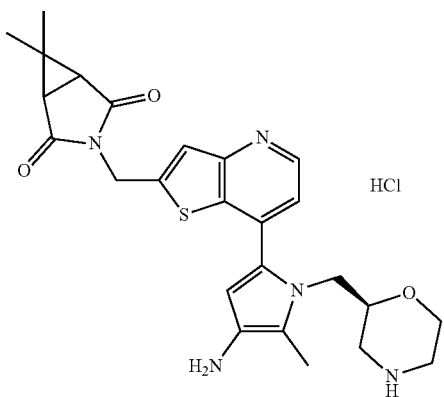 [SMILES: Cc1c(N)cc(-c2ccnc3cc(CN4C(=O)C5C(C4=O)C5(C)C)sc23)n1C[C@@H]1CNCCO1 ; Cl] | D*<br>HCl |
| 177. | 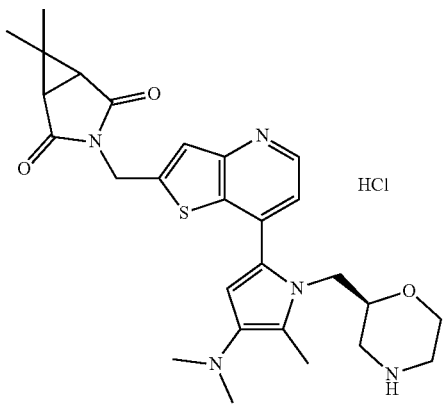 [SMILES: Cc1c(N(C)C)cc(-c2ccnc3cc(CN4C(=O)C5C(C4=O)C5(C)C)sc23)n1C[C@@H]1CNCCO1 ; Cl] | D*<br>HCl |
| 178. | 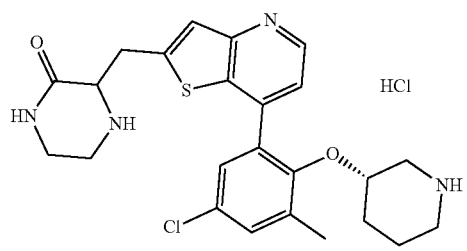 [SMILES: Cc1cc(Cl)cc(-c2ccnc3cc(CC4NCCNC4=O)sc23)c1O[C@H]1CCCNC1 ; Cl] | A<br>HCl |

| 179. | 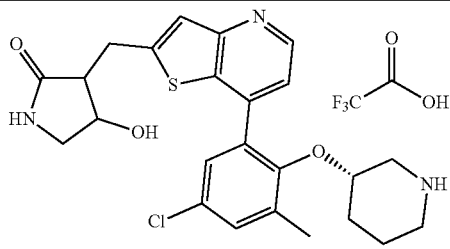 A single diastereoisomer | A |
| 180. | 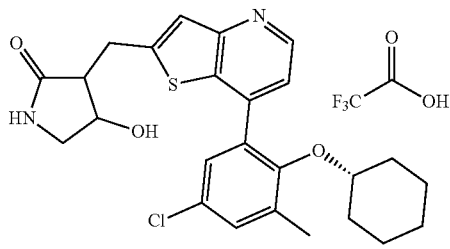 A single diastereoisomer | A |
| 181. | 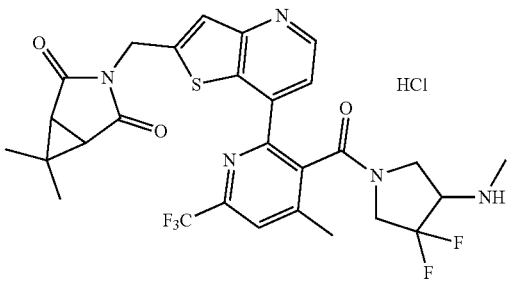 | HCl — |

General Synthetic Procedures

General Procedure I

Reaction of Appropriate Carboxylic Acid with an Appropriate Amine or Alcohols.

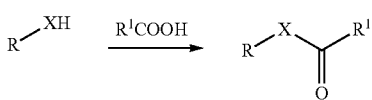

X = O, N

To the solution of carboxylic acid (1 equivalent) and diisopropylethylamine (DIPEA; 3 equivalents) or triethylamine ($Et_3N$; 3 equivalents) in dichloromethane (6 mL/mmol) or in DMF (5 mL/mmol) appropriate alcohol (1-1.2 equivalent) or amine (1 equivalent) was added. Then EDCl hydrochloride (1.1-1.5 equivalent) or HATU (1.1 equivalent) and DMAP (0.05-0.1 equivalent, when it was necessary) were added sequentially and the reaction mixture was stirred overnight at room temperature. After this time LC-MS control showed complete consumption of the starting materials and the reaction mixture was taken into DCM/water. An organic layer was washed with water and brine, dried over anhydrous $MgSO_4$, filtered and concentrated in vacuo and the crude product was further purified by flash column chromatography on silica.

General Procedure II

Acylation of Appropriate Amine with Acid Chloride.

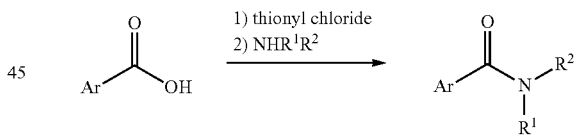

To the solution of carboxylic acid (1-1.5 equivalent) and triethylamine (4 equivalents) or pyridine (2.5 equivalents) in DCM or DMF (6 mL/mmol) thionyl chloride (1.7 equivalents) was added dropwise at 0° C. and the reaction mixture was stirred at this temperature for the time necessary for the complete consumption of the starting material (usually 1 to 3 hours) as judged by TLC or LC-MS. After this time thionyl chloride was concentrated in vacuo. Then to the residue a mixture of DCM (4 mL/mmol), triethylamine (2-7 equivalents), an appropriate amine (1-1.5 equivalents) and DMAP (0.1 equivalent) was added dropwise at 0° C. and the reaction mixture was stirred at 0° C. for 1 hour and then in room temperature and then heated at 40° C. After consumption of the starting material (confirmed by TLC or LC-MS analysis), to this mixture 1 M $K_2CO_3$ or 1 M NaOH was added. The layers were separated and the aqueous one was additionally extracted with DCM (3×). The combined organic extracts were dried over anhydrous $Na_2SO_4$, filtered and evaporated in vacuo. The crude product was purified by silica-gel chromatography or by preparative reversed-phase column chromatography.

General Procedure III
Protection of Amine Group by Di-Tert-Butyl Dicarbonate (Boc$_2$O).

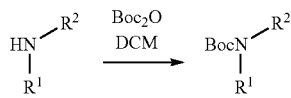

To the solution of appropriate amine (1 equivalent) in DCM (5 mL/mmol) Boc$_2$O (1.2 equivalents) was added and then stirred at room temperature overnight. The reaction progress was monitored by TLC and LC-MS. When analyses indicated completion of the reaction. DCM was removed in vacuo and the crude product was purified by silica-gel or flash column chromatography on silica.

General Procedure IVa
Removal of the Tert-Butoxycarbonyl (Boc-) Group from Amine with HCl.

The N-Boc protected amine was treated with a 4 M solution of HCl (5 mL/mmol of starting material) in an appropriate organic solvent (e.g., AcOEt, 1,4-dioxane, MeOH, DCM) for the time necessary for complete consumption of the starting material (typically 30 minutes-2 hours). The volatiles were then removed in vacuo providing de-protected amine in the form of its hydrochloride salt. The crude product was usually purified by preparative reversed-phase column chromatography to give the corresponding product.

General Procedure IVb
Removal of the Tert-Butoxycarbonyl (Boc-) Group from Amine with TFA.

The N-Boc protected amine was treated with solution of TFA (6 equivalents) in DCM for the time necessary for complete consumption of the starting material (typically 30 minutes-2 hours). The volatiles were then removed in vacuo providing de-protected amine in the form of its TFA salt. The crude product was usually purified by preparative reversed-phase column chromatography to give the corresponding product.

General Procedure Va
The Suzuki Coupling.

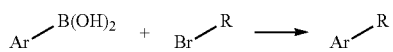

A palladium source (Pd(PPh$_3$)$_4$ or Pd(PPh$_3$)$_2$Cl$_2$ (0.05-0.1 equivalent)/PPh$_3$ (0.1-0.2 equivalent) or Pd(dppf)Cl$_2$ (0.05-0.1 equivalent) was dissolved in a combination of solvents such as dioxane (1-1.5 mL/mmol)/water (0.3 mL/mmol) and the mixture was degassed by bubbling with Ar. An appropriate halogen compound (1 equivalent) and K$_2$CO$_3$ (2-3 equivalents) were added and stirred for 5 minutes. Then to this mixture an organoboronic compound (1.1-2.5 equivalents) was added and the mixture was stirred vigorously at 90-110° C. (1-24 hours) under Ar. The reaction progress was monitored by TLC and LC-MS. After analytical control indicated completion of the reaction, the reaction was diluted with AcOEt (60 mL/mmol) and filtered through a Pad of Celite, evaporated thoroughly and redissolved in AcOEt/H$_2$O. The layers were separated and the aqueous one was extracted with AcOEt (3×). The combined organic layers were washed with brine, dried over anhydrous Na$_2$SO$_4$, filtered and concentrated in vacuo. The crude product was purified by flash column chromatography on silica.

General Procedure Vb
The Suzuki Coupling—Optional Cyclisation Reaction of Succinimide Ring in Case when Succinimide Ring Opening Product was Observed in Significant Amount.

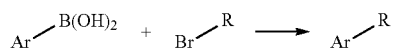

A palladium source (Pd(PPh$_3$)$_4$ or Pd(PPh$_3$)$_2$Cl$_2$ (0.05-0.1 equivalent)/PPh$_3$ (0.1-0.2 equivalent) or Pd(dppf)Cl$_2$ (0.05-0.1 equivalent) was dissolved in a combination of solvents such as dioxane (1-1.5 mL/mmol)/water (0.3 mL/mmol) and the mixture was degassed by bubbling with Ar. An appropriate halogen compound (1 equivalent) and K$_2$CO$_3$ (2-3 equivalents) were added and stirred for 5 minutes. Then to this mixture an organoboronic compound (1.1-2.5 equivalents) was added and the mixture was stirred vigorously at 90-110° C. (1-24 hours) under Ar. The reaction progress was monitored by TLC and LC-MS. The reaction mixture was concentrated in vacuo and dried under high vacuum. Then an acetic anhydride (5 ml/mmol) and sodium carbonate (2 equivalents) were added and the resulting suspension was stirred at 50° C. for 1 hour. The progress of cyclisation reaction was monitored by LC-MS. Then the mixture was concentrated in vacuo and the residue was purified by flash column chromatography on silica.

General Procedure VIa
Reductive Amination of the Cyclic Ketone with Appropriate Amine.

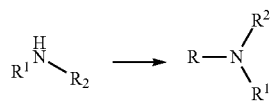

An appropriate amine or an amine hydrochloride (1 equivalent) was dissolved in DCE and acetic acid (AcOH, 2 equivalents) and appropriate ketone (2 equivalents) were added and the mixture was heated at 50° C. for 2 days. The reaction mixture was cooled to room temperature and sodium triacetoxyborohydride (NaBH(OAc)$_3$)(4 equivalents) was then added in one portion and the mixture was stirred overnight at room temperature. After this time a 5% aqueous solution of sodium bicarbonate (NaHCO$_3$) and dichloromethane (DCM) were added and the mixture was stirred for 30 minutes. The layers were separated and the aqueous layer was additionally extracted with dichloromethane. The organic extracts were combined, washed with brine, dried over anhydrous MgSO$_4$, filtered and evaporated to dryness. The crude product was purified by flash column chromatography on silica.

General Procedure VIb
Alternative Procedure for Reductive Amination of the Cyclic Ketone with Appropriate Amine.

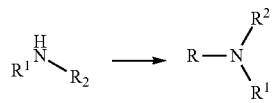

To the solution of an appropriate amine or an amine hydrochloride (1 equivalent) in dimethylformamide (DMF, 2 mL/mmol) under Ar, trimethylsilyl chloride (TMSCl, 2.5 equivalents) was added and the mixture was cooled to 0° C. and sodium borohydride (NaBH$_4$, 1 equivalent) was added. The reaction mixture was slowly warmed to room temperature and stirred overnight. After this time the mixture was taken into AcOEt/H$_2$O. The layers were separated and the aqueous layer was additionally extracted with AcOEt. The organic extracts were combined, washed with brine, dried over anhydrous MgSO$_4$, filtered and evaporated to dryness. The crude product was purified by flash column chromatography on silica.

General Procedure VII
Reduction of Morpholin-3-One to Morpholine or Amide to Amine.

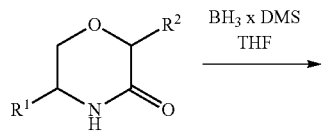

To the solution of either morpholin-3-one or 2-piperazinone or amide in THF (6 mL/mmol) borane-dimethylsulfide complex (BH$_3$×DMS; 5 equivalents) was added and the reaction mixture was refluxed overnight, after which time the TLC or LC-MS control indicated completed consumption of the starting material. Reaction mixture was cooled to room temperature and 2 M or 6 M HCl was cautiously added (6 equivalents with respect to the starting material). The resulting reaction mixture was refluxed for 2 hours and cooled back to room temperature. The pH of the solution was then adjusted to strongly alkaline (~10) by a dropwise addition of 6 M NaOH. The organic layer was separated and the aqueous layer was additionally extracted with diethyl ether or AcOEt. The combined organic extracts were then dried over anhydrous MgSO$_4$, filtered and the solvents were evaporated. The crude product obtained was, in most cases, sufficiently pure to be used to the next step without any additional purification.

General Procedure VIII
Installation of the Appropriate R-Group on the Primary or Secondary Amine or Alcohol

To a solution of the primary or secondary amine or alcohol in DCM (10 mL/mmol) or THF (4 mL/mmol). Et$_3$N (2-4 equivalents) or DIPEA (2 equivalents) followed by DMAP (0.1 equivalent, when it was necessary) were added and then appropriate carbamoyl chloride (2.5 equivalents) or appropriate isocyanate (1.1-2.5 equivalents) or acid chloride (1-2 equivalents) or appropriate anhydride (1.1-2 equivalents) was added at room temperature. The reaction progress was monitored by TLC and LC-MS. When analyses indicated completion of the reaction, the mixture was quenched by addition of 4 M NaOH or 5% NaHCO$_3$ (for tosylation). Product was extracted with DCM (2 times). The combined organic solutions were dried over anhydrous Na$_2$SO$_4$, filtered and concentrated in vacuo and the crude product was purified by preparative reversed-phase column chromatography or by silica-gel column chromatography.

Exemplary Synthetic Procedures

General Procedure A

Preparation of (2-((6,6-dimethyl-2,4-dioxo-3-azabicyclo[3.1.0]hexan-3-yl)methyl)thieno[3,2-b]yridin-7-yl)boronic acid (I)

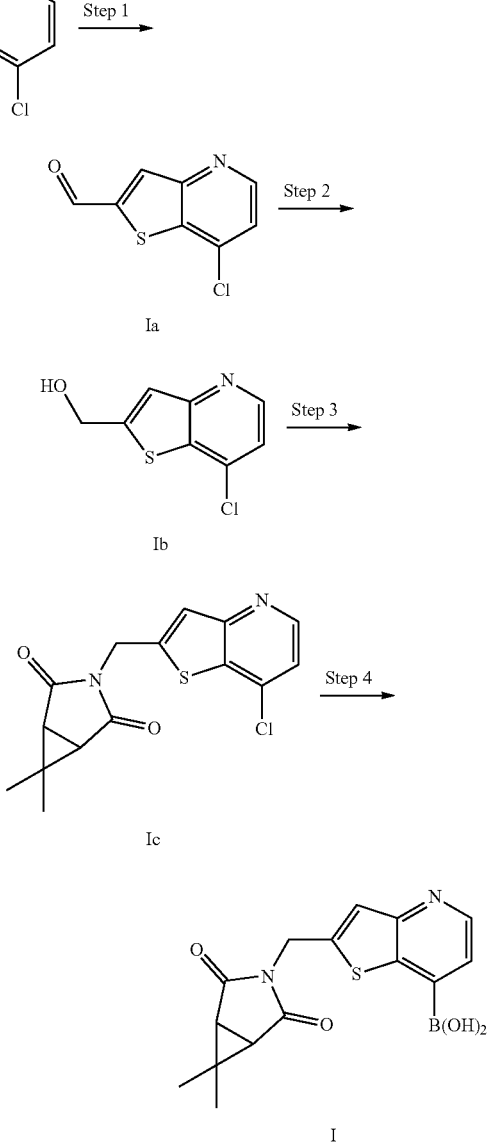

Step 1

Synthesis of 7-chlorothieno[3,2-b]pyridine-2-carbaldehyde (Ia)

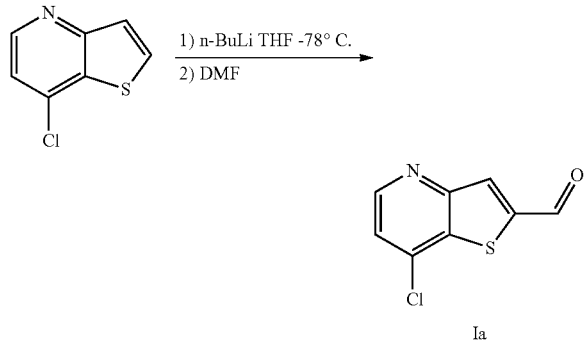

To a solution of 7-chlorothieno[3,2-b]pyridine (10 g; 58.96 mmol) in anhydrous THF (120 mL) n-BuLi (2.5 M in hexane; 26 mL; 64.86 mmol) was added dropwise over a period of 30 minutes at −78° C. The resulting yellow suspension was stirred for additional 30 minutes. Then an anhydrous N,N-dimethylformamide (45.4 mL; 589.60 mmol) was added dropwise over period of 30 minutes at −78° C. and the reaction was stirred at this temperature for 2 hours. The reaction progress was monitored by LC-MS. When analysis indicated completion of the reaction, MeOH (20 mL) was added dropwise at −78° C. and the reaction mixture was warmed to room temperature. Next 1 M HCl$_{aq}$ (100 mL) was slowly added and then the pH was adjusted to ~7 with 1 M HCl$_{aq}$. The resulting suspension was extracted with AcOEt (4×200 mL). The combined organic solutions were washed with water (1×100 mL) and brine (2×150 mL), dried over anhydrous Na$_2$SO$_4$, filtered and concentrated in vacuo. The crude product was triturated with cold MTBE, the solid was filtered, washed with hexane and dried. The crude product was used to the next step without additional purification. Compound Ia was obtained as a beige solid in 89% yield (10.34 g; 52.50 mmol).

ESI-MS m/z for C$_8$H$_5$ClNOS found 198.0/200.0 [M+H]$^+$, R$_t$=1.09 min; $^1$H NMR (700 MHz, CDCl$_3$) δ 10.21 (s, 1H), 8.72 (d, J=5.0 Hz, 1H), 8.25 (s, 1H), 7.44 (d, J=5.0 Hz, 1H).

Step 2

Synthesis of (7-chlorothieno[3,2-b]pyridin-2-yl)methanol (Ib)

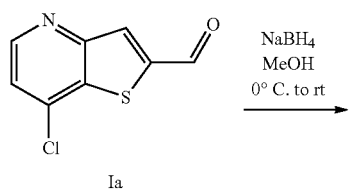

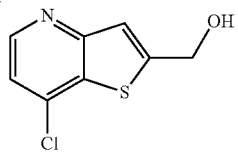

To a cooled to 0° C. suspension of aldehyde Ia (10.34 g; 52.50 mmol) in MeOH (120 mL), NaBH$_4$ (2.98 g; 78.75 mmol) was added portionwise. The resulting mixture was warmed to room temperature and stirred for 1 hour. Then the reaction mixture was quenched with water (100 mL) and MeOH was evaporated. The residue was extracted with AcOEt (3×100 mL). The combined organic solutions were dried over anhydrous Na$_2$SO$_4$, filtered and concentrated in vacuo. The crude product was used to the next step without additional purification. Compound Ib was obtained as a beige solid in 98% yield (10.28 g; 51.66 mmol).

ESI-MS m/z for C$_8$H$_7$ClNOS found 200.0/202.0 [M+H]$^+$; R$_t$=0.82 min; $^1$H NMR (700 MHz, CDCl$_3$) δ 8.55 (d, J=5.1 Hz, 1H), 7.44 (t, J=1.1 Hz, 1H), 7.26 (d, J=5.1 Hz, 1H), 5.01 (s, 2H).

Step 3

Synthesis of 3-((7-chlorothieno[3,2-b]pyridin-2-yl)methyl)-6,6-dimethyl-3-azabicyclo[3.1.0]hexane-2,4-dione (Ic)

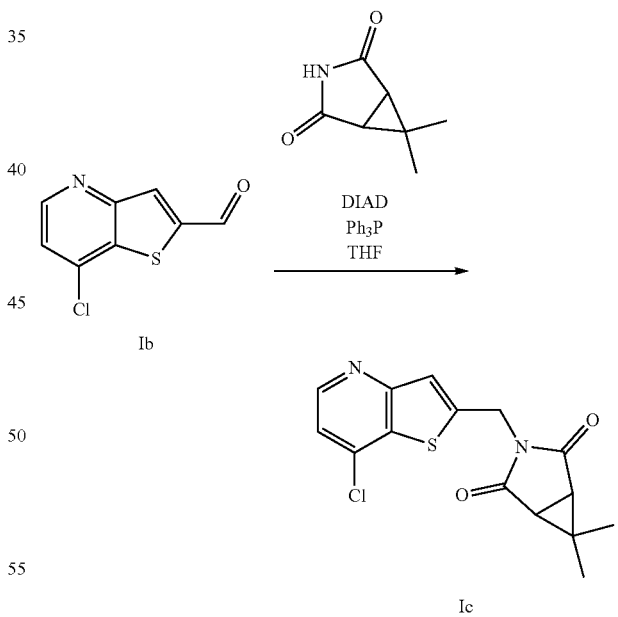

To a cooled to −10° C. solution of Ib (4.5 g; 22.5 mmol), 6,6-dimethyl-3-azabicyclo[3.1.0]hexane-2,4-dione (3.45 g; 24.8 mmol) and Ph$_3$P (7.1 g; 27.0 mmol) in THF (100 mL) DIAD (5.9 g; 5.7 mL; 29.3 mmol) was slowly added. The resulting mixture was stirred at room temperature overnight. The formed solid was filtered and washed with hexane (3×). The title compound Ic was obtained as a white solid in 72% yield (5.2 g; 16.2 mmol) (95% purity, P(O)Ph$_3$ contaminated product).

ESI-MS m/z for $C_{15}H_{14}ClN_2O_2S$ found 320.9/322.9 [M+H]$^+$; $R_t$=1.27 min

Step 4

Synthesis of (2-((6,6-dimethyl-2,4-dioxo-3-azabicyclo[3.1.0]hexan-3-yl)methyl)thieno[3,2-b]pyridin-7-yl)boronic acid (I)

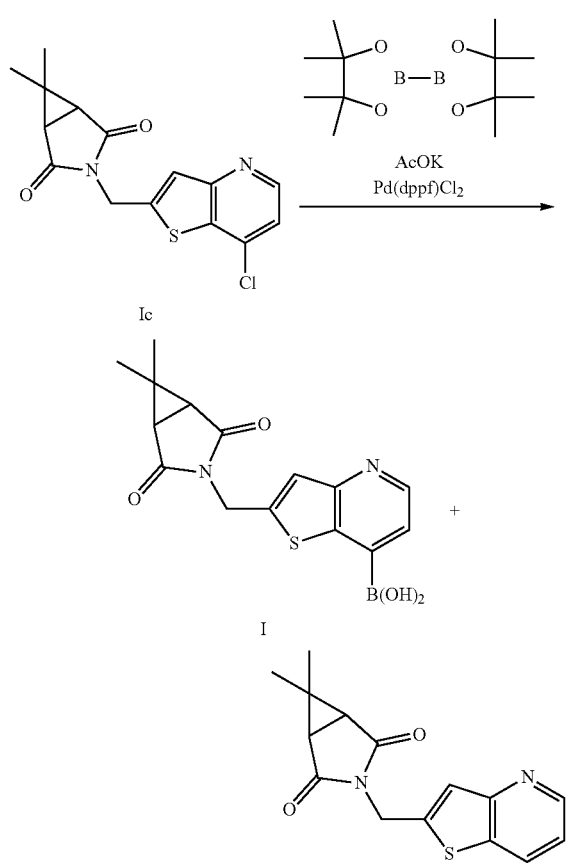

To the solution of Ic (5.62 g; 17.52 mmol) in dry dioxane (88.0 mL) bis(pinacolato)diboron (8.90 g; 35.05 mmol) and AcOK (5.16 g; 52.56 mmol) were added. The reaction mixture was intensively flushed with Ar. Then to this mixture Pd(dppf)Cl$_2$ (0.71 g; 0.876 mmol) was added in one portion and the reaction mixture was flushed with Ar. The mixture was stirred overnight at 100° C. in a sealed tube. The reaction progress was monitored by LC-MS. When analysis indicated completion of the reaction, the reaction mixture was filtered off and 1 M HCL$_{aq}$ (200 mL) was added to the filtrate and it was washed with Et$_2$O (2×300 mL). To the aqueous fraction the solid NaHCO$_3$ was carefully added portionwise to pH 8 and it was extracted with AcOEt (3×). The combined organic layers were dried over anhydrous MgSO$_4$, filtered and concentrated in vacuo. The solid residue was triturated with Et$_2$O and filtered off. The title compound I was obtained as a grey solid in 93% yield (5.40 g; 16.36 mmol). The crude product (included approx c.a 5-7% of dehalogenated substrate) was used to the next step without additional purification.

ESI-MS m/z for $C_{15}H_{16}BN_2O_4S$ found 330.8 [M+H]$^+$; $R_t$=0.84 min

General Procedure B

Preparation of 2-chloro-4-methyl-6-(trifluoromethyl)nicotinic acid (II)

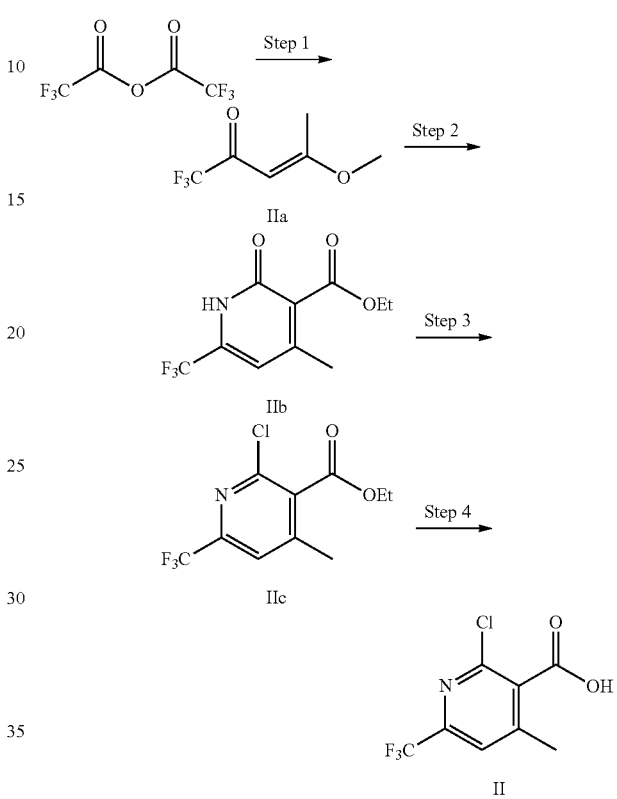

Step 1

Synthesis of (E)-1,1,1-trifluoro-4-methoxypent-3-en-2-one (IIa)

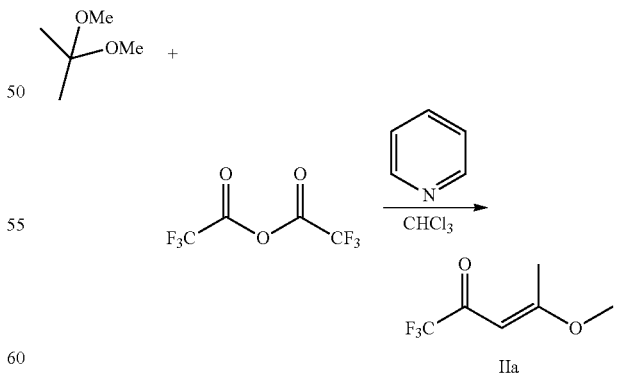

To a cooled to 0° C. solution of 2,2-dimethoxypropane (20 g; 192 mmol), pyridine (31 mL, 398 mmol) in chloroform (50 mL) a solution of 2,2,2-trifluoroacetic anhydride (53 mL; 381 mmol) in chloroform (50 mL) was added dropwise. The reaction mixture was stirred at room temperature overnight. Then the reaction mixture was cooled in ice-bath to 0° C. and quenched with 5% NaHCO₃. Next the reaction mixture was extracted with DCM (2×). The combined organic layers were washed again with 5% NaHCO₃, cold 1 M HCl, brine and dried over anhydrous Na₂SO₄, filtered and concentrated in vacuo. The crude product was distilled under reduced pressure (25 mmHg/45° C.). The title compound IIa was obtained as a yellow oil in 48% yield (15.7 g; 93.38 mmol).

ESI-MS m/z for $C_6H_8F_3O_2$ found 169.1 [M+H]⁺; $R_t$=1.14 min; ¹H NMR (700 MHz, CDCl₃) δ 5.70 (s, 1H), 3.81 (s, 3H), 2.43 (s, 1H).

Step 2

Synthesis of ethyl 4-methyl-2-oxo-6-(trifluoromethyl)-1,2-dihydropyridine-3-carboxylate (IIb)

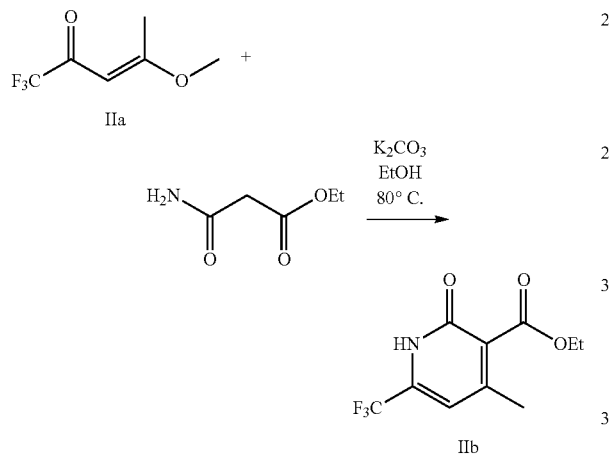

To a solution of ethyl-3-amino-3-oxopropanoate (0.78 g; 5.95 mmol) in EtOH (20 mL) compound IIa (1 g; 5.95 mmol) and K₂CO₃ (2.4 g; 17.85 mmol) were added. The reaction mixture was stirred at 80° C. for 3 hours. The reaction mixture was quenched with 2 M HCl. An aqueous residue was extracted with AcOEt (2×). The combined organic layers were washed with brine, dried over anhydrous Na₂SO₄, filtered and concentrated in vacuo and the crude product was used to the next step without additional purification. Compound IIb was obtained as an orange oil in 72% yield (1.07 g; 4.29 mmol).

ESI-MS m/z for $C_{10}H_{11}F_3NO_3$ found 250.0 [M+H]⁺; $R_t$=1.08 min; H NMR (700 MHz, CDCl₃) δ 7.06 (s, 1H), 4.55-4.49 (m, 2H), 2.62 (s, 3H), 1.47 (t, J=7.2 Hz, 3H).

Step 3

Synthesis of ethyl 2-chloro-4-methyl-6-(trifluoromethyl)nicotinate (IIc)

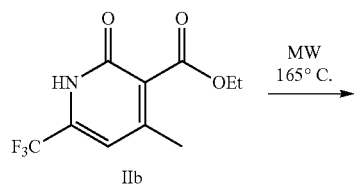

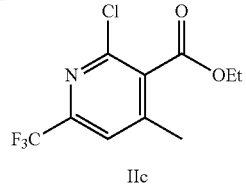

A mixture of IIb (1 g; 4.0 mmol) and phenyl dichlorophosphate (2.1 mL; 14.04 mmol) was heated under microwave irradiation using described method –1500 W, 165° C. (ramp temp. 10 minutes+hold temp. 20 minutes). The reaction mixture was poured into ice, stirred and diluted with AcOEt. Then the solution was adjusted to pH 8 by addition of 5% NaHCO₃. The layers were separated and an organic one was washed with brine, dried over anhydrous Na₂SO₄, filtered and concentrated in vacuo. The crude product was purified by flash column chromatography on silica (hexane/AcOEt, 100:0 to 80:20, 15 minutes, v/v). Compound IIc was obtained in 33% yield (0.33 g; 1.23 mmol).

¹H NMR (700 MHz, CDCl₃) δ 7.52 (s, 1H), 4.52-4.49 (m, 2H), 2.46 (s, 3H), 1.45 (t, J=7.2 Hz, 3H).

Step 4

Synthesis of 2-chloro-4-methyl-6-(trifluoromethyl)nicotinic acid (II)

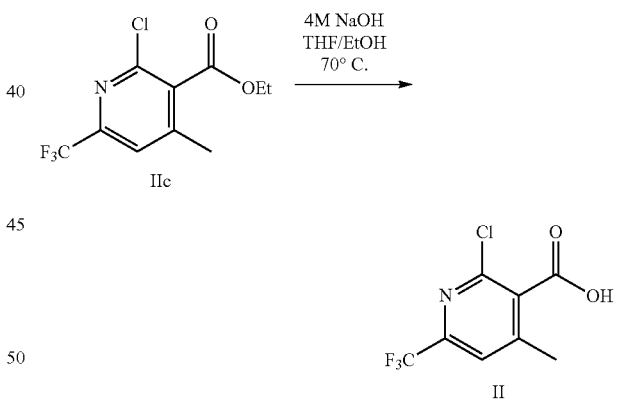

To the solution of IIc (6.9 g; 25.78 mmol) in THF/EtOH (30 mL/30 mL) a solution of 4 M NaOH (30 mL) was added. The reaction mixture was heated at 70° C. for 4 hours. Next solvents were evaporated in vacuo and an aqueous residue was acidified with 6 M HCl to pH 5 and then extracted with AcOEt (5×) and concentrated to small volume and again extracted with AcOEt (3×). The combined organic layers were dried over anhydrous Na₂SO₄, filtered and concentrated in vacuo and the crude product was used to the next step without additional purification. Compound II was obtained as a beige solid in 99% yield (6.10 g; 25.52 mmol).

ESI-MS m/z for $C_8H_6ClF_3NO_2$ found 237.7 [M–H]⁺; $R_t$=0.53 min; ¹H NMR (700 MHz, Methanol-d₄) δ 7.78 (s, 1H), 2.51 (s, 3H).

General Procedure C

Preparation of tert-butyl
(S)-ethyl(pyrrolidin-3-yl)carbamate (III)

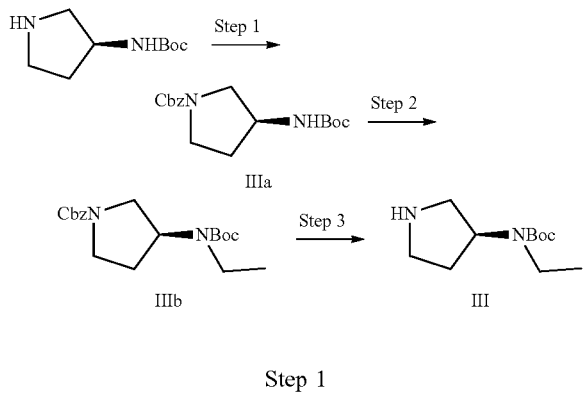

Step 1

Synthesis of benzyl (S)-3-((tert-butoxycarbonyl)
amino)pyrrolidine-1-carboxylate (IIIa)

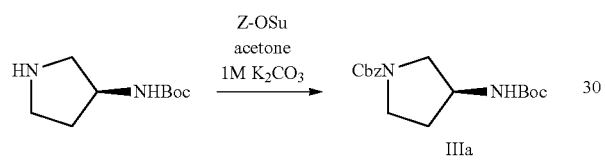

To the solution of tert-butyl (S)-pyrrolidin-3-ylcarbamate (0.26 g; 1.40 mmol) in a mixture of acetone (6.5 mL) and 1 M $K_2CO_3$ (5.2 mL) cooled to 0° C. a solution of Z—OSu (0.35 g; 1.40 mmol) in acetone (1 mL) was added dropwise. The reaction mixture was stirred at room temperature overnight. Then acetone was evaporated in vacuo. To the aqueous residue DCM was added and the product was extracted with DCM. Then an organic layer was washed with 1 M HCl, 1 M NaOH and brine. The organic layer was dried over anhydrous $Na_2SO_4$, filtered and concentrated in vacuo. The crude product was used to the next step without additional purification. Compound IIIa was obtained as a white solid in 95% yield (0.43 g; 1.34 mmol). ESI-MS m/z for $C_{17}H_{24}N_2O_4Na$ found 343.1 [M+Na]$^+$; $R_t$=1.5 min; $^1$H NMR (700 MHz, CDCl$_3$) δ 7.40-7.36 (m, 4H), 7.33 (ddd, J=12.3, 8.3, 2.4 Hz, 1H), 5.16 (s, 2H), 4.74-4.56 (m, 1H), 4.23 (s, 1H), 3.76-3.63 (m, 2H), 3.52 (dd, J=13.0, 6.7 Hz, 2H), 3.40-3.26 (m, 1H), 2.21-2.11 (m, 1H), 1.86 (dd, J=43.9, 16.8 Hz, 1H), 1.47 (s, 9H).

Step 2

Synthesis of benzyl (S)-3-((tert-butoxycarbonyl)
(ethyl)amino)pyrrolidine-1-carboxylate (IIIb)

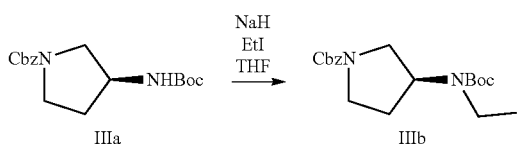 [SMILES: CC(C)(C)OC(=O)N[C@H]1CCN(C(=O)OCc2ccccc2)C1 ; CCN(C(=O)OC(C)(C)C)[C@H]1CCN(C(=O)OCc2ccccc2)C1]

To the solution of IIIa (0.21 g; 0.66 mmol) in THF (3.5 mL) under argon atmosphere NaH (60% in mineral oil; 40 mg; 1.65 mmol) was added. The reaction mixture was then stirred at room temperature for 20 minutes. Next EtI (0.18 mL; 2.64 mmol) was added and whole was stirred at room temperature for 1 hour. The reaction mixture was diluted with AcOEt and washed with 1 M HCl, 1 M NaOH and brine. An organic layer was dried over anhydrous $Na_2SO_4$, filtered and concentrated in vacuo and the crude product was purified by flash column chromatography on silica (hexane/AcOEt, 100:0 to 0:100, v/v). Compound IIIb was obtained in 48% yield (0.11 g; 0.32 mmol).

ESI-MS m/z for $C_{19}H_{28}N_2O_4Na$ found 371.1 [M+Na]$^+$; $R_t$=1.8 min; $^1$H NMR (700 MHz, CDCl$_3$) δ 7.42-7.37 (m, 4H), 7.35-7.32 (m, 1H), 5.16 (q, J=12.8 Hz, 2H), 4.58 (s, 1H), 3.66 (dd, J=30.7, 21.9 Hz, 2H), 3.30 (dd, J=36.6, 26.4 Hz, 2H), 3.22 (d, J=9.8 Hz, 2H), 2.04 (dd, J=31.9, 8.2 Hz, 2H), 1.48 (s, 9H), 1.13 (t, J=6.9 Hz, 3H).

Step 3

Synthesis of tert-butyl
(S)-ethyl(pyrrolidin-3-yl)carbamate (III)

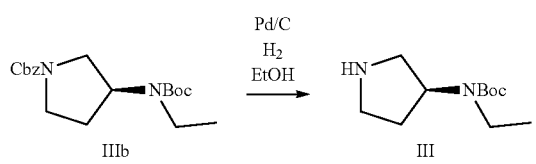

To the solution of IIIb (0.1 g; 0.29 mmol) in EtOH (3 mL) under argon atmosphere Pd/C (10 mol %; cat.) was added. Then argon was replaced by hydrogen and the reaction mixture was conducted under hydrogen atmosphere at room temperature for 2 hours. The reaction progress was monitored by LC-MS. When analysis indicated completion of the reaction, Pd/C was filtered off through a Celite pad and the solvent was stripped in vacuo. The crude product was used to the next step without additional purification. Compound III was obtained as a transparent oil in 98% yield (60 mg; 0.28 mmol).

ESI-MS m/z for $C_{11}H_{23}N_2O_2$ found 215.10 [M+H]$^+$; $R_t$=0.65 min; $^1$H NMR (700 MHz, Methanol-d$_4$) δ 4.32-4.06 (m, 1H), 3.31-3.23 (m, 3H), 3.02 (ddd, J=28.6, 19.8, 9.9 Hz, 3H), 2.17-1.88 (m, 2H), 1.49 (d, J=4.1 Hz, 9H), 1.15 (q, J=7.4 Hz, 3H).

Example 1

Synthesis of 6-(2-((6,6-dimethyl-2,4-dioxo-3-azabicyclo[3.1.0]hexan-3-yl)methyl)thieno[3,2-b]pyridin-7-yl)-4-methyl-5-(piperidin-3-yloxy)picolinonitrile 2,2,2-trifluoroacetate (1)

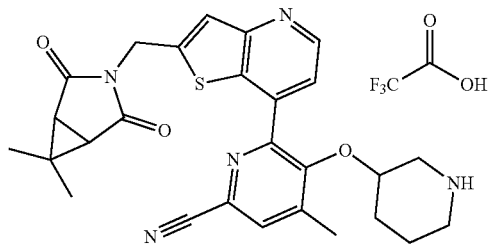

Step 1

Synthesis of 6-bromo-5-hydroxy-4-methylpicolinonitrile (1a)

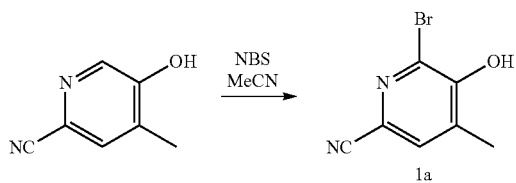

To the solution of 5-hydroxy-4-methylpicolinonitrile (136 mg; 1.01 mmol) in MeCN (3 mL) NBS (180 mg; 1.01 mmol) was added and then the reaction mixture was stirred at room temperature overnight. The reaction progress was monitored by LC-MS. When analysis indicated completion of the reaction, to this mixture 10% $Na_2S_2O_3$ was added and then extracted with AcOEt. The organic layer was washed with brine, dried over anhydrous $MgSO_4$, filtered and concentrated in vacuo and the crude product was used to the next step without additional purification. Compound 1a was obtained in 99% yield (214 mg; 1.01 mmol).

ESI-MS m/z for $C_7H_4BrN_2O$ found 211.0/213.0 $[M-H]^+$, $R_t$=0.86 min

Step 2

Synthesis of tert-butyl 3-((2-bromo-6-cyano-4-methylpyridin-3-yl)oxy)piperidine-1-carboxylate (1b)

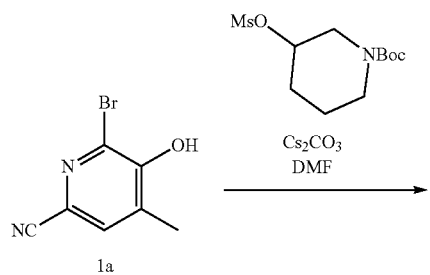

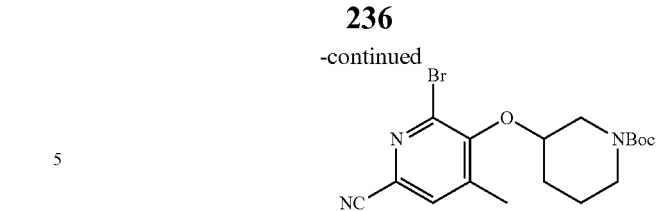

To the solution of 1a (84 mg; 0.39 mmol) in DMF (1.5 mL) tert-butyl 3-((methylsulfonyl)oxy)piperidine-1-carboxylate (132 mg; 0.47 mmol) and $Cs_2CO_3$ (257 mg; 0.79 mmol) were added and then the reaction mixture was heated at 70° C. overnight. The reaction progress was monitored by TLC and LC-MS. Next another portion of tert-butyl 3-((methylsulfonyl)oxy)piperidine-1-carboxylate (132 mg; 0.47 mmol) was added and stirred at 70° C. overnight. When analyses indicated completion of the reaction, this mixture was taken into AcOEt/water. An organic layer was washed with brine, dried over anhydrous $MgSO_4$, filtered and concentrated in vacuo and the crude product was purified by flash column chromatography on silica (hexane/AcOEt, 100:0 to 80:20, v/v, 15 minutes). Compound 1b was obtained in 10% yield (15 mg; 0.04 mmol).

ESI-MS m/z for $C_{13}H_{15}BrN_3O_3$ found 340.0/342.0 $[M+H-tBu]^+$; $R_t$=1.67 min

Step 3

Synthesis of tert-butyl 3-((6-cyano-2-(2-((6,6-dimethyl-2,4-dioxo-3-azabicyclo[3.1.0]hexan-3-yl)methyl)thieno[3,2-b]pyridin-7-yl)-4-methylpyridin-3-yl)oxy)piperidine-1-carboxylate (1c)

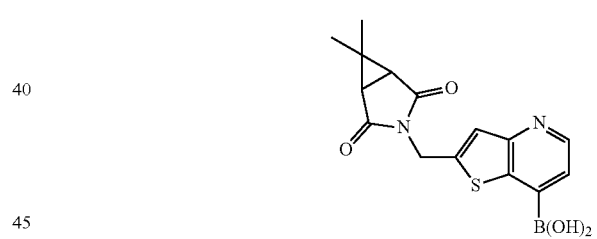

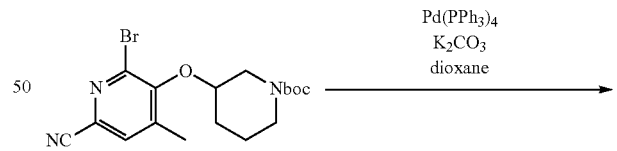

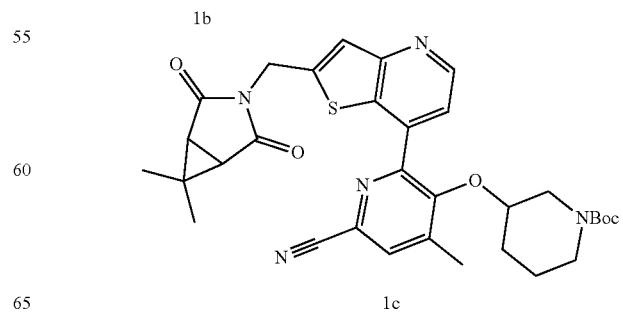

The title compound (1c) was obtained from 1b (15 mg; 0.040 mmol) and from boronic acid I (15 mg; 0.045 mmol) according to the General Procedure Va and after standard work-up all the crude product mixture was taken for the next step.

ESI-MS m/z for $C_{32}H_{36}N_5O_5S$ found 602.3 $[M+H]^+$; $R_t$=1.63 min

Step 4

Synthesis of 6-(2-((6,6-dimethyl-2,4-dioxo-3-azabi-cyclo[3.1.0]hexan-3-yl)methyl)thieno[3,2-b]pyridin-7-yl)-4-methyl-5-(piperidin-3-yloxy)picolinonitrile 2,2,2-trifluoroacetate (1)

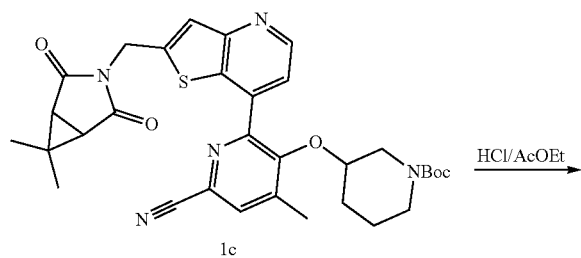

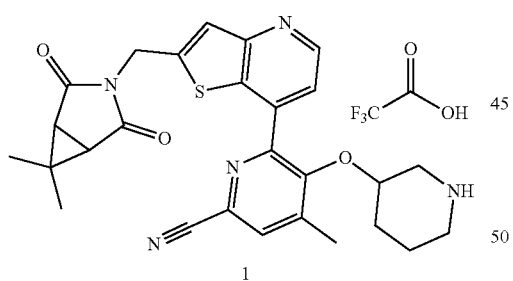

The title compound (1) was obtained as a racemate as a TFA salt from 1c (crude reaction mixture) according to the General Procedure IVa in 15% yield (per two steps) (4 mg; 0.006 mmol). The crude product was purified by preparative reversed-phase column chromatography (column: Cosmosil Cholester 20×250 mm, water/MeCN+1‰ TFA, 99:1 to 40:60, 30 min, 20 mL/min).

ESI-MS m/z for $C_{27}H_{28}N_5O_3S$ found 502.3 $[M+H]^+$; $R_t$=0.93 min; $^1$H NMR (700 MHz, $D_2O$) δ 8.82-8.78 (m, 1H), 8.05-8.01 (m, 1H), 7.98-7.95 (m, 1H), 7.67-7.64 (m, 1H), 4.99-4.90 (m, 2H), 4.07-3.95 (m, 1H), 3.27-3.17 (m, 1H), 3.17-3.09 (m, 1H), 2.99-2.89 (m, 2H), 2.61 (s, 2H), 2.46 (s, 3H), 1.56-1.44 (m, 2H), 1.33-1.22 (m, 2H), 1.18 (s, 3H), 1.01 (s, 3H).

Example 2

Synthesis of 3-((7-(6-chloro-4-methyl-3-(pyrrolidin-3-yloxy)pyridin-2-yl)thieno[3,2-b]pyridin-2-yl)methyl)-6,6-dimethyl-3-azabicyclo[3.1.0]hexane-2,4-dione hydrochloride (2)

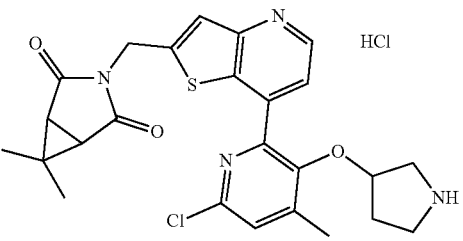

The title compound (2) was obtained as a hydrochloride salt as a racemate in 5% overall yield in a similar way to Example 1 with the exception that, in the first step of the synthesis, 6-chloro-4-methylpyridin-3-ol was used instead of 5-hydroxy-4-methylpicolinonitrile, in the second step of the synthesis, tert-butyl 3-((methylsulfonyl)oxy)pyrrolidine-1-carboxylate was used instead of tert-butyl 3-((methylsulfonyl)oxy)piperidine-1-carboxylate and in the last step of the synthesis the crude product was purified by preparative reversed-phase column chromatography (C-18, water+0.3‰ HCl (36%)/MeCN, 99:1 to 30:70, 30 min, 20 mL/min).

ESI-MS m/z for $C_{25}H_{26}ClN_4O_3S$ found 497.3/499.3 $[M+H]^+$; $R_t$=0.96 min; $^1$H NMR (700 MHz, $D_2O$) δ 8.75-8.72 (m, 1H), 8.03-7.98 (m, 1H), 7.62-7.58 (m, 1H), 7.49-7.46 (m, 1H), 4.94-4.84 (m, 2H), 4.50-4.37 (m, 1H), 3.46-3.36 (m, 1H), 3.30-3.17 (m, 2H), 3.07-2.94 (m, 1H), 2.61 (s, 2H), 2.38 (s, 3H), 1.79-1.69 (m, 2H), 1.18 (s, 3H), 1.02 (s, 3H).

Example 3

Synthesis of 3-((7-(6-chloro-4-methyl-3-(piperidin-3-yloxy)pyridin-2-yl)thieno[3,2-b]pyridin-2-yl)methyl)-6,6-dimethyl-3-azabicyclo[3.1.0]hexane-2,4-dione hydrochloride (3)

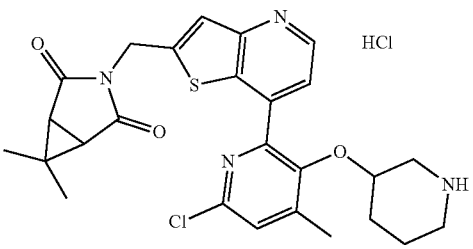

The title compound (3) was obtained as a hydrochloride salt as a racemate in 14% overall yield in a similar way to Example 1 with the exception that, in the first step of the synthesis, 6-chloro-4-methylpyridin-3-ol was used instead of 5-hydroxy-4-methylpicolinonitrile and in the last step of the synthesis the crude product was purified by preparative reversed-phase column chromatography (column: Cosmosil Cholester 20×250 mm, water+0.3‰ HCl (36%)/MeCN, 99:1 to 30:70, 30 min, 20 mL/min).

ESI-MS m/z for $C_{26}H_{28}ClN_4O_3S$ found 511.3/513.3 [M+H]$^+$; $R_t$=0.99 min; $^1$H NMR (700 MHz, D$_2$O) δ 8.81-8.76 (m, 1H), 8.11-8.08 (m, 1H), 7.66-7.63 (m, 1H), 7.52-7.49 (m, 1H), 4.98-4.86 (m, 2H), 3.96-3.88 (m, 1H), 3.27-3.20 (m, 1H), 3.15-3.07 (m, 1H), 3.04-2.97 (m, 1H), 2.94-2.86 (m, 1H), 2.61 (s, 2H), 2.39 (s, 3H), 1.57-1.46 (m, 2H), 1.33-1.25 (m, 1H), 1.25-1.21 (m, 1H), 1.19 (s, 3H), 1.02 (s, 3H).

Example 4

Synthesis of 3-((7-(6-chloro-4-methyl-3-(((S)-piperidin-3-yl)oxy)pyridin-2-yl)thieno[3,2-b]pyridin-2-yl)methyl)-6,6-dimethyl-3-azabicyclo[3.1.0]hexane-2,4-dione hydrochloride (4)

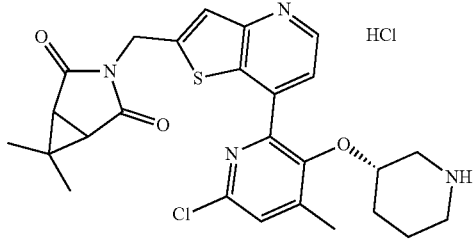

The title compound (4) was obtained as a hydrochloride salt as a single enantiomer of compound 3 in 1% overall yield in a similar way to Example 1 with the exception that, in the first step of the synthesis, 6-chloro-4-methylpyridin-3-ol was used instead of 5-hydroxy-4-methylpicolinonitrile, in the second step of the synthesis, tert-butyl (R)-3-((methylsulfonyl)oxy)piperidine-1-carboxylate was used instead of tert-butyl 3-((methylsulfonyl)oxy)piperidine-1-carboxylate and in the last step of the synthesis the crude product was purified by preparative reversed-phase column chromatography (C-18, water+0.3‰ HCl (36%)/MeCN, 99:1 to 30:70, 30 min, 20 mL/min).

ESI-MS m/z for $C_{26}H_{28}ClN_4O_3S$ found 511.4/513.4 [M+H]$^+$; $R_t$=0.99 min; $^1$H NMR (700 MHz, D$_2$O) δ 8.80-8.78 (m, 1H), 8.11-8.07 (m, 1H), 7.68-7.64 (m, 1H), 7.55-7.52 (m, 1H), 5.00-4.88 (m, 2H), 3.96-3.88 (m, 1H), 3.28-3.20 (m, 1H), 3.14-3.07 (m, 1H), 3.05-2.97 (m, 1H), 2.96-2.84 (m, 1H), 2.61 (s, 2H), 2.40 (s, 3H), 1.57-1.44 (m, 2H), 1.34-1.25 (m, 1H), 1.24-1.19 (m, 1H), 1.19 (s, 3H), 1.02 (s, 3H).

Example 5

Synthesis of 4-(2-((6,6-dimethyl-2,4-dioxo-3-azabicyclo[3.1.0]hexan-3-yl)methyl)thieno[3,2-b]pyridin-7-yl)-6-methyl-5-((S)-2-methylpiperazine-1-carbonyl)picolinonitrile 2,2,2-trifluoroacetate (5)

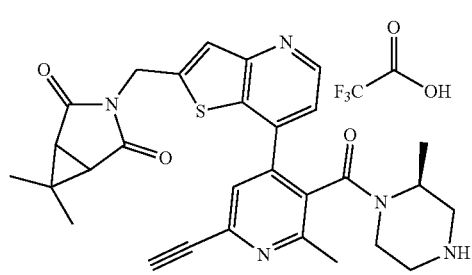

Step 1

Synthesis of tert-butyl 4,6-dichloro-2-methylnicotinate (5a)

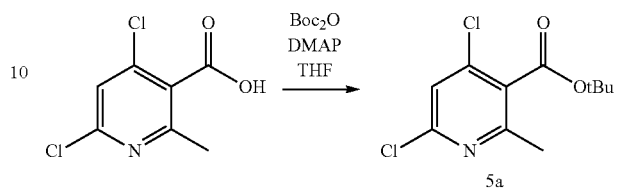

To the solution of 4,6-dichloro-2-methylnicotinic acid (1.1 g; 5.34 mmol) in THF (20 mL) Boc$_2$O (1.75 g; 8.00 mmol) and DMAP (0.33 g; 2.67 mmol) were added and then the reaction mixture was stirred at room temperature for 2 days. The reaction progress was monitored by LC-MS. Then another portion of Boc$_2$O (2.63 g; 10.00 mmol) and DMAP (0.33 g; 2.67 mmol) were added and then the reaction mixture was stirred at room temperature overnight. When analysis indicated completion of the reaction, the solvent was evaporated in vacuo and the residue was taken into water/AcOEt. An organic layer was washed with brine, dried over anhydrous MgSO$_4$, filtered and concentrated in vacuo and the crude product was purified by flash column chromatography on silica (hexane/AcOEt, 100:0 to 80:20, v/v, 15 minutes). Compound 5a was obtained in 67% yield (0.94 g; 3.60 mmol).

ESI-MS m/z for $C_{11}H_{14}Cl_2NO_2$ found 262.0/264.0 [M+H]$^+$; $R_t$=1.72 min Step 2

Synthesis of tert-butyl 4-chloro-6-cyano-2-methylnicotinate (5b)

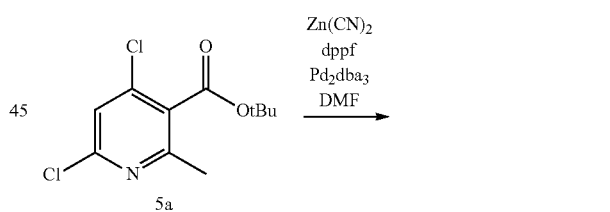

To the solution of 5a (0.84 g; 3.2 mmol) in DMF (16 mL) Zn(CN)$_2$ (376 mg; 2.2 mmol) was added and all was flushed with Ar. Next to this mixture dppf (0.18 g; 0.32 mmol) and Pd$_2$dba$_3$ (0.15 g; 0.16 mmol) were added and flushed with Ar. The mixture was heated at 70° C. overnight. The reaction progress was monitored by TLC. When analysis indicated completion of the reaction, this mixture was taken into AcOEt/water. An organic layer was washed with water and brine, dried over anhydrous MgSO$_4$, filtered and concentrated in vacuo and the crude product was purified by flash

Step 3

Synthesis of tert-butyl 6-cyano-4-(2-(((6,6-dimethyl-2,4-dioxo-3-azabicyclo[3.1.0]hexan-3-yl)methyl)thieno[3,2-b]pyridin-7-yl)-2-methylnicotinate (5c)

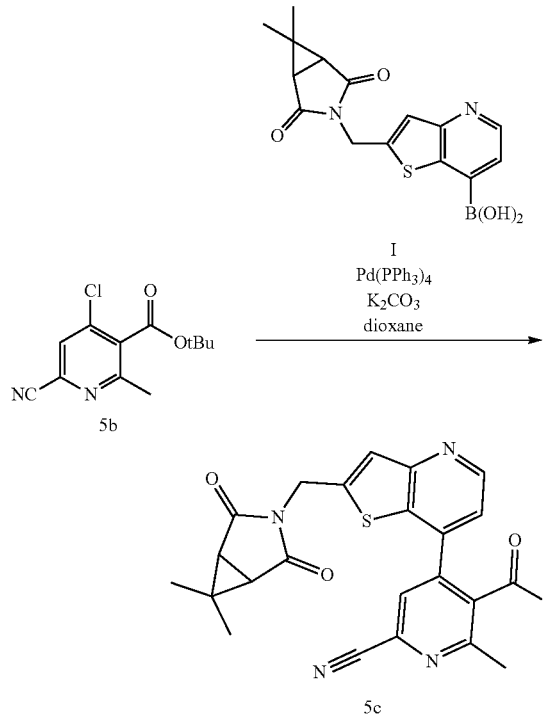

The title compound (5c) was obtained from 5b (200 mg; 0.79 mmol) and from boronic acid I (290 mg; 0.87 mmol) according to the General Procedure Va in 83% yield (330 mg; 0.66 mmol).

Step 4

Synthesis of 6-cyano-4-(2-(((6,6-dimethyl-2,4-dioxo-3-azabicyclo[3.1.0]hexan-3-yl)methyl)thieno[3,2-b]pyridin-7-yl)-2-methylnicotinic acid (5d)

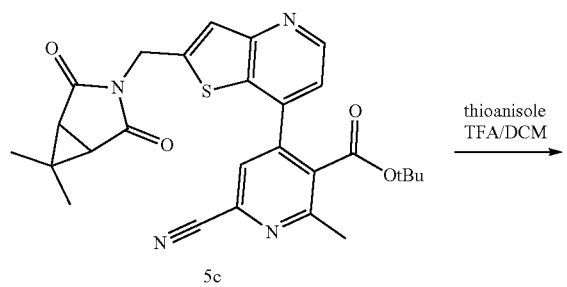

To the solution of 5c (0.28 g; 0.56 mmol) in DCM (3 mL) thioanisole (65 µL; 0.56 mmol) was added, followed by TFA (3 mL) and stirred at room temperature overnight. The reaction progress was monitored by LC-MS. When analysis indicated completion of the reaction, this solvents were evaporated to dryness and all the crude product mixture was taken to the next step without any additional purification.

ESI-MS m/z for $C_{23}H_{19}N_4O_4S$ found 447.0 $[M+H]^+$; $R_t$=1.10 min

Step 5

Synthesis of tert-butyl (3S)-4-(6-cyano-4-(2-(((6,6-dimethyl-2,4-dioxo-3-azabicyclo[3.1.0]hexan-3-yl)methyl)thieno[3,2-b]pyridin-7-yl)-2-methylnicotinoyl)-3-methylpiperazine-1-carboxylate (5e)

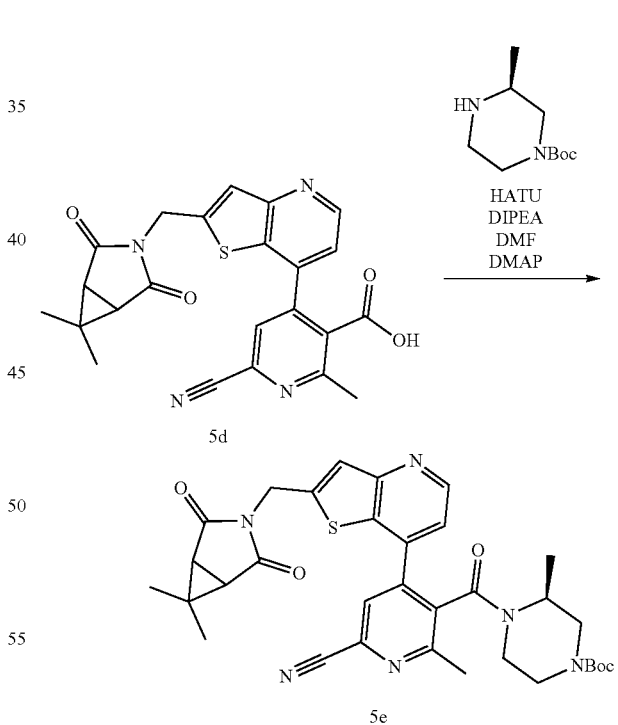

The title compound (5e) was obtained from 5d (the crude reaction mixture; 44 mg) and from tert-butyl (S)-3-methylpiperazine-1-carboxylate (22 mg; 0.11 mmol) according to the General Procedure VII and after standard work-up all the crude product mixture was taken to the next step without any additional purification.

ESI-MS m/z for $C_{33}H_{37}N_6O_5S$ found 629.0 $[M+H]^+$; $R_t$=1.51 min

Step 6

Synthesis of 4-(2-((6,6-dimethyl-2,4-dioxo-3-azabicyclo[3.1.0]hexan-3-yl)methyl)thieno[3,2-b]pyridin-7-yl)-6-methyl-5-((S)-2-methylpiperazine-1-carbonyl)picolinonitrile 2,2,2-trifluoroacetate (5)

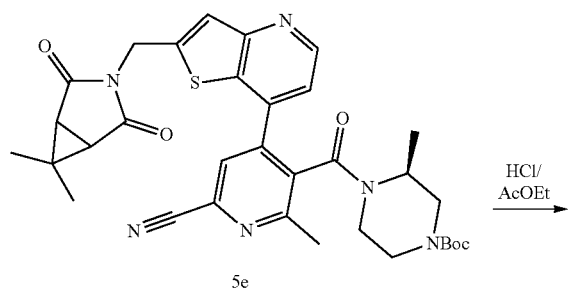

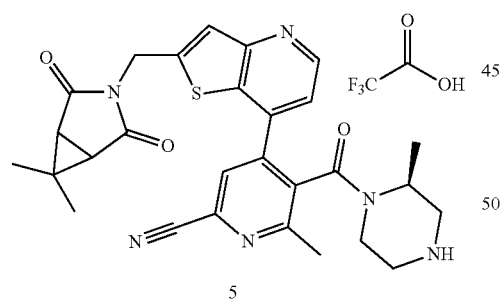

The title compound (5) was obtained as a TFA salt from 5e (the crude reaction mixture) according to the General Procedure IVa in 6% yield (per two steps) (4 mg; 0.006 mmol). The crude product was purified by preparative reversed-phase column chromatography (column: Cosmosil Cholester 20×250 mm, water/MeCN+1‰ TFA, 99:1 to 45:55, 30 min, 20 mL/min).

ESI-MS m/z for $C_{28}H_{29}N_6O_3S$ found 529.4 $[M+H]^+$; $R_t$=0.87 min; $^1$H NMR (700 MHz, $D_2O$) δ 8.78-8.70 (m, 1H), 8.23-8.03 (m, 1H), 7.67-7.62 (m, 1H), 7.44-7.33 (m, 1H), 4.96-4.75 (m, 3H), 3.55-2.92 (m, 5H), 2.70-2.53 (m, 5H), 1.36-0.95 (m, 8H), 0.55-0.44 (m, 2H).

Examples 6 and 7

Synthesis of 6,6-dimethyl-3-((7-(1-(morpholin-2-ylmethyl)-5-(trifluoromethyl)-1H-pyrazol-3-yl)thieno[3,2-b]pyridin-2-yl)methyl)-3-azabicyclo[3.1.0]hexane-2,4-dione 2,2,2-trifluoroacetate (6) and 6,6-dimethyl-3-((7-(1-(morpholin-2-ylmethyl)-3-(trifluoromethyl)-1H-pyrazol-5-yl)thieno[3,2-b]pyridin-2-yl)methyl)-3-azabicyclo[3.1.0]hexane-2,4-dione 2,2,2-trifluoroacetate (7)

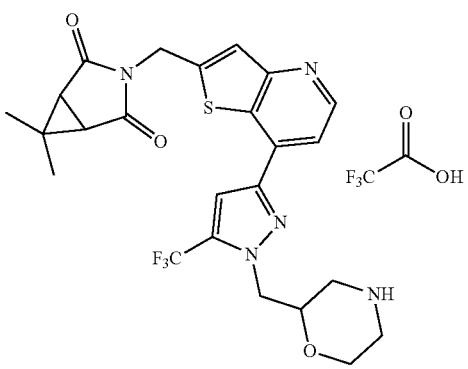

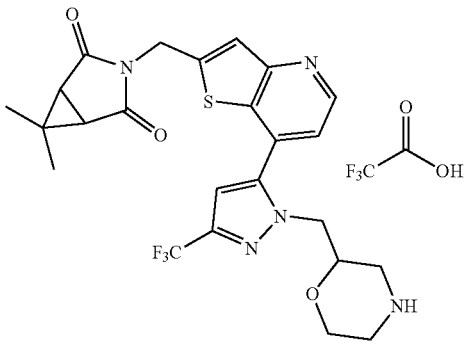

Step 1

Synthesis of tert-butyl 2-((3-bromo-5-(trifluoromethyl)-1H-pyrazol-1-yl)methyl)morpholine-4-carboxylate (6a) and tert-butyl 2-((5-bromo-3-(trifluoromethyl)-1H-pyrazol-1-yl)methyl)morpholine-4-carboxylate (6b)

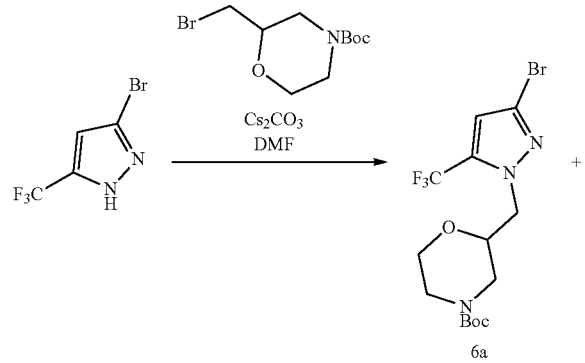

-continued

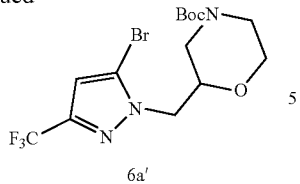

6a'

To the solution of 3-bromo-5-(trifluoromethyl)-1H-pyrazole (29 mg; 0.13 mmol) in DMF (0.5 mL) tert-butyl 2-(bromomethyl)morpholine-4-carboxylate (38 mg; 0.13 mmol) and Cs$_2$CO$_3$ (88 mg; 0.27 mmol) were added and then the reaction mixture was heated at 70° C. overnight. The reaction progress was monitored by LC-MS. When analysis indicated almost completion of the reaction, this mixture was taken into AcOEt/water. An organic layer was washed with water and brine, dried over anhydrous MgSO$_4$, filtered and concentrated in vacuo and the crude product mixture was used to the next step without additional purification. Compounds 6a and 6a' was obtained as a mixture of two regioisomers in 99% yield (55 mg; 0.13 mmol).

ESI-MS m/z for C$_{10}$H$_{12}$BrF$_3$N$_3$O$_3$ found 358.0/360.0 [M+H-tBu]$^+$; R$_t$=1.73, 1.76 min Step 2

Synthesis of tert-butyl 2-((3-(2-((6,6-dimethyl-2,4-dioxo-3-azabicyclo[3.1.0]hexan-3-yl)methyl)thieno[3,2-b]pyridin-7-yl)-5-(trifluoromethyl)-1H-pyrazol-1-yl)methyl)morpholine-4-carboxylate (6b) and tert-butyl 2-((5-(2-((6,6-dimethyl-2,4-dioxo-3-azabicyclo[3.1.0]hexan-3-yl)methyl)thieno[3,2-b]pyridin-7-yl)-3-(trifluoromethyl)-1H-pyrazol-1-yl)methyl)morpholine-4-carboxylate (6b')

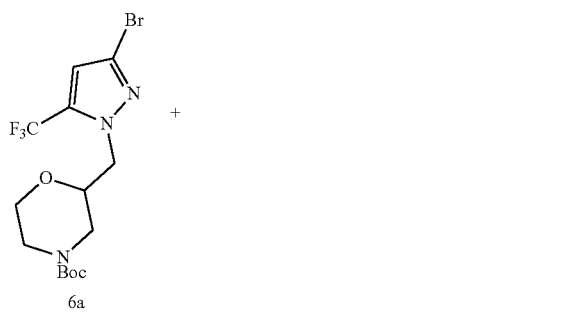

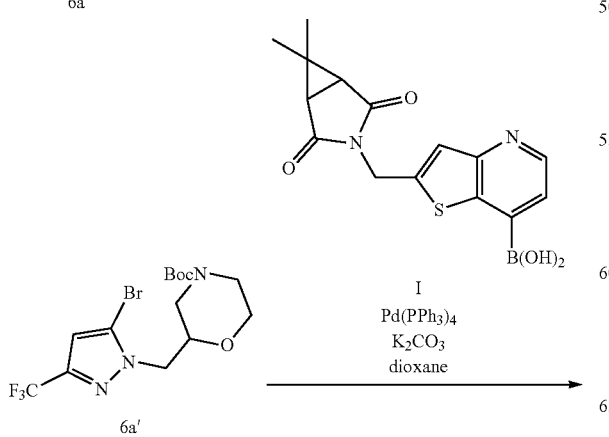

-continued

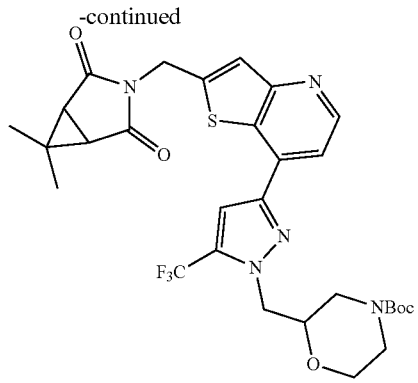

6b

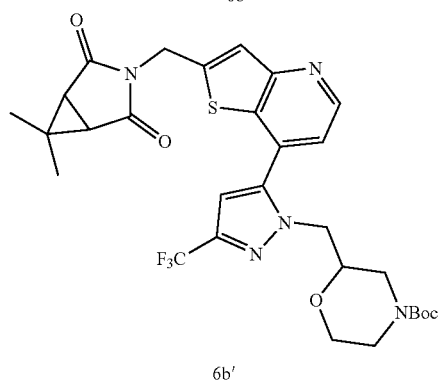

6b'

The title compounds (6b and 6b') was obtained from the mixture of regioisomers 6a and 6a' (55 mg; 0.13 mmol) and from boronic acid 1 (48 mg; 0.15 mmol) according to the General Procedure Va and after standard work-up all the crude products mixture was taken for the next step.

ESI-MS m/z for C$_{29}$H$_{33}$F$_3$N$_5$O$_5$S found 620.1 [M+H]$^+$; R$_t$=1.73, 1.79 min Step 3

Synthesis of 6,6-dimethyl-3-((7-(1-(morpholin-2-ylmethyl)-5-(trifluoromethyl)-1H-pyrazol-3-yl)thieno[3,2-b]pyridin-2-yl)methyl)-3-azabicyclo[3.1.0]hexane-2,4-dione 2,2,2-trifluoroacetate (6) and 6,6-dimethyl-3-((7-(1-(morpholin-2-ylmethyl)-3-(trifluoromethyl)-1H-pyrazol-5-yl)thieno[3,2-b]pyridin-2-yl)methyl)-3-azabicyclo[3.1.0]hexane-2,4-dione 2,2,2-trifluoroacetate (7)

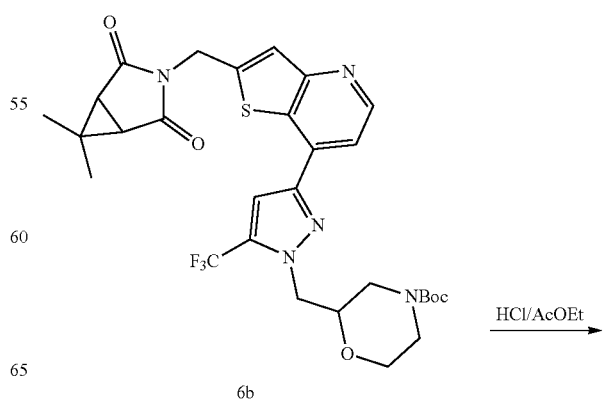

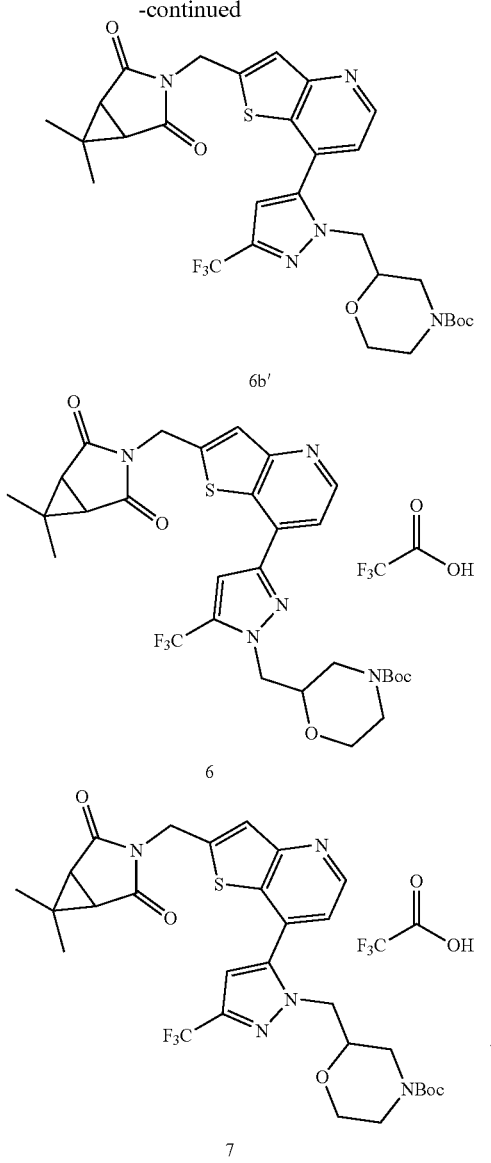

3.90 (m, 1H), 3.66-3.59 (m, 1H), 3.44-3.36 (m, 1H), 3.28-3.17 (m, 2H), 2.64 (s, 2H), 1.19 (s, 3H), 0.96 (s, 3H).

Example 8

Synthesis of 5-((R)-3-aminopyrrolidine-1-carbonyl)-4-(2-((6,6-dimethyl-2,4-dioxo-3-azabicyclo[3.1.0]hexan-3-yl)methyl)thieno[3,2-b]pyridin-7-yl)-6-methylpicolinonitrile 2,2,2-trifluoroacetate (8)

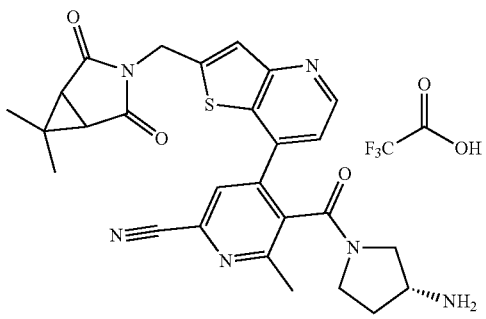

The title compound (8) was obtained as a TFA salt in 7% overall yield in a similar way to Example 5 with the exception that, in the fifth step of the synthesis, tert-butyl (R)-pyrrolidin-3-ylcarbamate was used instead of tert-butyl (S)-3-methylpiperazine-1-carboxylate and in the last step of the synthesis the crude product was purified by preparative reversed-phase column chromatography (column: Cosmosil Cholester 20×250 mm, water/MeCN+1‰ TFA, 99:1 to 45:55, 30 min, 20 mL/min).

ESI-MS m/z for $C_{27}H_{27}N_6O_3S$ found 515.4[M+H]$^+$; $R_t$=0.85 min; $^1$H NMR (700 MHz, D$_2$O, 333 K) δ 9.22-9.08 (m, 1H), 8.54-8.40 (m, 1H), 8.13-8.00 (m, 1H), 7.85-7.70 (m, 1H), 5.43-5.18 (m, 2H), 4.53-4.23 (m, 1H), 4.14-3.90 (m, 2H), 3.87-3.16 (m, 2H), 3.06-2.97 (m, 5H), 2.78-1.90 (m, 2H), 1.62 (s, 3H), 1.49-1.39 (m, 3H).

Example 9

Synthesis of 6,6-dimethyl-3-((7-(1-(morpholin-2-ylmethyl)-1H-pyrrol-2-yl)thieno[3,2-b]pyridin-2-yl)methyl)-3-azabicyclo[3.1.0]hexane-2,4-dione 2,2,2-trifluoroacetate (9)

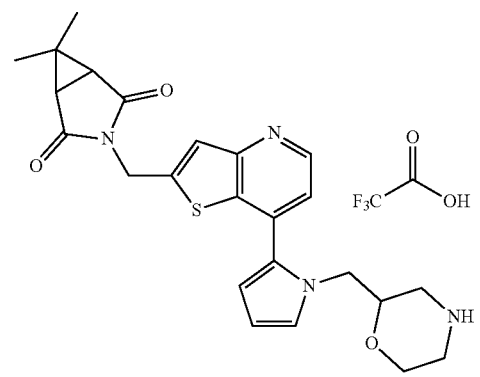

The title compounds (6 and 7) was obtained as separated single regioisomers as TFA salts from the mixture of 6b and 6b' (crude reaction mixture) according to the General Procedure IVa in 19% yield for 6 (per two steps) (16 mg; 0.025 mmol) and in 21% yield for 7 (per two steps) (17 mg; 0.027 mmol). The crude products were purified by preparative reversed-phase column chromatography (column: Cosmosil Cholester 20×250 mm, water/MeCN+1‰ TFA, 99:1 to 40:60, 30 min, 20 mL/min).

For 6: ESI-MS m/z for $C_{24}H_{25}F_3N_5O_3S$ found 520.5 [M+H]$^+$; $R_t$=1.01 min; $^1$H NMR (700 MHz, D$_2$O) δ 8.84-8.78 (m, 1H), 7.85-7.81 (m, 1H), 7.71 (s, 1H), 7.18 (s, 1H), 4.95 (s, 2H), 4.55-4.47 (m, 1H), 4.41-4.34 (m, 1H), 4.14-4.06 (m, 1H), 3.68-3.60 (m, 1H), 3.59-3.52 (m, 1H), 3.41-3.35 (m, 1H), 3.22-3.12 (m, 1H), 2.96-2.88 (m, 1H), 2.84-2.74 (m, 1H), 2.62 (s, 2H), 1.20 (s, 3H), 1.02 (s, 3H).

For 7: ESI-MS m/z for $C_{24}H_{25}F_3N_5O_3S$ found 520.5 [M+H]$^+$; $R_t$=0.93 min; $^1$H NMR (700 MHz, D$_2$O) δ 8.74-8.71 (m, 1H), 8.03-7.99 (m, 1H), 7.67 (s, 1H), 7.62 (s, 1H), 4.98 (s, 2H), 4.64-4.60 (m, 3H), 4.21-4.07 (m, 1H), 3.98-

Step 1

Synthesis of 3-((7-(1H-pyrrol-2-yl)thieno[3,2-b]pyridin-2-yl)methyl)-6,6-dimethyl-3-azabicyclo[3.1.0]hexane-2,4-dione (9a)

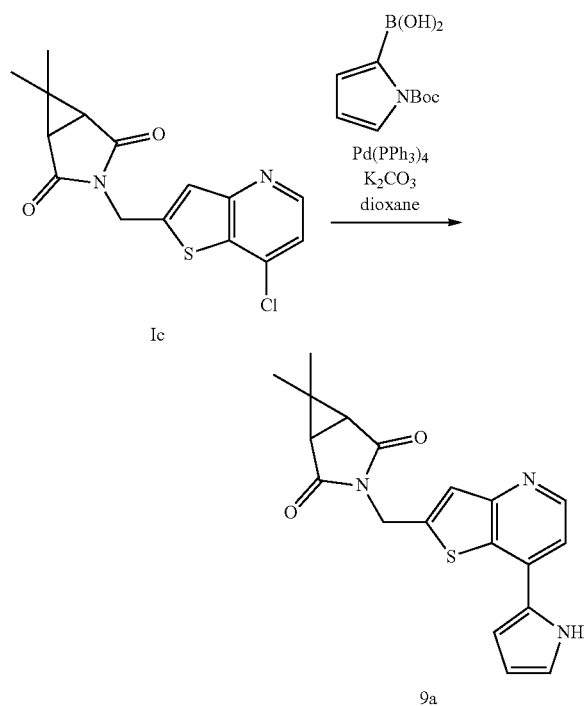

The title compound (9a) was obtained from Ic (210 mg; 0.65 mmol) and from (1-(tert-butoxycarbonyl)-1H-pyrrol-2-yl)boronic acid (276 mg; 1.31 mmol) according to the General Procedure Va in 9% yield (20 mg; 0.06 mmol).

ESI-MS m/z for $C_{19}H_{18}N_3O_2S$ found 352.1 [M+H]$^+$; $R_t$=0.96 min

Step 2

Synthesis of tert-butyl 2-((2-(2-(((6,6-dimethyl-2,4-dioxo-3-azabicyclo[3.1.0]hexan-3-yl)methyl)thieno[3,2-b]pyridin-7-yl)-1H-pyrrol-1-yl)methyl)morpholine-4-carboxylate (9b)

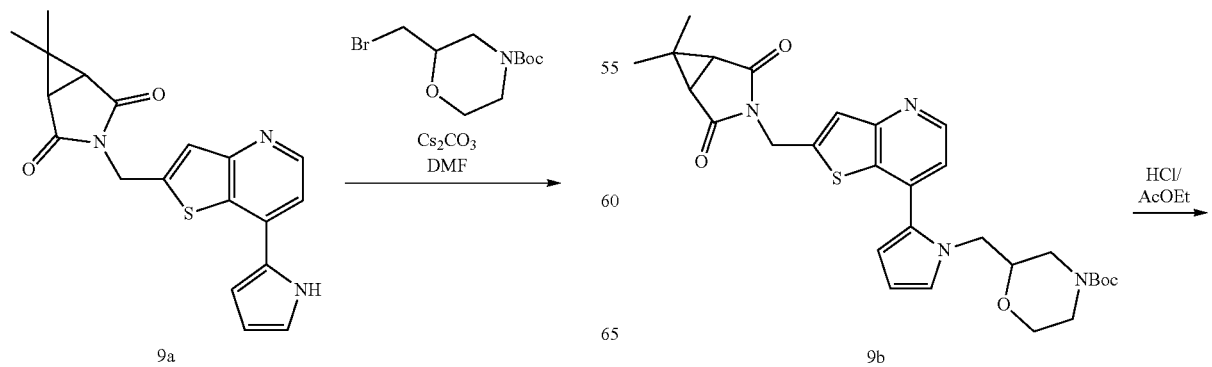

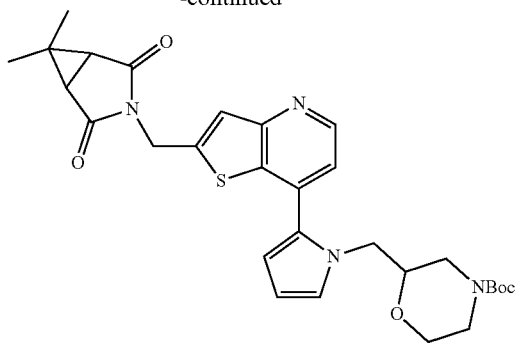

To the solution of 9a (20 mg; 0.06 mmol) in DMF (0.4 mL) tert-butyl 2-(bromomethyl)morpholine-4-carboxylate (16 mg; 0.06 mmol) and $Cs_2CO_3$ (37 mg; 0.11 mmol) were added and then the reaction mixture was stirred at room temperature overnight and then at 100° C. for 3 days. The reaction progress was monitored by LC-MS. When analysis indicated completion of the reaction, this mixture was taken into AcOEt/water. An organic layer was washed with water and brine, dried over anhydrous $MgSO_4$, filtered and concentrated in vacuo and the crude product was used to the next step without additional purification. Compound 9b was obtained in 83% yield (30 mg; 0.05 mmol).

ESI-MS m/z for $C_{29}H_{35}N_4O_5S$ found 551.0 [M+H]$^+$; $R_t$=1.49 min

Step 3

Synthesis of 6,6-dimethyl-3-((7-(1-(morpholin-2-ylmethyl)-1H-pyrrol-2-yl)thieno[3,2-b]pyridin-2-yl)methyl)-3-azabicyclo[3.1.0]hexane-2,4-dione 2,2,2-trifluoroacetate (9)

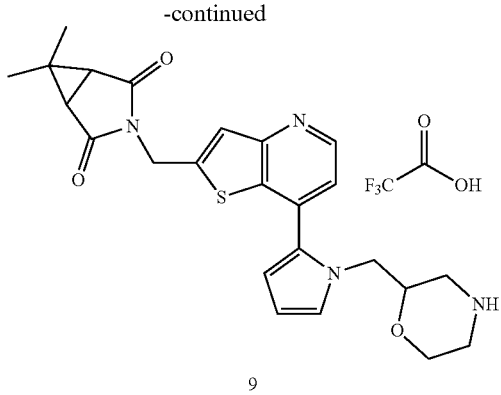

9

The title compounds (9) was obtained as a TFA salt from 9b (30 mg; 0.05 mmol) according to the General Procedure IVa in 14% yield (4 mg; 0.007 mmol). The crude product was purified by preparative reversed-phase column chromatography (column: Cosmosil Cholester 20×250 mm, water/MeCN+1 ‰ TFA, 99:1 to 45:55, 30 min, 20 mL/min).

ESI-MS m/z for $C_{24}H_{27}N_4O_3S$ found 451.1 $[M+H]^+$; $R_t$=0.84 min; $^1H$ NMR (700 MHz, $D_2O$, 300 K) δ 9.16-9.11 (m, 1H), 8.16-8.08 (m, 2H), 7.72-7.67 (m, 1H), 7.40-7.32 (m, 1H), 6.97-6.89 (m, 1H), 5.42 (s, 2H), 4.85-4.77 (m, 1H), 4.76-4.73 (m, 1H), 4.35-4.26 (m, 1H), 4.17-4.08 (m, 1H), 4.05-3.95 (m, 1H), 3.66-3.58 (m, 2H), 3.43-3.34 (m, 1H), 3.10 (s, 2H), 3.06-2.98 (m, 1H), 1.68 (s, 3H), 1.51 (s, 3H).

Example 10

Synthesis of 5-(3,3-difluoropyrrolidine-1-carbonyl)-4-(2-((6,6-dimethyl-2,4-dioxo-3-azabicyclo[3.1.0]hexan-3-yl)methyl)thieno[3,2-b]pyridin-7-yl)-6-methylpicolinonitrile 2,2,2-trifluoroacetate (10)

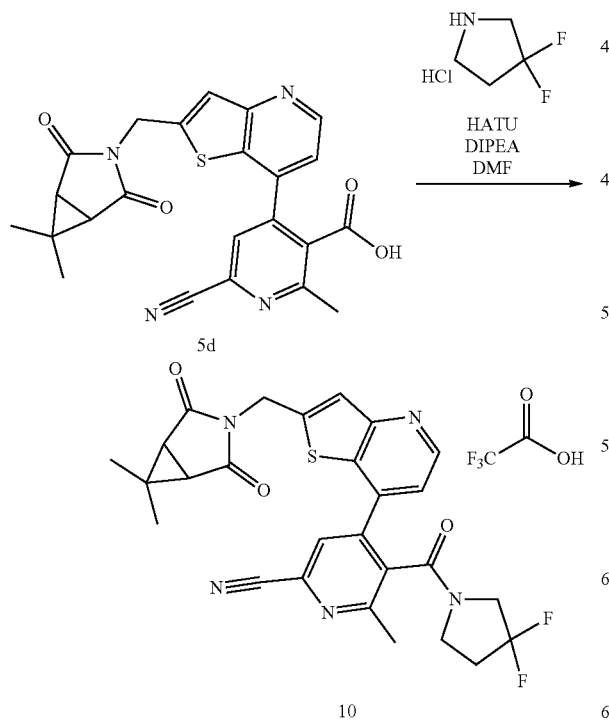

The title compound (10) was obtained as a TFA salt from 5d (47 mg; 0.100 mmol) and from 3,3-difluoropyrrolidine hydrochloride (16 mg; 0.11 mmol) according to the General Procedure I in 26% yield (17 mg; 0.026 mmol). The crude product was purified by preparative reversed-phase column chromatography (C-18, water/MeCN+1‰ TFA, 90:10 to 30:70, 30 min, 20 mL/min).

ESI-MS m/z for $C_7H_{24}F_2N_5O_3S$ found 536.1 $[M+H]^+$; $R_t$=1.33 min; $^1H$ NMR (700 MHz, $CD_3CN$-$d_3$) δ 8.76-8.73 (m, 1H), 7.98-7.95 (m, 1H), 7.62-7.59 (m, 1H), 7.32-7.29 (m, 1H), 4.87-4.80 (m, 2H), 3.87-3.68 (m, 1H), 3.54-3.43 (m, 1H), 3.35-3.25 (m, 1H), 3.12-2.89 (m, 1H), 2.64-2.59 (m, 3H), 2.46-2.41 (m, 2H), 2.38-2.12 (m, 2H), 1.26-1.18 (m, 3H), 1.08 (s, 3H).

Example 11

Synthesis of 4-(2-((6,6-dimethyl-2,4-dioxo-3-azabicyclo[3.1.0]hexan-3-yl)methyl)thieno[3,2-b]pyridin-7-yl)-5-((S)-3-hydroxypyrrolidine-1-carbonyl)-6-methylpicolinonitrile 2,2,2-trifluoroacetate (11)

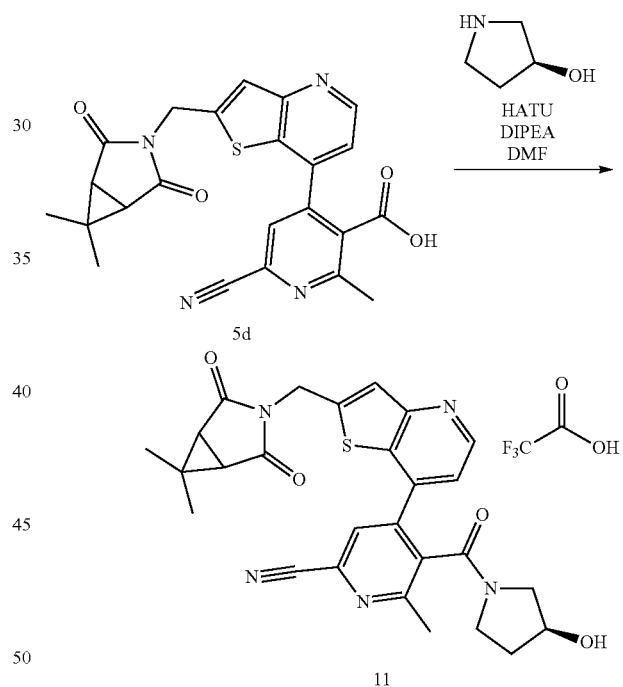

The title compound (11) was obtained as a TFA salt from 5d (47 mg; 0.10 mmol) and from (S)-pyrrolidin-3-ol (10 mg; 0.11 mmol) according to the General Procedure I in 40% yield (27 mg; 0.04 mmol). The crude product was purified by preparative reversed-phase column chromatography (column: Cosmosil Cholester 20×250 mm, water/MeCN+1‰ TFA, 99:1 to 40:60, 30 min, 20 mL/min).

ESI-MS m/z for $C_7H_{26}N_5O_4S$ found 516.3 $[M+H]^+$; $R_t$=1.07 min; $^1H$ NMR (700 MHz, $CD_3CN$-$d_3$) δ 8.75-8.70 (m, 1H), 7.99-7.93 (m, 1H), 7.63-7.57 (m, 1H), 7.49-7.32 (m, 1H), 4.89-4.77 (m, 2H), 4.28-3.98 (m, 1H), 3.60-3.42 (m, 1H), 3.26-3.04 (m, 2H), 2.93-2.69 (m, 1H), 2.65-2.59 (m, 3H), 2.47-2.42 (m, 2H), 1.90-1.31 (m, 2H), 1.26-1.18 (m, 3H), 1.12-1.02 (m, 3H).

Example 12

Synthesis of 4-(2-((6,6-dimethyl-2,4-dioxo-3-azabicyclo[3.1.0]hexan-3-yl)methyl)thieno[3,2-b]pyridin-7-yl)-5-((R)-3-hydroxypyrrolidine-1-carbonyl)-6-methylpicolinonitrile 2,2,2-trifluoroacetate (12)

Example 13

Synthesis of 5-(4,4-difluoropiperidine-1-carbonyl)-4-(2-((6,6-dimethyl-2,4-dioxo-3-azabicyclo[3.1.0]hexan-3-yl)methyl)thieno[3,2-b]pyridin-7-yl)-6-methylpicolinonitrile 2,2,2-trifluoroacetate (13)

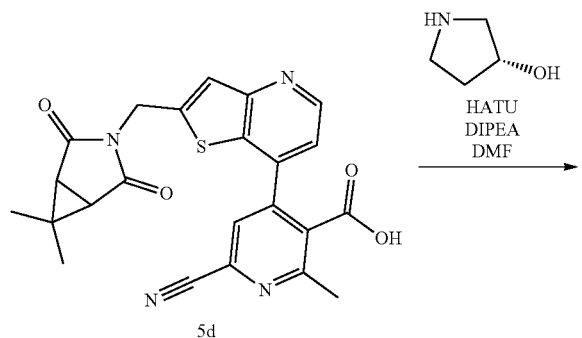

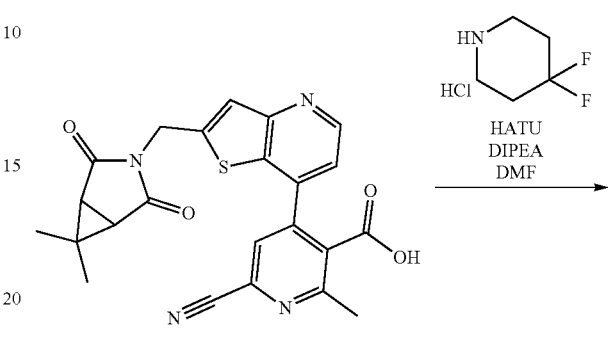

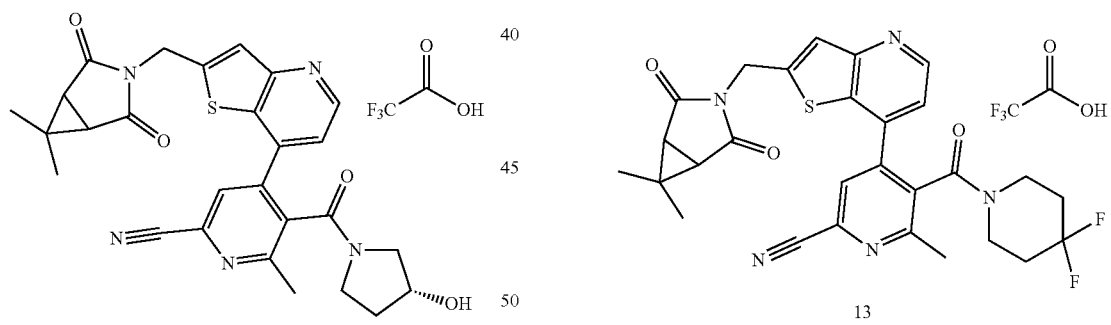

The title compound (12) was obtained as a TFA salt from 5d (47 mg; 0.10 mmol) and from (R)-pyrrolidin-3-ol (10 mg; 0.11 mmol) according to the General Procedure I in 30% yield (21 mg; 0.03 mmol). The crude product was purified by preparative reversed-phase column chromatography (column: Cosmosil Cholester 20×250 mm, water/MeCN+1‰ TFA, 99:1 to 40:60, 30 min, 20 mL/min).

ESI-MS m/z for $C_{27}H_{26}N_5O_4S$ found 516.3 [M+H]$^+$; $R_t$=1.07 min; $^1$H NMR (700 MHz, CD$_3$CN-d$_3$) δ 8.75-8.68 (m, 1H), 7.99-7.92 (m, 1H), 7.62-7.56 (m, 1H), 7.49-7.28 (m, 1H), 4.91-4.75 (m, 2H), 4.29-3.95 (m, 1H), 3.60-3.44 (m, 1H), 3.25-3.05 (m, 2H), 2.92-2.70 (m, 1H), 2.63-2.58 (m, 3H), 2.47-2.41 (m, 2H), 1.92-1.42 (m, 2H), 1.26-1.21 (m, 3H), 1.12-1.05 (m, 3H).

The title compound (13) was obtained as a TFA salt from 5d (47 mg; 0.100 mmol) and from 4,4-difluoropiperidine hydrochloride (18 mg; 0.11 mmol) according to the General Procedure I in 27% yield (18 mg; 0.027 mmol). The crude product was purified twice by preparative reversed-phase column chromatography (column: Cosmosil Cholester 20×250 mm, water/MeCN+1‰ TFA, 90:10 to 20:80, 30 min, 20 mL/min).

ESI-MS m/z for $C_{28}H_{26}F_2N_5O_3S$ found 550.4 [M+H]$^+$; $R_t$=1.39 min; $^1$H NMR (700 MHz, CD$_3$CN-d$_3$) δ 8.78-8.73 (m, 1H), 7.96-7.91 (m, 1H), 7.63-7.58 (m, 1H), 7.36-7.30 (m, 1H), 4.84 (s, 2H), 3.65-3.59 (m, 1H), 3.54-3.47 (m, 1H), 3.28-3.19 (m, 1H), 2.95-2.86 (m, 1H), 2.61 (s, 3H), 2.44 (s, 2H), 1.95-1.89 (m, 1H), 1.75-1.64 (m, 1H), 1.61-1.51 (m, 1H), 1.23 (s, 3H), 1.09 (s, 3H), 1.05-0.93 (m, 1H).

Example 14

Synthesis of 6-cyano-N-(3,3-difluorocyclobutyl)-4-(2-((6,6-dimethyl-2,4-dioxo-3-azabicyclo[3.1.0]hexan-3-yl)methyl)thieno[3,2-b]pyridin-7-yl)-2-methylnicotinamide 2,2,2-trifluoroacetate (14)

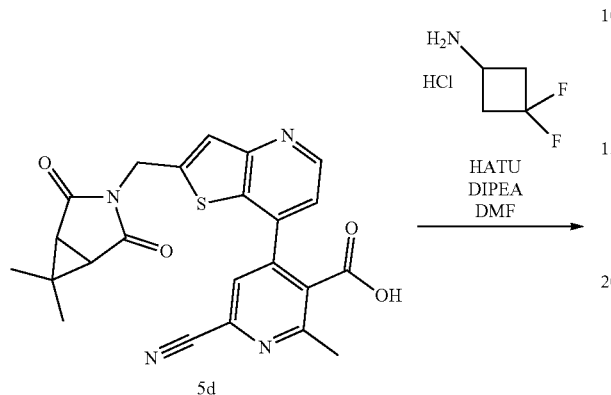

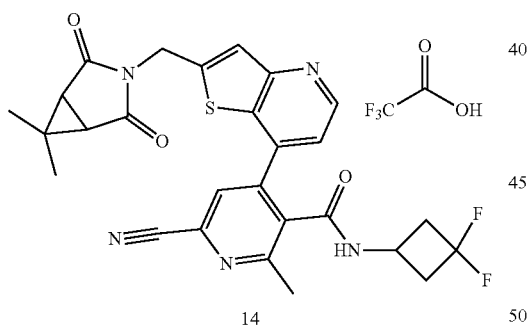

The title compound (14) was obtained as a TFA salt from 5d (47 mg; 0.100 mmol) and from 3,3-difluorocyclobutan-1-amine hydrochloride (16 mg; 0.11 mmol) according to the General Procedure I in 9% yield (6 mg; 0.009 mmol). The crude product was purified twice by preparative reversed-phase column chromatography (column: Cosmosil Cholester 20×250 mm, water/MeCN+1‰ TFA, 90:10 to 20:80, 30 min, 20 mL/min).

ESI-MS m/z for $C_{27}H_{24}F_2N_5O_3S$ found 536.2 [M+H]$^+$; $R_t$=1.30 min; $^1$H NMR (700 MHz, CD$_3$CN-d$_3$) δ 8.75-8.72 (m, 1H), 7.90-7.87 (m, 1H), 7.61-7.57 (m, 1H), 7.35-7.30 (m, 1H), 7.22 (d, J=6.3 Hz, 1H), 4.83 (d, J=0.9 Hz, 2H), 4.04-3.95 (m, 1H), 2.79-2.72 (m, 2H), 2.65 (s, 3H), 2.44 (s, 2H), 2.21-2.10 (m, 2H), 1.23 (s, 3H), 1.10 (s, 3H).

Example 15

Synthesis of 5-((S)-3-aminopyrrolidine-1-carbonyl)-4-(2-((6,6-dimethyl-2,4-dioxo-3-azabicyclo[3.1.0]hexan-3-yl)methyl)thieno[3,2-b]pyridin-7-yl)-6-methylpicolinonitrile 2,2,2-trifluoroacetate (15)

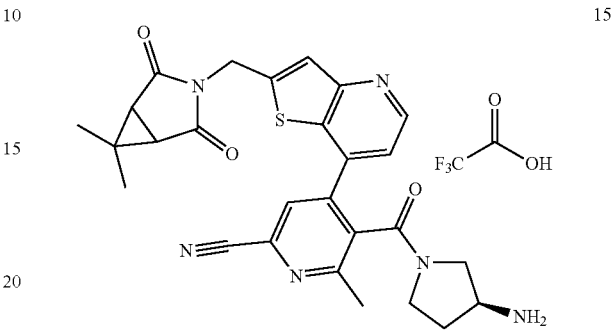

The title compound (15) was obtained as a TFA salt in 4% overall yield in a similar way to Example 5 with the exception that, in the fifth step of the synthesis, tert-butyl (S)-pyrrolidin-3-ylcarbamate was used instead of tert-butyl (S)-3-methylpiperazine-1-carboxylate and DCM was used instead of DMF and in the last step of the synthesis the crude product was purified by preparative reversed-phase column chromatography (column: Cosmosil Cholester 20×250 mm, water/MeCN+1‰ TFA, 99:1 to 45:55, 30 min, 20 mL/min).

ESI-MS m/z for $C_{27}H_{27}N_6O_3S$ found 515.3 [M+H]$^+$; $R_t$=0.84 min; $^1$H NMR (700 MHz, D$_2$O, 333 K) δ 9.22-9.13 (m, 1H), 8.59-8.50 (m, 1H), 8.12-8.02 (m, 1H), 7.85-7.75 (m, 1H), 5.48-5.21 (m, 2H), 4.57-4.30 (m, 1H), 4.20-3.93 (m, 2H), 3.87-3.28 (m, 2H), 3.14-3.00 (m, 5H), 2.80-1.94 (m, 2H), 1.74-1.59 (m, 3H), 1.54-1.39 (m, 3H).

Example 16

Synthesis of N-(azetidin-3-yl)-6-cyano-4-(2-((6,6-dimethyl-2,4-dioxo-3-azabicyclo[3.1.0]hexan-3-yl)methyl)thieno[3,2-b]pyridin-7-yl)-2-methylnicotinamide hydrochloride (16)

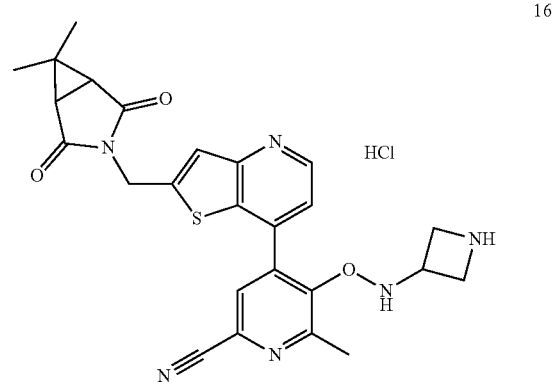 [SMILES: Cc1nc(C#N)cc(-c2ccnc3cc(CN4C(=O)C5C(C4=O)C5(C)C)sc23)c1ONC1CNC1 ; Cl]

The title compound (16) was obtained as a hydrochloride salt in 5% overall yield in a similar way to Example 5 with the exception that, in the fifth step of the synthesis, tert-butyl 3-aminoazetidine-1-carboxylate was used instead of tert-butyl (S)-3-methylpiperazane-1-carboxylate and DCM was used instead of DMF and in the last step of the synthesis the crude product was purified by preparative reversed-phase column chromatography (column: Cosmosil Cholester 20×250 mm, water+0.3‰ HCl (36%)/MeCN, 99:1 to 45:55, 30 min, 20 mL/min).

ESI-MS m/z for $C_{26}H_{25}N_6O_3S$ found 501.7 [M+H]$^+$; $R_t$=0.83 min; $^1$H NMR (700 MHz, D$_2$O, 300 K) δ 8.86-8.80 (m, 1H), 8.05 (s, 1H), 7.74 (s, 1H), 7.65-7.59 (m, 1H), 4.96 (s, 2H), 4.60-4.53 (m, 1H), 4.24-4.12 (m, 2H), 3.91-3.82 (m, 2H), 2.67 (s, 3H), 2.62 (s, 2H), 1.21 (s, 3H), 1.04 (s, 3H).

Example 17

Synthesis of 4-(2-((6,6-dimethyl-2,4-dioxo-3-azabicyclo[3.1.0]hexan-3-yl)methyl)thieno[3,2-b]pyridin-7-yl)-6-methyl-5-(piperazine-1-carbonyl)picolinonitrile hydrochloride (17)

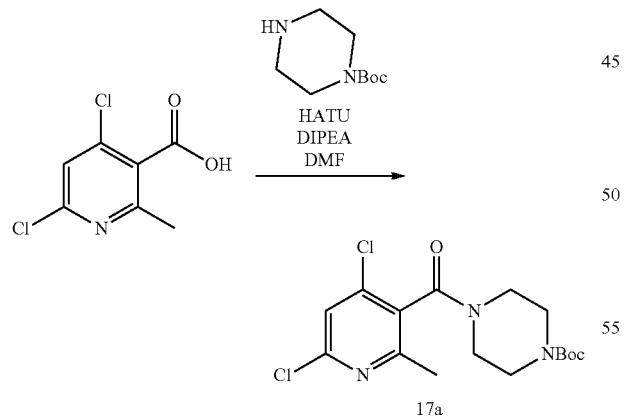

Step 1

Synthesis of tert-butyl 4-(4,6-dichloro-2-methylnicotinoyl)piperazine-1-carboxylate (17a)

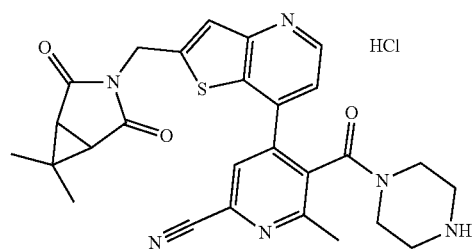

The title compound (17a) was obtained from 4,6-dichloro-2-methylnicotinic acid (0.47 g; 2.28 mmol) and from tert-butyl piperazine-1-carboxylate (0.42 g; 2.28 mmol) according to the General Procedure I in 47% yield (0.40 g; 1.07 mmol).

ESI-MS m/z for $C_{14}H_{16}Cl_2N_4O_3$ found 359.0/361.0 [M+MeCN-tBu]$^+$; $R_t$=1.35 min Step 2

Synthesis of tert-butyl 4-(4-chloro-6-cyano-2-methylnicotinoyl)piperazine-1-carboxylate (17b)

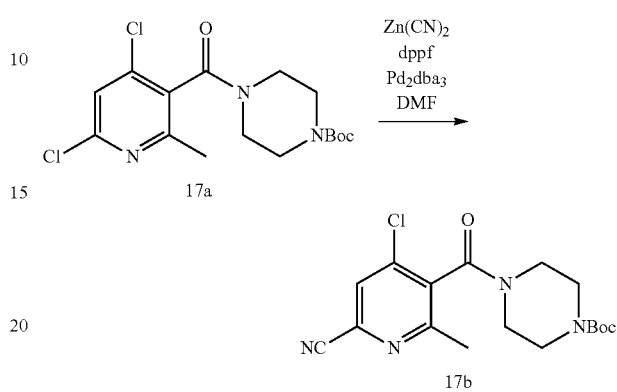

To the solution of 17a (85 mg; 0.23 mmol) in DMF (1.6 mL) Zn(CN)$_2$ (27 mg; 0.23 mmol) was added and all was flushed with Ar. Next to this mixture dppf (13 mg; 0.023 mmol) and Pd$_2$dba$_3$ (21 mg; 0.023 mmol) were added and flushed with Ar. The mixture was heated at 70° C. overnight. The reaction progress was monitored by TLC. When analysis indicated completion of the reaction, this mixture was taken into AcOEt/water. An organic layer was washed with water and brine, dried over anhydrous MgSO$_4$, filtered and concentrated in vacuo and the crude product was used to the next step without additional purification. Compound 17b was obtained in 99% yield (84 mg; 0.23 mmol).

ESI-MS m/z for $C_{15}H_{16}ClN_5O_3$ found 350.0/352.0 [M+MeCN-tBu]$^+$; $R_t$=1.33 min Step 3

Synthesis of tert-butyl 4-(6-cyano-4-(2-((6,6-dimethyl-2,4-dioxo-3-azabicyclo[3.1.0]hexan-3-yl)methyl)thieno[3,2-b]pyridin-7-yl)-2-methylnicotinoyl)piperazine-1-carboxylate (17c)

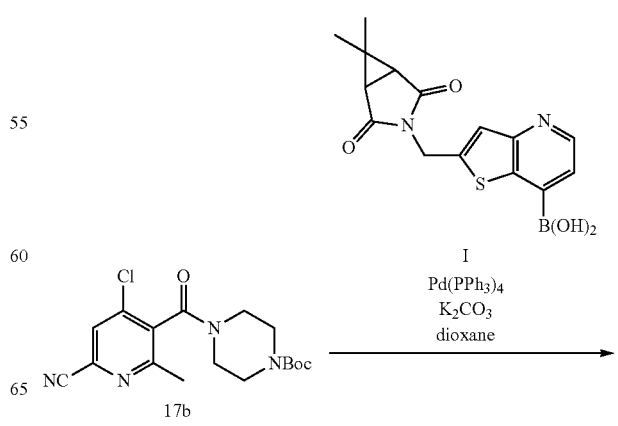

259

-continued

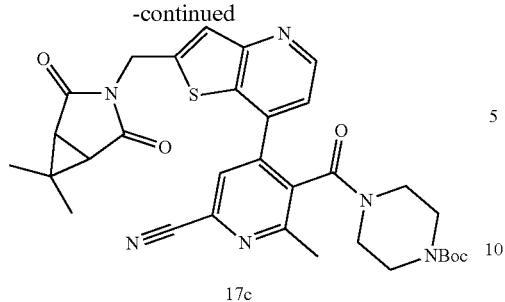

17c

The title compound (17c) was obtained from 17b (84 mg; 0.23 mmol) and from boronic acid I (196 mg; 0.59 mmol) according to the General Procedure Va and after standard work-up all the crude product mixture was taken to the next step without any additional purification.

ESI-MS m/z for $C_{32}H_{35}N_6O_5S$ found 615.0 $[M+H]^+$; $R_t$=1.49 min

Step 4

Synthesis of 4-(2-((6,6-dimethyl-2,4-dioxo-3-azabicyclo[3.1.0]hexan-3-yl)methyl)thieno[3,2-b]pyridin-7-yl)-6-methyl-5-(piperazine-1-carbonyl)picolinonitrile hydrochloride (17)

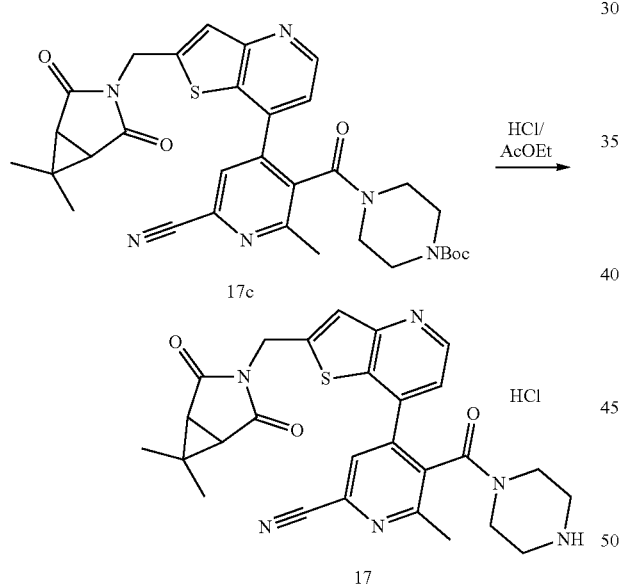

The title compound (17) was obtained as a hydrochloride salt from 17c (the crude reaction mixture) according to the General Procedure IVa in 2% yield (per two steps) (3 mg; 0.005 mmol). The crude product was purified twice by preparative reversed-phase column chromatography (column: Cosmosil Cholester 20×250 mm, water+0.3‰ HCl (36%)/MeCN, 99:1 to 45:55, 30 min, 20 mL/min).

ESI-MS m/z for $C_{27}H_{27}N_6O_3S$ found 515.6 $[M+H]^+$; $R_t$=0.84 min; $^1$H NMR (700 MHz, $D_2O$, 300 K) δ 8.82-8.76 (m, 1H), 8.12 (s, 1H), 7.70 (s, 1H), 7.50-7.44 (m, 1H), 4.98-4.86 (m, 2H), 3.90-3.82 (m, 1H), 3.56-3.49 (m, 2H), 3.27-3.20 (m, 1H), 3.20-3.11 (m, 1H), 3.04-2.98 (m, 1H), 2.88-2.79 (m, 1H), 2.64-2.59 (m, 5H), 2.38-2.25 (m, 1H), 1.21 (s, 3H), 1.03 (s, 3H).

260

Example 18

Synthesis of 6,6-dimethyl-3-((7-(4-methyl-3-(pyrrolidin-3-ylamino)-6-(trifluoromethyl)pyridin-2-yl)thieno[3,2-b]pyridin-2-yl)methyl)-3-azabicyclo[3.1.0]hexane-2,4-dione 2,2,2-trifluoroacetate (18)

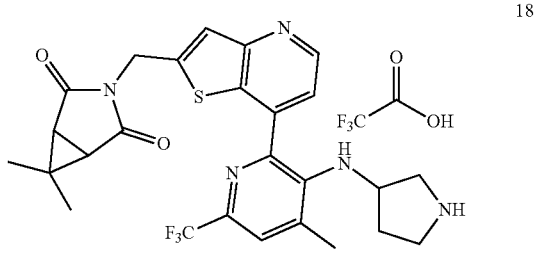

18

Step 1

Synthesis of tert-butyl 3-((4-methyl-6-(trifluoromethyl)pyridin-3-yl)amino)pyrrolidine-1-carboxylate (18a)

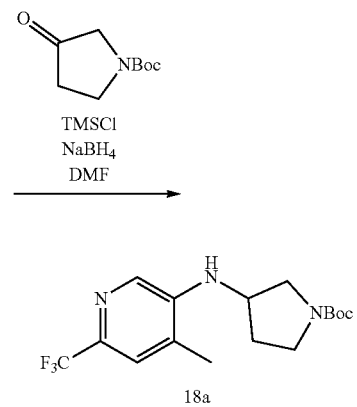

The title compound (18a) was obtained from 4-methyl-6-(trifluoromethyl)pyridin-3-amine (0.20 g; 1.16 mmol) and from tert-butyl 3-oxopyrrolidine-1-carboxylate (0.32 g; 1.74 mmol) according to the General Procedure VIb in 50% yield (0.20 g; 0.58 mmol).

ESI-MS m/z for $C_{16}H_{23}F_3N_3O_2$ found 346.0 $[M+H]^+$; $R_t$=1.51 min

Step 2

Synthesis of tert-butyl 3-((2-bromo-4-methyl-6-(trifluoromethyl)pyridin-3-yl)amino)pyrrolidine-1-carboxylate (18b)

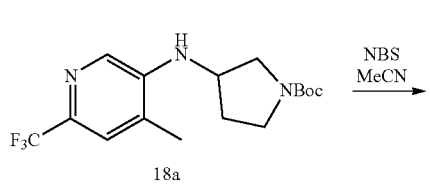

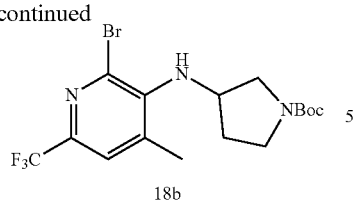

To the solution of 18a (0.2 g; 0.58 mmol) in MeCN (5 mL) NBS (103 mg; 0.58 mmol) was added and then the reaction mixture was stirred at room temperature overnight. The reaction progress was monitored by TLC and LC-MS. When analyses indicated completion of the reaction, to this mixture 10% $Na_2S_2O_3$ was added and then extracted with AcOEt. The organic layer was washed with brine, dried over anhydrous $MgSO_4$, filtered and concentrated in vacuo and the crude product was used to the next step without additional purification. Compound 18b was obtained in 98% yield (240 mg; 0.57 mmol).

ESI-MS m/z for $C_{12}H_{14}BrF_3N_3O_2$ found 368.0/370.0 $[M+H-tBu]^+$; $R_t$=1.70 min Step 3

Synthesis of tert-butyl 3-((2-(2-((6,6-dimethyl-2,4-dioxo-3-azabicyclo[3.1.0]hexan-3-yl)methyl)thieno[3,2-b]pyridin-7-yl)-4-methyl-6-(trifluoromethyl)pyridin-3-yl)amino)pyrrolidine-1-carboxylate (18c)

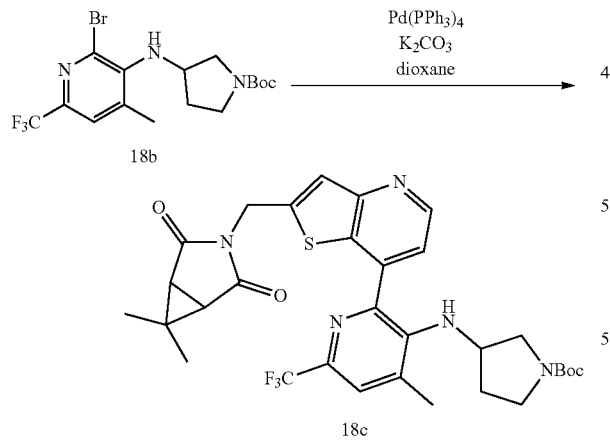

The title compound (18c) was obtained from 18b (120 mg; 0.28 mmol) and from boronic acid I (93 mg; 0.28 mmol) according to the General Procedure Va and after standard work-up all the crude product mixture was taken to the next step.

ESI-MS m/z for $C_{31}H_{35}F_3N_5O_4S$ found 630.1 $[M+H]^+$; $R_t$=1.62 min

Step 4

Synthesis of 6,6-dimethyl-3-((7-(4-methyl-3-(pyrrolidin-3-ylamino)-6-(trifluoromethyl)pyridin-2-yl)thieno[3,2-b]pyridin-2-yl)methyl)-3-azabicyclo[3.1.0]hexane-2,4-dione 2,2,2-trifluoroacetate (18)

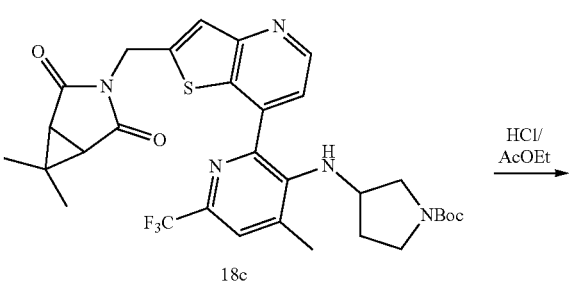

The title compound (18) was obtained as a TFA salt from 18c (the crude reaction mixture) according to the General Procedure IVa in 6% yield (per two steps) (10 mg; 0.016 mmol). The crude product was purified three times by preparative reversed-phase column chromatography (first: C-18, water/MeCN, 99:1 to 45:55, 30 min, 20 mL/min; second: column: Cosmosil Cholester 20×250 mm, water/MeCN, 99:1 to 50:50, 40 min, 20 mL/min; third: column: Cosmosil Cholester 20×250 mm, water/MeCN+1‰ TFA, 95:5 to 45:55, 30 min, 20 mL/min).

ESI-MS m/z for $C_{26}H_{27}F_3N_5O_2S$ found 530.7 $[M+H]^+$; $R_t$=1.03 min; $^1$H NMR (700 MHz, $D_2O$, 300 K) δ 8.85-8.80 (m, 1H), 8.15-8.11 (m, 1H), 7.81 (s, 1H), 7.72-7.68 (m, 1H), 4.96 (s, 2H), 3.52-3.40 (m, 1H), 3.35-3.23 (m, 1H), 3.05-2.92 (m, 3H), 2.63 (s, 2H), 2.45 (s, 3H), 1.90-1.79 (m, 1H), 1.79-1.68 (m, 1H), 1.20 (s, 3H), 1.02 (s, 3H).

Example 19

Synthesis of 5-(3,3-difluoroazetidine-1-carbonyl)-4-(2-((6,6-dimethyl-2,4-dioxo-3-azabicyclo[3.1.0]hexan-3-yl)methyl)thieno[3,2-b]pyridin-7-yl)-6-methylpicolinonitrile 2,2,2-trifluoroacetate (19)

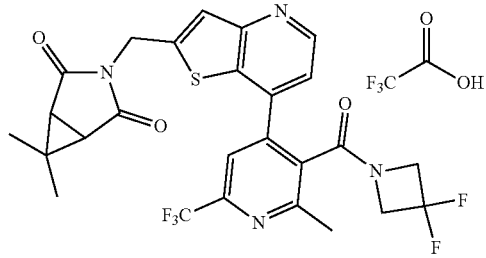

Step 1

Synthesis of (4,6-dichloro-2-methylpyridin-3-yl)(3,3-difluoroazetidin-1-yl)methanone (19a)

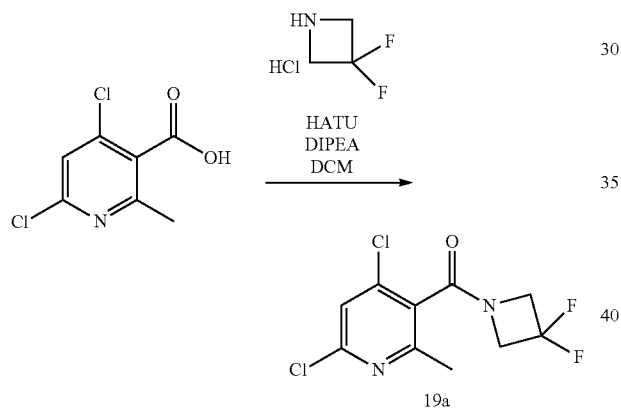

The title compound (19a) was obtained from 4,6-dichloro-2-methylnicotinic acid (0.47 g; 2.28 mmol) and from 3,3-difluoroazetidine hydrochloride (0.30 g; 2.28 mmol) according to the General Procedure I in 42% yield (0.33 g; 1.18 mmol).

ESI-MS m/z for $C_{12}H_{11}Cl_2F_2N_3O$ found 322.0/324.0 [M+MeCN]$^+$; $R_t$=1.06 min

Step 2

Synthesis of 4-chloro-5-(3,3-difluoroazetidine-1-carbonyl)-6-methylpicolinonitrile (19b)

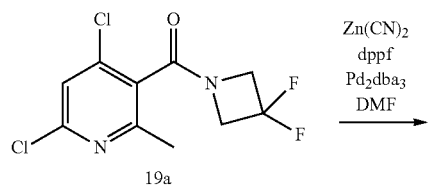

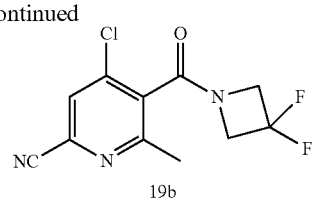

To the solution of 19a (65 mg; 0.23 mmol) in DMF (1.2 mL) Zn(CN)$_2$ (27 mg; 0.23 mmol) was added and all was flushed with Ar. Next to this mixture dppf (13 mg; 0.023 mmol) and Pd$_2$dba$_3$ (11 mg; 0.012 mmol) were added and flushed with Ar. The mixture was heated at 70° C. overnight. The reaction progress was monitored by TLC. When analysis indicated completion of the reaction, this mixture was taken into AcOEt/water. An organic layer was washed with water and brine, dried over anhydrous MgSO$_4$, filtered and concentrated in vacuo and the crude product was used to the next step without additional purification. Compound 19b was obtained in 99% yield (64 mg; 0.23 mmol).

ESI-MS m/z for $C_{11}H_9ClF_2N_3O$ found 272.0/274.0 [M+H]$^+$; $R_t$=0.91 min

Step 3

Synthesis of 5-(3,3-difluoroazetidine-1-carbonyl)-4-(2-((6,6-dimethyl-2,4-dioxo-3-azabicyclo[3.1.0]hexan-3-yl)methyl)thieno[3,2-b]pyridin-7-yl)-6-methylpicolinonitrile 2,2,2-trifluoroacetate (19)

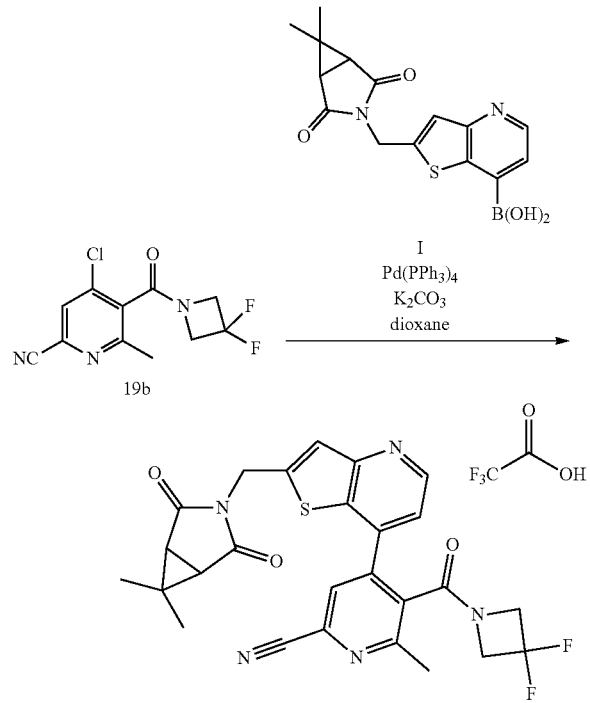

The title compound (19) was obtained as a TFA salt from 19b (64 mg; 0.23 mmol) and from boronic acid I (78 mg; 0.23 mmol) according to the General Procedure Va in 8% yield (12 mg; 0.019 mmol). The crude product was purified by flash column chromatography on silica (hexane/AcOEt, 100:0 to 80:20, v/v, 15 minutes) and then by preparative reversed-phase column chromatography (C-18, water/MeCN+1‰ TFA, 95:5 to 30:70, 30 min, 20 mL/min).

ESI-MS m/z for $C_{26}H_{22}F_2N_5O_3S$ found 522.3 [M+H]$^+$; $R_t$=1.23 min; $^1$H NMR (700 MHz, Methanol-$d_4$) δ 8.81-8.76 (m, 1H), 8.11 (s, 1H), 7.67-7.62 (m, 1H), 7.43-7.39 (m, 1H), 5.00-4.88 (m, 2H), 4.51-4.28 (m, 2H), 4.12-4.03 (m, 1H), 3.78-3.70 (m, 1H), 2.71 (s, 3H), 2.51 (s, 2H), 1.25 (s, 3H), 1.06 (s, 3H).

Example 20

Synthesis of 6-(2-((6,6-dimethyl-2,4-dioxo-3-azabicyclo[3.1.0]hexan-3-yl)methyl)thieno[3,2-b]pyridin-7-yl)-4-methyl-5-(pyrrolidin-3-ylamino)picolinonitrile dihydrochloride (20)

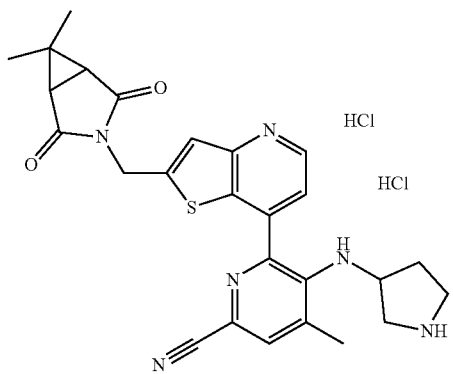

The title compound (20) was obtained as a dihydrochloride salt in 6% overall yield in a similar way to Example 18 with the exception that, in the first step of the synthesis, 5-amino-4-methylpicolinonitrile was used instead of 4-methyl-6-(trifluoromethyl)pyridin-3-amine and in the last step of the synthesis the crude product was purified three times by preparative reversed-phase column chromatography (first: C-18, water/MeCN, 99:1 to 45:55, 30 min, 20 mL/min; second: C-18, water/MeCN, 99:1 to 50:50, 40 min, 20 mL/min; third: column: Cosmosil Cholester 20×250 mm, water/MeCN+HCl, 99:1 to 45:55, 30 min, 20 mL/min).

ESI-MS m/z for $C_{26}H_{27}N_6O_2S$ found 487.5 [M+H]$^+$; $R_t$=0.93 min; $^1$H NMR (700 MHz, D$_2$O, 300 K) δ 8.79-8.74 (m, 1H), 7.88-7.85 (m, 1H), 7.71 (s, 1H), 7.64-7.60 (m, 1H), 4.91 (s, 2H), 3.46-3.38 (m, 1H), 3.32-3.25 (m, 1H), 3.02-2.86 (m, 3H), 2.61 (s, 2H), 2.38 (s, 3H), 1.79-1.69 (m, 2H), 1.20 (s, 3H), 1.04 (s, 3H).

Example 21

Synthesis of 6,6-dimethyl-3-((7-(2-methyl-3-(pyrrolidin-3-yloxy)-6-(trifluoromethyl)pyridin-4-yl)thieno[3,2-b]pyridin-2-yl)methyl)-3-azabicyclo[3.1.0]hexane-2,4-dione 2,2,2-trifluoroacetate (21)

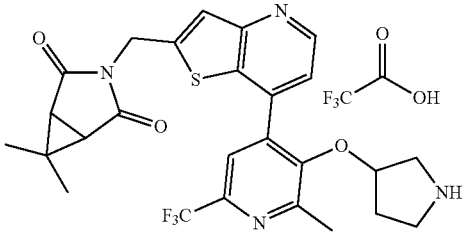

The title compound (21) was obtained as a TFA salt as a racemate in 10% overall yield in a similar way to Example 1 with the exception that, in the first step of the synthesis, 2-methyl-6-(trifluoromethyl)pyridin-3-ol was used instead of 5-hydroxy-4-methylpicolinonitrile, in the second step of the synthesis, tert-butyl 3-((methylsulfonyl)oxy)pyrrolidine-1-carboxylate was used instead of tert-butyl 3-((methylsulfonyl)oxy)piperidine-1-carboxylate and in the last step of the synthesis the crude product was purified by preparative reversed-phase column chromatography (C-18, water/MeCN+1‰ TFA, 99:1 to 45:55, 30 min, 20 mL/min).

ESI-MS m/z for $C_{26}H_{26}F_3N_4O_3S$ found 531.7 [M+H]$^+$; $R_t$=1.02 min; $^1$H NMR (700 MHz, D$_2$O, 300 K) δ 8.84-8.79 (m, 1H), 7.80 (s, 1H), 7.74-7.70 (m, 1H), 7.68-7.65 (m, 1H), 4.95-4.85 (m, 2H), 4.48-4.37 (m, 1H), 3.29-3.16 (m, 2H), 3.16-3.07 (m, 1H), 2.97-2.88 (m, 1H), 2.64 (s, 3H), 2.60 (s, 2H), 1.80-1.64 (m, 2H), 1.19 (s, 3H), 1.00 (s, 3H).

Example 22

Synthesis of 6,6-dimethyl-3-((7-(2-methyl-3-((S)-pyrrolidin-3-yl)oxy)-6-(trifluoromethyl)pyridin-4-yl)thieno[3,2-b]pyridin-2-yl)methyl)-3-azabicyclo[3.1.0]hexane-2,4-dione 2,2,2-trifluoroacetate (22)

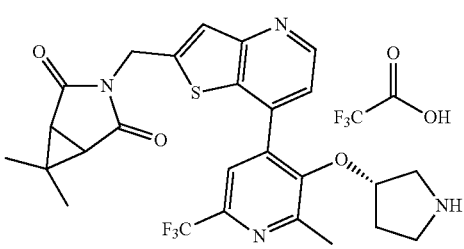

The title compound (22) was obtained as a TFA salt as a single enantiomer of compound 21 in 11% overall yield in a similar way to Example 1 with the exception that, in the first step of the synthesis, 2-methyl-6-(trifluoromethyl)pyridin-3-ol was used instead of 5-hydroxy-4-methylpicolinonitrile, in the second step of the synthesis, tert-butyl (S)-3-((methylsulfonyl)oxy)pyrrolidine-1-carboxylate was used instead of tert-butyl 3-((methylsulfonyl)oxy)piperidine-1-carboxylate and in the last step of the synthesis the crude product was purified by preparative reversed-phase column chromatography (C-18, water/MeCN+1‰ TFA, 99:1 to 45:55, 30 min, 20 mL/min).

ESI-MS m/z for $C_{26}H_{26}F_3N_4O_3S$ found 531.7 [M+H]$^+$; $R_t$=1.03 min; $^1$H NMR (700 MHz, D$_2$O, 300 K) δ 8.83-8.79 (m, 1H), 7.79-7.75 (m, 1H), 7.71-7.67 (m, 1H), 7.67-7.63 (m, 1H), 4.96-4.83 (m, 2H), 4.44-4.33 (m, 1H), 3.26-3.16 (m, 2H), 3.14-3.06 (m, 1H), 2.96-2.88 (m, 1H), 2.64 (s, 3H), 2.59 (s, 2H), 1.76-1.62 (m, 2H), 1.19 (s, 3H), 1.00 (s, 3H).

Example 23

Synthesis of 6,6-dimethyl-3-((7-(2-methyl-3-(((S)-piperidin-3-yl)oxy)-6-(trifluoromethyl)pyridin-4-yl) thieno[3,2-b]pyridin-2-yl)methyl)-3-azabicyclo [3.1.0]hexane-2,4-dione 2,2,2-trifluoroacetate (23)

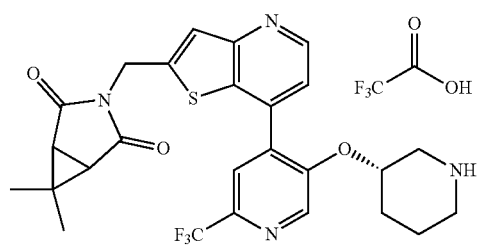

23

The title compound (23) was obtained as a TFA salt in 12% overall yield in a similar way to Example 1 with the exception that, in the first step of the synthesis, 2-methyl-6-(trifluoromethyl)pyridin-3-ol was used instead of 5-hydroxy-4-methylpicolinonitrile, in the second step of the synthesis, tert-butyl (R)-3-((methylsulfonyl)oxy)piperidine-1-carboxylate was used instead of tert-butyl 3-((methylsulfonyl)oxy)piperidine-1-carboxylate and in the last step of the synthesis the crude product was purified by preparative reversed-phase column chromatography (C-18, water/MeCN+1‰ TFA, 99:1 to 45:55, 30 min, 20 mL/min).

ESI-MS m/z for $C_{27}H_{28}F_3N_4O_3S$ found 545.7 [M+H]$^+$; $R_t$=1.05 min; $^1$H NMR (700 MHz, D$_2$O, 300 K) δ 8.83-8.79 (m, 1H), 7.81-7.78 (m, 1H), 7.72-7.69 (m, 1H), 7.68-7.65 (m, 1H), 4.96-4.85 (m, 2H), 3.95-3.87 (m, 1H), 3.06-2.98 (m, 1H), 2.98-2.91 (m, 3H), 2.65 (s, 3H), 2.59 (s, 2H), 1.48-1.39 (m, 2H), 1.32-1.20 (m, 2H), 1.19 (s, 3H), 1.00 (s, 3H).

Example 24

Synthesis of 5-(azetidin-3-ylamino)-6-(2-((6,6-dimethyl-2,4-dioxo-3-azabicyclo[3.1.0]hexan-3-yl) methyl)thieno[3,2-b]pyridin-7-yl)-4-methylpicolinonitrile 2,2,2-trifluoroacetate (24)

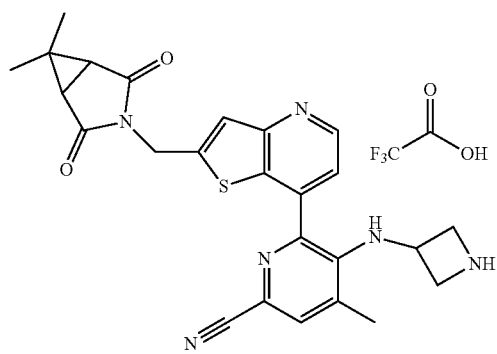

24

The title compound (24) was obtained as a TFA salt in 3% overall yield in a similar way to Example 18 with the exception that, in the first step of the synthesis, 5-amino-4-methylpicolinonitrile was used instead of 4-methyl-6-(trifluoromethyl)pyridin-3-amine and tert-butyl 3-oxoazetidine-1-carboxylate was used instead of tert-butyl 3-oxopyrrolidine-1-carboxylate and in the last step of the synthesis the crude product was purified by preparative reversed-phase column chromatography (C-18, water/MeCN+1‰ TFA, 99:1 to 45:55, 30 min, 20 mL/min).

ESI-MS m/z for $C_{25}H_{25}N_6O_2S$ found 473.6 [M+H]$^+$; $R_t$=0.88 min; $^1$H NMR (700 MHz, D$_2$O, 300 K) δ 8.82-8.79 (m, 1H), 7.89-7.86 (m, 1H), 7.71-7.67 (m, 2H), 4.94 (s, 2H), 3.95-3.89 (m, 2H), 3.86-3.79 (m, 1H), 3.65-3.56 (m, 2H), 2.63 (s, 2H), 2.38 (s, 3H), 1.21 (s, 3H), 1.07 (s, 3H).

Example 25

Synthesis of 6,6-dimethyl-3-((7-(2-methyl-3-(pyrrolidin-3-ylamino)-6-(trifluoromethyl)pyridin-4-yl) thieno[3,2-b]pyridin-2-yl)methyl)-3-azabicyclo [3.1.0]hexane-2,4-dione 2,2,2-trifluoroacetate (25)

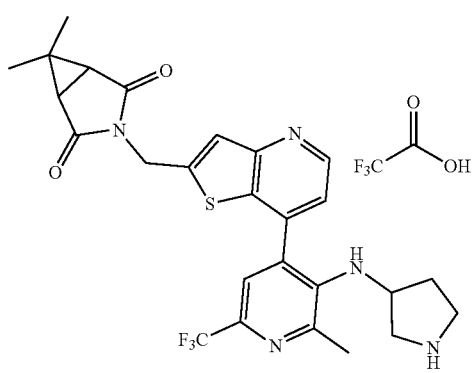

25

The title compound (25) was obtained as a TFA salt as a racemate in 11% overall yield in a similar way to Example 18 with the exception that, in the first step of the synthesis, 2-methyl-6-(trifluoromethyl)pyridin-3-amine was used instead of 4-methyl-6-(trifluoromethyl)pyridin-3-amine and in the last step of the synthesis the crude product was purified by preparative reversed-phase column chromatography (C-18, water/MeCN+1‰ TFA, 95:5 to 50:50, 30 min, 20 mL/min).

ESI-MS m/z for $C_{26}H_{27}F_3N_5O_2S$ found 530.8 [M+H]$^+$; $R_t$=1.03 min; $^1$H NMR (700 MHz, DMSO-d$_6$+D$_2$O, 348 K) δ 8.78-8.74 (m, 1H), 7.54-7.50 (m, 1H), 7.48-7.45 (m, 1H), 7.44-7.41 (m, 1H), 4.81-4.72 (m, 2H), 3.36-3.26 (m, 1H), 3.19-3.13 (m, 1H), 2.96-2.87 (m, 1H), 2.87-2.79 (m, 1H), 2.77-2.66 (m, 1H), 2.60 (s, 3H), 2.55-2.52 (m, 2H), 1.66-1.56 (m, 2H), 1.18 (s, 3H), 1.02 (s, 3H); $^{19}$F NMR (659 MHz, DMSO-d$_6$) δ −65.12 (s), −74.14 (s).

Example 26

Synthesis of 4-(2-((6,6-dimethyl-2,4-dioxo-3-azabicyclo[3.1.0]hexan-3-yl)methyl)thieno[3,2-b]pyridin-7-yl)-6-methyl-5-(pyrrolidin-3-ylamino)picolinonitrile 2,2,2-trifluoroacetate (26)

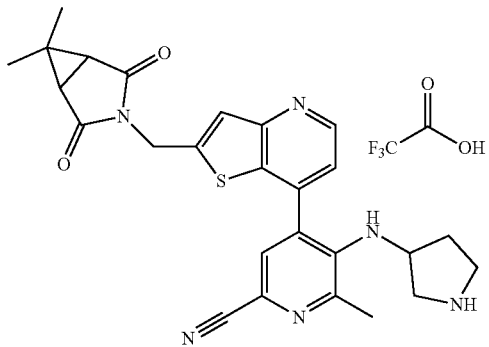

The title compound (26) was obtained as a TFA salt in 1% overall yield in a similar way to Example 18 with the exception that, in the first step of the synthesis, 5-amino-6-methylpicolinonitrile was used instead of 4-methyl-6-(trifluoromethyl)pyridin-3-amine and in the last step of the synthesis the crude product was purified by preparative reversed-phase column chromatography (C-18, water/MeCN+1‰ TFA, 99:1 to 45:55, 30 min, 20 mL/min).

ESI-MS m/z for $C_{26}H_{27}N_6O_2S$ found 487.6 [M+H]$^+$; $R_t$=0.86 min; $^1$H NMR (700 MHz, D$_2$O, 333 K) δ 9.29-9.25 (m, 1H), 8.33-8.28 (m, 1H), 8.15-8.12 (m, 1H), 8.08-8.04 (m, 1H), 5.38-5.24 (m, 2H), 3.73-3.60 (m, 2H), 3.43-3.19 (m, 3H), 2.99 (s, 2H), 2.95 (s, 3H), 2.19-2.00 (m, 2H), 1.57 (s, 3H), 1.40 (s, 3H).

Example 27

Synthesis of N-(6-cyano-4-(2-((6,6-dimethyl-2,4-dioxo-3-azabicyclo[3.1.0]hexan-3-yl)methyl)thieno[3,2-b]pyridin-7-yl)-2-methylpyridin-3-yl)azetidine-2-carboxamide 2,2,2-trifluoroacetate (27)

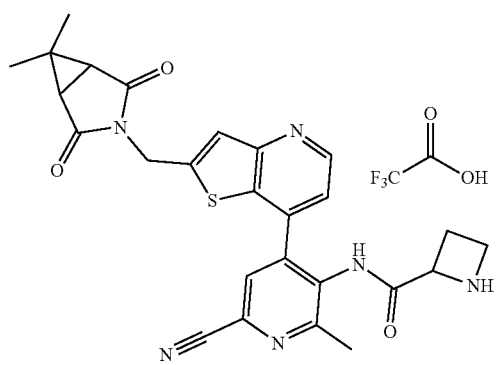

Step 1

Synthesis of 5-amino-4-bromo-6-methylpicolinonitrile (27a)

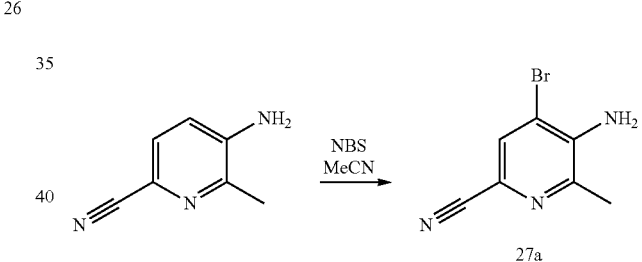

To the solution of 5-amino-6-methylpicolinonitrile (0.25 g; 1.88 mmol) in MeCN (10 mL) NBS (368 mg; 2.06 mmol) was added portionwise at 0° C. and then the reaction mixture was stirred at this temperature for 1 hour, then at room temperature for 1 hour. The reaction progress was monitored by TLC and LC-MS. When analyses indicated completion of the reaction, the reaction mixture was diluted with MeCN and filtered through a pad of Celite. The filtrate was concentrated in vacuo and the residue was dissolved in water/ AcOEt. The layers were separated and the aqueous one was extracted with AcOEt (3×). The combined organic solutions were washed with 10% Na$_2$S$_2$O$_3$ and brine, dried over anhydrous Na$_2$SO$_4$, filtered and concentrated in vacuo and the crude product was purified by flash column chromatography on silica (hexane 100%, 2 minutes and then hexane/ AcOEt 100:0 to 0:100, v/v, 20 minutes). Compound 27a was obtained in 68% yield (271 mg; 1.28 mmol).

ESI-MS m/z for $C_7H_7BrN_3$ found 212.0/214.0 [M+H]$^+$; $R_t$=0.79 min

Step 2

Synthesis of tert-butyl 2-((4-bromo-6-cyano-2-methylpyridin-3-yl)carbamoyl)azetidine-1-carboxylate (27b)

Step 3

Synthesis of tert-butyl 2-((6-cyano-4-(2-((6,6-dimethyl-2,4-dioxo-3-azabicyclo[3.1.0]hexan-3-yl)methyl)thieno[3,2-b]pyridin-7-yl)-2-methylpyridin-3-yl)carbamoyl)azetidine-1-carboxylate (27c)

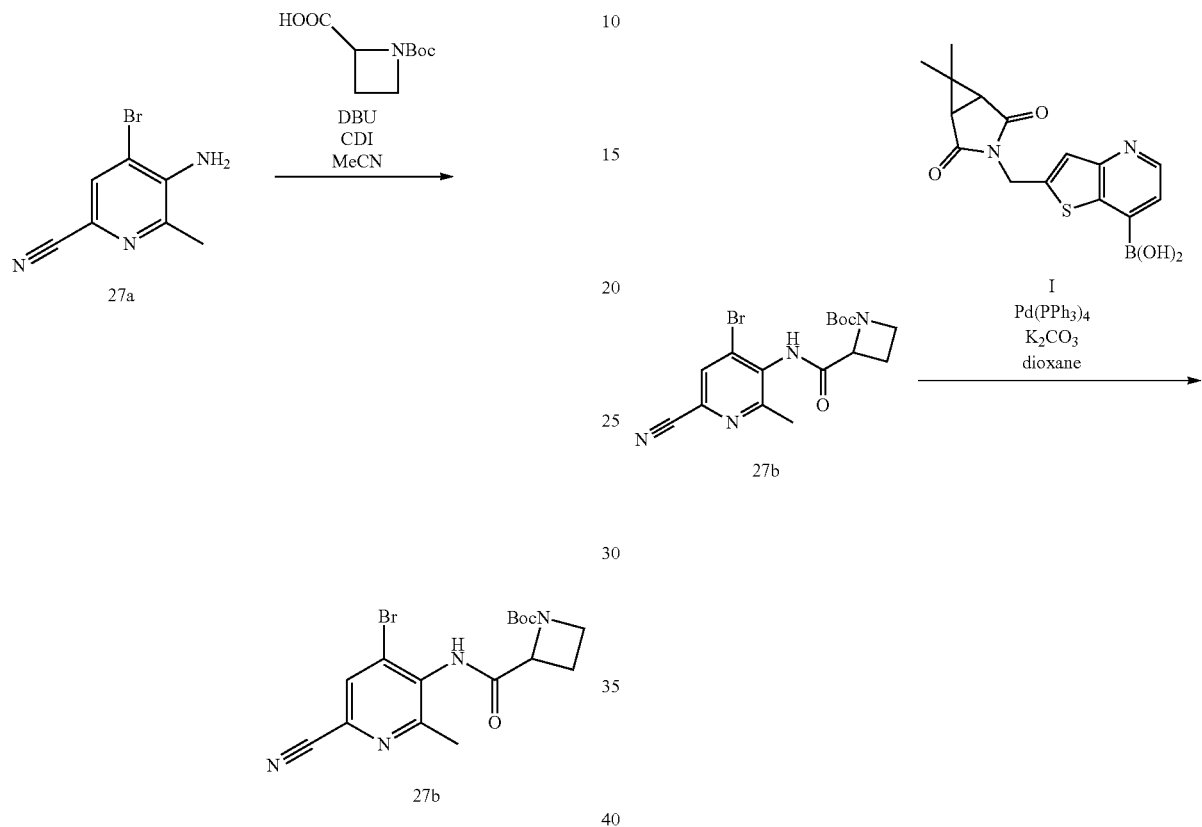

To the solution of 27a (79 mg; 0.37 mmol) in MeCN (0.8 mL) DBU (61 µL; 0.41 mmol) was added and stirred at room temperature for 1 hour. To the solution of 1-(tert-butoxycarbonyl)azetidine-2-carboxylic acid (75 mg; 0.37 mmol) in MeCN (0.8 mL) CDI (67 mg; 0.41 mmol) was added and stirred at room temperature for 1 hour, then added to the solution of substrate with DBU and stirred at 45° C. overnight. The reaction progress was monitored by LC-MS. When analysis indicated completion of the reaction, MeCN was evaporated to 30% vol. The residue was taken into AcOEt/water. An organic layer was washed with water and brine, dried over anhydrous MgSO$_4$, filtered and concentrated in vacuo and the crude product was purified by flash column chromatography on silica (hexane/AcOEt, 100:0 to 80:20, v/v, 15 minutes). Compound 27b was obtained in 76% yield (110 mg; 0.28 mmol).

ESI-MS m/z for $C_{16}H_{20}BrN_4O_3$ found 395.0/397.0 [M+H]$^+$; R$_t$=1.21 min The title compound (27c) was obtained from 27b (55 mg; 0.14 mmol) and from boronic acid I (60 mg; 0.18 mmol) according to the General Procedure Va and after standard work-up all the crude product mixture was taken to the next step.

ESI-MS m/z for $C_{31}H_{33}N_6O_5S$ found 601.1 [M+H]$^+$; R$_t$=1.36 min

Step 4

Synthesis of N-(6-cyano-4-(2-((6,6-dimethyl-2,4-dioxo-3-azabicyclo[3.1.0]hexan-3-yl)methyl)thieno[3,2-b]pyridin-7-yl)-2-methylpyridin-3-yl)azetidine-2-carboxamide 2,2,2-trifluoroacetate (27)

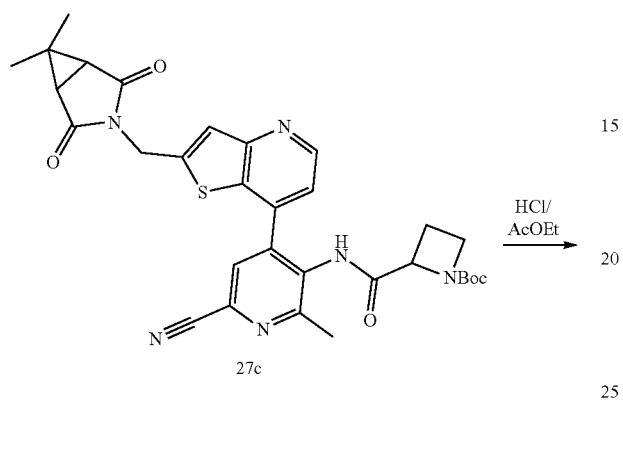

The title compound (27) was obtained as a TFA salt from 27c (the crude reaction mixture) according to the General Procedure IVa in 11% yield (per two steps) (9 mg; 0.015 mmol). The crude product was purified by preparative reversed-phase column chromatography (C-18, water/MeCN+1 ‰ TFA, 99:1 to 45:55, 30 min, 20 mL/min).

ESI-MS m/z for $C_{26}H_{25}N_6O_3S$ found 501.7 [M+H]$^+$; $R_t$=0.81 min; $^1$H NMR (700 MHz, D$_2$O, 333 K) 69.17-9.13 (m, 1H), 8.39-8.35 (m, 1H), 8.00-7.97 (m, 1H), 7.85-7.82 (m, 1H), 5.44-5.38 (m, 1H), 5.27 (s, 2H), 4.43-4.32 (m, 1H), 4.08-4.00 (m, 1H), 2.98 (s, 2H), 2.95 (s, 4H), 2.01-1.90 (m, 1H), 1.57 (s, 3H), 1.40 (s, 3H).

Example 28

Synthesis of N-(2-(2-((6,6-dimethyl-2,4-dioxo-3-azabicyclo[3.1.0]hexan-3-yl)methyl)thieno[3,2-b]pyridin-7-yl)-4-methyl-6-(trifluoromethyl)pyridin-3-yl)azetidine-3-carboxamide 2,2,2-trifluoroacetate (28)

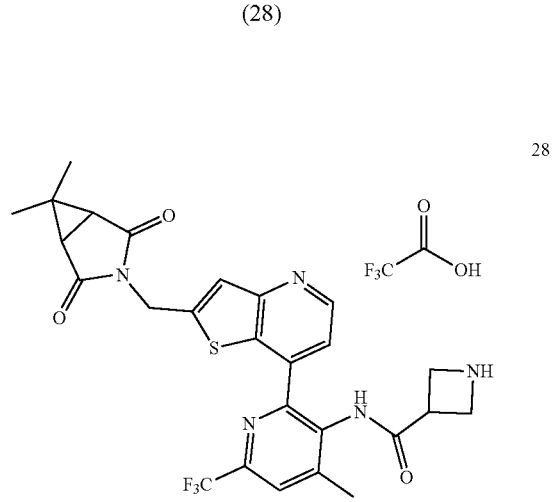

Step 1

Synthesis of 2-bromo-4-methyl-6-(trifluoromethyl)pyridin-3-amine (28a)

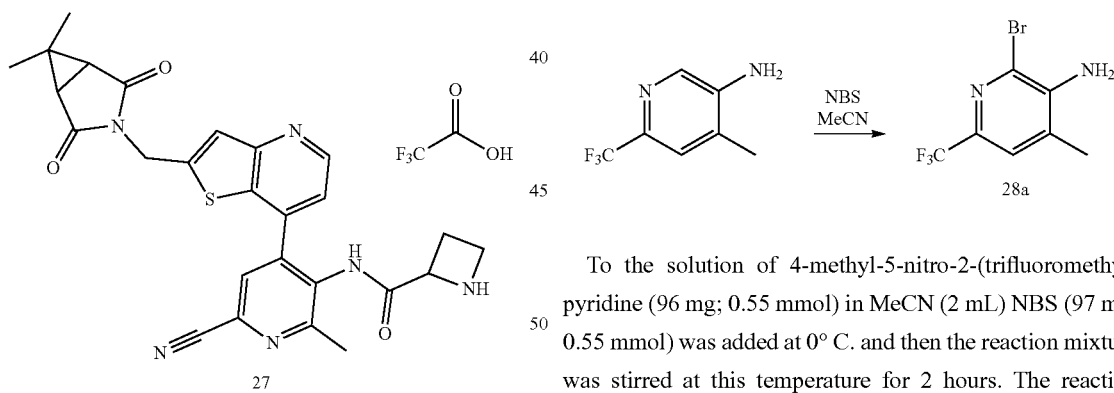

To the solution of 4-methyl-5-nitro-2-(trifluoromethyl)pyridine (96 mg; 0.55 mmol) in MeCN (2 mL) NBS (97 mg; 0.55 mmol) was added at 0° C. and then the reaction mixture was stirred at this temperature for 2 hours. The reaction progress was monitored by TLC and LC-MS. When analyses indicated completion of the reaction, to this mixture 10% Na$_2$S$_2$O$_3$ was added followed by AcOEt. The layers were separated and an organic layer was washed with 10% Na$_2$S$_2$O$_3$, brine, dried over anhydrous Na$_2$SO$_4$, filtered and concentrated in vacuo and the crude product was used to the next step without additional purification. Compound 28a was obtained in 84% yield (117 mg; 0.46 mmol).

ESI-MS m/z for $C_7H_7BrF_3N_2$ found 255.0/257.0 [M+H]$^+$; $R_t$=1.23 min

Step 2

Synthesis of tert-butyl 3-((2-bromo-4-methyl-6-(trifluoromethyl)pyridin-3-yl)carbamoyl)azetidine-1-carboxylate (28b)

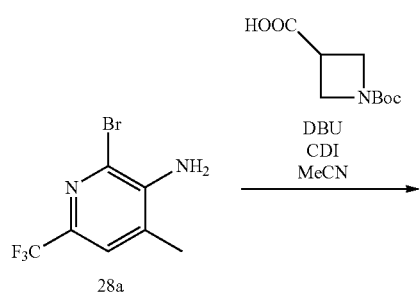

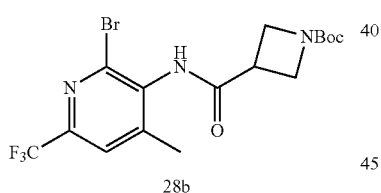

To the solution of 28ab (74 mg; 0.29 mmol) in MeCN (1 mL) DBU (48 µL; 0.32 mmol) was added and stirred at room temperature for 1 hour. To the solution of 1-(tert-butoxycarbonyl)azetidine-3-carboxylic acid (59 mg; 0.29 mmol) in MeCN (1 mL) CDI (52 mg; 0.32 mmol) was added and stirred at room temperature for 1 hour, then added to the solution of substrate with DBU and stirred at 45° C. overnight. The reaction progress was monitored by LC-MS. When analysis indicated completion of the reaction, MeCN was evaporated to 30% vol. The residue was taken into AcOEt/water. An organic layer was washed with water and brine, dried over anhydrous MgSO$_4$, filtered and concentrated in vacuo and the crude product was purified by flash column chromatography on silica (hexane/AcOEt, 100:0 to 80:20, v/v, 15 minutes). Compound 28b was obtained in 24% yield (31 mg; 0.07 mmol).

ESI-MS m/z for C$_{16}$H$_{20}$BrF$_3$N$_3$O$_3$ found 438.0/440.0 [M+H]$^+$; R$_t$=1.40 min

Step 3

Synthesis of tert-butyl 3-((2-(2-((6,6-dimethyl-2,4-dioxo-3-azabicyclo[3.1.0]hexan-3-yl)methyl)thieno[3,2-b]pyridin-7-yl)-4-methyl-6-(trifluoromethyl)pyridin-3-yl)carbamoyl)azetidine-1-carboxylate (28c)

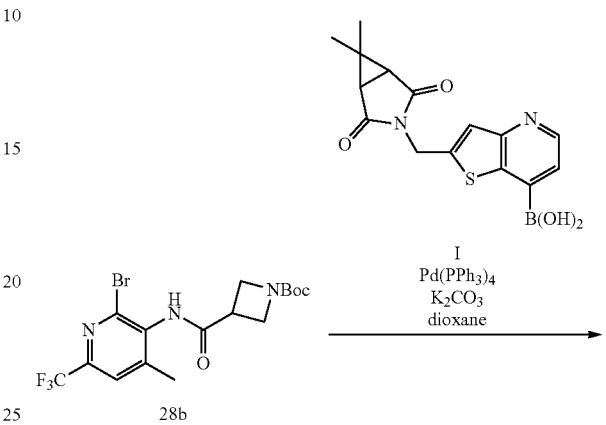

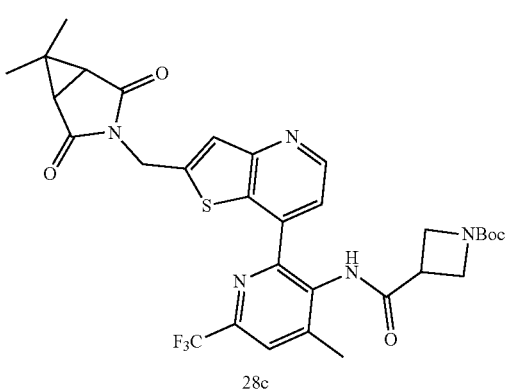

The title compound (28c) was obtained from 28b (31 mg; 0.07 mmol) and from boronic acid 1 (30 mg; 0.09 mmol) according to the General Procedure Va and after standard work-up all the crude product mixture was taken to the next step.

ESI-MS m/z for C$_{31}$H$_{32}$F$_3$N$_5$O$_5$S found 644.1 [M+H]$^+$; R$_t$=1.47 min

Step 5

Synthesis of N-(2-(2-((6,6-dimethyl-2,4-dioxo-3-azabicyclo[3.1.0]hexan-3-yl)methyl)thieno[3,2-b]pyridin-7-yl)-4-methyl-6-(trifluoromethyl)pyridin-3-yl)azetidine-3-carboxamide 2,2,2-trifluoroacetate (28)

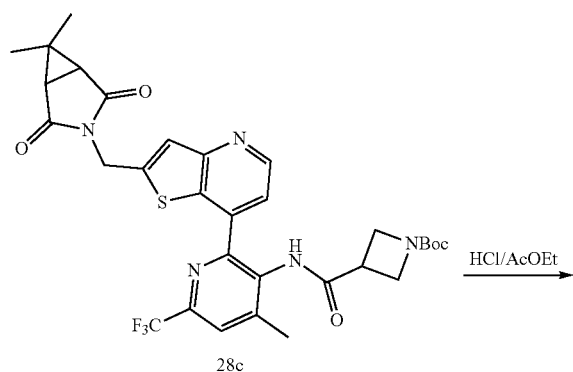

The title compound (28) was obtained as a TFA salt from 28c (the crude reaction mixture) according to the General Procedure IVa in 11% yield (per two steps) (5 mg; 0.008 mmol). The crude product was purified by preparative reversed-phase column chromatography (C-18, water/MeCN+1‰ TFA, 99:1 to 45:55, 30 min, 20 mL/min).

ESI-MS m/z for $C_{26}H_{25}F_3N_5O_3S$ found 544.6 [M+H]+; $R_t$=0.99 min; $^1$H NMR (700 MHz, $D_2O$, 333 K) δ 9.18-9.13 (m, 1H), 8.45-8.40 (m, 1H), 8.17-8.14 (m, 1H), 8.08-8.04 (m, 1H), 5.36-5.27 (m, 2H), 4.57-4.49 (m, 2H), 4.26-4.13 (m, 3H), 3.02-2.95 (m, 2H), 2.81 (s, 3H), 1.57 (s, 3H), 1.40 (s, 3H).

Example 29

Synthesis of N-(6-chloro-4-(2-((6,6-dimethyl-2,4-dioxo-3-azabicyclo[3.1.0]hexan-3-yl)methyl)thieno[3,2-b]pyridin-7-yl)-2-methylpyridin-3-yl)azetidine-3-carboxamide 2,2,2-trifluoroacetate (29)

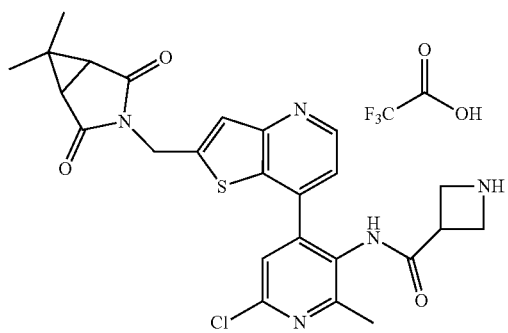

The title compound (29) was obtained as a TFA salt in 2% overall yield in a similar way to Example 27 with the exception that, the synthesis was started from the second step with commercially available 4-bromo-6-chloro-2-methylpyridin-3-amine and 1-(tert-butoxycarbonyl)azetidine-3-carboxylic acid instead of 1-(tert-butoxycarbonyl)azetidine-2-carboxylic acid and in the last step of the synthesis the crude product was purified by preparative reversed-phase column chromatography (C-18, water/MeCN+1‰ TFA, 99:1 to 45:55, 30 min, 20 mL/min).

ESI-MS m/z for $C_{25}H_{25}ClN_5O_3S$ found 510.0/512.0 [M+H]+; $R_t$=0.92 min; $^1$H NMR (700 MHz, $D_2O$, 333 K) δ 9.13-9.08 (m, 1H), 8.00-7.96 (m, 1H), 7.90 (s, 1H), 7.81-7.76 (m, 1H), 5.27 (s, 2H), 4.45-4.35 (m, 2H), 4.09-3.97 (m, 3H), 3.02-2.95 (m, 2H), 2.84 (s, 3H), 1.57 (s, 3H), 1.40 (s, 3H).

Example 30

Synthesis of N-(6-cyano-4-(2-((6,6-dimethyl-2,4-dioxo-3-azabicyclo[3.1.0]hexan-3-yl)methyl)thieno[3,2-b]pyridin-7-yl)-2-methylpyridin-3-yl)azetidine-3-carboxamide 2,2,2-trifluoroacetate (30)

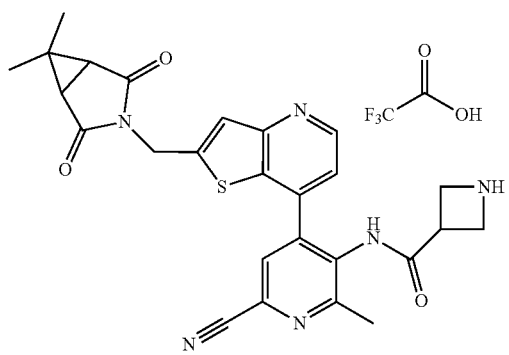

The title compound (30) was obtained as a TFA salt in 3% overall yield in a similar way to Example 27 with the

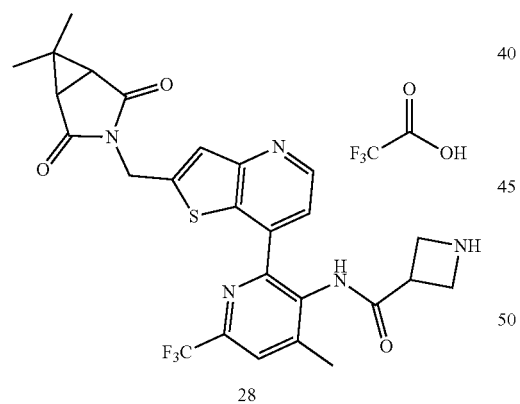

exception that, in the second step of the synthesis, 1-(tert-butoxycarbonyl)azetidine-3-carboxylic acid was used instead of 1-(tert-butoxycarbonyl)azetidine-2-carboxylic acid and in the last step of the synthesis the crude product was purified by preparative reversed-phase column chromatography (C-18, water/MeCN+1‰TFA, 95:5 to 50:50, 30 min, 20 mL/min).

ESI-MS m/z for $C_{26}H_{25}N_6O_3S$ found 501.8 [M+H]$^+$; $R_t$=0.83 min; $^1$H NMR (700 MHz, D$_2$O, 333 K) δ 9.13-9.11 (m, 1H), 8.38-8.35 (m, 1H), 8.02-7.98 (m, 1H), 7.84-7.79 (m, 1H), 5.32-5.23 (m, 2H), 4.46-4.37 (m, 2H), 4.09-4.00 (m, 3H), 2.99 (s, 2H), 2.94 (s, 3H), 1.57 (s, 3H), 1.40 (s, 3H).

Example 31

Synthesis of(S)-4-(5-chloro-3-methyl-2-(piperidin-3-yloxy)phenyl)thieno[2,3-b]pyridine 2,2,2-trifluoroacetate (31)

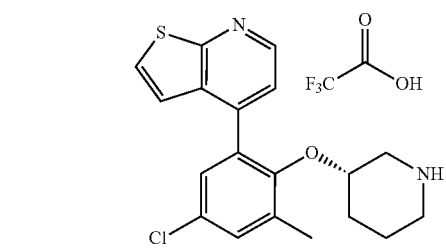

Step 1

Synthesis of tert-butyl (S)-3-(2-bromo-4-chloro-6-methylphenoxy)piperidine-1-carboxylate (31a)

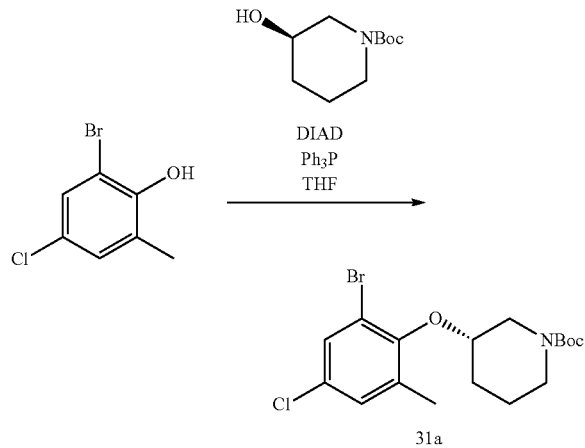

To a cooled to −10° C. solution of 2-bromo-4-chloro-6-methylphenol (9.9 g; 47.7 mmol), tert-butyl (R)-3-hydroxypiperidine-1-carboxylate (9.9 g; 49.2 mmol) and Ph$_3$P (14 g; 53.6 mmol) in THF (250 ml) DIAD (10.5 mL; 53.6 mmol) was slowly added. The resulting mixture was stirred at room temperature overnight. The formed solid was filtered and washed with hexane (3×), then purified by silica-gel column chromatography (hexane/AcOEt, 100:1 to 15:1, v/v). Compound 31a was obtained in 46% yield (8.9 g; 22.1 mmol).

ESI-MS m/z for $C_{17}H_{23}BrClNO_3Na$ found 427.8/429.8 [M+Na]$^+$; $R_t$=2.08 min; $^1$H NMR (700 MHz, CDCl$_3$) δ 7.45-7.35 (m, 1H), 7.17-7.05 (m, 1H), 4.16-4.01 (m, 2H), 3.17-2.89 (m, 2H), 2.30 (s, 3H), 2.17-2.04 (m, 1H), 1.87-1.80 (m, 1H), 1.79-1.72 (m, 1H), 1.52-1.48 (m, 1H), 1.45 (s, 9H), 1.33-1.26 (m, 1H).

Step 2

Synthesis of tert-butyl (S)-3-(4-chloro-2-methyl-6-(4,4,5,5-tetramethyl-1,3,2-dioxaborolan-2-yl)phenoxy)piperidine-1-carboxylate (31b)

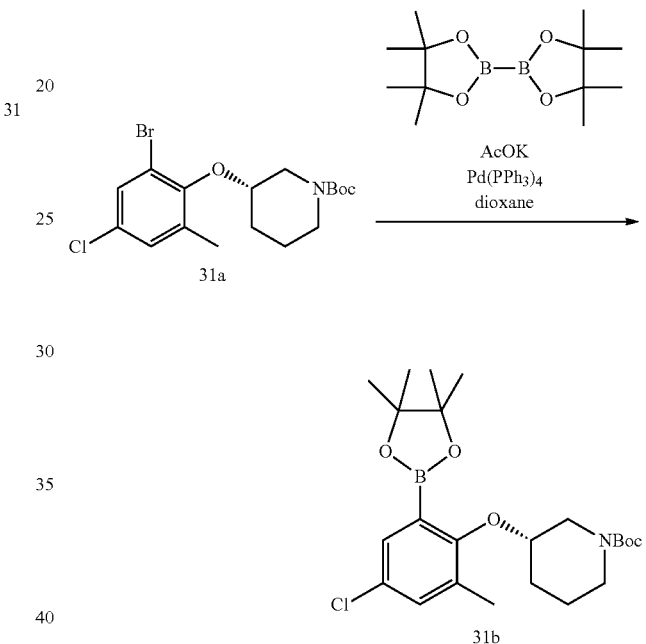

To the solution of 31a (5.00 g; 12.35 mmol) in dry dioxane (190 mL) bis(pinacolato)diboron (6.27 g; 24.70 mmol) and AcOK (3.60 g; 37.05 mmol) were added. The reaction mixture was intensively flushed with Ar. Then to this mixture Pd(PPh$_3$)$_4$ (0.71 g; 0.62 mmol) was added in one portion and the reaction mixture was flushed with Ar. The mixture was stirred overnight at 100° C. in a sealed tube. The reaction progress was monitored by LC-MS. Then another portion of Pd(PPh$_3$)$_4$ (0.30 g; 0.26 mmol), AcOK (2.42 g; 24.91 mmol) and bis(pinacolato)diboron (6.27 g; 24.70 mmol) was added and this mixture was stirred at 110° C. for 2 days. When analysis indicated completion of the reaction, dioxane was removed and the residue was dissolved in AcOEt/water and filtered through a pad of the Celite. The filtrate was separated and the aqueous layer was extracted with AcOEt. The combined organic layers were dried over anhydrous MgSO$_4$, filtered and concentrated in vacuo. The crude product was then purified by silica-gel column chromatography (hexane/AcOEt, 100:1 to 15:1, v/v). Compound 31b was obtained in 90% yield (5.00 g; 11.08 mmol).

ESI-MS m/z for $C_{23}H_{35}BClNO_5Na$ found 474.0/476.0 [M+Na]$^+$; $R_t$=2.24 min

Step 3

Synthesis of tert-butyl (S)-3-(4-chloro-2-methyl-6-(thieno[2,3-b]pyridin-4-yl)phenoxy)piperidine-1-carboxylate (31c)

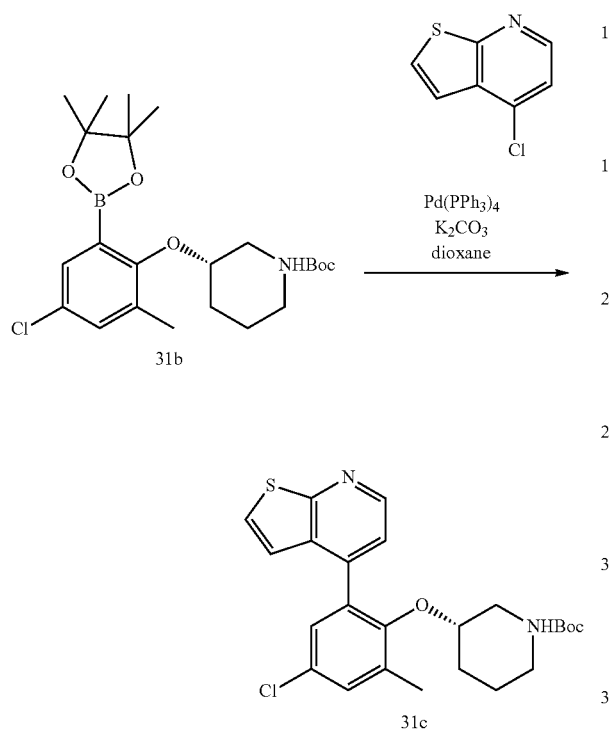

The title compound (31c) was obtained from 31b (257 mg; 0.57 mmol) and from 4-chlorothieno[2,3-b]pyridine (96 mg; 0.57 mmol) according to the General Procedure Va and after standard work-up all the crude product mixture was taken to the next step.

ESI-MS m/z for $C_{24}H_{28}ClN_2O_3S$ found 459.0/461.0 [M+H]$^+$; $R_t$=2.13 min

Step 4

Synthesis of (S)-4-(5-chloro-3-methyl-2-(piperidin-3-yloxy)phenyl)thieno[2,3-b]pyridine 2,2,2-trifluoroacetate (31)

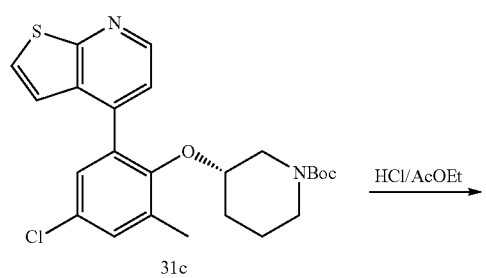

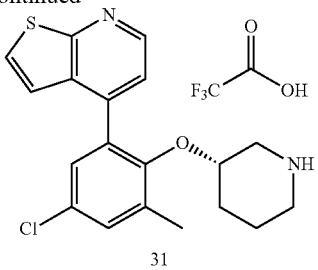

The title compound (31) was obtained as a TFA salt from 31c (the crude reaction mixture) according to the General Procedure IVa in 16% yield (per two steps) (42 mg; 0.09 mmol). The crude product was purified by preparative reversed-phase column chromatography (C-18, water/MeCN+1‰ TFA, 95:5 to 45:55, 30 min, 20 mL/min).

ESI-MS m/z for $C_{19}H_{20}ClN_2OS$ found 359.0/361.0 [M+H]$^+$; $R_t$=1.03 min; $^1$H NMR (700 MHz, DMSO-d$_6$+D$_2$O, 348 K) δ 8.64-8.61 (m, 1H), 7.84-7.81 (m, 1H), 7.45-7.40 (m, 2H), 7.26-7.20 (m, 1H), 7.11-7.06 (m, 1H), 3.66-3.59 (m, 1H), 2.91-2.79 (m, 2H), 2.75-2.68 (m, 1H), 2.55-2.52 (m, 1H), 2.35 (s, 3H), 1.59-1.49 (m, 1H), 1.45-1.34 (m, 1H), 1.24-1.08 (m, 2H).

Example 32

Synthesis of 2-(3,3-difluoroazetidin-1-yl)-N-(4-(2-((6,6-dimethyl-2,4-dioxo-3-azabicyclo[3.1.0]hexan-3-yl)methyl)thieno[3,2-b]pyridin-7-yl)-2-methyl-6-(trifluoromethyl)pyridin-3-yl)acetamide 2,2,2-trifluoroacetate (32)

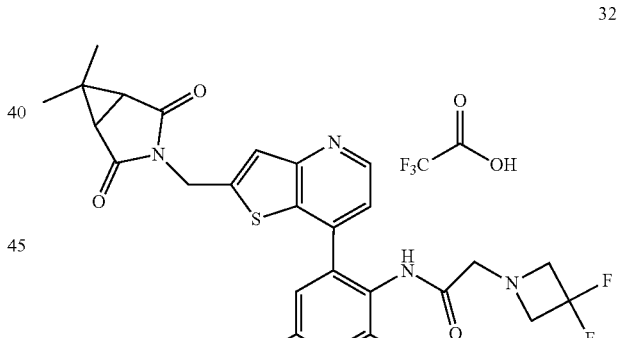

Step 1

Synthesis of 4-bromo-2-methyl-6-(trifluoromethyl)pyridin-3-amine (32a)

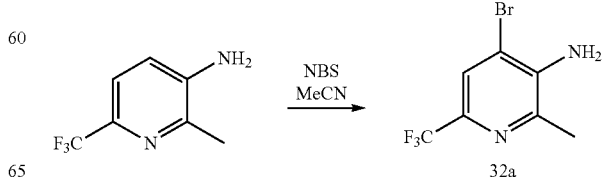

283

To the solution of 2-methyl-6-(trifluoromethyl)pyridin-3-amine (1.3 g; 7.38 mmol) in MeCN (70 mL) NBS (1.37 g; 7.71 mmol) was added portionwise at 0° C. and then the reaction mixture was stirred at this temperature for 1 hour. Then the cooling bath was removed and the mixture was stirred at room temperature for 5 hours. The reaction progress was monitored by LC-MS. When analysis indicated completion of the reaction, to this mixture 5% $Na_2S_2O_3$ (10 mL) was added and stirred for 10 minutes. The expected product was extracted with AcOEt (2×). The combined organic layers were dried over anhydrous $MgSO_4$, filtered and concentrated in vacuo and the crude product was used to the next step without additional purification. Compound 32a was obtained as a light orange oil in 96% yield (1.8 g; 7.09 mmol).

ESI-MS m/z for $C_7H_7BrF_3N_2$ found 254.8/256.8 $[M+H]^+$; $R_t$=1.27 min

Step 2

Synthesis of 2-bromo-N-(4-bromo-2-methyl-6-(trifluoromethyl)pyridin-3-yl)acetamide (32b)

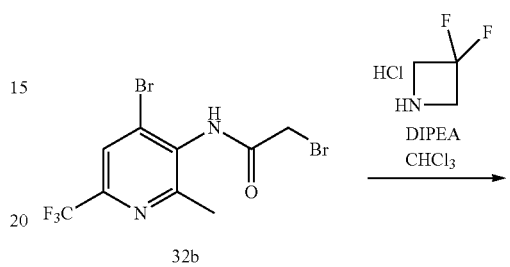

To the solution of 32a (155 mg; 0.61 mmol) and $Et_3N$ (0.17 mL; 1.22 mmol) in DCM (2 mL) bromoacetyl bromide (107 μL; 1.22 mmol) was added dropwise at 0° C. and then the reaction mixture was stirred at room temperature for 5 hours. The reaction progress was monitored by TLC and LC-MS. When analyses indicated completion of the reaction, the mixture was evaporated to dryness and the crude product was purified by flash column chromatography on silica (hexane/AcOEt, 100:0 to 80:20, 15 minutes, v/v). Compound 32b was obtained in 87% yield (200 mg; 0.53 mmol).

ESI-MS m/z for $C_9H_8Br_2F_3N_2O$ found 374.7/376.7/378.6 $[M+H]^+$; $R_t$=1.20 min

284

Step 3

Synthesis of N-(4-bromo-2-methyl-6-(trifluoromethyl)pyridin-3-yl)-2-(3,3-difluoroazetidin-1-yl)acetamide (32c)

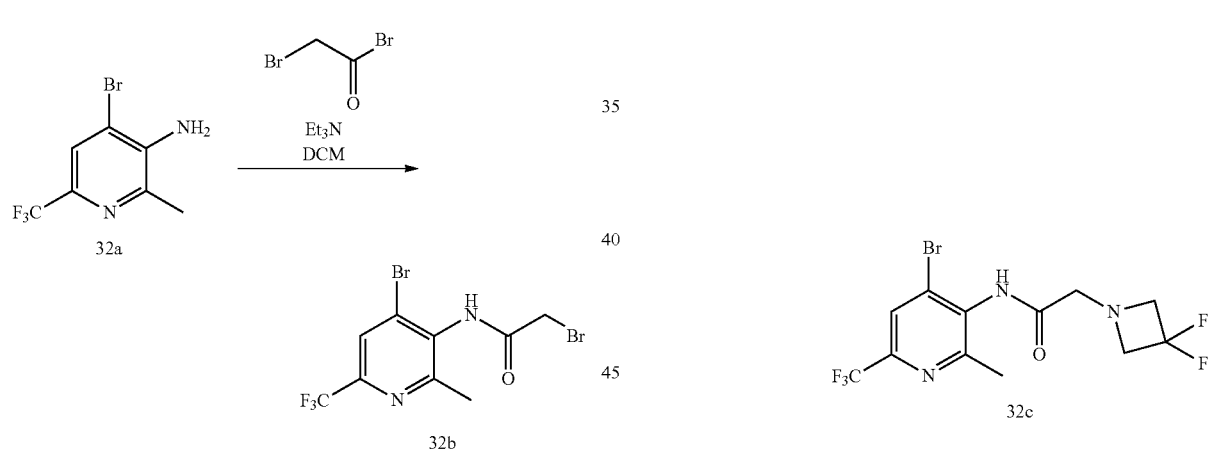

The solution of 32b (51 mg; 0.14 mmol), 3,3-difluoroazetidine hydrochloride (26 mg; 0.20 mmol) and DIPEA (0.06 mL; 0.34 mmol) in $CHCl_3$ (1 mL) was stirred at room temperature overnight. The reaction progress was monitored by TLC and LC-MS. When analyses indicated completion of the reaction, the mixture was diluted with DCM/water. The layers were separated and an organic one was washed with water, brine, dried over anhydrous $MgSO_4$, filtered and concentrated in vacuo and the crude product was used to the next step without additional purification. Compound 32c was obtained in 99% yield (54 mg; 0.14 mmol).

ESI-MS m/z for $C_{12}H_{12}BrF_5N_3O$ found 388.0/390.0 $[M+H]^+$; $R_t$=1.13 min Step 4

Synthesis of 2-(3,3-difluoroazetidin-1-yl)-N-(4-(2-((6,6-dimethyl-2,4-dioxo-3-azabicyclo[3.1.0]hexan-3-yl)methyl)thieno[3,2-b]pyridin-7-yl)-2-methyl-6-(trifluoromethyl)pyridin-3-yl)acetamide 2,2,2-trifluoroacetate (32)

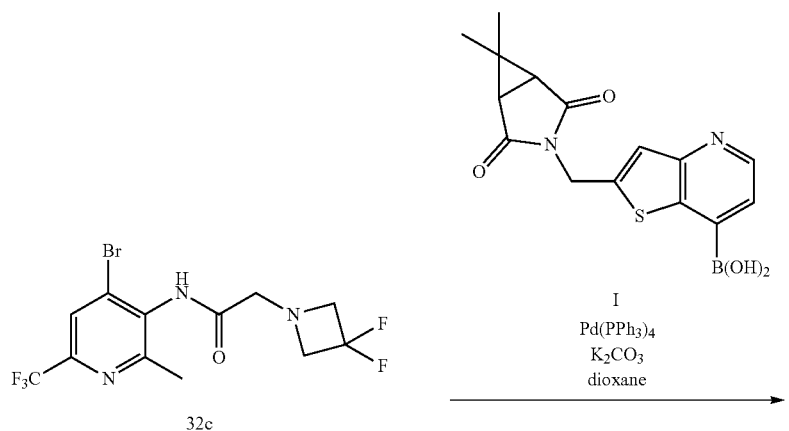

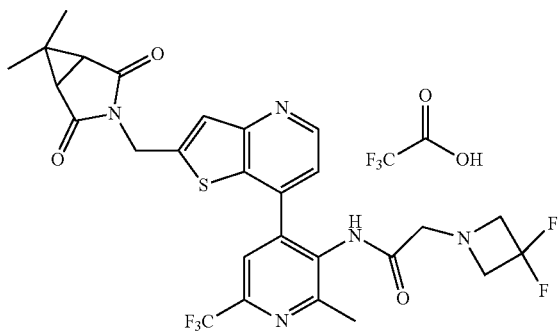

The title compound (32) was obtained as a TFA salt from 32c (54 mg; 0.14 mmol) and from boronic acid I (71 mg; 0.21 mmol) according to the General Procedure Va in 24% yield (24 mg; 0.034 mmol). The crude product was purified by preparative reversed-phase column chromatography (C-18, water/MeCN+1‰ TFA, 98:2 to 30:70, 30 min, 20 mL/min).

ESI-MS m/z for $C_{27}H_{25}F_5N_5O_3S$ found 594.8 [M+H]$^+$; R$_t$=1.37 min; $^1$H NMR (700 MHz, DMSO-d$_6$+D$_2$O, 348 K) δ 8.73-8.69 (m, 1H), 7.84-7.79 (m, 1H), 7.53-7.48 (m, 1H), 7.27-7.23 (m, 1H), 4.78-4.67 (m, 2H), 4.02-3.88 (m, 4H), 3.66 (s, 2H), 2.56-2.54 (m, 3H), 2.52 (s, 2H), 1.18 (s, 3H), 1.04 (s, 3H); $^{19}$F NMR (659 MHz, DMSO-d$_6$) δ −66.33 (s), −74.27 (s).

Example 33

Synthesis of N-(4-(2-((6,6-dimethyl-2,4-dioxo-3-azabicyclo[3.1.0]hexan-3-yl)methyl)thieno[3,2-b]pyridin-7-yl)-2-ethyl-6-(trifluoromethyl)pyridin-3-yl)piperidine-4-carboxamide 2,2,2-trifluoroacetate (33)

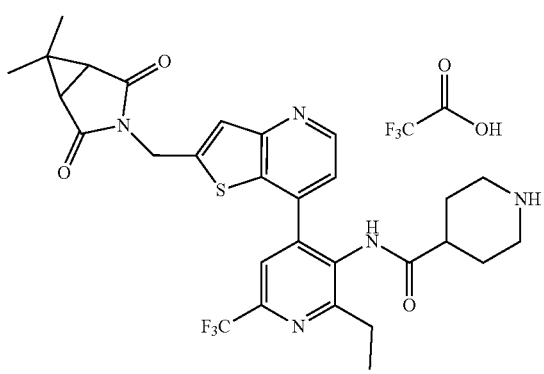

Step 1

Synthesis of 6-(trifluoromethyl)-2-vinylpyridin-3-amine (33a)

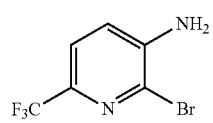

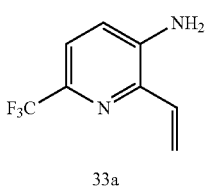

The title compound (33a) was obtained from 2-bromo-6-(trifluoromethyl)pyridin-3-amine (0.58 g; 2.41 mmol) and from potassium vinyltrifluoroborate (387 mg; 2.89 mmol) according to the General Procedure Va in 99% yield (449 mg; 2.39 mmol).

ESI-MS m/z for $C_8H_8F_3N_2$ found 189.1 [M+H]$^+$; $R_t$=1.15 min

Step 2

Synthesis of 2-ethyl-6-(trifluoromethyl)pyridin-3-amine (33b)

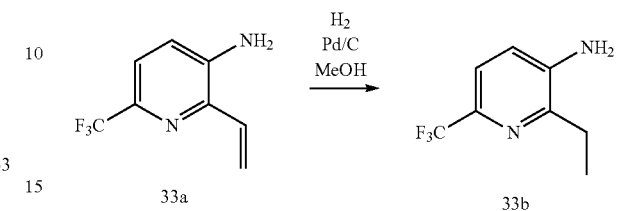

To the solution of 33a (449 mg; 2.39 mmol) in MeOH (12 mL) Pd/C (10 mol %; cat.) was added and the reaction mixture was conducted under hydrogen atmosphere at room temperature overnight. The reaction progress was monitored by LC-MS. When analysis indicated completion of the reaction, Pd/C was filtered off through a Celite pad and the solvents were concentrated in vacuo. The crude product was purified by flash column chromatography on silica (hexane/AcOEt, 100:0 to 80:20, 15 minutes, v/v). Compound 33b was obtained in 40% yield (180 mg; 0.95 mmol).

ESI-MS m/z for $C_8H_{10}F_3N_2$ found 191.0 [M+H]$^+$; $R_t$=1.12 min

Step 3

Synthesis of 4-bromo-2-ethyl-6-(trifluoromethyl)pyridin-3-amine (33c)

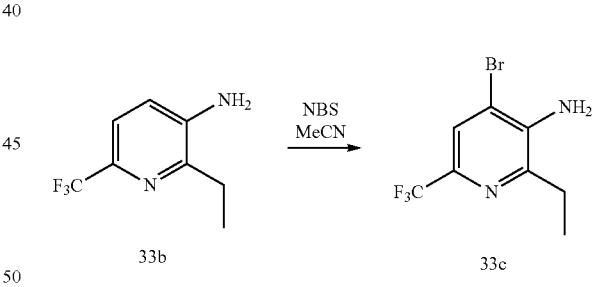

To the solution of 33b (180 mg; 0.95 mmol) in MeCN (4 mL) NBS (0.17 g; 0.95 mmol) was added portionwise at 0° C. and then the reaction mixture was stirred at this temperature for 1 hour. Then the cooling bath was removed and the mixture was stirred at room temperature overnight. The reaction progress was monitored by LC-MS. When analysis indicated completion of the reaction, to this mixture 5% Na$_2$S$_2$O$_3$ was added and stirred for 10 minutes. The expected product was extracted with AcOEt (2×). The combined organic layers were dried over anhydrous MgSO$_4$, filtered and concentrated in vacuo and the crude product was used to the next step without additional purification. Compound 33c was obtained in 98% yield (0.25 g; 0.93 mmol).

ESI-MS m/z for $C_8H_9BrF_3N_2$ found 269.0/271.0 [M+H]$^+$; $R_t$=1.48 min

Step 4

Synthesis of tert-butyl 4-((4-bromo-2-ethyl-6-(trifluoromethyl)pyridin-3-yl)carbamoyl)piperidine-1-carboxylate (33d)

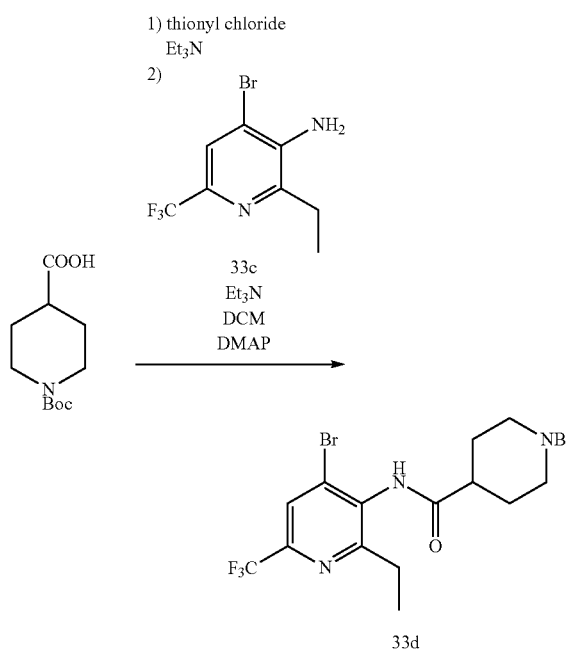

The title compound (33a) was obtained from 1-(tert-butoxycarbonyl)piperidine-4-carboxylic acid (128 mg; 0.56 mmol) and from 33c (100 mg; 0.37 mmol) according to the General Procedure II in 32% yield (58 mg; 0.12 mmol).

ESI-MS m/z for $C_{19}H_{26}BrF_3N_3O_3$ found 480.0/482.0 [M+H]$^+$; $R_t$=1.65 min

Step 5

Synthesis of tert-butyl 4-((4-(2-(((6,6-dimethyl-2,4-dioxo-3-azabicyclo[3.1.0]hexan-3-yl)methyl)thieno[3,2-b]pyridin-7-yl)-2-ethyl-6-(trifluoromethyl)pyridin-3-yl)carbamoyl)piperidine-1-carboxylate (33e)

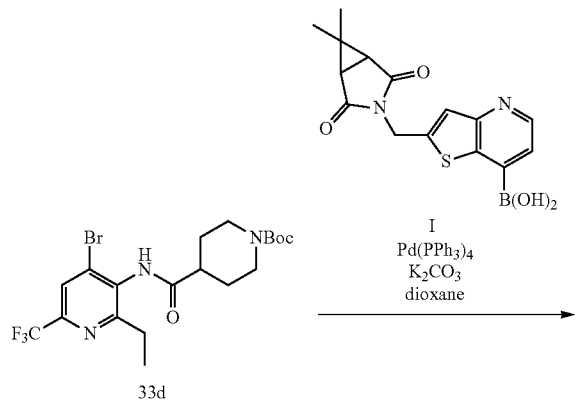

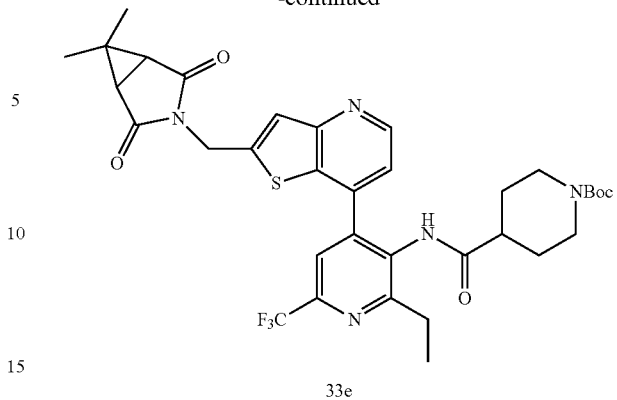

The title compound (33e) was obtained from 33d (42 mg; 0.09 mmol) and from boronic acid I (58 mg; 0.17 mmol) according to the General Procedure Va and after standard work-up all the crude product mixture was taken to the next step.

ESI-MS m/z for $C_{34}H_{39}F_3N_5O_5S$ found 686.1 [M+H]$^+$; $R_t$=1.69 min

Step 6

Synthesis of N-(4-(2-(((6,6-dimethyl-2,4-dioxo-3-azabicyclo[3.1.0]hexan-3-yl)methyl)thieno[3,2-b]pyridin-7-yl)-2-ethyl-6-(trifluoromethyl)pyridin-3-yl)piperidine-4-carboxamide 2,2,2-trifluoroacetate (33)

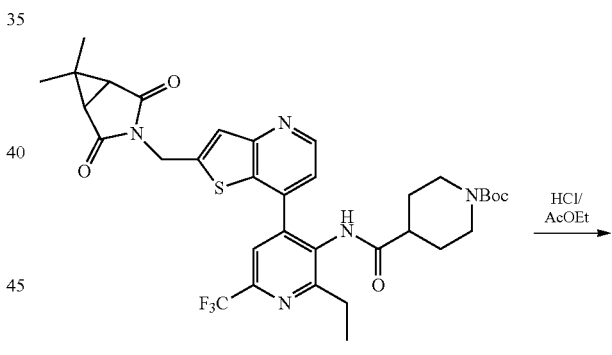

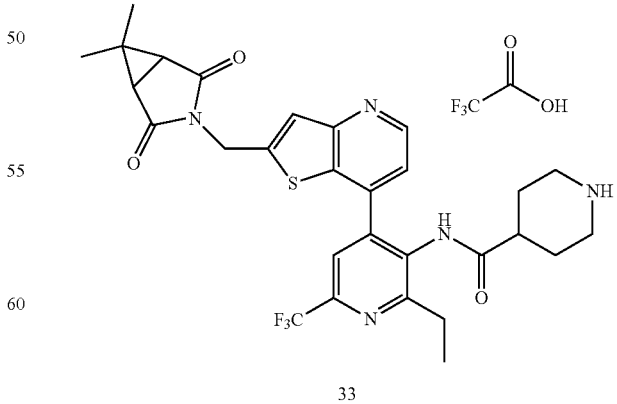

The title compound (33) was obtained as a TFA salt from 33e (the crude reaction mixture) according to the General Procedure IVa in 11% yield (per two steps) (8 mg; 0.01 mmol) with the exception that, to this reaction the molecular sieves were added. The crude product was purified by preparative reversed-phase column chromatography (C-18, water/MeCN+1‰ TFA, 95:5 to 50:50, 30 min, 20 mL/min).

$^{1}$H NMR (700 MHz, D$_{2}$O, 333 K) δ 9.14-9.09 (m, 1H), 8.27-8.23 (m, 1H), 8.00-7.95 (m, 1H), 7.84-7.78 (m, 1H), 5.27 (s, 2H), 4.11-4.03 (m, 1H), 3.61-3.53 (m, 2H), 3.30-3.20 (m, 4H), 2.98 (s, 2H), 2.94-2.90 (m, 1H), 1.99-1.88 (m, 2H), 1.76-1.66 (m, 2H), 1.59-1.55 (m, 5H), 1.40 (s, 3H).

Example 34

Synthesis of (3S)—N-(4-chloro-2-(2-((6,6-dimethyl-2,4-dioxo-3-azabicyclo[3.1.0]hexan-3-yl)methyl)thieno[3,2-b]pyridin-7-yl)-6-methylphenyl)pyrrolidine-3-carboxamide 2,2,2-trifluoroacetate (34)

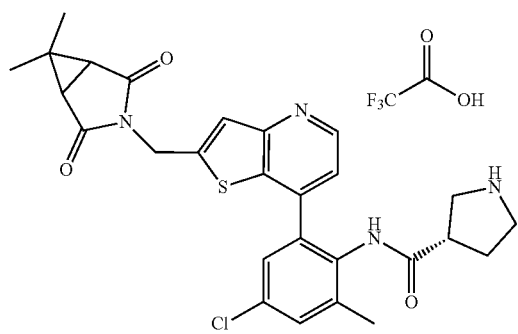

Step 1

Synthesis of tert-butyl (S)-3-((2-bromo-4-chloro-6-methylphenyl)carbamoyl)pyrrolidine-1-carboxylate (34a)

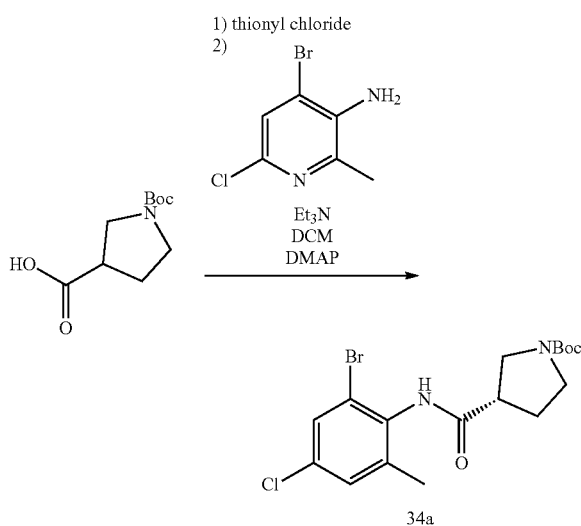

The title compound (34a) was obtained from (S)-1-(tert-butoxycarbonyl)pyrrolidine-3-carboxylic acid (200 mg; 0.87 mmol) and from 2-bromo-4-chloro-6-methylaniline (210 mg; 0.96 mmol) according to the General Procedure 11 in 26% yield (97 mg; 0.23 mmol).

ESI-MS m/z for C$_{17}$H$_{23}$BrClN$_{2}$O$_{3}$ found 417.0/419.0 [M+H]$^{+}$; R$_{t}$=1.56 min

Step 2

Synthesis of (S)-(2-(I-(tert-butoxycarbonyl)pyrrolidine-3-carboxamido)-5-chloro-3-methylphenyl)boronic acid (34b)

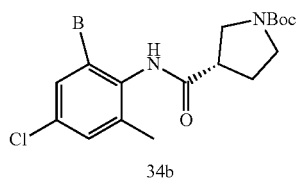

To the solution of 34a (104 mg; 0.25 mmol) in dry dioxane (2 mL) bis(pinacolato)diboron (127 mg; 0.50 mmol) and AcOK (73 mg; 0.75 mmol) were added. The reaction mixture was intensively flushed with Ar. Then to this mixture Pd(PPh$_{3}$)$_{4}$ (14 mg; 0.012 mmol) was added in one portion and the reaction mixture was flushed with Ar. The mixture was stirred overnight at 100° C. in a sealed tube. The reaction progress was monitored by LC-MS. When analysis indicated completion of the reaction, dioxane was removed and the residue was dissolved in AcOEt/water and filtered through a pad of the Celite. The filtrate was separated and the aqueous layer was extracted with AcOEt. The combined organic layers were dried over anhydrous MgSO$_{4}$, filtered and concentrated in vacuo. The crude product was then purified by flash column chromatography on silica (hexane/AcOEt, 100:1 to 15:1, v/v, 15 minutes). Compound 34b was obtained in 99% yield (95 mg; 0.25 mmol).

ESI-MS m/z for C$_{17}$H$_{23}$BClN$_{2}$O$_{5}$ found 381.0/383.0 [M−H]$^{+}$; R$_{t}$=1.07 min

Step 3

Synthesis of tert-butyl (3S)-3-((4-chloro-2-(2-((6,6-dimethyl-2,4-dioxo-3-azabicyclo[3.1.0]hexan-3-yl)methyl)thieno[3,2-b]pyridin-7-yl)-6-methylphenyl)carbamoyl)pyrrolidine-1-carboxylate (34c)

Step 4

Synthesis of (3S)—N-(4-chloro-2-(2-((6,6-dimethyl-2,4-dioxo-3-azabicyclo[3.1.0]hexan-3-yl)methyl)thieno[3,2-b]pyridin-7-yl)-6-methylphenyl)pyrrolidine-3-carboxamide 2,2,2-trifluoroacetate (34)

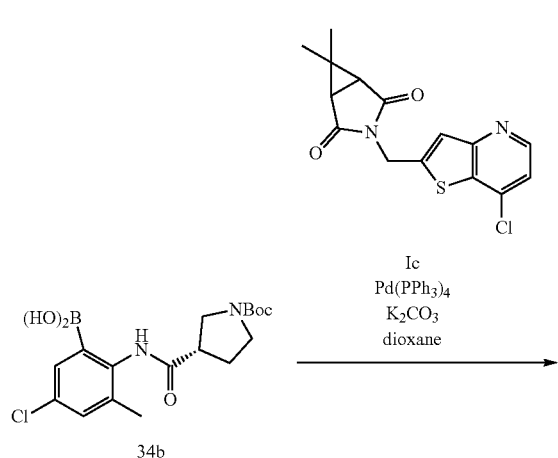

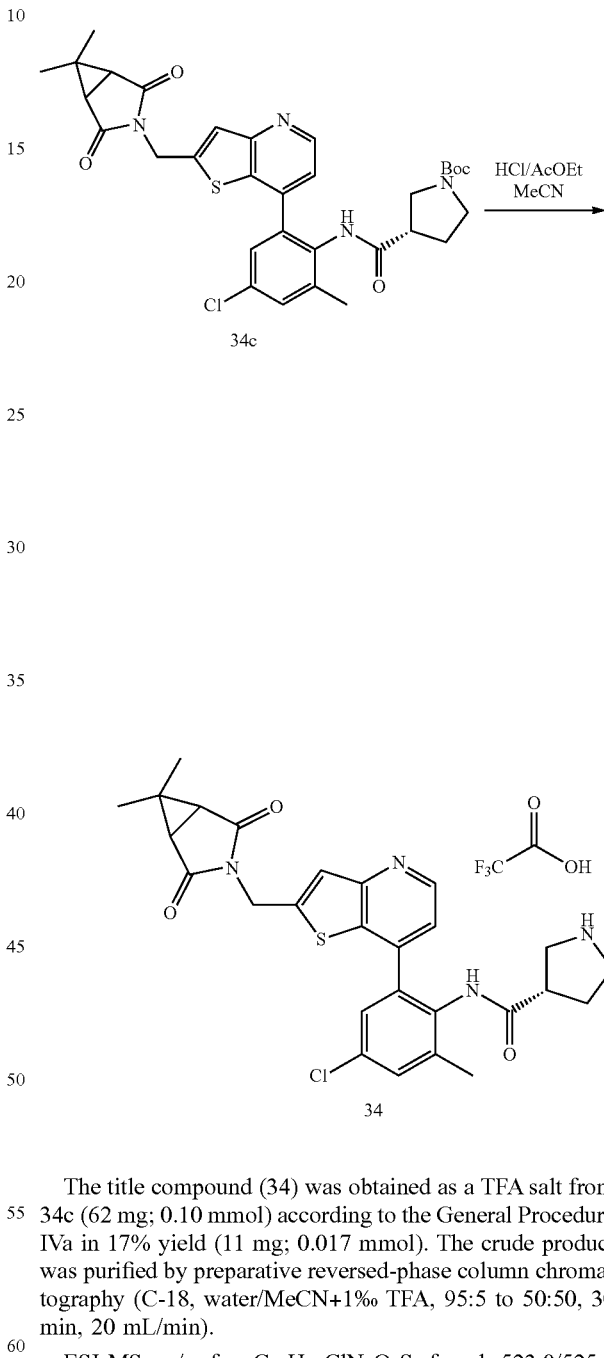

The title compound (34c) was obtained from 34b (95 mg; 0.25 mmol) and from Ic (84 mg; 0.26 mmol) according to the General Procedure Va in 40% yield (62 mg; 0.10 mmol).

ESI-MS m/z for $C_{32}H_{36}ClN_4O_5S$ found 623.0/625.0 [M+H]$^+$; $R_t$=1.57 min The title compound (34) was obtained as a TFA salt from 34c (62 mg; 0.10 mmol) according to the General Procedure IVa in 17% yield (11 mg; 0.017 mmol). The crude product was purified by preparative reversed-phase column chromatography (C-18, water/MeCN+1‰ TFA, 95:5 to 50:50, 30 min, 20 mL/min).

ESI-MS m/z for $C_{27}H_{29}ClN_4O_3S$ found 523.0/525.0 [M+H]$^+$; $R_a$=1.00 min; $^1$H NMR (700 MHz, D$_2$O, 333 K) δ 9.13-9.08 (m, 1H), 8.04-8.00 (m, 1H), 7.97-7.94 (m, 1H), 7.89-7.83 (m, 1H), 7.80-7.75 (m, 1H), 5.31-5.24 (m, 2H), 3.65-3.59 (m, 1H), 3.56-3.43 (m, 3H), 3.43-3.34 (m, 1H), 2.98 (s, 2H), 2.64 (s, 3H), 2.40-2.33 (m, 1H), 1.76-1.66 (m, 1H), 1.57 (s, 3H), 1.41 (s, 3H).

Example 35

Synthesis of 6,6-dimethyl-3-((7-(4-methyl-3-(piperazin-2-ylmethyl)-6-(trifluoromethyl)pyridin-2-yl)thieno[3,2-b]pyridin-2-yl)methyl)-3-azabicyclo[3.1.0]hexane-2,4-dione hydrochloride (35)

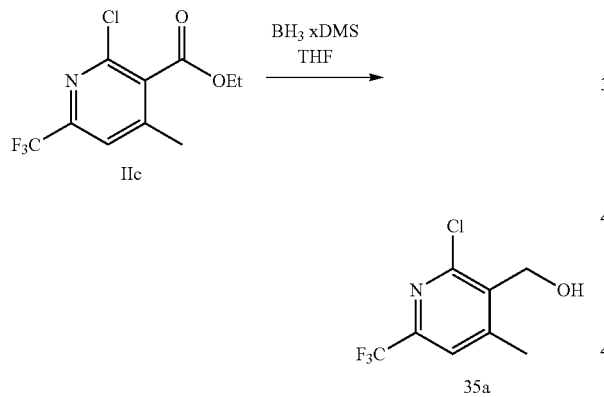

Step 1

Synthesis of (2-chloro-4-methyl-6-(trifluoromethyl)pyridin-3-yl)methanol (35a)

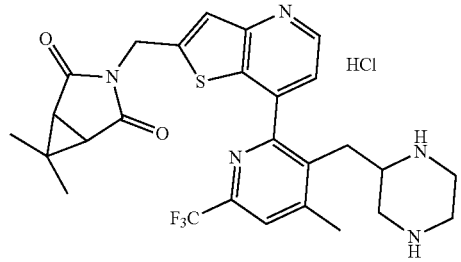

To the solution of IIc (5.1 g; 19.03 mmol) in THF (100 mL) BH$_3$×DMS (3.6 mL; 38.06 mmol) was added dropwise and then the reaction mixture was allowed to 60° C. and stirred at this temperature overnight. The reaction progress was monitored by LC-MS. When analysis indicated completion of the reaction, to this mixture 2 M HCl was added and all was extracted with Et$_2$O. The organic phase was washed with 1 M NaOH and brine and then dried over anhydrous MgSO$_4$, filtered and concentrated in vacuo and the crude product was crystallized from Et$_2$O/hexane. Compound 35a was obtained in 58% yield (2.5 g; 11.11 mmol).

ESI-MS m/z for C$_8$H$_8$ClF$_3$NO found 226.0/228.0 [M+H]$^+$; R$_t$=0.99 min

Step 2

Synthesis of 3-(bromomethyl)-2-chloro-4-methyl-6-(trifluoromethyl)pyridine (35b)

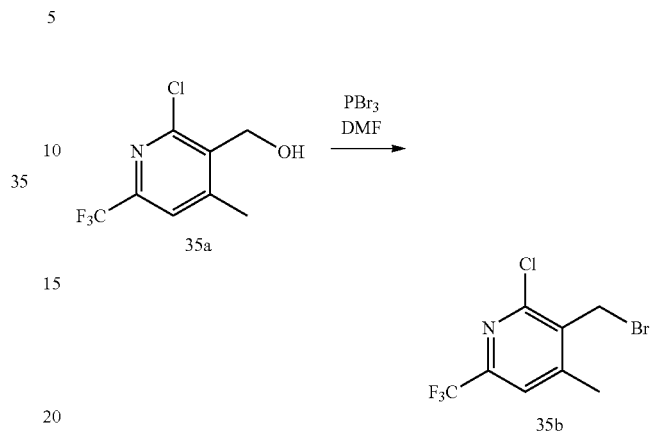

To a cooled to 0° C. solution of 35a (2.4 g; 10.64 mmol) in DMF (50 mL) PBr$_3$ (2 mL; 21.27 mmol) was added portionwise and then the reaction mixture was allowed to room temperature. The reaction progress was monitored by LC-MS. When analysis indicated completion of the reaction, the obtained solid precipitate was removed by filtration, washed with Et$_2$O. The filtrate was poured into saturated solution of NH$_4$Cl. The phases were separated and an organic one was dried over anhydrous MgSO$_4$, filtered and concentrated in vacuo and the crude product was purified by flash column chromatography on silica (hexane/AcOEt, 100:0 to 90:10, v/v, 10 minutes). Compound 35b was obtained in 70% yield (2.1 g; 7.28 mmol).

ESI-MS m/z for C$_8$H$_7$BrClF$_3$N found 287.7/289.7 [M+H]$^+$; R$_t$=1.55 min; $^1$H NMR (700 MHz, CDCl$_3$) δ 7.48 (s, 1H), 4.65 (s, 2H), 2.61-2.49 (m, 3H).

Step 3

Synthesis of ethyl 2-amino-3-(2-chloro-4-methyl-6-(trifluoromethyl)pyridin-3-yl)propanoate (35c)

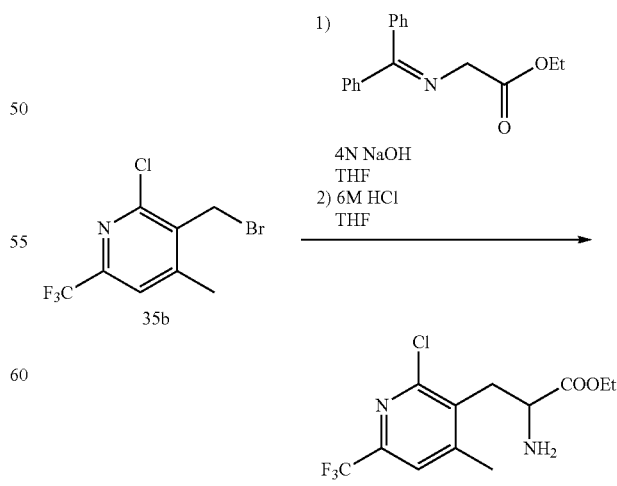

To a solution of 35b (2 g; 6.93 mmol) and ethyl 2-((di-phenylmethylene)amino)acetate (1.85 g; 6.93 mmol) in THF (100 mL) NaOH (4 N; 8.7 mL; 34.66 mmol) was added and then the reaction mixture was stirred at room temperature for 3 days. The reaction progress was monitored by LC-MS. When analysis indicated completion of the reaction, the mixture was diluted with AcOEt and washed with water and brine. An organic layer was dried over anhydrous $MgSO_4$, filtered and concentrated in vacuo and the crude product (2.7 g; 5.68 mmol) was dissolved in THF (28.5 mL), then whole was cooled to 0° C. and 6 M HCl (1.9 mL; 11.36 mmol) was added and the mixture was stirred at 0° C. for 1 hour. When analysis indicated completion of the reaction, to this mixture 1 M HCl (100 mL) was added and whole was washed with $Et_2O$ (2×). To the aqueous layer a solid $K_2CO_3$ was carefully added to pH 8-9 and extracted with AcOEt (2×). The combined organic solutions were dried over anhydrous $MgSO_4$, filtered and concentrated in vacuo and the crude product was used to the next step without additional purification. Compound 35c was obtained as a colorless oil in 68% yield (1.19 g; 3.84 mmol).

ESI-MS m/z for $C_{12}H_{15}ClF_3N_2O_2$ found 310.9/312.8 $[M+H]^+$; $R_t$=0.57 min; $^1H$ NMR (700 MHz, $CDCl_3$) δ 7.46 (s, 1H), 4.24-4.16 (m, 2H), 3.89-3.84 (m, 1H), 3.32-3.25 (m, 1H), 3.15-3.05 (m, 1H), 2.54 (s, 3H), 1.24 (t, J=7.2 Hz, 3H); $^{19}F$ NMR (235 MHz, $CDCl_3$) δ −65.24−−72.83 (m).

Step 4

Synthesis of ethyl 2-(2-((tert-butoxycarbonyl)amino)acetamido)-3-(2-chloro-4-methyl-6-(trifluoromethyl)pyridin-3-yl)propanoate (35d)

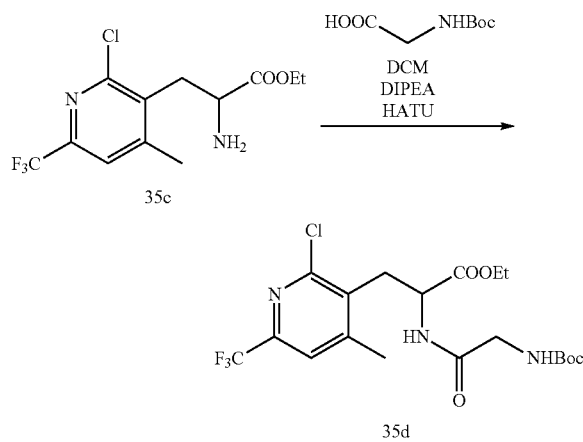

The title compound (35d) was obtained from 35c (500 mg; 1.62 mmol) and from (tert-butoxycarbonyl)glycine (283 mg; 1.62 mmol) according to the General Procedure I in 96% yield (730 mg; 1.56 mmol).

ESI-MS m/z for $C_{19}H_{25}ClF_3N_3O_5Na$ found 490.0/492.0 $[M+Na]^+$; $R_t$=1.51 min; $^1H$ NMR (700 MHz, $CDCl_3$) δ 7.46 (s, 1H), 6.92-6.88 (m, 1H), 5.10-5.01 (m, 1H), 4.86-4.78 (m, 1H), 4.23-4.09 (m, 2H), 3.83-3.75 (m, 2H), 3.41-3.36 (m, 1H), 3.35-3.28 (m, 1H), 2.61 (s, 3H), 1.49 (s, 9H), 1.17 (t, J=7.2 Hz, 3H).

Step 5

Synthesis of ethyl 2-(2-aminoacetamido)-3-(2-chloro-4-methyl-6-(trifluoromethyl)pyridin-3-yl)propanoate hydrochloride (35e)

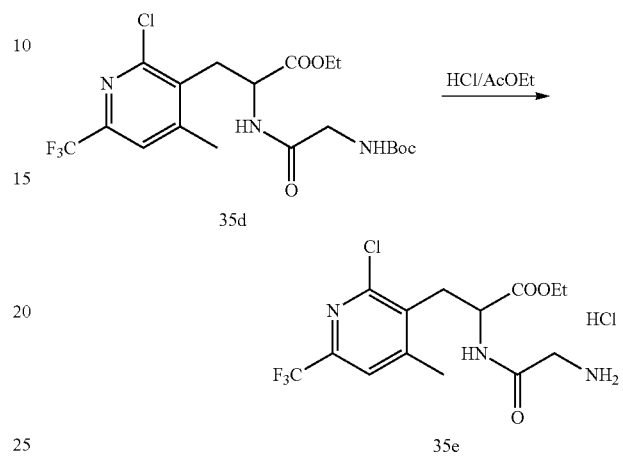

The title compound (35e) was obtained from 35d (730 mg; 1.56 mmol) according to the General Procedure IVa in 99% yield (730 mg; 1.56 mmol).

ESI-MS m/z for $C_{14}H_{18}ClF_3N_3O_3$ found 367.9/369.9 $[M+H]^+$; $R_t$=0.81 min Step 6

Synthesis of 3-((2-chloro-4-methyl-6-(trifluoromethyl)pyridin-3-yl)methyl)piperazine-2,5-dione (35f)

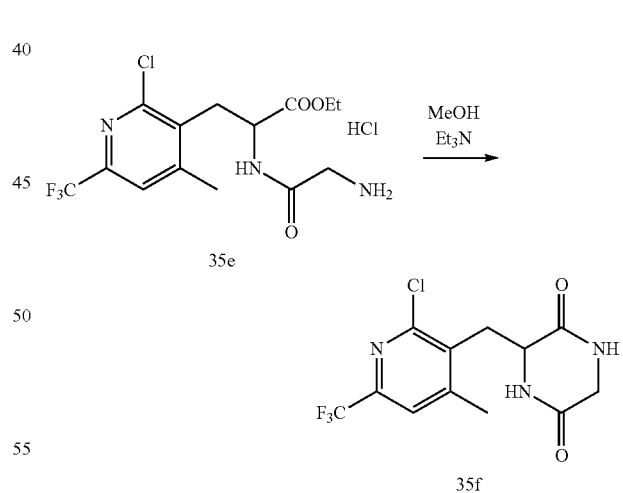

To a solution of 35e (730 mg; 1.56 mmol) in MeOH (20 mL) $Et_3N$ (0.91 mL; 6.53 mmol) was added and then the reaction mixture was stirred at room temperature overnight. The reaction progress was monitored by LC-MS. When analysis indicated completion of the reaction, the solvent was removed in vacuo and the residue was suspended in 5% $NaHCO_3$ and extracted with DCM (+10% of MeOH). The combined organic solutions were dried over anhydrous $MgSO_4$, filtered and concentrated in vacuo and the crude product was purified by preparative reversed-phase column chromatography (C-18, water/MeCN, 100:0 to 0:100, 30 min, 20 mL/min). Compound 35f was obtained as a white solid in 90% yield (0.45 g; 1.40 mmol).

ESI-MS m/z for $C_{12}H_{12}ClF_3N_3O_2$ found 321.9/323.9 [M+H]$^+$; $R_t$=0.83 min

Step 7

Synthesis of 2-((2-chloro-4-methyl-6-(trifluoromethyl)pyridin-3-yl)methyl)piperazine (35g)

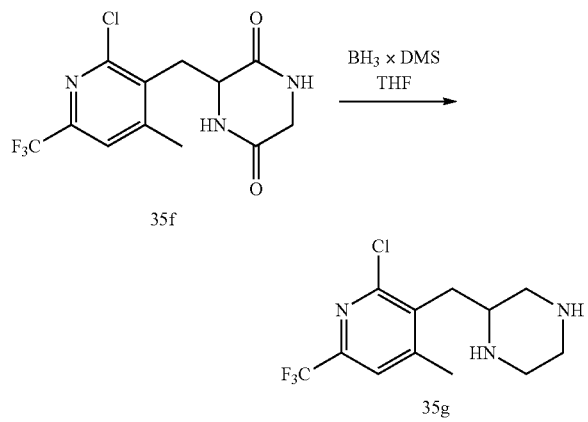

The title compound (35g) was obtained as a light yellow oil from 35f (430 mg; 1.33 mmol) according to the General Procedure VII in 67% yield (260 mg; 0.89 mmol).

ESI-MS m/z for $C_{12}H_{16}ClF_3N_3$ found 293.9/295.8 [M+H]$^+$; $R_t$=0.30 min

Step 8

Synthesis of di-tert-butyl 2-((2-chloro-4-methyl-6-(trifluoromethyl)pyridin-3-yl)methyl)piperazine-1,4-dicarboxylate (35h)

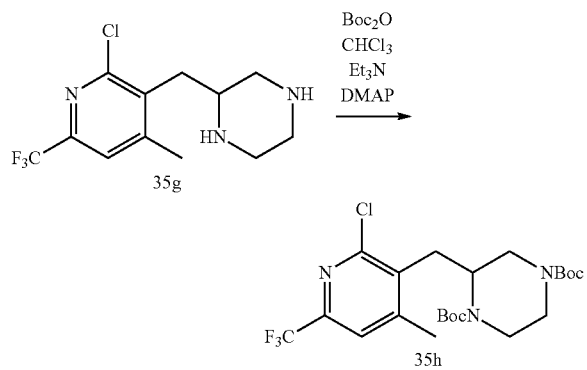

The title compound (35h) was obtained from 35g (260 mg; 0.89 mmol) according to the General Procedure VIII in 22% yield (100 mg; 0.20 mmol).

ESI-MS m/z for $C_{14}H_{16}ClF_3N_3O_4$ found 382.0/384.0 [M+H-tBu-tBu]$^+$; $R_t$=1.97 min

Step 9

Synthesis of di-tert-butyl 2-((2-(2-((6,6-dimethyl-2,4-dioxo-3-azabicyclo[3.1.0]hexan-3-yl)methyl)thieno[3,2-b]pyridin-7-yl)-4-methyl-6-(trifluoromethyl)pyridin-3-yl)methyl)piperazine-1,4-dicarboxylate (35i)

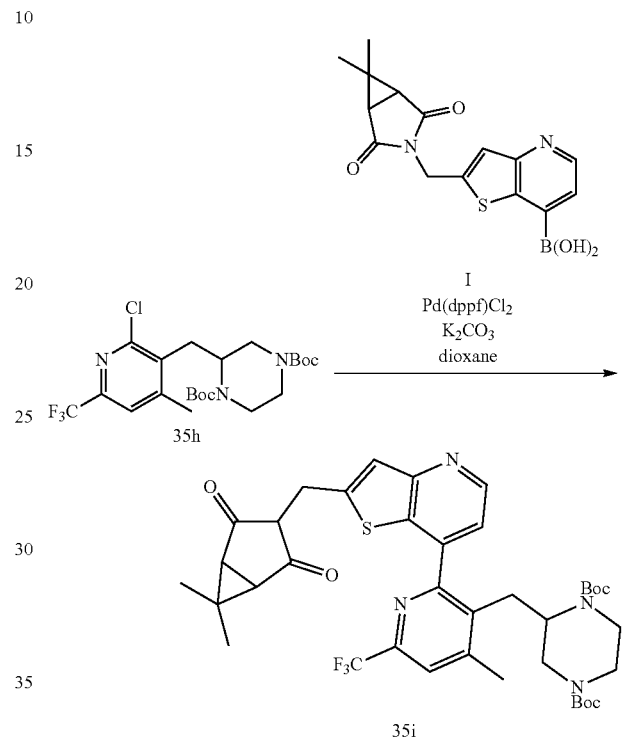

The title compound (35i) was obtained from 35h (50 mg; 0.10 mmol) and from I (34 mg; 0.10 mmol) according to the General Procedure Va and after standard work-up all the crude product mixture was taken to the next step.

ESI-MS m/z for $C_{37}H_{45}F_3N_5O_6S$ found 744.1 [M+H]$^+$; $R_t$=1.84 min

Step 10

Synthesis of 6,6-dimethyl-3-((7-(4-methyl-3-(piperazin-2-ylmethyl)-6-(trifluoromethyl)pyridin-2-yl)thieno[3,2-b]pyridin-2-yl)methyl)-3-azabicyclo[3.1.0]hexane-2,4-dione hydrochloride (35)

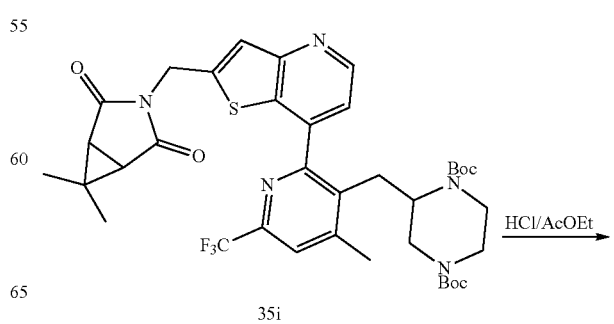

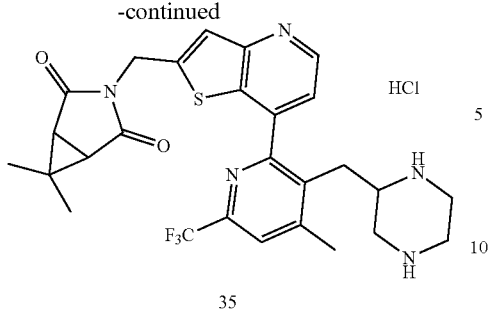

35

The title compound (35) was obtained as a racemate as a hydrochloride salt from 35i (the crude reaction mixture) according to the General Procedure IVa in 66% yield (per two steps)(38 mg; 0.066 mmol). The crude product was purified by preparative reversed-phase column chromatography (C-18, water+0.3%° HCl (36%)/MeCN, 90:10 to 90:10, 30 min, 20 mL/min).

ESI-MS m/z for $C_{27}H_{29}F_3N_5O_2S$ found 544.3 [M+H]$^+$; $R_t$=0.93 min; $^1$H NMR (700 MHz, DMSO-d$_6$+D$_2$O, 348 K) δ 8.84-8.80 (m, 1H), 7.96-7.92 (m, 1H), 7.58-7.55 (m, 1H), 7.55-7.52 (m, 1H), 4.85-4.72 (m, 2H), 3.64-3.57 (m, 1H), 3.39-3.35 (m, 2H), 3.29-3.24 (m, 1H), 3.19-3.13 (m, 1H), 3.12-3.07 (m, 1H), 3.06-3.01 (m, 2H), 2.76-2.69 (m, 1H), 2.64 (s, 3H), 2.53-2.52 (m, 2H), 1.19 (s, 3H), 1.05 (s, 3H); $^{19}$F NMR (659 MHz, DMSO-d$_6$) δ −66.36 (s).

Example 36

Synthesis of 3-((7-(3-((1H-1,2,4-triazol-1-yl) methyl)-4-methyl-6-(trifluoromethyl)pyridin-2-yl) thieno[3,2-b]pyridin-2-yl)methyl)-6,6-dimethyl-3-azabicyclo[3.1.0]hexane-2,4-dione hydrochloride (36)

36

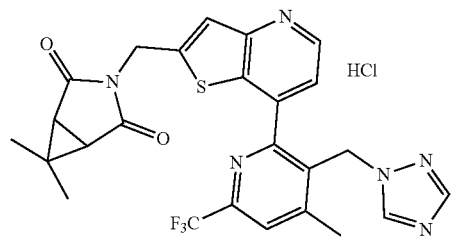

Step 1

Synthesis of 3-((1H-1,2,4-triazol-1-yl)methyl)-2-chloro-4-methyl-6-(trifluoromethyl)pyridine (36a)

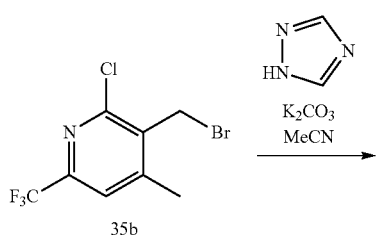

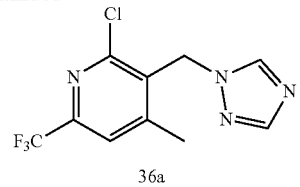

36a

To a solution of 35b (0.2 g; 0.70 mmol) in MeCN (4 mL) 1H-1,2,4-triazole (58 mg; 0.84 mmol) and K$_2$CO$_3$ (190 mg; 1.38 mmol) were added and then the reaction mixture was stirred in a sealed tube at 80° C. overnight. The reaction progress was monitored by LC-MS. When analysis indicated completion of the reaction, the mixture was diluted with DCM and filtered off. The filtrate was concentrated in vacuo and the crude product was purified by flash column chromatography on silica (DCM/MeOH, 100:0 to 85:15, v/v, 25 minutes). Compound 36a was obtained in 70% yield (135 mg; 0.49 mmol).

ESI-MS m/z for $C_{10}H_9ClF_3N_4$ found 276.9/278.9 [M+H]$^+$; $R_t$=1.11 min

Step 2

Synthesis of 3-((7-(3-((1H-1,2,4-triazol-1-yl) methyl)-4-methyl-6-(trifluoromethyl)pyridin-2-yl) thieno[3,2-b]pyridin-2-yl)methyl)-6,6-dimethyl-3-azabicyclo[3.1.0]hexane-2,4-dione hydrochloride (36)

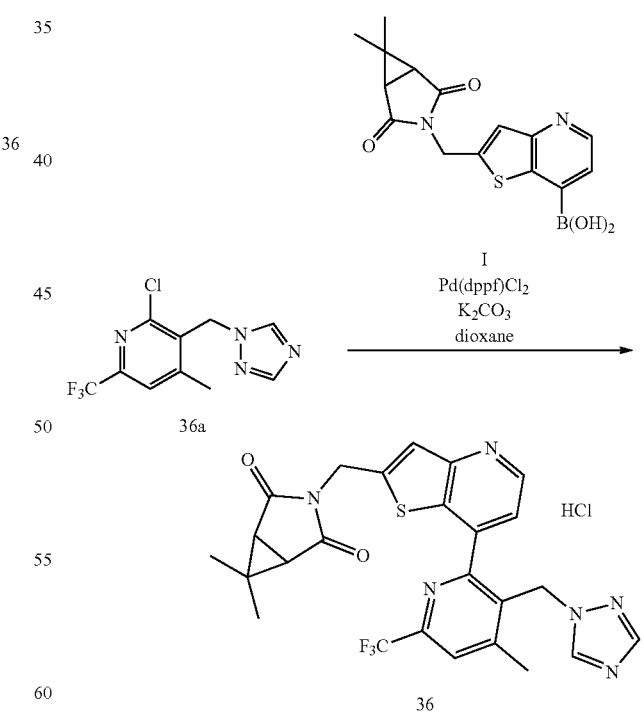

The title compound (36) was obtained as a hydrochloride salt from 36a (97 mg; 0.35 mmol) and from 1 (200 mg; 0.60 mmol) according to the General Procedure Va in 40% yield (80 mg; 0.14 mmol). The crude product was purified by flash column chromatography on silica (DCM/MeOH, 100:0 to 85:15, v/v, 30 minutes) and then by preparative reversed-phase column chromatography (C-18, water+0.5‰ HCL/MeCN, 98:2 to 30:70, 30 min, 20 mL/min).

ESI-MS m/z for $C_{25}H_{22}F_3N_6O_2S$ found 527.3 [M+H]$^+$; $R_t$=1.32 min; $^1$H NMR (700 MHz, DMSO-d$_6$+D$_2$O, 348 K) δ 8.77-8.73 (m, 1H), 8.20 (s, 1H), 7.95 (s, 1H), 7.80 (s, 1H), 7.55-7.48 (m, 2H), 5.47 (s, 2H), 4.77 (s, 2H), 2.54-2.52 (m, 2H), 2.48 (s, 3H), 1.18 (s, 3H), 1.02 (s, 3H); $^{19}$F NMR (659 MHz, DMSO-t) δ −66.56 (s).

Example 37

Synthesis of 3-((7-(3-((3,6-dioxopiperazin-2-yl)methyl)-4-methyl-6-(trifluoromethyl)pyridin-2-yl)thieno[3,2-b]pyridin-2-yl)methyl)-6,6-dimethyl-3-azabicyclo[3.1.0]hexane-2,4-dione hydrochloride (37)

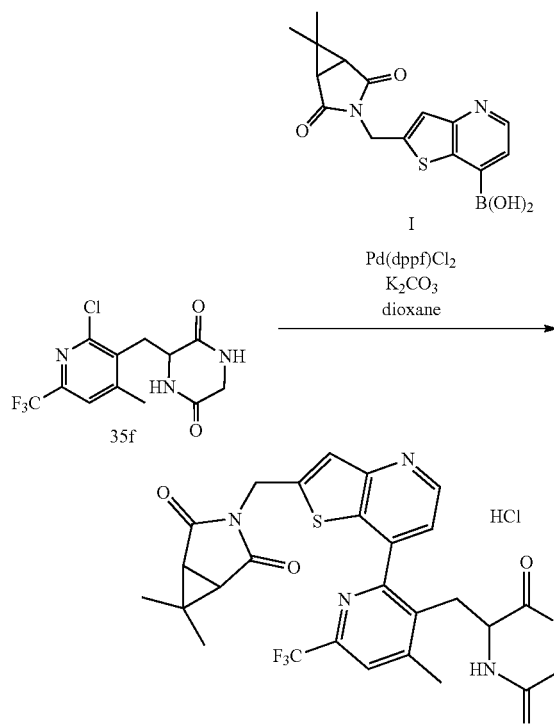

The title compound (37) was obtained as a hydrochloride salt from 35f (30 mg; 0.09 mmol) and from I (33 mg; 0.1 mmol) according to the General Procedure Va in 89% yield (48 mg; 0.08 mmol). The crude product was purified by flash column chromatography on silica (DCM/MeOH, 100:0 to 70:30, v/v, 30 minutes) and then by preparative reversed-phase column chromatography (C-18, water+0.5‰ HCl/MeCN, 90:10 to 10:90, 30 min, 20 mL/min).

ESI-MS m/z for $C_{27}H_{25}F_3N_5O_4S$ found 572.2 [M+H]$^+$; $R_t$=1.15 min; $^1$H NMR (700 MHz, DMSO-d$_6$+D$_2$O, 348 K) δ 8.75-8.72 (m, 1H), 7.84 (s, 1H), 7.53-7.51 (m, 1H), 7.47-7.43 (m, 1H), 4.80-4.72 (m, 2H), 3.68-3.60 (m, 1H), 3.48-3.42 (m, 1H), 3.34-3.27 (m, 1H), 3.16-3.09 (m, 1H), 3.09-3.01 (m, 1H), 2.55 (s, 3H), 2.50 (s, 2H), 1.16 (s, 3H), 0.99 (s, 3H); $^{19}$F NMR (659 MHz, DMSO-d$_6$) δ −66.29 (s).

Example 38

Synthesis of 6,6-dimethyl-3-((7-(4-methyl-3-((3-oxomorpholino)methyl)-6-(trifluoromethyl)pyridin-2-yl)thieno[3,2-b]pyridin-2-yl)methyl)-3-azabicyclo[3.1.0]hexane-2,4-dione hydrochloride (38)

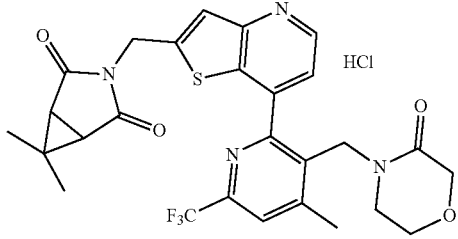

Step 1

Synthesis of 4-((2-chloro-4-methyl-6-(trifluoromethyl)pyridin-3-yl)methyl)morpholin-3-one (38a)

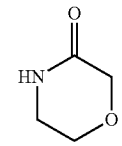

The solution of 35b (70 mg; 0.24 mmol) and morpholin-3-one (27 mg; 0.27 mmol) in THF (2 mL) was cooled to 0° C. and then to this mixture NaH (50%; 15 mg; 0.32 mmol) was added in one portion and then the cooling bath was removed and the mixture was stirred at room temperature for 1 hour. The reaction progress was monitored by LC-MS. When analysis indicated completion of the reaction, the mixture was diluted with AcOEt and washed carefully with water. The organic layer was dried over anhydrous MgSO$_4$, filtered and concentrated in vacuo and the crude product was used to the next step without additional purification. Compound 38a was obtained as a light yellow oil in 99% yield (74 mg; 0.24 mmol).

ESI-MS m/z for $C_{12}H_{13}ClF_3N_4O_2$ found 309.0/311.0 [M+H]$^+$; $R_t$=1.19 min

Step 2

Synthesis of 6,6-dimethyl-3-((7-(4-methyl-3-((3-oxomorpholino)methyl)-6-(trifluoromethyl)pyridin-2-yl)thieno[3,2-b]pyridin-2-yl)methyl)-3-azabicyclo[3.1.0]hexane-2,4-dione hydrochloride (38)

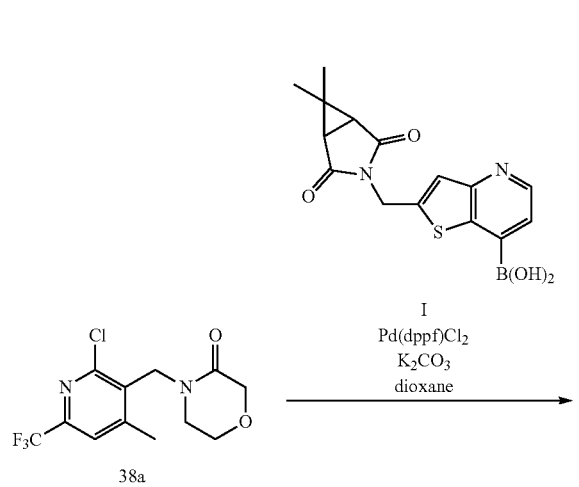

The title compound (38) was obtained as a hydrochloride salt from 38a (74 mg; 0.24 mmol) and from I (79 mg; 0.24 mmol) according to the General Procedure Va in 83% yield (121 mg; 0.20 mmol). The crude product was purified by flash column chromatography on silica (DCM/MeOH, 100:0 to 70:30, v/v, 30 minutes) and then by preparative reversed-phase column chromatography (C-18, water+0.5‰ HCl/MeCN, 99:1 to 40:60, 30 min, 20 mL/min).

ESI-MS m/z for $C_{27}H_{26}F_3N_4O_4S$ found 559.4 [M+H]$^+$; R$_t$=1.29 min; $^1$H NMR (700 MHz, DMSO-d$_6$+D$_2$O, 348 K) δ 8.74-8.69 (m, 1H), 7.88 (s, 1H), 7.50 (s, 1H), 7.42-7.36 (m, 1H), 4.80-4.75 (m, 2H), 4.63 (s, 2H), 3.67 (s, 2H), 3.41-3.40 (m, 2H), 2.76-2.69 (m, 2H), 2.54 (s, 3H), 1.17 (s, 3H), 1.03 (s, 3H); $^{19}$F NMR (235 MHz, DMSO-d$_6$) δ −66.55--66.90 (m).

Example 39

Synthesis of 6,6-dimethyl-3-((7-(4-methyl-3-((2-oxopyrrolidin-1-yl)methyl)-6-(trifluoromethyl)pyridin-2-yl)thieno[3,2-b]pyridin-2-yl)methyl)-3-azabicyclo[3.1.0]hexane-2,4-dione dihydrochloride (39)

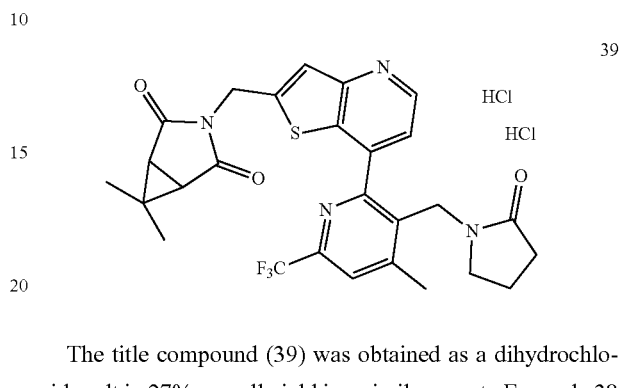

The title compound (39) was obtained as a dihydrochloride salt in 27% overall yield in a similar way to Example 38 with the exception that, in the first step of the synthesis pyrrolidin-2-one was used instead of morpholin-3-one and in the last step of the synthesis the crude product was purified by preparative reversed-phase column chromatography (C-18, water+0.5‰ HCl (6 M)/MeCN, 98:2 to 30:70, 30 min, 20 mL/min).

ESI-MS m/z for $C_{27}H_{26}F_3N_4O_3S$ found 543.2 [M+H]$^+$; R$_t$=1.33 min; $^1$H NMR (700 MHz, DMSO-d$_6$+D$_2$O, 348 K) δ 8.77-8.71 (m, 1H), 7.89 (s, 1H), 7.56-7.52 (m, 1H), 7.48-7.41 (m, 1H), 4.81-4.75 (m, 2H), 4.44 (s, 2H), 2.78-2.70 (m, 2H), 2.54-2.52 (m, 2H), 2.52 (s, 3H), 1.93-1.84 (m, 2H), 1.62-1.52 (m, 2H), 1.17 (s, 3H), 1.02 (s, 3H); $^{19}$F NMR (235 MHz, DMSO-d$_6$) δ −61.37--75.73 (m).

Example 40

Synthesis of 6,6-dimethyl-3-((7-(4-methyl-3-((2-oxopiperazin-1-yl)methyl)-6-(trifluoromethyl)pyridin-2-yl)thieno[3,2-b]pyridin-2-yl)methyl)-3-azabicyclo[3.1.0]hexane-2,4-dione dihydrochloride (40)

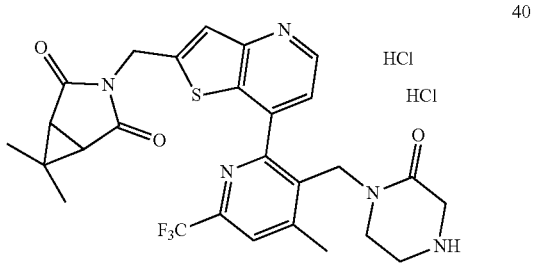 [SMILES: Cc1cc(C(F)(F)F)nc(-c2ccnc3cc(CN4C(=O)C5C(C4=O)C5(C)C)sc23)c1CN1CCNCC1=O ; Cl ; Cl]

Step 1

Synthesis of tert-butyl 4-((2-chloro-4-methyl-6-(trifluoromethyl)pyridin-3-yl)methyl)-3-oxopiperazine-1-carboxylate (40a)

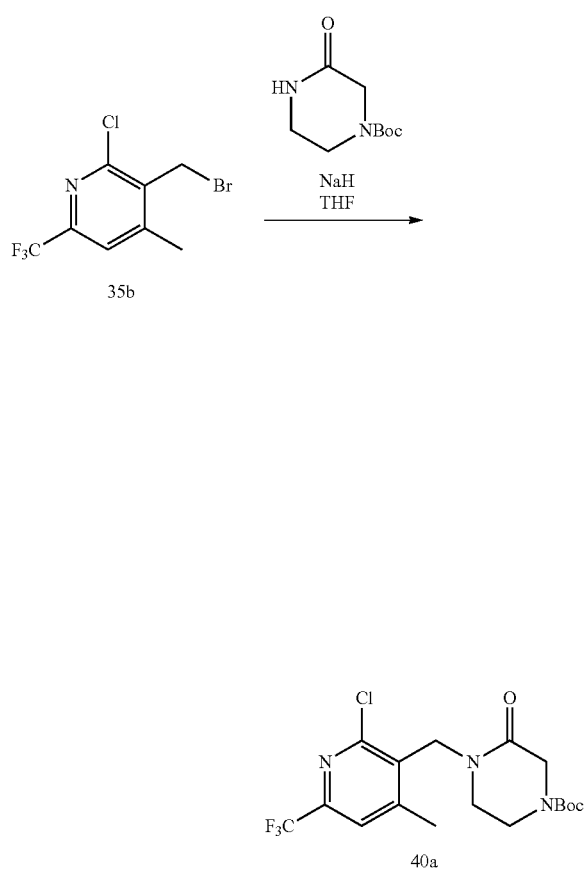

The solution of 35b (50 mg; 0.17 mmol) and tert-butyl 3-oxopiperazine-1-carboxylate (38 mg; 0.19 mmol) in THF (2 mL) was cooled to 0° C. and then to this mixture NaH (50%; 10 mg; 0.22 mmol) was added in one portion and then the cooling bath was removed and the mixture was stirred at room temperature for 30 minutes. The reaction progress was monitored by LC-MS. When analysis indicated completion of the reaction, to this mixture water was added and the product was extracted with AcOEt (2×). The combined organic solutions was dried over anhydrous $MgSO_4$, filtered and concentrated in vacuo and the crude product was purified by flash column chromatography on silica (hexane/AcOEt, 100:0 to 50:50, v/v, 30 minutes). Compound 40a was obtained in 82% yield (55 mg; 0.14 mmol).

ESI-MS m/z for $C_{17}H_{22}ClF_3N_3O_3$ found 407.5/409.5 $[M+H]^+$; $R_t$=1.47 min

Step 2

Synthesis of tert-butyl 4-((2-(2-(((6,6-dimethyl-2,4-dioxo-3-azabicyclo[3.1.0]hexan-3-yl)methyl)thieno[3,2-b]pyridin-7-yl)-4-methyl-6-(trifluoromethyl)pyridin-3-yl)methyl)-3-oxopiperazine-1-carboxylate (40b)

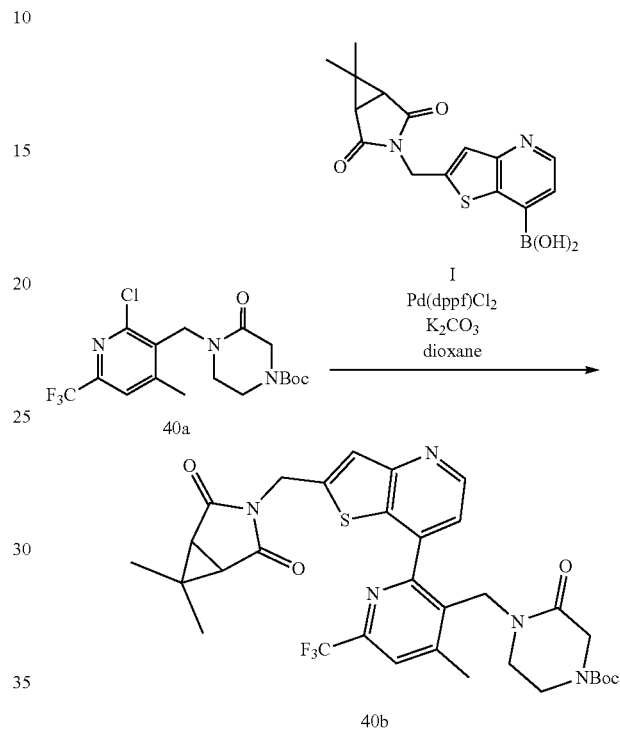

The title compound (40b) was obtained from 40a (55 mg; 0.14 mmol) and from I (53 mg; 0.16 mmol) according to the General Procedure Va and after standard work-up all the crude product mixture was taken to the next step.

ESI-MS m/z for $C_{32}H_{35}F_3N_5O_5S$ found 658.1 $[M+H]^+$; $R_t$=1.55 min

Step 3

Synthesis of 6,6-dimethyl-3-((7-(4-methyl-3-((2-oxopiperazin-1-yl)methyl)-6-(trifluoromethyl)pyridin-2-yl)thieno[3,2-b]pyridin-2-yl)methyl)-3-azabicyclo[3.1.0]hexane-2,4-dione dihydrochloride (40)

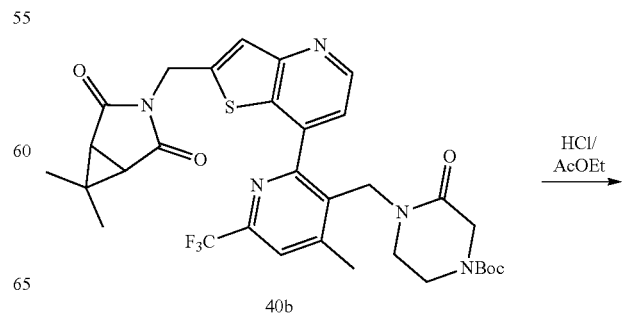

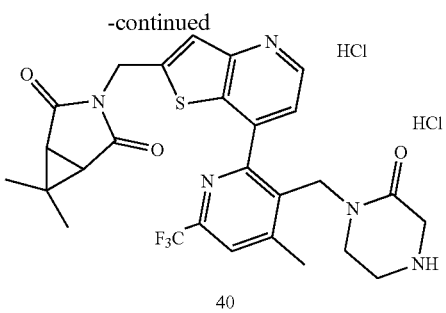

40

The title compound (40) was obtained as a dihydrochloride salt from 40b (the crude reaction mixture) according to the General Procedure IVa in 57% yield (per two steps)(52 mg; 0.08 mmol). The crude product was purified by flash column chromatography on silica (DCM/MeOH, 100:0 to 70:30, v/v, 30 minutes) and then by preparative reversed-phase column chromatography (C-18, water+0.5‰ HCl (36%)/MeCN, 98:2 to 30:70, 30 min, 20 mL/min).

ESI-MS m/z for $C_{27}H_{27}F_3N_5O_3S$ found 558.2 [M+H]$^+$; $R_t$=0.97 min; $^1$H NMR (700 MHz, DMSO-$d_6$+$D_2O$, 348 K) δ 8.77-8.74 (m, 1H), 7.91 (s, 1H), 7.55-7.51 (m, 1H), 7.48-7.44 (m, 1H), 4.84-4.74 (m, 2H), 4.64 (s, 2H), 3.54 (s, 2H), 3.16-3.07 (m, 2H), 3.05-2.95 (m, 2H), 2.53 (s, 3H), 2.52 (s, 2H), 1.18 (s, 3H), 1.03 (s, 3H); $^{19}$F NMR (235 MHz, DMSO-$d_6$) δ −66.78−−67.11 (m).

Example 41

Synthesis of 6,6-dimethyl-3-((7-(4-methyl-3-((4-methyl-2-oxopiperazin-1-yl)methyl)-6-(trifluoromethyl)pyridin-2-yl)thieno[3,2-b]pyridin-2-yl)methyl)-3-azabicyclo[3.1.0]hexane-2,4-dione dihydrochloride (41)

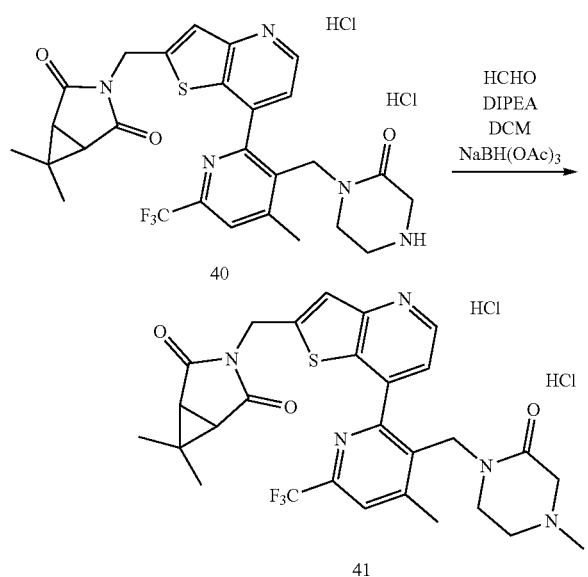

To the solution of 40 (35 mg; 0.06 mmol) in DCM (1 mL) DIPEA (0.03 mL; 0.19 mmol) and formalin (37% aqueous solution; 0.01 mL; 0.31 mmol) were added and this mixture was stirred at room temperature for 30 minutes. Then to this mixture NaBH(OAc)$_3$ (21 mg; 0.09 mmol) was added and whole was stirred at room temperature. The reaction progress was monitored by LC-MS. When analysis indicated completion of the reaction, the solvent was removed in vacuo and the residue was purified by preparative reversed-phase column chromatography (C-18, water+0.5‰ HCl (36%)/MeCN, 98:2 to 30:70, 30 min, 20 mL/min).

ESI-MS m/z for $C_{28}H_{29}F_3N_5O_3S$ found 572.1 [M+H]$^+$; $R_t$=0.99 min; $^1$H NMR (700 MHz, DMSO-$d_6$+$D_2O$, 348 K) δ 8.79-8.75 (m, 1H), 7.92-7.87 (m, 1H), 7.55-7.51 (m, 1H), 7.50-7.47 (m, 1H), 4.84-4.74 (m, 2H), 4.64 (s, 2H), 3.68 (s, 2H), 3.24 (s, 2H), 3.11-3.02 (m, 2H), 2.77 (s, 3H), 2.54-2.53 (m, 3H), 2.52 (s, 2H), 1.18 (s, 3H), 1.03 (s, 3H); $^{19}$F NMR (235 MHz, DMSO-$d_6$) δ −66.78−−67.06 (m).

Example 42

Synthesis of 6-cyano-2-(2-((6,6-dimethyl-2,4-dioxo-3-azabicyclo[3.1.0]hexan-3-yl)methyl)thieno[3,2-b]pyridin-7-yl)-N-(2-(dimethylamino)ethyl)-N,4-dimethylnicotinamide (42)

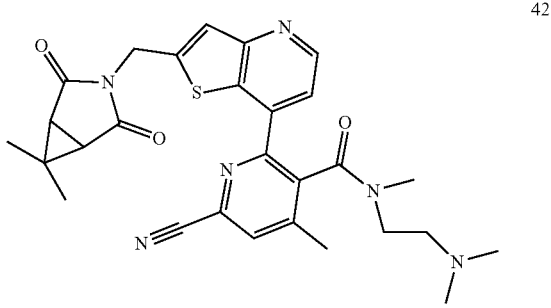

Step 1

Synthesis of tert-butyl 2-chloro-4-methylnicotinate (42a)

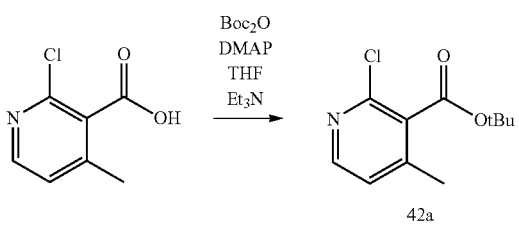

To the suspension of 2-chloro-4-methylnicotinic acid (4.14 g; 24.21 mmol) in THF (160 mL) Boc$_2$O (7.93 g; 36.31 mmol), DMAP (1.48 g; 12.10 mmol) and Et$_3$N (5 mL) were added and then the reaction mixture was stirred at room temperature overnight. Then DCM (30 mL) and another portion of Boc$_2$O (4 g; 15.00 mmol) were added and the reaction mixture was stirred at room temperature overnight. The reaction progress was monitored by LC-MS. When analysis indicated completion of the reaction, the solvent was evaporated in vacuo and the residue was purified by flash column chromatography on silica (hexane/AcOEt, 100:0 to 50:50, v/v, 25 minutes). Compound 42a was obtained in 76% yield (4.2 g; 18.50 mmol).

ESI-MS m/z for $C_{11}H_{15}ClNO_2$ found 228.0/230.0 [M+H]$^+$; $R_t$=1.44 min

Step 2

Synthesis of 3-(tert-butoxycarbonyl)-2-chloro-4-methylpyridine 1-oxide (42b)

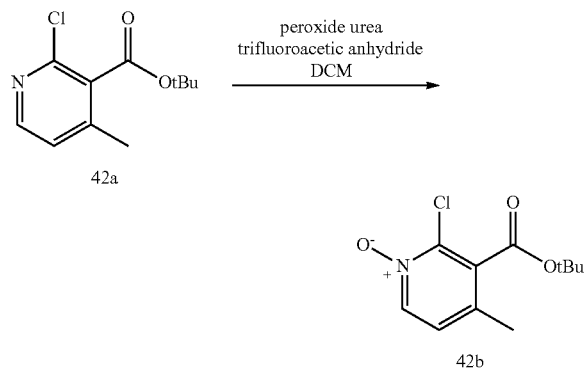

To the solution of 42a (3 g; 13.17 mmol) and peroxide urea (6.2 g; 65.84 mmol) in DCM (100 mL) trifluoroacetic anhydride (7.3 mL; 52.68 mmol) was added dropwise and this mixture was stirred at room temperature for 1 hour. The reaction progress was monitored by LC-MS. When analysis indicated completion of the reaction, to this mixture a mixture of 1 M K$_2$CO$_3$/5% NaHCO$_{3aq}$ (1:1, v/v) was carefully added to pH 8 and the product was extracted with DCM (3×). The combined organic solutions were dried over anhydrous MgSO$_4$, filtered and concentrated in vacuo and the crude product was used to the next step without additional purification. Compound 42b was obtained in 94% yield (3 g; 12.34 mmol).

ESI-MS m/z for $C_{11}H_{15}ClNO_3$ found 244.0/246.0 [M+H]$^+$; $R_t$=1.01 min

Step 3

Synthesis of tert-butyl 2-chloro-6-cyano-4-methylnicotinate (42c)

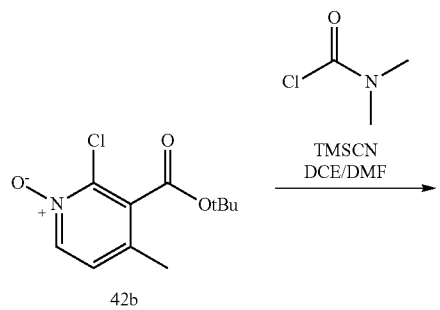

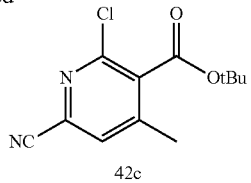

To the solution of 42b (3 g; 12.34 mmol) and dimethylcarbamic chloride (2.26 mL; 24.62 mmol) in DCE/DMF (36 mL/12 mL; 3:1, v/v) trimethylsilyl cyanate (4.95 mL; 36.93 mmol) was added dropwise and this mixture was stirred at 50° C. for 5 hours and then at room temperature for 3 days. The reaction progress was monitored by LC-MS. When analysis indicated completion of the reaction, the mixture was diluted with DCM and washed with 5% NaHCO$_3$ aq. The organic layer was dried over anhydrous MgSO$_4$, filtered and concentrated in vacuo and the crude product was purified by flash column chromatography on silica (hexane/AcOEt, 100:0 to 80:20, v/v, 30 minutes). Compound 42c was obtained in 61% yield (1.9 g; 7.54 mmol).

ESI-MS m/z for $C_{14}H_{17}ClN_3O_2$ found 294.0/296.0 [M+H+MeCN]$^+$; $R_t$=1.60 min Step 4

Synthesis of tert-butyl 6-cyano-2-(2-((6,6-dimethyl-2,4-dioxo-3-azabicyclo[3.1.0]hexan-3-yl)methyl)thieno[3,2-b]pyridin-7-yl)-4-methylnicotinate (42d)

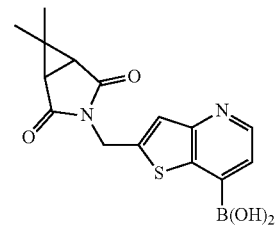

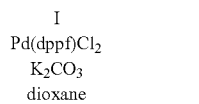

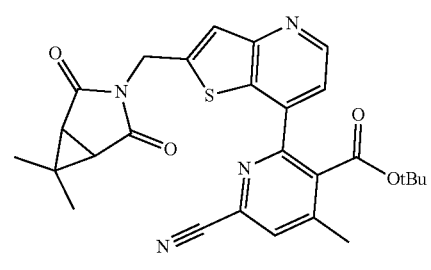

The title compound (42d) was obtained from 42c (300 mg; 1.98 mmol) and from boronic acid I (718 mg; 2.17 mmol) according to the General Procedure Va in 51% yield (500 mg; 1.00 mmol).

ESI-MS m/z for $C_{27}H_{27}N_4O_4S$ found 503.4 $[M+H]^+$; $R_t$=1.60 min

Step 5

Synthesis of 6-cyano-2-(2-((6,6-dimethyl-2,4-dioxo-3-azabicyclo[3.1.0]hexan-3-yl)methyl)thieno[3,2-b]pyridin-7-yl)-4-methylnicotinic acid (42e)

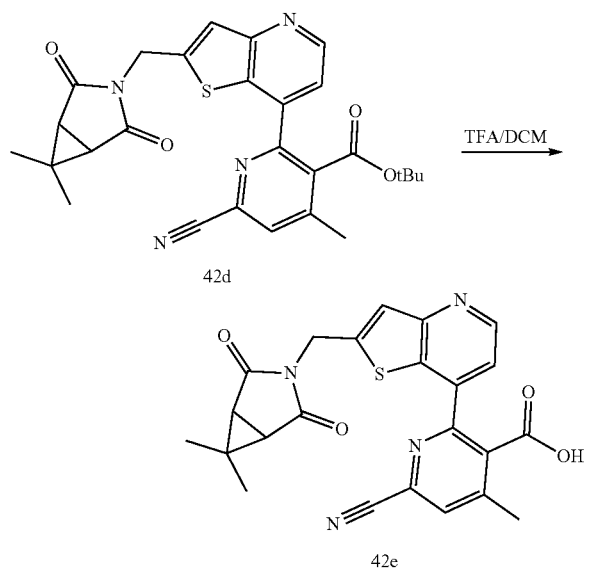

To the solution of 42d (0.6 g; 1.19 mmol) in DCM (12 mL) TFA (9 mL; 121 mmol) was added and this mixture was stirred at 45° C. for 4 hours. Then the solvent was evaporated in vacuo and the residue was purified by flash column chromatography on silica (DCM/MeOH, 100:0 to 50:50, v/v, 30 minutes). Compound 42e was obtained in 91% yield (480 mg; 1.08 mmol).

ESI-MS m/z for $C_{23}H_{19}N_4O_4S$ found 447.2 $[M+H]^+$; $R_t$=1.10 min

Step 6

Synthesis of 6-cyano-2-(2-((6,6-dimethyl-2,4-dioxo-3-azabicyclo[3.1.0]hexan-3-yl)methyl)thieno[3,2-b]pyridin-7-yl)-N-(2-(dimethylamino)ethyl)-N,4-dimethylnicotinamide (42)

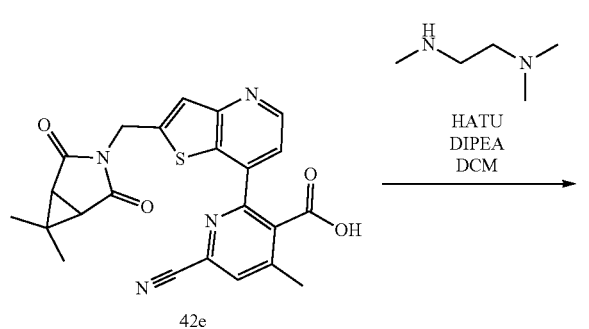

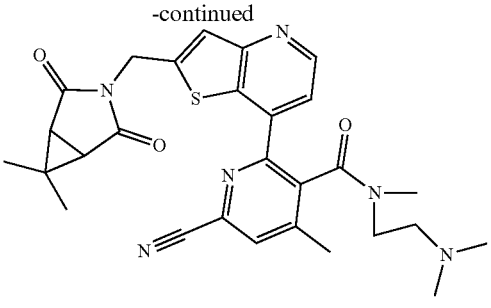

The title compound (42) was obtained from 42e (55 mg, 0.12 mmol) and from $N^1,N^1,N^2$-trimethylethane-1,2-diamine (0.02 mL; 0.15 mmol) according to the General Procedure 1 in 19% yield (12 mg; 0.023 mmol). The crude product was purified by preparative reversed-phase column chromatography (C-18, water/MeCN, 99:1 to 10:90, 30 min, 20 mL/min).

ESI-MS m/z for $C_{28}H_{30}N_6O_3S$ found 531.3 $[M+H]^+$; $R_t$=0.88 min; $^1$H NMR (700 MHz, $D_2O$) δ 8.71-8.66 (m, 1H), 8.05-8.02 (m, 1H), 7.58-7.54 (m, 1H), 7.40-7.36 (m, 1H), 4.91-4.81 (m, 2H), 3.76-3.70 (m, 1H), 3.58-3.50 (m, 1H), 2.99-2.92 (m, 1H), 2.92-2.85 (m, 1H), 2.78 (s, 6H), 2.58 (s, 2H), 2.55 (s, 3H), 2.41 (s, 3H), 1.17 (s, 3H), 0.95 (s, 3H).

Example 43

Synthesis of 6-(2-((6,6-dimethyl-2,4-dioxo-3-azabicyclo[3.1.0]hexan-3-yl)methyl)thieno[3,2-b]pyridin-7-yl)-5-(3-(dimethylamino)azetidine-1-carbonyl)-4-methylpicolinonitrile (43)

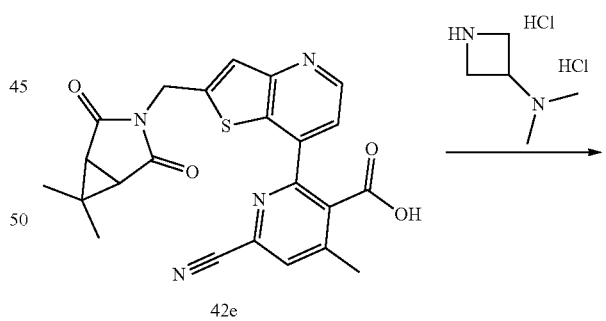

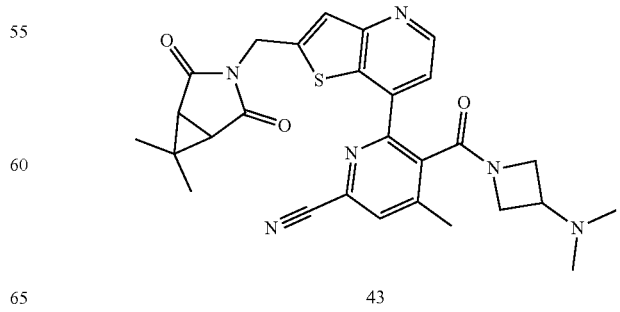

To the suspension of 42e (40 mg; 0.090 mmol) in DCM (1 mL) DMF (5 drops) was added and then an oxalyl chloride (0.008 mL; 0.098 mmol) was added dropwise at room temperature under an argon atmosphere. Then this mixture was stirred at room temperature for 1.5 hour. The reaction progress was monitored by LC-MS. Next to this mixture Et₃N (0.062 mL; 0.358 mmol) and N,N-dimethyl-azetidin-3-amine dihydrochloride (19 mg; 0.107 mmol) were added and whole was stirred at room temperature for 2 hours. When analysis indicated completion of the reaction, the mixture was concentrated in vacuo and the crude product was purified by preparative reversed-phase column chromatography (column: Cosmosil Cholester 20×250 mm, water/MeCN, 99:1 to 20:80, 30 min, 20 mL/min). The final compound (43) was obtained in 20% yield (10 mg; 0.018 mmol).

ESI-MS m/z for $C_{28}H_{29}N_6O_3S$ found 529.3 $[M+H]^+$; $R_t$=0.87 min; ¹H NMR (700 MHz, D₂O) δ 9.08-7.58 (m, 4H), 5.04-4.87 (m, 2H), 4.69-3.38 (m, 5H), 2.88-2.42 (m, 9H), 1.30-0.92 (m, 6H).

Example 44

Synthesis of 6-(2-((6,6-dimethyl-2,4-dioxo-3-azabicyclo[3.1.0]hexan-3-yl)methyl)thieno[3,2-b]pyridin-7-yl)-5-((S)-3-(dimethylamino)pyrrolidine-1-carbonyl)-4-methylpicolinonitrile hydrochloride (44)

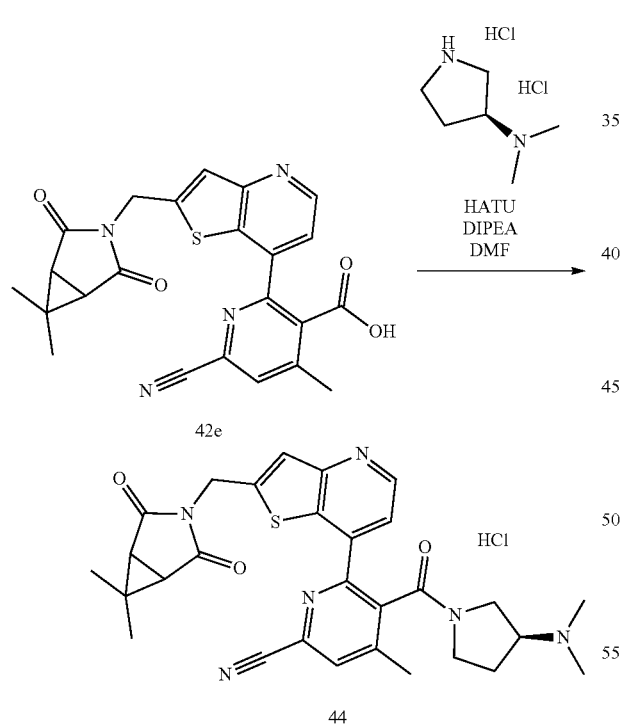

The title compound (44) was obtained as a hydrochloride salt from 42e (55 mg; 0.12 mmol) and from (S)—N,N-dimethylpyrrolidin-3-amine dihydrochloride (28 mg; 0.15 mmol) according to the General Procedure I in 25% yield (16 mg; 0.03 mmol). The crude product was purified by preparative reversed-phase column chromatography (C-18, water+0.5‰ HCl (36%)//MeCN, 98:2 to 40:60, 30 min, 20 mL/min).

ESI-MS m/z for $C_{29}H_{31}N_6O_3S$ found 543.4 $[M+H]^+$; $R_t$=0.89 min; ¹H NMR (700 MHz, DMSO-d₆+D₂O, 348 K) δ 8.78-8.72 (m, 1H), 8.15-8.08 (m, 1H), 7.53-7.37 (m, 2H), 4.87-4.76 (m, 2H), 4.07-3.41 (m, 3H), 3.24-3.07 (m, 1H), 2.86-2.73 (m, 2H), 2.70-2.52 (m, 6H), 2.49-2.39 (m, 4H), 2.38-1.65 (m, 2H), 1.22-1.17 (m, 3H), 1.12-1.03 (m, 3H).

Example 45

Synthesis of 6,6-dimethyl-3-((7-(4-methyl-3-(piperazine-1-carbonyl)pyridin-2-yl)thieno[3,2-b]pyridin-2-yl)methyl)-3-azabicyclo[3.1.0]hexane-2,4-dione hydrochloride (45)

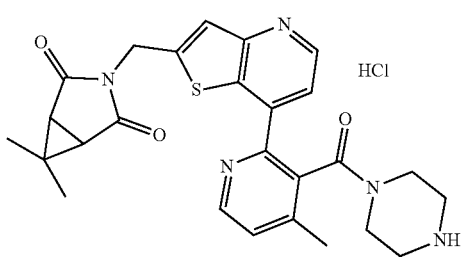

Step 1

Synthesis of tert-butyl 4-(2-chloro-4-methylnicotinoyl)piperazine-1-carboxylate (45a)

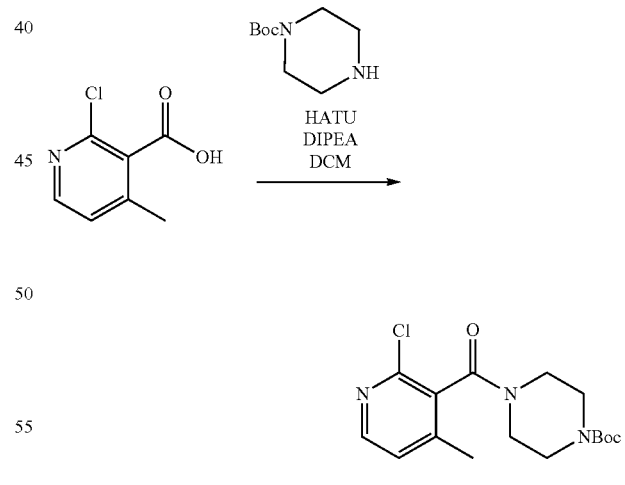

The title compound (45a) was obtained as a white solid from 2-chloro-4-methylnicotinic acid (200 mg; 1.17 mmol) and from tert-butyl piperazine-1-carboxylate (261 mg; 1.40 mmol) according to the General Procedure I in 88% yield (350 mg; 1.03 mmol).

ESI-MS m/z for $C_{16}H_{23}ClN_3O_3$ found 340.1/342.1 $[M+H]^+$; $R_t$=1.19 min

Step 2

Synthesis of tert-butyl 4-(2(2-(((6,6-dimethyl-2,4-dioxo-3-azabicyclo[3.1.0]hexan-3-yl)methyl)thieno[3,2-b]pyridin-7-yl)-4-methylnicotinoyl)piperazine-1-carboxylate (45b)

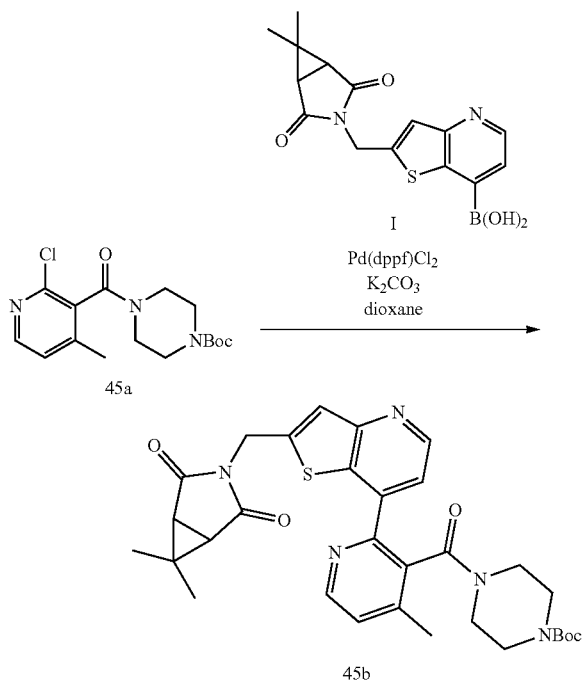

The title compound (45b) was obtained from 45a (76 mg; 0.23 mmol) and from I (60 mg; 0.18 mmol) according to the General Procedure Va and after standard work-up all the crude product mixture was taken to the next step.

ESI-MS m/z for $C_{31}H_{36}N_5O_5S$ found 590.6 [M+H]$^+$; $R_t$=1.39 min

Step 3

Synthesis of 6,6-dimethyl-3-((7-(4-methyl-3-(piperazine-1-carbonyl)pyridin-2-yl)thieno[3,2-b]pyridin-2-yl)methyl)-3-azabicyclo[3.1.0]hexane-2,4-dione hydrochloride (45)

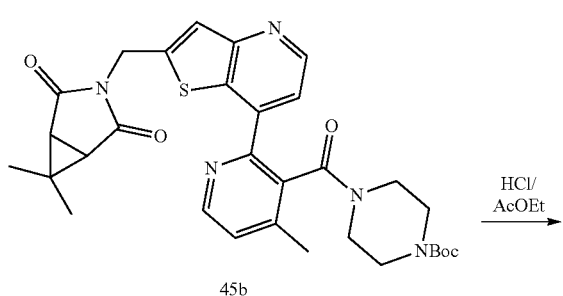

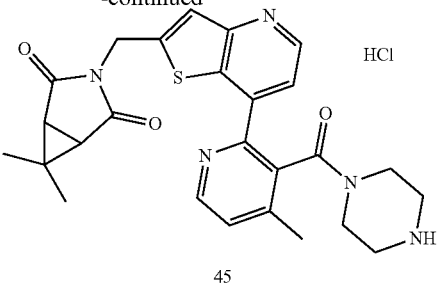

The title compound (45) was obtained as a hydrochloride salt from 45b (the crude reaction mixture) according to the General Procedure IVa in 26% yield (per two steps) (32 mg; 0.06 mmol). The crude product was purified by preparative reversed-phase column chromatography (C-18, water/MeCN, 98:2 to 20:80, 30 min, 20 mL/min). The obtained product was redissolved in water and to this solution 2 M HCl (3 drops) was added and then obtained hydrochloride salt was lyophilized.

ESI-MS m/z for $C_{26}H_{28}N_5O_3S$ found 490.4 [M+H]$^+$; $R_t$=0.82 min; $^1$H NMR (700 MHz, DMSO-d$_6$+D$_2$O, 348 K) δ 8.75-8.73 (m, 1H), 8.73-8.70 (m, 1H), 7.55-7.51 (m, 1H), 7.51-7.47 (m, 1H), 7.46-7.43 (m, 1H), 4.84-4.72 (m, 2H), 3.95-3.89 (m, 1H), 3.62-3.55 (m, 1H), 3.27-3.20 (m, 1H), 3.17-3.10 (m, 1H), 2.94-2.88 (m, 1H), 2.84-2.76 (m, 2H), 2.53-2.52 (m, 2H), 2.36 (s, 3H), 2.29-2.22 (m, 1H), 1.19 (s, 3H), 1.03 (s, 3H).

Example 46

Synthesis of 6,6-dimethyl-3-((7-(4-methyl-3-(piperazin-1-ylmethyl)pyridin-2-yl)thieno[3,2-b]pyridin-2-yl)methyl)-3-azabicyclo[3.1.0]hexane-2,4-dione hydrochloride (46)

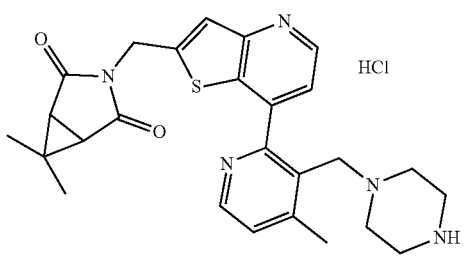

Step 1

Synthesis of tert-butyl 4-((2-chloro-4-methylpyridin-3-yl)methyl)piperazine-1-carboxylate (46a)

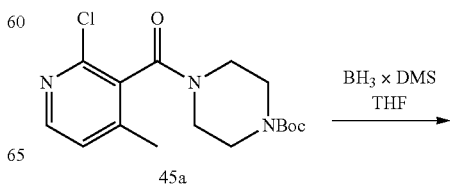

319

-continued

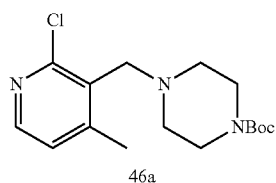

46a

The title compound (46a) was obtained as a white solid from 45a (274 mg; 0.80 mmol) according to the General Procedure VII in 14% yield (35 mg; 0.11 mmol).

ESI-MS m/z for $C_{16}H_{25}ClN_3O_2$ found 326.1/328.1 $[M+H]^+$, $R_t$=0.85 min Step 2

Synthesis of tert-butyl 4-((2-(2-((6,6-dimethyl-2,4-dioxo-3-azabicyclo[3.1.0]hexan-3-yl)methyl)thieno[3,2-b]pyridin-7-yl)-4-methylpyridin-3-yl)methyl)piperazine-1-carboxylate (46b)

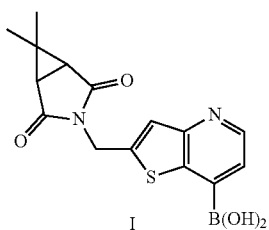

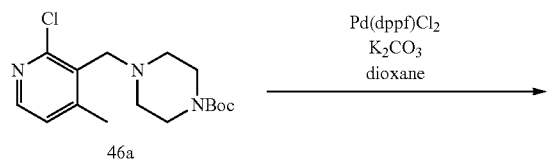

46b

The title compound (46b) was obtained from 46a (35 mg; 0.11 mmol) and from I (39 mg 0.12 mmol) according to the General Procedure Va and after standard work-up all the crude product mixture was taken to the next step.

ESI-MS m/z for $C_{31}H_{38}N_5O_4S$ found 576.6$[M+H]^+$, $R_t$=1.32 min

320

Step 3

Synthesis of 6,6-dimethyl-3-((7-(4-methyl-3-(piperazin-1-ylmethyl)pyridin-2-yl)thieno[3,2-b]pyridin-2-yl)methyl)-3-azabicyclo[3.1.0]hexane-2,4-dione hydrochloride (46)

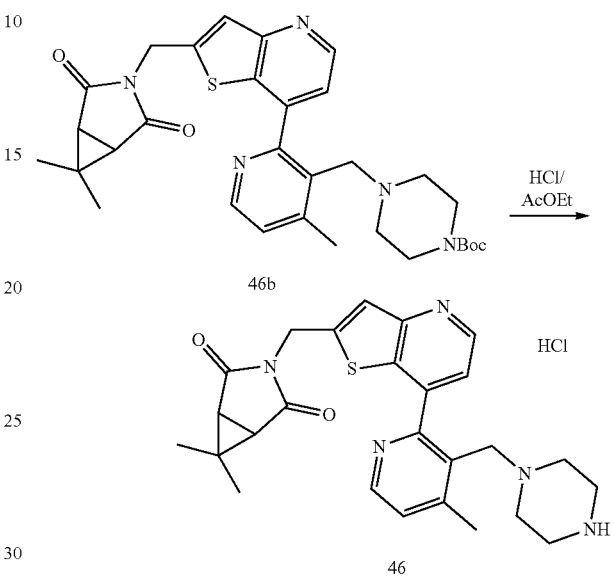

46

The title compound (46) was obtained as a hydrochloride salt from 46b (the crude reaction mixture) according to the General Procedure IVa in 36% yield (per two steps) (23 mg; 0.04 mmol). The crude product was purified by preparative reversed-phase column chromatography (C-18, water+0.5‰ HCl (36%)/MeCN, 99:1 to 30:70, 30 min, 20 mL/min).

ESI-MS m/z for $C_{26}H_{30}N_5O_2S$ found 476.5 $[M+H]^+$; $R_t$=0.73 min; $^1$H NMR (700 MHz, DMSO-$d_6$+$D_2O$, 348 K) δ 8.82-8.79 (m, 1H), 8.56-8.53 (m, 1H), 7.66-7.63 (m, 1H), 7.61-7.56 (m, 1H), 7.53-7.50 (n, 1H), 4.84-4.76 (m, 2H), 3.57 (s, 2H), 2.82-2.73 (m, 4H), 2.55 (s, 3H), 2.52 (s, 2H), 2.38-2.30 (m, 4H), 1.19 (s, 3H), 1.04 (s, 3H).

Example 47

Synthesis of 6-(2-((6,6-dimethyl-2,4-dioxo-3-azabicyclo[3.1.0]hexan-3-yl)methyl)thieno[3,2-b]pyridin-7-yl)-4-methyl-5-((S)-2-methylpiperazine-1-carbonyl)picolinonitrile hydrochloride (47)

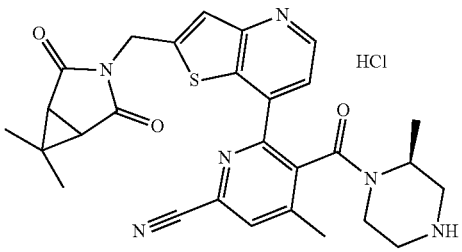

47

Step 1

Synthesis of tert-butyl (3S)-4-(6-cyano-2-(2-((6,6-dimethyl-2,4-dioxo-3-azabicyclo[3.1.0]hexan-3-yl)methyl)thieno[3,2-b]pyridin-7-yl)-4-methylnicotinoyl)-3-methylpiperazine-1-carboxylate (47a)

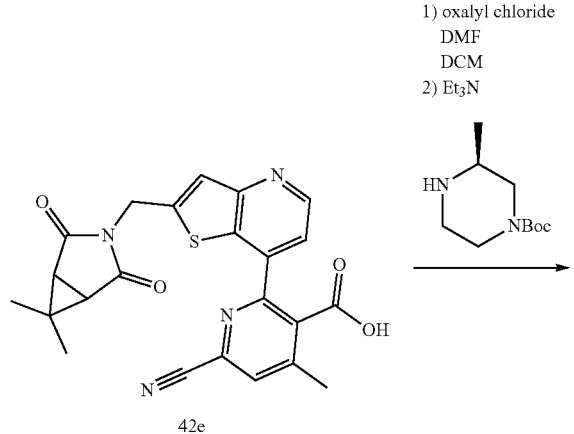

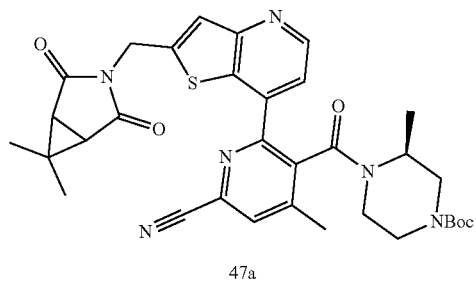

To the suspension of 42e (50 mg; 0.11 mmol) in DCM (1 mL) DMF (4 drops) was added and then an oxalyl chloride (0.011 mL; 0.12 mmol) was added dropwise at room temperature under an argon atmosphere. Then this mixture was stirred at room temperature for 1 hour. The reaction progress was monitored by LC-MS. Next to this mixture Et₃N (0.05 mL; 0.28 mmol) and tert-butyl (S)-3-methylpiperazine-1-carboxylate (25 mg; 0.12 mmol) were added and whole was stirred at room temperature for 2 hours. When analysis indicated completion of the reaction, the mixture was concentrated in vacuo and all the crude product mixture was taken to the next step.

ESI-MS m/z for $C_{33}H_{37}N_6O_5S$ found 629.3 [M+H]⁺; $R_t$=1.39 min

Step 2

Synthesis of 6-(2-((6,6-dimethyl-2,4-dioxo-3-azabicyclo[3.1.0]hexan-3-yl)methyl)thieno[3,2-b]pyridin-7-yl)-4-methyl-5-((S)-2-methylpiperazine-1-carbonyl)picolinonitrile hydrochloride (47)

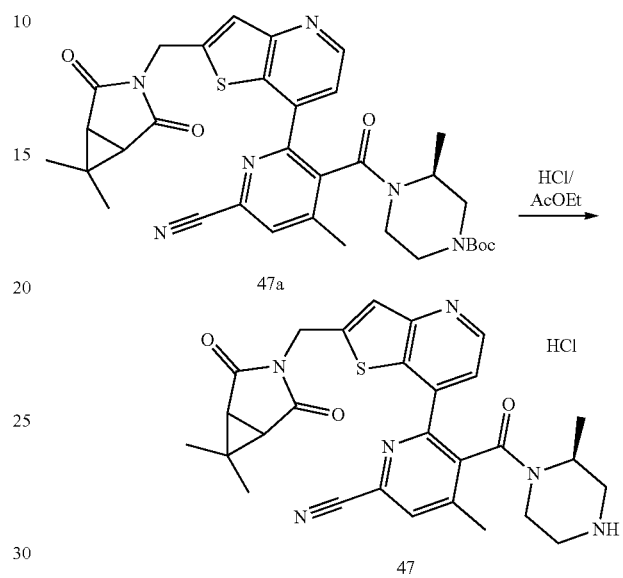

The title compound (47) was obtained as a hydrochloride salt from 47a (the crude reaction mixture) according to the General Procedure IVa in 55% yield (per two steps) (36 mg; 0.06 mmol). The crude product was purified by preparative reversed-phase column chromatography (C-18, water+0.3‰ HCl (36%)/MeCN, 98:2 to 30:70, 30 min, 20 mL/min).

ESI-MS m/z for $C_{28}H_{29}N_6O_3S$ found 529.3 [M+H]⁺; $R_t$=0.93 min; ¹H NMR (700 MHz, DMSO-d₆+D₂O, 348 K) δ 8.83-8.48 (m, 1H), 8.17-8.07 (m, 1H), 7.57-7.34 (m, 2H), 4.94-4.73 (m, 3H), 3.44-3.33 (m, 1H), 3.25-3.05 (m, 2H), 2.98-2.57 (m, 2H), 2.55-2.52 (m, 3H), 2.47-2.34 (m, 3H), 1.39-0.84 (m, 9H).

Example 48

Synthesis of 6,6-dimethyl-3-((7-(4-methyl-3-(morpholine-4-carbonyl)pyridin-2-yl)thieno[3,2-b]pyridin-2-yl)methyl)-3-azabicyclo[3.1.0]hexane-2,4-dione hydrochloride (48)

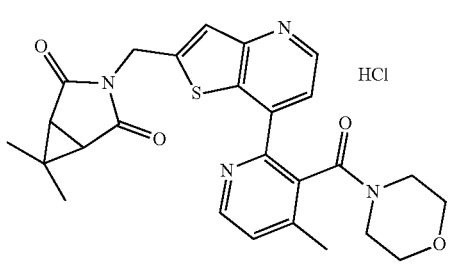

Step 1

Synthesis of (2-chloro-4-methylpyridin-3-yl)(morpholino)methanone (48a)

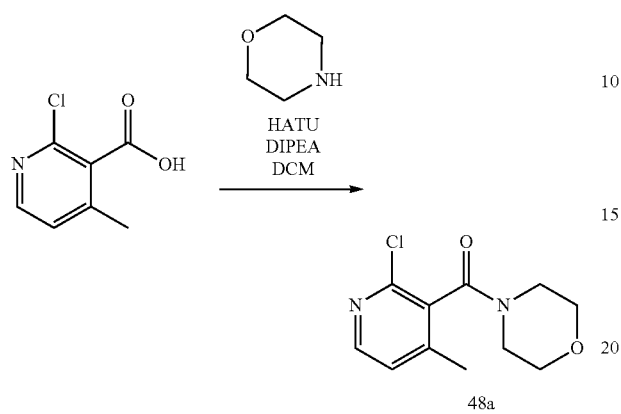

The title compound (48a) was obtained as a white solid from 2-chloro-4-methylnicotinic acid (200 mg; 1.17 mmol) and from morpholine (152 mg; 1.75 mmol) according to the General Procedure I in 59% yield (166 mg; 0.69 mmol).

ESI-MS m/z for $C_{11}H_{14}ClN_2O_2$ found 241.1/243.1 $[M+H]^+$; $R_t$=0.57 min

Step 2

Synthesis of 6,6-dimethyl-3-((7-(4-methyl-3-(morpholine-4-carbonyl)pyridin-2-yl)thieno[3,2-b]pyridin-2-yl)methyl)-3-azabicyclo[3.1.0]hexane-2,4-dione hydrochloride (48)

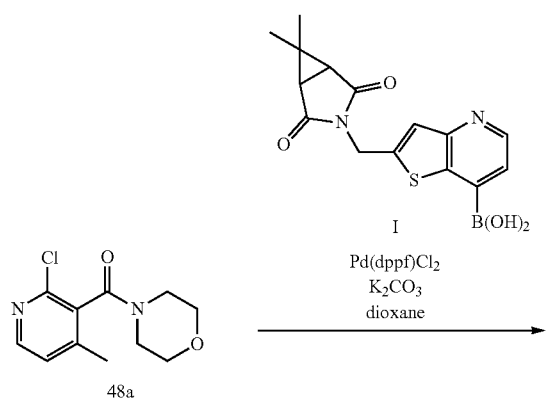

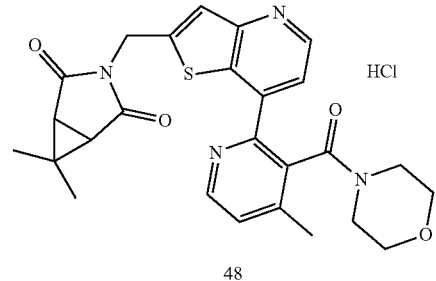

The title compound (48) was obtained from 48a (55 mg; 0.23 mmol) and from I (60 mg; 0.18 mmol) according to the General Procedure Va in 17% yield (18 mg; 0.03 mmol). The crude product was purified by preparative reversed-phase column chromatography (C-18, water+0.3‰ HCl (36%)/MeCN, 90:10 to 20:80, 30 min, 20 mL/min).

ESI-MS m/z for $C_{26}H_{27}N_4O_4S$ found 491.2 $[M+H]^+$; $R_t$=1.07 min; $^1$H NMR (700 MHz, DMSO-d$_6$+D$_2$O, 348 K) δ 8.70-8.68 (m, 1H), 8.69-8.65 (m, 1H), 7.49-7.44 (m, 3H), 4.81-4.70 (m, 2H), 3.61-3.45 (m, 3H), 3.24-3.10 (m, 2H), 3.02-2.90 (m, 1H), 2.63-2.52 (m, 4H), 2.33 (s, 3H), 1.17 (s, 3H), 1.00 (s, 3H).

Example 49

Synthesis of 3-((7-(3-(3,3-difluoropyrrolidine-1-carbonyl)-4-methylpyridin-2-yl)thieno[3,2-b]pyridin-2-yl)methyl)-6,6-dimethyl-3-azabicyclo[3.1.0]hexane-2,4-dione hydrochloride (49)

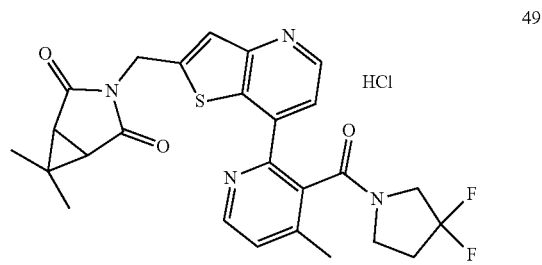 [SMILES: Cc1ccnc(-c2ccnc3cc(CN4C(=O)C5C(C4=O)C5(C)C)sc23)c1C(=O)N1CCC(F)(F)C1 ; Cl]

The title compound (49) was obtained as a hydrochloride salt in 27% overall yield in a similar way to Example 48 with the exception that, in the first step of the synthesis 3,3-difluoropyrrolidine hydrochloride was used instead of morpholine and in the last step of the synthesis the crude product was purified by preparative reversed-phase column chromatography (C-18, water+0.3‰ HCl (36%)/MeCN, 90:10 to 20:80, 30 min, 20 mL/min).

ESI-MS m/z for $C_{26}H_{25}F_2N_4O_3S$ found 511.2 $[M+H]^+$; $R_t$=1.23 min; $^1$H NMR (700 MHz, DMSO-d$_6$+D$_2$O, 348 K) δ 8.72-8.70 (m, 1H), 8.70-8.67 (m, 1H), 7.52-7.49 (m, 1H), 7.48-7.43 (m, 2H), 4.86-4.72 (m, 2H), 3.92-3.67 (m, 1H), 3.51-3.33 (m, 2H), 3.23-3.11 (m, 1H), 2.92-2.66 (m, 1H), 2.50-1.88 (m, 6H), 1.20-1.13 (m, 3H), 1.02-0.91 (m, 3H).

Example 50

Synthesis of 3-((7-(3-(3,3-difluoroazetidine-1-carbonyl)-4-methylpyridin-2-yl)thieno[3,2-b]pyridin-2-yl)methyl)-6,6-dimethyl-3-azabicyclo[3.1.0]hexane-2,4-dione hydrochloride (50)

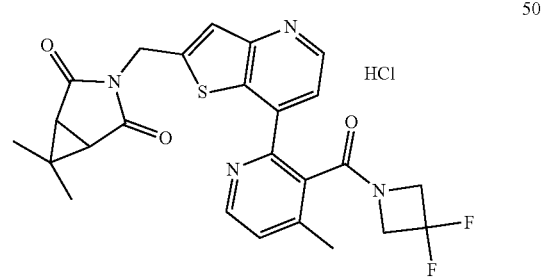 [SMILES: Cc1ccnc(-c2ccnc3cc(CN4C(=O)C5C(C4=O)C5(C)C)sc23)c1C(=O)N1CC(F)(F)C1 ; Cl]

The title compound (50) was obtained as a hydrochloride salt in 2% overall yield in a similar way to Example 48 with the exception that, in the first step of the synthesis 3,3-difluoroazetidine hydrochloride was used instead of morpholine and in the last step of the synthesis the crude product was purified by preparative reversed-phase column chromatography (C-18, water+0.3‰ HCl (36%)/MeCN, 90:10 to 20:80, 30 min, 20 mL/min).

ESI-MS m/z for $C_{26}H_{23}F_2N_4O_3S$ found 497.2 [M+H]$^+$; $R_t$=1.93 min; $^1$H NMR (700 MHz, DMSO-d$_6$+D$_2$O) δ 8.76-8.72 (m, 2H), 7.57-7.54 (m, 1H), 7.52-7.49 (m, 1H), 7.49-7.45 (m, 1H), 4.84-4.71 (m, 2H), 4.55-4.42 (m, 1H), 4.26-4.15 (m, 2H), 3.38-3.28 (m, 1H), 2.55 (s, 2H), 2.38 (s, 3H), 1.14 (s, 3H), 0.91 (s, 3H); $^{19}$F NMR (235 MHz, DMSO-d$_6$) δ−100.99−−101.33 (m).

Example 51

Synthesis of 5-(3,3-difluoroazetidine-1-carbonyl)-6-(2-((6,6-dimethyl-2,4-dioxo-3-azabicyclo[3.1.0]hexan-3-yl)methyl)thieno[3,2-b]pyridin-7-yl)-4-methylpicolinonitrile hydrochloride (51)

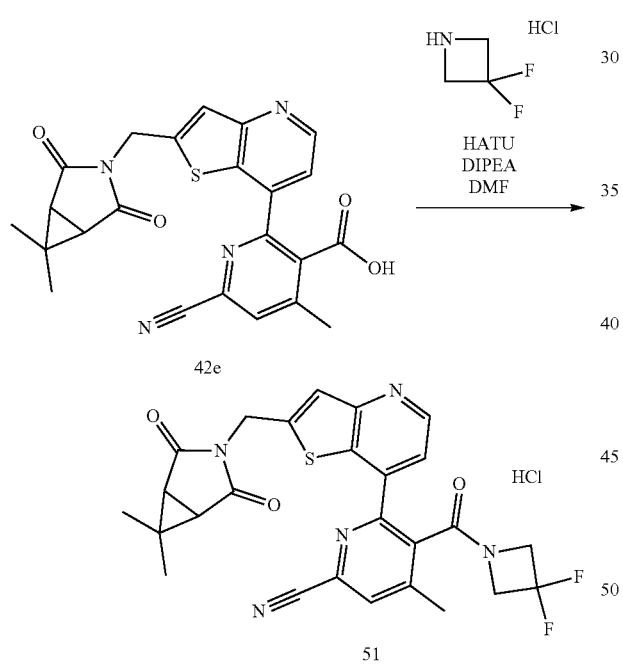

The title compound (51) was obtained as a hydrochloride salt from 42e (50 mg; 0.11 mmol) and from 3,3-difluoroazetidine hydrochloride (20 mg; 0.13 mmol) according to the General Procedure I in 27% yield (16 mg; 0.03 mmol). The crude product was purified twice by preparative reversed-phase column chromatography (first: C-18, water+0.3‰ HCl (36%)/MeCN, 98:2 to 30:70, 30 min, 20 mL/min; second: C-18, water+0.3‰ HCl (36%)/MeCN, 90:10 to 10:90, 30 min, 20 mL/min).

ESI-MS m/z for $C_{26}H_{22}F_2N_5O_3S$ found 522.3 [M+H]$^+$; $R_t$=1.35 min; $^1$H NMR (700 MHz, DMSO-d$_6$+D$_2$O) δ 8.78-8.75 (m, 1H), 8.19-8.15 (m, 1H), 7.55-7.51 (m, 1H), 7.47-7.43 (m, 1H), 4.89-4.75 (m, 2H), 4.54-4.43 (m, 1H), 4.38-4.19 (m, 2H), 3.44-3.33 (m, 1H), 2.58-2.54 (m, 2H), 2.45 (s, 3H), 1.14 (s, 3H), 0.93 (s, 3H).

Example 52

Synthesis of 6-(2-((6,6-dimethyl-2,4-dioxo-3-azabicyclo[3.1.0]hexan-3-yl)methyl)thieno[3,2-b]pyridin-7-yl)-5-((S)-2,4-dimethylpiperazine-1-carbonyl)-4-methylpicolinonitrile dihydrochloride (52)

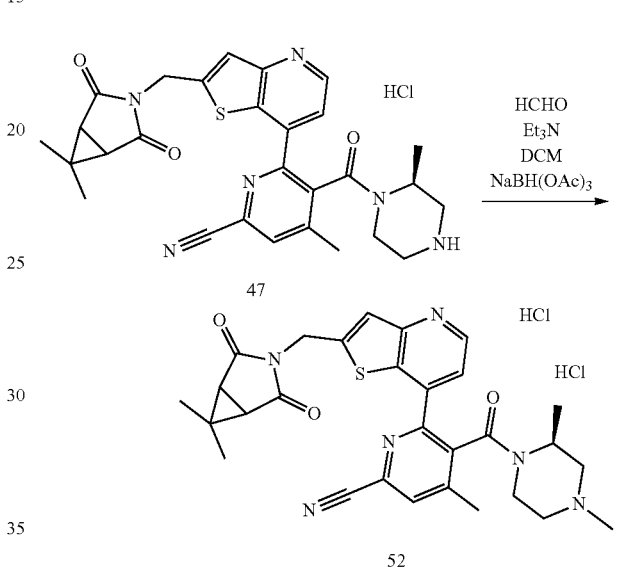

To the solution of 47 (100 mg; 0.19 mmol) in DCM (5 mL) Et$_3$N (0.13 mL; 0.76 mmol) and formalin (36% aqueous solution; 0.3 mL) were added and this mixture was stirred at room temperature for 5 minutes. Then to this mixture NaBH(OAc)$_3$ (62 mg; 0.287 mmol) was added and whole was stirred at room temperature for 2 hours. The reaction progress was monitored by LC-MS. Then another portion of formalin (36% aqueous solution; 0.1 mL) and NaBH(OAc)$_3$ (62 mg; 0.287 mmol) was added and stirred at room temperature for 1 hour. When analysis indicated completion of the reaction, the mixture was diluted with DCM and washed with 5% NaHCO$_3$. The organic layer was dried over anhydrous MgSO$_4$, filtered and concentrated in vacuo and the residue was purified by preparative reversed-phase column chromatography (C-18, water+0.3‰ HCl (36%)/MeCN, 98:2 to 30:70, 30 min, 20 mL/min). The title compound (52) was obtained as a dihydrochloride salt as a white solid in 47% yield (56 mg; 0.09 mmol).

ESI-MS m/z for $C_{29}H_{31}N_6O_3S$ found 543.6 [M+H]$^+$; $R_t$=0.94 min; $^1$H NMR (700 MHz, DMSO-d$_6$+D$_2$O, 348 K) δ 8.85-8.69 (m, 1H), 8.16-8.08 (m, 1H), 7.58-7.31 (m, 2H), 4.96-4.70 (m, 3H), 3.61-3.38 (m, 1H), 3.23-2.83 (m, 3H), 2.77-2.60 (m, 4H), 2.54-2.53 (m, 2H), 2.47-2.34 (m, 4H), 1.39-0.17 (m, 9H).

Example 53

Synthesis of 6-(2-((6,6-dimethyl-2,4-dioxo-3-azabicyclo[3.1.0]hexan-3-yl)methyl)thieno[3,2-b]pyridin-7-yl)-5-(3,3-dimethylpiperazine-1-carbonyl)-4-methylpicolinonitrile hydrochloride (53)

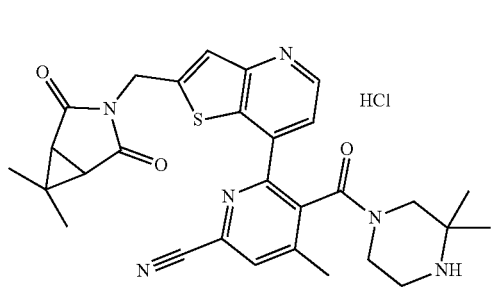

Step 1

Synthesis of tert-butyl 4-(6-cyano-2-(2-((6,6-dimethyl-2,4-dioxo-3-azabicyclo[3.1.0]hexan-3-yl)methyl)thieno[3,2-b]pyridin-7-yl)-4-methylnicotinoyl)-2,2-dimethylpiperazine-1-carboxylate (53a)

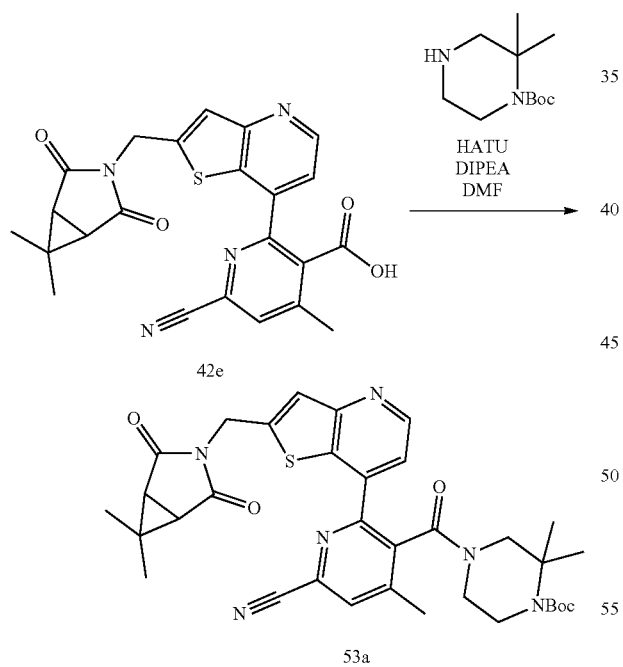

The title compound (53a) was obtained as a white solid from 42e (50 mg; 0.11 mmol) and from tert-butyl 2,2-dimethylpiperazine-1-carboxylate (29 mg; 0.13 mmol) according to the General Procedure I and after standard work-up all the crude product mixture was taken to the next step.

ESI-MS m/z for $C_{34}H_{39}N_6O_5S$ found 643.6 $[M+H]^+$; $R_t$=1.57 min

Step 2

Synthesis of 6-(2-((6,6-dimethyl-2,4-dioxo-3-azabicyclo[3.1.0]hexan-3-yl)methyl)thieno[3,2-b]pyridin-7-yl)-5-(3,3-dimethylpiperazine-1-carbonyl)-4-methylpicolinonitrile hydrochloride (53)

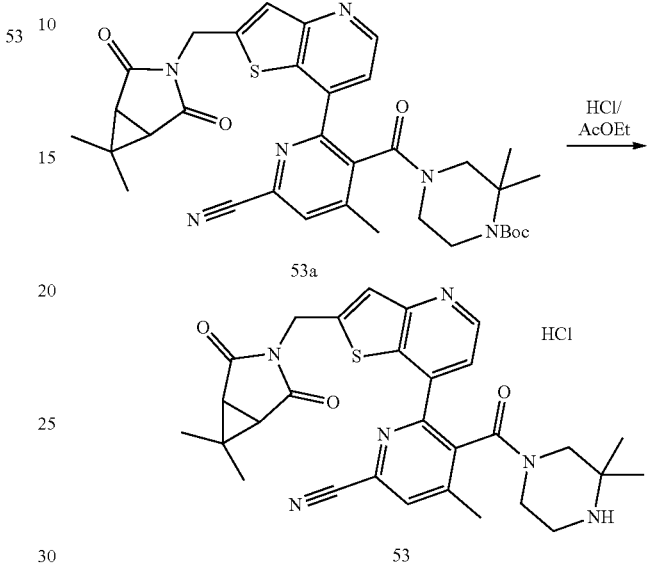

The title compound (53) was obtained as a hydrochloride salt as a white solid from 53a (the crude reaction mixture) according to the General Procedure IVa in 22% yield (per two steps) (14 mg; 0.024 mmol). The crude product was purified by preparative reversed-phase column chromatography (C-18, water/MeCN, 98:2 to 30:70, 30 min, 20 mL/min). The obtained product was redissolved in water and to this solution 2 M HCl (3 drops) was added and then obtained hydrochloride salt was lyophilized.

ESI-MS m/z for $C_{29}H_{31}N_6O_3S$ found 543.4 $[M+H]^+$; $R_t$=0.97 min; H NMR (700 MHz, DMSO-$d_6$+$D_2O$, 348 K) δ 8.76-8.71 (m, 1H), 8.15-8.08 (m, 1H), 7.54-7.36 (m, 2H), 4.86-4.76 (m, 2H), 4.05-3.61 (m, 1H), 3.28-3.15 (m, 1H), 3.03-2.73 (m, 2H), 2.55-2.52 (m, 2H), 2.49-2.37 (m, 5H), 1.34-1.19 (m, 5H), 1.09-0.94 (m, 6H), 0.62-0.45 (m, 1H).

Example 54

Synthesis of 6-(2-((6,6-dimethyl-2,4-dioxo-3-azabicyclo[3.1.0]hexan-3-yl)methyl)thieno[3,2-b]pyridin-7-yl)-4-methyl-5-((R)-2-methylpiperazine-1-carbonyl)picolinonitrile hydrochloride (54)

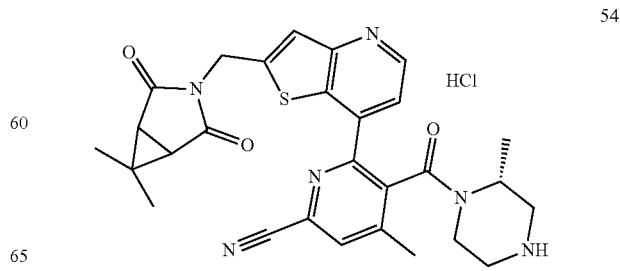

The title compound (54) was obtained as a hydrochloride salt in 6% overall yield in a similar way to Example 53 with the exception that, in the first step of the synthesis tert-butyl (R)-3-methylpiperazine-1-carboxylate was used instead of tert-butyl 2,2-dimethylpiperazine-1-carboxylate and in the last step of the synthesis the crude product was purified by preparative reversed-phase column chromatography (C-18, water/MeCN, 98:2 to 30:70, 30 min, 20 mL/min). The obtained product was redissolved in water and to this solution 2 M HCl (3 drops) was added and then obtained hydrochloride salt was lyophilized.

ESI-MS m/z for $C_{28}H_{29}N_6O_3S$ found 529.3 [M+H]$^+$; $R_t$=0.96 min; $^1$H NMR (700 MHz, DMSO-d$_6$+D$_2$O, 348 K) δ 8.82-8.68 (m, 1H), 8.16-8.06 (m, 1H), 7.60-7.33 (m, 2H), 4.93-4.71 (m, 3H), 3.49-3.33 (m, 1H), 3.24-2.57 (m, 5H), 2.55-2.52 (m, 2H), 2.49-2.35 (m, 3H), 1.53-0.16 (m, 9H).

Example 55

Synthesis of 6-(2-((6,6-dimethyl-2,4-dioxo-3-azabicyclo[3.1.0]hexan-3-yl)methyl)thieno[3,2-b]pyridin-7-yl)-4-methyl-5-(piperazine-1-carbonyl)picolinonitrile hydrochloride (55)

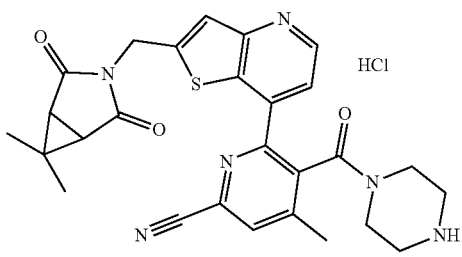

The title compound (55) was obtained as a hydrochloride salt in 45% overall yield in a similar way to Example 53 with the exception that, in the first step of the synthesis tert-butyl piperazine-1-carboxylate was used instead of tert-butyl 2,2-dimethylpiperazine-1-carboxylate and in the last step of the synthesis the crude product was purified by preparative reversed-phase column chromatography (C-18, water/MeCN, 98:2 to 30:70, 30 min, 20 mL/min). The obtained product was redissolved in water and to this solution 2 M HCl (3 drops) was added and then obtained hydrochloride salt was lyophilized.

ESI-MS m/z for $C_{27}H_{27}N_6O_3S$ found 515.4 [M+H]$^+$; $R_t$=0.94 min; $^1$H NMR (700 MHz, DMSO-d$_6$+D$_2$O, 348 K) δ 8.78-8.75 (m, 1H), 8.12-8.09 (m, 1H), 7.53-7.49 (m, 1H), 7.45-7.40 (m, 1H), 4.87-4.77 (m, 2H), 4.00-3.90 (m, 1H), 3.57-3.45 (m, 1H), 3.30-3.22 (m, 1H), 3.17-3.11 (m, 1H), 2.97-2.90 (m, 1H), 2.84-2.76 (m, 2H), 2.55-2.52 (m, 2H), 2.42 (s, 3H), 2.35-2.28 (m, 1H), 1.19 (s, 3H), 1.06 (s, 3H).

Example 56

Synthesis of N-(azetidin-3-yl)-6-cyano-2-(2-((6,6-dimethyl-2,4-dioxo-3-azabicyclo[3.1.0]hexan-3-yl)methyl)thieno[3,2-b]pyridin-7-yl)-4-methylnicotinamide hydrochloride (56)

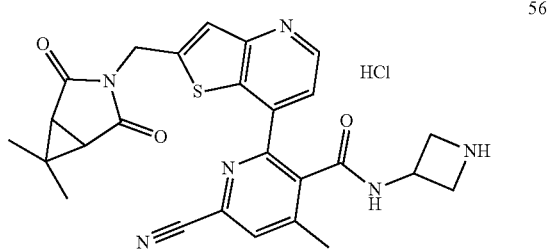 [SMILES: Cc1cc(C#N)nc(-c2ccnc3cc(CN4C(=O)C5C(C4=O)C5(C)C)sc23)c1C(=O)NC1CNC1 ; Cl]

The title compound (56) was obtained as a hydrochloride salt in 37% overall yield in a similar way to Example 53 with the exception that, in the first step of the synthesis tert-butyl 3-aminoazetidine-1-carboxylate was used instead of tert-butyl 2,2-dimethylpiperazine-1-carboxylate and in the last step of the synthesis the crude product was purified by preparative reversed-phase column chromatography (C-18, water/MeCN, 98:2 to 30:70, 30 min, 20 mL/min). The obtained product was redissolved in water and to this solution 2 M HCl (3 drops) was added and then obtained hydrochloride salt was lyophilized.

ESI-MS m/z for $C_{26}H_{25}N_6O_3S$ found 501.6 [M+H]$^+$; $R_t$=0.92 min; H NMR (700 MHz, DMSO-d$_6$+D$_2$O, 348 K) δ 8.73-8.69 (m, 1H), 8.12-8.05 (m, 1H), 7.57-7.54 (m, 1H), 7.50-7.45 (m, 1H), 4.83-4.77 (m, 2H), 4.66-4.58 (m, 1H), 4.20-4.09 (m, 2H), 3.91-3.81 (m, 2H), 2.54-2.53 (m, 2H), 2.46 (s, 3H), 1.20 (s, 3H), 1.10 (s, 3H).

Example 57

Synthesis of 6-cyano-N-(3,3-difluorocyclobutyl)-2-(2-((6,6-dimethyl-2,4-dioxo-3-azabicyclo[3.1.0]hexan-3-yl)methyl)thieno[3,2-b]pyridin-7-yl)-4-methylnicotinamide hydrochloride (57)

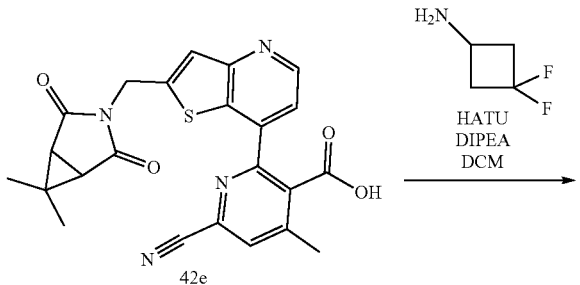

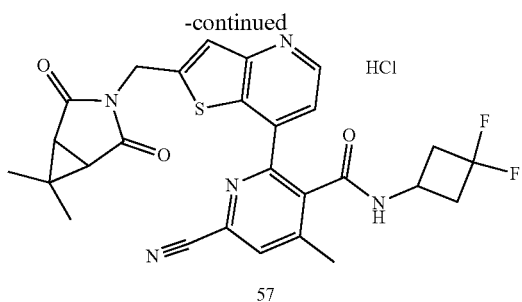

57

The title compound (57) was obtained as a hydrochloride salt from 42e (50 mg; 0.110 mmol) and from 3,3-difluoro-cyclobutan-1-amine (20 mg; 0.13 mmol) according to the General Procedure I in 62% yield (39 mg; 0.068 mmol). The crude product was purified by preparative reversed-phase column chromatography (C-18, water+0.3‰ HCl (36%)/MeCN, 98:2 to 30:70, 30 min, 20 mL/min).

ESI-MS m/z for $C_{27}H_{24}F_2N_5O_3S$ found 536.5 [M+H]$^+$; $R_t$=1.38 min; $^1$H NMR (700 MHz, DMSO-$d_6$+$D_2O$) δ 8.70-8.66 (m, 1H), 8.07-8.02 (m, 1H), 7.56-7.51 (m, 1H), 7.48-7.44 (m, 1H), 4.83-4.70 (m, 2H), 4.12-3.98 (m, 1H), 2.87-2.79 (m, 2H), 2.52 (s, 2H), 2.43 (s, 3H), 2.41-2.28 (m, 2H), 1.19 (s, 3H), 1.07 (s, 3H).

Example 58

Synthesis of 6-(2-((6,6-dimethyl-2,4-dioxo-3-azabicyclo[3.1.0]hexan-3-yl)methyl)thieno[3,2-b]pyridin-7-yl)-4-methyl-5-(morpholine-4-carbonyl)picolinonitrile hydrochloride (58)

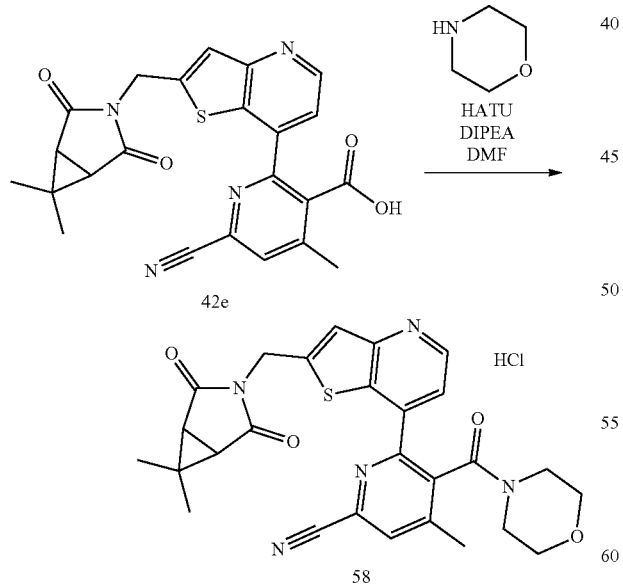

The title compound (58) was obtained as a hydrochloride salt from 42e (50 mg; 0.110 mmol) and from morpholine (16 mg; 0.180 mmol) according to the General Procedure I in 40% yield (24 mg; 0.044 mmol). The crude product was purified by preparative reversed-phase column chromatography (C-18, water+0.5‰ HCl (6 M)/MeCN, 98:2 to 30:70, 30 min, 20 mL/min).

ESI-MS m/z for $C_{27}H_{25}N_5O_4S$ found 516.3 [M+H]$^+$; $R_t$=1.23 min; $^1$H NMR (700 MHz, DMSO-$d_6$+$D_2O$) δ 8.76-8.72 (m, 1H), 8.11-8.04 (m, 1H), 7.51-7.46 (m, 2H), 4.83-4.76 (m, 2H), 3.58-3.54 (m, 1H), 3.51-3.47 (m, 2H), 3.26-3.19 (m, 2H), 3.05-2.98 (m, 1H), 2.64-2.56 (m, 2H), 2.55-2.52 (m, 1H), 2.50-2.47 (m, 1H), 2.40 (s, 3H), 1.18 (s, 3H), 1.03 (s, 3H).

Example 59

Synthesis of 5-(3,3-difluoropyrrolidine-1-carbonyl)-6-(2-((6,6-dimethyl-2,4-dioxo-3-azabicyclo[3.1.0]hexan-3-yl)methyl)thieno[3,2-b]pyridin-7-yl)-4-methylpicolinonitrile hydrochloride (59)

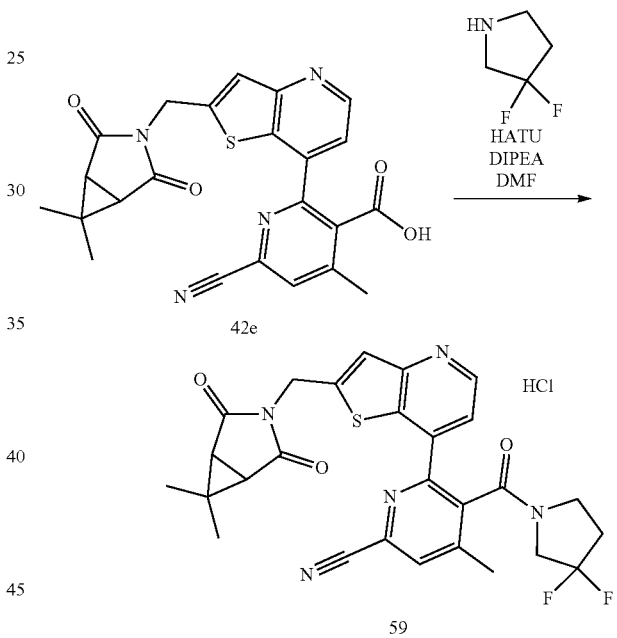

The title compound (59) was obtained as a hydrochloride salt from 42e (50 mg; 0.110 mmol) and from 3,3-difluoropyrrolidine (20 mg; 0.130 mmol) according to the General Procedure I in 57% yield (36 mg; 0.063 mmol). The crude product was purified by preparative reversed-phase column chromatography (C-18, water/MeCN, 98:2 to 30:70, 30 min, 20 mL/min). The obtained product was redissolved in water and to this solution 2 M HCl (3 drops) was added and then obtained hydrochloride salt was lyophilized.

ESI-MS m/z for $C_{27}H_{24}F_2N_5O_3S$ found 536.5 [M+H]$^+$; $R_t$=1.38 min; $^1$H NMR (700 MHz, DMSO-$d_6$+$D_2O$) δ 8.73-8.69 (m, 1H), 8.12-8.04 (m, 1H), 7.50-7.47 (m, 1H), 7.46-7.40 (m, 1H), 4.89-4.71 (m, 2H), 3.94-3.68 (m, 2H), 3.54-3.41 (m, 1H), 3.27-3.22 (m, 1H), 2.99-2.69 (m, 1H), 2.53-2.52 (m, 1H), 2.44-1.90 (m, 5H), 1.23-1.14 (m, 3H), 1.07-0.95 (m, 3H).

Example 60

Synthesis of N-(4-(2-(((6,6-dimethyl-2,4-dioxo-3-azabicyclo[3.1.0]hexan-3-yl)methyl)thieno[3,2-b]pyridin-7-yl)-2-methyl-6-(trifluoromethyl)pyridin-3-yl)-2-(methylamino)acetamide 2,2,2-trifluoroacetate (60)

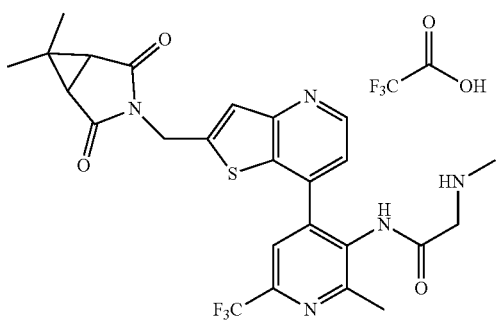

The title compound (60) was obtained as a TFA salt in 24% overall yield in a similar way to Example 27 with the exception that, in the first step of the synthesis, 2-methyl-6-(trifluoromethyl)pyridin-3-amine was used instead of 5-amino-6-methylpicolinonitrile, in the second step of the synthesis. N-(tert-butoxycarbonyl)-N-methylglycine was used instead of 1-(tert-butoxycarbonyl)azetidine-2-carboxylic acid and in the last step of the synthesis the crude product was purified by preparative reversed-phase column chromatography (C-18, water/MeCN+0.5‰ TFA, 90:10 to 30:70, 30 min, 20 mL/min).

ESI-MS m/z for $C_{25}H_{25}F_3N_6O_3S$ found 532.7 [M+H]$^+$; $R_t$=1.00 min; 1H NMR (700 MHz, DMSO-d$_6$+D$_2$O) δ 8.70 (d, J=4.8 Hz, 1H), 7.85 (s, 1H), 7.50 (s, 1H), 7.26 (d, J=4.9 Hz, 1H), 4.78 (s, 2H), 3.68 (s, 2H), 2.58 (s, 3H), 2.53 (s, 2H), 2.40 (s, 3H), 1.18 (s, 3H), 1.06 (s, 3H).

Example 61

Synthesis of N-(4-(2-(((6,6-dimethyl-2,4-dioxo-3-azabicyclo[3.1.0]hexan-3-yl)methyl)thieno[3,2-b]pyridin-7-yl)-2-methyl-6-(trifluoromethyl)pyridin-3-yl)-2-methoxyacetamide 2,2,2-trifluoroacetate (61)

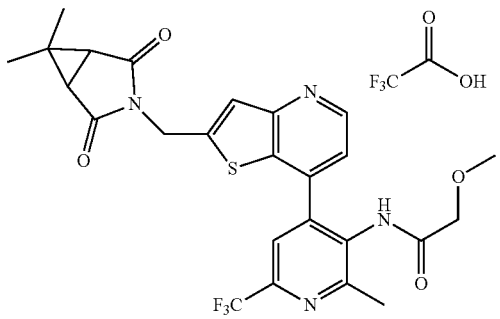

Step 1

Synthesis of N-(4-bromo-2-methyl-6-(trifluoromethyl)pyridin-3-yl)-2-methoxyacetamide (61a)

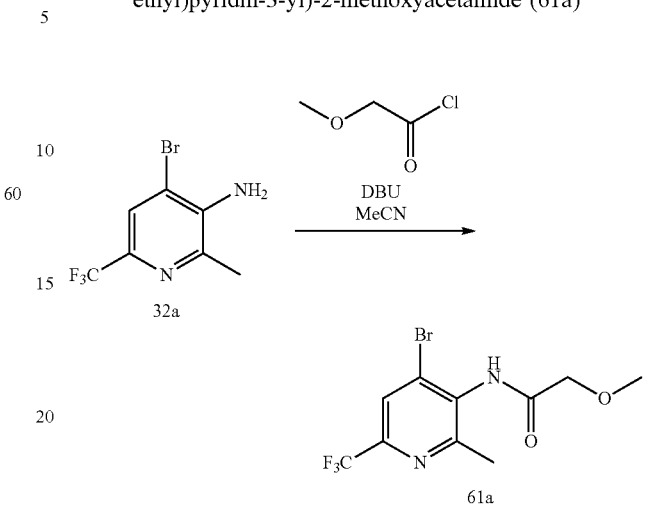

To the solution of 32a (100 mg; 0.39 mmol) in MeCN (1 mL) DBU (128 µL; 0.85 mmol) was added and stirred at room temperature for 30 minutes. Then to this solution 2-methoxyacetyl chloride (46 mg; 0.43 mmol) was added and stirred at room temperature for 6 hours. The reaction progress was monitored by LC-MS. When analysis indicated completion of the reaction, the mixture was diluted with AcOEt and washed with 5% NaHCO$_3$ and 1 M HCl. The organic layer was dried over anhydrous MgSO$_4$, filtered and concentrated in vacuo and the crude product was used to the next step without additional purification. Compound 61a was obtained as a light yellow foam in 60% yield (76 mg; 0.23 mmol).

ESI-MS m/z for $C_{10}H_{11}BrF_3N_2O_2$ found 326.7/328.6 [M+H]$^+$; $R_t$=1.01 min

Step 2

Synthesis of N-(4-(2-(((6,6-dimethyl-2,4-dioxo-3-azabicyclo[3.1.0]hexan-3-yl)methyl)thieno[3,2-b]pyridin-7-yl)-2-methyl-6-(trifluoromethyl)pyridin-3-yl)-2-methoxyacetamide 2,2,2-trifluoroacetate (61)

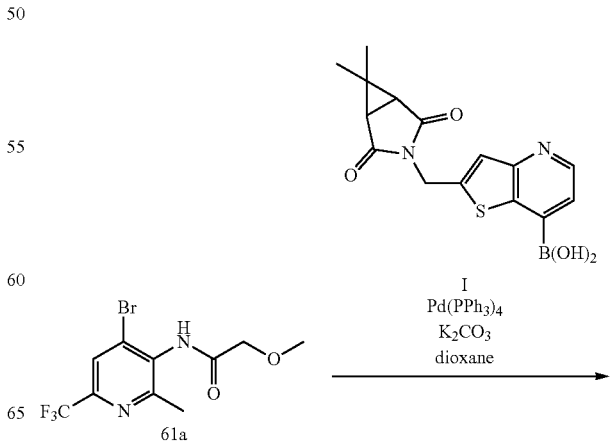

335

-continued

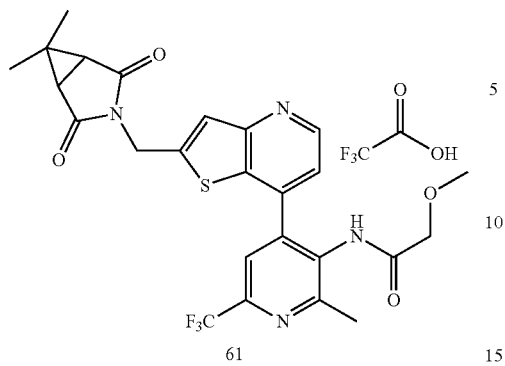

61

The title compound (61) was obtained as a TFA salt from 61a (70 mg; 0.21 mmol) and from boronic acid I (170 mg; 0.51 mmol) according to the General Procedure Va in 57% yield (76 mg; 0.12 mmol). The crude product was purified by flash column chromatography on silica (DCM/MeOH, 100:0 to 50:50, v/v, 30 minutes) and then by preparative reversed-phase column chromatography (C-18, water/MeCN+0.5‰ TFA, 90:10 to 30:70, 30 min, 20 mL/min).

ESI-MS m/z for $C_{25}H_{24}F_5N_4O_4S$ found 533.4 [M+H]$^+$; $R_t$=1.31 min; $^1$H NMR (700 MHz, DMSO-d$_6$+D$_2$O, 348 K) δ 8.68 (d, J=4.8 Hz, 1H), 7.81 (s, 1H), 7.49 (s, 1H), 7.27 (d, J=4.8 Hz, 1H), 4.77 (s, 2H), 3.72 (s, 2H), 3.08 (s, 3H), 2.54 (s, 3H), 2.52 (s, 2H), 1.17 (s, 3H), 1.03 (s, 3H).

Example 62

Synthesis of N-(4-(2-((6,6-dimethyl-2,4-dioxo-3-azabicyclo[3.1.0]hexan-3-yl)methyl)thieno[3,2-b]pyridin-7-yl)-2-methyl-6-(trifluoromethyl)pyridin-3-yl)-2,2,2-trifluoroacetamide 2,2,2-trifluoroacetate (62)

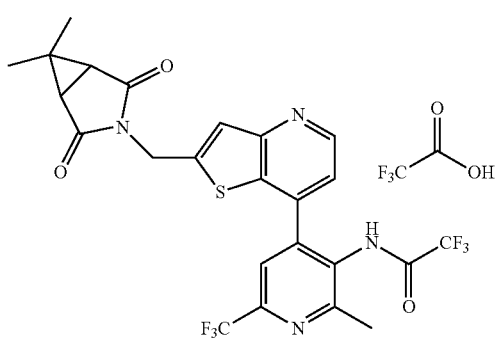

62

336

Step 1

Synthesis of 3-((7-(3-amino-2-methyl-6-(trifluoromethyl)pyridin-4-yl)thieno[3,2-b]pyridin-2-yl)methyl)-6,6-dimethyl-3-azabicyclo[3.1.0]hexane-2,4-dione 2,2,2-trifluoroacetate (62a)

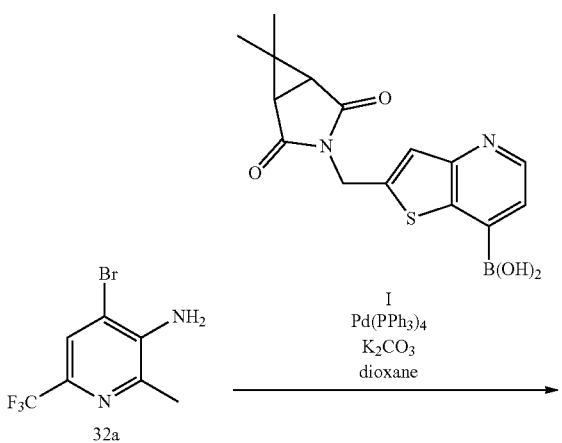

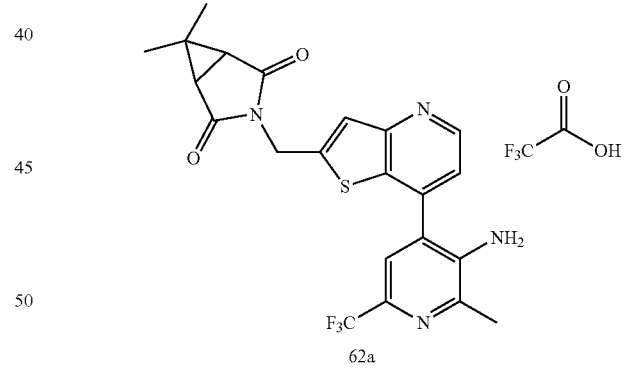

62a

The title compound (62a) was obtained as a TFA salt from 32a (104 mg; 0.41 mmol) and from boronic acid I (162 mg; 0.49 mmol) according to the General Procedure Va in 29% yield (70 mg; 0.12 mmol). The crude product was purified by preparative reversed-phase column chromatography (C-18, water/MeCN+1‰ TFA, 98:2 to 30:70, 30 min, 20 mL/min).

ESI-MS m/z for $C_{22}H_{20}F_3N_4O_2S$ found 461.1 [M+H]$^+$; $R_t$=1.40 min

337

Step 2

Synthesis of N-(4-(2-(((6,6-dimethyl-2,4-dioxo-3-azabicyclo[3.1.0]hexan-3-yl)methyl)thieno[3,2-b]pyridin-7-yl)-2-methyl-6-(trifluoromethyl)pyridin-3-yl)-2,2,2-trifluoroacetamide 2,2,2-trifluoroacetate (62)

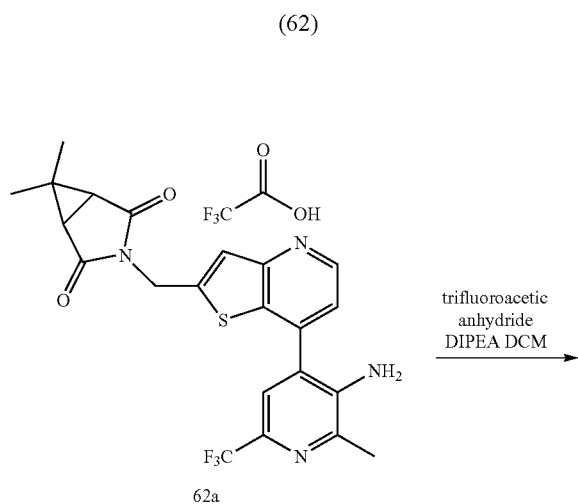

The title compound (62) was obtained as a TFA salt from 62a (50 mg; 0.086 mmol) according to the General Procedure VIII in 87% yield (50 mg; 0.075 mmol). The crude product was purified by preparative reversed-phase column chromatography (C-18, water/MeCN+0.5‰ TFA, 99:1 to 40:60, 30 min, 20 mL/min).

ESI-MS m/z for $C_{24}H_{19}F_6N_4O_3S$ found 557.6 [M+H]$^+$; $R_t$=1.46 min, $^1$H NMR (700 MHz, DMSO-d$_6$) δ 11.57 (s, 1H), 8.76 (d, J=4.7 Hz, 1H), 8.09 (s, 1H), 7.57 (s, 1H), 7.21 (d, J=4.8 Hz, 1H), 4.81 (s, 2H), 2.60 (s, 3H), 2.59 (s, 2H), 1.18 (s, 3H), 1.05 (s, 3H).

338

Example 63

Synthesis of N-(4-(2-(((6,6-dimethyl-2,4-dioxo-3-azabicyclo[3.1.0]hexan-3-yl)methyl)thieno[3,2-b]pyridin-7-yl)-2-methyl-6-(trifluoromethyl)pyridin-3-yl)nicotinamide 2,2,2-trifluoroacetate (63)

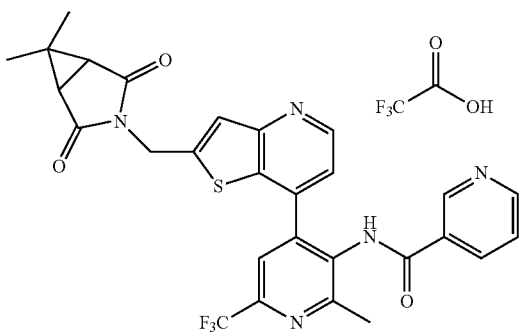

The title compound (63) was obtained as a TFA salt in 34% overall yield in a similar way to Example 61 with the exception that, in the first step of the synthesis, nicotinic acid was used instead of 2-methoxyacetyl chloride and this reaction was carried on with the addition of CDI (1.1 equivalents), and in the last step of the synthesis, the crude product was purified by preparative reversed-phase column chromatography (C-18, water/MeCN+0.5% TFA, 99:1 to 40:60, 30 min, 20 mL/min).

ESI-MS m/z for $C_{28}H_{23}F_3N_5O_3S$ found 566.0 [M+H]$^+$; $R_t$=1.34 min; $^1$H NMR (700 MHz, DMSO-d$_6$+D$_2$O, 348 K) δ 8.76 (dd, J=2.3, 0.9 Hz, 1H), 8.69 (dd, J=4.9, 1.6 Hz, 1H), 8.64 (d, J=4.8 Hz, 1H), 8.01 (dt, J=8.0, 1.9 Hz, 1H), 7.88 (d, J=0.7 Hz, 1H), 7.50 (ddd, J=7.9, 4.9, 0.9 Hz, 1H), 7.46 (s, 1H), 7.33 (d, J=4.8 Hz, 1H), 4.76 (s, 2H), 2.62 (s, 3H), 2.51 (s, 2H), 1.18 (s, 3H), 1.00 (s, 3H).

Example 64

Synthesis of N-(4-(2-(((6,6-dimethyl-2,4-dioxo-3-azabicyclo[3.1.0]hexan-3-yl)methyl)thieno[3,2-b]pyridin-7-yl)-2-methyl-6-(trifluoromethyl)pyridin-3-yl)pyrrolidine-3-carboxamide 2,2,2-trifluoroacetate (64)

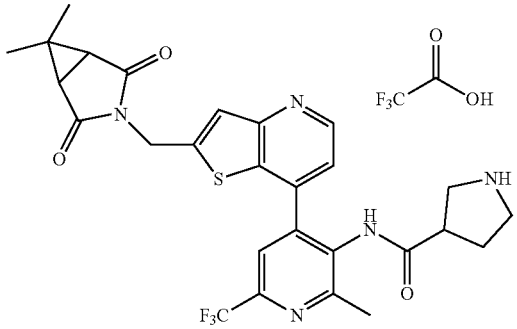

The title compound (64) was obtained as a TFA salt as a racemate in 54% overall yield in a similar way to Example 27 with the exception that, in the first step of the synthesis, 2-methyl-6-(trifluoromethyl)pyridin-3-amine was used instead of 5-amino-6-methylpicolinonitrile, in the second step of the synthesis, 1-(tert-butoxycarbonyl)pyrrolidine-3-carboxylic acid was used instead of 1-(tert-butoxycarbonyl)azetidine-2-carboxylic acid and in the last step of the synthesis, the crude product was purified by preparative reversed-phase column chromatography (C-18, water/MeCN+0.5‰ TFA, 99:1 to 40:60, 30 min, 20 mL/min).

ESI-MS m/z for $C_{27}H_{27}F_3N_5O_3S$ found 558.2 [M+H]$^+$; R$_t$=1.03 min; $^1$H NMR (700 MHz, DMSO-d$_6$+D$_2$O, 348 K) δ 8.70 (d, J=4.8 Hz, 1H), 7.83 (s, 1H), 7.50 (s, 1H), 7.25 (d, J=4.8 Hz, 1H), 4.78 (s, 2H), 3.24-3.15 (m, 1H), 3.12-3.01 (m, 3H), 2.98-2.80 (m, 1H), 2.57 (s, 3H), 2.53 (s, 2H), 2.12-1.84 (m, 1H), 1.60-1.42 (m, 1H), 1.19 (s, 3H), 1.05 (s, 3H).

Example 65

Synthesis of N-(4-(2-((6,6-dimethyl-2,4-dioxo-3-azabicyclo[3.1.0]hexan-3-yl)methyl)thieno[3,2-b]pyridin-7-yl)-2-methyl-6-(trifluoromethyl)pyridin-3-yl)-1-(2,2,2-trifluoroacetyl)pyrrolidine-3-carboxamide 2,2,2-trifluoroacetate (65)

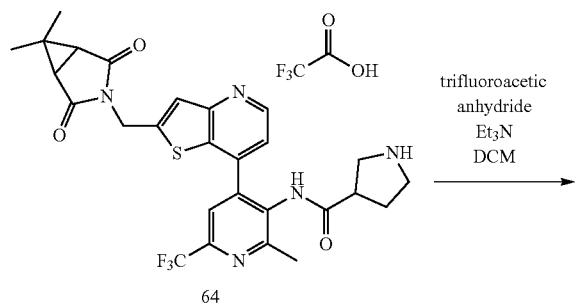

The title compound (65) was obtained as a TFA salt as a racemate from 64 (65 mg; 0.097 mmol) according to the General Procedure VIII in 57% yield (42 mg; 0.055 mmol). The crude product was purified by preparative reversed-phase column chromatography (C-18, water/MeCN+0.5‰ TFA, 99:1 to 40:60, 30 min, 20 mL/min).

ESI-MS m/z for $C_{29}H_{26}F_5N_5O_4S$ found 654.0 [M+H]$^+$; R$_t$=1.50 min; $^1$H NMR (700 MHz, DMSO-d$_6$+D$_2$O, 348 K) δ 8.68 (d, J=4.8 Hz, 1H), 7.80 (s, 1H), 7.49 (d, J=4.1 Hz, 1H), 7.23 (dd, J=4.8, 2.5 Hz, 1H), 4.77 (s, 2H), 3.64-3.44 (m, 2H), 3.37-3.19 (m, 3H), 3.14-2.91 (m, 1H), 2.62-2.52 (m, 4H), 2.06-1.85 (m, 1H), 1.76-1.44 (m, 1H), 1.17 (s, 3H), 1.01 (s, 3H).

Example 66

Synthesis of N-(4-(2-((6,6-dimethyl-2,4-dioxo-3-azabicyclo[3.1.0]hexan-3-yl)methyl)thieno[3,2-b]pyridin-7-yl)-2-methyl-6-(trifluoromethyl)pyridin-3-yl)azetidine-3-carboxamide 2,2,2-trifluoroacetate (66)

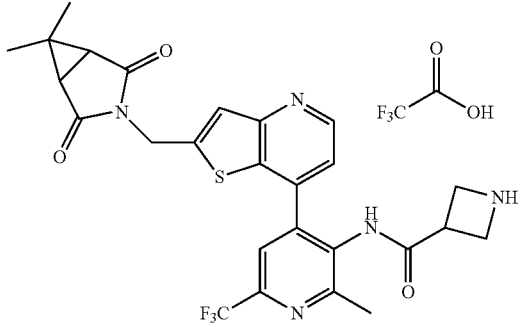

The title compound (66) was obtained as a TFA salt as a racemate in 8% overall yield in a similar way to Example 27 with the exception that, in the first step of the synthesis, 2-methyl-6-(trifluoromethyl)pyridin-3-amine was used instead of 5-amino-6-methylpicolinonitrile, in the second step of the synthesis, 1-(tert-butoxycarbonyl)azetidine-3-carboxylic acid was used instead of 1-(tert-butoxycarbonyl)azetidine-2-carboxylic acid and in the last step of the synthesis, the crude product was purified twice by preparative reversed-phase column chromatography (first: C-18, water/MeCN, 98:2 to 40:60, 30 min, 20 mL/min; second: C-18, water/MeCN+0.5‰ TFA, 99:1 to 40:60, 30 min, 20 mL/min).

ESI-MS m/z for $C_{26}H_{25}F_3N_5O_3S$ found 544.0 [M+H]$^+$; R$_t$=1.01 min; $^1$H NMR (700 MHz, DMSO-d$_6$+D$_2$O, 348 K) δ 8.70 (d, J=4.8 Hz, 1H), 7.84 (s, 1H), 7.50 (s, 1H), 7.24 (d, J=4.8 Hz, 1H), 4.78 (s, 2H), 3.94 (t, J=10.0 Hz, 2H), 3.72-3.66 (m, 2H), 3.61-3.58 (m, 1H), 2.57 (s, 3H), 2.54 (s, 2H), 1.19 (s, 3H), 1.06 (s, 3H).

Example 67

Synthesis of (S)-7-(5-chloro-3-methyl-2-(piperidin-3-yloxy)phenyl)-2-methyl-3H-imidazo[4,5-b]pyridine hydrochloride (67)

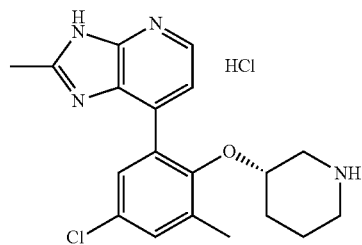

Step 1

Synthesis of 7-chloro-2-methyl-3H-imidazo[4,5-b]pyridine (67a)

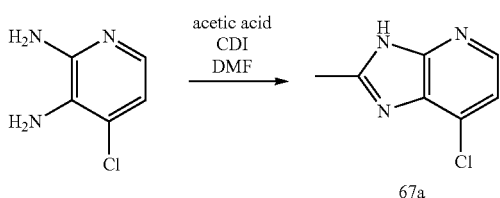

The solution of acetic acid (0.17 mL; 2.93 mmol) in DMF (3 mL) was cooled to 0° C. and then CDI (473 mg; 2.92 mmol) was added and stirred at this temperature for 20 minutes. Then to this mixture 4-chloropyridine-2,3-diamine (350 mg; 2.43 mmol) was added and whole was stirred at 160° C. for 30 minutes. The reaction progress was monitored by LC-MS. When analysis indicated completion of the reaction, DMF was evaporated in vacuo, the residue was diluted with DCM and washed with 5% NaHCO$_3$, brine, dried over anhydrous MgSO$_4$, filtered and concentrated in vacuo and the crude product was purified by flash column chromatography on silica (DCM 100%, 10 minutes, then DCM/MeOH, 100:0 to 95:5, v/v, 20 minutes). Compound 67a was obtained in 49% yield (200 mg; 1.20 mmol).

ESI-MS m/z for C$_7$H$_7$ClN$_3$ found 168.0/170.0 [M+H]$^+$; R$_t$=0.32 min

Step 2

Synthesis of tert-butyl (S)-3-(4-chloro-2-methyl-6-(2-methyl-3H-imidazo[4,5-b]pyridin-7-yl)phenoxy)piperidine-1-carboxylate (67b)

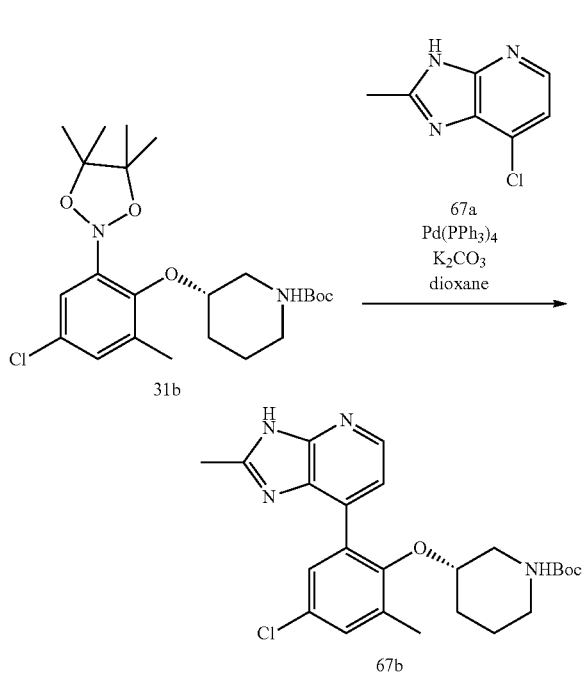

The title compound (67b) was obtained from 31b (134 mg; 0.3 mmol) and from 67a (50 mg; 0.3 mmol) according to the General Procedure Va and after standard work-up all the crude product mixture was taken to the next step.

ESI-MS m/z for C$_{24}$H$_{30}$ClN$_4$O$_3$ found 457.0/459.0 [M+H]$^+$; R$_t$=1.39 min

Step 3

Synthesis of (S)-7-(5-chloro-3-methyl-2-(piperidin-3-yloxy)phenyl)-2-methyl-3H-imidazo[4,5-b]pyridine hydrochloride (67)

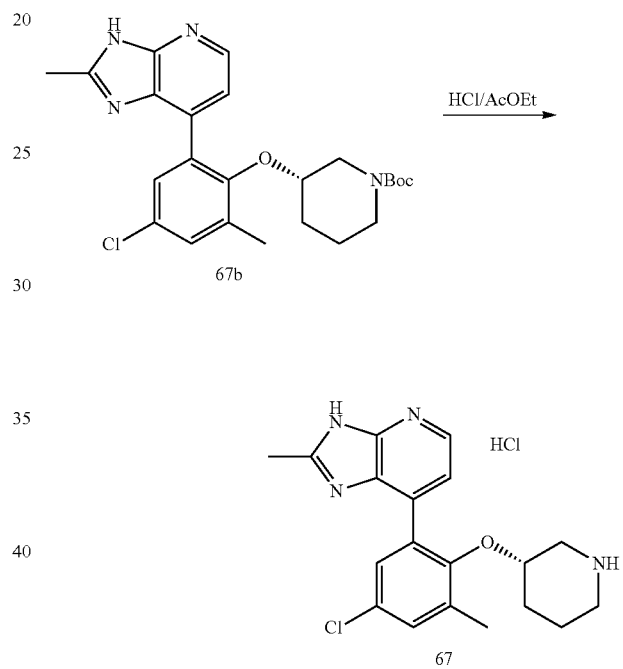

The title compound (67) was obtained as a hydrochloride salt from 67b (the crude reaction mixture) according to the General Procedure IVa in 45% yield (per two steps) (53 mg; 0.135 mmol). The crude product was purified by preparative reversed-phase column chromatography (C-18, water/MeCN+0.4‰ HCl (36%), 98:2 to 30:70, 30 min, 20 mL/min).

ESI-MS m/z for C$_{19}$H$_{22}$ClN$_4$O found 357.0/359.0 [M+H]$^+$; R$_t$=0.77 min; $^1$H NMR (700 MHz, DMSO-d$_6$+ D$_2$O, 348 K) δ 8.47 (d, J=5.1 Hz, 1H), 7.47 (dd, J=2.7, 0.8 Hz, 1H), 7.43 (d, J=5.2 Hz, 1H), 7.39 (dd, J=2.7, 0.7 Hz, 1H), 3.74-3.62 (m, 1H), 3.05-2.87 (m, 2H), 2.72 (ddd, J=13.1, 10.0, 3.6 Hz, 1H), 2.66 (s, 3H), 2.58 (dd, J=12.4, 8.4 Hz, 1H), 2.36 (s, 3H), 1.64-1.52 (m, 1H), 1.52-1.43 (m, 1H), 1.30-1.20 (m, 1H), 1.22-1.12 (m, 1H).

Example 68

Synthesis of (S)-7-(5-chloro-3-methyl-2-(piperidin-3-yloxy)phenyl)-2,3-dimethyl-3H-imidazo[4,5-b]pyridine hydrochloride (68)

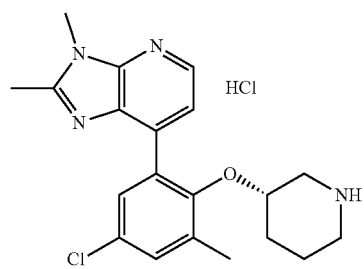

Step 1

Synthesis of 7-chloro-2,3-dimethyl-3H-imidazo[4,5-b]pyridine (68a) and 7-chloro-1,2-dimethyl-1H-imidazo[4,5-b]pyridine (68a')

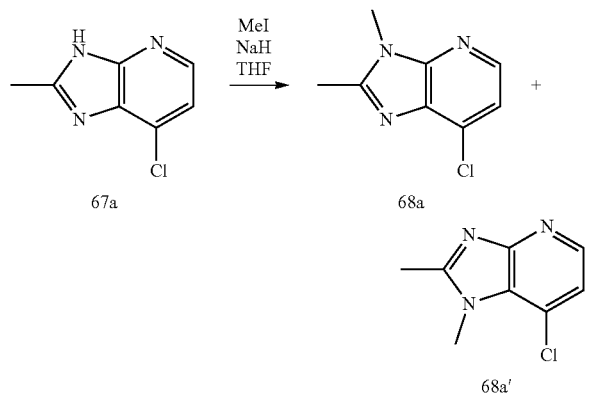

The solution of 67a (150 mg; 0.90 mmol) in THF (5 mL) was cooled to 0° C. and then NaH (60% in mineral oil; 43 mg; 1.07 mmol) was added in one portion and stirred at this temperature for 20 minutes. Then to this mixture MeI (0.07 mL; 1.07 mmol) was added and whole was stirred at 0° C. for 30 minutes. The reaction progress was monitored by LC-MS. The cooling bath was removed and the reaction mixture was stirred at room temperature overnight. Next another portion of NaH (60% in mineral oil; 20 mg; 0.50 mmol) and MeI (0.03 mL; 0.48 mmol) was added and stirred at 35° C. for 8 hours. When analysis indicated completion of the reaction, the solvent was removed in vacuo and the residue was purified by flash column chromatography on silica (DCM 100%, 10 minutes, then DCM/MeOH, 100:0 to 95:5, v/v, 20 minutes). Compound 68a was obtained as a single regioisomer in 21% yield (35 mg; 0.19 mmol) and compound 68a' was obtained as a second single regioisomer in 31% yield (50 mg; 0.28 mmol).

For 68a: ESI-MS m/z for $C_8H_9ClN_3$ found 181.9/183.9 $[M+H]^+$; $R_t$=0.54 min For 68a': ESI-MS m/z for $C_8H_9ClN_3$ found 181.9/183.9 $[M+H]^+$; $R_t$=0.59 min

Step 2

Synthesis of tert-butyl (S)-3-(4-chloro-2-(2,3-dimethyl-3H-imidazo[4,5-b]pyridin-7-yl)-6-methylphenoxy)piperidine-1-carboxylate (68b)

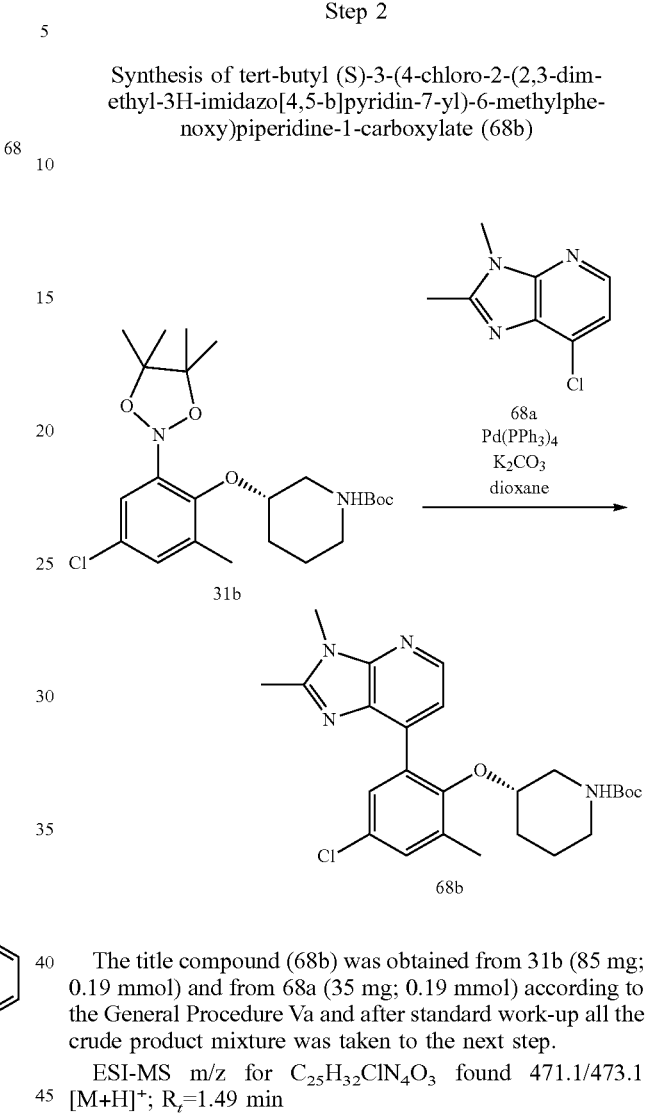

The title compound (68b) was obtained from 31b (85 mg; 0.19 mmol) and from 68a (35 mg; 0.19 mmol) according to the General Procedure Va and after standard work-up all the crude product mixture was taken to the next step.

ESI-MS m/z for $C_{25}H_{32}ClN_4O_3$ found 471.1/473.1 $[M+H]^+$; $R_t$=1.49 min

Step 3

Synthesis of (S)-7-(5-chloro-3-methyl-2-(piperidin-3-yloxy)phenyl)-2,3-dimethyl-3H-imidazo[4,5-b]pyridine hydrochloride (68)

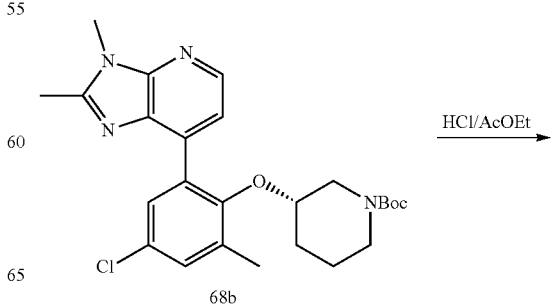

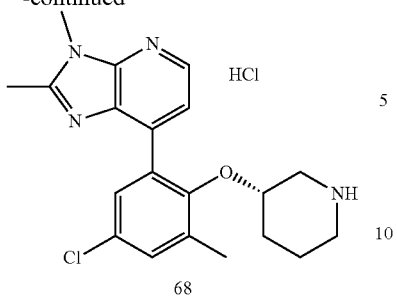

68

The title compound (68) was obtained as a hydrochloride salt from 68b (the crude reaction mixture) according to the General Procedure IVa in 62% yield (per two steps) (48 mg; 0.118 mmol). The crude product was purified by preparative reversed-phase column chromatography (C-18, water/MeCN+0.4‰ HCl (36%), 98:2 to 30:70, 30 min, 20 mL/min).

ESI-MS m/z for $C_{20}H_{24}ClN_4O$ found 371.0/373.0 [M+H]$^+$; $R_t$=0.82 min; $^1$H NMR (700 MHz, DMSO-d$_6$+ D$_2$O, 348 K) δ 8.49 (d, J=5.0 Hz, 1H), 7.47 (d, J=5.0 Hz, 1H), 7.45 (dd, J=2.6, 0.8 Hz, 1H), 7.42 (dd, J=2.7, 0.7 Hz, 1H), 3.87 (s, 3H), 3.79-3.64 (m, 1H), 3.04-2.86 (m, 2H), 2.76-2.71 (m, 1H), 2.71 (s, 3H), 2.61 (dd, J=12.4, 8.3 Hz, 1H), 2.36 (s, 3H), 1.66-1.48 (m, 2H), 1.40-1.10 (m, 2H).

Example 69

Synthesis of (S)-7-(5-chloro-3-methyl-2-(piperidin-3-yloxy)phenyl)-1,2-dimethyl-1H-imidazo[4,5-b]pyridine hydrochloride (69)

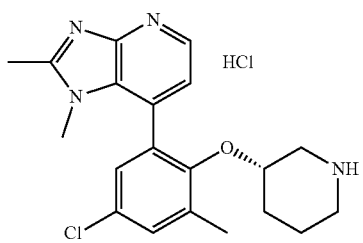

69

The title compound (69) was obtained as a hydrochloride salt in 12% overall yield in a similar way to Example 68 with the exception that, in the second step of the synthesis, the regioisomer 68a' was used instead of the regioisomer 68a and in the last step of the synthesis, the crude product was purified by preparative reversed-phase column chromatography (C-18, water/MeCN+0.4‰ HCl (36%), 98.2 to 30:70, 30 min, 20 mL/min).

ESI-MS m/z for $C_{20}H_{24}ClN_4O$ found 371.0/373.0 [M+H]$^+$; $R_t$=0.84 min; $^1$H NMR (700 MHz, DMSO-d$_6$+ D$_2$O, 348 K) δ 8.56 (dd, J=5.1, 1.7 Hz, 1H), 7.56-7.49 (m, 1H), 7.43 (dd, J=5.2, 3.7 Hz, 1H), 7.32 (t, J=2.7 Hz, 1H), 3.88-3.68 (m, 11H), 3.41 (d, J=4.9 Hz, 3H), 3.09 (dd, J=12.5, 3.6 Hz, 1H), 2.93-2.78 (m, 1H), 2.75-2.64 (m, 4H), 2.35 (d, J=3.8 Hz, 3H), 2.25 (dd, J=12.4, 8.1 Hz, 1H), 1.67 (d, J=10.2 Hz, 1H), 1.46-1.28 (m, 1H), 1.27-0.93 (m, 2H).

Example 70

Synthesis of N-(azetidin-3-yl)-2-(2-((6,6-dimethyl-2,4-dioxo-3-azabicyclo[3.1.0]hexan-3-yl)methyl)thieno[3,2-b]pyridin-7-yl)-4-methyl-6-(trifluoromethyl)nicotinamide dihydrochloride (70)

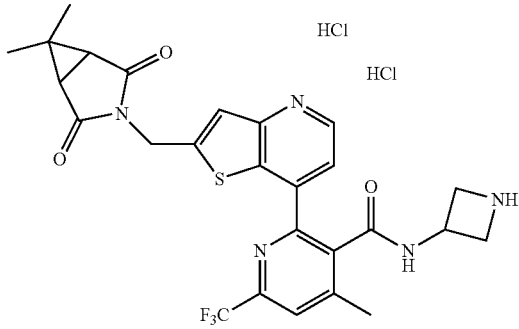

70

Step 1

Synthesis of tert-butyl 2-chloro-4-methyl-6-(trifluoromethyl)nicotinate (70a)

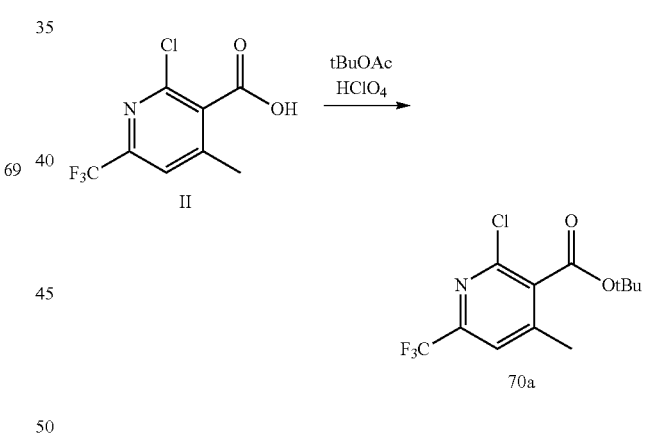

To the solution of acid II (2.9 g; 12.1 mmol) in tBuOAc (60 mL) HClO4 (70%; 2.19 mL; 36.3 mmol) was added dropwise at 0° C. and then the reaction mixture was warmed to at room temperature and stirred for 72 hours. The reaction progress was monitored by TLC. When analysis indicated completion of the reaction, the reaction mixture was cooled to 0° C. and 5% NaHCO$_3$ was added to this mixture followed by Et$_2$O. The layers were separated and the aqueous one was extracted with Et$_2$O (3×). The combined organic solutions were washed with brine, dried over anhydrous Na$_2$SO$_4$, filtered and concentrated in vacuo and the crude product was used to the next step without additional purification. Compound 70a was obtained in 9% yield (322 mg; 1.09 mmol).

ESI-MS m/z for $C_{12}H_{14}ClF_3NO_2$ found 296.0/298.0 [M+H]$^+$; $R_t$=1.86 min

Step 2

Synthesis of tert-butyl 2-(2-((6,6-dimethyl-2,4-di-oxo-3-azabicyclo[3.1.0]hexan-3-yl)methyl)thieno[3,2-b]pyridin-7-yl)-4-methyl-6-(trifluoromethyl)nicotinate (70b)

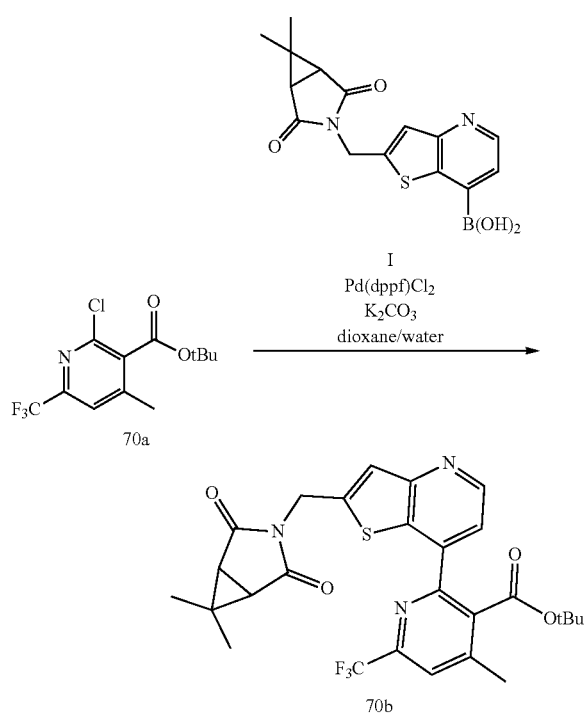

The title compound (70b) was obtained from 70a (311 mg; 1.05 mmol) and from boronic acid I (453 mg; 1.37 mmol) according to the General Procedure Va in 80% yield (458 mg; 0.84 mmol).

ESI-MS m/z for $C_{27}H_{27}F_3N_3O_4S$ found 546.4 [M+H]$^+$; $R_t$=1.75 min

Step 3

Synthesis of 2-(2-((6,6-dimethyl-2,4-dioxo-3-azabicyclo[3.1.0]hexan-3-yl)methyl)thieno[3,2-b]pyridin-7-yl)-4-methyl-6-(trifluoromethyl)nicotinic acid (70c)

To the solution of 70b (458 mg; 0.84 mmol) in DCM (10 mL) TFA (8 mL; 108 mmol) was added and this mixture was stirred at 40° C. for 3 hours. Then the solvent was evaporated in vacuo and the crude product was used to the next step without additional purification. Compound 70c was obtained in 99% yield (406 mg; 0.83 mmol).

ESI-MS m/z for $C_3H_{19}F_3N_3O_4S$ found 490.2 [M+H]$^+$; $R_t$=1.28 min

Step 4

Synthesis of tert-butyl 3-(2-(2-((6,6-dimethyl-2,4-dioxo-3-azabicyclo[3.1.0]hexan-3-yl)methyl)thieno[3,2-b]pyridin-7-yl)-4-methyl-6-(trifluoromethyl)nicotinamido)azetidine-1-carboxylate (70d)

The title compound (70d) was obtained from 70c (50 mg; 0.08 mmol) and from tert-butyl 3-aminoazetidine-1-carboxylate (16 mg; 0.09 mmol) according to the General Procedure I in 99% yield (51 mg; 0.08 mmol). The crude product was purified by flash column chromatography on silica (DCM/MeOH, 8:2, v/v, 30 min).

ESI-MS m/z for $C_{31}H_{33}F_3N_5O_5S$ found 644.3 [M+H]$^+$; $R_t$=1.54 min

Step 5

Synthesis of N-(azetidin-3-yl)-2-(2-((6,6-dimethyl-2,4-dioxo-3-azabicyclo[3.1.0]hexan-3-yl)methyl)thieno[3,2-b]pyridin-7-yl)-4-methyl-6-(trifluoromethyl)nicotinamide dihydrochloride (70)

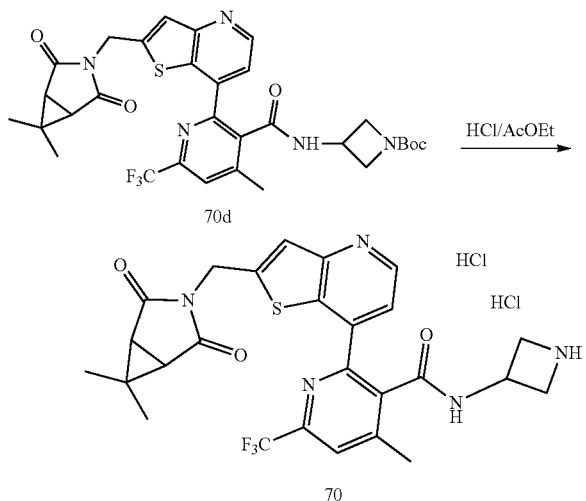

The title compound (70) was obtained as a dihydrochloride salt from 70d (51 mg; 0.08 mmol) according to the General Procedure IVa in 19% yield (10 mg; 0.016 mmol). The crude product was purified by preparative reversed-phase column chromatography (column: Cosmosil Cholester 20×250 mm, water+0.5‰ HCl (36%)/MeCN, 99:1 to 40:60, 30 min, 20 mL/min).

ESI-MS m/z for $C_{26}H_{25}F_3N_5O_3S$ found 544.4 $[M+H]^+$; $R_t$=1.63 min; $^1H$ NMR (700 MHz, Methanol-$d_4$) δ 9.04 (d, J=6.0 Hz, 1H), 8.20 (d, J=6.0 Hz, 1H), 8.12 (d, J=0.8 Hz, 1H), 7.80 (s, 1H), 5.03 (d, J=0.9 Hz, 2H), 4.78 (tt, J=8.3, 7.0 Hz, 1H), 4.41-4.31 (m, 2H), 4.24-4.13 (m, 2H), 2.66 (s, 3H), 2.56 (s, 2H), 1.29 (s, 3H), 1.18 (s, 3H).

Example 71

Synthesis of 6,6-dimethyl-3-((7-(4-methyl-3-(1,7-diazaspiro[4.4]nonane-7-carbonyl)-6-(trifluoromethyl)pyridin-2-yl)thieno[3,2-b]pyridin-2-yl)methyl)-3-azabicyclo[3.1.0]hexane-2,4-dione dihydrochloride (71)

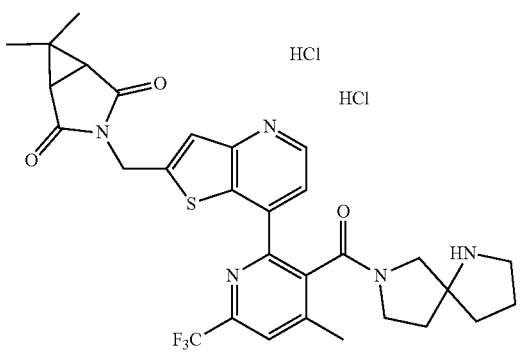

The title compound (71) was obtained as a dihydrochloride salt as a mixture of rotamers in 20% overall yield in a similar way to Example 45 with the exception that, in the first step of the synthesis tert-butyl 1,7-diazaspiro[4.4]nonane-1-carboxylate was used instead of tert-butyl piperazine-1-carboxylate and acid $H_1$ was used instead of 2-chloro-4-methylnicotinic acid and in the last step of the synthesis, the crude product was purified by preparative reversed-phase column chromatography (C-18, water+0.5‰ HCl (36%)/MeCN, 98:2 to 30:70, 30 min, 20 mL/min).

ESI-MS m/z for $C_{30}H_{31}F_3N_5O_3S$ found 598.1 $[M+H]^+$; $R_t$=1.10 min; $^1H$ NMR (700 MHz, DMSO-$d_6$+$D_2O$) δ 8.76-8.72 (m, 1H), 8.10-8.04 (m, 1H), 7.58-7.46 (m, 2H), 4.79 (s, 2H), 3.89-3.68 (m, 1H), 3.59-3.34 (m, 1H), 3.28-3.12 (m, 2H), 3.10-2.78 (m, 1H), 2.64-2.53 (m, 3H), 2.49-2.36 (m, 3H), 2.19-1.77 (m, 4H), 1.69-1.55 (m, 1H), 1.55-0.58 (m, 1H), 1.19-1.11 (m, 3H), 1.07-0.88 (m, 3H).

Example 72

Synthesis of 6,6-dimethyl-3-((7-(4-methyl-3-(octahydropyrrolo[3,4-b]pyrrole-1-carbonyl)-6-(trifluoromethyl)pyridin-2-yl)thieno[3,2-b]pyridin-2-yl)methyl)-3-azabicyclo[3.1.0]hexane-2,4-dione dihydrochloride (72)

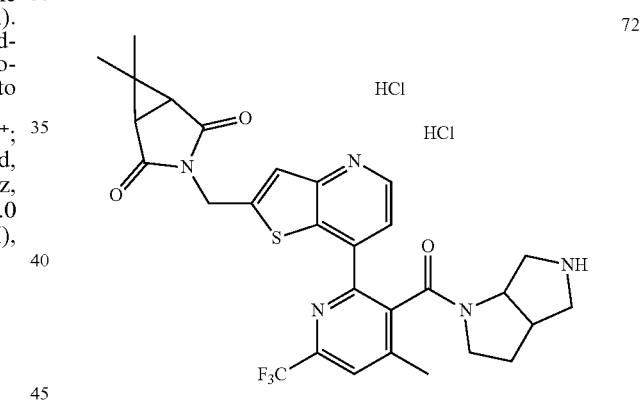

The title compound (72) was obtained as a dihydrochloride salt as a mixture of rotamers as a racemate in 20% overall yield in a similar way to Example 45 with the exception that, in the first step of the synthesis tert-butyl hexahydropyrrolo[3,4-b]pyrrole-5(1H)-carboxylate was used instead of tert-butyl piperazine-1-carboxylate and acid II was used instead of 2-chloro-4-methylnicotinic acid and in the last step of the synthesis, the crude product was purified by preparative reversed-phase column chromatography (C-18, water+0.5‰ HCl (36%)/MeCN, 98:2 to 30:70, 30 min, 20 mL/min).

ESI-MS m/z for $C_{29}H_{29}F_3N_5O_3S$ found 584.2 $[M+H]^+$; $R_b$=1.11 min; $^1H$ NMR (700 MHz, DMSO-$d_6$+$D_2O$) δ 8.84-8.70 (m, 1H), 8.22-8.00 (m, 1H), 7.64-7.40 (m, 2H), 5.01-4.75 (m, 2H), 4.74-4.39 (m, 1H), 3.68-3.52 (m, 1H), 3.42-3.17 (m, 2H), 3.13-2.97 (m, 2H), 2.96-2.74 (m, 2H), 2.68-2.54 (m, 1H), 2.41 (s, 3H), 2.00-1.65 (m, 1H), 1.62-1.54 (m, 1H), 1.31-1.08 (m, 4H), 1.06-0.86 (m, 3H).

Example 73

Synthesis of 3-((7-(3-((S)-3-(ethylamino)pyrrolidine-1-carbonyl)-4-methyl-6-(trifluoromethyl)pyridin-2-yl)thieno[3,2-b]pyridin-2-yl)methyl)-6,6-dimethyl-3-azabicyclo[3.1.0]hexane-2,4-dione dihydrochloride (73)

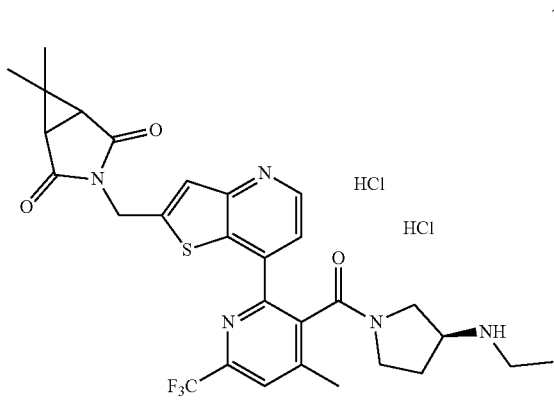

The title compound (73) was obtained as a dihydrochloride salt in 24% overall yield in a similar way to Example 45 with the exception that, in the first step of the synthesis the compound III was used instead of tert-butyl piperazine-1-carboxylate and acid II was used instead of 2-chloro-4-methylnicotinic acid and in the last step of the synthesis, the crude product was purified by preparative reversed-phase column chromatography (C-18, water+0.5‰HCl (36%)/MeCN, 98:2 to 30:70, 30 min, 20 mL/min).

ESI-MS m/z for $C_{29}H_{31}F_3N_5O_3S$ found 586.1 [M+H]$^+$; $R_t$=1.04 min; $^1$H NMR (700 MHz, DMSO-d$_6$+D$_2$O) δ 8.80-8.68 (m, 1H), 8.02-7.99 (m, 1H), 7.62-7.45 (m, 2H), 4.85-4.74 (m, 2H), 4.18-3.59 (m, 2H), 3.47-3.04 (m, 2H), 3.03-2.92 (m, 1H), 2.90-2.55 (m, 3H), 2.49-2.39 (m, 3H), 2.37-1.55 (m, 3H), 1.26-1.15 (m, 5H), 1.11-0.92 (m, 4H).

Example 74

Synthesis of 3-((7-(3-((S)-3-(isopropylamino)pyrrolidine-1-carbonyl)-4-methyl-6-(trifluoromethyl)pyridin-2-yl)thieno[3,2-b]pyridin-2-yl)methyl)-6,6-dimethyl-3-azabicyclo[3.1.0]hexane-2,4-dione dihydrochloride (74)

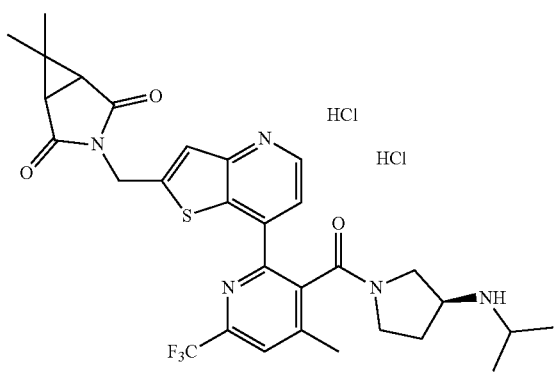

Step 1

Synthesis of tert-butyl (S)-(1-(2-chloro-4-methyl-6-(trifluoromethyl)nicotinoyl)pyrrolidin-3-yl)carbamate (74a)

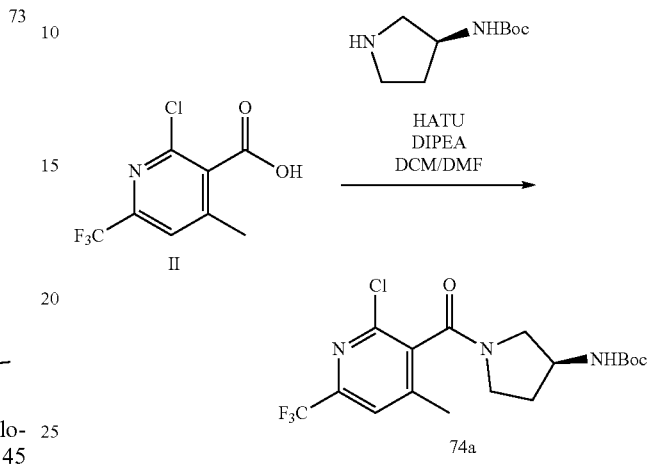

The title compound (74a) was obtained from II (100 mg; 0.42 mmol) and from tert-butyl (S)-pyrrolidin-3-ylcarbamate (86 mg; 0.46 mmol) according to the General Procedure I in 61% yield (104 mg; 0.26 mmol).

ESI-MS m/z for $C_{13}H_{14}ClF_3N_3O_3$ found 352.0/354.0 [M+H-tBu]$^+$; $R_t$=1.37 min

Step 2

Synthesis of (S)-(3-aminopyrrolidin-1-yl)(2-chloro-4-methyl-6-(trifluoromethyl)pyridin-3-yl)methanone hydrochloride (74b)

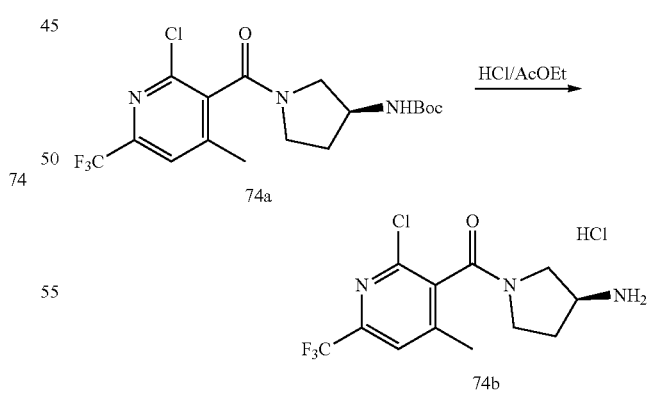

The title compound (74b) was obtained as a hydrochloride salt from 74a (31 mg; 0.076 mmol) according to the General Procedure IVa and after standard work-up all the crude product mixture was taken for the next step.

ESI-MS m/z for $C_{12}H_{14}ClF_3N_3O$ found 308.0/310.0 [M+H]$^+$; $R_t$=0.50 min

Step 3

Synthesis of (S)-2-chloro-4-methyl-6-(trifluoromethyl)pyridin-3-yl)(3-(isopropylamino)pyrrolidin-1-yl)methanone (74c)

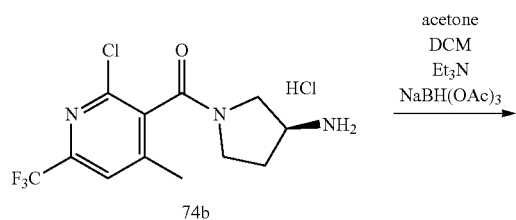

The title compound (74c) was obtained from 74b (crude reaction mixture) and from acetone (0.01 mL; 0.091 mmol) according to the General Procedure Via in 83% yield (per two steps)(22 mg; 0.063 mmol) with the exception that this reaction was carried on in DCM and Et$_3$N was added instead of acetic acid. The crude product was purified flash column chromatography on silica (DCM/MeOH, 95:5 to 50:50, v/v, 30 mm).

ESI-MS m/z for $C_{15}H_{20}ClF_3N_3O$ found 350.0/352.0 [M+H]$^+$; R$_t$=0.70 min

Step 4

Synthesis of 3-((7-(3-((S)-3-(isopropylamino)pyrrolidine-1-carbonyl)-4-methyl-6-(trifluoromethyl)pyridin-2-yl)thieno[3,2-b]pyridin-2-yl)methyl)-6,6-dimethyl-3-azabicyclo[3.1.0]hexane-2,4-dione dihydrochloride (74)

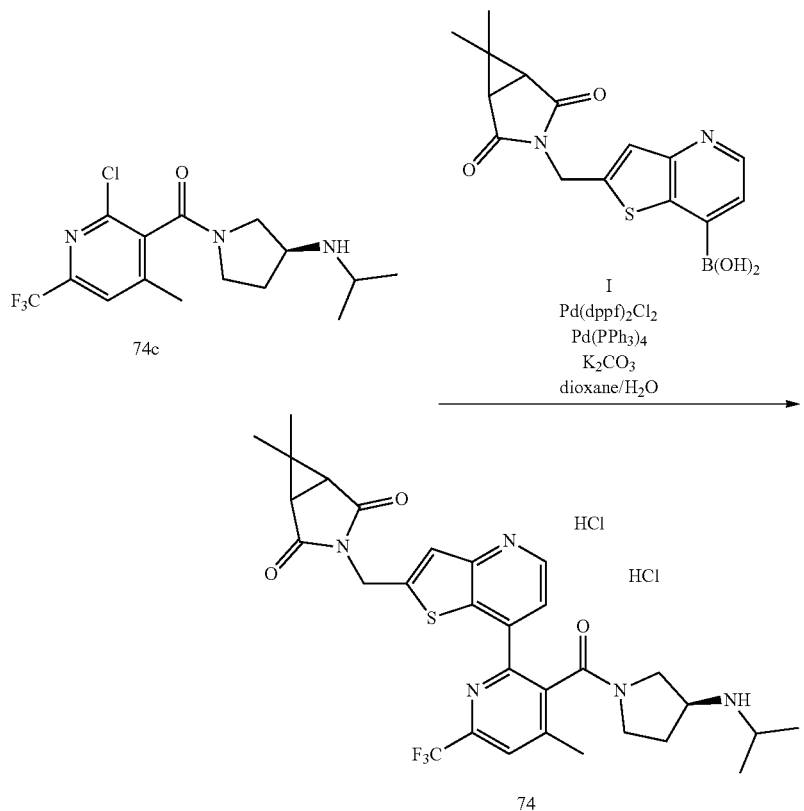

The title compound (74) was obtained as a dihydrochloride salt from 74c (20 mg; 0.057 mmol) and from boronic acid I (30 mg; 0.091 mmol) according to the General Procedure Va in 33% yield (13 mg; 0.019 mmol). The crude product was purified by preparative reversed-phase column chromatography (C-18, water+0.5‰ HCl (36%)/MeCN, 98:2 to 30:70, 30 min, 20 mL/min).

ESI-MS m/z for $C_{30}H_{33}F_3N_5O_3S$ found 600.0 [M+H]$^+$; R$_t$=1.08 min; $^1$H NMR (700 MHz, DMSO-d$_6$) δ 8.94-8.76 (m, 1H), 8.18-8.07 (m, 1H), 7.78-7.47 (m, 2H), 4.91-4.73 (m, 2H), 4.19-3.56 (m, 2H), 3.42-2.82 (m, 2H), 2.68-2.58 (m, 2H), 2.57-2.52 (m, 3H), 2.49-2.33 (m, 2H), 2.25-1.70 (m, 2H), 1.39-1.14 (m, 6H), 1.14-0.97 (m, 6H).

Example 75

Synthesis of 2-(2-((6,6-dimethyl-2,4-dioxo-3-azabicyclo[3.1.0]hexan-3-yl)methyl)thieno[3,2-b]pyridin-7-yl)-4-methyl-N—((S)-pyrrolidin-3-yl)-6-(trifluoromethyl)nicotinamide dihydrochloride (75)

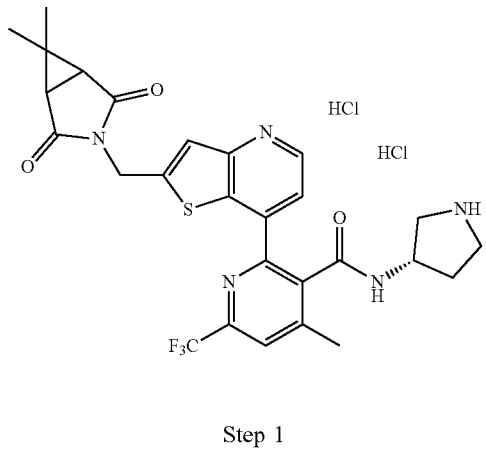

75

Step 1

Synthesis of benzyl (S)-3-aminopyrrolidine-1-carboxylate hydrochloride (75a)

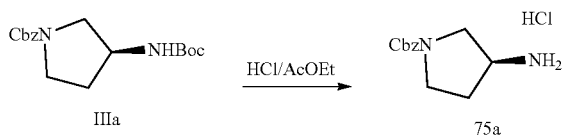 [SMILES: Cl ; CC(C)(C)OC(=O)N[C@H]1CCN(C(=O)OCc2ccccc2)C1 ; N[C@H]1CCN(C(=O)OCc2ccccc2)C1]

The title compound (75a) was obtained as a hydrochloride salt from IIIa (55 mg; 0.17 mmol) according to the General Procedure IVa and after standard work-up all the crude product mixture was taken to the next step.

ESI-MS m/z for $C_{12}H_{17}N_2O_2$ found 221.0 [M+H]$^+$; $R_t$=1.06 min

Step 2

Synthesis of benzyl (S)-3-(2-chloro-4-methyl-6-(trifluoromethyl)nicotinamido)pyrrolidine-1-carboxylate (75b)

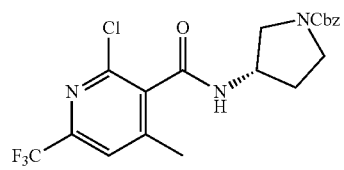

The title compound (75b) was obtained from II (67 mg; 0.28 mmol) and from 75a (the crude reaction mixture) according to the General Procedure I in 71% yield (per two steps)(53 mg; 0.12 mmol).

ESI-MS m/z for $C_{20}H_{18}ClF_3N_3O_3$ found 440.0/442.0 [M–H]$^-$; $R_t$=1.46 min

Step 3

Synthesis of benzyl (3S)-3-(2-(2-((6,6-dimethyl-2,4-dioxo-3-azabicyclo[3.1.0]hexan-3-yl)methyl)thieno[3,2-b]pyridin-7-yl)-4-methyl-6-(trifluoromethyl)nicotinamido)pyrrolidine-1-carboxylate (75c)

The title compound (75c) was obtained as a dihydrochloride salt from 75b (49 mg; 0.11 mmol) and from boronic acid I (55 mg; 0.17 mmol) according to the General Procedure Va in 36% yield (26 mg; 0.04 mmol).

ESI-MS m/z for $C_{35}H_{33}F_3N_5O_5S$ found 692.1 [M+H]$^+$; $R_t$=1.56 min

Step 4

Synthesis of 2-(2-((6,6-dimethyl-2,4-dioxo-3-azabicyclo[3.1.0]hexan-3-yl)methyl)thieno[3,2-b]pyridin-7-yl)-4-methyl-N—((S)-pyrrolidin-3-yl)-6-(trifluoromethyl)nicotinamide dihydrochloride (75)

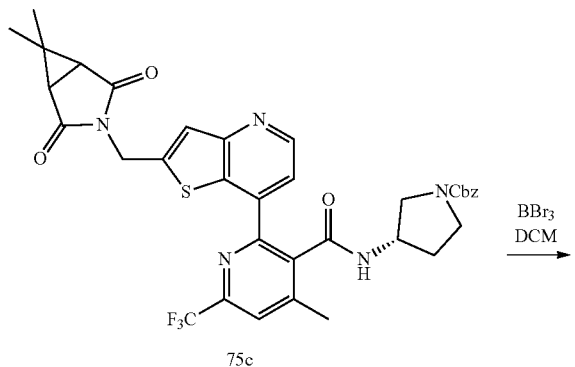

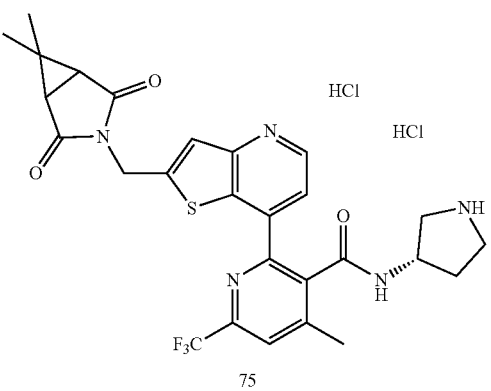

To the solution of 75c (26 mg; 0.04 mmol) in DCM (0.6 mL) under argon atmosphere a solution of BBr₃ in DCM (1 M; 0.6 mL; 0.6 mmol) was added and the reaction was stirred at room temperature for 50 minutes. The reaction progress was monitored by LC-MS. When analysis indicated completion of the reaction, the solvent was removed in vacuo and the residue was diluted with 1 M HCl and extracted with AcOEt. An aqueous layer was concentrated to dryness and purified by preparative reversed-phase column chromatography (C-18, water+0.5‰ HCl (36%)/MeCN, 97:3 to 40:60, 20 min, 20 mL/min). The title compound (75) was obtained as a dihydrochloride salt as a white solid in 15% yield (4 mg; 0.006 mmol).

ESI-MS m/z for $C_{27}H_{27}F_3N_5O_3S$ found 558.2 [M+H]⁺; $R_t$=1.02 min; ¹H NMR (700 MHz, DMSO-d₆+D₂O) δ 8.72 (d, J=5.0 Hz, 1H), 7.97 (s, 1H), 7.61 (d, J=5.0 Hz, 1H), 7.48 (s, 1H), 4.93 (s, 2H), 4.45-4.39 (m, 1H), 3.31 (s, 2H), 3.23-3.15 (m, 2H), 2.90 (dd, J=12.2, 5.8 Hz, 1H), 2.54-2.52 (m, 1H), 2.49 (s, 3H), 2.28-2.24 (m, 3H), 2.25-2.13 (m, 1H), 1.85 (s, 3H), 1.78-1.66 (m, 1H).

Example 76

Synthesis of 6,6-dimethyl-3-((7-(4-methyl-3-(piperazine-1-carbonyl)-6-(trifluoromethyl)pyridin-2-yl)thieno[3,2-b]pyridin-2-yl)methyl)-3-azabicyclo[3.1.0]hexane-2,4-dione dihydrochloride (76)

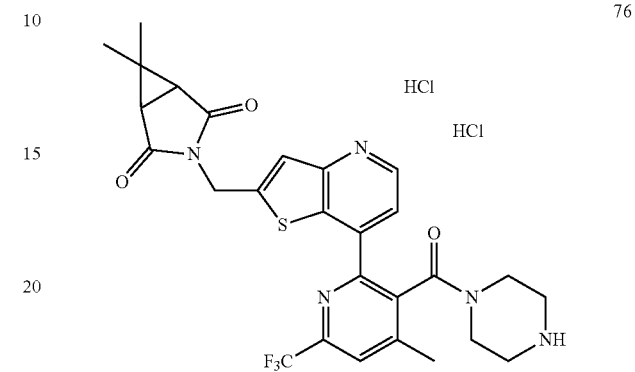

The title compound (76) was obtained as a dihydrochloride salt in 30% overall yield in a similar way to Example 45 with the exception that, in the first step of the synthesis tert-butyl piperazine-1-carboxylate was used instead of tert-butyl piperazine-1-carboxylate and acid II was used instead of 2-chloro-4-methylnicotinic acid and in the last step of the synthesis, the crude product was dissolved in water and to this solution 2 M HCl (3 drops) was added and then obtained dihydrochloride salt was lyophilized.

ESI-MS m/z for $C_{27}H_{27}F_3N_5O_3S$ found 558.2 [M+H]⁺; $R_t$=1.01 min; ¹H NMR (700 MHz, DMSO-d₆+D₂O) δ 8.76 (d, J=4.9 Hz, 1H), 8.06 (d, J=0.7 Hz, 1H), 7.52 (d, J=0.9 Hz, 1H), 7.44 (d, J=4.9 Hz, 1H), 4.83-4.75 (m, 2H), 3.52-3.42 (m, 1H), 3.23 (ddd, J=14.1, 6.3, 3.4 Hz, 1H), 3.10 (td, J=8.8, 4.2 Hz, 1H), 2.97 (dt, J=13.4, 4.6 Hz, 1H), 2.84-2.76 (m, 1H), 2.76-2.67 (m, 1H), 2.58-2.52 (m, 3H), 2.46-2.42 (m, 3H), 2.32-2.27 (m, 1H), 1.15 (s, 3H), 0.98 (s, 3H).

Example 77

Synthesis of 6,6-dimethyl-3-((7-(4-methyl-3-((S)-3-(methylamino)pyrrolidine-1-carbonyl)-6-(trifluoromethyl)pyridin-2-yl)thieno[3,2-b]pyridin-2-yl)methyl)-3-azabicyclo[3.1.0]hexane-2,4-dione dihydrochloride (77)

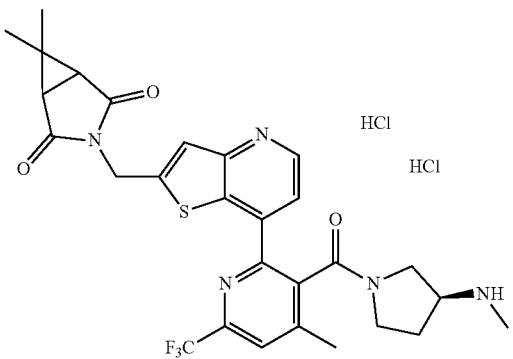

The title compound (77) was obtained as a dihydrochloride salt as a mixture of rotamers in 4% overall yield in a similar way to Example 45 with the exception that, in the first step of the synthesis the tert-butyl (S)-methyl(pyrrolidin-3-yl)carbamate was used instead of tert-butyl piperazine-1-carboxylate and acid II was used instead of 2-chloro-4-methylnicotinic acid and in the last step of the synthesis, the crude product was purified by preparative reversed-phase column chromatography (C-18, water+0.5‰ HCl (36%)/MeCN, 98:2 to 30:70, 30 min, 20 mL/min).

ESI-MS m/z for $C_{28}H_{29}F_3N_5O_3S$ found 572.2 [M+H]$^+$; $R_t$=1.00 min; $^1$H NMR (700 MHz, DMSO-$d_6$+$D_2$O) δ 8.77-8.69 (m, 1H), 8.10-7.94 (m, 1H), 7.60-7.44 (m, 2H), 4.83-4.74 (m, 2H), 4.12-3.58 (m, 2H), 3.42-3.05 (m, 2H), 2.93-2.80 (m, 3H), 2.68-2.56 (m, 2H), 2.49-2.29 (m, 3H), 2.23-1.78 (m, 2H), 1.63-1.55 (m, 1H), 1.21-1.15 (m, 3H), 1.10-0.99 (m, 3H).

Example 78

Synthesis of 6,6-dimethyl-3-((7-(4-methyl-3-((S)-2-methylpiperazine-1-carbonyl)-6-(trifluoromethyl)pyridin-2-yl)thieno[3,2-b]pyridin-2-yl)methyl)-3-azabicyclo[3.1.0]hexane-2,4-dione dihydrochloride (78)

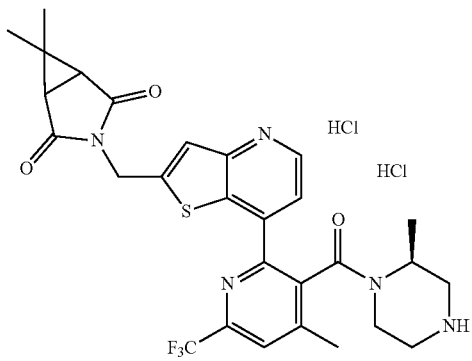

78

The title compound (78) was obtained as a dihydrochloride salt in 12% overall yield in a similar way to Example 53 with the exception that, in the first step of the synthesis tert-butyl (S)-3-methylpiperazine-1-carboxylate was used instead of tert-butyl 2,2-dimethylpiperazine-1-carboxylate and an acid 70c was used instead of an acid 42e and in the last step of the synthesis the crude product was purified by preparative reversed-phase column chromatography (column: Cosmosil Cholester 20×250 mm, water+0.5‰ HCl (36%)/MeCN, 99:1 to 40:60, 30 min, 20 mL/min).

ESI-MS m/z for $C_{28}H_{29}F_3N_5O_3S$ found 572.5 [M+H]$^+$; $R_t$=1.02 min; $^1$H NMR (700 MHz, DMSO-$d_6$) δ 8.86-8.65 (m, 1H), 8.06-7.95 (m, 1H), 7.67-7.33 (m, 2H), 5.00-4.53 (m, 3H), 3.55-3.36 (m, 1H), 3.25-3.03 (m, 2H), 3.00-2.89 (m, 1H), 2.90-2.73 (m, 1H), 2.72-2.56 (m, 1H), 2.50-2.38 (m, 5H), 1.51-1.21 (m, 1H), 1.21-1.07 (m, 3H), 1.08-0.99 (m, 3H), 0.96-0.14 (m, 2H).

Example 79

Synthesis of 3-((7-(3-((S)-2,4-dimethylpiperazine-1-carbonyl)-4-methyl-6-(trifluoromethyl)pyridin-2-yl)thieno[3,2-b]pyridin-2-yl)methyl)-6,6-dimethyl-3-azabicyclo[3.1.0]hexane-2,4-dione hydrochloride (79)

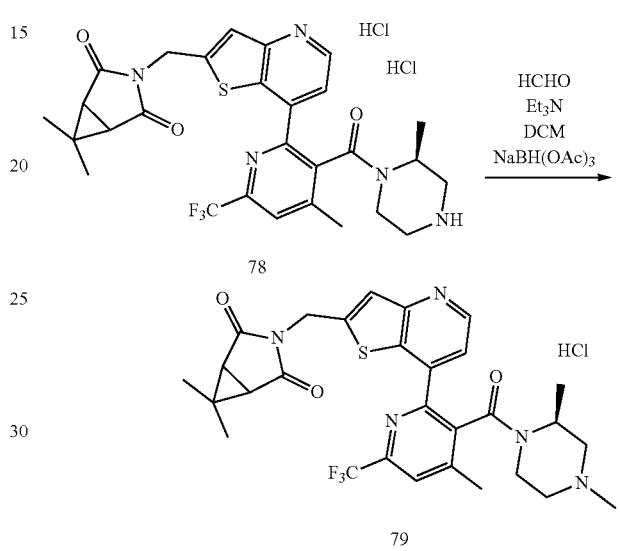

To the solution of 78 (9 mg; 0.014 mmol) in DCM (0.7 mL) Et$_3$N (0.01 mL; 0.058 mmol) and formalin (36% aqueous solution; 0.05 mL) were added and this mixture was stirred at room temperature for 1 hour. Then to this mixture NaBH(OAc)$_3$ (15 mg; 0.069 mmol) was added and whole was stirred at room temperature for 1 hour. The reaction progress was monitored by LC-MS. When analysis indicated completion of the reaction, the mixture was diluted with DCM and washed with 5% NaHCO$_3$. The organic layer was dried over anhydrous MgSO$_4$, filtered and concentrated in vacuo and the residue was purified by preparative reversed-phase column chromatography (C-18, water+0.5‰ HCl (36%)/MeCN, 98:2 to 30:70, 30 min, 20 mL/min). The title compound (79) was obtained as a hydrochloride salt as a mixture of rotamers in 71% yield (6 mg; 0.010 mmol).

ESI-MS m/z for $C_{29}H_{31}F_3N_5O_3S$ found 586.6 [M+H]$^+$; $R_t$=1.34 min; $^1$H NMR (700 MHz, D$_2$O) δ 9.22-9.11 (m, 1H), 8.46-8.35 (m, 1H), 8.18-7.95 (m, 2H), 5.39-4.87 (m, 3H), 4.06-3.71 (m, 2H), 3.68-3.40 (m, 2H), 3.34-3.15 (m, 3H), 2.95 (q, J=3.6 Hz, 3H), 2.87-2.48 (m, 3H), 1.75-1.60 (m, 1H), 1.56-1.42 (m, 3H), 1.40-1.30 (m, 3H), 1.25-0.52 (m, 2H).

Example 80

Synthesis of 6,6-dimethyl-3-((7-(4-methyl-3-(4-methylpiperazine-1-carbonyl)-6-(trifluoromethyl)pyridin-2-yl)thieno[3,2-b]pyridin-2-yl)methyl)-3-azabicyclo[3.1.0]hexane-2,4-dione dihydrochloride (80)

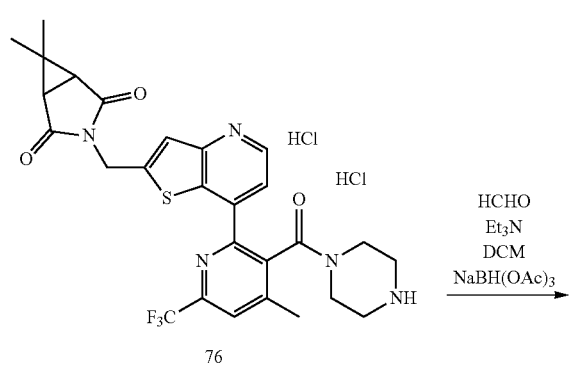

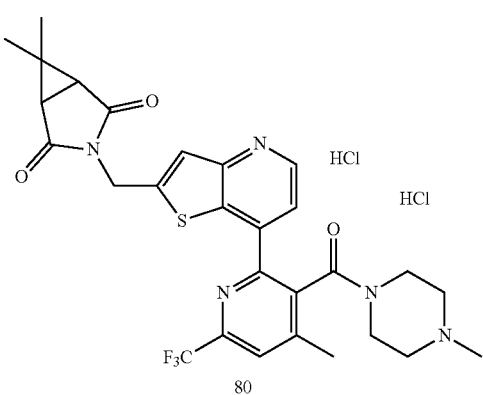

To the solution of 76 (9 mg; 0.014 mmol) in DCM (1 mL) Et₃N (0.008 ML; 0.057 mmol) and formalin (36% aqueous solution; 0.05 mL) were added and this mixture was stirred at room temperature for 1 hour. Then to this mixture NaBH(OAc)₃ (6 mg; 0.028 mmol) was added and whole was stirred at room temperature for 1 hour. The reaction progress was monitored by LC-MS. When analysis indicated completion of the reaction, the mixture was diluted with DCM and washed with 5% NaHCO₃. The organic layer was dried over anhydrous MgSO₄, filtered and concentrated in vacuo and the residue was purified by preparative reversed-phase column chromatography (C-18, water+0.5‰ HCl (36%)/MeCN, 98:2 to 30:70, 30 min, 20 mL/min). The title compound (80) was obtained as a dihydrochloride salt as a white solid in 71% yield (7 mg; 0.010 mmol).

ESI-MS m/z for $C_{28}H_{29}F_3N_5O_3S$ found 572.1 [M+H]⁺; $R_t$=1.01 min; ¹H NMR (700 MHz, DMSO-d₆+D₂O) δ 8.76 (d, J=5.0 Hz, 1H), 8.02 (s, 1H), 7.50 (t, J=0.9 Hz, 1H), 7.42 (d, J=4.9 Hz, 1H), 4.84-4.73 (m, 2H), 3.34-3.15 (m, 3H), 2.98-2.91 (m, 1H), 2.70 (s, 3H), 2.63-3.15 (m, 1H), 2.56-2.53 (m, 4H), 2.47 (s, 3H), 2.41 (p, J=1.9 Hz, 1H), 1.18 (s, 3H), 1.03 (s, 3H).

Example 81

Synthesis of 3-((7-(3-((S)-3-aminopyrrolidine-1-carbonyl)-4-methyl-6-(trifluoromethyl)pyridin-2-yl)thieno[3,2-b]pyridin-2-yl))methyl)-6,6-dimethyl-3-azabicyclo[3.1.0]hexane-2,4-dione dihydrochloride (81)

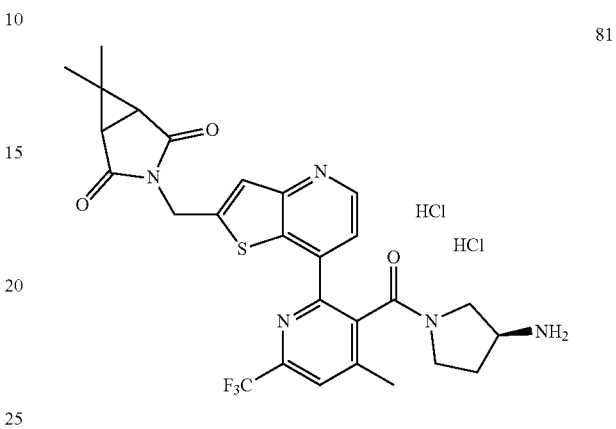

The title compound (81) was obtained as a dihydrochloride salt as a mixture of rotamers in 27% overall yield in a similar way to Example 45 with the exception that, in the first step of the synthesis tert-butyl (S)-pyrrolidin-3-ylcarbamate was used instead of tert-butyl piperazine-1-carboxylate and acid H was used instead of 2-chloro-4-methylnicotinic acid and in the last step of the synthesis, the crude product was dissolved in a solution of HCl in AcOEt and stirred at room temperature for 5 minutes. Then Et₂O was added to this mixture and the obtained white solid was filtered off, then washed with Et₂O. The solid was dissolved in water and lyophilized.

ESI-MS m/z for $C_{27}H_{27}F_3N_5O_3S$ found 558.4 [M+H]⁺; $R_t$=0.97 min; ¹H NMR (700 MHz, D₂O) δ 9.20-9.07 (m, 1H), 8.51-8.30 (m, 1H), 8.14-7.89 (m, 2H), 5.32-5.20 (m, 2H), 4.57-4.06 (m, 2H), 4.03-3.77 (m, 1H), 3.69-3.13 (m, 2H), 3.04-2.92 (m, 3H), 2.91-2.78 (m, 2H), 2.76-2.35 (m, 1H), 2.27-1.86 (m, 1H), 1.53 (d, J=9.7 Hz, 3H), 1.42-1.26 (m, 3H).

Example 82

Synthesis of 3-((7-(3-((S)-3-(dimethylamino)pyrrolidine-1-carbonyl)-4-methyl-6-(trifluoromethyl)pyridin-2-yl)thieno[3,2-b]pyridin-2-yl)methyl)-6,6-dimethyl-3-azabicyclo[3.1.0]hexane-2,4-dione dihydrochloride (82)

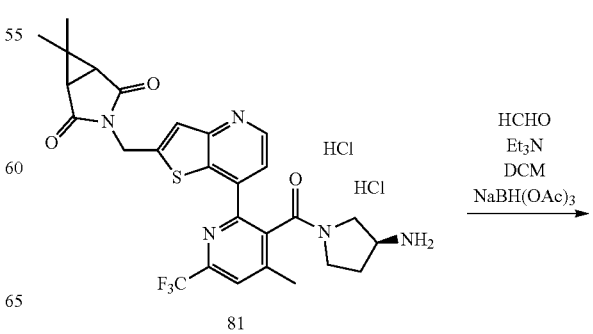

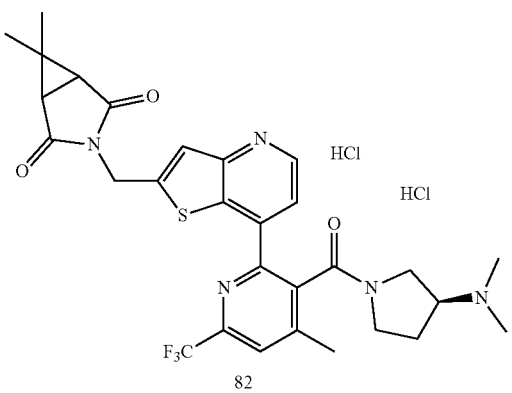

82

To the solution of 81 (20 mg; 0.032 mmol) in DCM (0.7 mL) Et$_3$N (0.018 mL; 0.120 mmol) and formalin (36% aqueous solution; 0.05 mL) were added and this mixture was stirred at room temperature for 1 hour. Then to this mixture NaBH(OAc)$_3$ (13 mg; 0.063 mmol) was added and whole was stirred at room temperature for 1 hour. The reaction progress was monitored by LC-MS. When analysis indicated completion of the reaction, the mixture was diluted with DCM and washed with 5% NaHCO$_3$. The organic layer was dried over anhydrous MgSO$_4$, filtered and concentrated in vacuo and the residue was purified by preparative reversed-phase column chromatography (C-18, water+0.5‰ HCl (36%)/MeCN, 98:2 to 30:70, 30 min, 20 mL/min). The title compound (82) was obtained as a dihydrochloride salt as a white solid in 44% yield (8 mg; 0.014 mmol).

ESI-MS m/z for C$_{29}$H$_{31}$F$_3$N$_5$O$_3$S found 586.2 [M+H]$^+$; R$_t$=1.06 min; $^1$H NMR (700 MHz, DMSO-d$_6$+D$_2$O) δ 8.81-8.61 (m, 1H), 8.15-7.96 (m, 1H), 7.54-7.44 (m, 2H), 4.86-4.73 (m, 2H), 4.11-3.78 (m, 1H), 3.77-3.60 (m, 1H), 3.49-3.32 (m, 1H), 3.28-3.05 (m, 1H), 2.77 (s, 2H), 2.63 (s, 3H), 2.58-2.52 (m, 4H), 2.49-2.43 (m, 3H), 2.39-1.59 (m, 3H), 1.21-1.15 (m, 2H), 1.09-0.98 (m, 3H).

Example 83

Synthesis of 3-((7-(3-(3,3-difluoropyrrolidine-1-carbonyl)-4-methyl-6-(trifluoromethyl)pyridin-2-yl)thieno[3,2-b]pyridin-2-yl)methyl)-6,6-dimethyl-3-azabicyclo[3.1.0]hexane-2,4-dione hydrochloride (83)

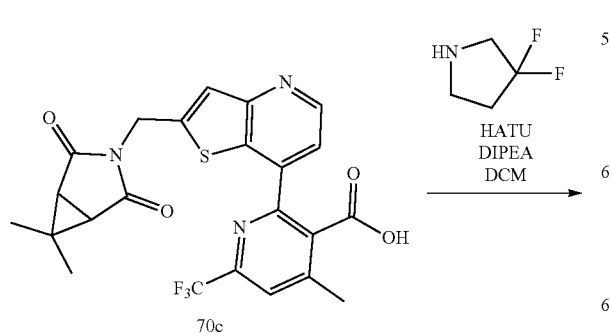

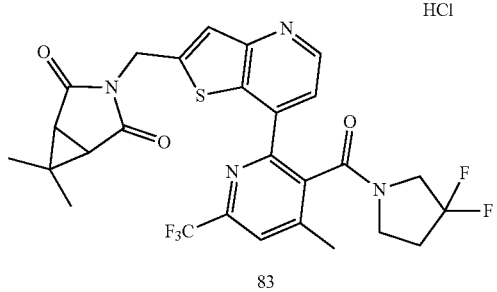

83

The title compound (83) was obtained as a hydrochloride salt from 70c (40 mg; 0.066 mmol) and from 3,3-difluoropyrrolidine (10 mg; 0.073 mmol) according to the General Procedure I in 59% yield (24 mg; 0.039 mmol). The crude product was purified by flash column chromatography on silica (hexane/AcOEt, 2:8, v/v, 30 min; then AcOEt, 100%) and then dissolved in a solution of HCl in AcOEt and stirred at room temperature for 5 minutes. Then Et$_2$O was added to this mixture and the obtained white solid was filtered off, then washed with Et$_2$O. The solid was dissolved in water and lyophilized.

ESI-MS m/z for C$_{27}$H$_{24}$F$_5$N$_4$O$_3$S found 579.3 [M+H]$^+$; R$_t$=1.45 min; $^1$H NMR (700 MHz, DMSO-d$_6$) δ 8.81-8.73 (m, 1H), 8.16-8.04 (m, 1H), 7.56-7.47 (m, 2H), 4.89-4.76 (m, 2H), 4.01-3.75 (m, 2H), 3.61-3.25 (m, 1H), 3.03-2.72 (m, 1H), 2.59-2.52 (m, 3H), 2.48-2.24 (m, 3H), 2.08-1.97 (m, 11H), 1.22-1.19 (m, 3H), 1.06-1.03 (m, 3H).

Example 84

Synthesis of 6,6-dimethyl-3-((7-(4-methyl-3-(morpholine-4-carbonyl)-6-(trifluoromethyl)pyridin-2-yl)thieno[3,2-b]pyridin-2-yl)methyl)-3-azabicyclo[3.1.0]hexane-2,4-dione hydrochloride (84)

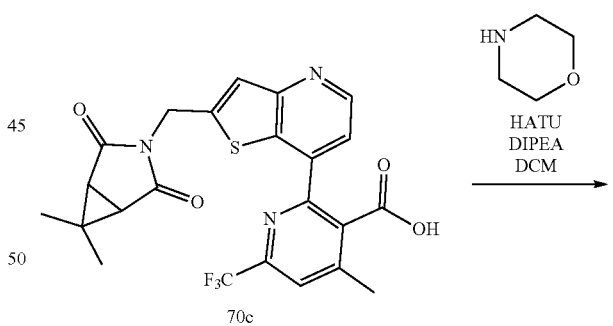

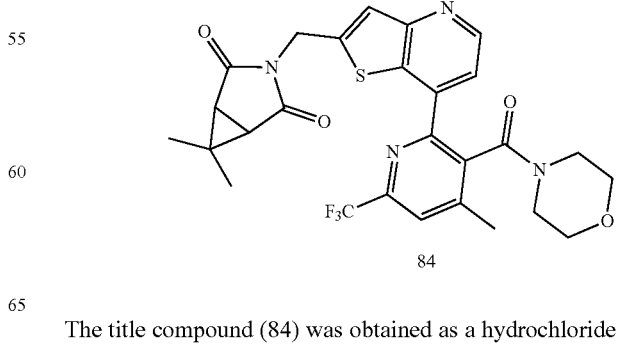

84

The title compound (84) was obtained as a hydrochloride salt from 70c (50 mg; 0.082 mmol) and from morpholine (9 mg; 0.090 mmol) according to the General Procedure I in 45% yield (22 mg; 0.037 mmol). The crude product was purified by flash column chromatography on silica (hexane/AcOEt, 2:8, v/v, 30 min; then AcOEt, 100%) and then dissolved in MeCN/water with addition of 2 N HCl (few drops), frozen and lyophilized.

ESI-MS m/z for $C_{27}H_{26}F_3N_4O_4S$ found 559.2 [M+H]$^+$; $R_t$=1.36 min; $^1$H NMR (700 MHz, DMSO-d$_6$) δ 8.78 (d, J=4.9 Hz, 1H), 8.09-7.94 (m, 1H), 7.56 (d, J=4.9 Hz, 1H), 7.51 (s, 1H), 4.81 (s, 2H), 3.69-3.46 (m, 3H), 3.37-3.30 (m, 2H), 3.06-3.01 (m, 1H), 2.66 (dddt, J=16.5, 13.3, 6.1, 3.1 Hz, 2H), 2.57-2.52 (m, 2H), 2.49 (s, 3H), 1.21 (s, 3H), 1.06 (s, 3H).

Example 85

Synthesis of 3-((7-(3-(3,3-difluoroazetidine-1-carbonyl)-4,6-dimethylpyridin-2-yl)thieno[3,2-b]pyridin-2-yl)methyl)-6,6-dimethyl-3-azabicyclo[3.1.0]hexane-2,4-dione hydrochloride (85)

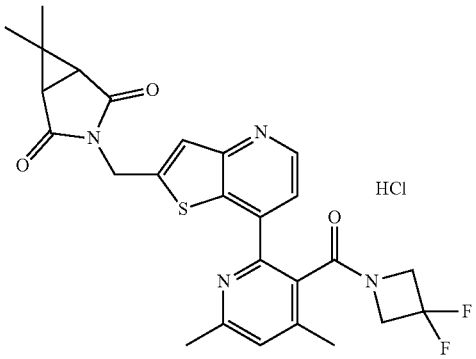

The title compound (85) was obtained as a hydrochloride salt in 2% overall yield in a similar way to Example 48 with the exception that, in the first step of the synthesis 3,3-difluoroazetidine hydrochloride was used instead of morpholine and 2-chloro-4,6-dimethylnicotinic acid was used instead of 2-chloro-4-methylnicotinic acid and in the last step of the synthesis the crude product was purified by preparative reversed-phase column chromatography (C-18, water+0.5‰ HCl (36%)/MeCN, 98:2 to 40:60, 30 min, 20 mL/min).

ESI-MS m/z for $C_{26}H_{24}F_2N_4O_3S$ found 511.7 [M+H]$^+$; $R_t$=1.23 min; $^1$H NMR (700 MHz, Methanol-d$_4$) δ 9.02 (d, J=6.1 Hz, 1H), 8.13 (d, J=6.0 Hz, 1H), 7.80 (s, 1H), 7.57 (s, 1H), 5.02 (d, J=0.8 Hz, 2H), 4.73-4.44 (m, 2H), 4.23 (d, J=12.0 Hz, 1H), 3.76 (d, J=11.8 Hz, 1H), 2.74 (s, 3H), 2.56 (s, 2H), 2.49 (d, J=0.6 Hz, 3H), 1.28 (s, 3H), 1.15 (s, 3H).

Example 86

Synthesis of N-(4-(2-((6,6-dimethyl-2,4-dioxo-3-azabicyclo[3.1.0]hexan-3-yl)methyl)thieno[3,2-b]pyridin-7-yl)-2-methyl-6-(trifluoromethyl)pyridin-3-yl)-3,3-difluorocyclobutane-1-carboxamide hydrochloride (86)

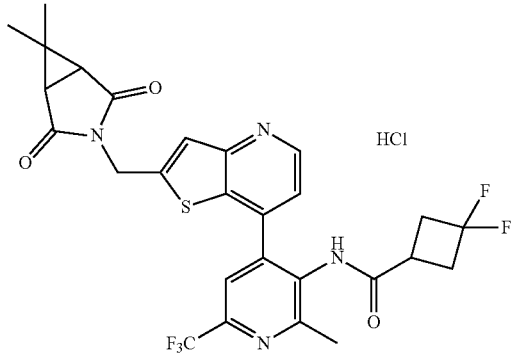

The title compound (86) was obtained as a hydrochloride salt as a white solid in 32% overall yield in a similar way to Example 61 with the exception that, in the first step of the synthesis, 3,3-difluorocyclobutane-1-carboxylic acid was used instead of 2-methoxyacetyl chloride and this reaction was carried on with the addition of CDI (1.1 equivalents), and in the last step of the synthesis, the crude product was purified by preparative reversed-phase column chromatography (C-18, water+0.5‰ HCl (36%)/MeCN, 98:2 to 30:70, 30 min, 20 mL/min).

ESI-MS m/z for $C_{27}H_{24}F_5N_4O_3S$ found 579.8 [M+H]$^+$; $R_t$=1.42 min; $^1$H NMR (700 MHz, Methanol-d$_4$) δ 8.95 (d, J=5.6 Hz, 1H), 7.92 (d, J=0.7 Hz, 1H), 7.76 (s, 1H), 7.73 (d, J=5.6 Hz, 1H), 4.98 (d, J=0.9 Hz, 2H), 3.65 (d, J=4.9 Hz, 1H), 3.02-2.90 (m, 1H), 2.70 (s, 3H), 2.60-2.55 (m, 2H), 2.54 (s, 2H), 2.38-2.23 (m, 2H), 1.27 (s, 3H), 1.15 (s, 3H).

Example 87

Synthesis of N-(4-(2-((6,6-dimethyl-2,4-dioxo-3-azabicyclo[3.1.0]hexan-3-yl)methyl)thieno[3,2-b]pyridin-7-yl)-2-methyl-6-(trifluoromethyl)pyridin-3-yl)piperidine-4-carboxamide hydrochloride (87)

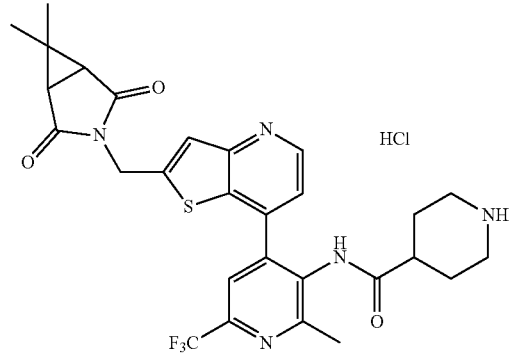

Step 1

Synthesis of tert-butyl 4-((4-bromo-2-methyl-6-(trifluoromethyl)pyridin-3-yl)carbamoyl)piperidine-1-carboxylate (87a)

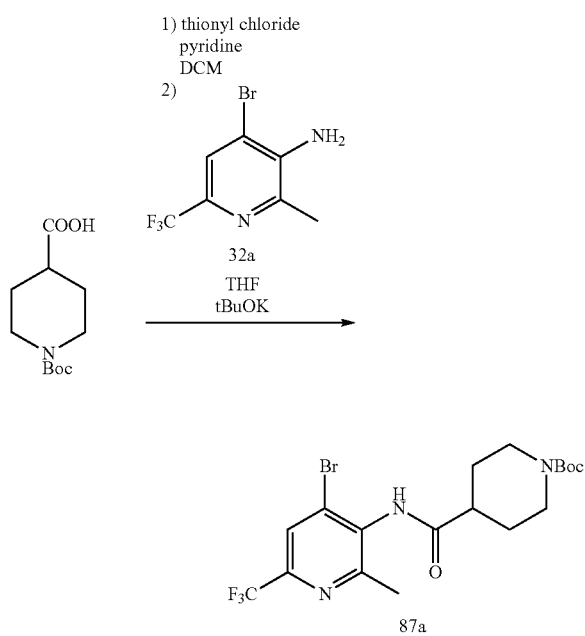

To the solution of 1-(tert-butoxycarbonyl)piperidine-4-carboxylic acid (1.3 g; 4.92 mmol) in DCM (10 mL) pyridine (1.97 mL; 24.61 mmol) was added and the reaction mixture was cooled to −20° C. Then thionyl chloride (0.41 mL; 5.71 mmol) was added dropwise under argon atmosphere and the reaction mixture was stirred at −10° C. for 1 hour. The reaction progress was monitored by LC-MS. To the solution of 32a (0.5 g; 1.97 mmol) in THF (5 mL) tBuOK (0.44 g; 3.94 mmol) was added under argon atmosphere and the reaction mixture was stirred at room temperature for 20 minutes. Next to this mixture a solution of generated acid chloride was added dropwise at room temperature and then the reaction mixture was heated at 50° C. for 24 hours, next at room temperature for 12 hours. After consumption of the starting material (confirmed by LC-MS analysis), to this mixture DCM was added and washed with 5% NaHCO$_3$, 10% citric acid, brine. The organic layer was dried over anhydrous Na$_2$SO$_4$, filtered and evaporated in vacuo. The crude product was purified by flash column chromatography on silica (hexane/AcOEt). The title compound 87a was obtained in 23% yield (0.21 g; 0.45 mmol).

ESI-MS m/z for $C_{14}H_{16}BrF_3N_3O_3$ found 410.0/412.0 [M-tBu]$^+$; R$_t$=1.53 min

Step 2

Synthesis of tert-butyl 4-((4-(2-(((6,6-dimethyl-2,4-dioxo-3-azabicyclo[3.1.0]hexan-3-yl)methyl)thieno[3,2-b]pyridin-7-yl)-2-methyl-6-(trifluoromethyl)pyridin-3-yl)carbamoyl)piperidine-1-carboxylate (87b)

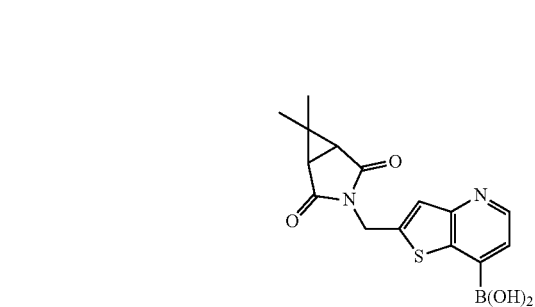

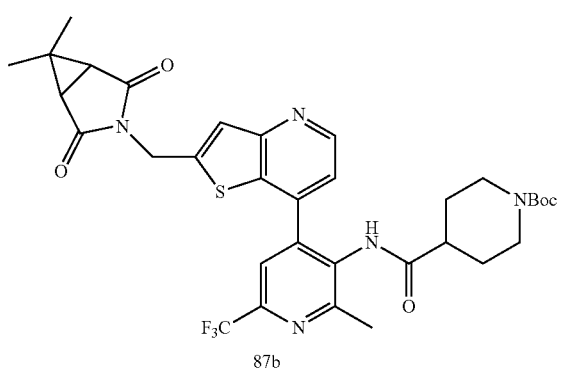

The title compound (87b) was obtained from 87a (50 mg; 0.11 mmol) and from boronic acid I (71 mg; 0.21 mmol) according to the General Procedure Va in 36% yield (27 mg; 0.04 mmol).

ESI-MS m/z for $C_{33}H_{37}F_3N_5O_5S$ found 672.1 [M+H]$^+$; R$_t$=1.58 min

371

Step 3

Synthesis of N-(4-(2-(((6,6-dimethyl-2,4-dioxo-3-azabicyclo[3.1.0]hexan-3-yl)methyl)thieno[3,2-b]pyridin-7-yl)-2-methyl-6-(trifluoromethyl)pyridin-3-yl)piperidine-4-carboxamide hydrochloride (87)

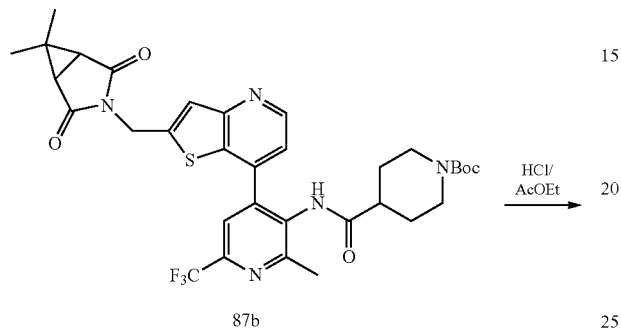

87b

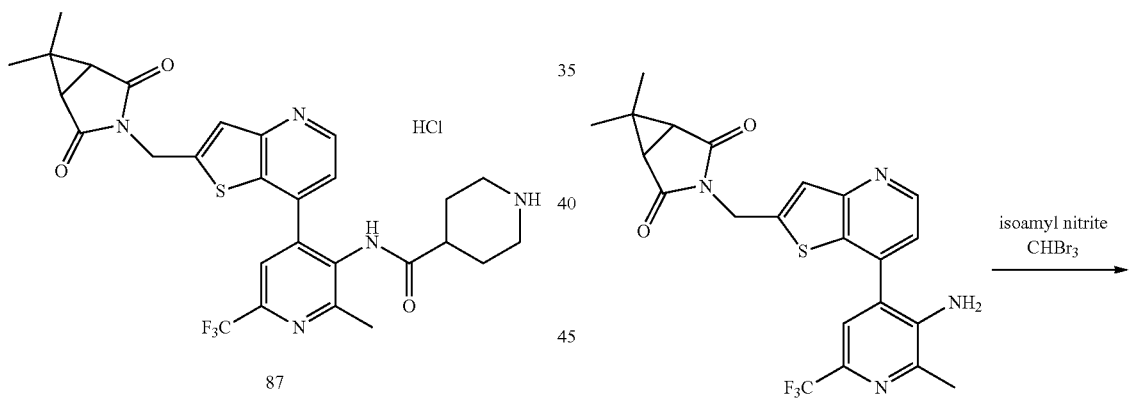

87

The title compound (87) was obtained as a hydrochloride salt as a white solid from 87b (27 mg; 0.040 mmol) according to the General Procedure IVa in 40% yield (10 mg; 0.014 mmol). The crude product was purified by preparative reversed-phase column chromatography (C-18, water+0.5‰ HCl (36%)/MeCN, 95:5 to 50:50, 30 min, 20 mL/min).

ESI-MS m/z for $C_{28}H_{29}F_3N_5O_3S$ found 572.7 [M+H]$^+$; $R_t$=0.99 min; $^1$H NMR (700 MHz, $D_2O$) δ 8.86 (d, J=5.7 Hz, 1H), 7.95 (s, 1H), 7.74 (s, 1H), 7.73-7.69 (m, 1H), 4.97 (d, J=1.0 Hz, 2H), 3.27 (d, J=13.0 Hz, 2H), 2.89 (td, J=13.0, 3.3 Hz, 2H), 2.63 (s, 2H), 2.60 (s, 4H), 1.72-1.55 (m, 2H), 1.48-1.28 (m, 2H), 1.20 (s, 3H), 1.05 (s, 3H).

372

Example 88

Synthesis of 6,6-dimethyl-3-((7-(2-methyl-3-(pyrrolidin-3-ylmethyl)-6-(trifluoromethyl)pyridin-4-yl)thieno[3,2-b]pyridin-2-yl)methyl)-3-azabicyclo[3.1.0]hexane-2,4-dione 2,2,2-trifluoroacetate (88)

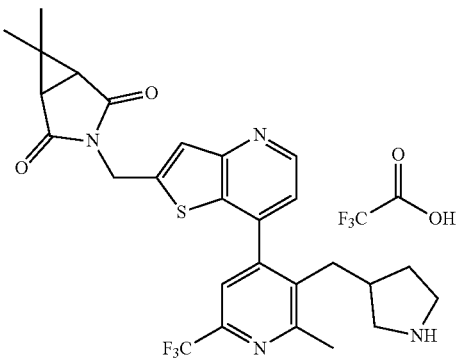

88

Step 1

Synthesis of 3-((7-(3-bromo-2-methyl-6-(trifluoromethyl)pyridin-4-yl)thieno[3,2-b]pyridin-2-yl)methyl)-6,6-dimethyl-3-azabicyclo[3.1.0]hexane-2,4-dione (88a)

62a

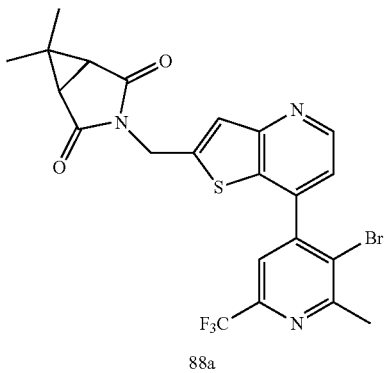

88a

To the solution of free amine 62a (465 mg; 1.01 mmol) in CHBr$_3$ (5 mL) isoamyl nitrite (0.2 mL; 1.51 mmol) was added and the reaction mixture was stirred at 85° C. overnight. The reaction progress was monitored by LC-MS. When analysis indicated completion of the reaction, to this mixture brine was added and the product was extracted with AcOEt. An organic layer was dried over anhydrous $Na_2SO_4$, filtered and concentrated in vacuo. The crude product was purified by flash column chromatography on silica (hexane/AcOEt, 4:6, v/v, 25 minutes). The title compound 88a was obtained in 40% yield (209 mg; 0.40 mmol).

ESI-MS m/z for $C_{22}H_{15}BrF_3N_3O_2S$ found 524.0/526.0 [M+H]$^+$; $R_t$=1.60 min; $^1$H NMR (700 MHz, DMSO-$d_6$) δ 8.77-8.75 (m, 1H), 7.74 (s, 1H), 7.54-7.52 (m, 1H), 7.37-7.33 (m, 1H), 4.80-4.74 (m, 2H), 3.36-3.34 (m, 2H), 2.80 (s, 3H), 1.17 (s, 3H), 1.01 (s, 3H); $^{19}$F NMR (235 MHz, DMSO-$d_6$) δ −65.71 (s).

Step 2

Synthesis of tert-butyl (E)-3-((4-(2-((6,6-dimethyl-2,4-dioxo-3-azabicyclo[3.1.0]hexan-3-yl)methyl)thieno[3,2-b]pyridin-7-yl)-2-methyl-6-(trifluoromethyl)pyridin-3-yl)methylene)pyrrolidine-1-carboxylate (88b)

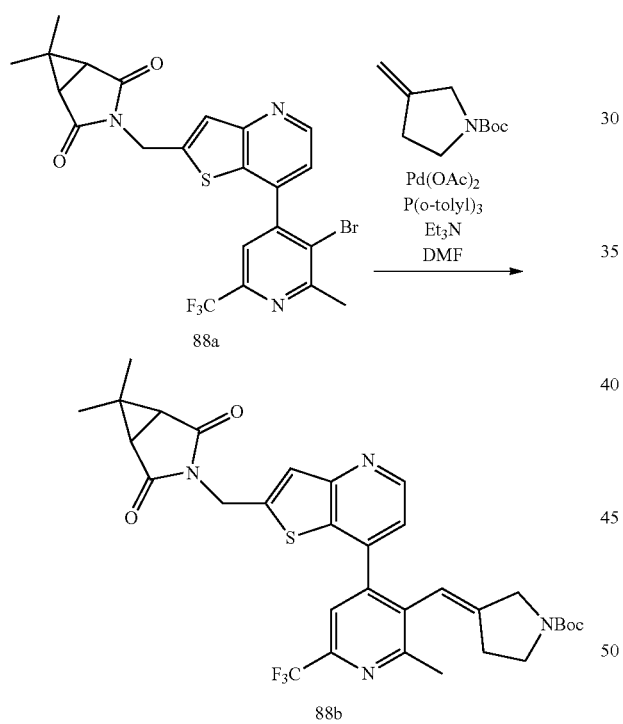

To the solution of 88a (120 mg; 0.230 mmol) in DMF (2 mL) tert-butyl 3-methylenepyrrolidine-1-carboxylate (54 mg; 0.297 mmol), Pd(OAc)$_2$ (4 mg; 0.023 mmol), P(o-tolyl)$_3$ (24 mg; 0.078 mmol) and Et$_3$N (0.1 mL; 0.690 mmol) were added and the reaction mixture was stirred at 100° C. overnight. The reaction progress was monitored by LC-MS. To the solution another portion of Pd(OAc)$_2$ (15 mg; 0.086 mmol) and P(o-tolyl)$_3$ (24 mg; 0.078 mmol) was added and stirred at 100° C. for 7 hours, then at 110° C. overnight. After consumption of the starting material (confirmed by LC-MS analysis), this mixture was taken between water/AcOEt. The layers were separated and the aqueous one was extracted with AcOEt. The organic layer was dried over anhydrous $MgSO_4$, filtered and concentrated in vacuo. The crude product was purified by flash column chromatography on silica (hexane/AcOEt, 2:8, v/v, 25 minutes). The title compound 88b was obtained in 22% yield (32 mg; 0.051 mmol).

ESI-MS m/z for $C_{32}H_{34}F_3N_4O_4S$ found 627.3 [M+H]$^+$; $R_t$=1.73 min

Step 3

Synthesis of tert-butyl 3-((4-(2-((6,6-dimethyl-2,4-dioxo-3-azabicyclo[3.1.0]hexan-3-yl)methyl)thieno[3,2-b]pyridin-7-yl)-2-methyl-6-(trifluoromethyl)pyridin-3-yl)methyl)pyrrolidine-1-carboxylate (88c)

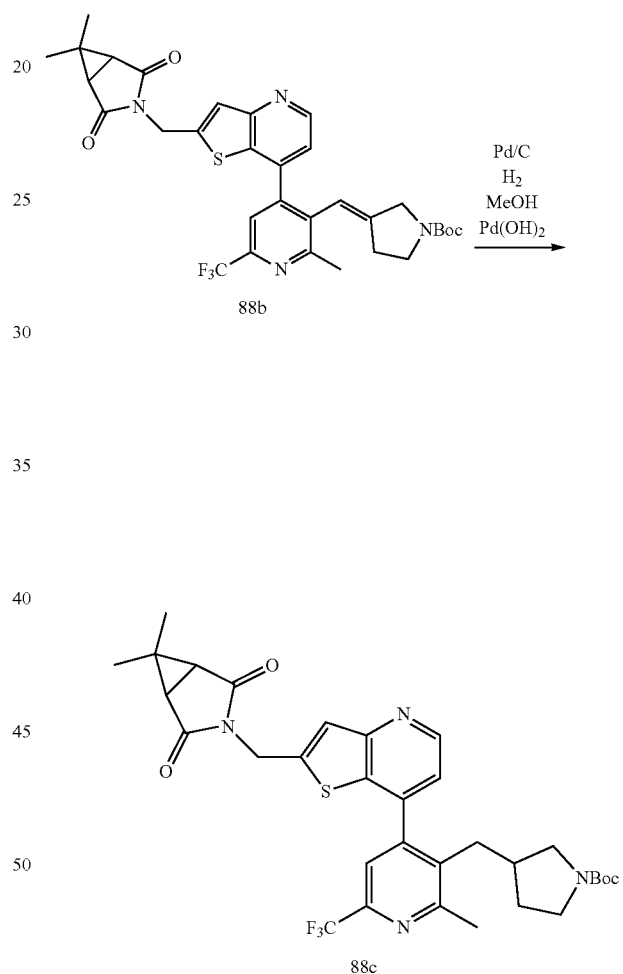

To the solution of 88b (46 mg; 0.073 mmol) in MeOH (1 mL) Pd/C (10 mol %; cat.) and Pd(OH)$_2$ (20 mol %; cat.) was added and the reaction mixture was conducted under hydrogen atmosphere at room temperature overnight. The reaction progress was monitored by LC-MS. When analysis indicated completion of the reaction, Pd/C was filtered off through a syringe filter and the solvent was stripped in vacuo. Compound 88c was obtained in 30% yield (14 mg; 0.022 mmol).

ESI-MS m/z for $C_{32}H_{36}F_3N_4O_4S$ found 629.3 [M+H]$^+$; $R_t$=1.73 min

Step 4

Synthesis of 6,6-dimethyl-3-((7-(2-methyl-3-(pyrrolidin-3-ylmethyl)-6-(trifluoromethyl)pyridin-4-yl)thieno[3,2-b]pyridin-2-yl)methyl)-3-azabicyclo[3.1.0]hexane-2,4-dione 2,2,2-trifluoroacetate (88)

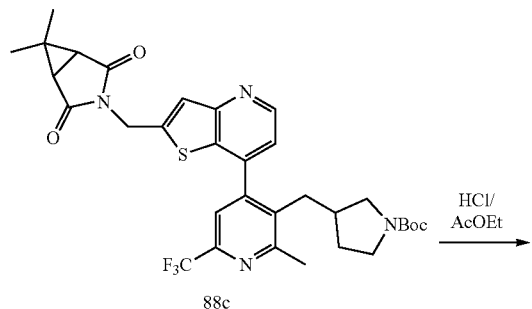

88c

HCl/AcOEt

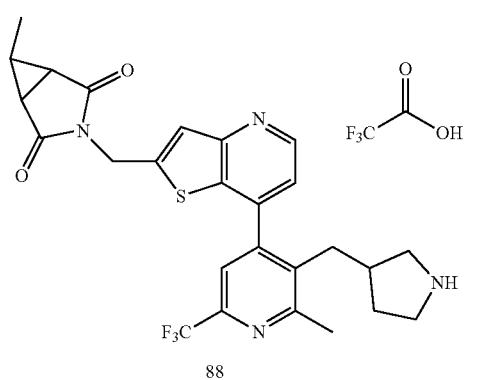

88

The title compound (88) was obtained as a TFA salt as a w % bite solid from 88c (14 mg; 0.022 mmol) according to the General Procedure IVa in 42% yield (6 mg; 0.009 mmol). The crude product was purified by preparative reversed-phase column chromatography (C-18, water/MeCN+1‰ TFA, 99:1 to 40:60, 30 min, 20 mL/min).

ESI-MS m/z for $C_{27}H_{28}F_3N_4O_2S$ found 529.9 [M+H]$^+$; $R_t$=1.02 min; $^1$H NMR (700 MHz, D$_2$O) δ 9.01-8.96 (m, 1H), 7.95-7.88 (m, 1H), 7.89-7.86 (m, 1H), 7.80 (d, J=17.9 Hz, 1H), 5.04 (s, 2H), 3.36-3.30 (m, 1H), 3.25-3.02 (m, 3H), 2.81 (s, 3H), 2.70 (s, 2H), 2.67-2.58 (m, 2H), 2.48-2.38 (m, 1H), 1.96-1.88 (m, 1H), 1.28 (s, 3H), 1.23-1.14 (m, 1H), 1.08 (d, J=6.2 Hz, 3H).

Example 89

Synthesis of 6,6-dimethyl-3-((7-(2-methyl-3-(pyrrolidin-3-ylmethyl)-6-(trifluoromethyl)pyridin-4-yl)thieno[3,2-b]pyridin-2-yl)methyl)-3-azabicyclo[3.1.0]hexane-2,4-dione hydrochloride (89)

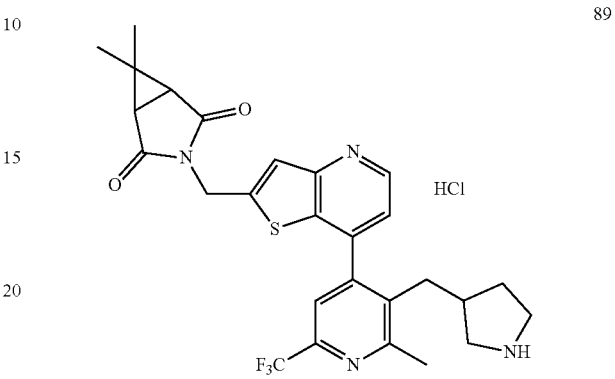

89

The title compound (89) was obtained as a hydrochloride salt as a single enantiomer of compound 88 in 2% overall yield in the same way as for Example 88 with the exception that, in the third step of the synthesis, the crude product was separated by chiral column chromatography (Cellulose-4, 250/21.2 mm, hexane/IPA:MeOH (10:2, v/v), 90:10 to 10:90.40 min, 15 mL/min)(confirmation of enantiomeric purity: Cellulose-4, 155/4.6 mm, hexane/IPA:MeOH (10:2, v/v), 90:10 to 10:90, 40 min, 20 mL/min, $R_t$=20.2 min), and in the last step of the synthesis, the crude product was lyophilized from water.

ESI-MS m/z for $C_{27}H_{28}F_3N_4O_2S$ found 529.8 [M+H]$^+$; $R_t$=1.06 min; $^1$H NMR (700 MHz, D$_2$O) δ 8.85-8.81 (m, 1H), 7.72-7.62 (m, 3H), 4.93-4.85 (m, 2H), 3.27-3.18 (m, 1H), 3.15-2.94 (m, 3H), 2.72 (s, 3H), 2.59 (s, 2H), 2.56-2.48 (m, 2H), 2.40-2.27 (m, 1H), 1.87-1.75 (m, 1H), 1.28-1.05 (nm 1H), 1.19 (s, 3H), 0.98 (d, J=7.5 Hz, 3H).

Example 90

Synthesis of 6,6-dimethyl-3-((7-(2-methyl-3-(pyrrolidin-3-ylmethyl)-6-(trifluoromethyl)pyridin-4-yl)thieno[3,2-b]pyridin-2-yl)methyl)-3-azabicyclo[3.1.0]hexane-2,4-dione hydrochloride (90)

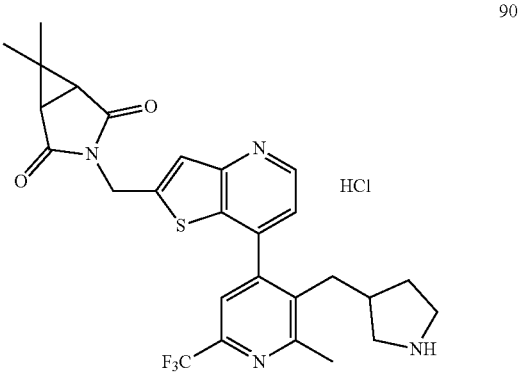 [SMILES: Cc1nc(C(F)(F)F)cc(-c2ccnc3cc(CN4C(=O)C5C(C4=O)C5(C)C)sc23)c1CC1CCNC1 ; Cl]

90

The title compound (90) was obtained as a hydrochloride salt as a second single enantiomer of compound 88 in 2% overall yield in the same way as for Example 88 with the exception that, in the third step of the synthesis, the crude product was separated by chiral column chromatography (Cellulose-4, 250/21.2 mm, hexane/IPA:MeOH (10:2, v/v), 90:10 to 10:90, 40 min, 15 mL/min)(confirmation of enantiomeric purity: Cellulose-4, 155/4.6 mm, hexane/IPA:MeOH (10:2, v/v), 90:10 to 10:90.40 min, 20 mL/min, $R_t$=21.4 min), and in the last step of the synthesis, the crude product was lyophilized from water.

ESI-MS m/z for $C_{27}H_{28}F_3N_4O_2S$ found 529.5 [M+H]$^+$; $R_t$=1.06 min; $^1$H NMR (700 MHz, D$_2$O) δ 8.85-8.80 (m, 1H), 7.72-7.62 (m, 3H), 4.93-4.85 (m, 2H), 3.27-3.18 (m, 1H), 3.15-2.94 (m, 3H), 2.71 (s, 3H), 2.59 (s, 2H), 2.56-2.48 (m, 2H), 2.40-2.27 (m, 1H), 1.87-1.75 (m, 1H), 1.28-1.05 (m, 1H), 1.19 (s, 3H), 0.98 (d, J=7.5 Hz, 3H).

Example 91

Synthesis of 6,6-dimethyl-3-((7-(2-methyl-3-(morpholin-2-ylmethyl)-6-(trifluoromethyl)pyridin-4-yl)thieno[3,2-b]pyridin-2-yl)methyl)-3-azabicyclo[3.1.0]hexane-2,4-dione 2,2,2-trifluoroacetate (91)

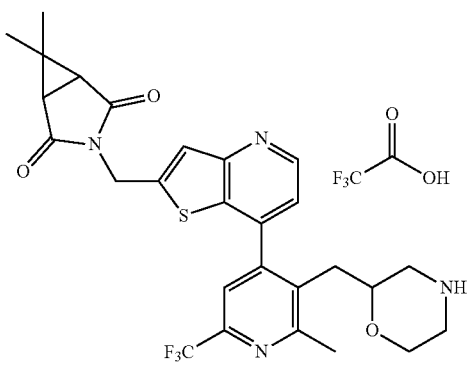

91

Step 1

Synthesis of tert-butyl 2-((4,4,5,5-tetramethyl-1,3,2-dioxaborolan-2-yl)methyl)morpholine-4-carboxylate (91a)

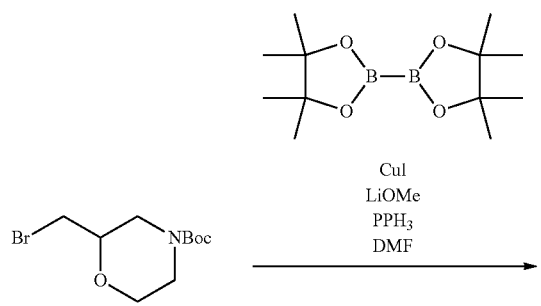

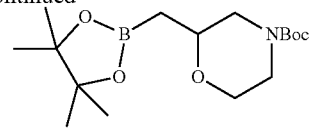

91a

A suspension of tert-butyl 2-(bromomethyl)morpholine-4-carboxylate (0.6 g; 2.14 mmol), CuI (41 mg; 0.21 mmol), LiOMe (162 mg; 4.28 mmol), PPh$_3$ (112 mg; 0.43 mmol) and bis(pinacolato)diboron (815 mg; 3.21 mmol) in DMF (12 mL) was purged with Ar and then stirred at 35° C. in a sealed capsule for 2 hours. The reaction completion was confirmed by LC-MS. Then DMF was evaporated in vacuo and the residue was purified by flash column chromatography on silica (hexane/AcOEt, 7:3, v/v, 20 minutes). The title compound 91a was obtained in 23% yield (160 mg; 0.49 mmol).

ESI-MS m/z for $C_{11}H_2BNO_3$ found 228.0 [M+H-Boc]$^+$; $R_t$=1.52 min

Step 2

Synthesis of tert-butyl 2-((4-(2-((6,6-dimethyl-2,4-dioxo-3-azabicyclo[3.1.0]hexan-3-yl)methyl)thieno[3,2-b]pyridin-7-yl)-2-methyl-6-(trifluoromethyl)pyridin-3-yl)methyl)morpholine-4-carboxylate (91b)

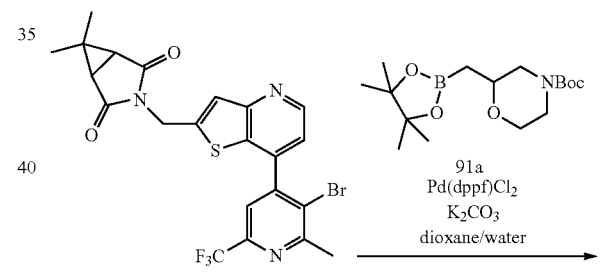

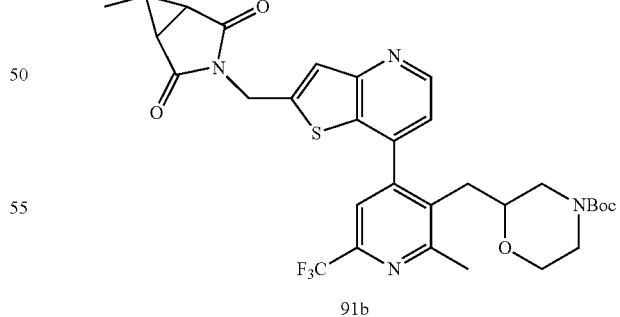

The title compound (91b) was obtained from 88a (60 mg; 0.114 mmol) and from 91a (45 mg; 0.137 mmol) according to the General Procedure Va and after standard work-up the crude product was taken to the next step.

ESI-MS m/z for $C_{32}H_{36}F_3N_4O_5S$ found 645.5 [M+H]$^+$; $R_t$=1.74 min

Step 3

Synthesis of 6,6-dimethyl-3-((7-(2-methyl-3-(morpholin-2-ylmethyl)-6-(trifluoromethyl)pyridin-4-yl)thieno[3,2-b]pyridin-2-yl)methyl)-3-azabicyclo[3.1.0]hexane-2,4-dione 2,2,2-trifluoroacetate (91)

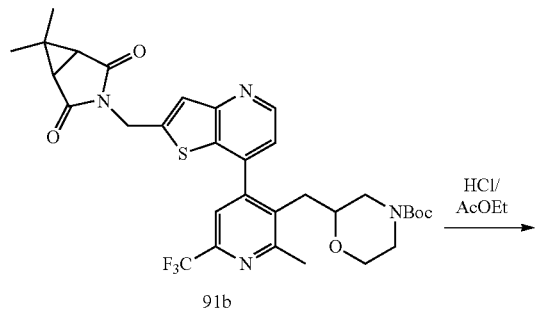

91b

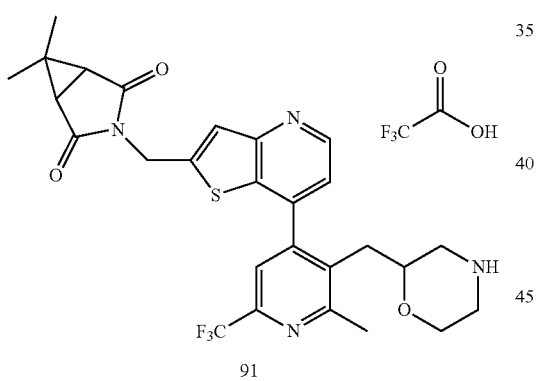

91

The title compound (91) was obtained as a TFA salt from 91b (the crude reaction mixture) according to the General Procedure IVa in 1% yield (per two steps)(1 mg; 0.001 mmol). The crude product was purified by preparative reversed-phase column chromatography (C-18, water/MeCN+1‰ TFA, 99:1 to 35:65, 30 min, 20 mL/min).

ESI-MS m/z for $C_7H_{28}F_3N_4O_3S$ found 545.5 [M+H]$^+$; $R_t$=1.05 min; $^1$H NMR (700 MHz, $D_2O$) δ 8.93 (m, 1H), 7.85-7.72 (m, 3H), 5.02 (s, 2H), 3.97-3.79 (m, 1H), 3.78-3.56 (m, 1H), 3.55-3.49 (m, 1H), 3.34-3.13 (m, 3H), 3.08-2.96 (m, 1H), 2.87-2.72 (m, 2H), 2.79 (s, 3H), 2.70 (s, 2H), 1.29 (s, 3H), 1.11 (d, J=9.5 Hz, 3H).

Example 92

Synthesis of 6,6-dimethyl-3-((7-(4-methyl-3-(morpholin-2-ylmethyl)-6-(trifluoromethyl)pyridin-2-yl)thieno[3,2-b]pyridin-2-yl)methyl)-3-azabicyclo[3.1.0]hexane-2,4-dione 2,2,2-trifluoroacetate (92)

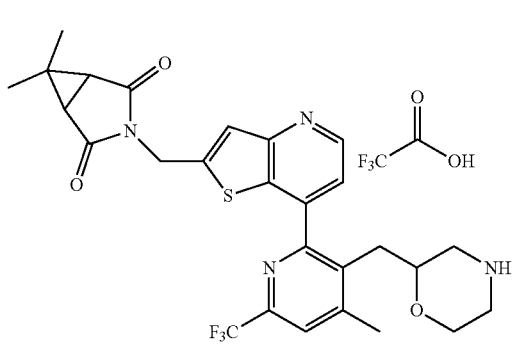

92

Step 1

Synthesis of 3-((7-(3-amino-4-methyl-6-(trifluoromethyl)pyridin-2-yl)thieno[3,2-b]pyridin-2-yl)methyl)-6,6-dimethyl-3-azabicyclo[3.1.0]hexane-2,4-dione (92a)

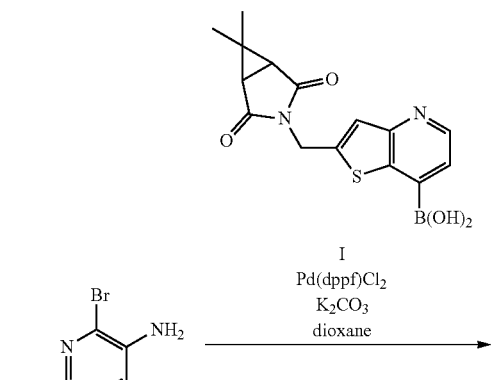

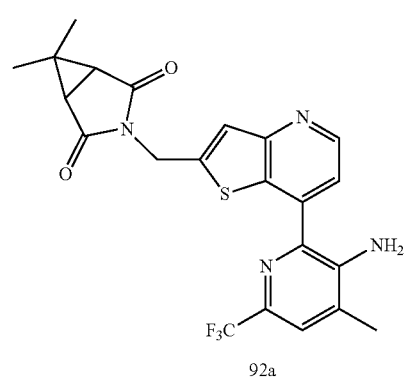

92a

The title compound (92a) was obtained from 28a (380 mg; 1.49 mmol) and from boronic acid I (541 mg; 1.64 mmol) according to the General Procedure Va in 38% yield (262 mg; 0.57 mmol). The crude product was purified by flash column chromatography on silica (AcOEt, 100%, 10 minutes, then AcOEt/MeOH, 9:1, v/v, 10 minutes).

ESI-MS m/z for $C_{22}H_{20}F_3N_4O_2S$ found 461.2 $[M+H]^+$; $R_t$=1.45 min; $^1H$ NMR (700 MHz, CDCl$_3$) δ 8.75 (s, 1H), 7.55 (s, 1H), 7.54-7.52 (m, 1H), 7.48-7.46 (m, 1H), 4.84 (s, 2H), 4.24 (s, 2H), 2.36 (s, 2H), 2.34 (s, 3H), 1.23 (s, 3H), 1.14 (s, 3H).

Step 2

Synthesis of 3-((7-(3-bromo-4-methyl-6-(trifluoromethyl)pyridin-2-yl)thieno[3,2-b]pyridin-2-yl)methyl)-6,6-dimethyl-3-azabicyclo[3.1.0]hexane-2,4-dione (92b)

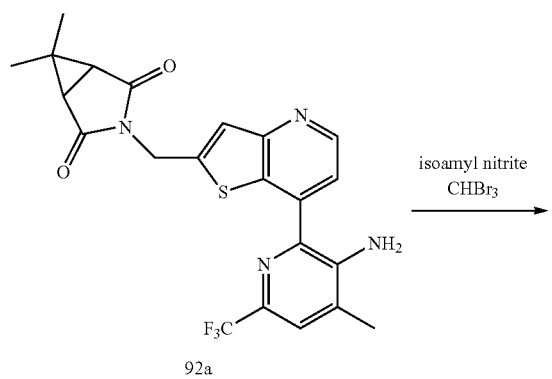

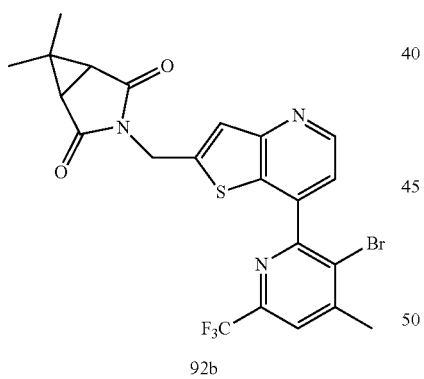

To the solution of 92a (228 mg; 0.49 mmol) in CHBr$_3$ (5 mL) isoamyl nitrite (0.13 mL; 0.99 mmol) was added and the reaction mixture was stirred at 100° C. overnight. The reaction progress was monitored by LC-MS. When analysis indicated completion of the reaction, to this mixture brine was added and the product was extracted with AcOEt. An organic layer was dried over anhydrous Na$_2$SO$_4$, filtered and concentrated in vacuo. The crude product was purified by flash column chromatography on silica (hexane/AcOEt, 2:8, v/v, 20 minutes). The title compound 92b was obtained in 8% yield (21 mg; 0.04 mmol).

ESI-MS m/z for $C_{22}H_{18}BrF_3N_3O_2S$ found 523.7/525.7 $[M+H]^+$; $R_t$=1.56 min

Step 3

Synthesis of tert-butyl 2-((2-(2-(((6,6-dimethyl-2,4-dioxo-3-azabicyclo[3.1.0]hexan-3-yl)methyl)thieno[3,2-b]pyridin-7-yl)-4-methyl-6-(trifluoromethyl)pyridin-3-yl)methyl)morpholine-4-carboxylate (92c)

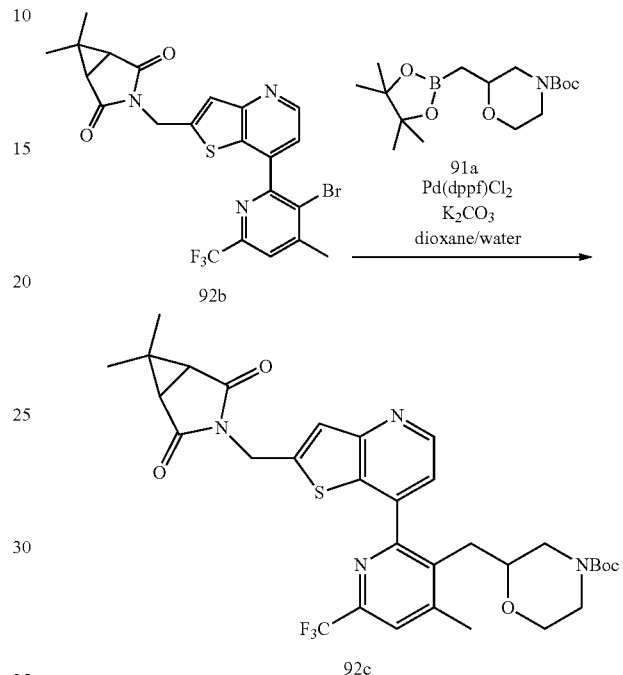

The title compound (92c) was obtained from 92b (25 mg; 0.048 mmol) and from 91a (39 mg; 0.120 mmol) according to the General Procedure Va and after standard work-up the crude product was taken to the next step.

ESI-MS m/z for $C_{32}H_{36}F_3N_4O_5S$ found 645.7 $[M+H]^+$; $R_t$=1.74 min

Step 4

Synthesis of 6,6-dimethyl-3-((7-(4-methyl-3-(morpholin-2-ylmethyl)-6-(trifluoromethyl)pyridin-2-yl)thieno[3,2-b]pyridin-2-yl)methyl)-3-azabicyclo[3.1.0]hexane-2,4-dione 2,2,2-trifluoroacetate (92)

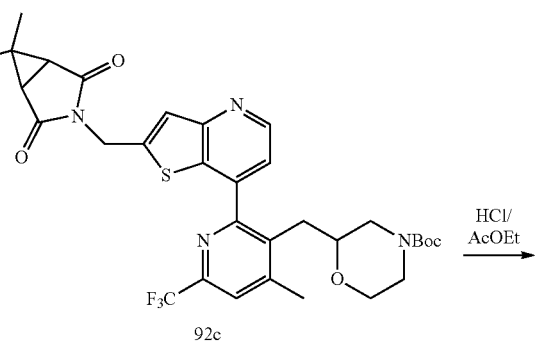

383
-continued

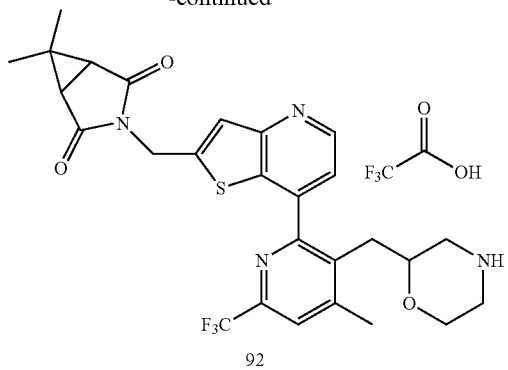

92

The title compound (92) was obtained as a TFA salt from 92c (the crude product) according to the General Procedure IVa in 7% yield (per two steps)(2 mg; 0.003 mmol). The crude product was purified by preparative reversed-phase column chromatography (C-18, water/MeCN+1‰ TFA, 99:1 to 35:65, 30 min, 20 mL/min).

ESI-MS m/z for $C_{27}H_{28}F_3N_4O_3S$ found 545.7 [M+H]$^+$; $R_t$=1.04 min; $^1$H NMR (700 MHz, D$_2$O) δ 8.91 (d, J=5.6 Hz, 1H), 8.01 (s, 1H), 7.82 (d, J=6.3 Hz, 1H), 7.78 (s, 1H), 5.01 (s, 2H), 3.79-3.65 (m, 2H), 3.46 (t, J=12.7 Hz, 1H), 3.26 (d, J=13.0 Hz, 1H), 3.19 (d, J=13.5 Hz, 1H), 3.14-3.09 (m, 1H), 3.07-2.98 (m, 1H), 2.97-2.88 (m, 1H), 2.77 (t, J=12.0 Hz, 1H), 2.69 (s, 2H), 2.65 (s, 3H), 1.29 (s, 3H), 1.10 (s, 3H).

Example 93

Synthesis of 6,6-dimethyl-3-((7-(4-methyl-2-(morpholin-2-ylmethyl)pyridin-3-yl)thieno[3,2-b]pyridin-2-yl)methyl)-3-azabicyclo[3.1.0]hexane-2,4-dione 2,2,2-trifluoroacetate (93)

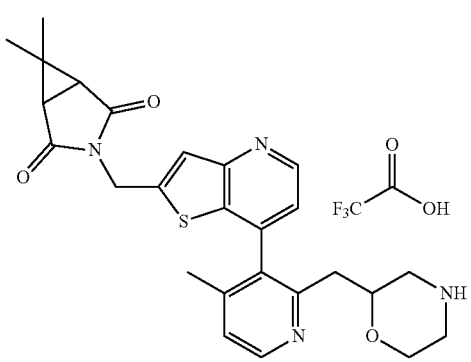

93

384
Step 1

Synthesis of tert-butyl 2-((3-bromo-4-methylpyridin-2-yl)methyl)morpholine-4-carboxylate (93a)

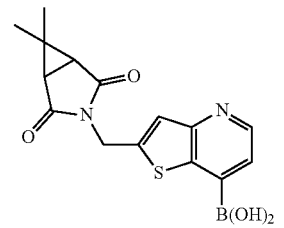

The title compound (93a) was obtained from 3-bromo-2-chloro-4-methylpyridine (80 mg; 0.39 mmol) and from 91a (157 mg; 0.47 mmol) according to the General Procedure Va in 8% yield (11 mg; 0.03 mmol).

ESI-MS m/z for $C_{16}H_{24}BrN_2O_3$ found 371.0/373.0 [M+H]$^+$; $R_t$=1.51 min Step 2

Synthesis of tert-butyl 2-((3-(2-(((6,6-dimethyl-2,4-dioxo-3-azabicyclo[3.1.0]hexan-3-yl)methyl)thieno[3,2-b]pyridin-7-yl)-4-methylpyridin-2-yl)methyl)morpholine-4-carboxylate (93b)

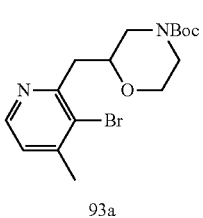

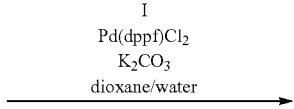

93a

-continued

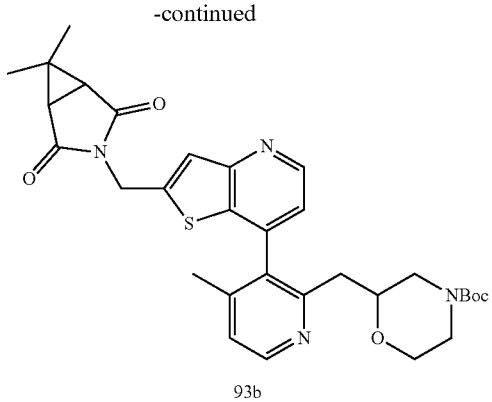

93b

The title compound (93b) was obtained from 93a (11 mg; 0.030 mmol) and from I (12 mg; 0.036 mmol) according to the General Procedure Va in 53% yield (9 mg; 0.016 mmol).

ESI-MS m/z for $C_{31}H_{37}N_4O_5S$ found 577.4 [M+H]$^+$; $R_t$=1.27 min

Step 3

Synthesis of 6,6-dimethyl-3-((7-(4-methyl-2-(morpholin-2-ylmethyl)pyridin-3-yl)thieno[3,2-b]pyridin-2-yl)methyl)-3-azabicyclo[3.1.0]hexane-2,4-dione 2,2,2-trifluoroacetate (93)

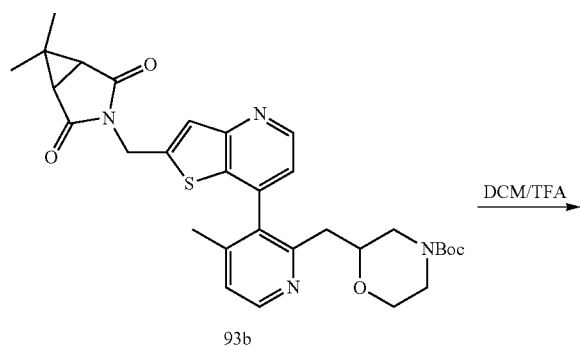

93b

DCM/TFA

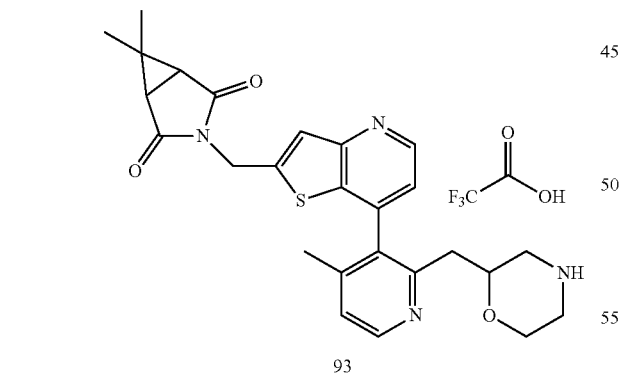

93

The title compound (93) was obtained as a TFA salt from 93b (9 mg; 0.016 mmol) according to the General Procedure IVb in 19% yield (2 mg; 0.003 mmol). The crude product was purified twice by preparative reversed-phase column chromatography (first: C-18, water/MeCN+1‰ TFA, 99:1 to 40:60, 30 min, 20 mL/min; second: C-18, water/MeCN+1‰ TFA, 99:1 to 50:50, 30 min, 20 mL/min).

ESI-MS m/z for $C_{26}H_{29}N_4O_3S$ found 477.3 [M+H]$^+$; $R_t$=0.81 min; $^1$H NMR (700 MHz, D$_2$O) δ 8.94 (d, J=5.0 Hz, 1H), 8.75 (d, J=5.8 Hz, 1H), 8.01 (d, J=5.8 Hz, 1H), 7.81 (s, 1H), 7.67 (d, J=5.1 Hz, 1H), 5.06-4.94 (m, 3H), 4.10-3.95 (m, 1H), 3.86-3.59 (m, 2H), 3.33-3.11 (m, 3H), 3.10-2.81 (m, 2H), 2.70 (s, 2H), 2.29 (s, 3H), 1.28 (s, 3H), 1.06 (d, J=12.3 Hz, 3H).

Example 94

Synthesis of 6-(2-((6,6-dimethyl-2,4-dioxo-3-azabicyclo[3.1.0]hexan-3-yl)methyl)thieno[3,2-b]pyridin-7-yl)-4-methyl-5-(morpholin-2-ylmethyl)picolinonitrile 2,2,2-trifluoroacetate (94)

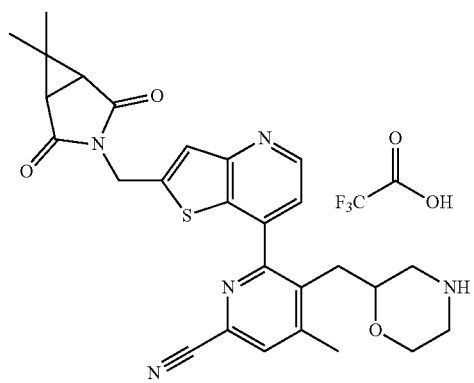

94

The title compound (94) was obtained as a TFA salt in 1% overall yield in a similar way to Example 92 with the exception that, in the first step of the synthesis, 5-amino-4-bromo-6-methylpicolinonitrile (27a) was used instead of compound 28a and in the last step of the synthesis, the crude product was purified by preparative reversed-phase column chromatography (C-18, water/MeCN+1‰ TFA, 99:1 to 40:60, 30 min, 20 mL/min).

ESI-MS m/z for $C_{27}H_{28}N_5O_3S$ found 502.4 [M+H]$^+$; $R_t$=0.90 min; $^1$H NMR (700 MHz, D$_2$O) δ 8.93-8.91 (m, 1H), 8.05 (s, 1H), 7.82-7.80 (m, 1H), 7.79 (s, 1H), 5.03 (s, 2H), 3.75-3.68 (m, 2H), 3.46 (t, J=12.9 Hz, 1H), 3.26 (d, J=13.0 Hz, 1H), 3.19 (d, J=12.8 Hz, 1H), 3.11 (d, J=14.9 Hz, 1H), 3.03-2.90 (m, 2H), 2.76 (t, J=12.0 Hz, 1H), 2.71 (s, 2H), 2.63 (s, 3H), 1.29 (s, 3H), 1.13 (s, 3H).

Example 95

Synthesis of 6,6-dimethyl-3-((7-(4-methyl-3-(((S)-morpholin-2-yl)methyl)-6-(trifluoromethyl)pyridin-2-yl)thieno[3,2-b]pyridin-2-yl)methyl)-3-azabicyclo[3.1.0]hexane-2,4-dione dihydrochloride (95)

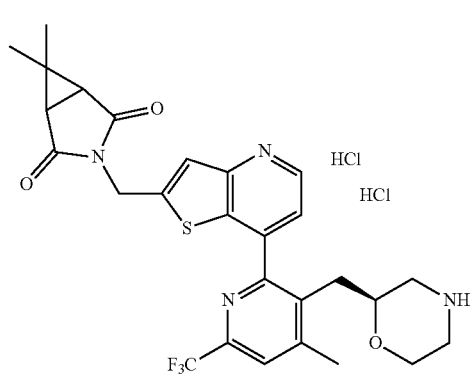

95

The title compound (95) was obtained as a dihydrochloride salt in 6% overall yield in a similar way to Example 91 with the exception that, in the first step of the synthesis, tert-butyl (R)-2-(bromomethyl)morpholine-4-carboxylate was used instead of tert-butyl 2-(bromomethyl)morpholine-4-carboxylate, in the second step of the synthesis, compound 92b was used instead of compound 88a and in the last step of the synthesis, the crude product was purified by preparative reversed-phase column chromatography (C-18, water+ 0.3‰ HCl (12 M)/MeCN, 99:1 to 40:60, 30 min, 20 mL/min).

ESI-MS m/z for $C_{27}H_{28}F_3N_4O_3S$ found 545.5 [M+H]$^+$; R$_t$=1.03 min;

$^1$H NMR (700 MHz, D$_2$O) δ 8.98-8.95 (m, 1H), 8.05-8.03 (m, 1H), 7.98-7.96 (m, 1H), 7.85-7.82 (m, 1H), 5.05 (s, 2H), 3.75 (t, J=10.4 Hz, 1H), 3.71-3.67 (m, 1H), 3.50-3.44 (m, 1H), 3.32 (d, J=12.7 Hz, 1H), 3.22-3.14 (m, 2H), 3.02 (dd, J=15.0, 9.9 Hz, 1H), 2.94 (td, J=12.5, 3.8 Hz, 1H), 2.79 (t, J=12.1 Hz, 1H), 2.71 (s, 2H), 2.66 (s, 3H), 1.29 (s, 3H), 1.12 (s, 3H).

Example 96

Synthesis of 6,6-dimethyl-3-((7-(4-methyl-3-(((R)-morpholin-2-yl)methyl)-6-(trifluoromethyl)pyridin-2-yl)thieno[3,2-b]pyridin-2-yl)methyl)-3-azabicyclo[3.1.0]hexane-2,4-dione dihydrochloride (96)

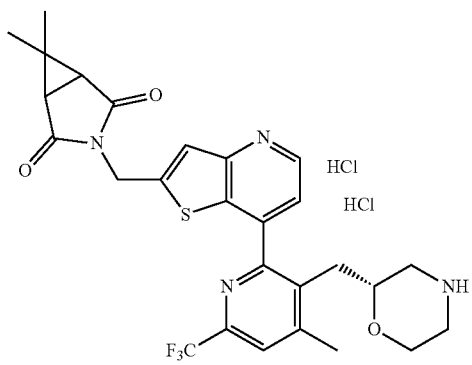

96

The title compound (96) was obtained as a dihydrochloride salt in 3% overall yield in a similar way to Example 91 with the exception that, in the first step of the synthesis, tert-butyl (S)-2-(bromomethyl)morpholine-4-carboxylate was used instead of tert-butyl 2-(bromomethyl)morpholine-4-carboxylate, in the second step of the synthesis, compound 92b was used instead of compound 88a and in the last step of the synthesis, the crude product was purified by preparative reversed-phase column chromatography (C-18, water+ 0.3‰ HCl (12 M)/MeCN, 99:1 to 40:60, 30 min. 20 mL/min).

ESI-MS m/z for $C_{27}H_{28}F_3N_4O_3S$ found 545.4 [M+H]$^+$; R$_t$=1.04 min; $^1$H NMR (700 MHz, D$_2$O) δ 8.98-8.95 (m, 1H), 8.03 (s, 1H), 7.98-7.93 (m, 1H), 7.84-7.81 (m, 1H), 5.04 (s, 2H), 3.77-3.67 (m, 2H), 3.47 (td, J=12.9, 2.1 Hz, 1H), 3.31 (d, J=12.8 Hz, 1H), 3.22-3.13 (m, 2H), 3.06-2.99 (m, 1H), 2.97-2.91 (m, 1H), 2.81-2.76 (m, 1H), 2.70 (s, 2H), 2.66 (s, 3H), 1.29 (s, 3H), 1.11 (s, 3H).

Example 97

Synthesis of 6,6-dimethyl-3-((7-(4-methyl-3-(((S)-4-methylmorpholin-2-yl)methyl)-6-(trifluoromethyl)pyridin-2-yl)thieno[3,2-b]pyridin-2-yl)methyl)-3-azabicyclo[3.1.0]hexane-2,4-dione dihydrochloride (97)

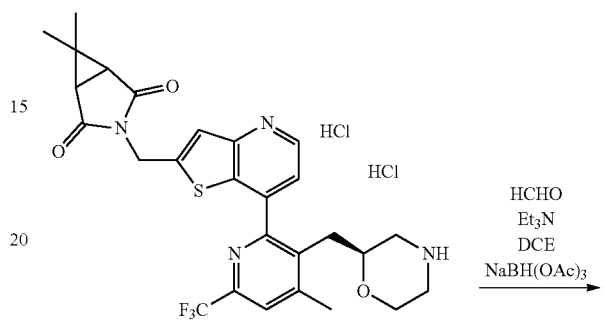

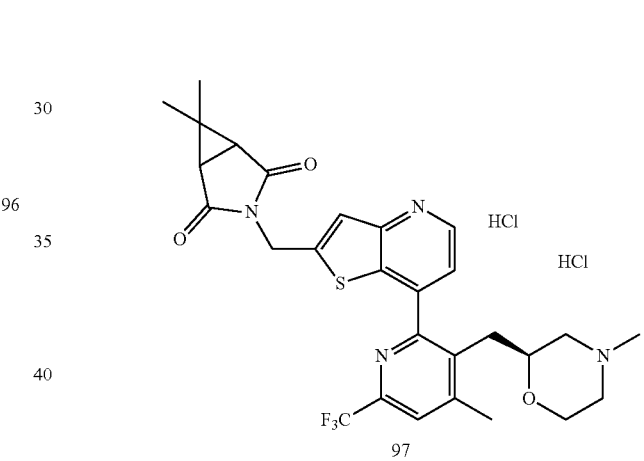

To the solution of 95 (12 mg; 0.019 mmol) in DCE (0.5 mL) Et$_3$N (0.008 mL; 0.057 mmol) and formalin (36% aqueous solution; 0.003 mL; 0.038 mmol) were added and this mixture was stirred at room temperature for 1 hour. Then to this mixture NaBH(OAc)$_3$ (8 mg; 0.038 mmol) was added and whole was stirred at room temperature for 1 hour. The reaction progress was monitored by LC-MS. When analysis indicated completion of the reaction, the mixture was diluted with DCM and washed with 5% NaHCO$_3$. The organic layer was dried over anhydrous MgSO$_4$, filtered and concentrated in vacuo and the residue was purified by preparative reversed-phase column chromatography (C-18, water+0.3‰ HCl (36%)/MeCN, 99:1 to 40:60, 30 min, 20 mL/min). The title compound (97) was obtained as a dihydrochloride salt in 31% yield (4 mg; 0.006 mmol).

ESI-MS m/z for $C_{28}H_{30}F_3N_4O_3S$ found 559.3 [M+H]$^+$; R$_t$=1.02 min; $^1$H NMR (700 MHz, D$_2$O) δ 8.98 (d, J=5.7 Hz, 1H), 8.03 (s, 1H), 8.01 (d, J=5.6 Hz, 1H), 7.85 (s, 1H), 5.04 (s, 2H), 3.74-3.68 (m, 2H), 3.67-3.47 (m, 2H), 3.32 (d, J=12.7 Hz, 1H), 3.16 (dd, J=15.1, 3.2 Hz, 1H), 3.04-2.97 (m, 1H), 2.90-2.83 (m, 1H), 2.82 (s, 3H), 2.75-2.69 (m, 1H), 2.69 (s, 2H), 2.64 (s, 3H), 1.27 (s, 3H), 1.10 (s, 3H).

Example 98

Synthesis of 6,6-dimethyl-3-((7-(4-methyl-3-(((R)-4-methylmorpholin-2-yl)methyl)-6-(trifluoromethyl)pyridin-2-yl)thieno[3,2-b]pyridin-2-yl)methyl)-3-azabicyclo[3.1.0]hexane-2,4-dione dihydrochloride (98)

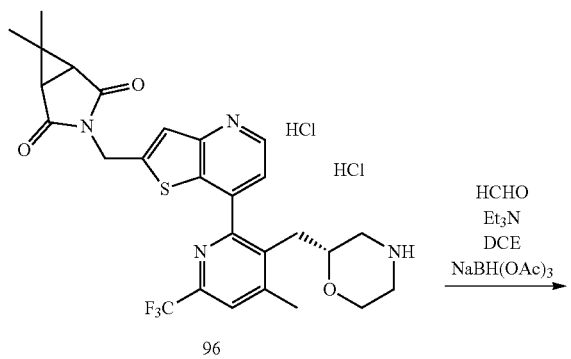

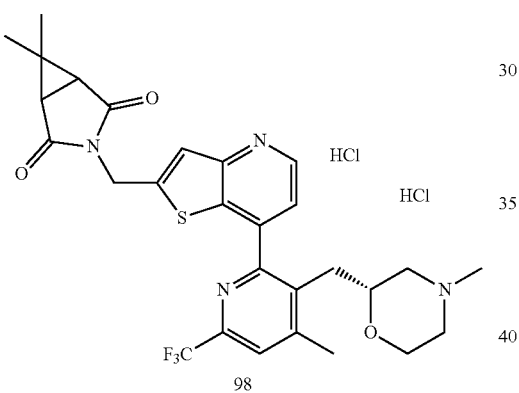

To the solution of 96 (23 mg; 0.037 mmol) in DCE (1 mL) Et₃N (0.016 mL; 0.112 mmol) and formalin (36% aqueous solution; 0.006 mL; 0.074 mmol) were added and this mixture was stirred at room temperature for 1 hour. Then to this mixture NaBH(OAc)₃ (16 mg; 0.076 mmol) was added and whole was stirred at room temperature for 1 hour. The reaction progress was monitored by LC-MS. When analysis indicated completion of the reaction, the mixture was diluted with DCM and washed with 5% NaHCO₃. The organic layer was dried over anhydrous MgSO₄, filtered and concentrated in vacuo and the residue was purified by preparative reversed-phase column chromatography (C-18, water+0.3‰ HCl (36%)/MeCN, 99:1 to 40:60, 30 min, 20 mL/min). The title compound (97) was obtained as a dihydrochloride salt in 72% yield (17 mg; 0.027 mmol).

ESI-MS m/z for $C_{28}H_{30}F_3N_4O_3S$ found 559.2 [M+H]1; $R_t$=1.03 min; ¹H NMR (700 MHz, D₂O) δ 8.92 (d, J=5.5 Hz, 1H), 8.01 (s, 1H), 7.86 (d, J=5.5 Hz, 1H), 7.79 (s, 1H), 5.02-5.00 (m, 2H), 3.77-3.73 (m, 1H), 3.71-3.65 (m, 1H), 3.47-3.40 (m, 1H), 3.40-3.36 (m, 1H), 3.33 (d, J=12.8 Hz, 1H), 3.13 (dd, J=15.0, 3.6 Hz, 1H), 3.05-3.00 (m, 1H), 2.88 (td, J=12.4, 3.8 Hz, 1H), 2.81 (s, 3H), 2.73-2.68 (m, 1H), 2.69 (s, 2H), 2.64 (s, 3H), 1.28 (s, 3H), 1.10 (s, 3H).

Example 99

Synthesis of 6,6-dimethyl-3-((7-(2-(((R)-morpholin-2-yl)methyl)-5-(trifluoromethyl)pyridin-3-yl)thieno[3,2-b]pyridin-2-yl)methyl)-3-azabicyclo[3.1.0]hexane-2,4-dione 2,2,2-trifluoroacetate (99)

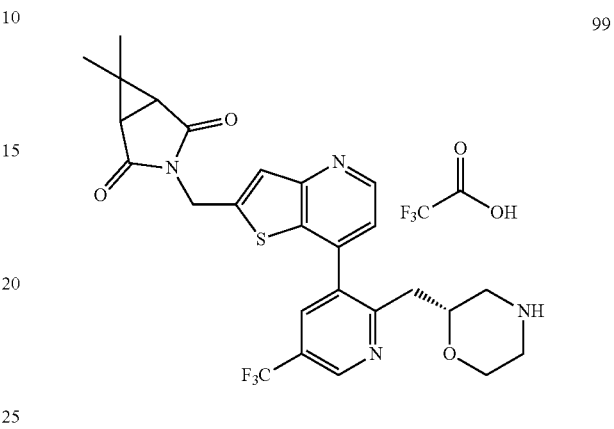

Step 1

Synthesis of tert-butyl (R)-2-((4,4,5,5-tetramethyl-1,3,2-dioxaborolan-2-yl)methyl)morpholine-4-carboxylate (99a)

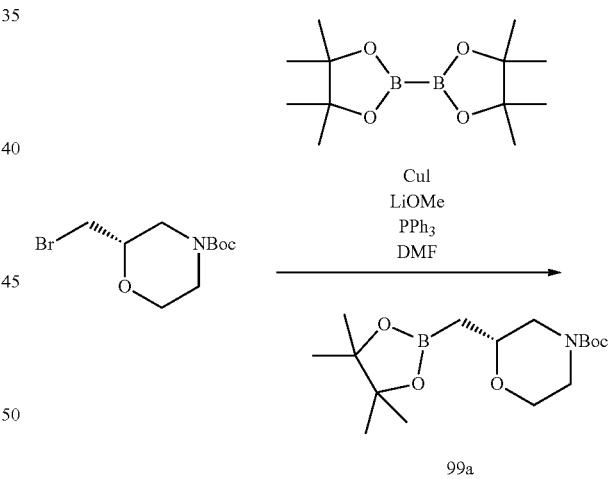

A suspension of tert-butyl (S)-2-(bromomethyl)morpholine-4-carboxylate (0.9 g; 3.21 mmol), CuI (61 mg; 0.32 mmol), LiOMe (244 mg; 6.42 mmol), PPh₃ (168 mg; 0.64 mmol) and bis(pinacolato)diboron (1.22 g; 4.82 mmol) in DMF (18 mL) was purged with Ar and then stirred at 35° C. in a sealed capsule for 2 hours. The reaction completion was confirmed by LC-MS. Then DMF was evaporated in vacuo and the residue was purified by flash column chromatography on silica (hexane/AcOEt, 7:3, v/v, 20 minutes). The title compound 99a was obtained in 99% yield (1.04 g; 3.18 mmol).

ESI-MS m/z for $C_{11}H_{23}BNO_3$ found 228.0 [M+H-Boc]⁺; $R_t$=1.52 min

Step 2

Synthesis of tert-butyl (R)-2-((3-chloro-5-(trifluoromethyl)pyridin-2-yl)methyl)morpholine-4-carboxylate (99b)

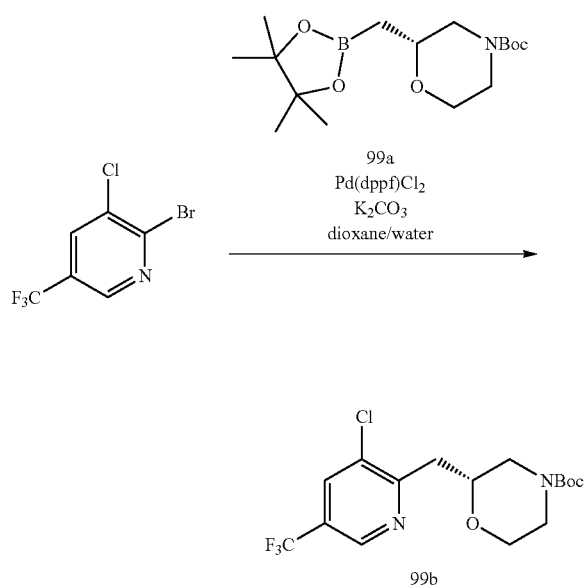

The title compound (99b) was obtained from 2-bromo-3-chloro-5-(trifluoromethyl)pyridine (80 mg; 0.310 mmol) and from 99a (100 mg; 0.310 mmol) according to the General Procedure Va in 8% yield (10 mg; 0.025 mmol).

ESI-MS m/z for $C_{12}H_{13}ClF_3N_2O_3$ found 325.0/327.0 [M+H-tBu]$^+$; $R_t$=1.71 min

Step 3

Synthesis of tert-butyl (2R)-2-((3-(2-((6,6-dimethyl-2,4-dioxo-3-azabicyclo[3.1.0]hexan-3-yl)methyl)thieno[3,2-b]pyridin-7-yl)-5-(trifluoromethyl)pyridin-2-yl)methyl)morpholine-4-carboxylate (99c)

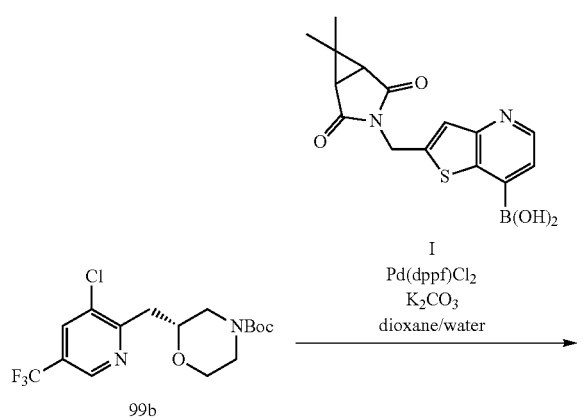

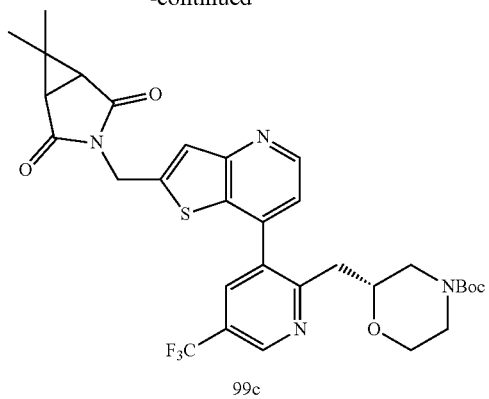

The title compound (99c) was obtained from 99b (10 mg; 0.025 mmol) and from I (13 mg; 0.039 mmol) according to the General Procedure Va and after standard work-up the crude product was taken to the next step.

ESI-MS m/z for $C_{27}H_{26}F_3N_4O_5S$ found 575.2 [M+H-tBu]$^+$; $R_t$=1.69 min

Step 4

Synthesis of 6,6-dimethyl-3-((7-(2-(((R)-morpholin-2-yl)methyl)-5-(trifluoromethyl)pyridin-3-yl)thieno[3,2-b]pyridin-2-yl)methyl)-3-azabicyclo[3.1.0]hexane-2,4-dione 2,2,2-trifluoroacetate (99)

The title compound (99) was obtained as a TFA salt from 99c (the crude product) according to the General Procedure IVa in 6% yield (per two stepsx mg; 0.002 mmol). The crude product was purified by preparative reversed-phase column chromatography (C-18, water/MeCN+1‰ TFA, 40:60, 50 min, 20 mL/min).

ESI-MS m/z for $C_{26}H_{26}F_3N_4O_3S$ found 531.2 [M+H]$^+$; $R_t$=0.92 min; $^1$H NMR (700 MHz, $D_2O$) δ 9.10 (s, 1H), 8.89 (d, J=5.4 Hz, 1H), 8.31 (s, 1H), 7.79 (s, 1H), 7.75-7.66 (s, 1H), 5.00 (s, 2H), 4.22-4.12 (s, 2H), 3.97-3.77 (m, 1H), 3.71-3.60 (s, 2H), 3.37 (d, J=12.7 Hz, 1H), 3.29-3.24 (s, 1H), 3.12-3.02 (s, 1H), 2.88-2.79 (s, 1H), 2.68 (s, 2H), 1.27 (s, 3H), 1.08 (s, 3H).

Example 100

Synthesis of 3-((7-(3-(hydroxy((S)-morpholin-2-yl)methyl)-4-methylpyridin-2-yl)thieno[3,2-b]pyridin-2-yl)methyl)-6,6-dimethyl-3-azabicyclo[3.1.0]hexane-2,4-dione 2,2,2-trifluoroacetate (100)

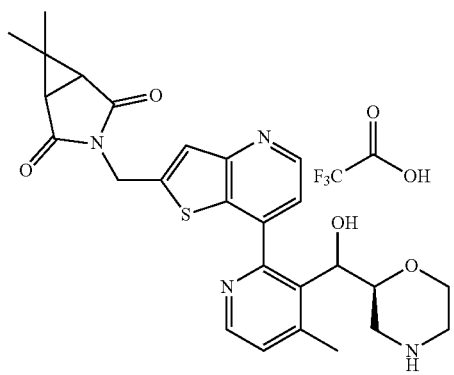

Step 1

Synthesis of tert-butyl (S)-2-(methoxy(methyl)carbamoyl)morpholine-4-carboxylate (100a)

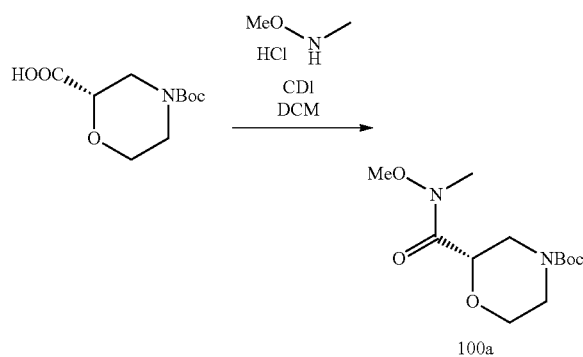

A suspension of (S)-4-(tert-butoxycarbonyl)morpholine-2-carboxylic acid (0.4 g; 1.73 mmol), CDI (309 mg; 1.91 mmol) and MeNHOMe×HCl (185 mg; 1.91 mmol) in DCM (12 mL) was stirred at room temperature overnight. The reaction progress was monitored by LC-MS. When analysis indicated completion of the reaction, this mixture was diluted with DCM and washed with 2 M HCl and brine. An organic layer was dried over anhydrous MgSO$_4$, filtered and concentrated in vacuo and the crude product was used to the next step without additional purification. Compound 100a was obtained in 65% yield (308 mg; 1.12 mmol).

ESI-MS m/z for $C_8H_{15}N_2O_5$ found 219.0 [M+H-tBu]$^+$; $R_t$=1.02 min

Step 2

Synthesis of tert-butyl (S)-2-(2-chloro-4-methylnicotinoyl)morpholine-4-carboxylate (100b)

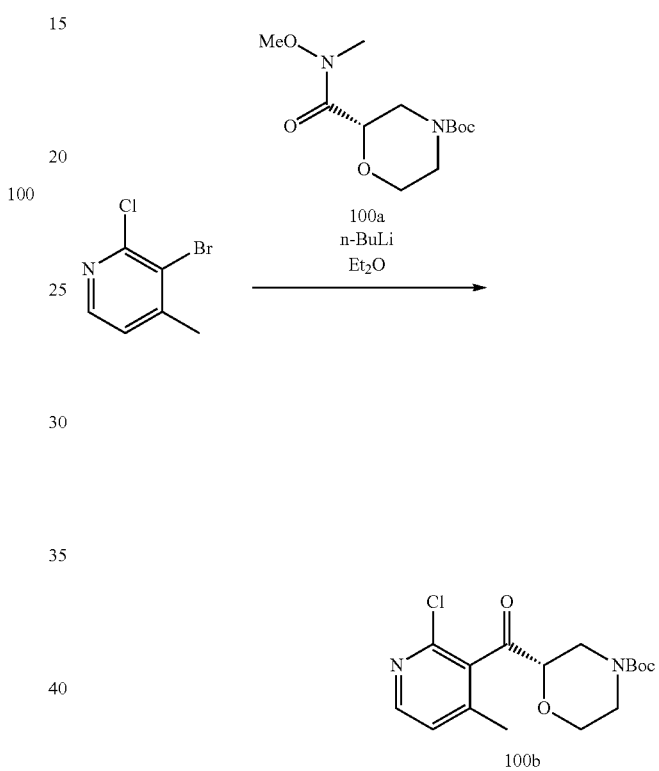

To a solution of 3-bromo-2-chloro-4-methylpyridine (209 mg; 1.01 mmol) in anhydrous Et$_2$O (8 mL) n-BuLi (2.5 M in hexane; 0.81 mL; 2.02 mmol) was added dropwise at −78° C. The resulting suspension was stirred for 2 hours at −78° C. Then a solution of 100a (306 mg; 1.12 mmol) in Et$_2$O (5 mL) was added dropwise and the reaction was stirred at −78° C. for 1 hour and then at room temperature for 30 minutes. The reaction progress was monitored by LC-MS. When analysis indicated completion of the reaction, water was added and whole was extracted with AcOEt. The organic solution was dried over anhydrous Na$_2$SO$_4$, filtered and concentrated in vacuo. The crude product was purified by flash column chromatography on silica (hexane/AcOEt, 6:4, v/v, 20 minutes). The title compound 100b was obtained in 28% yield (95 mg; 0.28 mmol).

ESI-MS m/z for $C_{12}H_{14}ClN_2O_4$ found 285.0/287.0 [M+H-tBu]$^+$, $R_t$=1.46 min; $^1$H NMR (700 MHz, DMSO-d$_6$+D$_2$O, 348 K) δ 8.31-8.29 (m, 1H), 7.34-7.31 (m, 1H), 4.49-4.42 (m, 1H), 4.08-4.02 (m, 1H), 3.81-3.75 (m, 1H), 3.66-3.60 (m, 1H), 3.55-3.48 (m, 1H), 3.16-3.08 (m, 1H), 3.03-2.95 (m, 1H), 2.22 (s, 3H), 1.41 (s, 9H).

Step 3

Synthesis of tert-butyl (2S)-2-((2-chloro-4-methylpyridin-3-yl)(hydroxy)methyl)morpholine-4-carboxylate (100c)

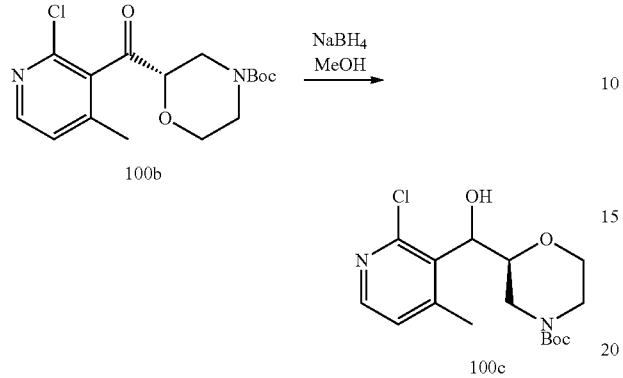

To a solution of 100b (79 mg; 0.23 mmol) in MeOH (4 mL) NaBH$_4$ (13 mg; 0.35 mmol) was added and the resulting mixture was stirred at room temperature for 2 hours. The reaction progress was monitored by LC-MS. Then another portion of NaBH$_4$ (7 mg; 0.19 mmol) was added and the resulting mixture was stirred at room temperature for 1 hour. When analysis indicated completion of the reaction, water was added and MeOH was evaporated in vacuo. The product was extracted with AcOEt. The organic solution was dried over anhydrous Na$_2$SO$_4$, filtered and concentrated in vacuo. The crude product was purified by flash column chromatography on silica (hexane/AcOEt, 6:4, v/v, 20 minutes). The title compound 100c was obtained in 61% yield (48 mg; 0.14 mmol) as a mixture of diastereoisomers.

Diastereoisomer 1: ESI-MS m/z for C$_2$H$_{16}$ClN$_2$O$_4$ found 287.0/289.0 [M+H-tBu]$^+$; R$_t$=1.16 min Diastereoisomer 2: ESI-MS m/z for C$_{12}$H$_{16}$ClN$_2$O$_4$ found 287.0/289.0 [M+H-tBu]$^+$; R$_t$=1.24 min

Step 4

Synthesis of tert-butyl (2S)-2-((2-(2-((6,6-dimethyl-2,4-dioxo-3-azabicyclo[3.1.0]hexan-3-yl)methyl)thieno[3,2-b]pyridin-7-yl)-4-methylpyridin-3-yl)(hydroxy)methyl)morpholine-4-carboxylate (100d and 100d')

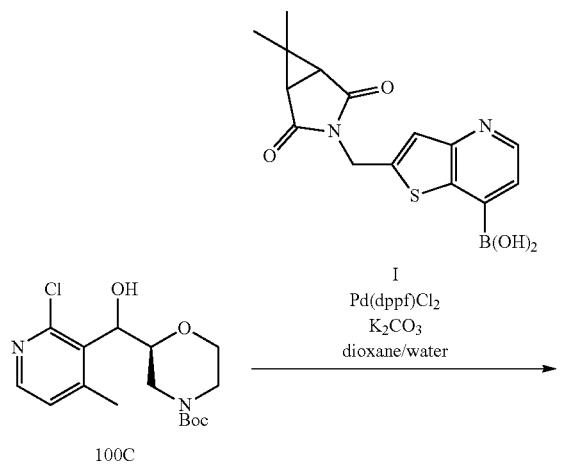

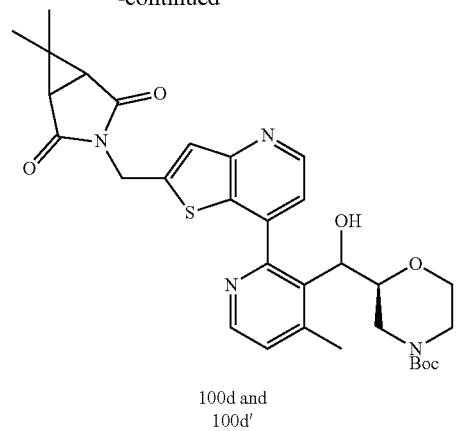

The title compounds (100d and 100d') were obtained from 100c (31 mg; 0.09 mmol) and from I (150 mg; 0.45 mmol) according to the General Procedure Va. The crude product mixture was purified by flash column chromatography on silica (AcOEt 100%, 15 minutes, then AcOEt/MeOH, 8:2, v/v, 10 minutes). The collected fractions were repurified by NP HPLC (silica-based preparative column) with isocratic flow of Hexane:IPA:MeOH, 6:3:1, v/v/v, 20 mL/min to isolate pure diastereomers. The title compounds 100d and 100d' were obtained in 11% yield (for 100d)(6 mg; 0.01 mmol) and in 11% (for 100d')(6 mg; 0.01 mmol).

For 100d: ESI-MS m/z for C$_{31}$H$_{37}$N$_4$O$_6$S found 593.2 [M+H]$^+$, R$_t$=1.24 min For 100d': ESI-MS m/z for C$_{31}$H$_{37}$N$_4$O$_6$S found 593.4 [M+H]$^+$; R$_t$=1.31 min

Step 5

Synthesis of 3-((7-(3-(hydroxy((S)-morpholin-2-yl)methyl)-4-methylpyridin-2-yl)thieno[3,2-b]pyridin-2-yl)methyl)-6,6-dimethyl-3-azabicyclo[3.1.0]hexane-2,4-dione 2,2,2-trifluoroacetate (100)

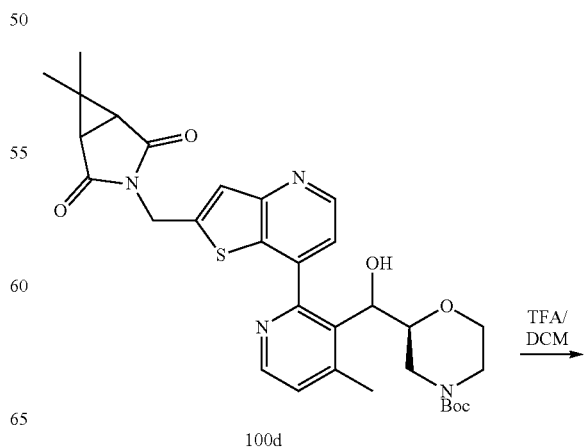

397

-continued

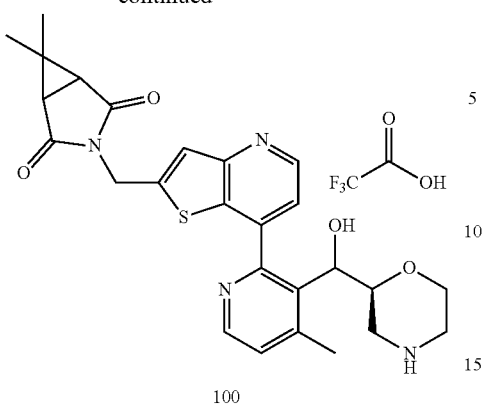

100

The title compound (100) was obtained as a TFA salt from 100d (6 mg; 0.010 mmol) according to the General Procedure IVb in 33% yield (2 mg; 0.003 mmol). The crude product was purified by preparative reversed-phase column chromatography (C-18, water/MeCN+1‰ TFA, 99:1 to 50:50, 30 min, 20 mL/min).

ESI-MS m/z for $C_{26}H_{29}N_4O_4S$ found 493.2 [M+H]$^+$, $R_t$=0.68 min; $^1$H NMR (700 MHz, D$_2$O) δ 8.97-8.93 (m, 1H), 8.65-8.61 (m, 1H), 7.91-7.87 (m, 1H), 7.86-7.82 (m, 2H), 5.06-5.00 (m, 2H), 4.92-4.85 (m, 1H), 3.96-3.88 (m, 2H), 3.59-3.51 (m, 2H), 3.27 (d, J=13.3 Hz, 1H), 3.09-3.00 (m, 1H), 2.90-2.83 (m, 1H), 2.81-2.76 (m, 3H), 2.69 (s, 2H), 1.27 (s, 3H), 1.10 (s, 3H).

Example 101

Synthesis of 3-((7-(3-(hydroxy((S)-morpholin-2-yl)methyl)-4-methylpyridin-2-yl)thieno[3,2-b]pyridin-2-yl)methyl)-6,6-dimethyl-3-azabicyclo[3.1.0]hexane-2,4-dione 2,2,2-trifluoroacetate (101)

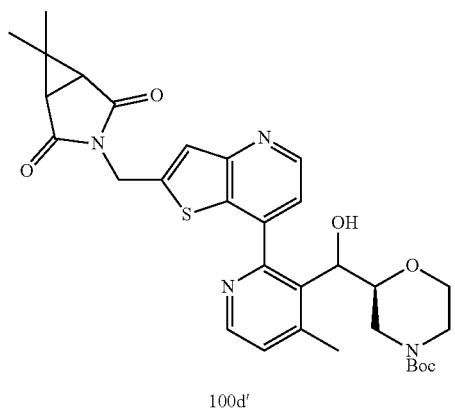

100d'

398

-continued

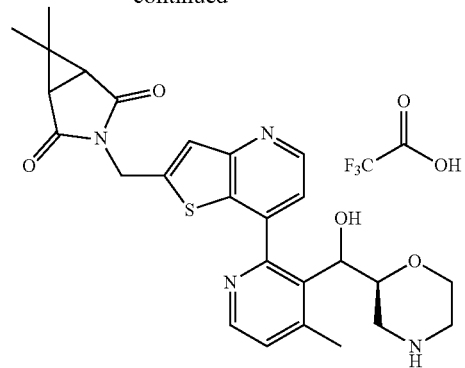

101

The title compound (101) was obtained as a TFA salt from 100d' (6 mg; 0.010 mmol) according to the General Procedure IVb in 23% yield (1 mg; 0.002 mmol). The crude product was purified by preparative reversed-phase column chromatography (C-18, water/MeCN+1‰ TFA, 99:1 to 50:50, 30 min, 20 mL/min).

ESI-MS m/z for $C_{26}H_{29}N_4O_4S$ found 493.1 [M+H]$^+$; $R_t$=0.61 min; $^1$H NMR (700 MHz, D$_2$O) δ 8.91 (d, J=5.6 Hz, 1H), 8.60 (d, J=5.3 Hz, 1H), 7.86 (d, J=5.6 Hz, 1H), 7.81 (s, 1H), 7.75 (d, J=5.5 Hz, 1H), 5.03-5.01 (m, 2H), 4.99 (d, J=5.2 Hz, 1H), 4.12 (ddd, J=11.5, 5.3, 2.2 Hz, 1H), 4.04 (dd, J=13.4, 3.4 Hz, 1H), 3.74 (td, J=13.1, 2.5 Hz, 1H), 3.28 (d, J=13.1 Hz, 1H), 3.15 (d, J=12.5 Hz, 1H), 3.01 (td, J=12.8, 4.0 Hz, 1H), 2.82-2.77 (m, 1H), 2.73 (s, 3H), 2.69 (s, 2H), 1.27 (s, 3H), 1.09 (s, 3H).

Example 102

Synthesis of 6,6-dimethyl-3-((7-(2-methyl-3-(piperazin-1-ylmethyl)-6-(trifluoromethyl)pyridin-4-yl)thieno[3,2-b]pyridin-2-yl)methyl)-3-azabicyclo[3.1.0]hexane-2,4-dione 2,2,2-trifluoroacetate (102)

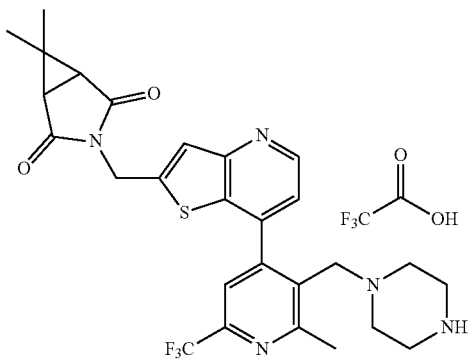

102

Step 1

Synthesis of 6,6-dimethyl-3-((7-(2-methyl-6-(trifluoromethyl)-3-vinylpyridin-4-yl)thieno[3,2-b]pyridin-2-yl)methyl)-3-azabicyclo[3.1.0]hexane-2,4-dione (102a)

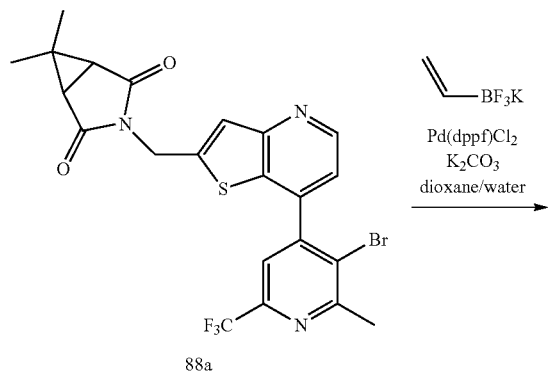

The title compound (102a) was obtained from 88a (185 mg; 0.35 mmol) and from potassium vinyltrifluoroborate (71 mg; 0.53 mmol) according to the General Procedure Va in 62% (104 mg; 0.22 mmol).

ESI-MS m/z for $C_{24}H_{21}F_3N_3O_2S$ found 472.5 $[M+H]^+$, $R_t$=1.53 min

Step 2

Synthesis of 3-((7-(3-(hydroxymethyl)-2-methyl-6-(trifluoromethyl)pyridin-4-yl)thieno[3,2-b]pyridin-2-yl)methyl)-6,6-dimethyl-3-azabicyclo[3.1.0]hexane-2,4-dione (102b)

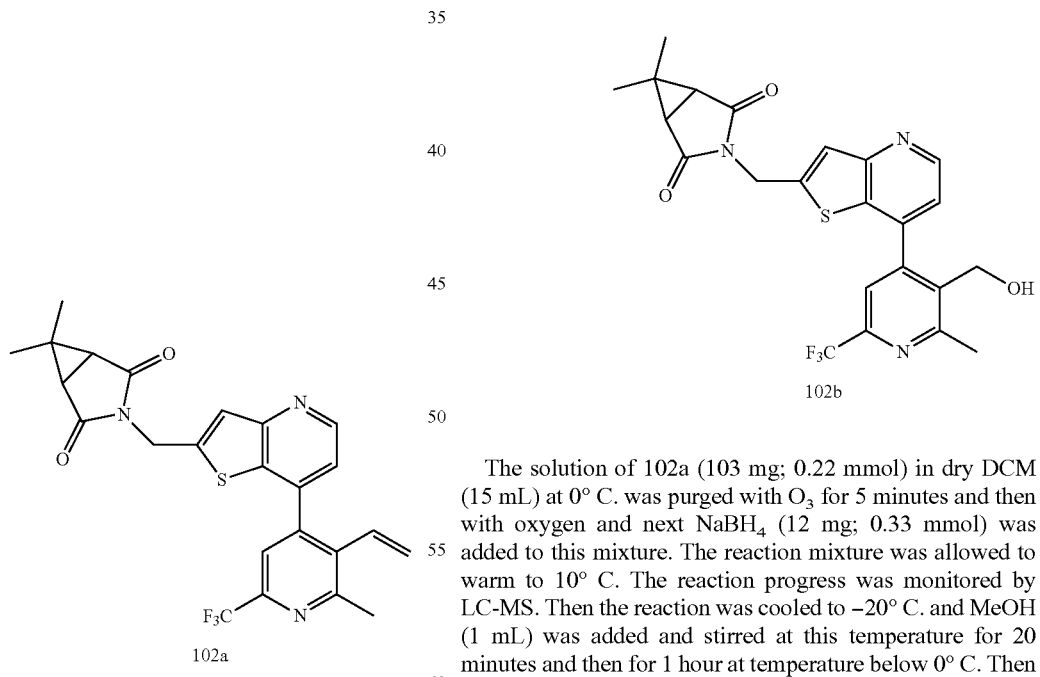

The solution of 102a (103 mg; 0.22 mmol) in dry DCM (15 mL) at 0° C. was purged with $O_3$ for 5 minutes and then with oxygen and next $NaBH_4$ (12 mg; 0.33 mmol) was added to this mixture. The reaction mixture was allowed to warm to 10° C. The reaction progress was monitored by LC-MS. Then the reaction was cooled to −20° C. and MeOH (1 mL) was added and stirred at this temperature for 20 minutes and then for 1 hour at temperature below 0° C. Then $NH_4Cl$ (0.5 mL) was added and the resulting mixture was concentrated in vacuo. The crude product was purified by flash column chromatography on silica (AcOEt, 100%, 12 min; then AcOEt/MeOH, 9:1, v/v). The title compound 102b was obtained in 23% yield (24 mg; 0.05 mmol).

ESI-MS m/z for $C_{23}H_{21}F_3N_3O_3S$ found 476.5 $[M+H]^+$, $R_t$=1.27 min

Step 3

Synthesis of (4-(2-(((6,6-dimethyl-2,4-dioxo-3-azabi-cyclo[3.1.0]hexan-3-yl)methyl)thieno[3,2-b]pyridin-7-yl)-2-methyl-6-(trifluoromethyl)pyridin-3-yl) methyl methanesulfonate (102c)

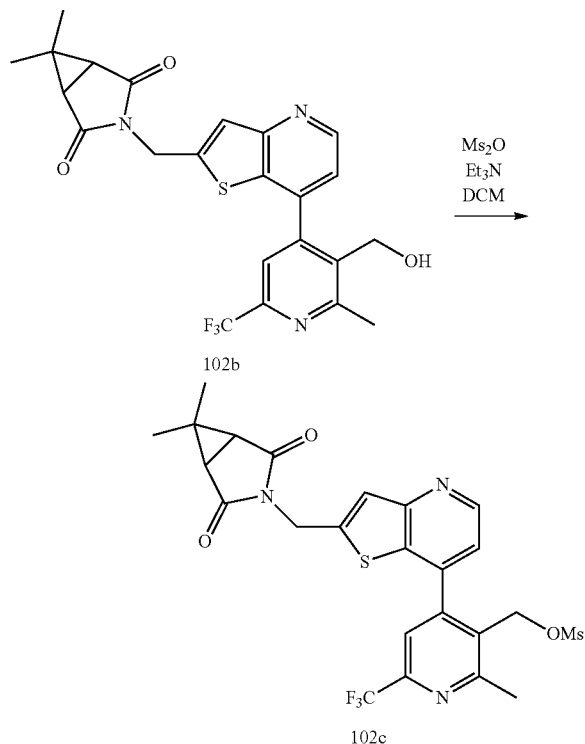

The title compound (102c) was obtained from 102b (61 mg; 0.128 mmol) according to the General Procedure VIII in 70% yield (49 mg; 0.089 mmol).

ESI-MS m/z for $C_{24}H_{23}F_3N_3O_5S_2$ found 554.1 [M+H]$^+$; $R_t$=1.42 min

Step 4

Synthesis of tert-butyl 4-((4-(2-(((6,6-dimethyl-2,4-dioxo-3-azabicyclo[3.1.0]hexan-3-yl)methyl)thieno[3,2-b]pyridin-7-yl)-2-methyl-6-(trifluoromethyl)pyridin-3-yl)methyl)piperazine-1-carboxylate (102d)

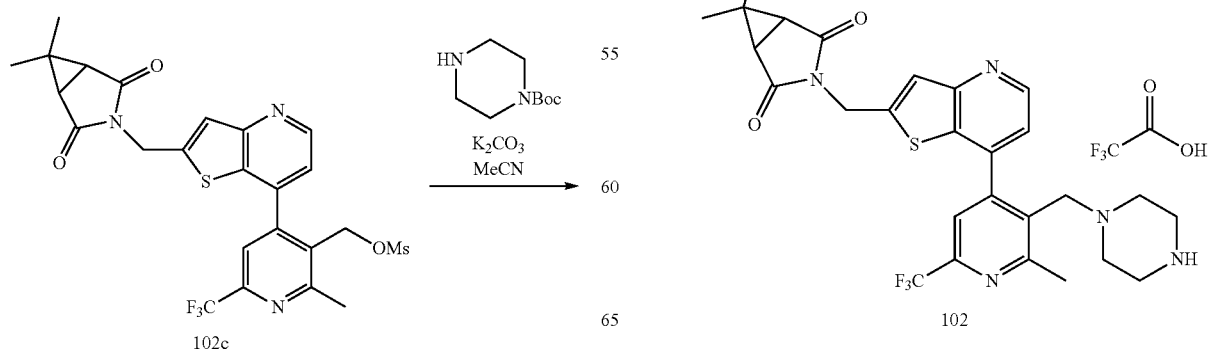

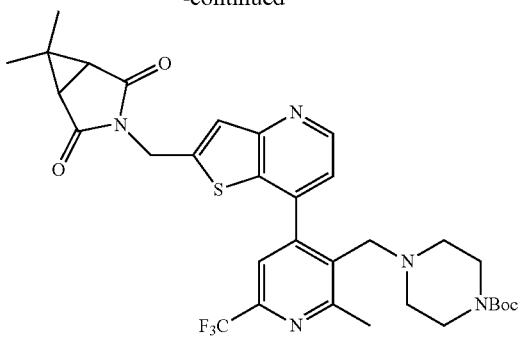

To a solution of 102c (49 mg; 0.089 mmol) in MeCN (1.5 mL) tert-butyl piperazine-1-carboxylate (25 mg; 0.133 mmol) and $K_2CO_3$ (25 mg; 0.178 mmol) were added and then the reaction mixture was stirred at 50° C. for 1.5 hours. The reaction progress was monitored by LC-MS. When analysis indicated completion of the reaction, the mixture was concentrated in vacuo and the crude product was purified by flash column chromatography on silica (hexane to hexane/AcOEt 3:7, v/v, 20 minutes). Compound 102d was obtained in 23% yield (13 mg; 0.020 mmol).

ESI-MS m/z for $C_{32}H_{37}F_3N_5O_4S$ found 644.3 [M+H]$^+$; $R_t$=1.74 min

Step 5

Synthesis of 6,6-dimethyl-3-((7-(2-methyl-3-(piperazin-1-ylmethyl)-6-(trifluoromethyl)pyridin-4-yl)thieno[3,2-b]pyridin-2-yl)methyl)-3-azabicyclo[3.1.0]hexane-2,4-dione 2,2,2-trifluoroacetate (102)

The title compound (102) was obtained as a TFA salt from 102d (13 mg; 0.020 mmol) according to the General Procedure IVa in 26% yield (3 mg; 0.005 mmol). The crude product was purified by preparative reversed-phase column chromatography (C-18, water/MeCN+1‰ TFA, 99:1 to 50:50, 30 min, 20 mL/min).

ESI-MS m/z for $C_{27}H_{29}F_3N_5O_2S$ found 544.5 $[M+H]^+$; $R_t$=1.1 min; $^1$H NMR (700 MHz, $D_2O$) δ 8.92 (d, J=5.4 Hz, 1H), 7.84-7.82 (m, 2H), 7.80 (d, J=5.4 Hz, 1H), 5.03 (s, 2H), 3.86 (d, J=13.9 Hz, 1H), 3.58 (d, J=14.3 Hz, 1H), 2.88-2.75 (m, 7H), 2.70 (s, 2H), 2.48-2.37 (m, 4H), 1.29 (s, 3H), 1.11 (s, 3H).

Example 103

Synthesis of 3-((7-(3-((3,3-difluoroazetidin-1-yl)methyl)-2-methyl-6-(trifluoromethyl)pyridin-4-yl)thieno[3,2-b]pyridin-2-yl)methyl)-6,6-dimethyl-3-azabicyclo[3.1.0]hexane-2,4-dione 2,2,2-trifluoroacetate (103)

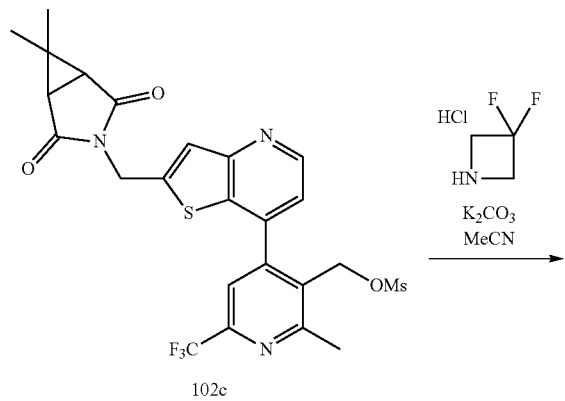

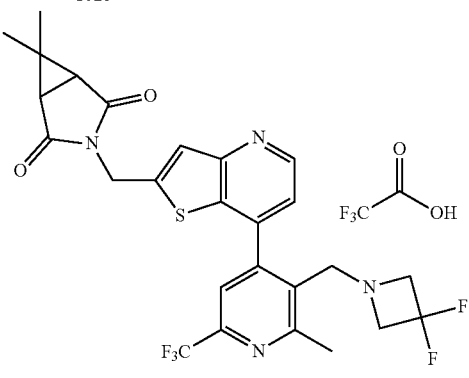

To a solution of 102c (34 mg; 0.061 mmol) in MeCN (2 mL) 3,3-difluoroazetidine hydrochloride (12 mg; 0.092 mmol) and $K_2CO_3$ (34 mg; 0.240 mmol) were added and then the reaction mixture was stirred at 50° C. for 2 hours and then at 80° C. for 2 hours. The reaction progress was monitored by LC-MS. Then another portion of 3,3-difluoroazetidine hydrochloride (6 mg; 0.046 mmol) was added and the reaction mixture was stirred at 80° C. for 2 hours. When analysis indicated completion of the reaction, the mixture was concentrated in vacuo and the crude product was purified by flash column chromatography on silica (hexane to hexane/AcOEt 3:7, v/v, 20 minutes) and then by preparative reversed-phase column chromatography (C-18, water/MeCN+1‰ TFA, 99:1 to 30:70, 30 min, 20 mL/min). The title compound (103) was obtained as a TFA salt in 7% yield (3 mg; 0.004 mmol).

ESI-MS m/z for $C_{26}H_{24}F_5N_4O_2S$ found 551.7 $[M+H]^+$; $R_t$=1.57 min; $^1$H NMR (700 MHz, Methanol-$d_4$) δ 8.84-8.82 (m, 1H), 7.66 (s, 1H), 7.64 (s, 1H), 7.52-7.48 (m, 1H), 4.92-4.88 (m, 2H), 3.97-3.88 (m, 1H), 3.72-3.65 (m, 1H), 3.41-3.33 (m, 4H), 2.84 (s, 3H), 2.50 (s, 2H), 1.25 (s, 3H), 1.08 (s, 3H).

Example 104

Synthesis of 3-((7-(3-((S)-3-(difluoromethyl)pyrrolidine-1-carbonyl)-4-methyl-6-(trifluoromethyl)pyridin-2-yl)thieno[3,2-b]pyridin-2-yl)methyl)-6,6-dimethyl-3-azabicyclo[3.1.0]hexane-2,4-dione hydrochloride (104)

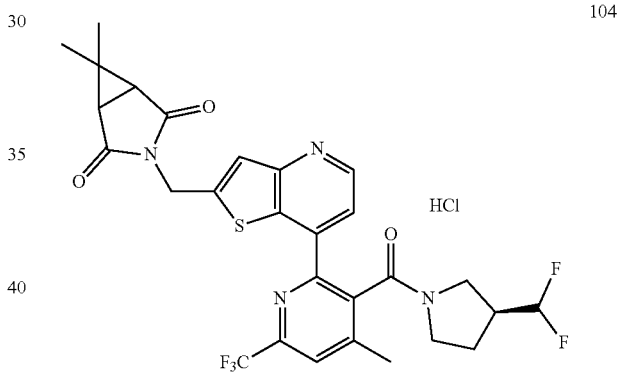

The title compound (104) was obtained as a hydrochloride salt in 11% overall yield in a similar way to Example 48 with the exception that, in the first step of the synthesis (S)-3-(difluoromethyl)pyrrolidine hydrochloride was used instead of a morpholine and an acid II was used instead of 2-chloro-4-methylnicotinic acid and in the last step of the synthesis the crude product was purified by flash column chromatography on silica (hexane, 100%, 15 min) and then by preparative reversed-phase column chromatography (C-18, water+0.3‰ HCl (36%)/MeCN, 99:1 to 20:80, 30 min, 20 mL/min).

ESI-MS m/z for $C_{28}H_{26}F_5N_4O_3S$ found 593.2 $[M+H]^+$; $R_t$=1.45 min; $^1$H NMR (700 MHz, Methanol-$d_4$) δ 8.76-8.72 (m, 1H), 8.00-7.97 (m, 1H), 7.72-7.68 (m, 1H), 7.58-7.55 (m, 1H), 6.03-5.17 (m, 1H), 4.91-4.89 (m, 2H), 3.80-3.63 (m, 1H), 3.58-3.41 (m, 1H), 3.16-3.00 (m, 1H), 2.74-2.55 (m, 1H), 2.54-2.51 (m, 3H), 2.50-2.47 (m, 2H), 2.09-1.82 (m, 1H), 1.76-1.43 (m, 1H), 1.33-1.27 (m, 1H), 1.24-1.21 (m, 3H), 1.10-1.04 (m, 3H).

Example 105

Synthesis of 3-((7-(3-((S)-3-(fluoromethyl)pyrrolidine-1-carbonyl)-4-methyl-6-(trifluoromethyl)pyridin-2-yl)thieno[3,2-b]pyridin-2-yl)methyl)-6,6-dimethyl-3-azabicyclo[3.1.0]hexane-2,4-dione hydrochloride (105)

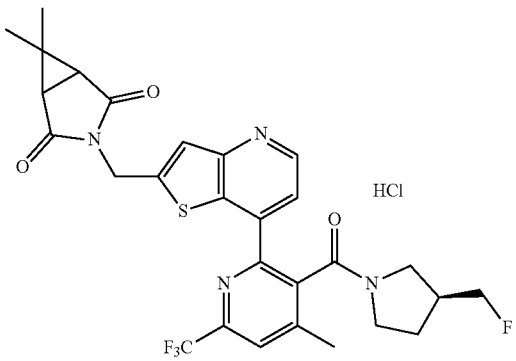

The title compound (105) was obtained as a hydrochloride salt in 6% overall yield in a similar way to Example 48 with the exception that, in the first step of the synthesis (S)-3-(fluoromethyl)pyrrolidine hydrochloride was used instead of a morpholine and an acid II was used instead of 2-chloro-4-methylnicotinic acid and in the last step of the synthesis the crude product was purified by preparative reversed-phase column chromatography (C-18, water+0.3‰ HCl (36%)/MeCN, 99:1 to 20:80, 30 min, 20 mL/min).

ESI-MS m/z for $C_{28}H_{27}F_4N_4O_3S$ found 575.2 [M+H]$^+$, $R_t$=1.47 min; $^1$H NMR (700 MHz, Methanol-d$_4$) δ 8.81-8.76 (m, 1H), 8.02-7.99 (m, 1H), 7.80-7.74 (m, 1H), 7.61-7.56 (m, 1H), 4.92-4.89 (m, 2H), 4.47-4.28 (m, 1H), 4.26-4.02 (m, 1H), 4.00-3.75 (m, 1H), 3.66-3.50 (m, 2H), 3.16-2.98 (m, 1H), 2.91-2.70 (m, 1H), 2.55-2.51 (m, 3H), 2.50-2.46 (m, 2H), 2.04-1.85 (m, 1H), 1.77-1.50 (m, 1H), 1.25-1.21 (m, 3H), 1.11-1.04 (m, 3H).

Example 106

Synthesis of 3-((7-(3-((3S,4S)-3-amino-4-methylpyrrolidine-1-carbonyl)-4-methyl-6-(trifluoromethyl)pyridin-2-yl)thieno[3,2-b]pyridin-2-yl)methyl)-6,6-dimethyl-3-azabicyclo[3.1.0]hexane-2,4-dione hydrochloride (106)

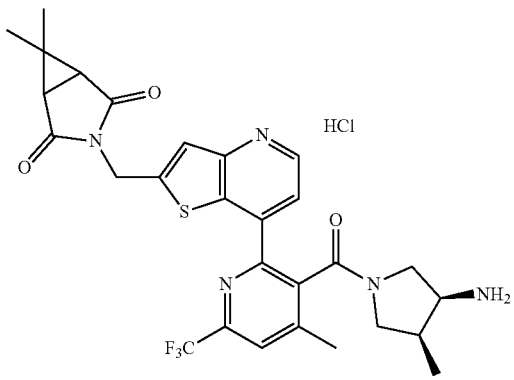

The title compound (106) was obtained as a hydrochloride salt in 8% overall yield in a similar way to Example 45 with the exception that, in the first step of the synthesis an acid II and tert-butyl ((3S,4S)-4-methylpyrrolidin-3-yl)carbamate were used instead of 2-chloro-4-methylnicotinic acid and tert-butyl piperazine-1-carboxylate and in the last step of the synthesis the crude product was purified by preparative reversed-phase column chromatography (C-18, water+0.3‰ HCl (36%)/MeCN, 98:2 to 30:70, 30 min, 20 mL/min).

ESI-MS m/z for $C_{28}H_{29}F_3N_5O_3S$ found 572.3 [M+H], $R_t$=1.11 min; $^1$H NMR (700 MHz, Methanol-d$_4$) δ 8.98-8.83 (m, 1H), 8.15-8.07 (m, 1H), 8.05-7.85 (m, 1H), 7.74-7.67 (m, 1H), 5.03-4.95 (m, 2H), 4.20-3.93 (m, 1H), 3.89-3.78 (m, 1H), 3.73-3.60 (m, 1H), 3.53-3.45 (m, 1H), 3.16-2.94 (m, 1H), 2.66-2.60 (m, 2H), 2.58-2.52 (m, 3H), 2.52-2.28 (m, 1H), 1.39-1.23 (m, 3H), 1.23-1.11 (m, 3H), 1.08-0.42 (m, 3H).

Example 107

Synthesis of 3-((7-(3-((3S,4R)-3-amino-4-methylpyrrolidine-1-carbonyl)-4-methyl-6-(trifluoromethyl)pyridin-2-yl)thieno[3,2-b]pyridin-2-yl)methyl)-6,6-dimethyl-3-azabicyclo[3.1.0]hexane-2,4-dione hydrochloride (107)

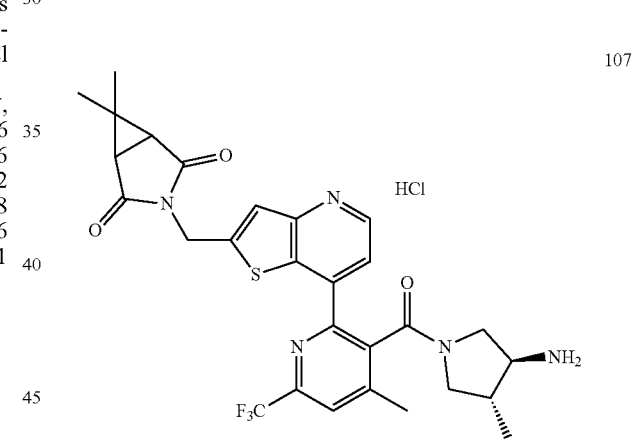

The title compound (107) was obtained as a hydrochloride salt in 9% overall yield in a similar way to Example 45 with the exception that, in the first step of the synthesis an acid II and tert-butyl ((3S,4R)-4-methylpyrrolidin-3-yl)carbamate hydrochloride were used instead of 2-chloro-4-methylnicotinic acid and tert-butyl piperazine-1-carboxylate and in the last step of the synthesis the crude product was purified by preparative reversed-phase column chromatography (C-18, water+0.3‰ HCl (36%)/MeCN, 98:2 to 30:70, 30 min, 20 mL/min).

ESI-MS m/z for $C_{28}H_{29}F_3N_5O_3S$ found 572.1 [M+H], $R_t$=1.12 min; $^1$H NMR (700 MHz, Methanol-d$_4$) δ 8.96-8.75 (m, 1H), 8.10-8.05 (m, 1H), 7.95-7.80 (m, 1H), 7.68-7.61 (m, 1H), 4.98-4.92 (m, 2H), 4.30-3.92 (m, 1H), 3.69-3.46 (m, 1H), 3.38-3.36 (m, 1H), 3.30-3.01 (m, 1H), 2.64-2.56 (m, 3H), 2.56-2.50 (m, 2H), 2.40-2.04 (m, 2H), 1.31-1.26 (m, 3H), 1.20-1.13 (m, 3H), 1.04-0.45 (m, 3H).

Example 108

Synthesis of 6,6-dimethyl-3-((7-(4-methyl-3-((3aR,6aR)-octahydropyrrolo[3,4-b]pyrrole-5-carbonyl)-6-(trifluoromethyl)pyridin-2-yl)thieno[3,2-b]pyridin-2-yl)methyl)-3-azabicyclo[3.1.0]hexane-2,4-dione dihydrochloride (108)

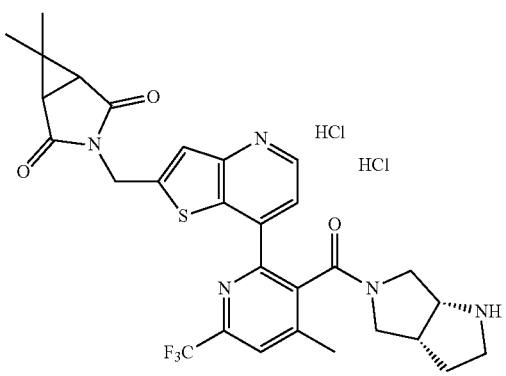

The title compound (108) was obtained as a dihydrochloride salt in 12% overall yield in a similar way to Example 45 with the exception that, in the first step of the synthesis an acid II and tert-butyl (3aR,6aR)-hexahydropyrrolo[3,4-b]pyrrole-1(2H)-carboxylate were used instead of 2-chloro-4-methylnicotinic acid and tert-butyl piperazine-1-carboxylate and in the last step of the synthesis the crude product was purified by preparative reversed-phase column chromatography (C-18, water+0.3‰ HCl (36%)/MeCN, 98:2 to 30:70, 30 min, 20 mL/min).

ESI-MS m/z for $C_{29}H_{29}F_3N_5O_3S$ found 584.0 [M+H]$^+$, $R_t$=1.17 min; $^1$H NMR (700 MHz, Methanol-d$_4$) δ 8.90-8.80 (n, 1H), 8.09-8.01 (m, 1H), 7.87-7.76 (m, 1H), 7.67-7.59 (m, 1H), 4.97-4.91 (m, 2H), 4.39-4.17 (m, 1H), 4.15-4.04 (m, 1H), 3.83-3.73 (m, 1H), 3.49-3.37 (m, 1H), 3.07-2.84 (m, 2H), 2.84-2.73 (m, 1H), 2.66-2.58 (m, 2H), 2.55-2.49 (m, 4H), 2.23-2.11 (m, 1H), 1.91-1.70 (m, 1H), 1.28-1.23 (m, 3H), 1.20-1.08 (m, 3H).

Example 109

Synthesis of (2S)-2-amino-N-((3S)-1-(2-(2-((6,6-dimethyl-2,4-dioxo-3-azabicyclo[3.1.0]hexan-3-yl)methyl)thieno[3,2-b]pyridin-7-yl)-4-methyl-6-(trifluoromethyl)nicotinoyl)pyrrolidin-3-yl)-3-methylbutanamide dihydrochloride (109)

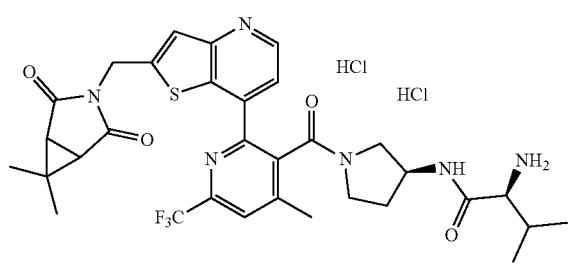

Step 1

Synthesis of tert-butyl ((2S)-1-(((3S)-1-(2-(2-((6,6-dimethyl-2,4-dioxo-3-azabicyclo[3.1.0]hexan-3-yl)methyl)thieno[3,2-b]pyridin-7-yl)-4-methyl-6-(trifluoromethyl)nicotinoyl)pyrrolidin-3-yl)amino)-3-methyl-1-oxobutan-2-yl)carbamate (109a)

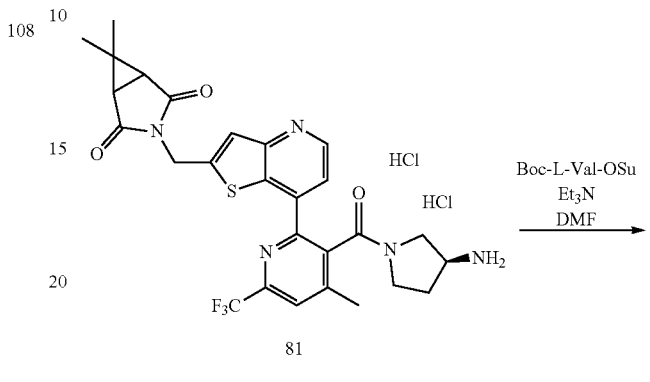

To a stirred solution of 81 (25 mg; 0.04 mmol) in DMF (0.5 mL), Boc-L-Val-OSu (14 mg; 0.04 mmol) and Et$_3$N (28 μL; 0.20 mmol) were added and the resulting mixture was stirred at room temperature overnight. The reaction progress was monitored by LC-MS. When analysis indicated completion of the reaction, DMF was evaporated under reduced pressure. The residue was dissolved in AcOEt (20 mL) and washed with 5% NaHCO$_3$ (1×10 mL), 1 M KHSO$_4$ (1×10 mL) and water (1×10 mL). The organic phase was dried over anhydrous NaSO$_4$, filtered and concentrated in vacuo. The crude product was used to the next step without additional purification. The title compound (109a) was obtained as a colorless oil in 99% yield (29 mg; 0.04 mmol).

ESI-MS m/z for $C_{37}H_{44}F_3N_6O_6S$ found 757.1 [M+H]$^+$; $R_t$=1.57 min

Step 2

Synthesis of (2S)-2-amino-N-((3S)-1-(2-(2-((6,6-dimethyl-2,4-dioxo-3-azabicyclo[3.1.0]hexan-3-yl)methyl)thieno[3,2-b]pyridin-7-yl)-4-methyl-6-(trifluoromethyl)nicotinoyl)pyrrolidin-3-yl)-3-methylbutanamide dihydrochloride (109)

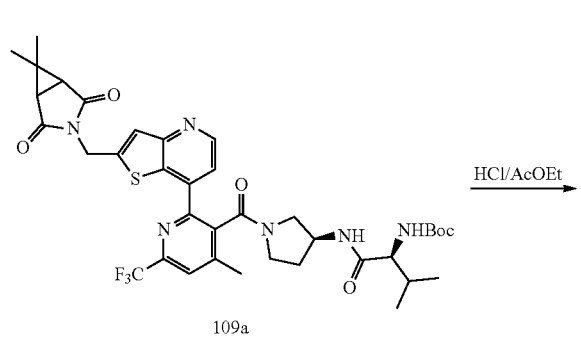

109a

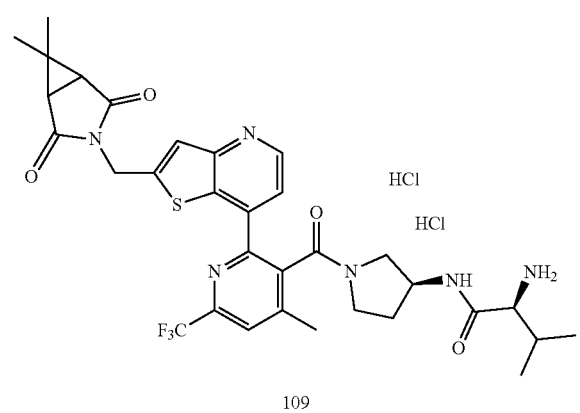

109

The title compound (109) was obtained as a white solid as a dihydrochloride salt from 109a (29 mg; 0.040 mmol) according to the General Procedure IVa in in 85% yield (25 mg; 0.034 mmol). The crude product was purified by preparative reversed-phase column chromatography (C-18, water+0.3‰ HCl (36%)/MeCN, 98:2 to 30:70, 30 min, 20 mL/min).

ESI-MS m/z for $C_{32}H_{36}F_3N_6O_4S$ found 657.1 [M+H]$^+$, $R_t$=1.09 min; $^1$H NMR (700 MHz, $D_2O$) δ 8.92-8.82 (m, 1H), 8.18-8.12 (m, 1H), 7.88-7.69 (m, 2H), 5.06-4.99 (m, 2H), 4.39-3.90 (m, 1H), 3.83-3.67 (m, 1H), 3.66-3.51 (m, 1H), 3.47-3.20 (m, 1H), 2.96-2.76 (m, 1H), 2.72-2.69 (m, 2H), 2.58-2.54 (m, 3H), 2.32-2.20 (m, 1H), 2.18-2.02 (m, 1H), 1.99-1.86 (m, 1H), 1.83-1.60 (m, 1H), 1.30-1.25 (m, 3H), 1.15-1.04 (m, 4H), 0.96-0.87 (m, 3H), 0.57-0.51 (m, 2H).

Example 110

Synthesis of (2S)-2-amino-N-((3S)-1-(2-(2-((6,6-dimethyl-2,4-dioxo-3-azabicyclo[3.1.0]hexan-3-yl)methyl)thieno[3,2-b]pyridin-7-yl)-4-methyl-6-(trifluoromethyl)nicotinoyl)pyrrolidin-3-yl)propanamide dihydrochloride (110)

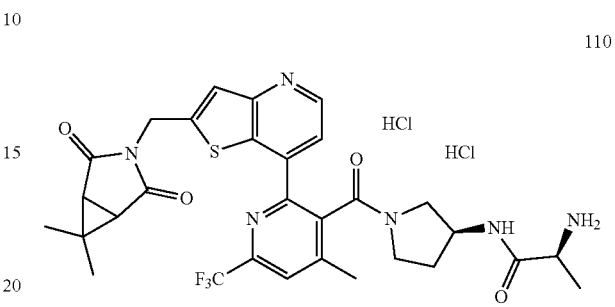

110

The title compound (110) was obtained as a dihydrochloride salt in 81% overall yield in a similar way to Example 109 with the exception that, in the first step of the synthesis Boc-L-Ala-OSu was used instead of Boc-L-Val-OSu and in the last step of the synthesis the crude product was purified by preparative reversed-phase column chromatography (C-18, water+0.3‰ HCl (36%)/MeCN, 98:2 to 30:70, 30 min, 20 mL/min).

ESI-MS m/z for $C_{30}H_{32}F_3N_6O_4S$ found 629.1 [M+H]$^+$, $R_t$=1.05 min; $^1$H NMR (700 MHz, $D_2O$) δ 8.89-8.80 (m, 1H), 8.17-8.11 (m, 1H), 7.78-7.66 (m, 2H), 5.05-4.95 (m, 2H), 4.33-3.76 (m, 2H), 3.69-3.55 (m, 1H), 3.45-3.19 (m, 2H), 3.03-2.73 (m, 1H), 2.72-2.67 (m, 2H), 2.60-2.52 (m, 3H), 2.31-1.97 (m, 2H), 1.87-1.78 (m, 1H), 1.58-1.45 (m, 2H), 1.37-1.24 (m, 3H), 1.14-0.94 (m, 3H).

Example 111

Synthesis of 2-(2-((6,6-dimethyl-2,4-dioxo-3-azabicyclo[3.1.0]hexan-3-yl)methyl)thieno[3,2-b]pyridin-7-yl)-4-methyl-N-(piperidin-4-yl)-6-(trifluoromethyl)nicotinamide dihydrochloride (111)

111

The title compound (111) was obtained as a dihydrochloride salt in 36% overall yield in a similar way to Example 45 with the exception that, in the first step of the synthesis an acid II and tert-butyl 4-aminopiperidine-1-carboxylate were used instead of 2-chloro-4-methylnicotinic acid and tert-butyl piperazine-1-carboxylate and in the last step of the synthesis the crude product was purified by preparative reversed-phase column chromatography (C-18, water+0.3‰ HCl (36%)/MeCN, 99:1 to 25:75, 30 mm, 18 mL/min).

ESI-MS m/z for $C_{28}H_{298}F_3N_5O_3S$ found 572.2 [M+H]$^+$, $R_t$=1.07 min; $^1$H NMR (700 MHz, D$_2$O) δ 8.82 (d, J=5.3 Hz, 1H), 8.09 (s, 1H), 7.74 (d, J=5.3 Hz, 1H), 7.69 (s, 1H), 4.99 (s, 2H), 4.07-4.01 (m, 1H), 3.36-3.31 (m, 2H), 3.08 (td, J=13.0, 3.1 Hz, 2H), 2.69 (s, 2H), 2.59 (s, 3H), 1.94 (d, J=12.9 Hz, 2H), 1.48 (dd, J=22.7, 11.0 Hz, 2H), 1.27 (s, 3H), 1.09 (s, 3H).

Example 112

Synthesis of 3-((7-(3-(4-aminopiperidine-1-carbonyl)-4-methyl-6-(trifluoromethyl)pyridin-2-yl)thieno[3,2-b]pyridin-2-yl)methyl)-6,6-dimethyl-3-azabicyclo[3.1.0]hexane-2,4-dione dihydrochloride (112)

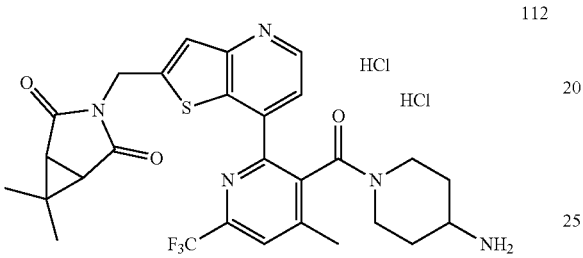

The title compound (112) was obtained as a dihydrochloride salt in 35% overall yield in a similar way to Example 45 with the exception that, in the first step of the synthesis an acid II and tert-butyl piperidin-4-ylcarbamate were used instead of 2-chloro-4-methylnicotinic acid and tert-butyl piperazine-1-carboxylate and in the last step of the synthesis the crude product was purified by preparative reversed-phase column chromatography (C-18, water+0.3‰ HCl (36%)/MeCN, 99:1 to 30:70, 30 min, 20 mL/min).

ESI-MS m/z for $C_{28}H_{29}F_3N_5O_3S$ found 572.1 [M+H]$^+$, $R_t$=1.12 min; $^1$H NMR (70) MHz, D$_2$O) δ 8.79-8.75 (m, 1H), 8.06-8.00 (m, 1H), 7.74-7.57 (m, 2H), 4.96-4.87 (m, 2H), 4.65-4.59 (m, 1H), 3.35-3.12 (m, 2H), 2.98-2.73 (m, 1H), 2.61 (d, J=2.8 Hz, 2H), 2.57-2.44 (m, 4H), 2.19-2.06 (m, 1H), 1.83-1.64 (m, 1H), 1.57-1.45 (m, 1H), 1.20 (s, 3H), 1.15 (ddd, J=16.9, 12.7, 4.6 Hz, 1H), 1.01 (d, J=14.5 Hz, 3H).

Example 113

Synthesis of 3-((7-(3-((S)-3-hydroxypyrrolidine-1-carbonyl)-4-methyl-6-(trifluoromethyl)pyridin-2-yl)thieno[3,2-b]pyridin-2-yl)methyl)-6,6-dimethyl-3-azabicyclo[3.1.0]hexane-2,4-dione hydrochloride (113)

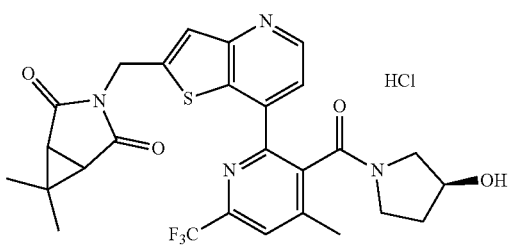

The title compound (113) was obtained as a hydrochloride salt in 10% overall yield in a similar way to Example 48 with the exception that, in the first step of the synthesis (S)-3-hydroxypyrrolidine was used instead of a morpholine and an acid II was used instead of 2-chloro-4-methylnicotinic acid and in the last step of the synthesis the crude product was purified by preparative reversed-phase column chromatography (C-18, water+0.3‰ HCl (36%)/MeCN, 99:1 to 25:75, 30 min, 18 mL/min).

ESI-MS m/z for $C_{27}H_{26}F_3N_4O_4S$ found 559.3 [M+H]$^+$, $R_t$=1.25 min; $^1$H NMR (700 MHz, DMSO-d$_6$) δ 8.81-8.69 (m, 1H), 8.14-8.09 (m, 1H), 7.72-7.50 (m, 2H), 4.82 (s, 2H), 4.28-4.12 (m, 1H), 3.96-3.61 (m, 1H), 3.22-2.97 (m, 1H), 2.71-2.61 (m, 1H), 2.60-2.58 (m, 2H), 2.48-2.45 (m, 3H), 2.00-1.57 (m, 2H), 1.53-1.26 (m, 1H), 1.21-1.14 (m, 3H), 1.02 (dd, J=19.4, 14.4 Hz, 3H).

Example 114

Synthesis of 3-((7-(3-((S)-3-fluoropyrrolidine-1-carbonyl)-4-methyl-6-(trifluoromethyl)pyridin-2-yl)thieno[3,2-b]pyridin-2-yl)methyl)-6,6-dimethyl-3-azabicyclo[3.1.0]hexane-2,4-dione hydrochloride (114)

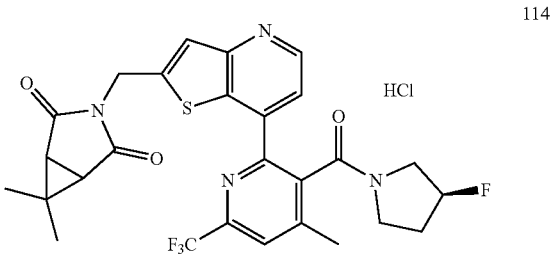 [SMILES: Cc1cc(C(F)(F)F)nc(-c2ccnc3cc(CN4C(=O)C5C(C4=O)C5(C)C)sc23)c1C(=O)N1CC[C@H](F)C1 ; Cl]

Step 1

Synthesis of 7-chloro-2-(((tetrahydro-2H-pyran-2-yl)oxy)methyl)thieno[3,2-b]pyridine (114a)

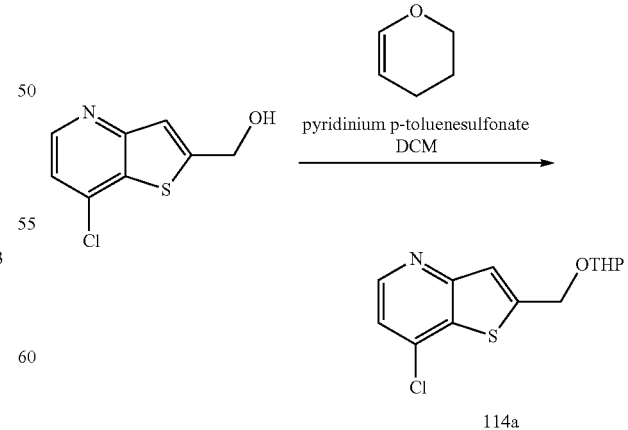

To a solution of (7-chlorothieno[3,2-b]pyridin-2-yl)methanol (0.6 g; 3.01 mmol) in anhydrous DCM (17 mL) 3,4-dihydro-2H-pyran (0.41 mL; 4.51 mmol) and pyri-

413 dinium p-toluenesulfonate (0.76 g; 3.01 mmol) were added and the reaction mixture was stirred at room temperature overnight. Then another part of 3,4-dihydro-2H-pyran (0.27 mL; 3.01 mmol) was added and the reaction mixture was stirred at room temperature additional day. The reaction progress was monitored by LC-MS. When analysis indicated completion of the reaction, it was washed with an aqueous saturated solution of Na-2CO$_3$ (1×15 mL). The organic phase was dried over anhydrous Na$_2$SO$_4$, filtered and concentrated in vacuo and the crude product was purified by flash column chromatography on silica (hexane/AcOEt, 100:0 to 0:100, v/v). The title compound (114a) was obtained as a colorless oil in 96% yield (0.82 g; 2.88 mmol).

ESI-MS m/z for C$_{13}$H$_{15}$ClNO$_2$S found 284.0/286.0 [M+H]$^+$; R$_t$=1.55 min; $^1$H NMR (700 MHz, CDCl$_3$) 8.55 (d, J=5.1 Hz, 1H), 7.45 (t, J=1.1 Hz, 1H), 7.24 (d, J=5.1 Hz, 1H), 5.03 (dd, J=13.4, 1.2 Hz, 1H), 4.86 (dd, J=13.4, 1.0 Hz, 1H), 4.80 (t, J=3.4 Hz, 1H), 3.96-3.89 (m, 1H), 3.61-3.56 (m, 1H), 1.92-1.84 (m, 1H), 1.80-1.74 (m, 1H), 1.73-1.68 (m, 1H), 1.65-1.61 (m, 1H), 1.59-1.54 (m, 2H).

Step 2

Synthesis of (2-(((tetrahydro-2H-pyran-2-yl)oxy)methyl)thieno[3,2-b]pyridin-7-yl)boronic acid (114b)

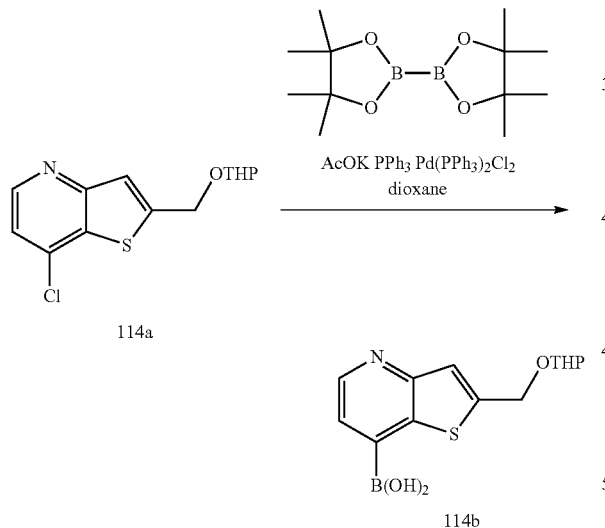

In a Schlenk flask was placed the compound 114a (100 mg; 0.35 mmol), potassium acetate (104 mg; 0.42 mmol), Pd(PPh$_3$)$_2$Cl$_2$ (25 mg; 0.035 mmol), PPh$_3$ (19 mg; 0.07 mmol) and anhydrous, degassed dioxane (2 mL). The flask was backfilled with an argon and stirred for 10 minutes. Then bis(pinacolo)diboron (25 mg; 0.035 mmol) was added and the resulting mixture was stirred at 90° C. overnight. The reaction progress was monitored by LC-MS. When analysis indicated completion of the reaction, the mixture was cooled to room temperature and the product was not isolated. It was used to the next step without purification.

ESI-MS m/z for C$_{13}$H$_{17}$BNO$_4$S found 293.9 [M+H]$^+$, R$_t$=1.04 min

414

Step 3

Synthesis of (S)-(2-chloro-4-methyl-6-(trifluoromethyl)pyridin-3-yl)(3-fluoropyrrolidin-1-yl)methanone (114c)

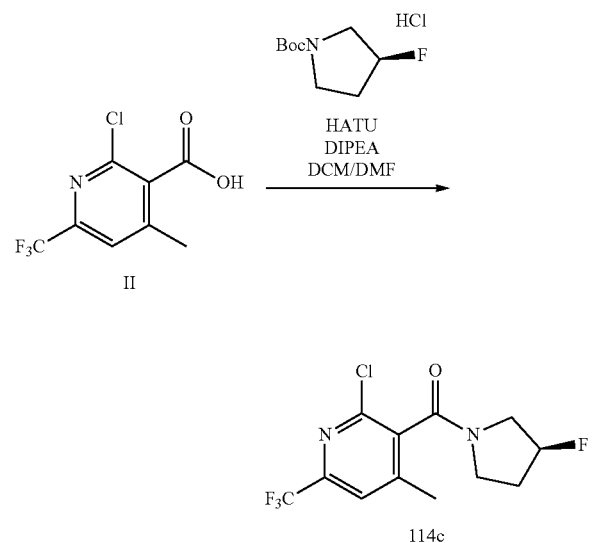

The title compound (114c) was obtained from an acid II (100 mg; 0.42 mmol) and from tert-butyl (S)-3-fluoropyrrolidine-1-carboxylate hydrochloride (58 mg; 0.46 mmol) according to the General Procedure I as a colorless oil in 99% yield (128 mg; 0.41 mmol).

ESI-MS m/z for C$_{12}$H$_{12}$ClF$_4$N$_2$O found 310.9 [M+H]$^+$; R$_t$=1.21 min; $^1$H NMR (700 MHz, Methanol-d$_4$) δ 7.86-7.78 (m, 1H), 5.49-5.22 (m, 1H), 4.10-3.90 (m, 1H), 3.85-3.68 (m, 1H), 3.63-3.37 (m, 2H), 2.47-2.42 (m, 3H), 2.41-2.15 (m, 2H).

Step 4

Synthesis of ((S)-3-fluoropyrrolidin-1-yl)(4-methyl-2-(2-(((tetrahydro-2H-pyran-2-yl)oxy)methyl)thieno[3,2-b]pyridin-7-yl)-6-(trifluoromethyl)pyridin-3-yl)methanone (114d)

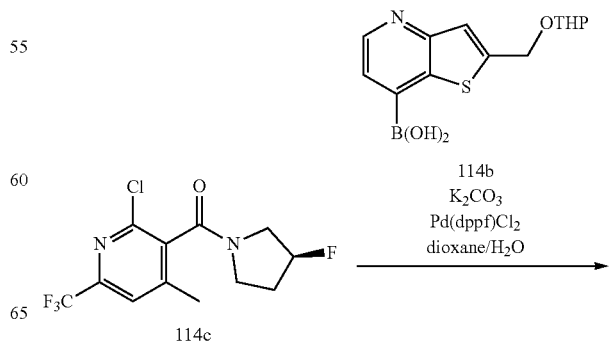

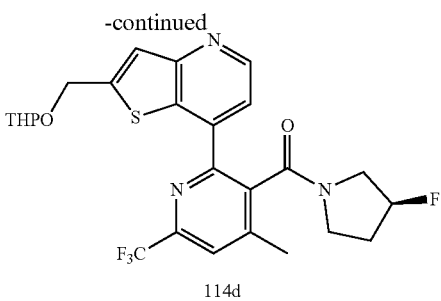

114d

The title compound (114d) was obtained from 114b (the crude product) and from 114c (109 mg; 0.35 mmol) according to the General Procedure Va as a yellow oil in 70% yield (130 mg; 0.25 mmol).

ESI-MS m/z for $C_{25}H_{26}F_4N_3O_3S$ found 524.2 $[M+H]^+$; $R_t$=1.61 min

Step 5

Synthesis of (S)-(3-fluoropyrrolidin-1-yl)(2-(2-(hydroxymethyl)thieno[3,2-b]pyridin-7-yl)-4-methyl-6-(trifluoromethyl)pyridin-3-yl)methanone (114e)

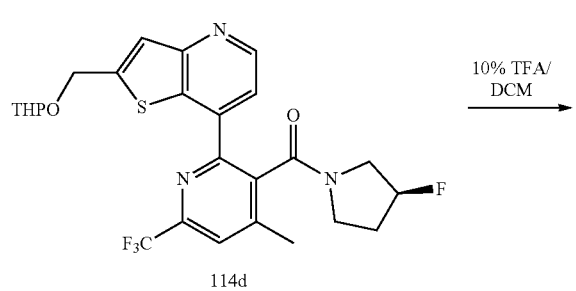

The solution of 114d (100 mg; 0.19 mmol) in DCM (9 mL) and TFA (1 mL) was stirred at room temperature for 3 h. The reaction progress was monitored by LC-MS. When analysis indicated completion of the reaction, the mixture of TFA/DCM was removed in vacuo and the residue was redissolved in AcOEt (20 mL) and washed with 5% NaHCO$_3$ (1×20 mL). The organic phase was dried over anhydrous Na$_2$SO$_4$, filtered and concentrated in vacuo. The crude product was purified by flash column chromatography on silica (hexane/AcOEt, 100:0 to 0:100, v/v, then: AcOEt/MeOH, 90:10, v/v). The title compound (114e) was obtained as a colorless oil in 71% yield (60 mg; 0.14 mmol).

ESI-MS m/z for $C_{20}H_{18}F_4N_3O_2S$ found 440.0 $[M+H]^+$; $R_t$=1.17 min

Step 6

Synthesis of (S)-(7-(3-(3-fluoropyrrolidine-1-carbonyl)-4-methyl-6-(trifluoromethyl)pyridin-2-yl)thieno[3,2-b]pyridin-2-yl)methyl methanesulfonate (114f)

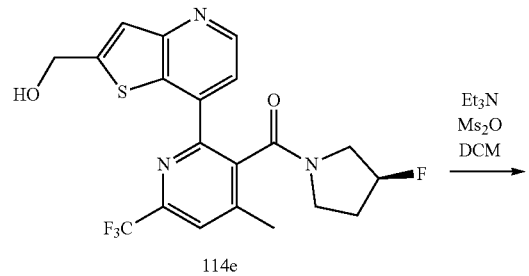

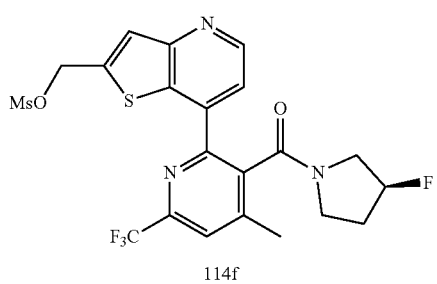

114f

The title compound (114f) was obtained as a brown oil from 114e (50 mg; 0.11 mmol) according to the General Procedure VIII in 98% yield (58 mg; 0.11 mmol).

ESI-MS m/z for $C_{21}H_{20}F_4N_3O_4S_2$ found 518.0 $[M+H]^+$; $R_a$=1.38 min

Step 7

Synthesis of 3-((7-(3-((S)-3-fluoropyrrolidine-1-carbonyl)-4-methyl-6-(trifluoromethyl)pyridin-2-yl)thieno[3,2-b]pyridin-2-yl)methyl)-6,6-dimethyl-3-azabicyclo[3.1.0]hexane-2,4-dione hydrochloride (114)

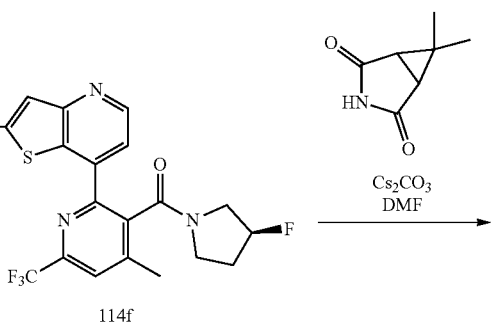

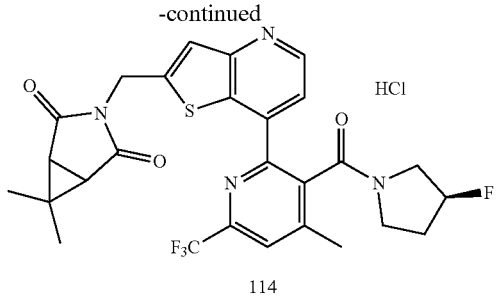

114

To a solution of 114f (55 mg; 0.11 mmol) in anhydrous DMF (3 mL), 6,6-dimethy-3-aza-bicyclo[3.1.0]hexane 2,4-dione (16 mg; 0.12 mmol) and $Cs_2CO_3$ (69 mg; 0.21 mmol) were added. The resulting mixture was stirred at room temperature overnight. The reaction progress was monitored by LC-MS. When analysis indicated completion of the reaction, DMF was removed in vacuo and the residue was dissolved in AcOEt (20 mL) and washed with water (1×15 mL). The organic phase was dried over anhydrous $Na_2SO_4$, filtered and concentrated in vacuo. The crude product was purified by preparative reversed-phase column chromatography (C-18, water+0.3 HCl (36%)/MeCN, 98:2 to 20:80, 30 min, 20 mL/min). The title compound (114) was obtained as a hydrochloride salt as a white solid in 33% yield (21 mg; 0.035 mmol).

ESI-MS m/z for $C_{27}H_{25}F_4N_4O_3S$ found 561.3 [M+H]$^+$; $R_t$=1.48 min; $^1$H NMR (700 MHz, Methanol-$d_4$) δ 8.90-8.81 (m, 1H), 8.10-8.06 (m, 1H), 7.93-7.86 (m, 1H), 7.69-7.63 (m, 1H), 5.33-5.03 (m, 1H), 5.00-4.96 (m, 2H), 4.12-3.54 (m, 2H), 3.44-3.16 (m, 1H), 2.98-2.63 (m, 1H), 2.60-2.56 (m, 3H), 2.56-2.52 (m, 2H), 2.32-1.87 (m, 2H), 1.28 (dd, J=21.7, 14.5 Hz, 3H), 1.13 (dd, J=21.7, 14.5 Hz, 3H).

Example 115

Synthesis of 3-((7-(3-((R)-3-(aminomethyl)pyrrolidine-1-carbonyl)-4-methyl-6-(trifluoromethyl)pyridin-2-yl)thieno[3,2-b]pyridin-2-yl)methyl)-6,6-dimethyl-3-azabicyclo[3.1.0]hexane-2,4-dione dihydrochloride (115)

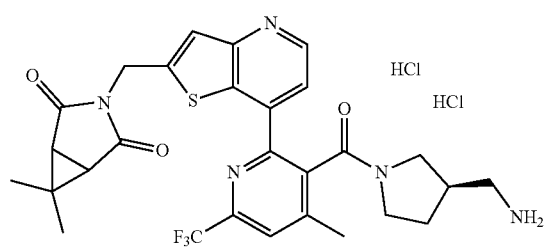

115

Step 1

Synthesis of (S)-tert-butyl 3-(((methylsulfonyl)oxy)methyl)pyrrolidine-1-carboxylate (115a)

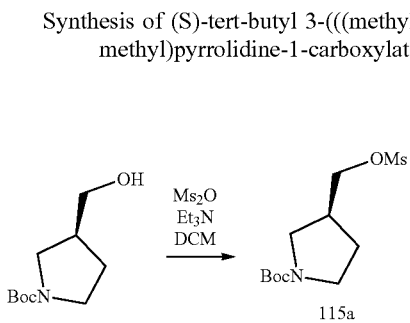

The title compound (115a) was obtained as a yellow oil from tert-butyl (S)-3-(hydroxymethyl)pyrrolidine-1-carboxylate (0.30 g; 1.49 mmol) according to the General Procedure VIII in 99% yield (0.41 mg; 1.49 mmol).

ESI-MS m/z for $C_{11}H_{21}NO_5SNa$ found 302.0 [M+Na]$^+$; $R_t$=1.21 min; $^1$H NMR (700 MHz, CDCl$_3$) δ 4.25-4.11 (m, 2H), 3.63-3.28 (m, 3H), 3.20-3.09 (m, 1H), 3.03 (s, 3H), 2.68-2.58 (m, 1H), 2.09-2.01 (m, 1H), 1.82-1.65 (m, 1H), 1.47 (s, 9H).

Step 2

Synthesis of (S)-tert-butyl 3-(azidomethyl)pyrrolidine-1-carboxylate (115b)

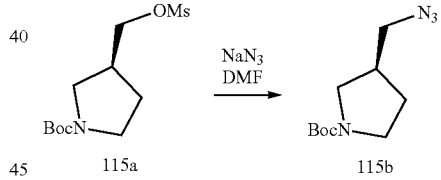

A compound 115a (0.42 g; 1.49 mmol) and sodium azide (0.19 g; 2.98 mmol) in DMF (5 mL) were stirred at 70° C. overnight. The reaction progress was monitored by LC-MS. When analysis indicated completion of the reaction, the mixture was poured into a saturated solution of NaCl (20 mL) and extracted with $Et_2O$ (3×20 mL). The combined organic layers were dried over anhydrous $NaSO_4$, filtered and concentrated in vacuo. The crude product was purified by flash column chromatography on silica (hexane/AcOEt, 100:0 to 0:100, v/v). The title compound (115b) was obtained as a colorless oil in 94% yield (0.31 mg; 1.4 mmol).

ESI-MS m/z for $C_6H_{11}N_4O_2$ found 171.2 [M+H-tBu]$^+$; $R_t$=1.44 min; $^1$H NMR (700 MHz, CDCl$_3$) δ 3.62-3.37 (m, 2H), 3.39-3.22 (m, 3H), 3.13-2.99 (m, 1H), 2.48-2.37 (m, 1H), 2.08-1.96 (m, 1H), 1.73-1.63 (m, 1H), 1.46 (s, 9H).

Step 3

Synthesis of (S)-3-(azidomethyl)pyrrolidine hydrochloride (115c)

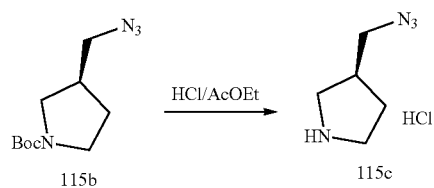 [SMILES: CC(C)(C)OC(=O)N1CC[C@H](CN=[N+]=[N-])C1 ; [N-]=[N+]=NC[C@H]1CCNC1 ; Cl]

The title compounds (115c) was obtained as a hydrochloride salt as a colorless oil from 115b (0.11 g; 0.49 mmol) according to the General Procedure IVa in 99% yield (79 mg; 0.48 mmol).

ESI-MS m/z for $C_5H_{11}N_4$ found 127.3 [M+H]$^+$; $R_t$=0.18 min; $^1$H NMR (700 MHz, Methanol-d$_4$) δ 3.52 (ddd, J=46.1, 12.4, 6.4 Hz, 2H), 3.43 (dd, J=11.9, 8.1 Hz, 1H), 3.38 (ddd, J=11.7, 8.4, 5.1 Hz, 1H), 3.30-3.24 (m, 1H), 3.03 (dd, J=11.9, 7.8 Hz, 1H), 2.66-2.58 (m, 1H), 2.20 (dtd, J=13.0, 7.8, 5.1 Hz, 1H), 1.80 (dq, J=13.3, 8.2 Hz, 1H).

Step 4

Synthesis of (S)-(3-(azidomethyl)pyrrolidin-1-yl)(2-chloro-4-methyl-6-(trifluoromethyl)pyridin-3-yl)methanone (115d)

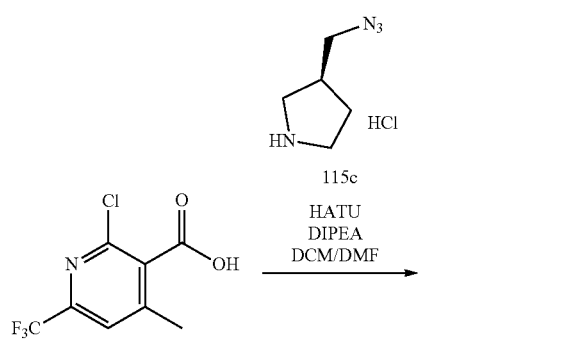

The title compound (115d) was obtained from an acid II (110 mg; 0.44 mmol) and from the compound 115c (79 mg; 0.49 mmol) according to the General Procedure I as a colorless oil in 44% yield (68 mg; 0.2 mmol).

ESI-MS m/z for $C_{13}H_{14}ClF_3N_5O$ found 348.0/350.0 [M+H]$^+$; $R_t$=1.42 min; $^1$H NMR (700 MHz, CDCl$_3$) δ 7.53-7.49 (m, 1H), 3.90-3.82 (m, 1H), 3.72-3.63 (m, 1H), 3.45-3.39 (m, 2H), 3.32-3.27 (m, 1H), 3.14-3.07 (m, 1H), 2.63-2.56 (m, 1H), 2.43-2.40 (m, 3H), 2.21-2.13 (m, 1H), 1.87-1.80 (m, 1H).

Step 5

Synthesis of 3-((7-(3-((S)-3-(azidomethyl)pyrrolidine-1-carbonyl)-4-methyl-6-(trifluoromethyl)pyridin-2-yl)thieno[3,2-b]pyridin-2-yl)methyl)-6,6-dimethyl-3-azabicyclo[3.1.0]hexane-2,4-dione (115e)

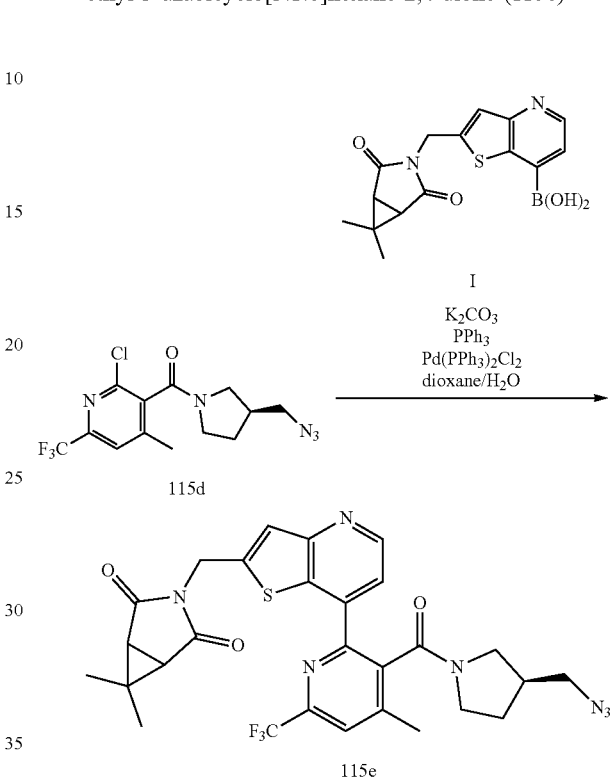

The title compound (115e) was obtained from 115d (67 mg; 0.19 mmol) and from the boronic acid I (76 mg; 0.23 mmol) according to the General Procedure Va. The crude product was used to the next step without purification.

ESI-MS m/z for $C_{28}H_{27}F_3N_7O_3S$ found 598.1 [M+H]$^+$; $R_t$=1.34 min

Step 6

Synthesis of 3-((7-(3-((R)-3-(aminomethyl)pyrrolidine-1-carbonyl)-4-methyl-6-(trifluoromethyl)pyridin-2-yl)thieno[3,2-b]pyridin-2-yl)methyl)-6,6-dimethyl-3-azabicyclo[3.1.0]hexane-2,4-dione dihydrochloride (115)

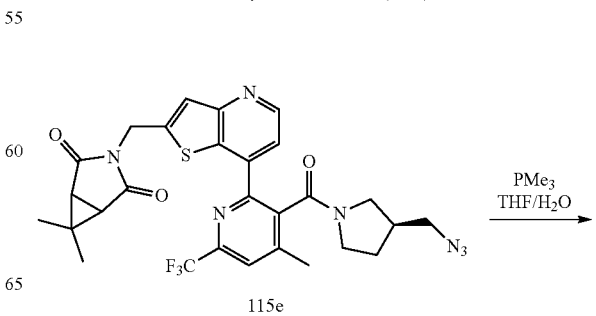

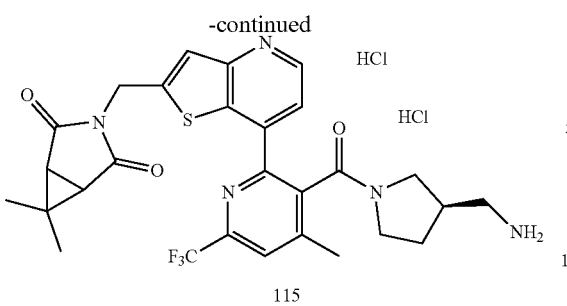

115

To the solution of 115e (the crude product) in THF (1.8 mL) water (0.2 mL) and PMe₃ (1 M solution in THF; 0.58 mL; 0.58 mmol) were added and the mixture was stirred at room temperature overnight. The reaction progress was monitored by LC-MS. When analysis indicated completion of the reaction, the mixture was concentrated in vacuo and the residue was purified by preparative reversed-phase column chromatography (C-18, water+0.3‰ HCl (36%)/MeCN, 98:2 to 30:70, 30 min, 20 mL/min). The title compound (115) was obtained as a dihydrochloride salt as a white solid in 6% yield (per two steps)(8 mg; 0.01 mmol).

ESI-MS m/z for $C_{28}H_{29}F_3N_5O_3S$ found 572.3 [M+H]⁺; $R_t$=1.10 min; ¹H NMR (700 MHz, D₂O) δ 8.83-8.73 (m, 1H), 8.09-8.02 (m, 1H), 7.76-7.59 (m, 2H), 4.97-4.87 (m, 2H), 3.93-3.60 (m, 1H), 3.55-3.23 (m, 1H), 3.13-2.84 (m, 2H), 2.78-2.64 (m, 1H), 2.63-2.58 (m, 2H), 2.56-2.37 (m, 4H), 2.30-2.09 (m, 1H), 1.95-1.70 (m, 1H), 1.59-1.40 (m, 1H), 1.22-1.16 (m, 3H), 1.04-0.92 (m, 3H).

Example 116

Synthesis of 6,6-dimethyl-3-((7-(4-methyl-3-((3aR,6aR)-octahydropyrrolo[3,4-b]pyrrole-1-carbonyl)-6-(trifluoromethyl)pyridin-2-yl)thieno[3,2-b]pyridin-2-yl)methyl)-3-azabicyclo[3.1.0]hexane-2,4-dione dihydrochloride (116)

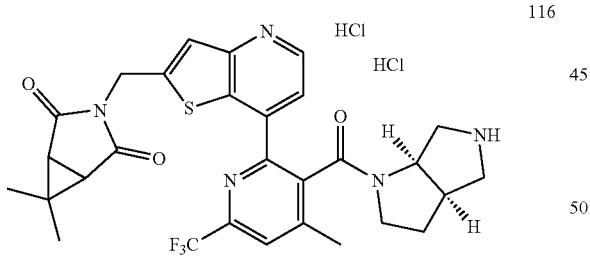

116

The title compound (116) was obtained as a dihydrochloride salt in 46% overall yield in a similar way to Example 45 with the exception that, in the first step of the synthesis an acid II and tert-butyl (3aR,6aR)-hexahydropyrrolo[3,4-b]pyrrole-5(1H)-carboxylate were used instead of 2-chloro-4-methylnicotinic acid and tert-butyl piperazine-1-carboxylate and in the last step of the synthesis the crude product was purified by preparative reversed-phase column chromatography (C-18, water+0.3‰ HCl (36%)/MeCN, 98:2 to 30:70, 30 min, 20 mL/min).

ESI-MS m/z for $C_{29}H_{29}F_3N_5O_3S$ found 584.3 [M+H]⁺; $R_t$=1.18 min; ¹H NMR (700 MHz, DMSO-d₆) δ 8.78-8.70 (m, 1H), 8.09-8.01 (m, 1H), 7.52-7.40 (m, 2H), 4.81-4.74 (m, 2H), 4.70-4.41 (m, 1H), 3.62-3.52 (m, 1H), 3.39-3.16 (m, 2H), 3.13-2.53 (m, 5H), 2.53-2.51 (m, 2H), 2.48-2.37 (m, 3H), 1.60-1.52 (m, 1H), 1.17-1.10 (m, 3H), 1.03-0.90 (m, 3H).

Example 117

Synthesis of 3-((7-(3-((3R,4R)-3-amino-4-fluoropyrrolidine-1-carbonyl)-4-methyl-6-(trifluoromethyl)pyridin-2-yl)thieno[3,2-b]pyridin-2-yl)methyl)-6,6-dimethyl-3-azabicyclo[3.1.0]hexane-2,4-dione dihydrochloride (117)

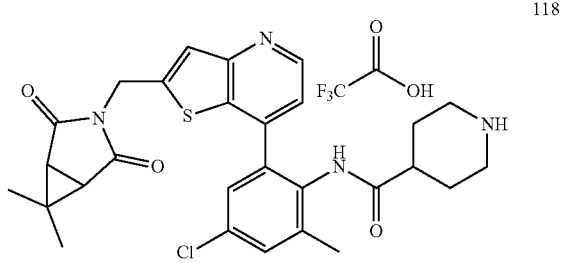

117

The title compound (117) was obtained as a dihydrochloride salt in 3% overall yield in a similar way to Example 45 with the exception that, in the first step of the synthesis an acid II and tert-butyl ((3R,4R)-4-fluoropyrrolidin-3-yl)carbamate hydrochloride were used instead of 2-chloro-4-methylnicotinic acid and tert-butyl piperazine-1-carboxylate and in the last step of the synthesis the crude product was purified by preparative reversed-phase column chromatography (C-18, water+0.3‰ HCl (36%)/MeCN, 99:1 to 20:80, 30 min, 20 mL/min).

ESI-MS m/z for $C_{27}H_{26}F_4N_5O_3S$ found 576.2 [M+H]⁺; $R_t$=1.15 min; ¹H NMR (700 MHz, Methanol-d₄) δ 9.00-8.91 (m, 1H), 8.18-7.93 (m, 2H), 7.73 (dd, J=9.5, 7.0 Hz, 1H), 5.40-5.14 (m, 1H), 5.04-4.94 (m, 2H), 4.49-3.14 (m, 5H), 3.10-2.65 (m, 2H), 2.60-2.49 (m, 3H), 1.32-1.23 (m, 3H), 1.21-1.08 (m, 3H).

Example 118

Synthesis of N-(4-chloro-2-(2-((6,6-dimethyl-2,4-dioxo-3-azabicyclo[3.1.0]hexan-3-yl)methyl)thieno[3,2-b]pyridin-7-yl)-6-methylphenyl)piperidine-4-carboxamide 2,2,2-trifluoroacetate (118)

118

The title compound (118) was obtained as a TFA salt in 5% overall yield in a similar way to Example 34 with the exception that, in the first step of the synthesis 1-(tert-butoxycarbonyl)piperidine-4-carboxylic acid was used instead of (S)-1-(tert-butoxycarbonyl)pyrrolidine-3-carboxylic acid and in the last step of the synthesis, the General Procedure IVb was used instead of the General Procedure IVa and the crude product was purified by preparative reversed-phase column chromatography (C-18, water+0.4‰ TFA/MeCN+0.4‰ TFA, 85:15 to 55:45, 30 min, 20 mL/min).

ESI-MS m/z for $C_{28}H_{30}ClN_4O_3S$ found 537.0/539.0 [M+H]$^+$; R$_t$=1.00 min; $^1$H NMR (700 MHz, Methanol-d$_4$) δ 8.69-8.65 (m, 1H), 7.56-7.54 (m, 1H), 7.53-7.51 (m, 1H), 7.41-7.38 (m, 1H), 7.31-7.28 (m, 1H), 4.89-4.87 (m, 2H), 3.27-3.18 (m, 2H), 2.95-2.83 (m, 2H), 2.53 (s, 2H), 2.51-2.45 (m, 1H), 2.34 (s, 3H), 1.69-1.58 (m, 2H), 1.58-1.45 (m, 2H), 1.27 (s, 3H), 1.15 (s, 3H).

Example 119

Synthesis of 6,6-dimethyl-3-((7-(2-methyl-5-(((S)-piperidin-3-yl)oxy)pyridin-4-yl)thieno[3,2-b]pyridin-2-yl)methyl)-3-azabicyclo[3.1.0]hexane-2,4-dione 2,2,2-trifluoroacetate (119)

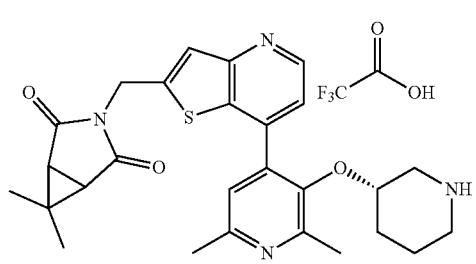

119

The title compound (119) was obtained as a TFA salt in 3% overall yield in a similar way to Example 31 with the exception that, in the first step of the synthesis 4-bromo-6-methylpyridin-3-ol was used instead of 2-bromo-4-chloro-6-methylphenol, in the third step of the synthesis, the compound Ic was used instead of 4-chlorothieno[2,3-b]pyridine, and in the last step of the synthesis, the General Procedure IVb was used instead of the General Procedure IVa and the crude product was purified by preparative reversed-phase column chromatography (C-18, water+0.4‰ TFA/MeCN+0.4‰ TFA, 95:5 to 50:50, 30 min, 20 mL/min).

ESI-MS m/z for $C_{26}H_{29}N_4O_3S$ found 477.0 [M+H]$^+$; R$_t$=0.75 min; $^1$H NMR (700 MHz, Methanol-d$_4$) δ 8.81-8.78 (m, 1H), 8.64 (s, 1H), 7.72 (s, 1H), 7.61-7.58 (m, 1H), 7.57-7.54 (m, 1H), 4.93-4.89 (m, 2H), 4.79-4.73 (m, 1H), 3.41-3.37 (m, 1H), 3.31-3.27 (m, 1H), 3.15-3.10 (m, 2H), 2.70 (s, 3H), 2.52 (s, 2H), 2.00-1.92 (m, 1H), 1.85-1.74 (m, 2H), 1.74-1.67 (m, 1H), 1.26 (s, 3H), 1.12 (s, 3H).

Example 120

Synthesis of (3R)—N-(6-chloro-4-(2-((6,6-dimethyl-2,4-dioxo-3-azabicyclo[3.1.0]hexan-3-yl)methyl)thieno[3,2-b]pyridin-7-yl)-2-methylpyridin-3-yl)pyrrolidine-3-carboxamide 2,2,2-trifluoroacetate (120)

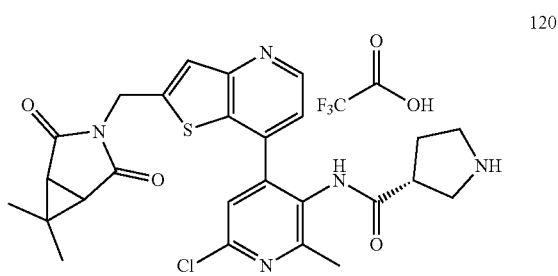

120

Step 1

Synthesis of benzyl (S)-3-((4-bromo-6-chloro-2-methylpyridin-3-yl)carbamoyl)pyrrolidine-1-carboxylate (120a)

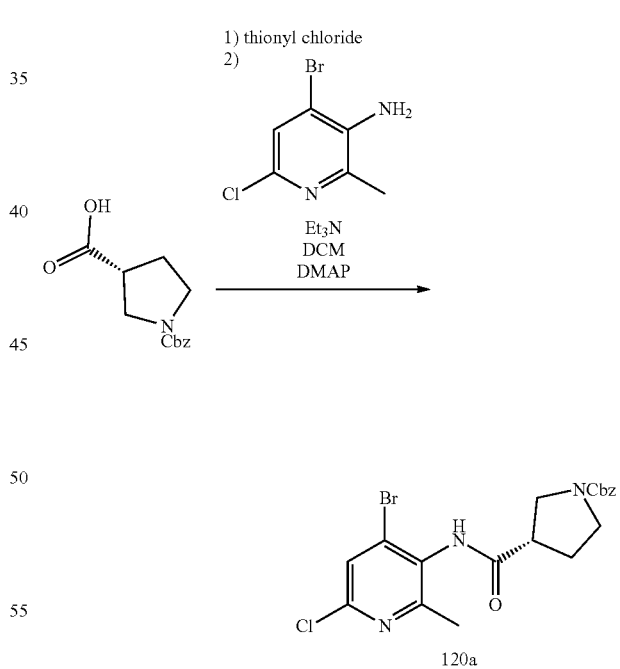

120a

The title compound (120a) was obtained from (R)-1-((benzyloxy)carbonyl)pyrrolidine-3-carboxylic acid (354 mg; 1.42 mmol) and from commercially available 4-bromo-6-chloro-2-methylpyridin-3-amine (183 mg; 0.83 mmol) according to the General Procedure II in 16% yield (59 mg; 0.13 mmol).

ESI-MS m/z for $C_{19}H_{20}BrClN_3O_3$ found 451.9/453.9 [M+H]$^+$; R$_t$=1.36 min

Step 2

Synthesis of benzyl (3S)-3-((6-chloro-4-(2-((6,6-dimethyl-2,4-dioxo-3-azabicyclo[3.1.0]hexan-3-yl)methyl)thieno[3,2-b]pyridin-7-yl)-2-methylpyridin-3-yl)carbamoyl)pyrrolidine-1-carboxylate (120b)

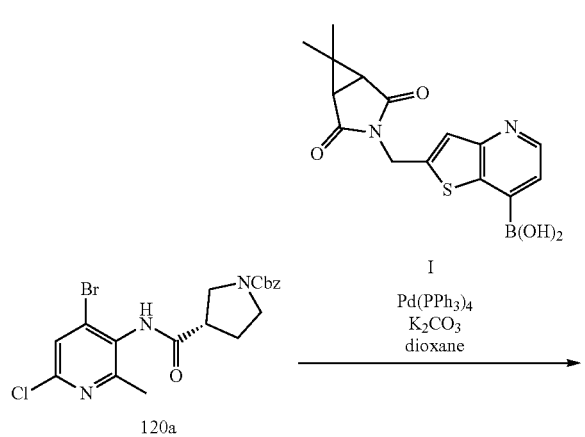

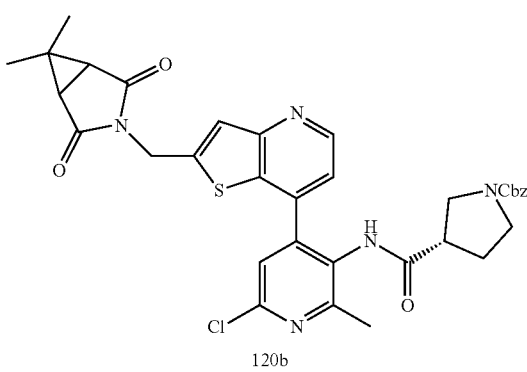

The title compound (120b) was obtained from 120a (59 mg; 0.13 mmol) and from boronic acid I (53 mg; 0.16 mmol) according to the General Procedure Va and after standard work-up the crude product was taken to the next step.

ESI-MS m/z for $C_{34}H_{33}ClN_5O_5S$ found 658.4/660.4 [M+H]$^+$; R$_t$=1.44

Step 3

Synthesis of (3R)—N-(6-chloro-4-(2-((6,6-dimethyl-2,4-dioxo-3-azabicyclo[3.1.0]hexan-3-yl)methyl)thieno[3,2-b]pyridin-7-yl)-2-methylpyridin-3-yl)pyrrolidine-3-carboxamide 2,2,2-trifluoroacetate (120)

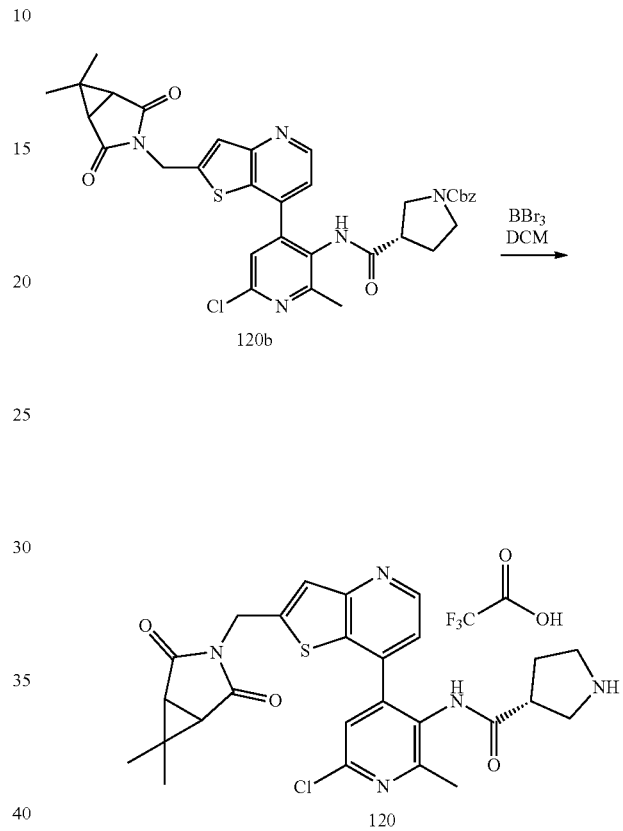

To the cooled to −10° C. solution of 120b (the crude product) in anhydrous DCM (1.5 mL) under an argon atmosphere BBr$_3$ (1 M solution in DCM; 0.15 mL; 0.15 mmol) was added dropwise and then the mixture was stirred at room temperature for 1.5 hours. The reaction progress was monitored by LC-MS. When analysis indicated completion of the reaction, the reaction mixture was cooled to 0° C. and to this mixture 1 M NaOH (1 mL) was added dropwise and whole was then stirred to allow to room temperature. Then brine was added and the phases were separated. An aqueous phase was extracted with AcOEt (3×). The combined organic solutions were dried over anhydrous Na$_2$SO$_4$, filtered and concentrated in vacuo. The crude product was purified by preparative reversed-phase column chromatography (C-18, water+0.4‰ TFA/MeCN+0.4‰ TFA, 90:10 to 50:50, 40 min, 20 mL/min). The title compound (120) was obtained as a TFA salt in 2% yield (per two steps)(2 mg; 0.003 mmol).

ESI-MS m/z for $C_{26}H_{27}ClN_5O_3S$ found 524.3/526.3 [M+H]$^+$; R$_t$=0.90 min; $^1$H NMR (700 MHz, D$_2$O) δ 8.86-8.80 (m, 1H), 7.72 (s, 1H), 7.66-7.61 (m, 1H), 7.56 (s, 1H), 4.96 (s, 2H), 3.30-3.11 (m, 4H), 3.12-3.04 (m, 1H), 3.03-2.94 (m, 1H), 2.62 (s, 2H), 2.49 (s, 3H), 2.05-1.92 (m, 1H), 1.20 (s, 3H), 1.04 (s, 3H).

Example 121

Synthesis of 3-((7-(6-chloro-4-methyl-3-(2-oxotetrahydropyrimidin-1(2H)-yl)pyridin-2-yl)thieno[3,2-b]pyridin-2-yl)methyl)-6,6-dimethyl-3-azabicyclo[3.1.0]hexane-2,4-dione 2,2,2-trifluoroacetate (121)

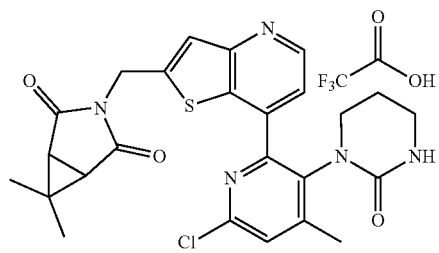

Step 1

Synthesis of 2-bromo-6-chloro-4-methylpyridin-3-amine (121a)

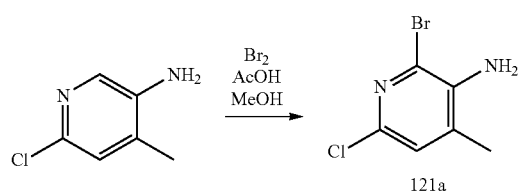

To the solution of 6-chloro-4-methylpyridin-3-amine (1.00 g; 7.01 mmol) in MeOH (10 mL) AcOH (0.80 mL; 14.02 mmol) was added and then the reaction mixture was cooled to 0° C. and then to this mixture a bromine (0.36 mL; 7.01 mmol) was added dropwise and the resulting mixture was stirred at room temperature for 1.5 hours. The reaction progress was monitored by TLC and LC-MS. When analyses indicated almost completion of the reaction, to this mixture 10% $Na_2S_2O_3$ was added and then a whole was stirred for a time necessary to obtain a precipitate. The precipitate was filtered off and dried in oven overnight. The title compound (121a) was obtained in 93% yield (1.43 g; 6.50 mmol).

ESI-MS m/z for $C_6H_7BrClN_2$ found 220.9/222.9 [M+H]$^+$; $R_t$=0.98 min; $^1$H NMR (700 MHz, CDCl$_3$) δ 7.02-6.96 (m, 1H), 4.09 (s, 2H), 2.23 (s, 3H).

Step 2

Synthesis of tert-butyl (3-((2-bromo-6-chloro-4-methylpyridin-3-yl)amino)propyl)carbamate (121b)

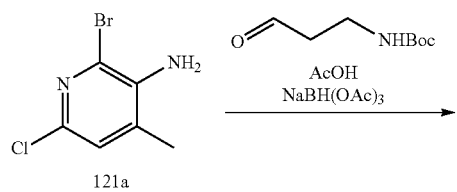

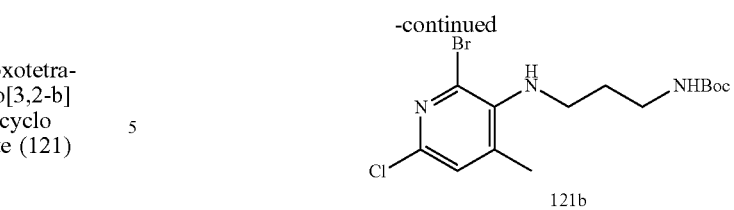

The title compound (121b) was obtained from 121a (154 mg, 0.70 mmol) and from tert-butyl (3-oxopropyl)carbamate (145 mg; 0.84 mmol) according to the General Procedure VIa in 14% yield (37 mg; 0.10 mmol) with the exception that this reaction was carried on only in AcOH (2 mL) without addition of DCE. The crude product was purified by silica-gel column chromatography (hexane/AcOEt, 2:1, v/v) and then by preparative reversed-phase column chromatography (C-18, water/MeCN, 70:30 to 10:90, 30 min, 20 mL/min).

ESI-MS m/z for $C_{14}H_{22}BrClN_3O_2$ found 377.9/379.9[M+H]$^+$; $R_t$=1.57 min

Step 3

Synthesis of tert-butyl (3-((6-chloro-2-(2-((6,6-dimethyl-2,4-dioxo-3-azabicyclo[3.1.0]hexan-3-yl)methyl)thieno[3,2-b]pyridin-7-yl)-4-methylpyridin-3-yl)amino)propyl)carbamate (121c)

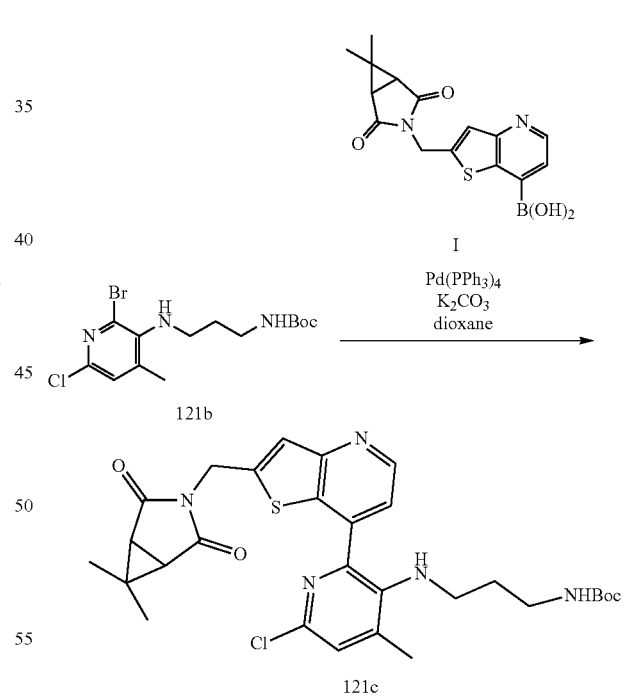

The title compound (121c) was obtained from 121b (33 mg; 0.086 mmol) and from boronic acid I (34 mg; 0.103 mmol) according to the General Procedure Va in 53% yield (27 mg; 0.046 mmol). The crude product was purified by preparative reversed-phase column chromatography (C-18, water/MeCN, 50:50 to 10:90, 30 min, 20 mL/min).

ESI-MS m/z for $C_{29}H_{35}ClN_5O_4S$ found 584.3/586.3 [M+H]$^+$; $R_t$=1.54 min

Step 4

Synthesis of 3-((7-(3-((3-aminopropyl)amino)-6-chloro-4-methylpyridin-2-yl)thieno[3,2-b]pyridin-2-yl)methyl)-6,6-dimethyl-3-azabicyclo[3.1.0]hexane-2,4-dione tetrahydrochloride (121d)

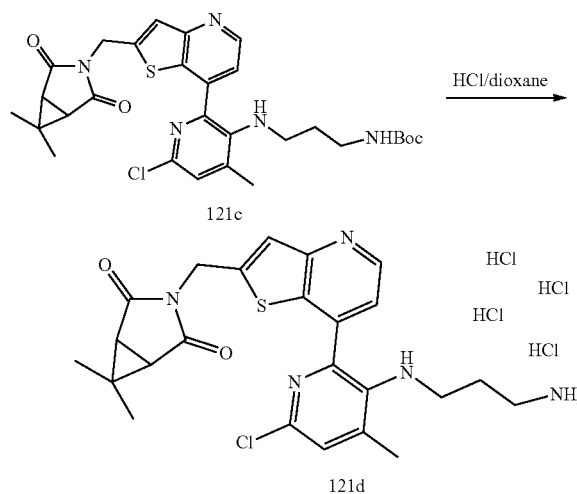

The title compound (121d) was obtained as a tetrahydrochloride salt from 121c (27 mg; 0.046 mmol) according to the General Procedure IVa in 89% yield (26 mg; 0.041 mmol). ESI-MS m/z for $C_{24}H_{27}ClN_5O_2S$ found 484.3/486.3 [M+H]$^+$; $R_t$=0.96 min

Step 5

Synthesis of 3-((7-(6-chloro-4-methyl-3-(2-oxotetrahydropyrimidin-1(2H)-yl)pyridin-2-yl)thieno[3,2-b]pyridin-2-yl)methyl)-6,6-dimethyl-3-azabicyclo[3.1.0]hexane-2,4-dione 2,2,2-trifluoroacetate (121)

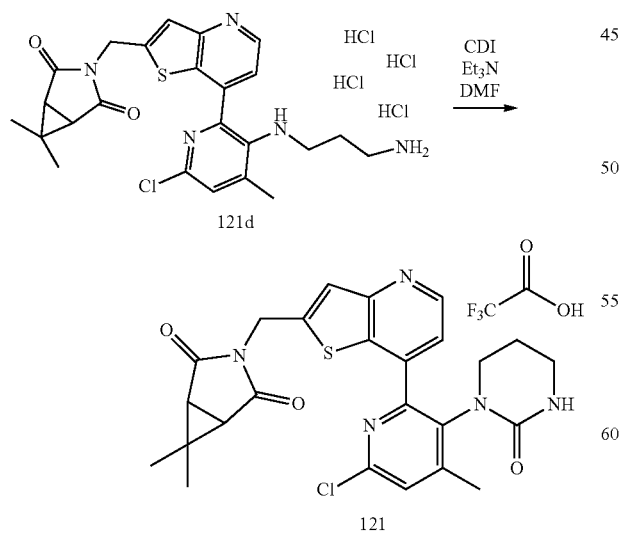

A solution of 121d (26 mg; 0.041 mmol), CDI (10 mg; 0.062 mmol) and Et$_3$N (114 µL; 0.820 mmol) in dry DMF (0.4 mL) was stirred at 85° C. in a sealed vial for 3 hours. The reaction progress was monitored by LC-MS. When analysis indicated completion of the reaction, this mixture was concentrated in vacuo and the crude product was purified by preparative reversed-phase column chromatography (C-18, water+0.4‰ TFA/MeCN+0.4‰ TFA, 75:25 to 45:55, 30 min, 20 mL/min). The title compound (121) was obtained as a TFA salt in 13% yield (5 mg; 0.008 mmol).

ESI-MS m/z for $C_{25}H_{25}CN_5O_3S$ found 510.3/512.3 [M+H]$^+$; $R_t$=1.52 min; $^1$H NMR (700 MHz, Methanol-d$_4$) δ 8.82-8.79 (m, 1H), 7.71-7.68 (m, 1H), 7.65-7.62 (m, 1H), 7.62-7.60 (m, 1H), 4.96-4.89 (m, 2H), 3.38-3.34 (m, 2H), 3.25-3.19 (m, 1H), 2.89-2.84 (m, 1H), 2.52 (s, 2H), 2.41 (s, 3H), 1.93-1.82 (m, 1H), 1.66-1.56 (m, 1H), 1.26 (s, 3H), 1.12 (s, 3H).

Example 122

Synthesis of 3-((7-(3-(azetidin-3-ylamino)-6-chloro-4-methylpyridin-2-yl)thieno[3,2-b]pyridin-2-yl)methyl)-6,6-dimethyl-3-azabicyclo[3.1.0]hexane-2,4-dione tetrahydrochloride (122)

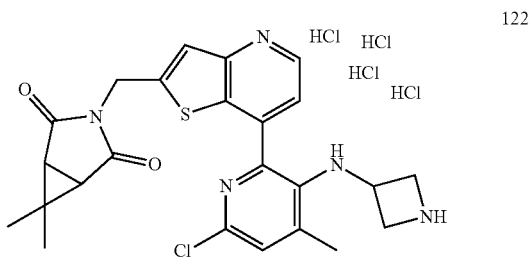 [SMILES: Cl ; Cc1cc(Cl)nc(-c2ccnc3cc(CN4C(=O)C5C(C4=O)C5(C)C)sc23)c1NC1CNC1 ; Cl ; Cl ; Cl]

Step 1

Synthesis of tert-butyl 3-((6-chloro-4-methylpyridin-3-yl)amino)azetidine-1-carboxylate (122a)

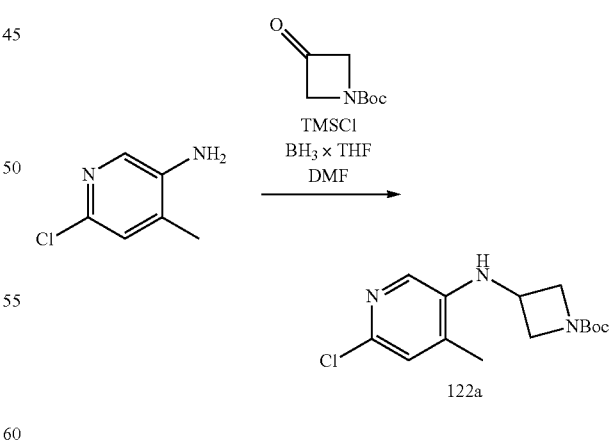

To the solution of 6-chloro-4-methylpyridin-3-amine (212 mg; 1.49 mmol) and tert-butyl 3-oxoazetidine-1-carboxylate (200 mg; 1.17 mmol) in DMF (3.5 mL) under an argon atmosphere TMSCl (0.46 mL; 3.65 mmol) was added and then the reaction mixture was cooled to 0° C. and then to this mixture BH$_3$×THF (1.17 mL; 1.17 mmol) was added dropwise and the resulting mixture was stirred at 0° C. for 1 hour and then at room temperature for 30 minutes. The reaction progress was monitored by TLC and LC-MS. When analyses indicated completion of the reaction, the reaction mixture was cooled to 0° C. and quenched with water and stirred to obtain room temperature. Then this mixture was diluted with water and to this mixture a saturated solution of NaHCO₃ was added and then a whole was extracted with AcOEt (3×). The combined organic solutions were dried over anhydrous Na₂SO₄, filtered and concentrated in vacuo. The crude product was purified by preparative reversed-phase column chromatography (C-18, water/MeCN, 75:25 to 15:85, 30 min, 20 mL/min). The title compound (122a) was obtained in 64% yield (224 mg; 0.75 mmol).

ESI-MS m/z for $C_{14}H_{21}ClN_3O_2$ found 298.2/300.2 [M+H]⁺; $R_t$=1.35 min; ¹H NMR (700 MHz, CDCl₃) δ 7.44 (s, 1H), 7.08-7.04 (m, 1H), 4.39-4.34 (m, 2H), 4.29-4.23 (m, 1H), 3.79-3.75 (m, 3H), 2.19 (s, 3H), 1.47 (s, 9H).

Step 2

Synthesis of tert-butyl 3-((2-bromo-6-chloro-4-methylpyridin-3-yl)amino)azetidine-1-carboxylate (122b)

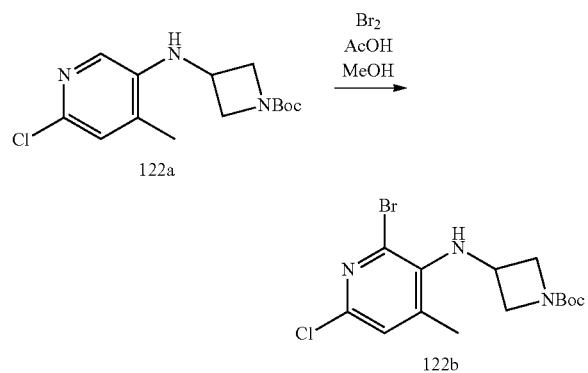

To the solution of 122a (224 mg; 0.75 mmol) in MeOH (2.25 mL) AcOH (86 μL; 1.50 mmol) was added and then the reaction mixture was cooled to 0° C. and then to this mixture a bromine (38 μL; 0.75 mmol) was added dropwise and the resulting mixture was stirred at room temperature overnight. The reaction progress was monitored by TLC and LC-MS. When analyses indicated almost completion of the reaction, to this mixture 10% Na₂S₂O₃ was added and then a whole was stirred for a several minutes. Then this mixture was alkalized by addition of 1 M K₂CO₃. Then MeOH was evaporated in vacuo and the residue was extracted with AcOEt (3×). The combined organic solutions were dried over anhydrous Na₂SO₄, filtered and concentrated in vacuo. The crude product was purified by silica-gel column chromatography (hexane/AcOEt, 100:0 to 70:30, v/v). The title compound (122b) was obtained in 29% yield (82 mg; 0.22 mmol).

ESI-MS m/z for $C_{14}H_{20}BrClN_3O_2$ found 375.9/377.9 [M+H]⁺; $R_t$=1.61 min; ¹H NMR (700 MHz, CDCl₃) δ 7.08-7.06 (m, 1H), 4.27-4.22 (m, 2H), 4.10-4.05 (m, 2H), 3.90-3.85 (m, 2H), 2.30 (s, 3H), 1.47 (s, 9H).

Step 3

Synthesis of tert-butyl 3-((6-chloro-2-(2-((6,6-dimethyl-2,4-dioxo-3-azabicyclo[3.1.0]hexan-3-yl)methyl)thieno[3,2-b]pyridin-7-yl)-4-methylpyridin-3-yl)amino)azetidine-1-carboxylate (122c)

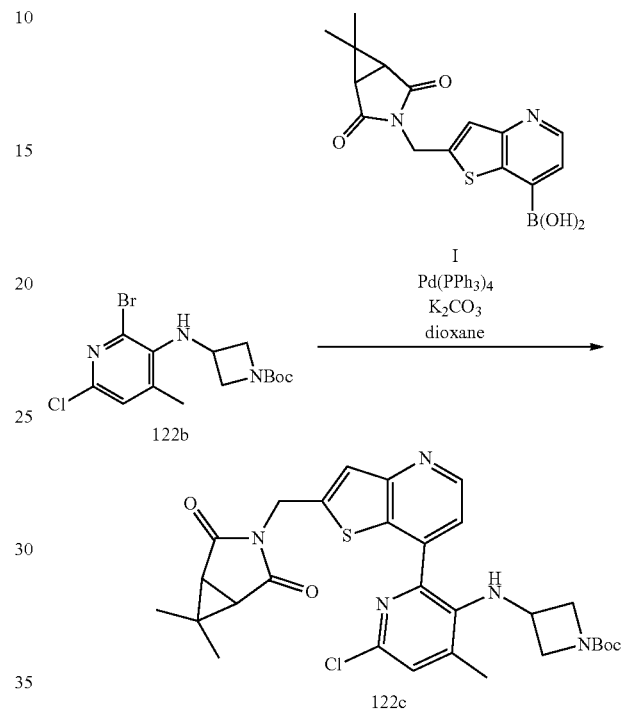

The title compound (122c) was obtained from 122b (82 mg; 0.22 mmol) and from boronic acid I (86 mg; 0.26 mmol) according to the General Procedure Va in 27% yield (36 mg; 0.06 mmol). The crude product was purified by preparative reversed-phase column chromatography (C-18, water/MeCN, 70:30 to 10:90, 30 min, 20 mL/min).

ESI-MS m/z for $C_{29}H_{33}ClN_5O_4S$ found 582.5/584.5 [M+H]⁺; $R_t$=1.57 min

Step 4

Synthesis of 3-((7-(3-(azetidin-3-ylamino)-6-chloro-4-methylpyridin-2-yl)thieno[3,2-b]pyridin-2-yl)methyl)-6,6-dimethyl-3-azabicyclo[3.1.0]hexane-2,4-dione tetrahydrochloride (122)

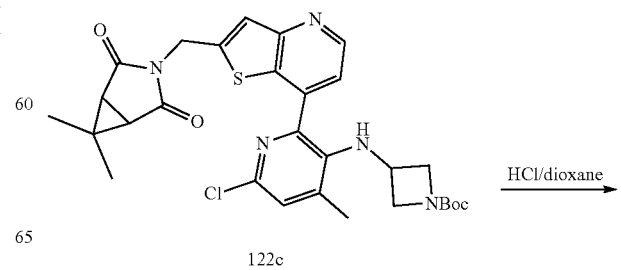

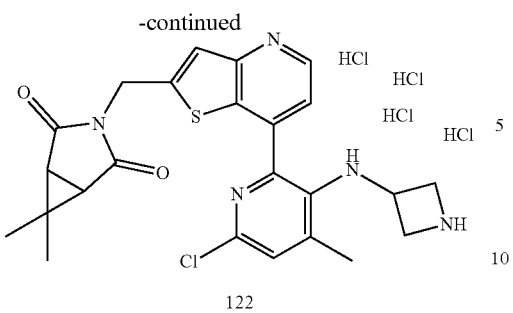

122

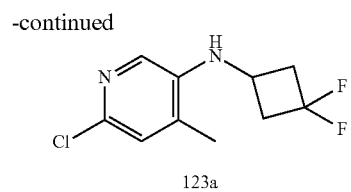

The title compound (122) was obtained as a tetrahydrochloride salt from 122c (36 mg; 0.060 mmol) according to the General Procedure IVa in 18% yield (7 mg; 0.011 mmol). The crude product was purified twice by preparative reversed-phase column chromatography (first: C-18, water/MeCN, 80:20 to 50:50, 30 min, 20 mL/min; second: C-18, water/MeCN, 83:17 to 63:37, 60 min, 20 mL/min).

ESI-MS m/z for $C_{24}H_{25}ClN_5O_2S$ found 482.3/484.3 [M+H]$^+$; $R_t$=0.96 min; $^1$H NMR (700 MHz, Methanol-d$_4$) δ 8.77-8.74 (m, 1H), 7.73-7.69 (m, 1H), 7.57-7.54 (m, 1H), 7.37 (d, J=0.8 Hz, 1H), 4.92-4.86 (m, 2H), 3.91-3.85 (m, 2H), 3.82-3.74 (m, 1H), 3.62-3.52 (m, 2H), 2.52 (s, 2H), 2.42 (d, J=0.8 Hz, 3H), 1.27 (s, 3H), 1.15 (s, 3H).

Example 123

Synthesis of 3-((7-(6-chloro-3-((3,3-difluorocyclobutyl)amino)-4-methylpyridin-2-yl)thieno[3,2-b]pyridin-2-yl)methyl)-6,6-dimethyl-3-azabicyclo[3.1.0]hexane-2,4-dione 2,2,2-trifluoroacetate (123)

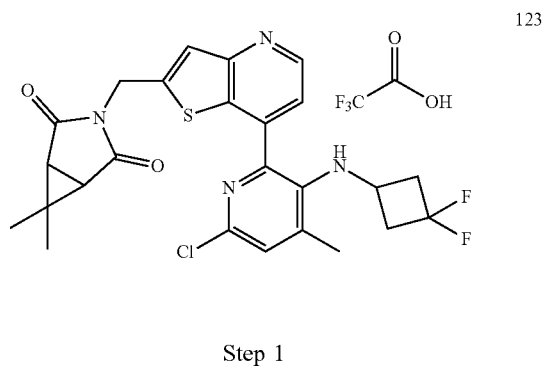

123

Step 1

Synthesis of 6-chloro-N-(3,3-difluorocyclobutyl)-4-methylpyridin-3-amine (123a)

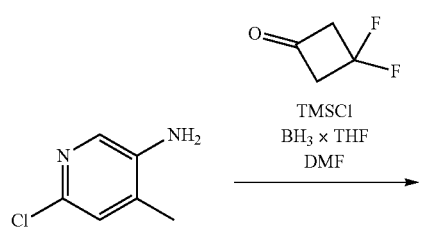

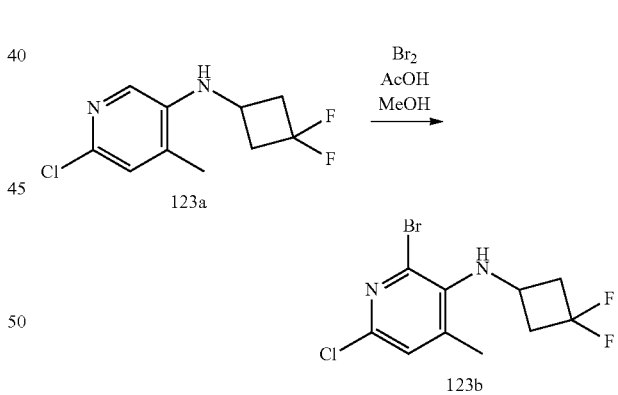

123a

To the solution of 6-chloro-4-methylpyridin-3-amine (130 mg; 0.84 mmol) and 3,3-difluorocyclobutan-1-one (89 mg; 0.84 mmol) in DMF (2.5 mL) under an argon atmosphere TMSCl (0.27 mL; 2.10 mmol) was added and then the reaction mixture was cooled to 0° C. and then to this mixture BH$_3$×THF (0.84 mL; 0.84 mmol) was added dropwise and the resulting mixture was stirred at 0° C. for 30 minutes. The reaction progress was monitored by TLC and LC-MS. When analyses indicated completion of the reaction, the reaction mixture was quenched with water and stirred to obtain room temperature. Then this mixture was diluted with water and next to this mixture a saturated solution of NaHCO$_3$ was added and then a whole was extracted with AcOEt (3×). The combined organic solutions were dried over anhydrous Na$_2$SO$_4$, filtered and concentrated in vacuo. The crude product was purified by silica-gel column chromatography (hexane/AcOEt, 100:0 to 70:30, v/v). The title compound (123a) was obtained in 45% yield (88 mg; 0.38 mmol).

ESI-MS m/z for $C_{10}H_{12}ClF_2N_2$ found 233.1/235.1 [M+H]$^+$; $R_t$=1.26 min; $^1$H NMR (700 MHz, CDCl$_3$) δ 7.54 (s, 1H), 7.06-7.05 (m, 1H), 3.96-3.89 (m, 1H), 3.68-3.59 (m, 1H), 3.17-3.09 (m, 2H), 2.54-2.43 (m, 2H), 2.17 (s, 3H).

Step 2

Synthesis of 2-bromo-6-chloro-N-(3,3-difluorocyclobutyl)-4-methylpyridin-3-amine (122b)

To the solution of 123a (84 mg; 0.36 mmol) in MeOH (0.8 mL) AcOH (41 μL; 0.72 mmol) was added and then the reaction mixture was cooled to 0° C. and then to this mixture a bromine (18 μL; 0.36 mmol) was added dropwise and the resulting mixture was stirred at room temperature for 1.5 hours. The reaction progress was monitored by TLC and LC-MS. When analyses indicated almost completion of the reaction, to this mixture 10% Na$_2$S$_2$O$_3$ was added and then a whole was stirred for a several minutes. Then this mixture was alkalized by addition of 1 M K$_2$CO$_3$. Then MeOH was evaporated n vacuo and the residue was extracted with AcOEt (3×). The combined organic solutions were dried over anhydrous Na$_2$SO$_4$, filtered and concentrated in vacuo.

The crude product was purified by silica-gel column chromatography (hexane/AcOEt, 100:0 to 80:20, v/v). The title compound (123b) was obtained in 55% yield (63 mg; 0.20 mmol).

ESI-MS m/z for $C_{10}H_{11}BrClF_2O_2$ found 310.8/312.8 $[M+H]^+$; $R_t$=1.52 min; $^1H$ NMR (700 MHz, $CDCl_3$) δ 7.08 (s, 1H), 3.89-3.83 (m, 1H), 3.80-3.73 (m, 1H), 3.00-2.93 (m, 2H), 2.60-2.50 (m, 2H), 2.34 (s, 3H), 1.56 (s, 2H).

Step 3

Synthesis of 3-((7-(6-chloro-3-((3,3-difluorocyclobutyl)amino)-4-methylpyridin-2-yl)thieno[3,2-b]pyridin-2-yl)methyl)-6,6-dimethyl-3-azabicyclo[3.1.0]hexane-2,4-dione 2,2,2-trifluoroacetate (123)

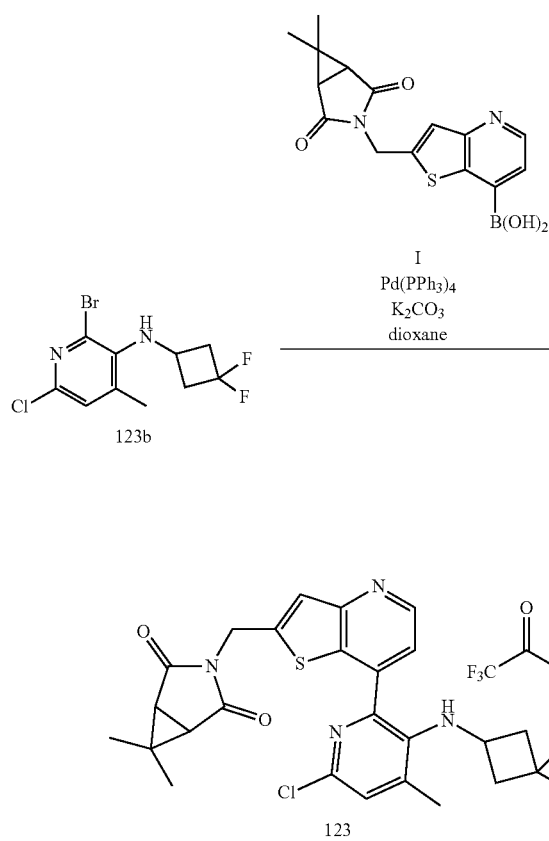

The title compound (123) was obtained as a TFA salt from 123b (63 mg; 0.200 mmol) and from boronic acid I (60 mg; 0.180 mmol) according to the General Procedure Va in 27% yield (30 mg; 0.048 mmol). The crude product was purified by silica-gel column chromatography (hexane/AcOEt, 50:50 to 0:100, v/v) and then by preparative reversed-phase column chromatography (C-18, water+0.4‰ TFA/MeCN+0.4‰ TFA, 70:30 to 30:70, 30 min, 20 mL/min).

ESI-MS m/z for $C_{25}H_{24}ClF_2N_4O_2S$ found 517.4/519.4 $[M+H]^+$; $R_t$=1.50 min; $^1H$ NMR (700 MHz, Methanol-$d_4$) δ 8.81-8.79 (m, 1H), 8.05-8.03 (m, 1H), 7.64-7.62 (m, 1H), 7.40-7.37 (m, 1H), 4.97-4.92 (m, 2H), 3.16-3.11 (m, 1H), 2.52 (s, 2H), 2.43 (s, 3H), 2.43-2.37 (m, 4H), 1.26 (s, 3H), 1.11 (s, 3H).

Example 124

Synthesis of 3-((7-(4,6-dimethyl-3-(pyrrolidin-3-ylamino)pyridin-2-yl)thieno[3,2-b]pyridin-2-yl)methyl)-6,6-dimethyl-3-azabicyclo[3.1.0]hexane-2,4-dione 2,2,2-trifluoroacetate (124)

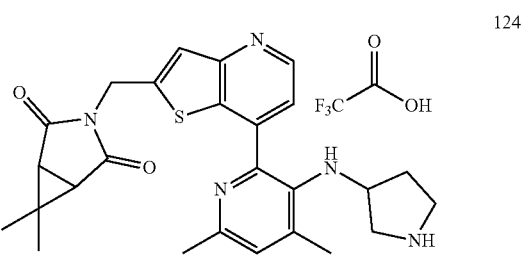

Step 1

Synthesis of tert-butyl 3-((2-bromo-4,6-dimethylpyridin-3-yl)amino)pyrrolidine-1-carboxylate (124a)

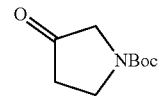

TMSCl
$BH_3 \times THF$
DMF

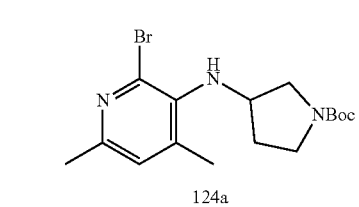

To the solution of 2-bromo-4,6-dimethylpyridin-3-amine (107 mg; 0.53 mmol) and tert-butyl 3-oxopyrrolidine-1-carboxylate (78 mg; 0.42 mmol) in DMF (1.5 mL) under an argon atmosphere TMSCl (0.17 mL; 1.33 mmol) was added and then the reaction mixture was cooled to 0° C. and then to this mixture $BH_3 \times THF$ (0.42 mL; 0.42 mmol) was added dropwise over 10 minutes and the resulting mixture was stirred at 0° C. for 40 minutes. The reaction progress was monitored by TLC and LC-MS. When analyses indicated completion of the reaction, the reaction mixture was quenched with water and stirred to obtain room temperature. Then the reaction mixture was poured into water (11 mL) and alkalized with a saturated solution of $NaHCO_3$ and then extracted with AcOEt (3×). The combined organic solutions were dried over anhydrous $Na_2SO_4$, filtered and concentrated in vacuo. The crude product was purified by preparative reversed-phase column chromatography (C-18, water/MeCN, 60:40 to 10:90, 30 min, 20 mL/min). The title compound (124a) was obtained in 29% yield (46 mg; 0.12 mmol).

ESI-MS m/z for $C_{16}H_{25}BrN_3O_2$ found 369.9/371.9 [M+H]$^+$; R=1.47 min

Step 2

Synthesis of tert-butyl 3-((2-(2-(((6,6-dimethyl-2,4-dioxo-3-azabicyclo[3.1.0]hexan-3-yl)methyl)thieno[3,2-b]pyridin-7-yl)-4,6-dimethylpyridin-3-yl)amino)pyrrolidine-1-carboxylate (124b)

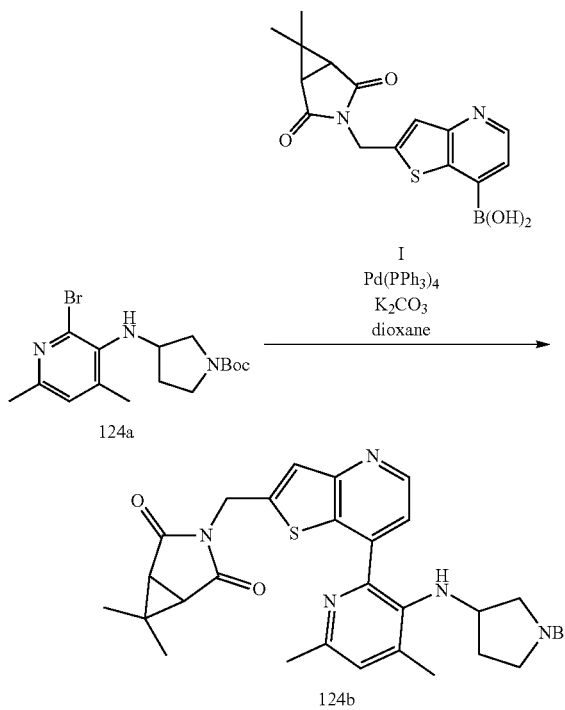

The title compound (124b) was obtained from 124a (46 mg; 0.120 mmol) and from boronic acid I (47 mg; 0.144 mmol) according to the General Procedure Va in 43% yield (30 mg; 0.052 mmol). The crude product was purified by planar liquid chromatography (AcOEt, 100%).

ESI-MS m/z for $C_{31}H_{38}N_5O_4S$ found 576.8 [M+H]$^+$; R$_t$=1.29 min

Step 3

Synthesis of 3-((7-(4,6-dimethyl-3-(pyrrolidin-3-ylamino)pyridin-2-yl)thieno[3,2-b]pyridin-2-yl)methyl)-6,6-dimethyl-3-azabicyclo[3.1.0]hexane-2,4-dione 2,2,2-trifluoroacetate (124)

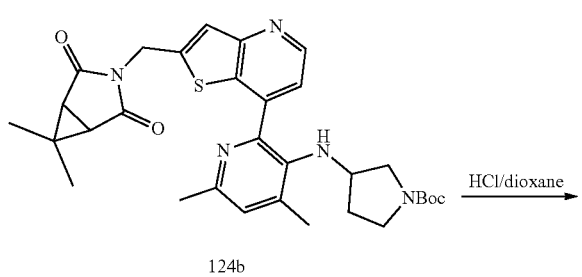

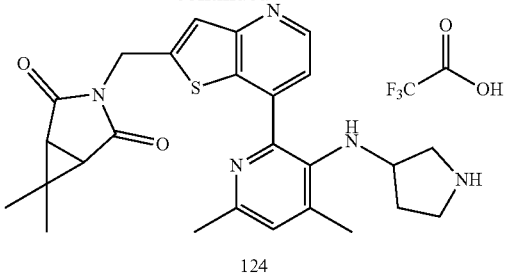

124

The title compound (124) was obtained as a TFA salt as a racemate from 124b (30 mg; 0.052 mmol) according to the General Procedure IVa in 79% yield (24 mg; 0.041 mmol). The crude product was purified twice by preparative reversed-phase column chromatography (C-18, water+0.4% TFA/MeCN+0.4‰ TFA, 85:15 to 60:40, 30 min, 20 mL/min).

ESI-MS m/z for $C_{26}H_{30}N_5O_2S$ found 476.5 [M+H]$^+$; R$_t$=1.21 min; $^1$H NMR (700 MHz, Methanol-d$_4$) δ 8.90-8.86 (m, 1H), 8.03-7.98 (m, 1H), 7.64-7.60 (m, 1H), 7.54 (s, 1H), 4.95-4.89 (m, 2H), 3.47-3.41 (m, 1H), 3.31-3.26 (m, 1H), 3.09-3.03 (m, 1H), 2.97-2.92 (m, 2H), 2.62 (s, 3H), 2.54 (s, 3H), 2.52 (s, 2H), 1.89-1.82 (m, 1H), 1.78-1.70 (m, 1H), 1.26 (s, 3H), 1.13 (s, 3H).

Example 125

Synthesis of 3-((7-(6-chloro-2-methyl-3-(pyrrolidin-3-ylamino)pyridin-4-yl)thieno[3,2-b]pyridin-2-yl)methyl)-6,6-dimethyl-3-azabicyclo[3.1.0]hexane-2,4-dione 2,2,2-trifluoroacetate (125)

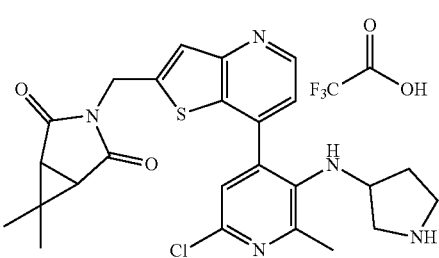

125

The title compound (125) was obtained as a TFA salt as a racemate in 23% overall yield in a similar way to Example 124 with the exception that, in the first step of the synthesis 4-bromo-6-chloro-2-methylpyridin-3-amine was used instead of 2-bromo-4,6-dimethylpyridin-3-amine and in the last step of the synthesis, the crude product was purified by preparative reversed-phase column chromatography (C-18, water+0.4‰ TFA/MeCN+0.4‰ TFA, 85:15 to 50:50, 30 min, 20 mL/min).

ESI-MS m/z for $C_{25}H_{27}ClN_5O_2S$ found 496.4/498.2 [M+H]$^+$; R$_t$=0.93 min; $^1$H NMR (700 MHz, Methanol-d$_4$) δ 9.06-9.01 (m, 1H), 8.07-8.01 (m, 1H), 7.81 (s, 1H), 7.36 (s, 1H), 5.00 (s, 2H), 3.39-3.34 (m, 1H), 3.31-3.27 (m, 1H), 3.11-3.03 (m, 1H), 3.03-2.87 (m, 2H), 2.65 (s, 3H), 2.55 (s, 2H), 1.94-1.82 (m, 1H), 1.79-1.68 (m, 1H), 1.28 (s, 3H), 1.17 (s, 3H).

Example 126

Synthesis of 3-((7-(6-chloro-4-methyl-3-(pyrrolidin-3-ylamino)pyridin-2-yl)thieno[3,2-b]pyridin-2-yl)methyl)-6,6-dimethyl-3-azabicyclo[3.1.0]hexane-2,4-dione tetrahydrochloride (126)

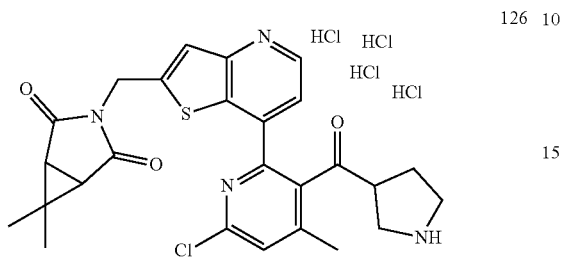

The title compound (126) was obtained as a tetrahydrochloride salt as a racemate in 12% overall yield in a similar way to Example 124 with the exception that, in the first step of the synthesis 2-bromo-6-chloro-4-methylpyridin-3-amine (121a) was used instead of 2-bromo-4,6-dimethylpyridin-3-amine and in the last step of the synthesis, the crude product was purified by preparative reversed-phase column chromatography (C-18, water/MeCN, 99:1 to 20:80, 30 min, 20 mL/min).

ESI-MS m/z for $C_{25}H_{27}ClN_5O_2S$ found 496.4/498.2 [M+H]$^+$; $R_t$=0.93 min; $^1$H NMR (700 MHz, Methanol-d$_4$) δ 8.79-8.74 (m, 1H), 7.95-7.87 (m, 1H), 7.57-7.49 (m, 1H), 7.41-7.34 (m, 1H), 4.91-4.88 (m, 2H), 3.48-3.42 (m, 1H), 3.31-3.25 (m, 1H), 3.07-2.98 (m, 2H), 2.97-2.91 (m, 1H), 2.52 (s, 2H), 2.46 (s, 3H), 1.95-1.86 (m, 1H), 1.80-1.72 (m, 1H), 1.26 (s, 3H), 1.14 (s, 3H).

Example 127

Synthesis of 3-((7-(6-chloro-4-methyl-3-(piperidin-4-ylamino)pyridin-2-yl)thieno[3,2-b]pyridin-2-yl)methyl)-6,6-dimethyl-3-azabicyclo[3.1.0]hexane-2,4-dione tetrahydrochloride (127)

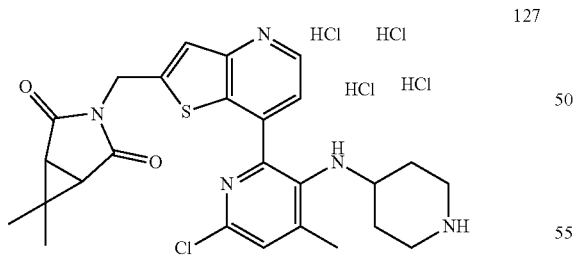

The title compound (127) was obtained as a tetrahydrochloride salt in 15% overall yield in a similar way to Example 124 with the exception that, in the first step of the synthesis 2-bromo-6-chloro-4-methylpyridin-3-amine (121a) and tert-butyl 4-oxopiperidine-1-carboxylate were used instead of 2-bromo-4,6-dimethylpyridin-3-amine and tert-butyl 3-oxopyrrolidine-1-carboxylate, and in the last step of the synthesis, the crude product was purified by preparative reversed-phase column chromatography (C-18, water/MeCN, 80:20 to 40:60, 20 min, 20 mL/min).

ESI-MS m/z for $C_{26}H_{29}ClN_5O_2S$ found 510.4/512.4 [M+H]$^+$; $R_t$=1.00 min; $^1$H NMR (700 MHz, Methanol-d$_4$) δ 8.73-8.70 (m, 1H), 7.96-7.93 (m, 1H), 7.53-7.49 (m, 1H), 7.41-7.37 (m, 1H), 4.89-4.88 (m, 2H), 3.24-3.17 (m, 2H), 2.75-2.68 (m, 1H), 2.63-2.58 (m, 2H), 2.52 (s, 2H), 2.45 (s, 3H), 1.81-1.75 (m, 2H), 1.54-1.45 (m, 2H), 1.26 (s, 3H), 1.14 (s, 3H).

Example 128

Synthesis of 6,6-dimethyl-3-((7-(4-methyl-3-(piperidin-4-ylamino)-6-(trifluoromethyl)pyridin-2-yl)thieno[3,2-b]pyridin-2-yl)methyl)-3-azabicyclo[3.1.0]hexane-2,4-dione tetrahydrochloride (128)

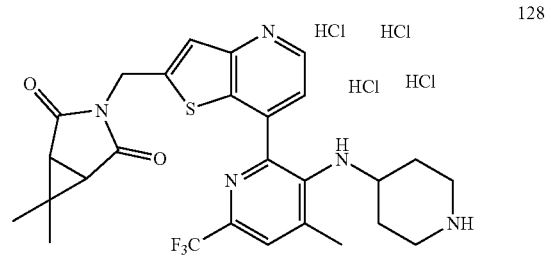 [SMILES: Cl ; Cl ; Cc1cc(C(F)(F)F)nc(-c2ccnc3cc(CN4C(=O)C5C(C4=O)C5(C)C)sc23)c1NC1CCNCC1 ; Cl ; Cl]

The title compound (128) was obtained as a tetrahydrochloride salt in 10% overall yield in a similar way to Example 122 with the exception that, in the first step of the synthesis 4-methyl-6-(trifluoromethyl)pyridin-3-amine and tert-butyl 4-oxopiperidine-1-carboxylate were used instead of 6-chloro-4-methylpyridin-3-amine and tert-butyl 3-oxoazetidine-1-carboxylate, and in the last step of the synthesis, the crude product was purified by preparative reversed-phase column chromatography (C-18, water+0.3‰ HCl (36%)/MeCN+0.3‰ HCl (36%), 90:10 to 40:60, 30 min, 20 mL/min).

ESI-MS m/z for $C_{27}H_{29}F_3N_5O_2S$ found 544.4 [M+H]$^+$; $R_t$=1.02 min; $^1$H NMR (700 MHz, Methanol-d$_4$) δ 8.92-8.89 (m, 1H), 8.61-8.57 (m, 1H), 7.82-7.79 (m, 1H), 7.72-7.69 (m, 1H), 5.02-4.96 (m, 2H), 3.30-3.24 (m, 2H), 3.04-2.93 (m, 1H), 2.79-2.66 (m, 2H), 2.57-2.52 (m, 5H), 1.98-1.90 (m, 2H), 1.75-1.66 (m, 2H), 1.28 (s, 3H), 1.18 (s, 3H); $^{19}$F NMR (235 MHz, Methanol-d$_4$) δ −63.68.

Example 129

Synthesis of 3-((7-(6-chloro-4-methyl-3-(piperidin-3-ylamino)pyridin-2-yl)thieno[3,2-b]pyridin-2-yl)methyl)-6,6-dimethyl-3-azabicyclo[3.1.0]hexane-2,4-dione tetrahydrochloride (129)

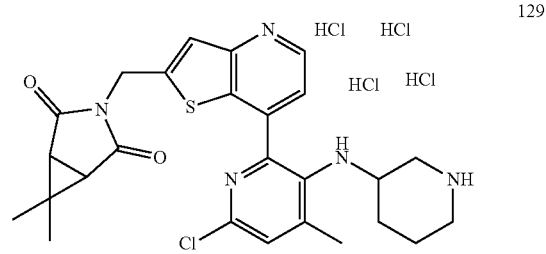 [SMILES: Cl ; Cl ; Cc1cc(Cl)nc(-c2ccnc3cc(CN4C(=O)C5C(C4=O)C5(C)C)sc23)c1NC1CCCNC1 ; Cl ; Cl]

The title compound (129) was obtained as a tetrahydrochloride salt in 12% overall yield in a similar way to Example 124 with the exception that, in the first step of the synthesis 2-bromo-6-chloro-4-methylpyridin-3-amine (121a) and tert-butyl 3-oxopiperidine-1-carboxylate were used instead of 2-bromo-4,6-dimethylpyridin-3-amine and tert-butyl 3-oxopyrrolidine-1-carboxylate, and in the last step of the synthesis, the crude product was purified by preparative reversed-phase column chromatography (C-18, water/MeCN, 90:10 to 30:70, 30 min, 20 mL/min).

ESI-MS m/z for $C_{26}H_{29}ClN_5O_2S$ found 510.1/512.1 [M+H]$^+$; R$_t$=1.05 min; $^1$H NMR (700 MHz, Methanol-d$_4$) δ 8.76-8.73 (m, 1H), 8.03-7.98 (m, 1H), 7.55-7.50 (m, 1H), 7.43-7.38 (m, 1H), 4.89 (d, J=0.9 Hz, 2H), 3.16-3.10 (m, 1H), 3.09-3.04 (m, 1H), 2.84-2.78 (m, 1H), 2.78-2.70 (m, 2H), 2.52 (s, 2H), 2.44 (s, 3H), 1.83-1.77 (m, 2H), 1.42-1.33 (m, 1H), 1.32-1.24 (m, 4H), 1.16 (s, 3H).

Example 130

Synthesis of 6,6-dimethyl-3-((7-(4-methyl-3-(piperidin-3-ylamino)-6-(trifluoromethyl)pyridin-2-yl)thieno[3,2-b]pyridin-2-yl)methyl)-3-azabicyclo[3.1.0]hexane-2,4-dione tetrahydrochloride (130)

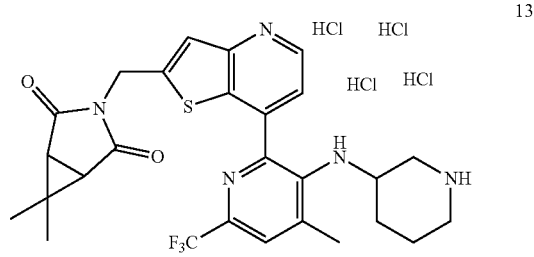

The title compound (130) was obtained as a tetrahydrochloride salt in 1% overall yield in a similar way to Example 122 with the exception that, in the first step of the synthesis 4-methyl-6-(trifluoromethyl)pyridin-3-amine and tert-butyl 3-oxopiperidine-1-carboxylate were used instead of 6-chloro-4-methylpyridin-3-amine and tert-butyl 3-oxoazetidine-1-carboxylate, and in the last step of the synthesis, the crude product was purified by preparative reversed-phase column chromatography (C-18, water+0.3‰ HCl (36%)/MeCN+0.3%0 HCl (36%), 75:25 to 35:65, 30 min, 20 mL/min).

ESI-MS m/z for $C_{27}H_{29}F_3N_5O_2S$ found 544.5 [M+H]$^+$; R$_t$=1.07 min; $^1$H NMR (700 MHz, Methanol-d$_4$) δ 8.92-8.83 (m, 1H), 8.40-8.32 (m, 1H), 7.82-7.75 (m, 1H), 7.68-7.63 (m, 1H), 4.95 (d, J=0.8 Hz, 2H), 3.22-3.12 (m, 2H), 3.08-2.99 (m, 1H), 2.89-2.82 (m, 1H), 2.80-2.73 (m, 1H), 2.57-2.52 (m, 5H), 1.91-1.86 (m, 1H), 1.86-1.79 (m, 1H), 1.54-1.45 (m, 1H), 1.39-1.34 (m, 1H), 1.28 (s, 3H), 1.17 (s, 3H).

Example 131

Synthesis of 3-((7-(3-((2-azaspiro[3.3]heptan-6-yl)amino)-6-chloro-4-methylpyridin-2-yl)thieno[3,2-b]pyridin-2-yl)methyl)-6,6-dimethyl-3-azabicyclo[3.1.0]hexane-2,4-dione hydrobromide (131)

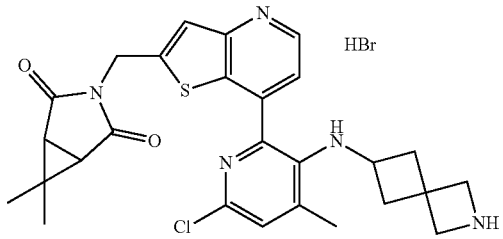

The title compound (131) was obtained as a hydrobromide salt in 3% overall yield in a similar way to Example 124 with the exception that, in the first step of the synthesis 2-bromo-6-chloro-4-methylpyridin-3-amine (121a) and tert-butyl 6-oxo-2-azaspiro[3.3]heptane-2-carboxylate were used instead of 2-bromo-4,6-dimethylpyridin-3-amine and tert-butyl 3-oxopyrrolidine-1-carboxylate, and the last step was different (the synthesis was described below) and in the last step of the synthesis, the crude product was purified by preparative reversed-phase column chromatography (C-18, water/MeCN, 99.9:0.1 to 40:60, 30 min, 20 mL/min).

ESI-MS m/z for $C_{27}H_{29}ClN_5O_2S$ found 522.4/524.4 [M+H]$^+$; R$_t$=1.04 min; $^1$H NMR (700 MHz, Methanol-d$_4$) δ 8.85 (s, 1H), 7.95 (s, 1H), 7.57 (s, 1H), 7.37-7.31 (m, 1H), 4.91 (s, 2H), 3.90 (s, 2H), 3.79 (s, 2H), 3.17-3.10 (m, 1H), 2.53 (s, 2H), 2.40 (s, 3H), 2.25-2.17 (m, 2H), 2.10-2.02 (m, 2H), 1.27 (s, 3H), 1.15 (s, 3H).

The last step of the synthesis:

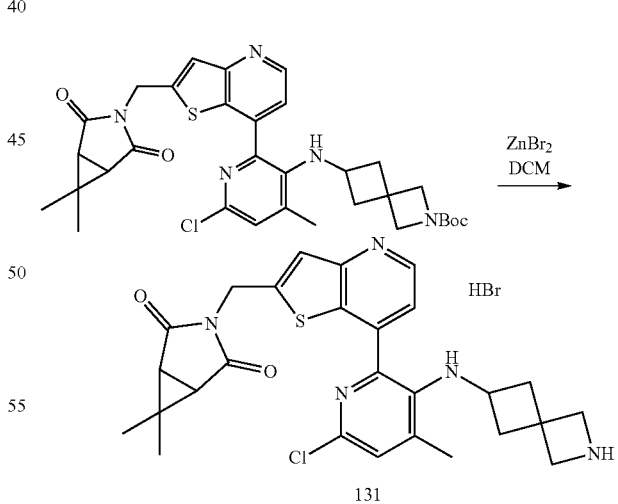

To the solution of tert-butyl 6-((6-chloro-2-(2-((6,6-dimethyl-2,4-dioxo-3-azabicyclo[3.1.0]hexan-3-yl)methyl)thieno[3,2-b]pyridin-7-yl)-4-methylpyridin-3-yl)amino)-2-azaspiro[3.3]heptane-2-carboxylate (61 mg; 0.099 mmol) in dry DCM (0.20 mL) ZnBr$_2$ (44 mg, 0.198 mmol) was added and then the reaction mixture was stirred at room temperature overnight. The reaction progress was monitored by LC-MS. When analysis indicated completion of the reaction, to the reaction mixture water (2.5 mL) and 2 M HCl (49 µL) were added to obtain a precipitate. Then the precipitate was filtered off and the residue was purified by preparative reversed-phase column chromatography. The title compound (131) was obtained as a hydrobromide salt in 8% yield (5 mg; 0.008 mmol).

Example 132

Synthesis of 3-((7-(3-((2-azaspiro[3.3]heptan-6-yl)amino)-4-methyl-6-(trifluoromethyl)pyridin-2-yl)thieno[3,2-b]pyridin-2-yl)methyl)-6,6-dimethyl-3-azabicyclo[3.1.0]hexane-2,4-dione 2,2,2-trifluoroacetate (132)

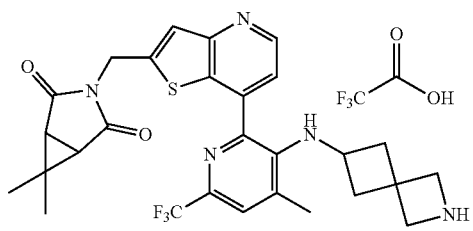

132

The title compound (132) was obtained as a TFA salt in 2% overall yield in a similar way to Example 122 with the exception that, in the first step of the synthesis 4-methyl-6-(trifluoromethyl)pyridin-3-amine and tert-butyl 6-oxo-2-azaspiro[3.3]heptane-2-carboxylate were used instead of 6-chloro-4-methylpyridin-3-amine and tert-butyl 3-oxoazetidine-1-carboxylate, and in the last step of the synthesis, the General Procedure IVb was used instead of the General Procedure IVa and the crude product was purified by preparative reversed-phase column chromatography (C-18, water+0.4‰ TFA/MeCN+0.4‰ TFA, 75:25 to 45:55, 30 min, 20 mL/min).

ESI-MS m/z for $C_{28}H_{29}F_3N_5O_2S$ found 556.2 [M+H]$^+$; R$_t$=1.07 min; $^1$H NMR (700 MHz, Methanol-d$_4$) δ 8.74 (s, 1H), 7.85-7.83 (m, 1H), 7.65-7.62 (m, 1H), 7.57-7.54 (m, 1H), 4.91-4.89 (m, 2H), 3.90 (s, 2H), 3.77 (s, 2H), 3.25-3.19 (m, 1H), 2.52 (s, 2H), 2.46 (s, 3H), 2.23-2.17 (m, 2H), 2.16-2.08 (m, 2H), 1.27 (s, 3H), 1.14 (s, 3H).

Example 133

Synthesis of N-(2-(2-(((6,6-dimethyl-2,4-dioxo-3-azabicyclo[3.1.0]hexan-3-yl)methyl)thieno[3,2-b]pyridin-7-yl)-4,6-dimethylpyridin-3-yl)azetidine-3-carboxamide 2,2,2-trifluoroacetate (133)

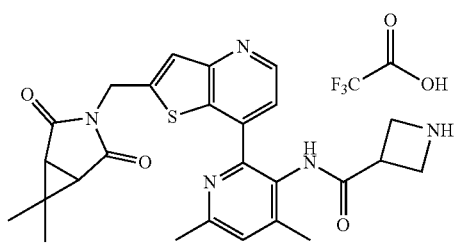

133

Step 1

Synthesis of 3-((7-(3-amino-4,6-dimethylpyridin-2-yl)thieno[3,2-b]pyridin-2-yl)methyl)-6,6-dimethyl-3-azabicyclo[3.1.0]hexane-2,4-dione (133a)

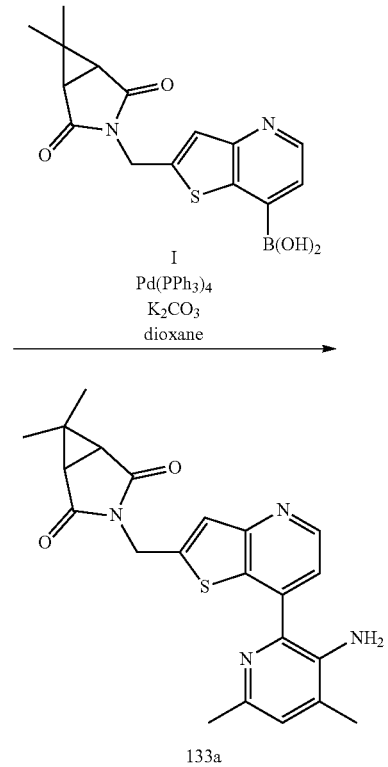

133a

The title compound (133a) was obtained from 2-bromo-4,6-dimethylpyridin-3-amine (194 mg; 0.960 mmol) and from boronic acid I (150 mg; 0.450 mmol) according to the General Procedure Va in 23% yield (43 mg; 0.106 mmol). The crude product was purified by silica-gel column chromatography (hexane/AcOEt, 70:30 to 0:100, v/v, then: AcOEt/MeOH, 99:1 to 90:10, v/v).

ESI-MS m/z for $C_{22}H_{23}N_4O_2S$ found 407.8 [M+H]$^+$; R$_t$=0.81 min

Step 2

Synthesis of tert-butyl 3-((2-(2-(((6,6-dimethyl-2,4-dioxo-3-azabicyclo[3.1.0]hexan-3-yl)methyl)thieno[3,2-b]pyridin-7-yl)-4,6-dimethylpyridin-3-yl)carbamoyl)azetidine-1-carboxylate (133b)

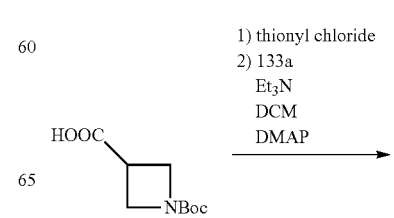

445

-continued

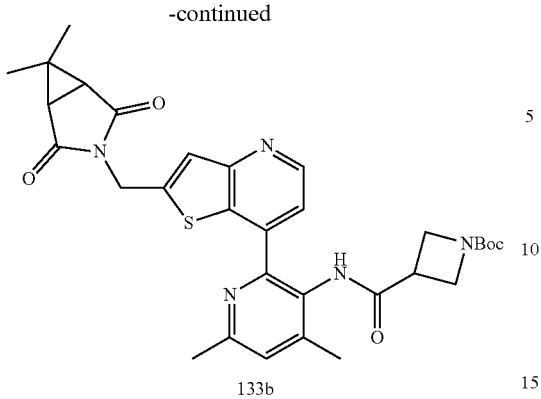

133b

The title compound (133b) was obtained from 1-(tert-butoxycarbonyl)azetidine-3-carboxylic acid (66 mg; 0.330 mmol) and from the amine 133a (43 mg; 0.106 mmol) according to the General Procedure II in 90% yield (56 mg; 0.095 mmol).

ESI-MS m/z for $C_{31}H_{36}N_5O_5S$ found 590.6 [M+H]$^+$, R=1.28 min

Step 3

Synthesis of N-(2-(2-(((6,6-dimethyl-2,4-dioxo-3-azabicyclo[3.1.0]hexan-3-yl)methyl)thieno[3,2-b]pyridin-7-yl)-4,6-dimethylpyridin-3-yl)azetidine-3-carboxamide 2,2,2-trifluoroacetate (133)

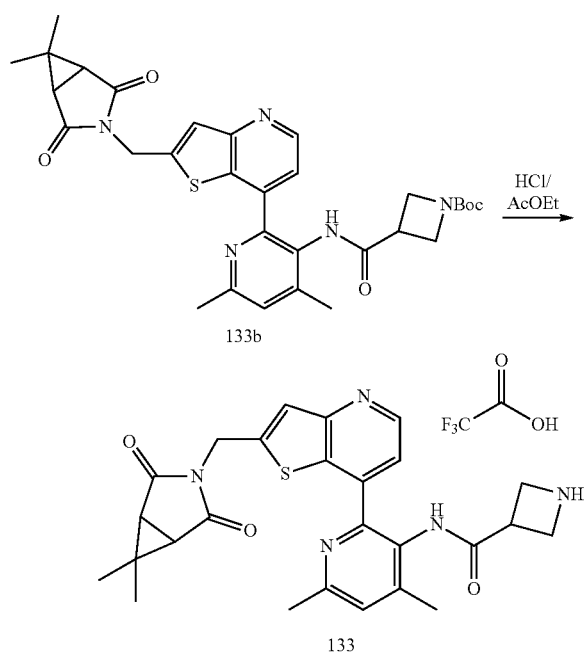

133

The title compound (133) was obtained as a TFA salt from 133b (56 mg; 0.095 mmol) according to the General Procedure IVa in 2% yield (1 mg; 0.002 mmol). The crude product was purified by preparative reversed-phase column chromatography (column: Cosmosil Cholester 20×250 mm, water+0.4‰ TFA/MeCN+0.4‰ TFA, 80:20 to 60:40, 30 min, 40 mL/min).

446

ESI-MS m/z for $C_{26}H_{28}N_5O_3S$ found 490.6 [M+H]$^+$; R$_t$=0.78 min; $^1$H NMR (700 MHz, D$_2$O) δ 8.83-8.79 (m, 1H), 7.74-7.69 (m, 2H), 7.63 (s, 1H), 4.98-4.93 (m, 2H), 4.12-4.05 (m, 2H), 3.82-3.68 (m, 3H), 2.65-2.55 (m, 5H), 2.36 (s, 3H), 1.20 (s, 3H), 1.04 (s, 3H).

Example 134

Synthesis of N-(2-(2-(((6,6-dimethyl-2,4-dioxo-3-azabicyclo[3.1.0]hexan-3-yl)methyl)thieno[3,2-b]pyridin-7-yl)-4,6-dimethylpyridin-3-yl)piperidine-4-carboxamide 2,2,2-trifluoroacetate (134)

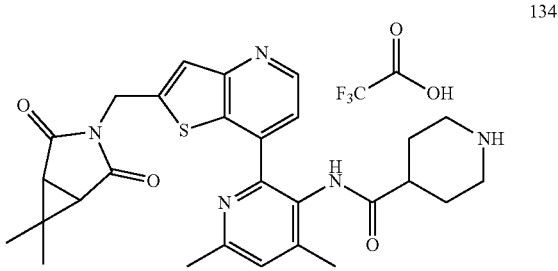

134

Step 1

Synthesis of benzyl 4-((2-bromo-4,6-dimethylpyridin-3-yl)carbamoyl)piperidine-1-carboxylate (134a)

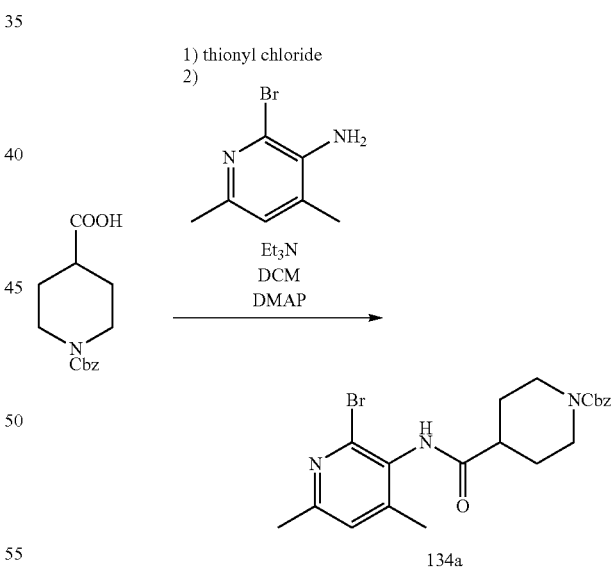

134a

The title compound (134a) was obtained from 1-((benzyloxy)carbonyl)piperidine-4-carboxylic acid (671 mg; 2.55 mmol) and from 2-bromo-4,6-dimethylpyridin-3-amine (170 mg; 0.85 mmol) according to the General Procedure II in 18% yield (65 mg; 0.15 mmol). The crude product was purified by silica-gel column chromatography (hexane/AcOEt, 70:30 to 10:90, v/v).

ESI-MS m/z for $C_{21}H_{25}BrN_3O_3$ found 445.9/447.9 [M+H]$^+$; R$_t$=1.30 min; $^1$H NMR (700 MHz, CDCl$_3$) δ 7.42-7.26 (m, 5H), 6.97 (s, 1H), 5.17 (s, 2H), 4.37-4.20 (m, 2H), 3.06-2.92 (m, 2H), 2.64-2.54 (m, 1H), 2.51 (s, 3H), 2.25 (s, 3H), 2.09-2.0) (m, 2H), 1.89-1.81 (m, 2H).

Step 2

Synthesis of benzyl 4-((2-(2-((6,6-dimethyl-2,4-dioxo-3-azabicyclo[3.1.0]hexan-3-yl)methyl)thieno[3,2-b]pyridin-7-yl)-4,6-dimethylpyridin-3-yl)carbamoyl)piperidine-1-carboxylate (134b)

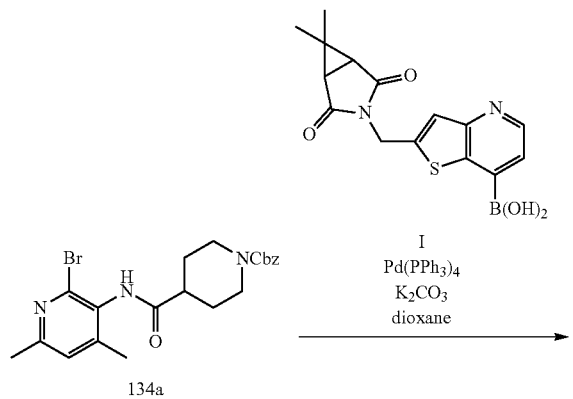

The title compound (134b) was obtained from 134a (65 mg; 0.15 mmol) and from boronic acid I (59 mg; 0.18 mmol) according to the General Procedure Va in 40% yield (40 mg; 0.06 mmol). The crude product was purified by silica-gel column chromatography (AcOEt/MeOH, 100:0 to 92.5:7.5, v/v).

ESI-MS m/z for $C_{36}H_{38}N_5O_5S$ found 652.9 [M+H]$^+$; $R_t$=1.35 min

Step 3

Synthesis of N-(2-(2-((6,6-dimethyl-2,4-dioxo-3-azabicyclo[3.1.0]hexan-3-yl)methyl)thieno[3,2-b]pyridin-7-yl)-4,6-dimethylpyridin-3-yl)piperidine-4-carboxamide 2,2,2-trifluoroacetate (134)

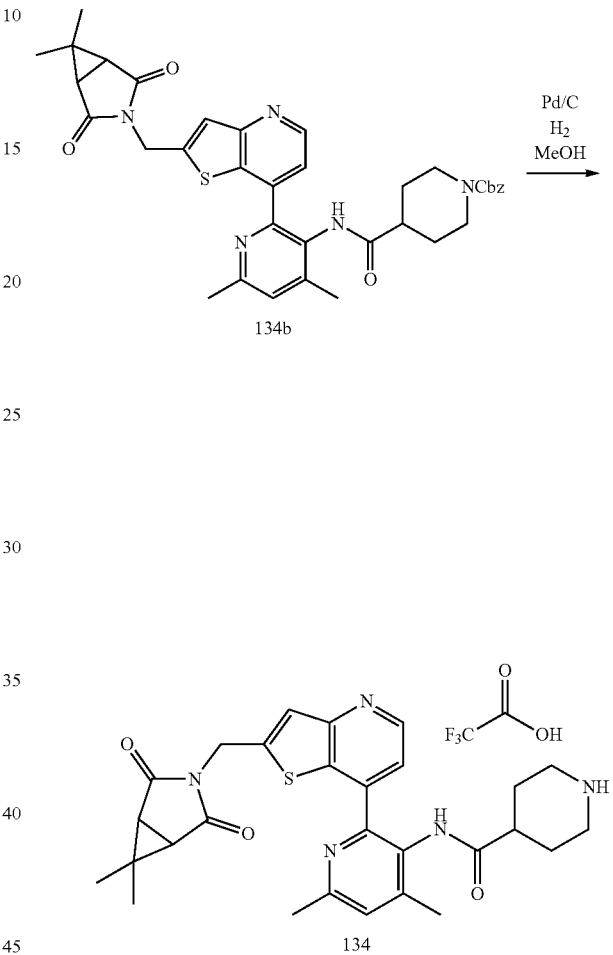

To the solution of 134b (40 mg; 0.06 mmol) in MeOH (0.25 mL) under argon atmosphere Pd/C (10 mol %; cat.) was added. Then argon was replaced by hydrogen and the reaction mixture was conducted under hydrogen atmosphere at room temperature overnight. The reaction progress was monitored by LC-MS. When analysis indicated completion of the reaction, Pd/C was filtered off through a Celite pad and the solvent was evaporated in vacuo. The crude product was purified by preparative reversed-phase column chromatography (C-18, water+0.4‰ TFA/MeCN+0.4‰ TFA, 85:15 to 55:45, 30 min, 20 mL/min). The title compound (134) was obtained as a TFA salt in 50% yield (19 mg; 0.03 mmol).

ESI-MS m/z for $C_{28}H_{32}N_5O_3S$ found 518.4 [M+H]$^+$; $R_t$=0.75 min; $^1$H NMR (700 MHz, Methanol-d$_4$) δ 8.75-8.71 (m, 1H), 7.59-7.53 (m, 2H), 7.48-7.45 (m, 1H), 4.91-4.88 (m, 2H), 3.56-3.49 (m, 1H), 3.38-3.34 (m, 1H), 3.02-2.95 (m, 2H), 2.67-2.59 (m, 4H), 2.54-2.50 (m, 2H), 2.37 (s, 2H), 1.91-1.82 (m, 2H), 1.72-1.63 (m, 2H), 1.26 (s, 3H), 1.13 (s, 3H).

Example 135

Synthesis of 3-((7-(6-chloro-4-methyl-3-(piperazine-1-carbonyl)pyridin-2-yl)thieno[3,2-b]pyridin-2-yl)methyl)-6,6-dimethyl-3-azabicyclo[3.1.0]hexane-2,4-dione 2,2,2-trifluoroacetate (135)

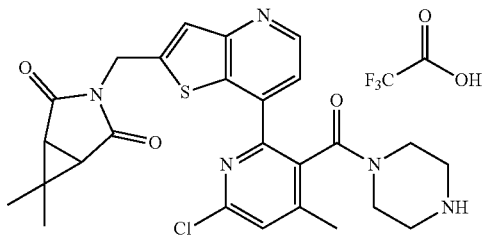

Step 1

Synthesis of 2-bromo-3-(ethoxycarbonyl)-4-methylpyridine 1-oxide (135a)

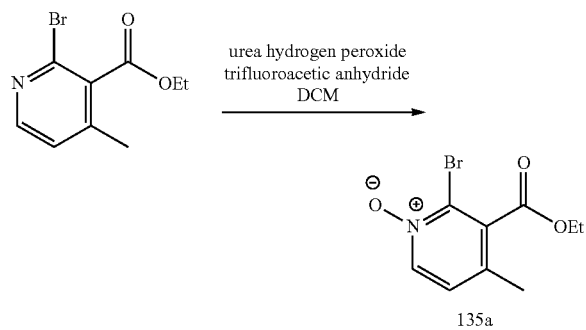

To the solution of ethyl 2-bromo-4-methylnicotinate (5.00 g; 20.48 mmol) in DCM (150 mL) urea hydrogen peroxide (9.63 g; 102.40 mmol) was added at room temperature. Then the reaction mixture was cooled to 0° C. and to this mixture trifluoroacetic anhydride (11.40 mL; 81.92 mmol) was added dropwise and the whole was stirred at room temperature for 1 hour. The reaction progress was monitored by TLC. When analysis indicated completion of the reaction, 5% NaHCO$_3$ (150 mL) was carefully added and this mixture was stirred for a while. The layers were separated and an aqueous one was carefully alkalized by solid K$_2$CO$_3$ and then extracted with DCM (3×). The combined organic solutions were washed with brine and dried over anhydrous Na$_2$SO$_4$, filtered and concentrated in vacuo. The title compound (135a) was obtained in 99% yield (5.25 g; 20.27 mmol).

ESI-MS m/z for C$_9$H$_{11}$BrNO$_3$ found 259.9/261.9 [M+H]$^+$; R$_t$=0.68 min; $^1$H NMR (700 MHz, CDCl$_3$) δ 8.36-8.31 (m, 1H), 7.14-7.10 (m, 1H), 4.50 (q, J=7.2 Hz, 2H), 2.36 (s, 3H), 1.45 (t, J=7.2 Hz, 3H).

Step 2

Synthesis of ethyl 2-bromo-6-chloro-4-methylnicotinate (135b)

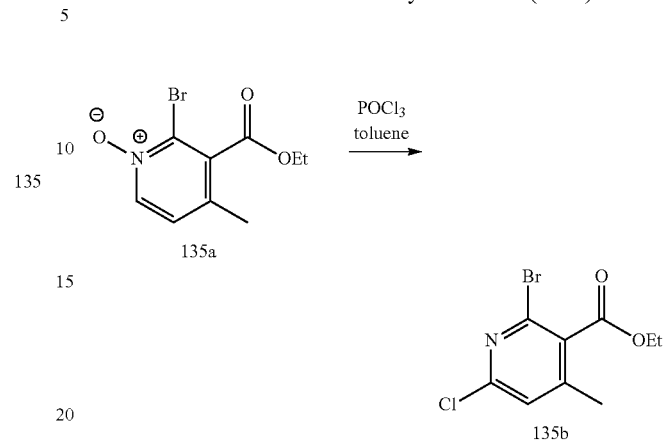

To the cooled to 0° C. solution of 135a (1.85 g; 7.14 mmol) in anhydrous toluene (50 mL) POCl$_3$ (13 mL; 139.50 mmol) was added dropwise and the resulting mixture was allowed to warm to room temperature and then it was stirred at 120° C. for 3 hours. The reaction progress was monitored by TLC. When analysis indicated completion of the reaction, the reaction mixture was cooled to room temperature and to this mixture an ice was added. When an ice had melt, the mixture was alkalized to pH 8 by addition of solid K$_2$CO$_3$ and then extracted with AcOEt (3×). The combined organic solutions were dried over anhydrous Na$_2$SO$_4$, filtered and concentrated in vacuo. The crude product was purified by silica-gel column chromatography (hexane/AcOEt, 100:0 to 92:8, v/v). The title compound (135b) was obtained in 41% yield (0.82 g; 2.96 mmol).

ESI-MS m/z for C$_9$H$_{10}$BrClNO$_2$ found 277.8/279.8 [M+H]$^+$; R$_t$=1.46 min; $^1$H NMR (700 MHz, CDCl$_3$) δ 8.51 (s, 1H), 4.49 (q, J=7.1 Hz, 2H), 2.42 (s, 3H), 1.44 (t, J=7.1 Hz, 3H).

Step 3

Synthesis of 2-bromo-6-chloro-4-methylnicotinic acid (135c)

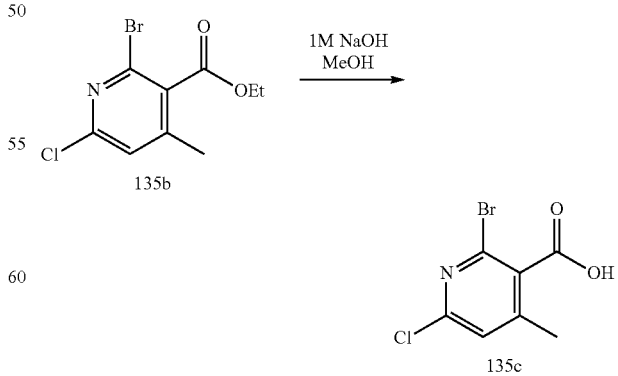

To the solution of 135b (648 mg; 2.33 mmol) in MeOH (6 mL) 1 M NaOH (9.32 mL; 9.32 mmol) was added and the resulting mixture was stirred at room temperature overnight. Then another portions of 1 M NaOH (3×2 mL) were added and stirred for 2 days. The reaction progress was monitored by LC-MS. When analysis indicated almost completion of the reaction, MeOH was evaporated and the residue was neutralized to pH 7 and this solution was cooled in acetone/dry ice bath and lyophilized. Then the product was extracted with 2-propanol (3×) from the precipitate. The combined organic solutions were concentrated in vacuo. The crude product was purified by silica-gel column chromatography (AcOEt/MeOH, 70:30 to 50:50, v/v). The title compound (135c) was obtained in 61% yield (357 mg; 1.43 mmol).

ESI-MS m/z for $C_7H_6BrClNO_2$ found 249.9/251.9 $[M+H]^+$; $R_t$=0.56 min

Step 4

Synthesis of tert-butyl 4-(2-bromo-6-chloro-4-methylnicotinoyl)piperazine-1-carboxylate (135d)

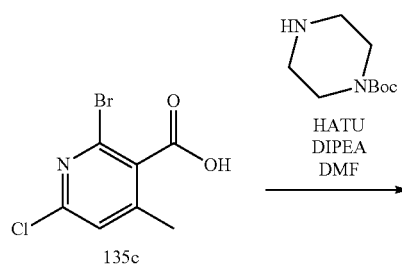

Step 5

Synthesis of tert-butyl 4-(6-chloro-2-(2-(((6,6-dimethyl-2,4-dioxo-3-azabicyclo[3.1.0]hexan-3-yl)methyl)thieno[3,2-b]pyridin-7-yl)-4-methylnicotinoyl)piperazine-1-carboxylate (135e)

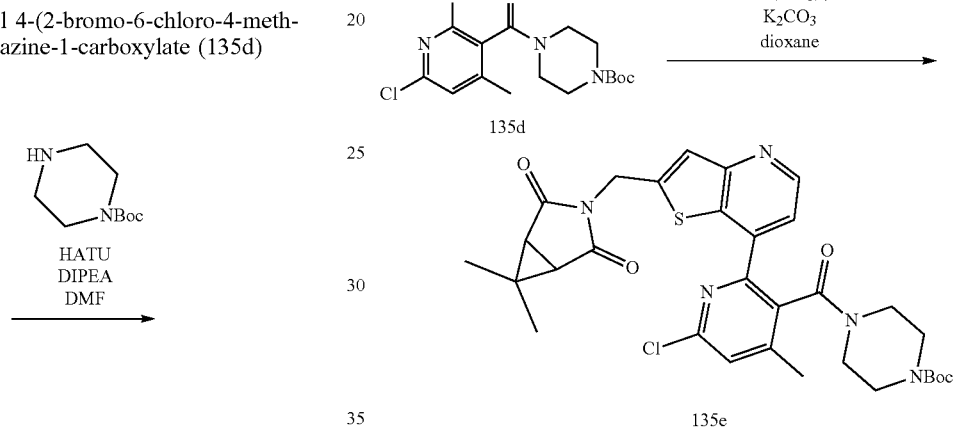

The title compound (135e) was obtained from 135d (217 mg; 0.52 mmol) and from boronic acid I (172 mg; 0.52 mmol) according to the General Procedure Va in 10% yield (30 mg; 0.05 mmol). The crude product was purified by silica-gel column chromatography (hexane/AcOEt, 100:0 to 40:60, v/v) and then by preparative reversed-phase column chromatography (C-18, water/MeCN, 70:30 to 20:80, 30 min, 20 mL/min).

ESI-MS m/z for $C_{31}H_{35}ClN_5O_5S$ found 624.4/626.4 $[M+H]^+$; $R_t$=1.72 min Step 6

Synthesis of 3-((7-(6-chloro-4-methyl-3-(piperazine-1-carbonyl)pyridin-2-yl)thieno[3,2-b]pyridin-2-yl)methyl)-6,6-dimethyl-3-azabicyclo[3.1.0]hexan-2,4-dione 2,2,2-trifluoroacetate (135)

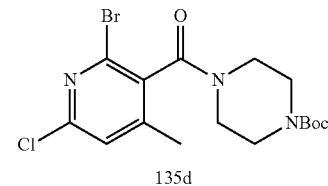

The title compound (135d) was obtained from 135c (197 mg; 0.79 mmol) and from tert-butyl piperazine-1-carboxylate (531 mg; 2.85 mmol) according to the General Procedure I in 66% yield (217 mg; 0.52 mmol).

ESI-MS m/z for $C_{12}H_{14}BrClN_3O_3$ found 361.8/363.8 $[M+H-tBu]^+$; $R_t$=1.58 min

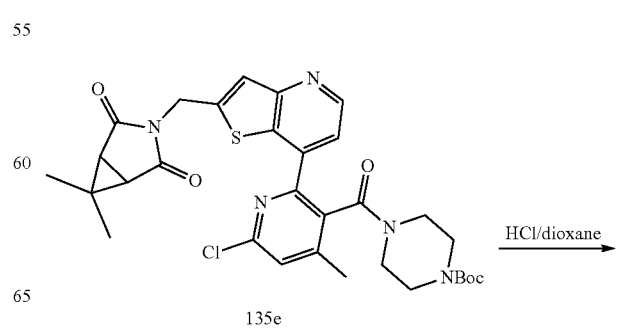

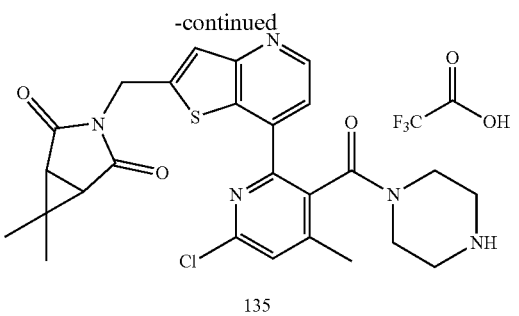

135

The title compound (135) was obtained as a TFA salt from 135e (32 mg; 0.051 mmol) according to the General Procedure IVa in 4% yield (1 mg; 0.002 mmol). The crude product was purified by preparative reversed-phase column chromatography (Cosmosil Cholester 20×250 mm, water+ 0.4‰ TFA/MeCN+0.4‰ TFA, 80:20 to 50:50, 30 min, 20 mL/min).

ESI-MS m/z for $C_{26}H_{27}ClN_5O_3S$ found 524.2/526.2 $[M+H]^+$; $R_t$=1.21 min

Example 136

Synthesis of 1-((3S)-1-(2-(2-((6,6-dimethyl-2,4-dioxo-3-azabicyclo[3.1.0]hexan-3-yl)methyl)thieno[3,2-b]pyridin-7-yl)-4-methyl-6-(trifluoromethyl)nicotinoyl)pyrrolidin-3-yl)urea dihydrochloride (136)

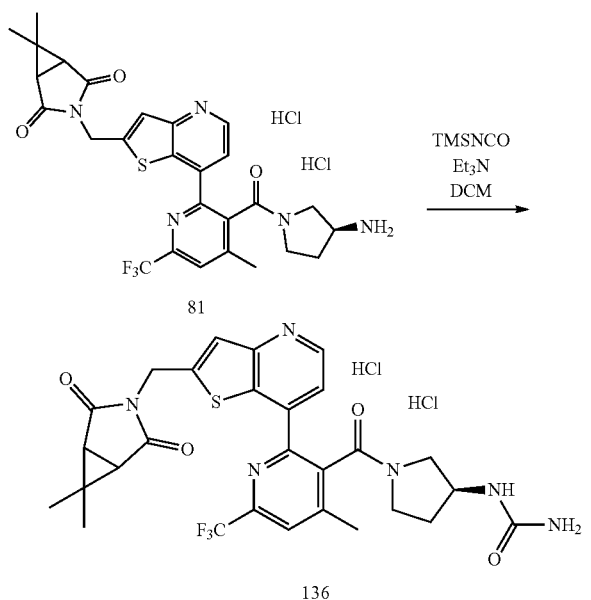

To a stirred solution of 81 (28 mg; 0.045 mmol) in DCM (0.25 mL) TMSNCO (18 µL; 0.135 mmol) and Et₃N (25 µL; 0.180 mmol) were added and the resulting mixture was stirred at room temperature for 2 hours. The reaction progress was monitored by LC-MS. When analysis indicated completion of the reaction, the mixture was cooled to 0° C. and quenched with MeOH. The cooling bath was removed and this mixture was stirred to allow to room temperature. Then the solvents were evaporated under reduced pressure. To the residue 1 M HCl (1.5 mL) was added and a whole was washed with AcOEt (2×), the aqueous phase was then purified twice by preparative reversed-phase column chromatography (first: C-18, water+0.3‰ HCl (36%)/MeCN+ 0.3‰ HCl (36%), 75:25 to 35:65, 30 min, 20 mL/min; second: C-18, water+0.3‰ HCl (36%)/MeCN+0.3‰ HCl (36%), 70:30 to 40:60, 30 min, 20 mL/min). The title compound (136) was obtained as a dihydrochloride salt in 1% yield (4 mg, 0.006 mmol).

ESI-MS m/z for $C_{28}H_{28}F_3N_6O_4S$ found 601.0 $[M+H]^+$; $R_t$=1.28 min; $^1$H NMR (700 MHz, Methanol-d₄) δ 8.88-8.80 (m, 1H), 8.06-8.01 (m, 1H), 7.88-7.81 (m, 1H), 7.66-7.58 (m, 1H), 4.97-4.89 (m, 2H), 4.20-2.63 (m, 7H), 2.58-2.51 (m, 3H), 2.22-1.65 (m, 2H), 1.42-1.08 (m, 6H).

Example 137

Synthesis of 3-((7-(3-(3-amino-3-methylpyrrolidine-1-carbonyl)-4-methyl-6-(trifluoromethyl)pyridin-2-yl)thieno[3,2-b]pyridin-2-yl)methyl)-6,6-dimethyl-3-azabicyclo[3.1.0]hexane-2,4-dione trihydrochloride (137)

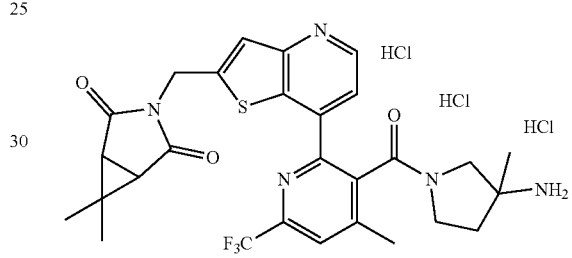

Step 1

Synthesis of tert-butyl (1-(2-chloro-4-methyl-6-(trifluoromethyl)nicotinoyl)-3-methylpyrrolidin-3-yl)carbamate 2,2,2-trifluoroacetate (137a)

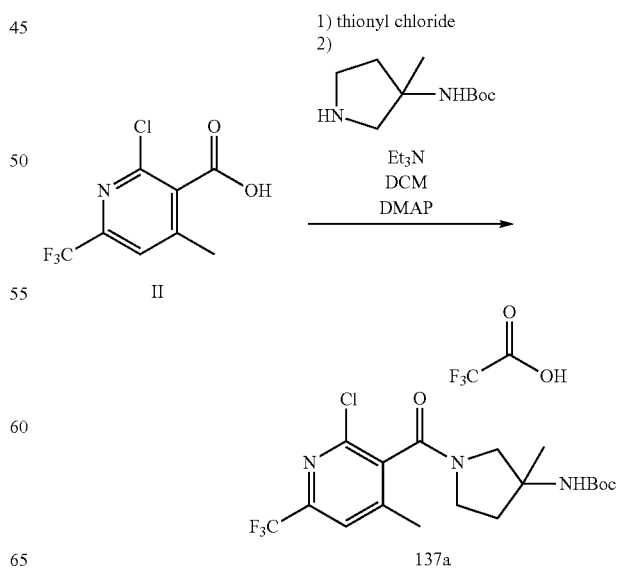

The title compound (137a) was obtained as a TFA salt from an acid II (99 mg; 0.41 mmol) and from tert-butyl (3-methylpyrrolidin-3-yl)carbamate (124 mg; 0.62 mmol) according to the General Procedure 11 in 37% yield (79 mg; 0.15 mmol). The crude product was purified by silica-gel column chromatography (hexane/AcOEt, 100:0 to 20:80, v/v) and then by preparative reversed-phase column chromatography (C-18, water/MeCN+1‰ TFA, 70:30 to 30:70, 30 min, 20 mL/min).

ESI-MS m/z for $C_{14}H_{16}ClF_3N_3O_3$ found 365.9/367.9 [M+H-tBu]$^+$; $R_t$=1.59 min; $^1$H NMR (700 MHz, Methanol-$d_4$) δ 7.88-7.77 (m, 1H), 4.34-3.67 (m, 2H), 3.51-3.35 (m, 1H), 3.29-3.10 (m, 1H), 2.49-2.36 (m, 3H), 2.33-1.94 (m, 2H), 1.53-1.35 (n, 12H).

Step 2

Synthesis of tert-butyl (1-(2-(2-((6,6-dimethyl-2,4-dioxo-3-azabicyclo[3.1.0]hexan-3-yl)methyl)thieno[3,2-b]pyridin-7-yl)-4-methyl-6-(trifluoromethyl)nicotinoyl)-3-methylpyrrolidin-3-yl)carbamate (137b)

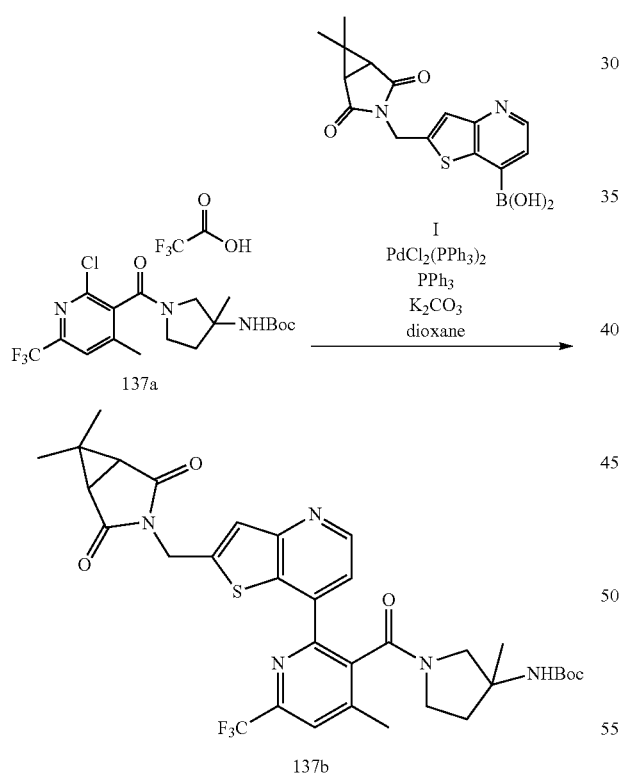

The title compound (137b) was obtained from 137a (75 mg; 0.14 mmol) and from boronic acid I (69 mg; 0.21 mmol) according to the General Procedure Va in 43% yield (43 mg; 0.06 mmol). The crude product was purified by silica-gel column chromatography (hexane/AcOEt, 100:0 to 0:100, v/v, then AcOEt/MeOH, 95:5 to 90:10, v/v).

ESI-MS m/z for $C_{33}H_{37}F_3N_5O_5S$ found 672.2 [M+H]$^+$; $R_t$=1.69 min

Step 3

Synthesis of 3-((7-(3-(3-amino-3-methylpyrrolidine-1-carbonyl)-4-methyl-6-(trifluoromethyl)pyridin-2-yl)thieno[3,2-b]pyridin-2-yl)methyl)-6,6-dimethyl-3-azabicyclo[3.1.0]hexane-2,4-dione trihydrochloride (137)

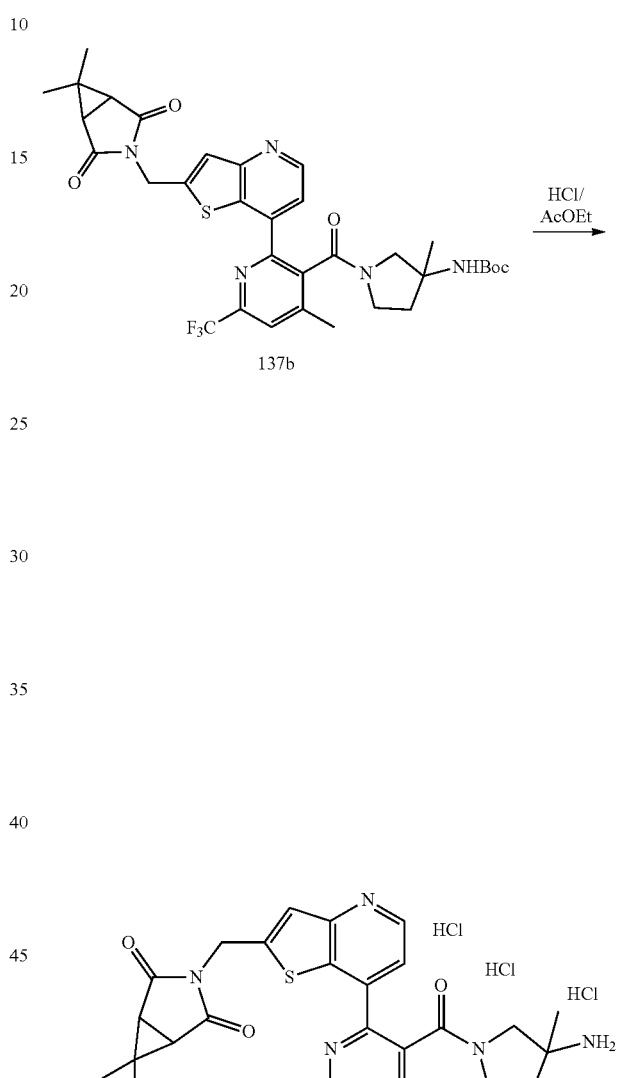

The title compound (137) was obtained as a trihydrochloride salt from 137b (43 mg; 0.06 mmol) according to the General Procedure IVa in 33% yield (14 mg; 0.02 mmol). The crude product was purified by preparative reversed-phase column chromatography (C-18, water+0.3% HCl (36%)/MeCN+0.3‰ HCl (36%), 90:10 to 40:60, 30 min, 20 mL/min).

ESI-MS m/z for $C_{28}H_{29}F_3N_5O_3S$ found 572.0 [M+H]$^+$; $R_t$=1.17 min; $^1$H NMR (700 MHz, Methanol-$d_4$) δ 9.06-8.96 (m, 1H), 8.17-8.10 (m, 1H), 8.06-7.98 (m, 1H), 7.79-7.69 (m, 1H), 5.04-4.96 (m, 2H), 4.00-3.68 (m, 2H), 3.29-2.74 (m, 3H), 2.65-2.51 (m, 3H), 2.24-1.80 (m, 3H), 1.55-0.94 (m, 9H).

Example 138

Synthesis of 3-((7-(3-((3S)-3-(1-aminoethyl)pyrrolidine-1-carbonyl)-4-methyl-6-(trifluoromethyl)pyridin-2-yl)thieno[3,2-b]pyridin-2-yl)methyl)-6,6-dimethyl-3-azabicyclo[3.1.0]hexane-2,4-dione trihydrochloride (138)

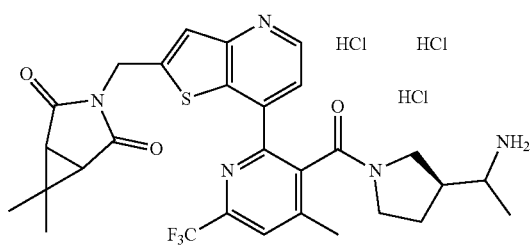

Step 1

Synthesis of tert-butyl (S)-3-formylpyrrolidine-1-carboxylate (138a)

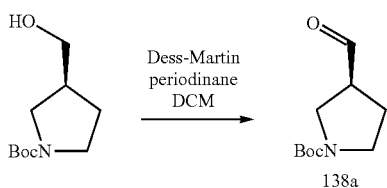 [SMILES: CC(C)(C)OC(=O)N1CC[C@H](CO)C1 ; CC(C)(C)OC(=O)N1CC[C@H](C=O)C1]

To a solution of tert-butyl (S)-3-(hydroxymethyl)pyrrolidine-1-carboxylate (3.08 g; 15.32 mmol) in DCM (60 mL) Dess-Martin periodinane (8.45 g; 19.92 mmol) was added at 0° C. and the reaction mixture was warmed to room temperature and stirred for 1 hour. The reaction progress was monitored by TLC. When analysis indicated completion of the reaction, to this mixture 10% $Na_2S_2O_3$ was added and stirred for 30 minutes, then phases were separated and an organic one was washed with water (1×), 1 M NaOH (2×) and water (1×). An aqueous layer was extracted with DCM (3×). The combined organic layers were dried over anhydrous $Na_2SO_4$, filtered and concentrated in vacuo. The crude product was purified by silica-gel column chromatography (hexane/AcOEt, 100:0 to 40:60, v/v). The title compound (138a) was obtained in 78% yield (2.38 g; 11.95 mmol).

ESI-MS m/z for $C_6H_{10}NO_3$ found 144.2 [M+H-tBu]+; $R_t$=0.92 min; $^1$H NMR (700 MHz, CDCl$_3$) δ 9.71 (d, J=1.6 Hz, 1H), 3.80-3.65 (m, 1H), 3.60-3.47 (m, 1H), 3.47-3.34 (m, 2H), 3.08-2.97 (m, 1H), 2.27-2.08 (m, 2H), 1.48 (s, 9H).

Step 2

Synthesis of tert-butyl (S)-3-((R)-1-hydroxyethyl)pyrrolidine-1-carboxylate (138b)

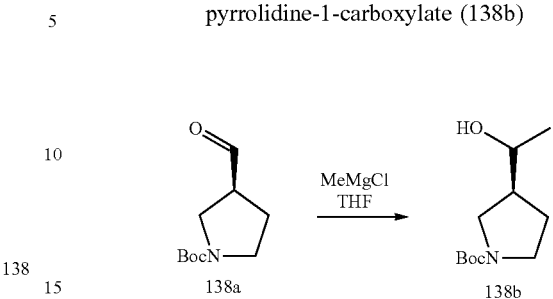

To a cooled to −20° C. solution of 138a (2.38 g; 11.95 mmol) in anhydrous THF (45 mL) under an argon atmosphere MeMgCl (3 M in THF; 6 mL; 18.00 mmol) was added dropwise. After this reaction was allowed to warm up to room temperature and stirred for 2 hours. The reaction progress was monitored by TLC analysis of small aliquots of the crude reaction mixture. When analyses were indicated completion of the reaction, the mixture was poured into saturated solution of $NH_4Cl$. An organic phase was separated, and the aqueous phase was extracted with AcOEt (3×). The combined organic phases were dried over anhydrous $MgSO_4$, filtered and concentrated in vacuo. The crude product was purified by silica-gel column chromatography (hexane/AcOEt, 80:20 to 30:70, v/v). The title compound (138b) was obtained in 82% yield (2.12 g; 9.85 mmol).

$^1$H NMR (700 MHz, CDCl$_3$) δ 3.77-3.66 (m, 1H), 3.66-3.40 (m, 2H), 3.33-2.96 (m, 2H), 2.21-2.07 (m, 1H), 1.95-1.63 (m, 2H), 1.48 (s, 9H), 1.28-1.23 (m, 3H).

Step 3

Synthesis of tert-butyl (S)-3-((R)-1-((methylsulfonyl)oxy)ethyl)pyrrolidine-1-carboxylate (138c)

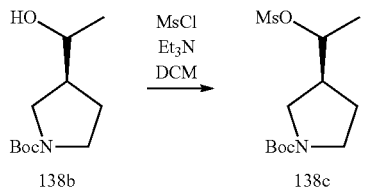 [SMILES: CC(O)[C@H]1CCN(C(=O)OC(C)(C)C)C1 ; CC(OS(C)(=O)=O)[C@H]1CCN(C(=O)OC(C)(C)C)C1]

The title compound (138c) was obtained from 138b (2.12 g; 9.85 mmol) according to the General Procedure VIII in 99% yield (2.86 g; 9.75 mmol).

ESI-MS m/z for $C_{12}H_{23}NO_5SNa$ found 316.0 [M+Na]+; $R_t$=1.37 min; $^1$H NMR (700 MHz, CDCl$_3$) δ 4.80-4.68 (m, 1H), 3.70-2.99 (m, 7H), 2.47-1.67 (m, 3H), 1.52-1.44 (m, 12H).

Step 4

Synthesis of tert-butyl (S)-3-((R)-1-azidoethyl)pyrrolidine-1-carboxylate (138d)

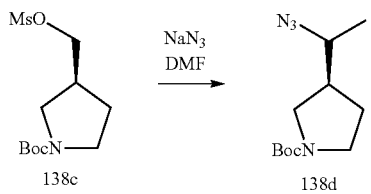 [SMILES: CC(C)(C)OC(=O)N1CC[C@H](COS(C)(=O)=O)C1 ; CC(N=[N+]=[N-])[C@H]1CCN(C(=O)OC(C)(C)C)C1]

A compound 138c (2.86 g; 9.75 mmol) and sodium azide (1.26 g; 19.46 mmol) in DMF (50 mL) were stirred at 70° C. overnight. The reaction progress was monitored by LC-MS. When analysis indicated completion of the reaction, the mixture was cooled to room temperature. The obtained precipitate was filtered off and the residue was diluted with Et$_2$O (250 mL) and washed with water (3×) and then dried over anhydrous NaSO$_4$, filtered and concentrated in vacuo. The crude product was purified by flash column chromatography on silica (hexane/AcOEt, 100:0 to 20:80, v/v, 35 min). The title compound (138d) was obtained as a single isomer in 36% yield (0.85 g; 3.54 mmol).

$^1$H NMR (700 MHz, CDCl$_3$) δ 3.58-3.51 (m, 1H), 3.51-3.36 (m, 2H), 3.32-3.24 (m, 1H), 3.04-2.96 (m, 1H), 2.28-2.15 (m, 1H), 2.12-2.06 (m, 1H), 1.76-1.66 (m, 1H), 1.48 (s, 9H), 1.33 (d, J=6.5 Hz, 3H).

Step 5

Synthesis of (S)-3-((R)-1-azidoethyl)pyrrolidine hydrochloride (138e)

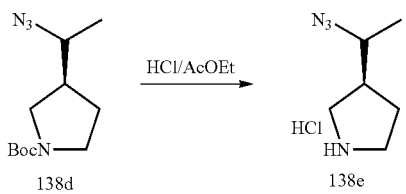

The title compounds (138e) was obtained as a hydrochloride salt from 138d (0.85 g; 3.54 mmol) according to the General Procedure IVa in 99% yield (618 mg; 3.50 mmol).

ESI-MS m/z for C$_6$H$_{13}$N$_4$ found 141.2 [M+H]$^+$; R$_t$=0.20 min; $^1$H NMR (700 MHz, Methanol-d$_4$) δ 3.79-3.72 (m, 1H), 3.45-3.37 (m, 2H), 3.29-3.22 (m, 1H), 3.08-3.02 (m, 1H), 2.52-2.40 (m, 1H), 2.22-2.13 (m, 1H), 1.93-1.80 (m, 1H), 1.37 (d, J=6.6 Hz, 3H).

Step 6

Synthesis of ((S)-3-((S)-1-azidoethyl)pyrrolidin-1-yl)(2-chloro-4-methyl-6-(trifluoromethyl)pyridin-3-yl)methanone (138f)

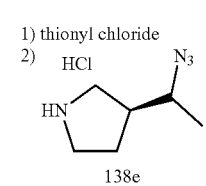

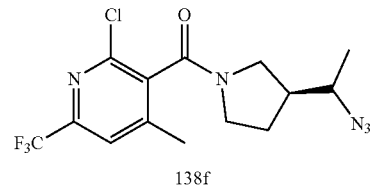

The title compound (138f) was obtained from an acid II (100 mg; 0.42 mmol) and from 138e (115 mg; 0.65 mmol) according to the General Procedure II in 67% yield (102 mg; 0.28 mmol). The crude product was purified by silica-gel column chromatography (hexane/AcOEt, 80:20 to 30:70, v/v).

ESI-MS m/z for C$_{14}$H$_{16}$ClF$_3$N$_5$O found 362.0/364.0 [M+H]$^+$; R$_t$=1.49 mm; $^1$H NMR (700 MHz, CDCl$_3$) δ 7.55-7.50 (m, 1H), 3.99-3.07 (m, 4H), 2.47-2.41 (m, 2H), 2.41-2.16 (m, 3H), 1.95-1.75 (m, 1H), 1.44-1.26 (m, 4H).

Step 7

Synthesis of 3-((7-(3-((3S)-3-(1-aminoethyl)pyrrolidine-1-carbonyl)-4-methyl-6-(trifluoromethyl)pyridin-2-yl)thieno[3,2-b]pyridin-2-yl)methyl)-6,6-dimethyl-3-azabicyclo[3.1.0]hexane-2,4-dione trihydrochloride (138)

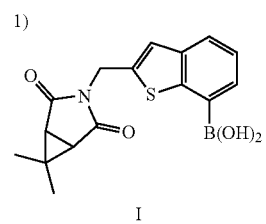

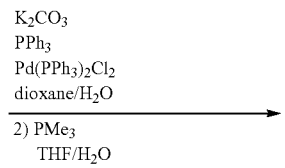

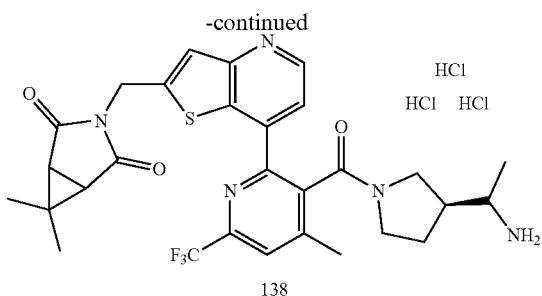

138

The title compound (138) was obtained as a trihydrochloride salt in 4% yield (5 mg; 0.007 mmol) from 138f (102 mg; 0.28 mmol) and from the boronic acid I (139 mg; 0.42 mmol) according to the General Procedure Va. Then the crude product was dissolved in THF/water (5:1; v/v; 1 mL) and PMe$_3$ (1 M solution in THF; 0.20 mL; 0.200 mmol) was added to this solution and the mixture was stirred at room temperature for 1 hour. The reaction progress was monitored by LC-MS. When analysis indicated completion of the reaction, the mixture was concentrated in vacuo and to the residue 1 M HCl (1.5 mL) was added and then extracted with AcOEt (2×). The aqueous layer was purified twice by preparative reversed-phase column chromatography (first: C-18, water+0.3‰ HCl (36%)/MeCN+0.3‰ HCl (36%), 75:25 to 50:50, 30 min. 20 mL/min, second: C-18, water+0.3‰ HCl (36%)/MeCN+0.3%, HCl (36%), 85:15 to 50:50.35 min, 20 mL/min).

ESI-MS m/z for C$_{29}$H$_{31}$F$_3$N$_5$O$_3$S found 586.2 [M+H]$^+$; R$_t$=1.11 min; $^1$H NMR (700 MHz, Methanol-d$_4$) δ 8.88-8.84 (m, 1H), 8.09-8.02 (m, 1H), 7.91-7.77 (m, 1H), 7.68-7.61 (m, 1H), 4.99-4.92 (m, 2H), 4.03-3.60 (m, 2H), 3.45-3.36 (m, 1H), 3.25-3.05 (m, 1H), 2.91-2.64 (m, 1H), 2.59-2.51 (m, 3H), 2.43-2.28 (m, 1H), 2.18-1.84 (m, 2H), 1.76-1.45 (m, 2H), 1.37-0.83 (m, 9H).

Example 139

Synthesis of 3-((7-(3-(3-(aminomethyl)pyrrolidine-1-carbonyl)-4-methyl-6-(trifluoromethyl)pyridin-2-yl)thieno[3,2-b]pyridin-2-yl)methyl)-6,6-dimethyl-3-azabicyclo[3.1.0]hexane-2,4-dione trihydrochloride (139)

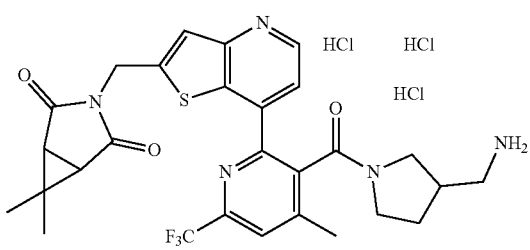

139

The title compound (139) was obtained as a racemate as a trihydrochloride salt in 10% overall yield in a similar way to Example 137 with the exception that, in the first step of the synthesis tert-butyl (pyrrolidin-3-ylmethyl)carbamate was used instead of tert-butyl (3-methylpyrrolidin-3-yl)carbamate, and in the last step of the synthesis, the General Procedure IVb was used instead of the General Procedure IVa and the crude product was purified by preparative reversed-phase column chromatography (C-18, water+0.3‰ HCl (36%)/MeCN+0.3‰ HCl (36%), 80:20 to 40:60, 30 min, 20 mL/min).

ESI-MS m/z for C$_{28}$H$_{29}$F$_3$N$_5$O$_3$S found 572.0 [M+H]$^+$; R$_t$=1.03 min; $^1$H NMR (700 MHz, Methanol-d$_4$) δ 9.07-8.93 (m, 1H), 8.19-8.05 (m, 2H), 7.80-7.75 (m, 1H), 5.04-4.98 (m, 2H), 4.10-3.38 (m, 3H), 3.30-2.89 (m, 3H), 2.82-2.70 (m, 1H), 2.64-2.36 (m, 5H), 2.28-1.90 (m, 1H), 1.86-1.49 (m, 1H), 1.33-1.25 (m, 3H), 1.21-1.12 (m, 3H).

Example 140

Synthesis of 3-((7-(3-(3-((isopropylamino)methyl)pyrrolidine-1-carbonyl)-4-methyl-6-(trifluoromethyl)pyridin-2-yl)thieno[3,2-b]pyridin-2-yl)methyl)-6,6-dimethyl-3-azabicyclo[3.1.0]hexane-2,4-dione trihydrochloride (140)

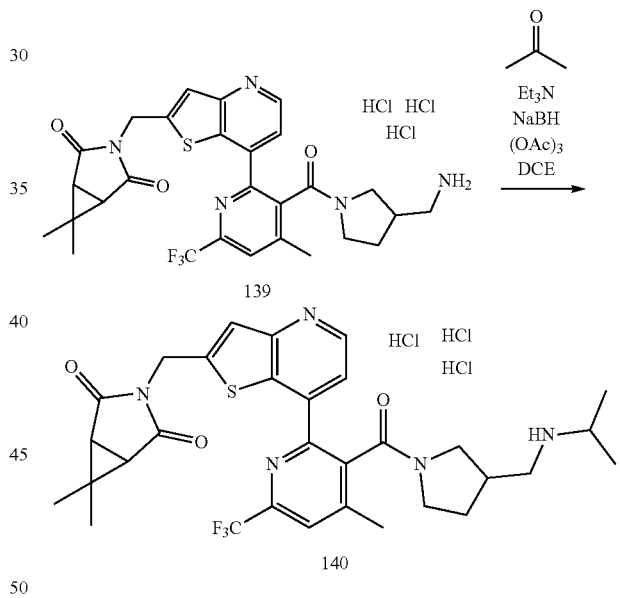

The title compound (140) was as a racemate as a trihydrochloride salt obtained from 139 (13 mg, 0.020 mmol) and from acetone (2 µL; 0.027 mmol) according to the General Procedure VIa in 70% yield (10 mg; 0.014 mmol) with the exception that in this reaction Et$_3$N was used instead of AcOH. The crude product was purified by preparative reversed-phase column chromatography (C-18, water+0.3‰ HCl (36%)/MeCN+0.3‰ HCl (36%), 80:20 to 40:60, 30 min, 20 mL/min ESI-MS m/z for C$_{31}$H$_{35}$F$_3$N$_5$O$_3$S found 614.1 [M+H]$^+$; R$_t$=0.97 min; $^1$H NMR (700 MHz, Methanol-d$_4$) δ 8.97-8.87 (m, 1H), 8.11-8.05 (m, 1H), 8.01-7.88 (m, 1H), 7.70-7.64 (m, 1H), 5.02-4.91 (m, 2H), 4.10-3.49 (m, 4H), 3.28-2.75 (m, 3H), 2.70-2.48 (m, 3H), 2.47-1.59 (m, 5H), 1.37-1.12 (m, 12H).

Example 141

Synthesis of 3-((7-(3-((2S,6S)-2,6-dimethylpiperazine-1-carbonyl)-4-methyl-6-(trifluoromethyl)pyridin-2-yl)thieno[3,2-b]pyridin-2-yl)methyl)-6,6-dimethyl-3-azabicyclo[3.1.0]hexane-2,4-dione 2,2,2-trifluoroacetate (141)

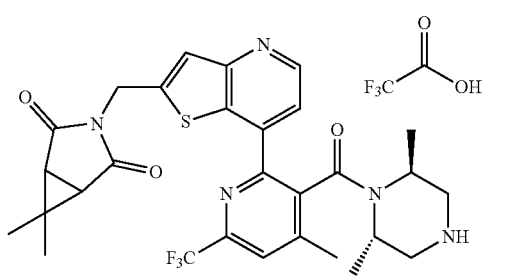

141

The title compound (141) was obtained as a mixture of two isomers (in ratio 7:10) as a TFA salt in 4% overall yield in a similar way to Example 137 with the exception that, in the first step of the synthesis tert-butyl (3S,5S)-3,5-dimethylpiperazine-1-carboxylate was used instead of tert-butyl (3-methylpyrrolidin-3-yl)carbamate, and in the last step of the synthesis, the General Procedure IVb was used instead of the General Procedure IVa and the crude product was purified by preparative reversed-phase column chromatography (C-18, water+0.4‰ TFA/MeCN+0.4‰ TFA, 90:10 to 50:50, 30 min, 20 mL/min).

ESI-MS m/z for $C_{29}H_{31}F_3N_5O_3S$ found 586.2 [M+H]$^+$; $R_t$=0.93 min; $^1$H NMR (700 MHz, Methanol-d$_4$) δ 8.79-8.72 (m, 1H), 8.08-7.51 (m, 3H), 4.95-4.86 (m, 2H), 4.67-4.49 (m, 1H), 3.66-3.61 (m, 1H), 3.46-3.34 (m, 1H), 3.31-2.82 (m, 3H), 2.62-2.08 (m, 5H), 1.65-0.45 (m, 12H).

Example 142

Synthesis of 3-((7-(3-((2R,6R)-2,6-dimethylpiperazine-1-carbonyl)-4-methyl-6-(trifluoromethyl)pyridin-2-yl)thieno[3,2-b]pyridin-2-yl)methyl)-6,6-dimethyl-3-azabicyclo[3.1.0]hexane-2,4-dione 2,2,2-trifluoroacetate (142)

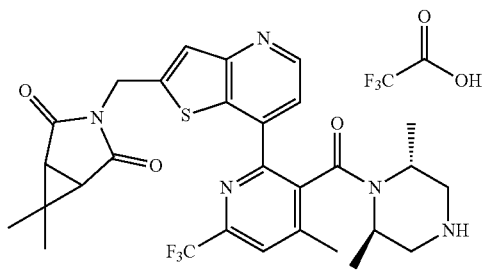

142

The title compound (142) was obtained as a mixture of two isomers (in ratio 10:12) as a TFA salt in 1% overall yield in a similar way to Example 137 with the exception that, in the first step of the synthesis tert-butyl (3R,5R)-3,5-dimethylpiperazine-1-carboxylate was used instead of tert-butyl (3-methylpyrrolidin-3-yl)carbamate, and in the last step of the synthesis, the General Procedure IVb was used instead of the General Procedure IVa and the crude product was purified by preparative reversed-phase column chromatography (C-18, water+0.4‰ TFA/MeCN+0.4‰ TFA, 80:20 to 40:60, 30 min, 20 mL/min).

ESI-MS m/z for $C_{29}H_{31}F_3N_5O_3S$ found 586.2 [M+H]$^+$; $R_t$=0.96 min; $^1$H NMR (700 MHz, Methanol-d$_4$) δ 8.79-8.72 (m, 1H), 8.07-7.50 (m, 3H), 4.96-4.87 (m, 2H), 4.67-4.53 (m, 1H), 3.85-3.36 (m, 3H), 3.24-2.77 (m, 2H), 2.64-2.42 (m, 3H), 2.34-2.10 (m, 1H), 1.71-0.45 (m, 13H).

Example 143

Synthesis of 3-((7-(3-(4-ethylpiperazine-1-carbonyl)-4-methyl-6-(trifluoromethyl)pyridin-2-yl)thieno[3,2-b]pyridin-2-yl)methyl)-6,6-dimethyl-3-azabicyclo[3.1.0]hexane-2,4-dione trihydrochloride (143)

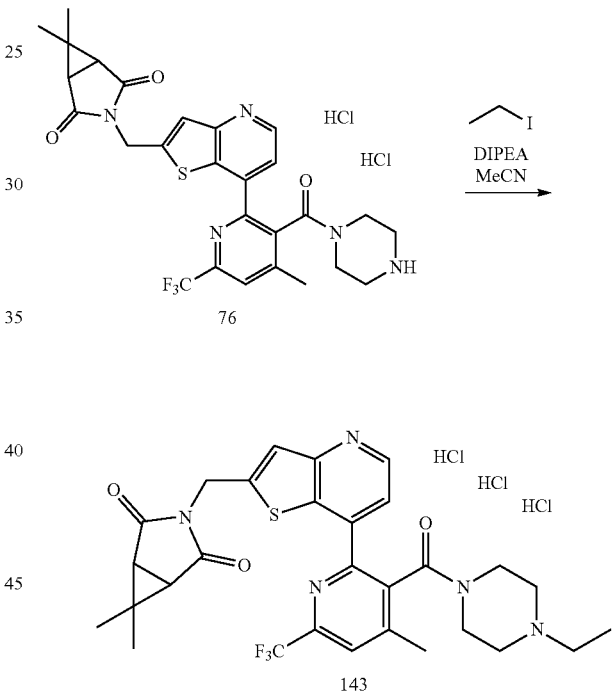

The mixture of compound 76 (10 mg; 0.015 mmol), MeCN (0.5 mL), DIPEA (10 μL; 0.060 mmol) and iodoethane (2 μL; 0.018 mmol) was stirred at room temperature for 2 days. Then the reaction mixture was concentrated under reduced pressure and the residue was purified by preparative reversed-phase column chromatography (C-18, water+0.396 HCl (36%)/MeCN, 90:10 to 40:60, 20 min, 20 mL/min). The title compound (143) was obtained as a trihydrochloride salt in 87% yield (9 mg; 0.013 mmol).

ESI-MS m/z for $C_{29}H_{31}F_3N_5O_3S$ found 586.2 [M+H]$^+$; $R_t$=1.04 min, $^1$H NMR (700 MHz, Methanol-d$_4$) δ 8.98-8.95 (m, 1H), 8.12 (s, 1H), 7.99-7.82 (m, 1H), 7.72 (d, J=2.2 Hz, 1H), 5.01-4.95 (m, 2H), 3.73-3.63 (m, 1H), 3.60-3.37 (m, 2H), 3.30-3.09 (m, 5H), 2.93-2.86 (m, 1H), 2.84-2.77 (m, 1H), 2.63 (d, J=10.3 Hz, 2H), 2.56-2.52 (m, 3H), 1.33-1.26 (m, 6H), 1.17 (s, 3H).

Example 144

Synthesis of 6,6-dimethyl-3-((7-(4-methyl-3-((S)-3-(methylamino)piperidine-1-carbonyl)-6-(trifluoromethyl)pyridin-2-yl)thieno[3,2-b]pyridin-2-yl)methyl)-3-azabicyclo[3.1.0]hexane-2,4-dione trihydrochloride (144)

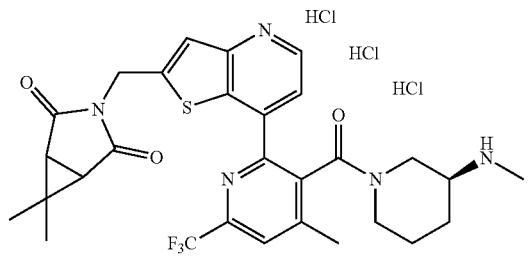

144

The title compound (144) was obtained as a trihydrochloride salt in 15% overall yield in a similar way to Example 45 with the exception that, in the first step of the synthesis an acid II and (S)-3-N-Boc-3-(methylamino)piperidine were used instead of 2-chloro-4-methylnicotinic acid and tert-butyl piperazine-1-carboxylate and in the last step of the synthesis the crude product was purified by preparative reversed-phase column chromatography (C-18, water+0.3‰ HCl (36%)/MeCN, 90:10 to 40:60, 20 min, 20 mL/min).

ESI-MS m/z for $C_{29}H_{31}F_3N_5O_3S$ found 586.10 [M+H]$^+$; $R_t$=0.98 min; $^1$H NMR (700 MHz, Methanol-$d_4$) δ 8.99-8.83 (m, 1H), 8.11-8.02 (m, 1H), 7.97-7.77 (m, 1H), 7.71-7.61 (m, 1H), 4.99-4.94 (m, 2H), 3.29-3.14 (m, 1H), 3.08-2.93 (m, 2H), 2.85-2.76 (m, 3H), 2.66-2.59 (m, 2H), 2.57-2.50 (m, 4H), 2.46-2.20 (m, 1H), 2.01-1.66 (m, 1H), 1.54-1.31 (m, 2H), 1.20 (d, J=15.1 Hz, 4H), 1.13 (d, J=8.2 Hz, 2H).

Example 145

Synthesis of 4-methyl-6-((7-(4-methyl-3-(pyrrolidin-3-ylamino)-6-(trifluoromethyl)pyridin-2-yl)thieno[3,2-b]pyridin-2-yl)methyl)-4,6-diazaspiro[2.4]heptane-5,7-dione dihydrochloride (145)

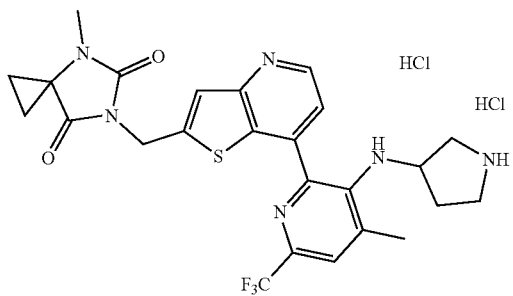

145

Step 1

Synthesis of 2-((7-chlorothieno[3,2-b]pyridin-2-yl)methyl)isoindoline-1,3-dione (145a)

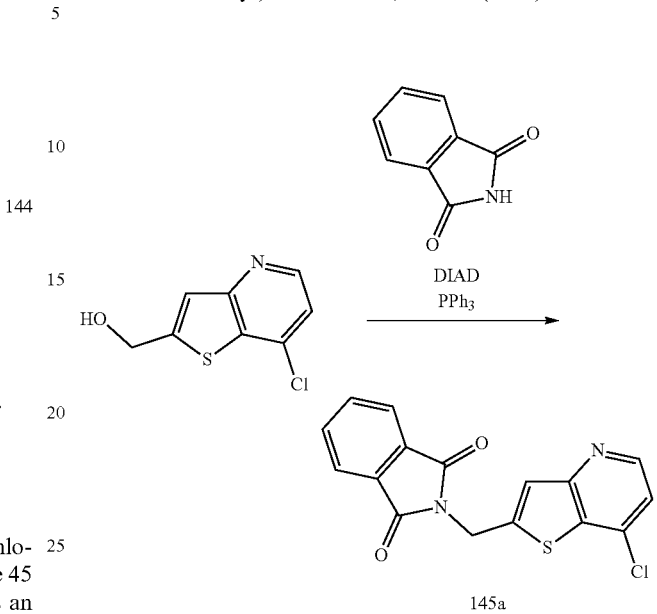

145a

To a cooled to −10° C. solution of (7-chlorothieno[3,2-b]pyridin-2-yl)methanol (500 mg; 2.50 mmol), phthalimide (440 mg; 3.00 mmol) and Ph$_3$P (780 mg; 3.00 mmol) in THF (10 ml) DIAD (0.64 mL; 3.25 mmol) was slowly added. The resulting mixture was stirred at room temperature for 2 hours and then concentrated in vacuo. The residue was taken into DCM and filtered to afford the title compound 145a as a white solid in 66% yield (540 mg; 1.64 mmol).

ESI-MS m/z for $C_{16}H_{10}ClN_2O_2S$ found 329.0/331.0 [M+H]$^+$; $R_t$=1.40 min; $^1$H NMR (700 MHz, DMSO-$d_6$) δ 8.62 (d, J=5.1 Hz, 1H), 7.96-7.92 (m, 2H), 7.90-7.86 (m, 2H), 7.67 (s, 1H), 7.55 (d, J=5.1 Hz, 1H), 5.15 (d, J=0.8 Hz, 2H).

Step 2

Synthesis of (7-chlorothieno[3,2-b]pyridin-2-yl)methanamine (145b)

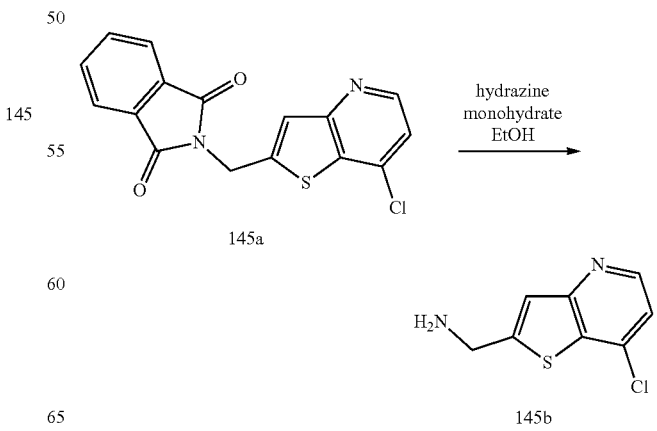

145b

A compound 145a (0.54 g; 1.64 mmol) was dissolved in ethanol (5 mL), and to this mixture hydrazine monohydrate (0.4 mL, 8.21 mmol) was added. The reaction mixture was heated to 70° C. for 1 hour. The reaction mixture was concentrated in vacuo, diluted with water (5 mL) and AcOEt (15 mL), and the aqueous layer was extracted with AcOEt (25 mL). The combined organic layers were washed with brine, dried over anhydrous MgSO$_4$, filtered, and concentrated in vacuo to afford the title product 145b in 78% yield (250 mg; 1.25 mmol).

Step 3

Synthesis of tert-butyl (1-(((7-chlorothieno[3,2-b]pyridin-2-yl)methyl)carbamoyl)cyclopropyl)carbamate (145c)

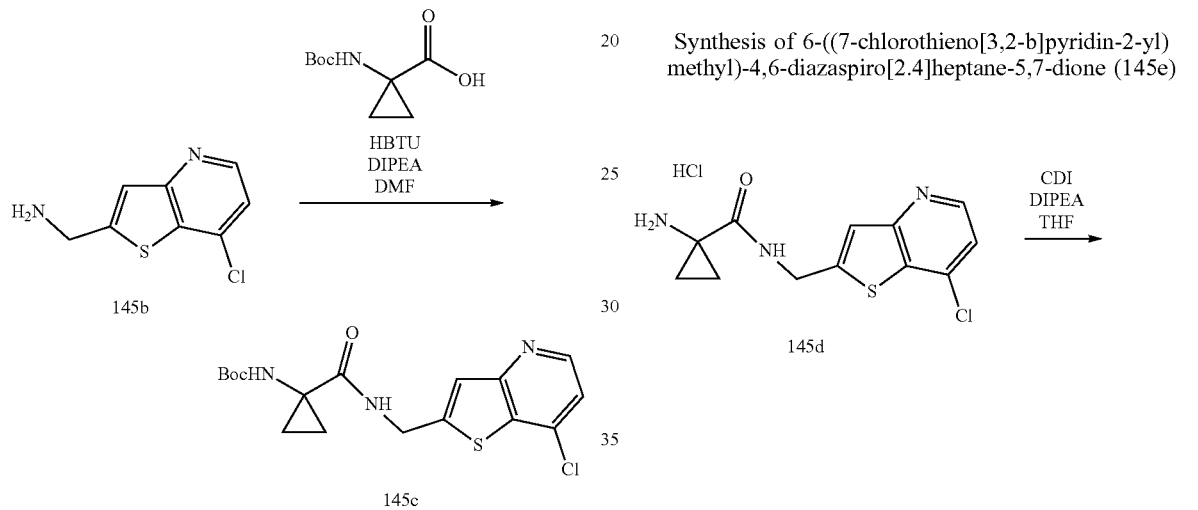

The title compound (145c) was obtained from 145b (250 mg; 1.25 mmol) and from 1-((tert-butoxycarbonyl)amino)cyclopropane-1-carboxylic acid (250 mg; 1.25 mmol) according to the General Procedure I (with the exception that HBTU was used instead of HATU) in 99% yield (465 mg; 1.22 mmol).

ESI-MS m/z for C$_{17}$H$_{21}$ClN$_3$O$_3$S found 382.1/384.1 [M+H]$^+$; R$_t$=1.25 min; $^1$H NMR (700 MHz, DMSO-d$_6$) δ 8.55 (d, J=5.1 Hz, 1H), 7.44 (s, 1H), 7.42 (d, J=5.1 Hz, 1H), 4.62 (s, 2H), 1.35 (s, 9H), 1.31-1.27 (m, 2H), 0.95 (q, J=4.3 Hz, 2H).

Step 4

Synthesis of 1-amino-N-((7-chlorothieno[3,2-b]pyridin-2-yl)methyl)cyclopropane-1-carboxamide (145d)

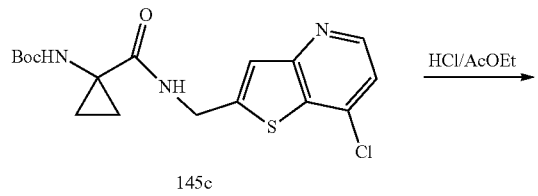

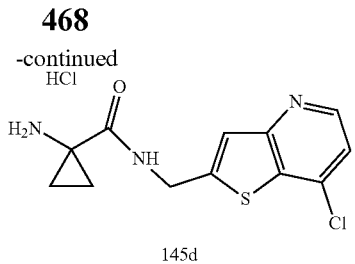

The title compound (145d) was obtained as a hydrochloride salt from 145c (465 mg; 1.22 mmol) according to the General Procedure IVa in 99% yield (387 mg; 1.22 mmol).

ESI-MS m/z for C$_{12}$H$_{13}$ClN$_3$OS found 282.0/284.0 [M+H]$^+$; R$_t$=0.39 min Step 5

Synthesis of 6-((7-chlorothieno[3,2-b]pyridin-2-yl)methyl)-4,6-diazaspiro[2.4]heptane-5,7-dione (145e)

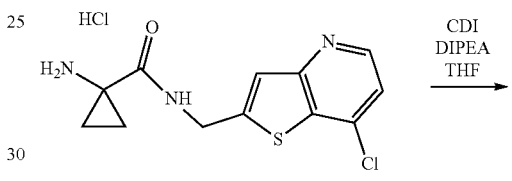

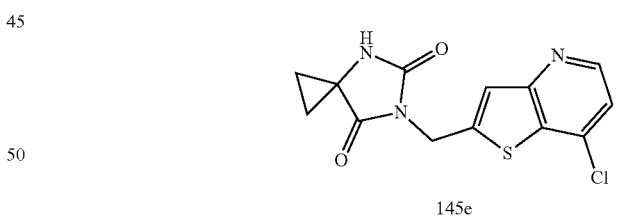

To the solution of 145d (387 mg; 1.22 mmol) in dry THF (4 mL) CDI (198 mg; 1.22 mmol) and DIPEA (449 mL; 2.44 mmol) were added and the reaction mixture was stirred at 50° C. for 3 days. The reaction progress was monitored by LC-MS. When analysis indicated completion of the reaction, the reaction mixture was concentrated to dryness. The residue was taken into AcOEt (10 mL), washed with water (10 mL) and brine (10 mL), dried over anhydrous MgSO$_4$, filtered, and concentrated under reduced pressure to afford the title compound 145e in 98% (370 mg; 1.20 mmol) which was used to the next step without any additional purification.

ESI-MS m/z for C$_{13}$H$_{11}$ClN$_3$O$_2$S found 307.9/309.9 [M+H]$^+$; R$_t$=1.05 min

Step 6

Synthesis of 6-((7-chlorothieno[3,2-b]pyridin-2-yl)methyl)-4-methyl-4,6-diazaspiro[2.4]heptane-5,7-dione (145f)

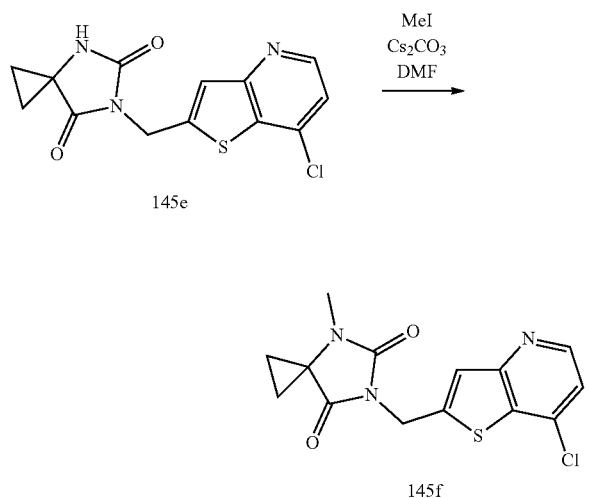

To the solution of compound 145e (370 mg; 1.20 mmol) in DMF (5 mL) Cs₂CO₃ (430 mg; 1.30 mmol) and MeI (0.075 mL; 1.20 mmol) were added and the reaction mixture was stirred at room temperature overnight. The reaction progress was monitored by LC-MS. When analysis indicated completion of the reaction, the reaction mixture was diluted with water (5 mL) and extracted with AcOEt, dried over anhydrous MgSO₄, filtered and concentrated in vacuo. The crude product was purified by flash column chromatography on silica (DCM/MeOH, 100:1 to 10:1, v/v) to give the title compound 145f in 45% yield (170 mg; 0.53 mmol).

ESI-MS m/z for $C_{14}H_{13}ClN_3O_2S$ found 321.9/323.9 [M+H]⁺; R$_t$=1.14 min

Step 7

Synthesis of (2-((4-methyl-5,7-dioxo-4,6-diazaspiro[2.4]heptan-6-yl)methyl)thieno[3,2-b]pyridin-7-yl)boronic acid (145g)

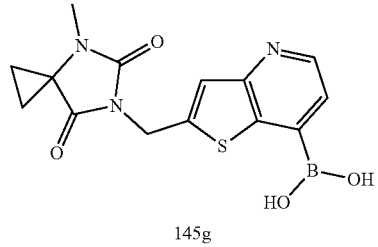

To the solution of 145f (170 mg; 0.53 mmol) in dry dioxane (190 mL) bis(pinacolato)diboron (270 mg; 1.06 mmol) and AcOK (150 mg; 1.59 mmol) were added. The reaction mixture was intensively flushed with Ar. Then to this mixture Pd(dppf)Cl₂ (43 mg; 0.53 mmol) was added in one portion and the reaction mixture was flushed with Ar. The mixture was stirred overnight at 100° C. in a sealed tube. The reaction progress was monitored by LC-MS. Then another portion of Pd(dppf)Cl₂ (43 mg; 0.53 mmol) and bis(pinacolato)diboron (270 mg; 1.06 mmol) was added and this mixture was stirred at 110° C. for 2 days. When analysis indicated completion of the reaction, dioxane was removed and the residue was dissolved in AcOEt/1 M HCl and extracted with AcOEt. Then an aqueous layer was alkalized with solid NaHCO₃ to pH 7 and extracted with AcOEt. The combined organic layers were dried over anhydrous MgSO₄, filtered and concentrated in vacuo. The title compound 145g was obtained as a mixture with bis-arylated product (150 mg) and directly used to the next step without further purification.

ESI-MS m/z for $C_{14}H_{15}BN_3O_4S$ found 332.1 [M+H]⁺; R$_t$=0.71 min

Step 8

Synthesis of tert-butyl 3-((4-methyl-2-(2-((4-methyl-5,7-dioxo-4,6-diazaspiro[2.4]heptan-6-yl)methyl)thieno[3,2-b]pyridin-7-yl)-6-(trifluoromethyl)pyridin-3-yl)amino)pyrrolidine-1-carboxylate (145h)

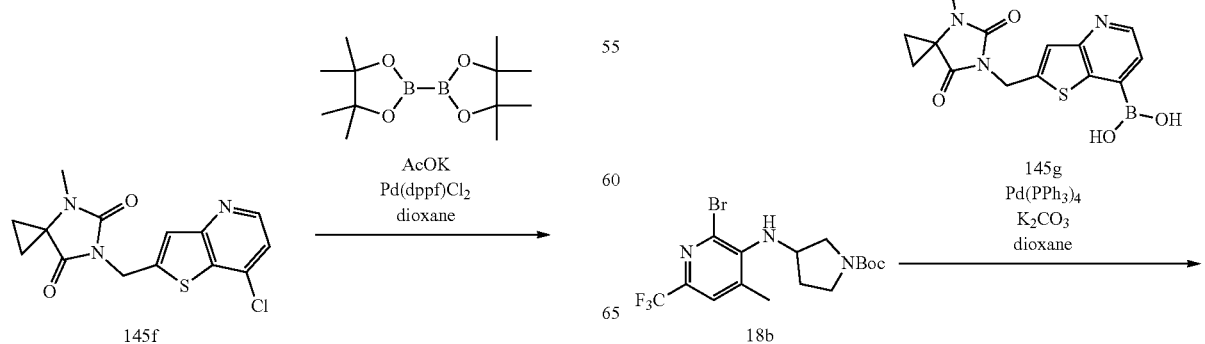

-continued

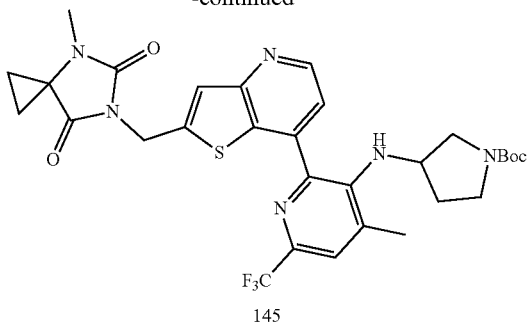

145

The title compound (145h) was obtained from 18b (150 mg; 0.36 mmol) and from 145g (150 mg; 0.36 mmol) according to the General Procedure Va in 20% yield (45 mg; 0.07 mmol).

ESI-MS m/z for $C_{30}H_{34}F_3N_6O_4S$ found 631.5 $[M+H]^+$; $R_t$=1.155 min

Step 9

Synthesis of 4-methyl-6-((7-(4-methyl-3-(pyrrolidin-3-ylamino)-6-(trifluoromethyl)pyridin-2-yl)thieno[3,2-b]pyridin-2-yl)methyl)-4,6-diazaspiro[2.4]heptane-5,7-dione dihydrochloride (145)

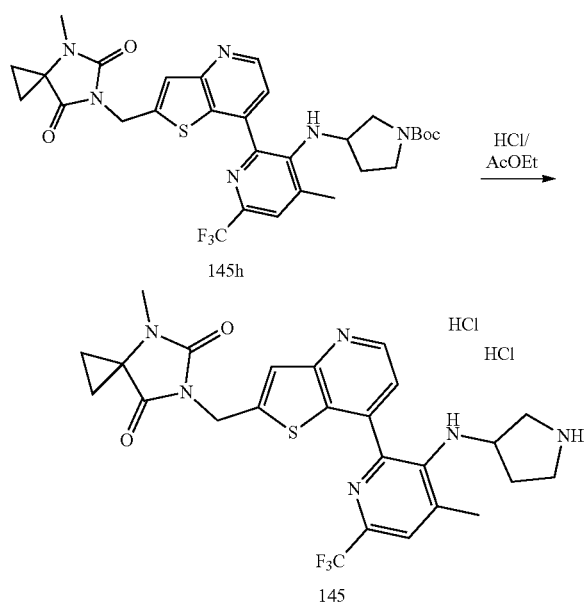

The title compound (145) was obtained as a dihydrochloride salt from 145h (45 mg; 0.07 mmol) according to the General Procedure IVa in 56% yield (28 mg; 0.04 mmol). The crude product was purified by preparative reversed-phase column chromatography (C-18, water+0.3‰ HCl (36%)/MeCN, 99:1 to 30:70, 30 min, 20 mL/min).

ESI-MS m/z for $C_{25}H_{26}F_3N_6O_2S$ found 531.4 $[M+H]^+$; $R_t$=0.93 min; $^1$H NMR (700 MHz, Methanol-$d_4$) δ 8.91 (d, J=5.7 Hz, 1H), 8.37 (d, J=5.7 Hz, 1H), 7.80 (d, J=0.6 Hz, 1H), 7.72 (t, J=0.9 Hz, 1H), 5.16 (d, J=0.9 Hz, 2H), 3.67 (p, J=7.0 Hz, 1H), 3.43-3.35 (m, 1H), 3.25-3.20 (m, 1H), 3.10 (ddd, J=16.1, 9.4, 5.5 Hz, 2H), 2.79 (s, 3H), 2.57 (s, 3H), 2.12-2.01 (m, 1H), 1.93-1.85 (m, 1H), 1.59 (dd, J=8.3, 5.6 Hz, 2H), 1.38 (dd, J=8.2, 5.6 Hz, 2H).

Examples 146 and 147

Synthesis of 3-((7-(1H-imidazol-2-yl)thieno[3,2-b]pyridin-2-yl)methyl)-6,6-dimethyl-3-azabicyclo[3.1.0]hexane-2,4-dione 2,2,2-trifluoroacetate (146) and 6,6-dimethyl-3-((7-(1-(morpholin-2-ylmethyl)-1H-imidazol-2-yl)thieno[3,2-b]pyridin-2-yl)methyl)-3-azabicyclo[3.1.0]hexane-2,4-dione 2,2,2-trifluoroacetate (147)

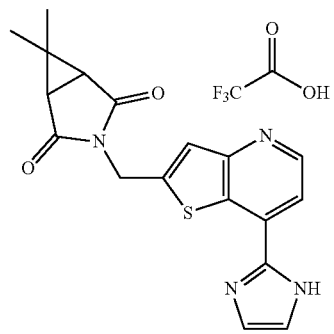

146

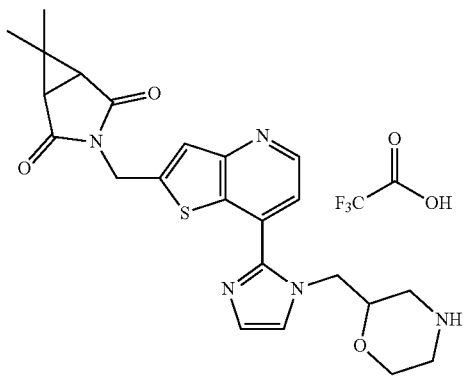

147

The title compounds (146 and 147) were obtained as TFA salts in 1% and 3% overall yield in a similar way to Examples 6 and 7 with the exception that, in the first step of the synthesis 2-bromo-1H-imidazole was used instead of 3-bromo-5-(trifluoromethyl)-1H-pyrazole and this step was carried out in a different way (the synthesis was described below) and in the last step of the synthesis the crude product was purified by preparative reversed-phase column chromatography (C-18, water/MeCN+1‰ TFA, 99:1 to 50:50, 30 min, 20 mL/min).

For 146. ESI-MS m/z for $C_{15}H_7N_4O_2S$ found 353.2 $[M+H]^+$; $R_t$=0.88 min; $^1$H NMR (700 MHz, Methanol-$d_4$) δ 8.72 (d, J=5.3 Hz, 1H), 7.81 (d, J=5.3 Hz, 1H), 7.57-7.54 (m, 1H), 7.44 (s, 2H), 4.93 (s, 2H), 2.53 (s, 2H), 1.26 (s, 3H), 1.11 (s, 3H).

For 147: ESI-MS m/z for $C_{23}H_{26}N_5O_3S$ found 452.2 $[M+H]^+$; $R_t$=1.11 min; $^1$H NMR (700 MHz, $D_2O$) δ 8.86-8.83 (m, 1H), 7.80-7.77 (m, 1H), 7.77-7.74 (m, 1H), 7.71-7.68 (m, 1H), 7.68 (s, 1H), 4.94 (s, 2H), 4.53-4.45 (m, 1H), 4.35-4.27 (m, 1H), 4.13-4.05 (m, 1H), 3.78-3.72 (m, 1H), 3.67-3.56 (m, 1H), 3.37-3.33 (m, 1H), 3.25-3.16 (m, 1H), 3.02-2.92 (m, 1H), 2.84-2.77 (m, 1H), 2.63 (s, 2H), 1.20 (s, 3H), 1.02 (s, 3H).

473

Step 1

Synthesis of tert-butyl 2-((2-bromo-1H-imidazol-1-yl)methyl)morpholine-4-carboxylate (146a)

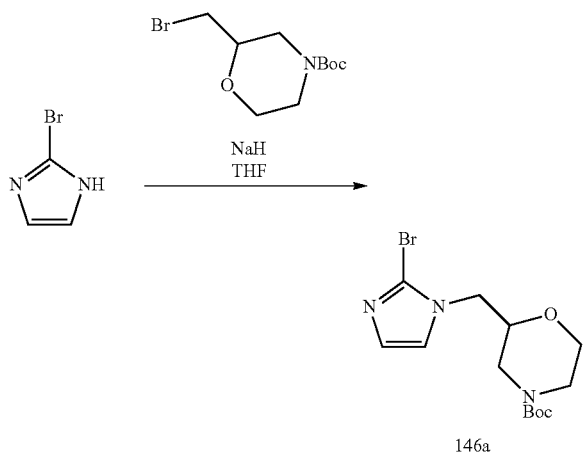

To the solution of 2-bromo-1H-imidazole (30 mg; 0.20 mmol) in THF (2 mL) NaH (60%; 17 mg; 0.40 mmol) was added at 0° C. and after 5 minutes tert-butyl 2-(bromomethyl)morpholine-4-carboxylate (67 mg; 0.24 mmol) was added and then the mixture was stirred at room temperature overnight and then at 60° C. overnight. The reaction progress was monitored by LC-MS. When analysis indicated completion of the reaction, THF was evaporated under reduced pressure and to the residue water was added and then extracted with AcOEt. The organic layer was dried over anhydrous MgSO$_4$, filtered and concentrated in vacuo and the crude product was used to the next step without additional purification. Compound 146a was obtained in 99% yield (69 mg; 0.20 mmol).

ESI-MS m/z for C$_{13}$H$_{21}$BrN$_3$O$_3$ found 346.0/348.0 [M+H]$^+$; R$_t$=1.12 min

Example 148

Synthesis of ethyl 5-(2-((6,6-dimethyl-2,4-dioxo-3-azabicyclo[3.1.0]hexan-3-yl)methyl)thieno[3,2-b]pyridin-7-yl)-2-methyl-1-(((S)-morpholin-2-yl)methyl)-1H-pyrrole-3-carboxylate 2,2,2-trifluoroacetate (148)

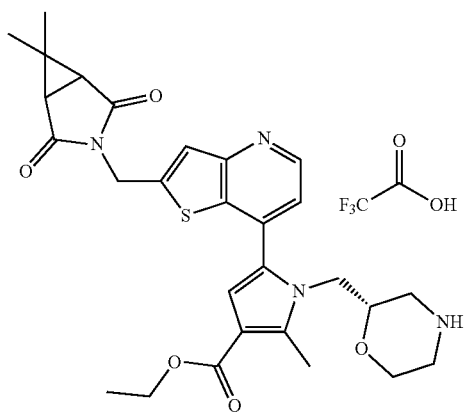

148

474

Step 1

Synthesis of tert-butyl (R)-2-((3-(ethoxycarbonyl)-2-methyl-1H-pyrrol-1-yl)methyl)morpholine-4-carboxylate (148a)

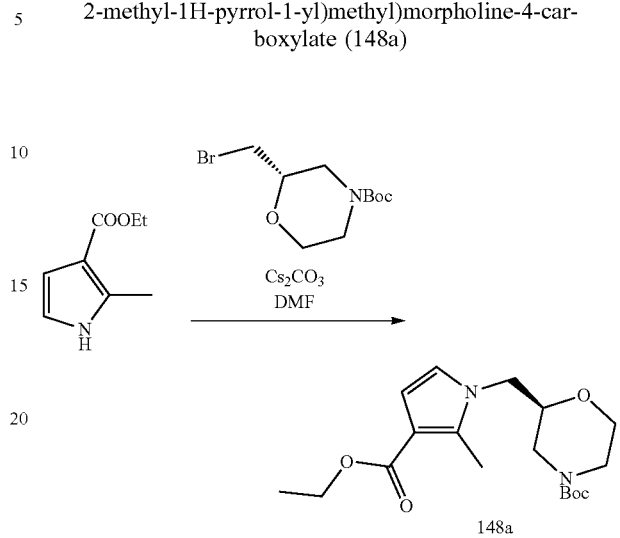

To the solution of ethyl 2-methyl-1H-pyrrole-3-carboxylate (100 mg; 0.65 mmol) in DMF (2 mL) tert-butyl (S)-2-(bromomethyl)morpholine-4-carboxylate (201 mg; 0.72 mmol) and Cs$_2$CO$_3$ (423 mg; 1.30 mmol) were added and then the reaction mixture was heated at 60° C. overnight. The reaction progress was monitored by TLC and LC-MS. Next another portion of tert-butyl (S)-2-(bromomethyl)morpholine-4-carboxylate (100 mg; 0.36 mmol) was added and the mixture was stirred at 60° C. overnight and then to this reaction Cs$_2$CO$_3$ (211 mg; 0.65 mmol) was added and stirred at 60° C. for 4 hours. When analyses indicated almost completion of the reaction, the mixture was concentrated in vacuo and the crude product was purified by flash column chromatography on silica (hexane/AcOEt, 70:30, v/v, 20 minutes). Compound 148a was obtained in 45% yield (101 mg; 0.29 mmol).

ESI-MS m/z for C$_{18}$H$_{28}$N$_2$O$_5$Na found 375.0 [M+Na]$^+$; R$_t$=1.54 min; $^1$H NMR (700 MHz, CDCl$_3$) δ 6.57-6.53 (m, 2H), 4.28 (q, J=7.1 Hz, 2H), 3.96-3.75 (m, 5H), 3.65-3.58 (m, 1H), 3.50-3.44 (m, 1H), 2.99-2.88 (m, 1H), 2.67-2.52 (m, 4H), 1.48 (s, 9H), 1.35 (t, J=7.1 Hz, 3H).

Step 2

Synthesis of tert-butyl (S)-2-((5-bromo-3-(ethoxycarbonyl)-2-methyl-1H-pyrrol-1-yl)methyl)morpholine-4-carboxylate (148b)

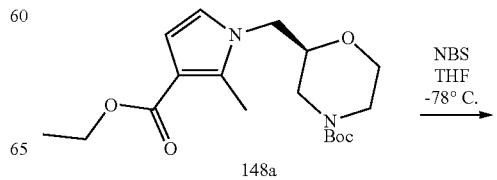

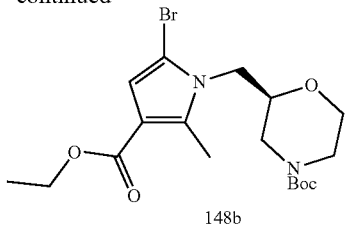

148b

To the solution of 148a (89 mg; 0.252 mmol) in THF (3 mL) NBS (45 mg; 0.252 mmol) was added at −78° C. and then the reaction mixture was stirred in this temperature for 2 hours. The reaction progress was monitored by LC-MS. When analysis indicated completion of the reaction, to this mixture an aqueous solution of $NH_4Cl$ was added and then extracted with AcOEt. The organic layer was washed with brine, dried over anhydrous $MgSO_4$, filtered and concentrated in vacuo and the crude product was used to the next step without additional purification. Compound 148b was obtained in 85% yield (92 mg; 0.214 mmol).

ESI-MS m/z for $C_{18}H_{27}BrN_3O_5Na$ found 455.0/457.0 $[M+Na]^+$; $R_t$=1.77 min Step 3

Synthesis of tert-butyl (2R)-2-((5-(2-((6,6-dimethyl-2,4-dioxo-3-azabicyclo[3.1.0]hexan-3-yl)methyl)thieno[3,2-b]pyridin-7-yl)-3-(ethoxycarbonyl)-2-methyl-1H-pyrrol-1-yl)methyl)morpholine-4-carboxylate (148c)

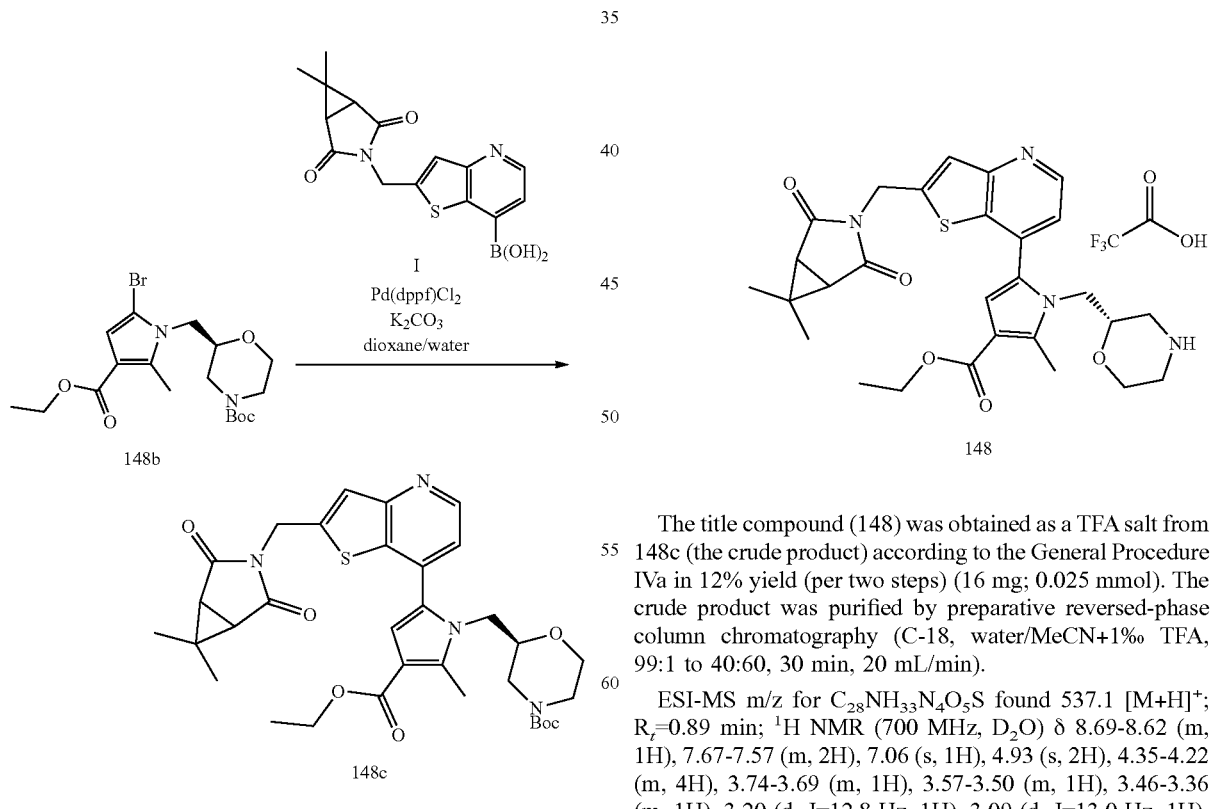

The title compound (148c) was obtained from 148b (99 mg; 0.294 mmol) and from boronic acid I (86 mg; 0.199 mmol) according to the General Procedure Va and after standard work-up the crude product was taken to the next step.

ESI-MS m/z for $C_{33}H_{41}N_4O_7S$ found 637.1 $[M+H]^+$; $R_t$=1.60 min

Step 4

Synthesis of ethyl 5-(2-((6,6-dimethyl-2,4-dioxo-3-azabicyclo[3.1.0]hexan-3-yl)methyl)thieno[3,2-b]pyridin-7-yl)-2-methyl-1-(((S)-morpholin-2-yl)methyl)-1H-pyrrole-3-carboxylate 2,2,2-trifluoroacetate (148)

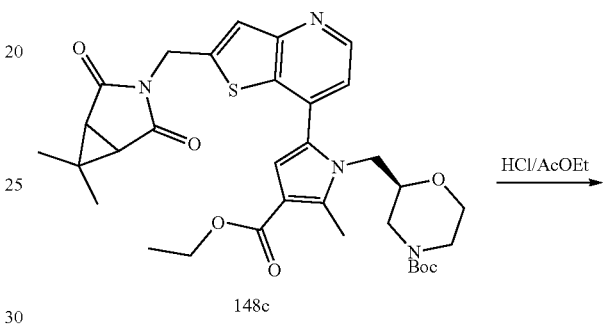

148

The title compound (148) was obtained as a TFA salt from 148c (the crude product) according to the General Procedure IVa in 12% yield (per two steps) (16 mg; 0.025 mmol). The crude product was purified by preparative reversed-phase column chromatography (C-18, water/MeCN+1‰ TFA, 99:1 to 40:60, 30 min, 20 mL/min).

ESI-MS m/z for $C_{28}NH_{33}N_4O_5S$ found 537.1 $[M+H]^+$; $R_t$=0.89 min; $^1H$ NMR (700 MHz, $D_2O$) δ 8.69-8.62 (m, 1H), 7.67-7.57 (m, 2H), 7.06 (s, 1H), 4.93 (s, 2H), 4.35-4.22 (m, 4H), 3.74-3.69 (m, 1H), 3.57-3.50 (m, 1H), 3.46-3.36 (m, 1H), 3.20 (d, J=12.8 Hz, 1H), 3.09 (d, J=13.0 Hz, 1H), 2.87-2.78 (m, 1H), 2.64-2.59 (m, 3H), 2.59 (s, 3H), 1.31 (t, J=7.1 Hz, 3H), 1.20 (s, 3H), 1.05 (s, 3H).

Example 149

Synthesis of 6,6-dimethyl-3-((7-(1-(((S)-morpholin-2-yl)methyl)-4-(trifluoromethyl)-1H-imidazol-2-yl)thieno[3,2-b]pyridin-2-yl)methyl)-3-azabicyclo[3.1.0]hexane-2,4-dione 2,2,2-trifluoroacetate (149)

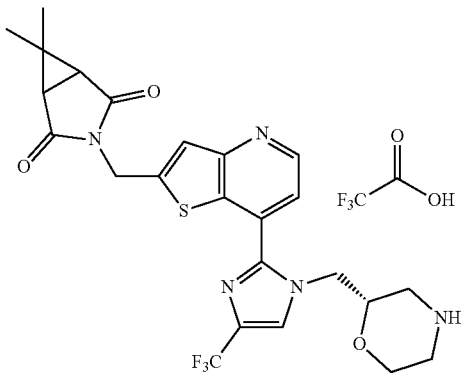

149

The title compound (149) was obtained as a TFA salt in 1% overall yield in a similar way to Example 148 with the exception that, in the first step of the synthesis 4-(trifluoromethyl)-1H-imidazole was used instead of ethyl 2-methyl-1H-pyrrole-3-carboxylate and the second step of the synthesis was carried out in a different way (the synthesis is described below) and in the last step of the synthesis the crude product was purified by preparative reversed-phase column chromatography (C-18, water/MeCN+1‰ TFA, 99:1 to 50:50, 30 min, 20 mL/min).

ESI-MS m/z for $C_{24}H_{25}F_3N_5O_3S$ found 520.0 [M+H]$^+$; $R_t$=0.99 min; $^1$H NMR (700 MHz, D$_2$O) δ 8.82-8.76 (m, 1H), 7.97 (s, 1H), 7.79-7.74 (m, 1H), 7.64 (s, 1H), 4.93 (s, 2H), 4.45-4.37 (m, 1H), 4.35-4.26 (m, 1H), 4.04-3.97 (m, 1H), 3.81-3.75 (m, 1H), 3.64-3.54 (m, 1H), 3.31 (d, J=12.8 Hz, 1H), 3.20 (d, J=13.1 Hz, 1H), 3.04-2.95 (m, 1H), 2.83-2.74 (m, 1H), 2.61 (s, 2H), 1.20 (s, 3H), 1.02 (s, 3H).

Step 2

Synthesis of tert-butyl (S)-2-((2-bromo-4-(trifluoromethyl)-1H-imidazol-1-yl)methyl)morpholine-4-carboxylate (149b)

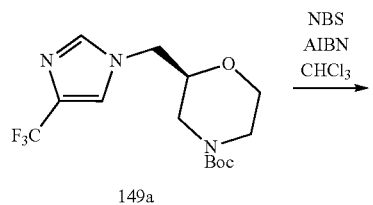

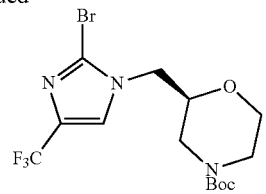

149b

To the solution of tert-butyl (R)-2-((4-(trifluoromethyl)-1H-imidazol-1-yl)methyl)morpholine-4-carboxylate (149a) (106 mg; 0.316 mmol) in CHCl$_3$ (3 mL) NBS (68 mg; 0.379 mmol) and AIBN (3 mg; 0.016 mmol) were added and then stirred at 60° C. overnight. Then another portions of NBS (2×68 mg; 0.758 mmol) were added and stirred at 60° C. two days. The reaction progress was monitored by LC-MS. When analysis indicated completion of the reaction, to this mixture 5% NaHCO$_3$ was added and then extracted with CHCl$_3$. The organic layer was dried over anhydrous MgSO$_4$, filtered and concentrated in vacuo and the crude product was purified by flash column chromatography on silica (hexane/AcOEt, 60:40, v/v, 20 minutes, 6 mL/min). Compound 149b was obtained in 5% yield (7 mg; 0.016 mmol).

ESI-MS m/z for $C_{14}H_{20}BrF_3N_3O_3$ found 414.0/416.0 [M+H]$^+$; $R_t$=1.53 min

Example 150

Synthesis of (S)-7-(5-chloro-3-methyl-2-(piperidin-3-yloxy)phenyl)furo[3,2-b]pyridine 2,2,2-trifluoroacetate (150)

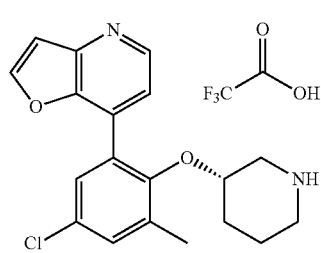

150

The title compound (150) was obtained as a TFA salt in 7% overall yield in a similar way to Example 31 with the exception that, in the third step of the synthesis 7-chlorofuro[3,2-b]pyridine was used instead of from 4-chlorothieno[2,3-b]pyridine and in the fourth step of the synthesis the General Procedure IVb was used instead of the General Procedure IVa and the crude product was purified by preparative reversed-phase column chromatography (Luna Phenyl-Hexyl 5 μm, 250×21.2 mm, water/MeCN+1‰ TFA, 90:10 to 10:90.45 min, 17 mL/min).

ESI-MS m/z for $C_{19}H_{20}ClN_2O_2$ found 343.2/345.2 [M+H]$^+$; $R_t$=5.74 min; $^1$H NMR (700 MHz, Methanol-d$_4$) δ 8.65-8.59 (m, 1H), 8.27-8.21 (m, 1H), 7.61-7.56 (m, 1H), 7.50-7.45 (m, 2H), 7.19-7.14 (m, 1H), 3.80-3.72 (m, 1H), 3.08-3.01 (m, 1H), 3.01-2.89 (m, 2H), 2.83-2.70 (m, 1H), 2.43 (s, 3H), 1.70-1.53 (m, 2H), 1.40-1.31 (m, 3H).

Example 151

Synthesis of 3-((7-(5-chloro-3-methyl-2-(((S)-piperidin-3-yl)oxy)phenyl)thiazolo[4,5-b]pyridin-2-yl)methyl)-6,6-dimethyl-3-azabicyclo[3.1.0]hexane-2,4-dione dihydrochloride (151)

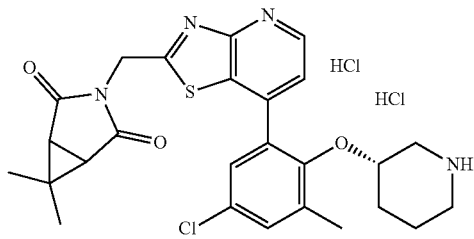

The title compound (151) was obtained as a dihydrochloride salt in 5% overall yield in a similar way to Example 31 with the exception that, in the third step of the synthesis 3-((7-chlorothiazolo[4,5-b]pyridin-2-yl)methyl)-6,6-dimethyl-3-azabicyclo[3.1.0]hexane-2,4-dione (151f—the synthesis of this compound is described below) was used instead of from 4-chlorothieno[2,3-b]pyridine and in the fourth step of the synthesis the crude product was purified by preparative reversed-phase column chromatography (C-18, water+0.3%0 HCl (36%)/MeCN, 99:1 to 35:65, 30 min, 17 mL/min).

ESI-MS m/z for $C_{26}H_{28}ClN_4O_3S$ found 511.1/513.1 [M+H]$^+$; $R_t$=1.07 min; $^1$H NMR (700 MHz, D$_2$O) δ 8.84 (d, J=6.1 Hz, 1H), 8.28 (d, J=6.1 Hz, 1H), 7.63 (dd, J=2.7, 0.7 Hz, 1H), 7.47 (d, J=2.6 Hz, 1H), 5.21 (s, 2H), 3.92-3.87 (m, 1H), 3.20-3.15 (m, 1H), 3.06-3.01 (m, 1H), 2.94-2.88 (m, 2H), 2.76 (s, 2H), 2.43 (s, 3H), 1.55-1.50 (m, 1H), 1.42-1.36 (m, 1H), 1.35-1.33 (m, 1H), 1.33 (s, 3H), 1.28 (s, 3H), 1.16-1.09 (m, 1H).

Synthesis of 3-((7-chlorothiazolo[4,5-b]pyridin-2-yl)methyl)-6,6-dimethyl-3-azabicyclo[3.1.0]hexane-2,4-dione (151f)

Step 1

Synthesis of 7-chlorothiazolo[4,5-b]pyridine-2-thiol (151a)

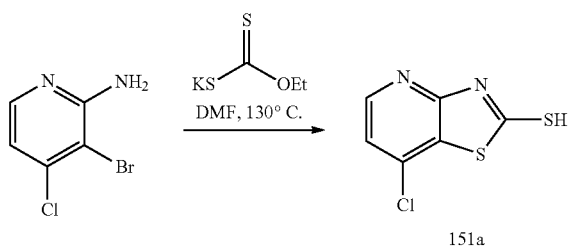

3-Bromo-4-chloropyridin-2-amine (1 g; 4.82 mmol) and potassium O-ethyl carbonodithioate (1.08 g; 6.75 mmol) were dissolved in DMF (8 ml) and stirred at 130° C. overnight. To the reaction mixture water (15 mL) was added and then pH was adjusted to 6 with 2 M HCl. The solid was collected by filtration and dried by air. Compound 151a was obtained as a yellow solid in 59% yield (0.58 g; 2.86 mmol).

ESI-MS m/z for $C_6H_4ClN_2S_2$ found 202.9/204.9 [M+H]$^+$; $R_t$=1.05 min; $^1$H NMR (700 MHz, DMSO-d$_6$) δ 8.31 (d, J=5.5 Hz, 1H), 7.27 (d, J=5.5 Hz, 1H).

Step 2

Synthesis of 2-bromo-7-chlorothiazolo[4,5-b]pyridine (151b)

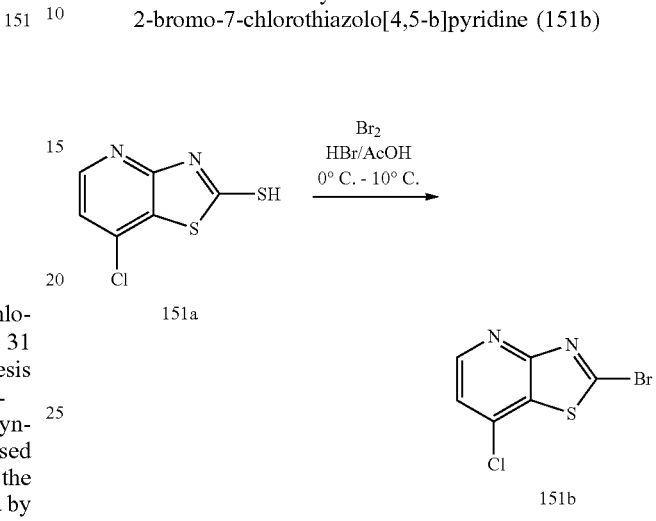

To a cooled to 0° C. solution of 151a (0.56 g; 2.79 mmol) in HBr/AcOH (6 mL), bromine (0.22 mL; 4.18 mmol) was added dropwise. The resulting mixture was stirred at 10° C. for 2 hours. Then it was quenched with water with ice (20 mL) and pH was adjusted to 5 with 2 M NaOH. The residue was extracted with DCM (4×20 mL). The combined organic layers were dried over anhydrous Na$_2$SO$_4$, filtered and concentrated in vacuo and the crude product was purified by flash column chromatography on silica gel (hexane/AcOEt, 100:0 to 80:20, v/v). Compound 151b was obtained as a beige solid in 42% yield (0.29 g; 1.16 mmol).

$^1$H NMR (700 MHz, CDCl$_3$) δ 8.43 (d, J=5.5 Hz, 1H), 7.81 (d, J=5.5 Hz, 1H).

Step 3

Synthesis of 7-chlorothiazolo[4,5-b]pyridine-2-carbaldehyde (151c)

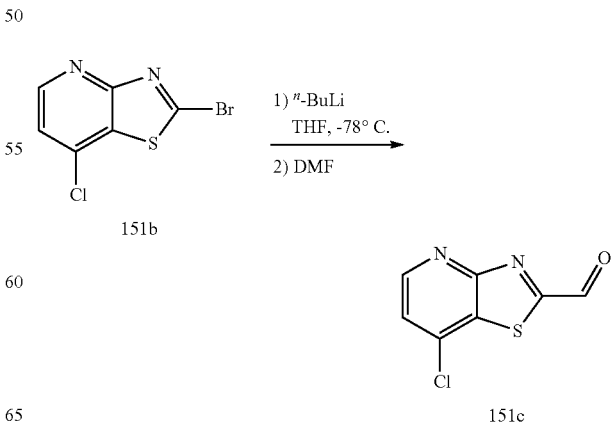

To a solution of 151b (0.28 g; 1.12 mmol) in anhydrous THF (7 mL) n-BuLi (2.5 M in hexane; 0.58 mL; 1.46 mmol) was added dropwise at −78° C. The resulting mixture was stirred additional 30 minutes. Anhydrous DMF (0.43 mL; 5.61 mmol) was then added dropwise at −78° C. and the reaction was stirred at this temperature for 1 hour. The reaction progress was monitored by LC-MS. When analysis indicated completion of the reaction, a saturated solution of NH$_4$Cl (25 mL) was added dropwise and the reaction mixture was warmed to room temperature. The reaction was extracted with AcOEt (3×20 mL). The combined organic solutions were washed with water (1×40 mL) and brine (2×40 mL), dried over anhydrous Na$_2$SO$_4$, filtered and concentrated in vacuo. The compound was used to the next step without additional purification. Compound 151c was obtained as a brown solid in 99% yield (0.22 g; 1.11 mmol).

$^1$H NMR (700 MHz, CDCl$_3$) δ 8.43 (d, J=5.5 Hz, 1H), 7.81 (d, J=5.5 Hz, 1H).

Step 4

Synthesis of (7-chlorothiazolo[4,5-b]pyridin-2-yl)methanol (151d)

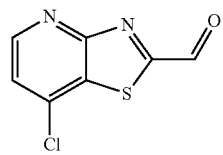
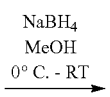

To a cooled to 0° C. suspension of 151c (0.22 g; 1.1 mmol) in MeOH (10 mL), NaBH$_4$ (63 mg; 1.66 mmol) was added portionwise. The resulting mixture was warmed to room temperature and stirred for 0.5 hour. Then, the reaction mixture was quenched with water (20 mL) and MeOH was evaporated in vacuo. The residue was extracted with AcOEt (3×100 mL). The combined organic solutions were dried over anhydrous Na$_2$SO$_4$, filtered and concentrated in vacuo. The crude product was purified by flash column chromatography on silica (hexane/AcOEt, 100:0 to 70:30, v/v). Compound 151d was obtained as a beige solid in 45% yield (0.1 g; 0.5 mmol).

ESI-MS m/z for C$_7$H$_6$ClN$_2$OS found 201.0 [M+H]$^+$; R$_t$=0.71 min; $^1$H NMR (700 MHz, CDCl$_3$) δ 8.43 (d, J=5.5 Hz, 1H), 7.79 (d, J=5.5 Hz, 1H), 5.14 (d, J=5.9 Hz, 2H).

Step 5

Synthesis of (7-chlorothiazolo[4,5-b]pyridin-2-yl)methyl methanesulfonate (151e)

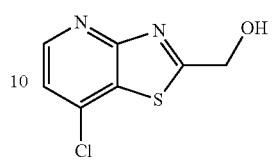
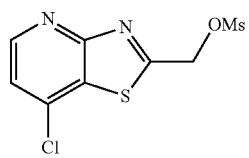

The title compound (151e) was obtained from 151d (95 mg; 0.47 mmol) according to the General Procedure VIII in 96% yield (126 mg; 0.45 mmol).

$^1$H NMR (700 MHz, CDCl$_3$) δ 8.49 (d, J=5.6 Hz, 1H), 7.86 (d, J=5.6 Hz, 1H), 5.63 (s, 2H), 3.21 (s, 3H).

Step 6

Synthesis of 3-((7-chlorothiazolo[4,5-b]pyridin-2-yl)methyl)-6,6-dimethyl-3-azabicyclo[3.1.0]hexane-2,4-dione (151f)

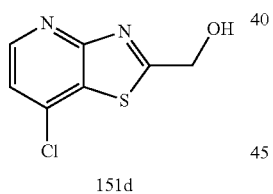
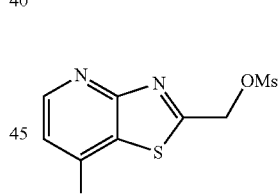
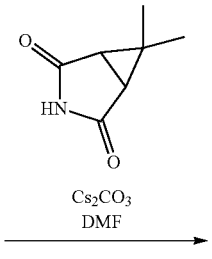
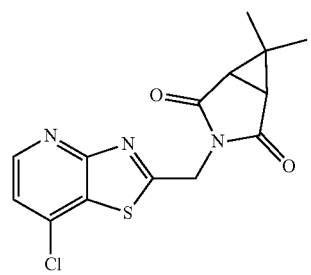

To a solution of 151e (124 mg; 0.45 mmol) in anhydrous DMF (4 mL), 6,6-dimethy-3-aza-bicyclo[3.1.0]hexane 2,4-dione (210 mg; 0.49 mmol) and Cs$_2$CO$_3$ (290 mg; 0.89 mmol) were added. The resulting mixture was stirred at room temperature overnight. The reaction progress was monitored by LC-MS. When analysis indicated completion of the reaction, DMF was removed in vacuo and the residue was dissolved in AcOEt (50 mL) and washed with water (1×40 mL) and brine (1×30 mL). The organic phase was dried over anhydrous NaSO$_4$, filtered and concentrated in vacuo. The crude product was purified by flash column chromatography on silica (hexane/AcOEt, 100:0 to 80:20, v/v). Compound 151f was obtained as a yellow solid in 52% yield (75 mg; 0.23 mmol).

$^1$H NMR (700 MHz, CDCl$_3$) δ 8.42 (d, J=5.5 Hz, 1H), 7.80 (d, J=5.5 Hz, 1H), 5.01 (s, 2H), 2.48 (s, 2H), 1.31 (s, 3H), 1.30 (s, 3H).

Example 152

Synthesis of 3-((7-(5-fluoro-2-(((S)-piperidin-3-yl)oxy)pyridin-3-yl)thieno[3,2-b]pyridin-2-yl)methyl)-6,6-dimethyl-3-azabicyclo[3.1.0]hexane-2,4-dione dihydrochloride (152)

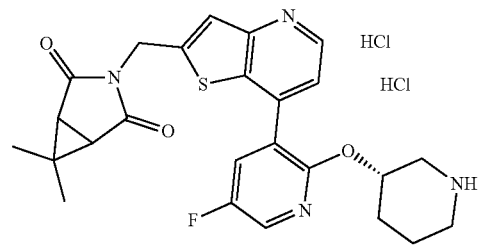

152

Step 1

Synthesis of tert-butyl (S)-3-((3-bromo-5-fluoropyridin-2-yl)oxy)piperidine-1-carboxylate (152a)

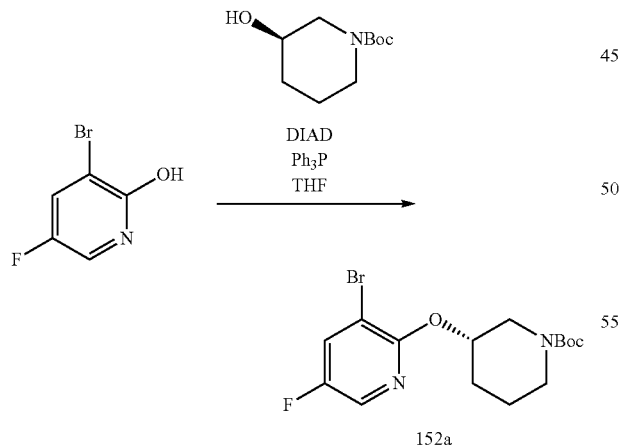

152a

To a cooled to −10° C. solution of 3-bromo-5-fluoropyridin-2-ol (50 mg; 0.26 mmol), tert-butyl (R)-3-hydroxypiperidine-1-carboxylate (63 mg; 0.31 mmol) and Ph$_3$P (81 mg; 0.31 mmol) in dry THF (3 ml) DIAD (67 µL; 0.34 mmol) was slowly added. The resulting mixture was stirred at room temperature overnight. Then the reaction mixture was concentrated in vacuo and the residue was purified by flash column chromatography on silica (hexane/AcOEt, 100:0 to 0:100, v/v, 17 min, 8 mL/min). Compound 152a was obtained in 50% yield (48 mg; 0.13 mmol).

ESI-MS m/z for C$_{11}$H$_{13}$BrFN$_2$O$_3$ found 318.8/320.8 [M+H-tBu]$^+$; R$_t$=1.76 min Step 2

Synthesis of tert-butyl (3S)-3-((3-(2-((6,6-dimethyl-2,4-dioxo-3-azabicyclo[3.1.0]hexan-3-yl)methyl)thieno[3,2-b]pyridin-7-yl)-5-fluoropyridin-2-yl)oxy)piperidine-1-carboxylate (152b)

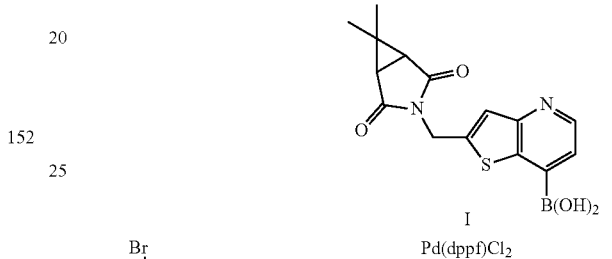

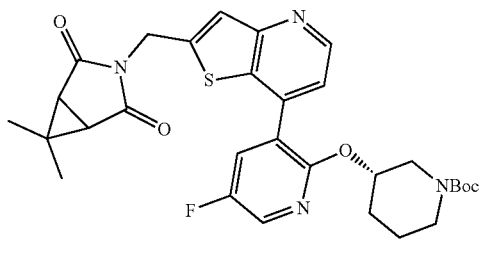

152b

The title compound (152b) was obtained from 152a (44 mg; 0.117 mmol) and from boronic acid I (46 mg; 0.141 mmol) according to the General Procedure Va in 55% yield (38 mg; 0.065 mmol). The crude product was purified by flash column chromatography on silica (hexane/AcOEt, 100:0 to 0:100, v/v, 27 min, 8 mL/min).

ESI-MS m/z for C$_{30}$H$_{34}$FN$_4$O$_5$S found 581.1 [M+H]$^+$; R$_t$=1.74 min

Step 3

Synthesis of 3-((7-(5-fluoro-2-(((S)-piperidin-3-yl)oxy)pyridin-3-yl)thieno[3,2-b]pyridin-2-yl)methyl)-6,6-dimethyl-3-azabicyclo[3.1.0]hexane-2,4-dione dihydrochloride (152)

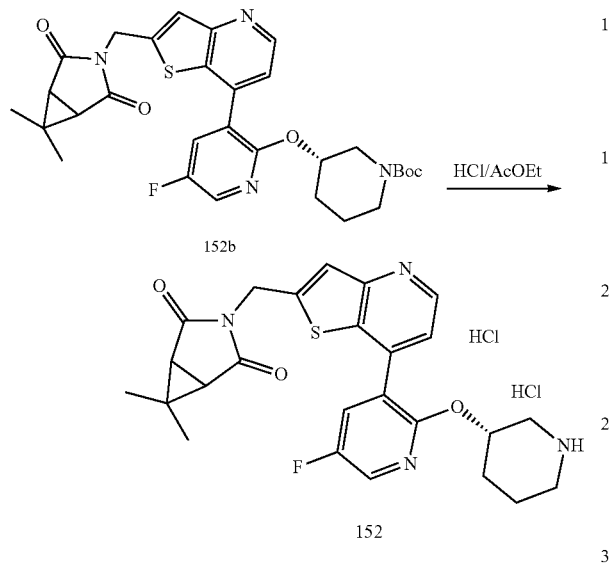

The title compound (152) was obtained as a dihydrochloride salt from 152b (37 mg; 0.064 mmol) according to the General Procedure IVa in 67% yield (24 mg; 0.043 mmol). The crude product was purified by preparative reversed-phase column chromatography (C-18, water+0.3‰ HCl (36%)/MeCN, 98:2 to 30:70, 30 min, 20 mL/min).

ESI-MS m/z for $C_{25}H_{26}FN_4O_3S$ found 481.4 [M+H]$^+$; 1&=0.91 min; $^1$H NMR (700 MHz, Methanol-d$_4$) δ 9.01-8.98 (m, 1H), 8.39-8.37 (m, 1H), 8.08-8.05 (m, 1H), 8.05-8.03 (m, 1H), 7.82-7.79 (m, 1H), 5.60-5.51 (m, 1H), 5.03-4.98 (m, 2H), 3.54-3.48 (m, 1H), 3.48-3.42 (m, 1H), 3.19-3.11 (m, 2H), 2.57 (s, 2H), 2.12-2.05 (m, 1H), 2.05-1.99 (m, 1H), 1.88-1.74 (m, 2H), 1.29 (s, 3H), 1.18 (s, 3H); $^{19}$F NMR (659 MHz, Methanol-d$_4$) δ -137.98 (d, J=7.9 Hz).

Example 153

Synthesis of 3-((7-(3-(((3aR,6aR)-hexahydropyrrolo[3,4-b]pyrrol-1(2H)-yl)methyl)-4-methyl-6-(trifluoromethyl)pyridin-2-yl)thieno[3,2-b]pyridin-2-yl)methyl)-6,6-dimethyl-3-azabicyclo[3.1.0]hexane-2,4-dione trihydrochloride (153)

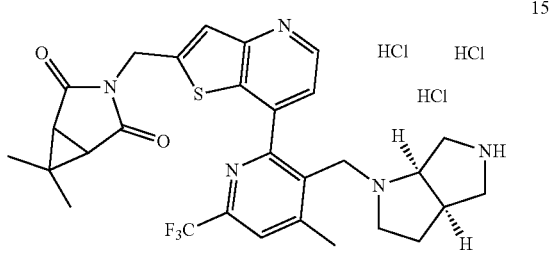

The title compound (153) was obtained as a trihydrochloride salt as a racemate in 30% overall yield in a similar way to Example 40 with the exception that, in the first step of the synthesis tert-butyl (3aR,6aR)-hexahydropyrrolo[3,4-b]pyrrole-5(1H)-carboxylate was used instead of tert-butyl 3-oxopiperazine-1-carboxylate. This synthesis step was carried out in a different way (the synthesis was described below). In the last step of the synthesis the crude product was purified by preparative reversed-phase column chromatography (C-18, water+0.3‰ HCl (36%)/MeCN, 98:2 to 30:70, 30 min, 20 mL/min).

ESI-MS m/z for $C_{29}H_{31}F_3N_5O_2S$ found 570.6 [M+H]$^+$; R$_t$=0.98 min; $^1$H NMR (700 MHz, Methanol-d$_4$) δ 8.92-8.87 (m, 1H), 7.92 (s, 1H), 7.80-7.76 (m, 1H), 7.71-7.66 (m, 1H), 4.95-4.92 (m, 2H), 4.12-4.03 (m, 1H), 3.78-3.68 (m, 1H), 3.21-3.14 (m, 1H), 3.13-3.04 (m, 2H), 3.04-2.95 (m, 2H), 2.94-2.85 (m, 1H), 2.78 (s, 3H), 2.65-2.58 (m, 1H), 2.54-2.49 (m, 2H), 1.99-1.86 (m, 2H), 1.46-1.36 (m, 1H), 1.26 (s, 3H), 1.11 (s, 3H); $^{19}$F NMR (659 MHz, Methanol-d$_4$) δ -69.32.

Step 1

Synthesis of tert-butyl (3aR,6aR)-1-((2-chloro-4-methyl-6-(trifluoromethyl)pyridin-3-yl)methyl)hexahydropyrrolo[3,4-b]pyrrole-5(1H)-carboxylate (153a)

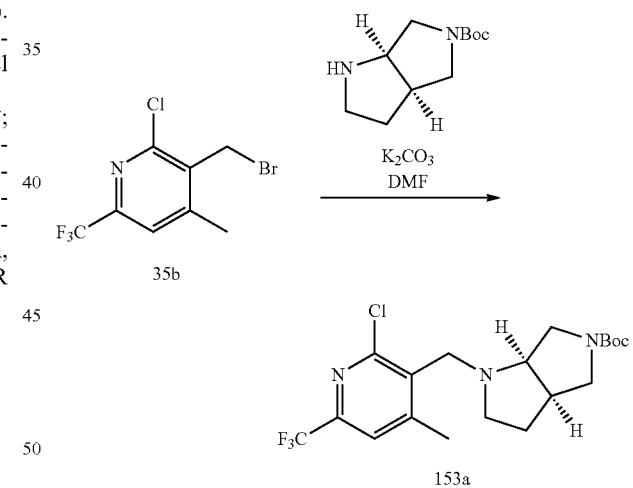

To a solution of 35b (97 mg; 0.336 mmol) and tert-butyl (3aR,6aR)-hexahydropyrrolo[3,4-b]pyrrole-5(1H)-carboxylate (60 mg; 0.280 mmol) in DMF (1 mL) K$_2$CO$_3$ (58 mg; 0.420 mmol) was added and then the reaction mixture was stirred at 50° C. for 3 hours. The reaction progress was monitored by LC-MS. When analysis indicated completion of the reaction, the mixture was diluted with AcOEt (20 mL) and washed with brine (15 mL). The organic layer was dried over anhydrous NaSO$_4$, filtered and concentrated in vacuo. The title compound 153a was obtained as a colorless oil in 99% yield (117 mg; 0.279 mmol).

ESI-MS m/z for $C_{19}H_{26}ClF_3N_3O_2$ found 420.0/422.0 [M+H]$^+$; R$_t$=1.43 min

Example 154

Synthesis of 6,6-dimethyl-3-((7-(5-methyl-1-(((S)-morpholin-2-yl)methyl)-4-nitro-1H-pyrrol-2-yl)thieno[3,2-b]pyridin-2-yl)methyl)-3-azabicyclo[3.1.0]hexane-2,4-dione hydrochloride (154)

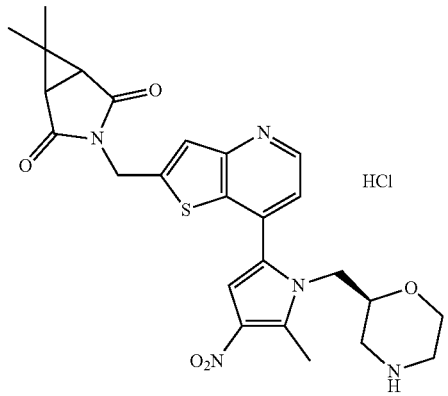

154

The title compound (154) was obtained as a hydrochloride salt in 5% overall yield in a similar way to Example 148 with the exception that, in the first step of the synthesis 2-methyl-3-nitro-1H-pyrrole was used instead of 2-methyl-1H-pyrrole-3-carboxylate and in the last step of the synthesis the crude product was purified by preparative reversed-phase column chromatography (C-18, water+0.3‰ HCl (36%)/MeCN, 99:1 to 40:60, 30 min, 20 mL/min).

ESI-MS m/z for $C_{28}H_{28}N_5O_5S$ found 510.4[M+H]$^+$; $R_t$=0.90 min; $^1$H NMR (700 MHz, Methanol-$d_4$) δ 8.79-8.75 (m, 1H), 7.62-7.57 (m, 2H), 7.15 (s, 1H), 4.93-4.92 (m, 2H), 4.39-4.31 (m, 1H), 4.30-4.23 (m, 1H), 3.82-3.76 (m, 1H), 3.75-3.68 (m, 1H), 3.59-3.49 (m, 1H), 3.23-3.19 (m, 1H), 3.18-3.11 (m, 1H), 3.01-2.92 (m, 1H), 2.80 (s, 3H), 2.80-2.72 (m, 1H), 2.56 (s, 2H), 1.28 (s, 3H), 1.16 (s, 3H).

Example 155

Synthesis of ethyl 2-(2-((6,6-dimethyl-2,4-dioxo-3-azabicyclo[3.1.0]hexan-3-yl)methyl)thieno[3,2-b]pyridin-7-yl)-5-methyl-1-(((S)-morpholin-2-yl)methyl)-4-(trifluoromethyl)-1H-pyrrole-3-carboxylate hydrochloride (155)

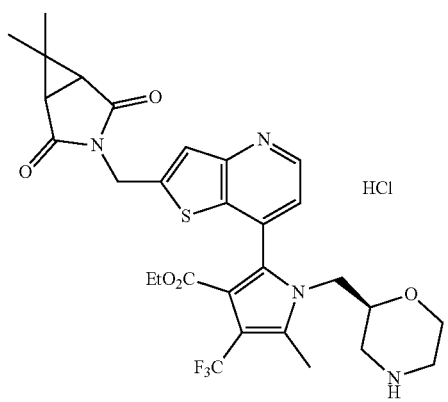

155

The title compound (155) was obtained as a hydrochloride salt in 23% overall yield in a similar way to Example 148 with the exception that, in the first step of the synthesis ethyl 5-methyl-4-(trifluoromethyl)-1H-pyrrole-3-carboxylate 155a (the synthesis of this compound was described below) was used instead of 2-methyl-1H-pyrrole-3-carboxylate and in the last step of the synthesis the crude product was purified by preparative reversed-phase column chromatography (C-18, water+0.3‰ HCl (36%)/MeCN, 90:10 to 40:60, 30 min, 20 mL/min).

ESI-MS m/z for $C_{29}H_{32}F_3N_4O_5S$ found 605.4 [M+H]$^+$; $R_t$=1.01 min; $^1$H NMR (700 MHz, $D_2O$) δ 8.83-8.78 (m, 1H), 7.68-7.61 (m, 2H), 4.98-4.85 (m, 2H), 4.18-4.13 (m, 1H), 4.05-3.97 (m, 1H), 3.84-3.75 (m, 3H), 3.61-3.40 (m, 3H), 3.27-2.94 (m, 2H), 2.75-2.58 (m, 2H), 2.48-2.42 (m, 3H), 1.20 (s, 3H), 1.09-1.02 (m, 3H), 0.55-0.47 (m, 3H).

Synthesis of ethyl 5-methyl-4-(trifluoromethyl)-1H-pyrrole-3-carboxylate (155a)

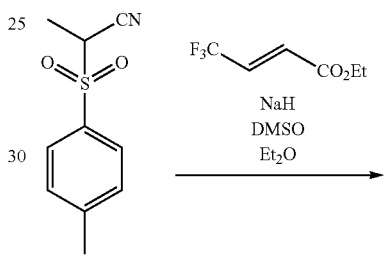

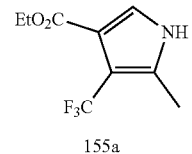

155a

The solution of 2-tosylpropanenitrile (2.05 g; 8.81 mmol) and ethyl (E)-4,4,4-trifluorobut-2-enoate (1.50 g; 8.92 mmol) in DMSO (12 mL) and $Et_2O$ (18 mL) was added dropwise to the suspension of NaH (60% in mineral oil; 784 mg; 19.62 mmol) in $Et_2O$ (30 mL) and the mixture was stirred at room temperature for 1.5 hours. The reaction progress was monitored by LC-MS. When analysis indicated completion of the reaction, the mixture was diluted with AcOEt and washed with water. The organic layer was dried over anhydrous $MgSO_4$, filtered and concentrated in vacuo and the crude product was purified by flash column chromatography on silica (hexane/AcOEt, 100:0 to 0:100, v/v, 20 min, 30 mL/min). The title compound 155a was obtained in 82% yield (1.60 g; 7.24 mmol).

ESI-MS m/z for $C_9H_{11}F_3NO_2$ found 222.0 [M+H]$^+$; $R_t$=1.25 min

Example 156

Synthesis of 3-((7-(3-(2,5-diazabicyclo[2.2.2]octane-2-carbonyl)-4-methyl-6-(trifluoromethyl)pyridin-2-yl)thieno[3,2-b]pyridin-2-yl)methyl)-6,6-dimethyl-3-azabicyclo[3.1.0]hexane-2,4-dione hydrochloride (156)

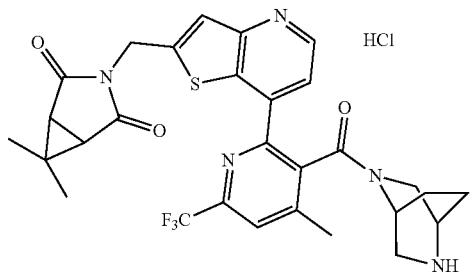

156

The title compound (156) was obtained as a hydrochloride salt in 43% overall yield in a similar way to Example 45 with the exception that, in the first step of the synthesis tert-butyl 2,5-diazabicyclo[2.2.2]octane-2-carboxylate was used instead of tert-butyl piperazine-1-carboxylate and acid II was used instead of 2-chloro-4-methylnicotinic acid and in the last step of the synthesis, the crude product was purified by preparative reversed-phase column chromatography (C-18, water+0.3‰ HCl (36%)/MeCN, 98:2 to 30:70, 30 min, 20 mL/min).

ESI-MS m/z for $C_{29}H_{29}F_3N_5O_3S$ found 584.5 $[M+H]^+$; $R_f$=0.94 min; $^1H$ NMR (700 MHz, DMSO-$d_6$+$D_2O$, 348 K) δ 8.81-8.73 (m, 1H), 8.09-7.99 (m, 1H), 7.66-7.47 (m, 2H), 4.85-4.67 (m, 2H), 3.95-3.72 (m, 2H), 3.60-3.44 (m, 1H), 3.40-3.33 (m, 1H), 3.24-2.99 (m, 2H), 2.91-2.56 (m, 1H), 2.48-2.40 (m, 3H), 2.09-1.93 (m, 1H), 1.89-1.71 (m, 2H), 1.64-1.23 (m, 2H), 1.20-1.15 (m, 3H), 1.09-0.99 (m, 3H); $^{19}F$ NMR (659 MHz, DMSO-$d_6$) δ -66.48--66.55 (m).

Example 157

Synthesis of 3-((7-(5-fluoro-2-(((S)-pyrrolidin-3-yl)oxy)pyridin-3-yl)thieno[3,2-b]pyridin-2-yl)methyl)-6,6-dimethyl-3-azabicyclo[3.1.0]hexane-2,4-dione dihydrochloride (157)

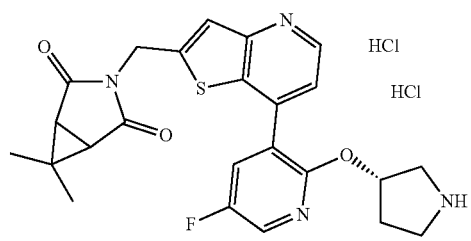

157

The title compound (157) was obtained as a dihydrochloride salt in 30% overall yield in a similar way to Example 152 with the exception that, in the first step of the synthesis tert-butyl (R)-3-hydroxypyrrolidine-1-carboxylate was used instead of tert-butyl (R)-3-hydroxypiperidine-1-carboxylate and in the last step of the synthesis, the crude product was purified by preparative reversed-phase column chromatography (C-18, water+0.3‰ HCl (36%)/MeCN, 98:2 to 30:70, 30 min, 20 mL/min).

ESI-MS m/z for $C_{24}H_{24}FN_4O_3S$ found 467.5 $[M+H]^+$; $R_f$=0.83 min; $^1H$ NMR (700 MHz, Methanol-$d_4$) δ 8.86-8.83 (m, 1H), 8.35-8.31 (m, 1H), 7.97-7.93 (m, 1H), 7.78-7.74 (m, 1H), 7.68-7.65 (m, 1H), 5.84-5.79 (m, 1H), 4.96-4.93 (m, 2H), 3.70-3.65 (m, 1H), 3.55-3.50 (m, 1H), 3.46-3.40 (m, 1H), 3.31-3.24 (m, 1H), 2.55 (s, 2H), 2.43-2.35 (m, 1H), 2.32-2.25 (m, 1H), 1.28 (s, 3H), 1.14 (s, 3H).

Example 158

Synthesis of 3-((7-(5-fluoro-2-(((R)-pyrrolidin-3-yl)oxy)pyridin-3-yl)thieno[3,2-b]pyridin-2-yl)methyl)-6,6-dimethyl-3-azabicyclo[3.1.0]hexane-2,4-dione hydrochloride (158)

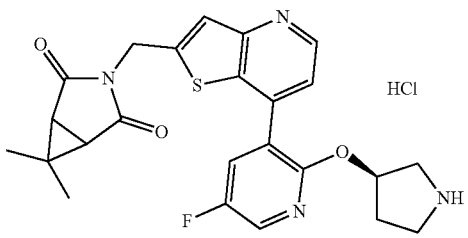

158

The title compound (158) was obtained as a hydrochloride salt in 26% overall yield in a similar way to Example 152 with the exception that, in the first step of the synthesis tert-butyl (S)-3-hydroxypyrrolidine-1-carboxylate was used instead of tert-butyl (R)-3-hydroxypiperidine-1-carboxylate and in the last step of the synthesis, the crude product was purified by preparative reversed-phase column chromatography (C-18, water+0.3%0 HCl (36%)/MeCN, 98:2 to 30:70, 30 min, 20 mL/min).

ESI-MS m/z for $C_{24}H_{24}FN_4O_3S$ found 467.3 $[M+H]^+$; $R_f$=0.84 min; $^1H$ NMR (700 MHz, Methanol-$d_4$) δ 8.81-8.78 (m, 1H), 8.33-8.29 (m, 1H), 7.94-7.89 (m, 1H), 7.67-7.64 (m, 1H), 7.63-7.60 (m, 1H), 5.83-5.78 (m, 1H), 4.93-4.91 (m, 2H), 3.70-3.65 (m, 1H), 3.54-3.49 (m, 1H), 3.46-3.40 (m, 1H), 3.30-3.23 (m, 1H), 2.54 (s, 2H), 2.43-2.34 (m, 1H), 2.32-2.25 (m, 1H), 1.27 (s, 3H), 1.13 (s, 3H).

Example 159

Synthesis of 3-((7-(3-(((3aR,6aR)-hexahydropyrrolo[3,4-b]pyrrol-1(2H)-yl)methyl)-4-methyl-6-(trifluoromethyl)pyridin-2-yl)thieno[3,2-b]pyridin-2-yl)methyl)-6,6-dimethyl-3-azabicyclo[3.1.0]hexane-2,4-dione trihydrochloride (159)

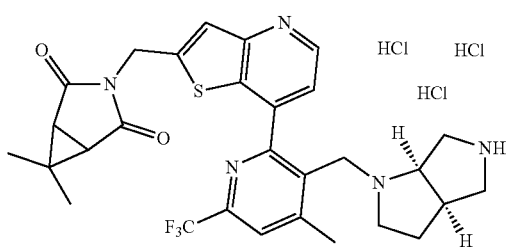

159

The title compound (159) was obtained as a trihydrochloride salt as a single enantiomer in 28% overall yield in the same way as Example 153 with the exception that in the first step of the synthesis optically pure tert-butyl (3aR,6aR)-hexahydropyrrolo[3,4-b]pyrrole-5(1H)-carboxylate was used instead of racemate. In the last step of the synthesis the crude product was purified by preparative reversed-phase column chromatography (C-18, water+0.3‰ HCl (36%)/MeCN, 98:2 to 30:70, 30 min, 20 mL/min).

ESI-MS m/z for $C_{29}H_{31}F_3N_5O_2S$ found 570.3 [M+H]$^+$; $R_t$=0.99 min; $^1$H NMR (700 MHz, Methanol-d$_4$) δ 8.88-8.84 (m, 1H), 7.89 (s, 1H), 7.75-7.70 (m, 1H), 7.67-7.63 (m, 1H), 4.93-4.89 (m, 2H), 4.11-4.00 (m, 1H), 3.78-3.66 (m, 1H), 3.18-3.11 (m, 1H), 3.10-3.00 (m, 2H), 3.00-2.92 (m, 2H), 2.89-2.82 (m, 1H), 2.76 (s, 3H), 2.64-2.55 (m, 1H), 2.50 (s, 2H), 1.98-1.84 (m, 2H), 1.46-1.36 (m, 1H), 1.24 (s, 3H), 1.08 (s, 3H).

Example 160

Synthesis of 6,6-dimethyl-3-((7-(4-methyl-3-(((S)-3-(methylamino)pyrrolidin-1-yl)methyl)-6-(trifluoromethyl)pyridin-2-yl)thieno[3,2-b]pyridin-2-yl)methyl)-3-azabicyclo[3.1.0]hexane-2,4-dione hydrochloride (160)

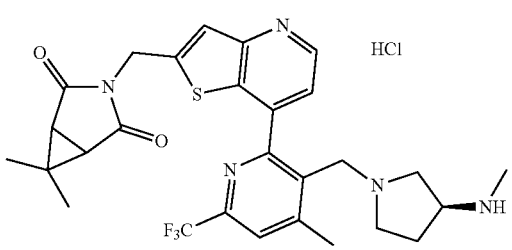

160

The title compound (160) was obtained as a hydrochloride salt in 20% overall yield in a similar way to Example 153 with the exception that, in the first step of the synthesis tert-butyl (S)-methyl(pyrrolidin-3-yl)carbamate was used instead of tert-butyl 3-oxopiperazine-1-carboxylate, and in the last step of the synthesis the crude product was purified by preparative reversed-phase column chromatography (C-18, water+0.3‰ HCl (36%)/MeCN, 99:1 to 40:60, 30 min, 20 mL/min).

ESI-MS m/z for $C_{28}H_{31}F_3N_5O_2S$ found 558.4 [M+H]$^+$; $R_t$=0.98 min; $^1$H NMR (700 MHz, D$_2$O) δ 8.85 (s, 1H), 8.03 (s, 1H), 7.71 (s, 1H), 7.68 (s, 1H), 4.99-4.95 (m, 2H), 4.20-4.09 (m, 2H), 3.66-3.58 (m, 1H), 2.97-2.90 (m, 1H), 2.76-2.70 (m, 5H), 2.68 (s, 2H), 2.57-2.50 (m, 4H), 2.21-2.11 (m, 1H), 1.83-1.75 (m, 1H), 1.27 (s, 3H), 1.07 (s, 3H).

Example 161

Synthesis of 3-((7-(5-chloro-2-(((S)-piperidin-3-yl)oxy)pyridin-3-yl)thieno[3,2-b]pyridin-2-yl)methyl)-6,6-dimethyl-3-azabicyclo[3.1.0]hexane-2,4-dione dihydrochloride (161)

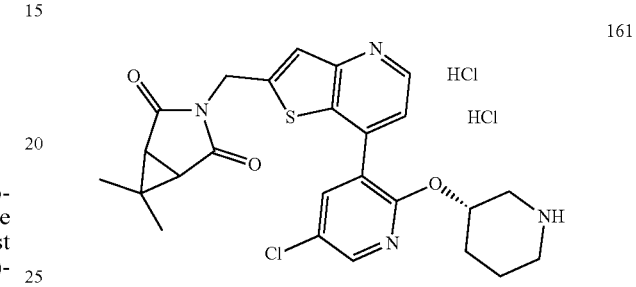

161

The title compound (161) was obtained as a dihydrochloride salt in 28% overall yield in a similar way to Example 152 with the exception that, in the first step of the synthesis 3-bromo-5-chloropyridin-2-ol was used instead of 3-bromo-5-fluoropyridin-2-ol and in the last step of the synthesis, the crude product was purified by preparative reversed-phase column chromatography (C-18, water+0.3‰ HCl (36%)/MeCN, 98:2 to 30:70, 30 min, 20 mL/min).

ESI-MS m/z for $C_{25}H_{26}ClN_4O_3S$ found 497.2/499.2 [M+H]$^+$; $R_t$=0.96 min; $^1$H NMR (700 MHz, Methanol-d$_4$) δ 8.82-8.78 (m, 1H), 8.40-8.36 (m, 1H), 8.08-8.05 (m, 1H), 7.72-7.68 (m, 1H), 7.64-7.61 (m, 1H), 5.53-5.49 (m, 1H), 4.93-4.89 (m, 2H), 3.53-3.47 (m, 1H), 3.42-3.37 (m, 1H), 3.16-3.09 (m, 2H), 2.53 (s, 2H), 2.10-2.04 (m, 1H), 1.99-1.94 (m, 1H), 1.83-1.74 (m, 2H), 1.25 (s, 3H), 1.12 (s, 3H).

Example 162

Synthesis of 3-((7-(4-chloro-5-methyl-1-(((S)-morpholin-2-yl)methyl)-1H-pyrrol-2-yl)thieno[3,2-b]pyridin-2-yl)methyl)-6,6-dimethyl-3-azabicyclo[3.1.0]hexane-2,4-dione hydrochloride (162)

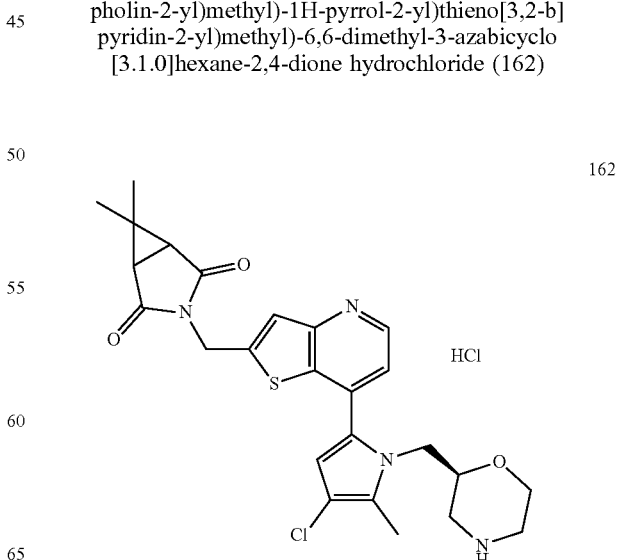

162

Step 1

Synthesis of tert-butyl (R)-2-((3-chloro-5-(ethoxycarbonyl)-2-methyl-1H-pyrrol-1-yl)methyl)morpholine-4-carboxylate (162a)

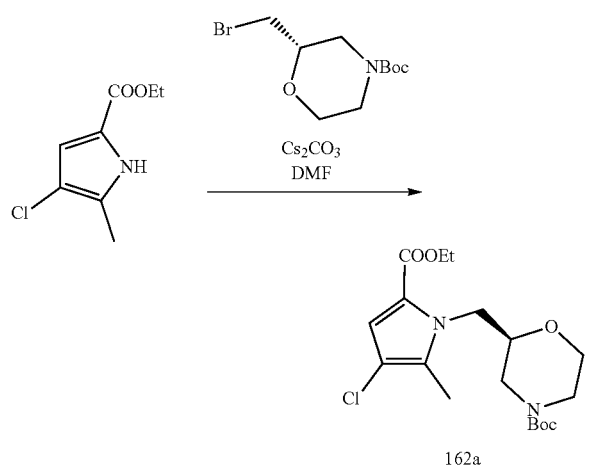

To the solution of ethyl 4-chloro-5-methyl-1H-pyrrole-2-carboxylate (92 mg; 0.49 mmol) in DMF (2 mL) tert-butyl (S)-2-(bromomethyl)morpholine-4-carboxylate (165 mg; 0.59 mmol) and Cs$_2$CO$_3$ (319 mg; 0.98 mmol) were added and then the reaction mixture was heated at 60° C. overnight. The reaction progress was monitored by TLC and LC-MS. When analyses indicated completion of the reaction, the mixture was concentrated in vacuo and the crude product was purified by flash column chromatography on silica (hexane/AcOEt, 60:40, v/v, 20 minutes, 14 mL/min). The title compound 162a was obtained in 99% yield (185 mg; 0.48 mmol).

ESI-MS m/z for C$_{15}$H$_{27}$ClN$_2$O$_5$Na found 409.0/411.0 [M+Na]$^+$; R$_t$=1.91 min; $^1$H NMR (700 MHz, Methanol-d$_4$) δ 4.64-4.51 (m, 1H), 4.32-4.23 (m, 2H), 4.22-4.13 (m, 1H), 4.03-3.95 (m, 1H), 3.87-3.79 (m, 2H), 3.69-3.60 (m, 1H), 3.39-3.34 (m, 1H), 2.96-2.63 (m, 2H), 2.28 (s, 3H), 1.48 (s, 9H), 1.35 (t, J=7.1 Hz, 3H).

Step 2

Synthesis of (R)-1-((4-(tert-butoxycarbonyl)morpholin-2-yl)methyl)-4-chloro-5-methyl-1H-pyrrole-2-carboxylic acid (162b)

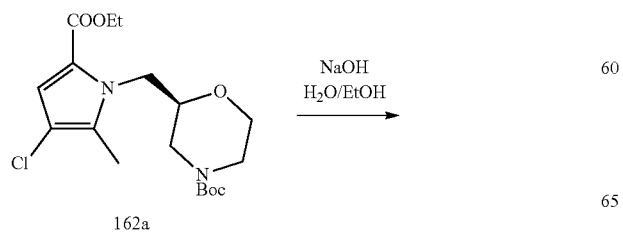

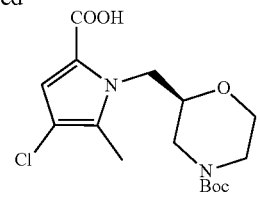

The solution of 162a (226 mg; 0.58 mmol) and NaOH (70 mg; 1.75 mmol) in H$_2$O/EtOH (3 mL/3 mL) was stirred at 100° C. for 1 hour and then at 85° C. for 3 hours. The reaction progress was monitored by LC-MS. When analysis indicated completion of the reaction, EtOH was evaporated in vacuo and the residue was acidified with 2M HCl to pH~2. Product was extracted with Et$_2$O. The organic layer was dried over anhydrous Na$_2$SO$_4$, filtered and concentrated in vacuo and the crude product was used to the next step without additional purification. The title compound 162b was obtained in 99% yield (207 mg; 0.58 mmol).

ESI-MS m/z for C$_{16}$H$_{23}$ClN$_2$O$_5$Na found 381.0/383.0 [M+Na]; R$_t$=1.54 min; $^1$H NMR (700 MHz, Methanol-d$_4$) δ 4.67-4.56 (m, 1H), 4.26-4.11 (m, 1H), 4.03-3.94 (m, 1H), 3.89-3.76 (m, 2H), 3.69-3.61 (m, 1H), 3.40-3.35 (m, 1H), 3.00-2.87 (m, 1H), 2.76-2.57 (m, 1H), 2.28 (s, 3H), 1.47 (s, 9H).

Step 3

Synthesis of tert-butyl (2R)-2-((3-chloro-5-(2-((6,6-dimethyl-2,4-dioxo-3-azabicyclo[3.1.0]hexan-3-yl)methyl)thieno[3,2-b]pyridin-7-yl)-2-methyl-1H-pyrrol-1-yl)methyl)morpholine-4-carboxylate (162c)

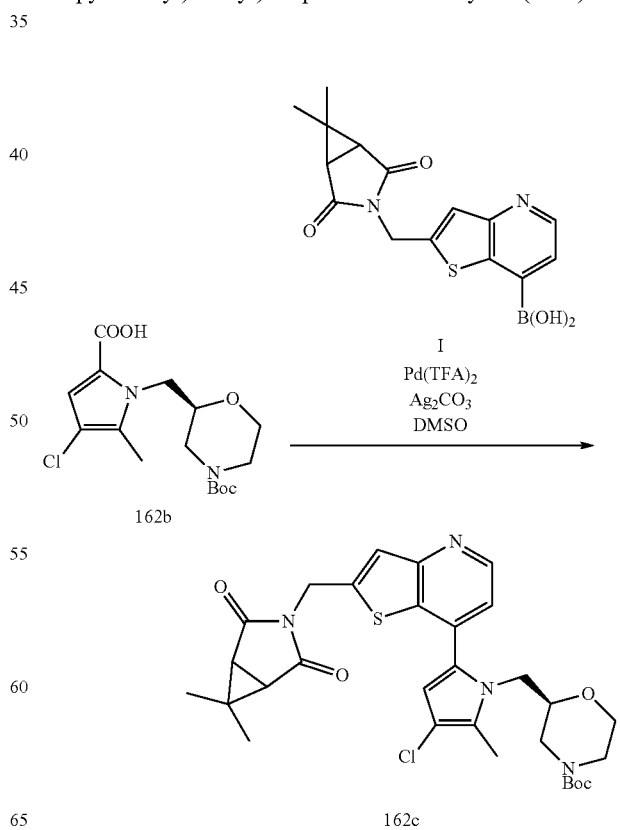

The mixture of 162b (194 mg; 0.540 mmol), a boronic acid I (338 mg; 1.020 mmol), Pd(TFA)$_2$ (34 mg; 0.102 mmol) and Ag$_2$CO$_3$ (393 mg; 1.530 mmol) was placed to the vial under an argon atmosphere. Then to this mixture DMSO (6 mL) was added and a whole was stirred at 110° C. for 1 hour. The reaction progress was monitored by LC-MS. When analysis indicated completion of the reaction, the mixture was diluted with Et$_2$O and then was washed with H$_2$O and brine. The organic layer was dried over anhydrous Na$_2$SO$_4$, filtered and concentrated in vacuo and the crude product was purified by flash column chromatography on silica (hexane/AcOEt, 0:100 to 100:0, v/v, 20 minutes, 14 mL/min). The title compound 162c was obtained in 5% yield (15 mg; 0.025 mmol).

ESI-MS m/z for C$_{30}$H$_{36}$ClN$_4$O$_5$S found 599.3/601.3 [M+H]$^+$; R$_t$=1.70 min Step 4

Synthesis of 3-((7-(4-chloro-5-methyl-1-(((S)-morpholin-2-yl)methyl)-1H-pyrrol-2-yl)thieno[3,2-b]pyridin-2-yl)methyl)-6,6-dimethyl-3-azabicyclo[3.1.0]hexane-2,4-dione hydrochloride (162)

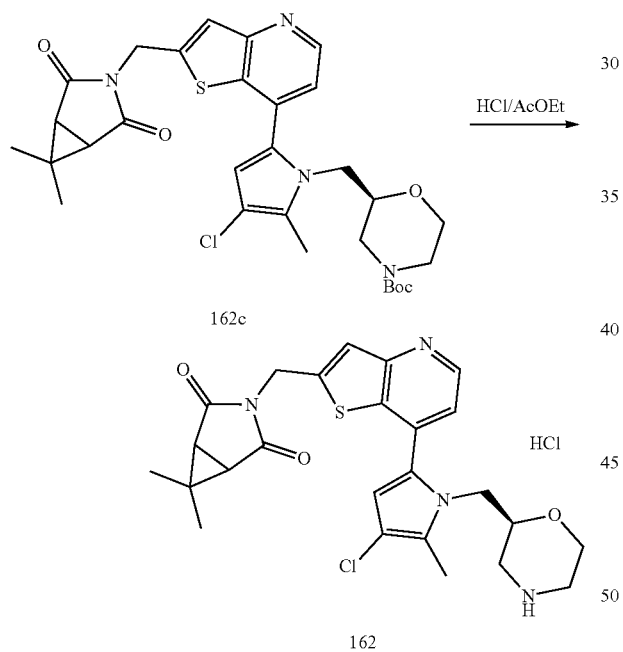

The title compound (162) was obtained as a hydrochloride salt from 162c (15 mg; 0.025 mmol) according to the General Procedure IVa in 44% yield (6 mg; 0.011 mmol). The crude product was purified by preparative reversed-phase column chromatography (C-18, water+0.3‰ HCl (36%)/MeCN, 98:2 to 30:70, 30 min, 20 mL/min).

ESI-MS m/z for C$_{25}$H$_{28}$ClN$_4$O$_3$S found 499.3/501.3 [M+H]$^+$; R$_t$=0.96 min; $^1$H NMR (700 MHz, Methanol-d$_4$) δ 8.72 (s, 1H), 7.65 (s, 1H), 7.61 (s, 1H), 6.70 (s, 1H), 4.93 (s, 2H), 4.34-4.25 (m, 2H), 3.77-3.72 (m, 1H), 3.71-3.66 (m, 1H), 3.55-3.49 (m, 1H), 3.18-3.09 (m, 2H), 2.98-2.91 (m, 1H), 2.72-2.66 (m, 1H), 2.54 (s, 2H), 2.39 (s, 3H), 1.27 (s, 3H), 1.15 (s, 3H).

Example 163

Synthesis of 6,6-dimethyl-3-((7-(4-methyl-3-((3aS,6aS)-octahydropyrrolo[3,4-b]pyrrole-5-carbonyl)-6-(trifluoromethyl)pyridin-2-yl)thieno[3,2-b]pyridin-2-yl)methyl)-3-azabicyclo[3.1.0]hexane-2,4-dione hydrochloride (163)

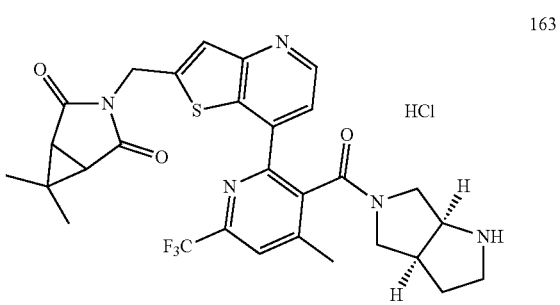 [SMILES: Cc1cc(C(F)(F)F)nc(-c2ccnc3cc(CN4C(=O)C5C(C4=O)C5(C)C)sc23)c1C(=O)N1C[C@@H]2CCN[C@@H]2C1 ; Cl]

The title compound (163) was obtained as a hydrochloride salt in 10% overall yield in a similar way to Example 45 with the exception that, in the first step of the synthesis tert-butyl (3aS,6aS)-hexahydropyrrolo[3,4-b]pyrrole-1(2H)-carboxylate was used instead of tert-butyl piperazine-1-carboxylate and acid II was used instead of 2-chloro-4-methylnicotinic acid and in the last step of the synthesis, the crude product was purified by preparative reversed-phase column chromatography (C-18, water+0.3‰ HCl (36%)/MeCN, 98:2 to 30:70, 30 min, 20 mL/min).

ESI-MS m/z for C$_{29}$H$_{29}$F$_3$N$_5$O$_3$S found 584.4 [M+H]$^+$; R$_t$=0.96 min; $^1$H NMR (700 MHz, Methanol-d$_4$) δ 8.85-8.79 (m, 1H), 8.07-8.01 (m, 1H), 7.92-7.71 (m, 1H), 7.62-7.58 (m, 1H), 4.95-4.90 (m, 2H), 4.38-4.00 (m, 2H), 3.79-3.67 (m, 1H), 3.05-2.93 (m, 1H), 2.88-2.78 (m, 1H), 2.78-2.71 (m, 1H), 2.58 (s, 2H), 2.56-2.46 (m, 3H), 2.16-2.06 (m, 1H), 1.75-1.57 (m, 2H), 1.29 (s, 3H), 1.13 (s, 3H), 0.93-0.63 (m, 1H).

Example 164

Synthesis of 3-((7-(5-chloro-2-(((S)-pyrrolidin-3-yl)oxy)pyridin-3-yl)thieno[3,2-b]pyridin-2-yl)methyl)-6,6-dimethyl-3-azabicyclo[3.1.0]hexane-2,4-dione dihydrochloride (164)

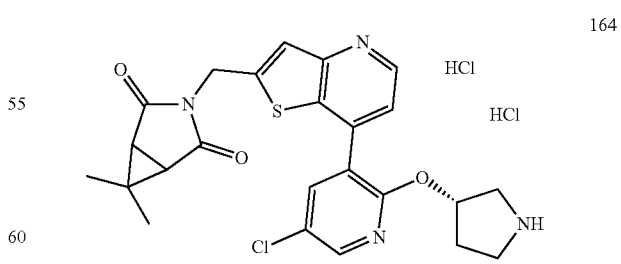

The title compound (164) was obtained as a dihydrochloride salt in 37% overall yield in a similar way to Example 152 with the exception that, in the first step of the synthesis 3-bromo-5-chloropyridin-2-ol and tert-butyl (R)-3-hydroxypyrrolidine-1-carboxylate were used instead of 3-bromo-5- fluoropyridin-2-ol and tert-butyl (R)-3-hydroxypiperidine-1-carboxylate and in the last step of the synthesis, the crude product was purified by preparative reversed-phase column chromatography (C-18, water+0.3‰ HCl (36%)/MeCN, 98:2 to 30:70, 30 min, 20 mL/min).

ESI-MS m/z for $C_{24}H_{24}ClN_4O_3S$ found 483.2/485.2 [M+H]$^+$; $R_t$=0.93 min; $^1$H NMR (700 MHz, Methanol-$d_4$) δ 8.77-8.74 (m, 1H), 8.39-8.36 (m, 1H), 8.05-8.01 (m, 1H), 7.61-7.55 (m, 2H), 5.84-5.78 (m, 1H), 4.91-4.88 (m, 2H), 3.67-3.63 (m, 1H), 3.51-3.47 (m, 1H), 3.43-3.38 (m, 1H), 3.26-3.20 (m, 1H), 2.52 (s, 2H), 2.40-2.33 (m, 1H), 2.30-2.24 (m, 1H), 1.25 (s, 3H), 1.12 (s, 3H).

Example 165

Synthesis of 6,6-dimethyl-3-((7-(4-methyl-3-((3-oxopiperazin-2-yl)methyl)-6-(trifluoromethyl)pyridin-2-yl)thieno[3,2-b]pyridin-2-yl)methyl)-3-azabicyclo[3.1.0]hexane-2,4-dione hydrochloride (165)

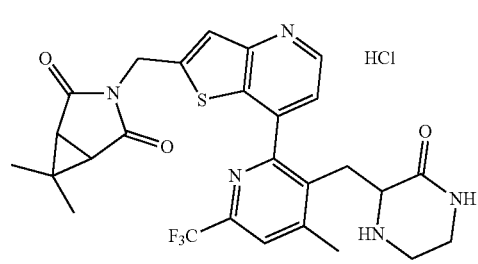

Step 1

Synthesis of di-tert-butyl 2-oxopiperazine-1,4-dicarboxylate (165a)

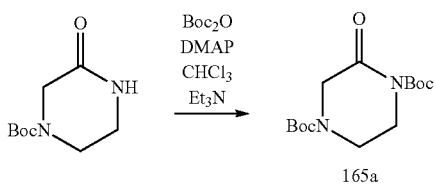 [SMILES: CC(C)(C)OC(=O)N1CCNC(=O)C1 ; CC(C)(C)OC(=O)N1CCN(C(=O)OC(C)(C)C)C(=O)C1]

To the suspension of tert-butyl 3-oxopiperazine-1-carboxylate (1.00 g; 4.99 mmol) in CHCl$_3$ (20 mL) Boc$_2$O (1.30 g; 5.98 mmol), DMAP (183 mg; 1.49 mmol) and Et$_3$N (0.83 mL; 5.98 mmol) were added and then the reaction mixture was stirred at room temperature overnight. Then Boc$_2$O (1.30 g; 5.98 mmol) and DMAP (183 mg; 1.49 mmol) were added and the reaction mixture was stirred at room temperature for 3 hours. The reaction progress was monitored by LC-MS. When analysis indicated completion of the reaction, the solvent was evaporated in vacuo and the residue was purified by flash column chromatography on silica (hexane/AcOEt, 100:0 to 50:50, v/v, 35 minutes). Compound 165a was obtained in 83% yield (1.25 g; 4.16 mmol).

ESI-MS m/z for $C_{14}H_{25}N_2O_5$ found 301.0 [M+H]$^+$; $R_t$=1.32 min; $^1$H NMR (700 MHz, CDCl$_3$) δ 4.23-4.18 (m, 2H), 3.83-3.79 (m, 2H), 3.67-3.60 (m, 2H), 1.57 (s, 10H), 1.49 (s, 9H).

Step 2

Synthesis of di-tert-butyl 2-((2-chloro-4-methyl-6-(trifluoromethyl)pyridin-3-yl)methyl)-3-oxopiperazine-1,4-dicarboxylate (165b)

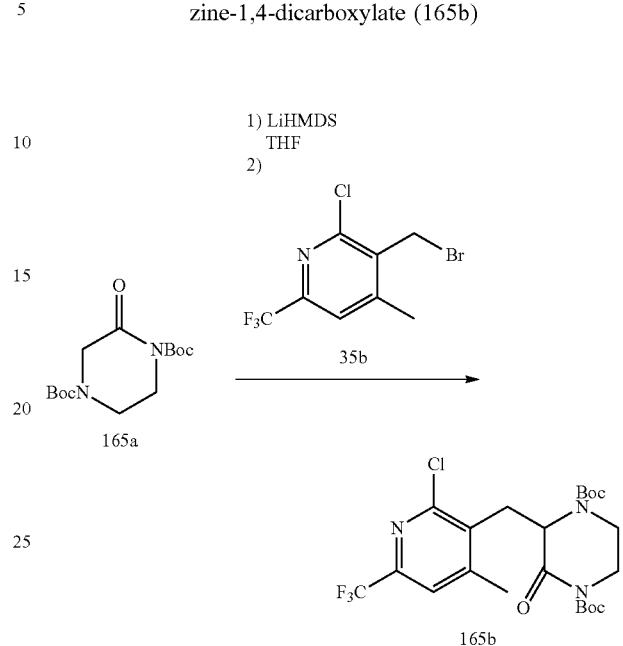

To a cooled to −78° C. solution of 165a (0.90 g; 3.00 mmol) in THF (50 mL) LiHMDS (1 M in THF; 3.30 mL; 3.30 mmol) was added dropwise and then the reaction mixture was stirred at this temperature for 1 hour. Then to this mixture a solution of 35b (867 mg; 3.00 mmol) in THF (5 mL) was added and the resulting mixture was stirred at −78° C. for 5 hours and then the mixture was slowly warmed up to room temperature and stirred overnight. The reaction progress was monitored by LC-MS. When analysis indicated completion of the reaction, the mixture was diluted with Et$_2$O and washed with NH$_4$Cl. An organic layer was dried over anhydrous MgSO$_4$, filtered and concentrated in vacuo and the crude product was purified by flash column chromatography on silica (hexane/AcOEt, 100:0 to 60:40, v/v, 25 minutes). The title compound 165b was obtained as a colorless oil in 52% yield (795 mg; 1.57 mmol).

ESI-MS m/z for $C_{22}H_{29}ClF_3N_3O_5Na$ found 530.1/532.1 [M+Na]$^+$; $R_t$=1.84 min Step 3

Synthesis of tert-butyl 2-((2-chloro-4-methyl-6-(trifluoromethyl)pyridin-3-yl)methyl)-3-oxopiperazine-1-carboxylate (165c)

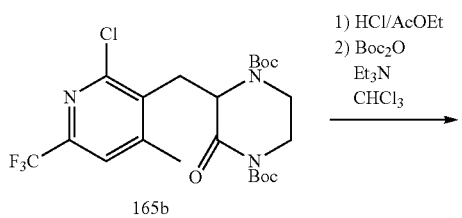

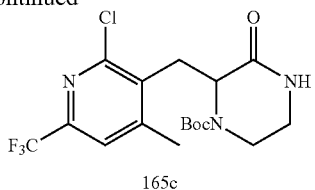

165c

The title compound (165c) was obtained from 165b (730 mg; 1.44 mmol) according to the General Procedure IVa and then the General Procedure III in 99% yield (per two steps)(578 mg; 1.42 mmol). The crude product was purified by flash column chromatography on silica (DCM/MeOH, 100:0 to 0:100, v/v, 30 minutes).

ESI-MS m/z for $C_{17}H_{22}ClF_3N_3O_3$ found 407.9/409.8 [M+H]$^+$; $R_t$=1.34 min; $^1$H NMR (700 MHz, CDCl$_3$) δ 7.45 (s, 1H), 6.22-6.08 (m, 1H), 5.03-4.86 (m, 1H), 4.38-4.07 (m, 1H), 3.55-3.31 (m, 4H), 2.60 (s, 3H), 1.20 (s, 9H); $^{19}$F NMR (659 MHz, CDCl$_3$) δ −68.05.

Step 4

Synthesis of tert-butyl 2-((2-(2-((6,6-dimethyl-2,4-dioxo-3-azabicyclo[3.1.0]hexan-3-yl)methyl)thieno[3,2-b]pyridin-7-yl)-4-methyl-6-(trifluoromethyl)pyridin-3-yl)methyl)-3-oxopiperazine-1-carboxylate (165d)

The title compound (165d) was obtained from 165c (40 mg; 0.098 mmol) and from boronic acid I (31 mg; 0.098 mmol) according to the General Procedure Va and the crude product was used to the next step without additional purification.

ESI-MS m/z for $C_{32}H_{35}F_3N_5O_5S$ found 658.5 [M+H]$^+$; $R_t$=1.81 min

Step 5

Synthesis of 6,6-dimethyl-3-((7-(4-methyl-3-((3-oxopiperazin-2-yl)methyl)-6-(trifluoromethyl)pyridin-2-yl)thieno[3,2-b]pyridin-2-yl)methyl)-3-azabicyclo[3.1.0]hexane-2,4-dione hydrochloride (165)

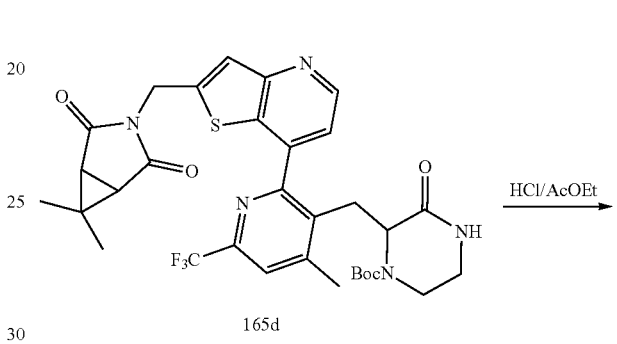

165d

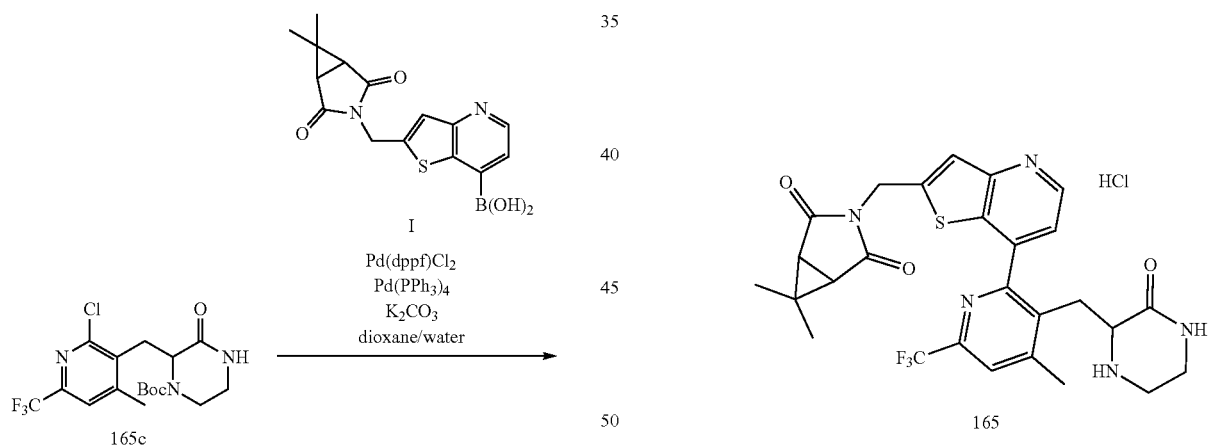

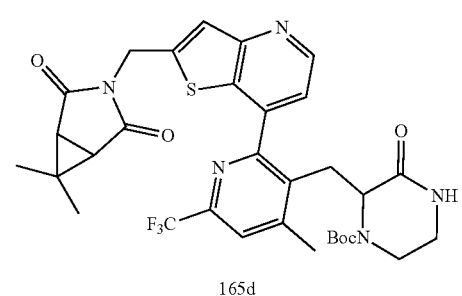

165d

The title compound (165) was obtained as a hydrochloride salt from 165d (the crude product) according to the General Procedure IVa in 18% yield (per two steps)(11 mg; 0.018 mmol). The crude product was purified by preparative reversed-phase column chromatography (column: Cosmosil Cholester 20×250 mm, water+0.3‰ HCl (36%)/MeCN, 99:1 to 40:60, 30 min, 20 mL/min).

ESI-MS m/z for $C_{27}H_{27}F_3N_5O_3S$ found 558.5 [M+H]$^+$; $R_t$=0.92 min; $^1$H NMR (700 MHz, DMSO-d$_6$+D$_2$O, 348 K) δ 8.77-8.73 (m, 1H), 7.84 (s, 1H), 7.53-7.50 (m, 1H), 7.48-7.42 (m, 1H), 4.83-4.73 (m, 2H), 3.79-3.72 (m, 1H), 3.60-3.54 (m, 1H), 3.33-3.23 (m, 3H), 3.17-3.05 (m, 2H), 2.61-2.56 (m, 3H), 2.55-2.52 (m, 2H), 1.18 (s, 3H), 1.03 (s, 3H); $^{19}$F NMR (659 MHz, DMSO-d$_6$) δ −66.23.

Example 166

Synthesis of 6,6-dimethyl-3-((7-(2-((3-oxopiper-azin-2-yl)methyl)-5-(trifluoromethyl)pyridin-3-yl)thieno[3,2-b]pyridin-2-yl)methyl)-3-azabicyclo[3.1.0]hexane-2,4-dione hydrochloride (166)

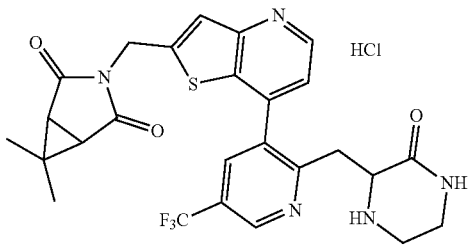

166

The title compound (166) was obtained as a hydrochloride salt in 13% overall yield in a similar way to Example 165 with the exception that, in the second step of the synthesis 2-(bromomethyl)-3-chloro-5-(trifluoromethyl)pyridine was used instead of the compound 35b and the third step of the synthesis was carried out without using the General Procedure III and in the last step of the synthesis, the crude product was purified by preparative reversed-phase column chromatography (column: Cosmosil Cholester 20×250 mm, water+0.3‰ HCl (36%)/MeCN, 99:1 to 40:60, 30 min, 20 mL/min).

ESI-MS m/z for $C_{26}H_{25}F_3N_5O_3S$ found 544.5 [M+H]$^+$; $R_t$=0.87 min; $^1$H NMR (700 MHz, DMSO-d$_6$+D$_2$O, 348 K) δ 9.05-9.00 (m, 1H), 8.81-8.70 (m, 1H), 8.25-8.12 (m, 1H), 7.58-7.53 (m, 1H), 7.42-7.33 (m, 1H), 4.82-4.74 (m, 2H), 4.47-4.37 (m, 1H), 3.55-3.46 (m, 2H), 3.40-3.37 (m, 1H), 3.37-3.30 (m, 2H), 3.28-3.23 (m, 1H), 2.55-2.52 (m, 2H), 1.18 (s, 3H), 1.03 (s, 3H); $^{19}$F NMR (659 MHz, DMSO-d$_6$) δ-60.57.

Example 167

Synthesis of 6,6-dimethyl-3-((7-(5-methyl-1-(((R)-morpholin-2-yl)methyl)-4-nitro-1H-pyrrol-2-yl)thieno[3,2-b]pyridin-2-yl)methyl)-3-azabicyclo[3.1.0]hexane-2,4-dione hydrochloride (167)

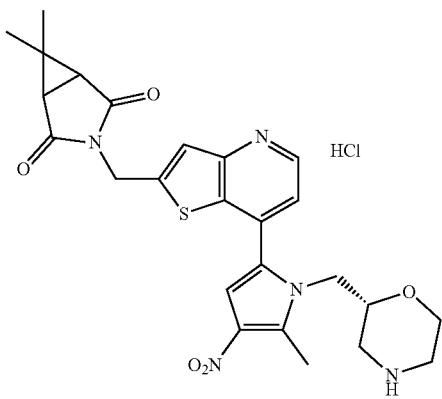

167

The title compound (167) was obtained as a hydrochloride salt in 12% overall yield in a similar way to Example 148 with the exception that, in the first step of the synthesis 2-methyl-3-nitro-1H-pyrrole and tert-butyl (R)-2-(bromomethyl)morpholine-4-carboxylate were used instead of 2-methyl-1H-pyrrole-3-carboxylate and tert-butyl (S)-2-(bromomethyl)morpholine-4-carboxylate and in the last step of the synthesis the crude product was purified by preparative reversed-phase column chromatography (C-18, water+0.3‰ HCl (36%)/MeCN, 99:1 to 40:60, 30 min, 20 mL/min).

ESI-MS m/z for $C_{25}H_{28}N_5O_5S$ found 510.5 [M+H]$^+$; $R_t$=0.91 min; $^1$H NMR (700 MHz, Methanol-d$_4$) δ 8.81 (s, 1H), 7.71-7.66 (m, 1H), 7.66-7.62 (m, 1H), 7.20 (s, 1H), 4.95 (s, 2H), 4.41-4.35 (m, 1H), 4.34-4.24 (m, 1H), 3.79-3.69 (m, 2H), 3.56-3.50 (m, 1H), 3.25-3.19 (m, 1H), 3.18-3.09 (m, 1H), 3.01-2.92 (m, 1H), 2.79 (s, 3H), 2.78-2.75 (m, 1H), 2.54 (s, 2H), 1.26 (s, 3H), 1.15 (s, 3H).

Example 168

Synthesis of 6,6-dimethyl-3-((7-(4-methyl-3-((3R,4S)-3-methyl-4-(methylamino)pyrrolidine-1-carbonyl)-6-(trifluoromethyl)pyridin-2-yl)thieno[3,2-b]pyridin-2-yl)methyl)-3-azabicyclo[3.1.0]hexane-2,4-dione hydrochloride (168)

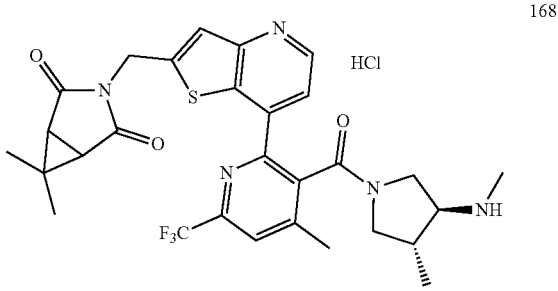

168

The title compound (168) was obtained as a hydrochloride salt in 6% overall yield in a similar way to Example 45 with the exception that, in the first step of the synthesis tert-butyl methyl((3S,4R)-4-methylpyrrolidin-3-yl)carbamate (this compound was synthesized according to the General Procedure C with the exception that, in the first step of the synthesis tert-butyl ((3S,4R)-4-methylpyrrolidin-3-yl)carbamate was used instead of tert-butyl (S)-pyrrolidin-3-yl-carbamate and in the second step of the synthesis, MeI and DMF were used instead of EtI and THF and this reaction was carried out at 0° C. and slowly raised to room temperature and the whole was stirred overnight) was used instead of tert-butyl piperazine-1-carboxylate and acid II was used instead of 2-chloro-4-methylnicotinic acid and in the last step of the synthesis, the General Procedure IVb was used instead of the General Procedure IVa and the crude product was purified by preparative reversed-phase column chromatography (C-18, water+0.3‰ HCl (36%)/MeCN, 100:0 to 45:55, 30 min, 20 mL/min).

ESI-MS m/z for $C_{29}H_{31}F_3N_5O_3S$ found 586.6 [M+H]$^+$; $R_t$=1.07 min; $^1$H NMR (700 MHz, D$_2$O) δ 8.89-8.84 (m, 1H), 8.18-8.13 (m, 1H), 7.79-7.68 (m, 2H), 5.08-4.96 (m, 2H), 4.36-3.77 (m, 2H), 3.65-3.23 (m, 2H), 3.09-2.95 (n, 1H), 2.75-2.67 (m, 3H), 2.64-2.51 (m, 4H), 2.36-1.94 (m, 2H), 1.31-1.14 (m, 3H), 1.11-0.12 (m, 6H); $^{19}$F NMR (376 MHz, D$_2$O) δ −67.82−−67.87 (m).

Example 169

Synthesis of 3-((7-(3-((3R,4S)-3-amino-4-fluoropyrrolidine-1-carbonyl)-4-methyl-6-(trifluoromethyl)pyridin-2-yl)thieno[3,2-b]pyridin-2-yl)methyl)-6,6-dimethyl-3-azabicyclo[3.1.0]hexane-2,4-dione hydrochloride (169)

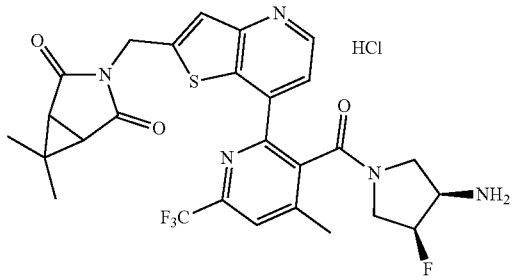

169

The title compound (169) was obtained as a hydrochloride salt in 14% overall yield in a similar way to Example 45 with the exception that, in the first step of the synthesis an acid II and tert-butyl ((3R,4S)-4-fluoropyrrolidin-3-yl)carbamate were used instead of 2-chloro-4-methylnicotinic acid and tert-butyl piperazine-1-carboxylate and in the last step of the synthesis, the crude product was purified by preparative reversed-phase column chromatography (C-18, water+0.4‰ HCl (36%)/MeCN, 99:1 to 20:80, 30 min, 18 mL/min).

ESI-MS m/z for C$_2$H$_{26}$F$_4$N$_5$O$_3$S found 576.5 [M+H]$^+$; R$_t$=1.11 min; $^1$H NMR (700 MHz, Methanol-d$_4$) δ 8.98-8.90 (m, 1H), 8.15-7.89 (m, 2H), 7.73-7.69 (m, 1H), 5.46-5.06 (m, 1H), 5.02-4.92 (m, 2H), 4.32-3.93 (m, 2H), 3.89-3.35 (m, 2H), 3.26-3.06 (m, 1H), 2.61-2.56 (m, 2H), 2.56-2.50 (m, 3H), 1.28-1.23 (m, 3H), 1.20-1.09 (m, 3H).

Example 170

Synthesis of 3-((7-(3-((3S,4S)-3-amino-4-fluoropyrrolidine-1-carbonyl)-4-methyl-6-(trifluoromethyl)pyridin-2-yl)thieno[3,2-b]pyridin-2-yl)methyl)-6,6-dimethyl-3-azabicyclo[3.1.0]hexane-2,4-dione hydrochloride (170)

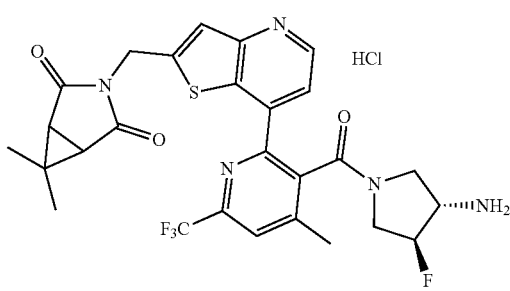

170

The title compound (170) was obtained as a hydrochloride salt in 16% overall yield in a similar way to Example 45 with the exception that, in the first step of the synthesis an acid II and tert-butyl ((3S,4S)-4-fluoropyrrolidin-3-yl)carbamate were used instead of 2-chloro-4-methylnicotinic acid and tert-butyl piperazine-1-carboxylate and in the last step of the synthesis, the crude product was purified by preparative reversed-phase column chromatography (column: Cosmosil Cholester 20×250 mm, water+0.3‰ HCl (36%)/MeCN, 99:1 to 20:80, 30 min, 20 mL/min).

ESI-MS m/z for C$_{27}$H$_{26}$F$_4$N$_5$O$_3$S found 576.3 [M+H]$^+$; R=1.14 min; $^1$H NMR (700 MHz, Methanol-d$_4$) δ 9.03-8.97 (m, 1H), 8.17-7.97 (m, 2H), 7.79-7.75 (m, 1H), 5.47-5.05 (m, 1H), 5.02-4.96 (m, 2H), 4.32-3.83 (m, 2H), 3.78-3.39 (m, 2H), 3.28-2.67 (m, 1H), 2.64-2.57 (m, 2H), 2.57-2.52 (m, 3H), 1.29-1.23 (m, 3H), 1.21-1.10 (m, 3H).

Example 171

Synthesis of 3-((7-(3-((3S,4R)-3-amino-4-fluoropyrrolidine-1-carbonyl)-4-methyl-6-(trifluoromethyl)pyridin-2-yl)thieno[3,2-b]pyridin-2-yl)methyl)-6,6-dimethyl-3-azabicyclo[3.1.0]hexane-2,4-dione hydrochloride (171)

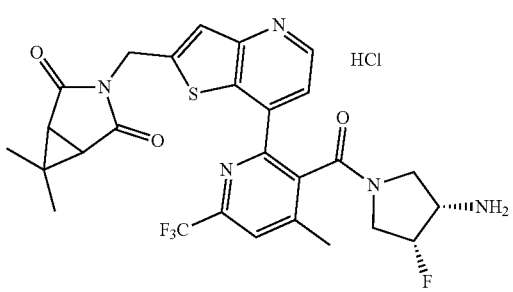

171

The title compound (171) was obtained as a hydrochloride salt in 17% overall yield in a similar way to Example 45 with the exception that, in the first step of the synthesis an acid H$_1$ and tert-butyl ((3S,4R)-4-fluoropyrrolidin-3-yl)carbamate were used instead of 2-chloro-4-methylnicotinic acid and tert-butyl piperazine-1-carboxylate and in the last step of the synthesis, the crude product was purified by preparative reversed-phase column chromatography (column: Cosmosil Cholester 20×250 mm, water+0.3‰ HCl (36%)/MeCN, 99:1 to 20:80, 30 min, 20 mL/min).

ESI-MS m/z for C$_{27}$H$_{26}$F$_4$N$_5$O$_3$S found 576.5 [M+H]$^+$; R$_t$=1.09 min; $^1$H NMR (700 MHz, Methanol-d$_4$) δ 9.03-8.97 (m, 1H), 8.17-7.96 (m, 2H), 7.79-7.75 (m, 1H), 5.47-5.05 (m, 1H), 5.02-4.96 (m, 2H), 4.32-3.39 (m, 4H), 3.28-2.66 (m, 1H), 2.63-2.57 (m, 2H), 2.57-2.52 (m, 3H), 1.29-1.23 (m, 3H), 1.21-1.10 (m, 3H).

Example 172

Synthesis of 3-((7-(3-((3S,4R)-3-(dimethylamino)-4-methylpyrrolidine-1-carbonyl)-4-methyl-6-(trifluoromethyl)pyridin-2-yl)thieno[3,2-b]pyridin-2-yl)methyl)-6,6-dimethyl-3-azabicyclo[3.1.0]hexane-2,4-dione hydrochloride (172)

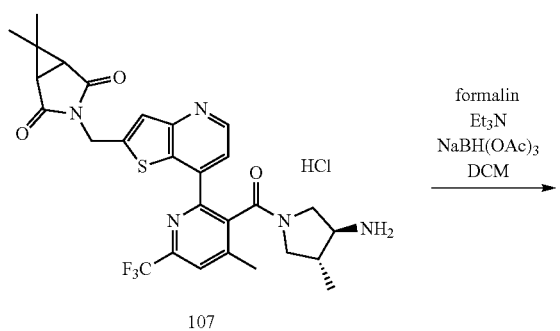

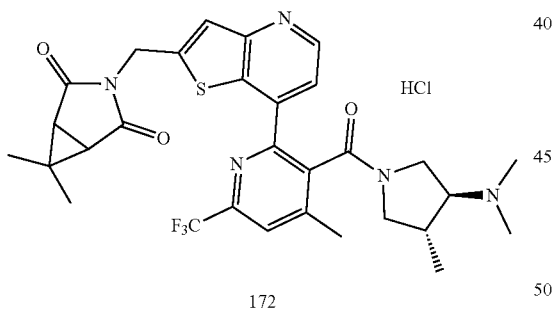

The title compound (172) was obtained as a hydrochloride salt from the compound 107 (6.5 mg, 0.0107 mmol) and from the formalin (36-38%; 3.3 µL; 0.0424 mmol) according to the General Procedure VIa in 82% yield (5.6 mg; 0.0088 mmol) with the exception that in this reaction Et$_3$N was used instead of AcOH. The crude product was purified by preparative reversed-phase column chromatography (column: Cosmosil Cholester 20×250 mm, water+0.3‰ HCl (36%)/MeCN, 99:1 to 20:80, 30 min, 20 mL/min).

ESI-MS m/z for C$_{30}$H$_{33}$F$_3$N$_5$O$_3$S found 600.4 [M+H]$^+$; R$_t$=1.18 min; $^1$H NMR (700 MHz, Methanol-d$_4$) δ 9.10-8.99 (m, 1H), 8.16-8.07 (m, 2H), 7.78-7.74 (m, 1H), 5.01-4.94 (m, 2H), 4.32-3.91 (m, 2H), 3.71-3.38 (m, 2H), 3.29-3.08 (m, 2H), 2.94-2.66 (m, 5H), 2.64-2.38 (m, 7H), 1.27-1.22 (m, 3H), 1.19-0.67 (m, 6H).

Example 173

Synthesis of 3-((7-(3-((S)-7-amino-5-azaspiro[2.4]heptane-5-carbonyl)-4-methyl-6-(trifluoromethyl)pyridin-2-yl)thieno[3,2-b]pyridin-2-yl)methyl)-6,6-dimethyl-3-azabicyclo[3.1.0]hexane-2,4-dione hydrochloride (173)

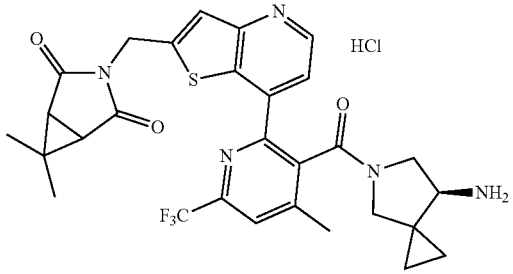

The title compound (173) was obtained as a hydrochloride salt in 1% overall yield in a similar way to Example 45 with the exception that, in the first step of the synthesis an acid II and tert-butyl (S)-(5-azaspiro[2.4]heptan-7-yl)carbamate were used instead of 2-chloro-4-methylnicotinic acid and tert-butyl piperazine-1-carboxylate and in the last step of the synthesis, the crude product was purified by preparative reversed-phase column chromatography (column: Cosmosil Cholester 20×250 mm, water+0.3‰ HCl (36%)/MeCN, 98:2 to 30:70, 30 min, 20 mL/min).

ESI-MS m/z for C$_{29}$H$_{29}$F$_3$N$_5$O$_3$S found 584.3 [M+H]$^+$; R$_t$=1.11 min; $^1$H NMR (700 MHz, Methanol-d$_4$) δ 9.02-8.94 (m, 1H), 8.24-7.92 (m, 2H), 7.75-7.71 (m, 1H), 5.00-4.94 (m, 2H), 4.41-3.91 (m, 1H), 3.82-3.32 (m, 3H), 3.28-3.06 (m, 1H), 2.83-2.62 (m, 2H), 2.58-2.45 (m, 3H), 1.30-1.24 (m, 3H), 1.20-1.12 (m, 3H), 1.09--0.58 (m, 4H).

Example 174

Synthesis of 3-((3-fluoro-7-(4-methyl-3-((S)-3-(methylamino)pyrrolidine-1-carbonyl)-6-(trifluoromethyl)pyridin-2-yl)thieno[3,2-b]pyridin-2-yl)methyl)-6,6-dimethyl-3-azabicyclo[3.1.0]hexane-2,4-dione hydrochloride (174)

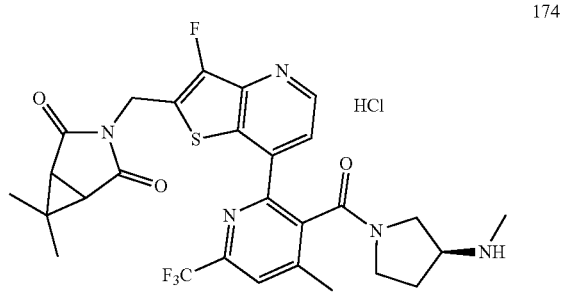

Step 1

Synthesis of 7-chloro-3-fluoro-2-(((tetrahydro-2H-pyran-2-yl)oxy)methyl)thieno[3,2-b]pyridine (174a)

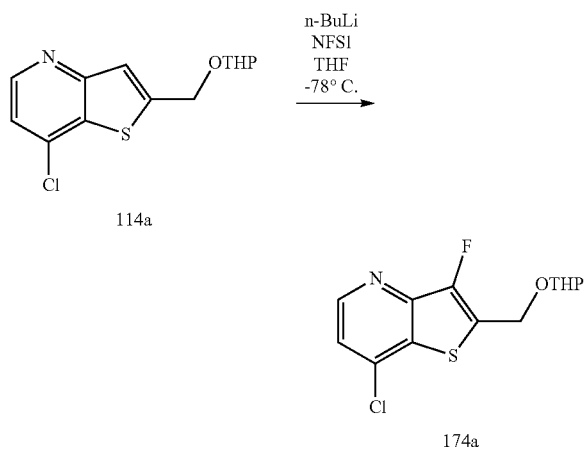

To a solution of 114a (0.55 g; 1.94 mmol) in anhydrous THF (6 mL) n-BuLi (2.5 M in hexane; 1.55 mL; 3.88 mmol) was added dropwise at −78° C. The resulting mixture was stirred for additional 30 minutes. Then N-fluorobenzenesulfonimide (NFSI)(734 mg; 2.33 mmol) was added at −78° C. and the reaction was stirred at this temperature for 2 hours. The reaction progress was monitored by LC-MS. When analysis indicated completion of the reaction, the reaction was quenched by addition of saturated solution of NH₄Cl (30 mL) and then extracted with extracted with AcOEt (3×30 mL). The combined organic solutions were washed with brine (1×50 mL), dried over anhydrous Na₂SO₄, filtered and concentrated in vacuo. The crude product was purified by flash column chromatography on silica (hexane/AcOEt, 100:0 to 0:100, v/v, 25 min, 20 mL/min). The title compound (174a) was obtained in 9% yield (52 mg; 0.17 mmol).

ESI-MS m/z for $C_{13}H_{14}ClFNO_2S$ found 301.9/303.7 $[M+H]^+$; $R_t$=1.56 min

Step 2

Synthesis of (3-fluoro-2-(((tetrahydro-2H-pyran-2-yl)oxy)methyl)thieno[3,2-b]pyridin-7-yl)boronic acid (174b)

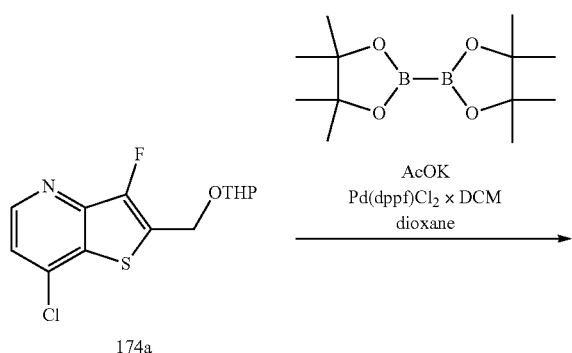

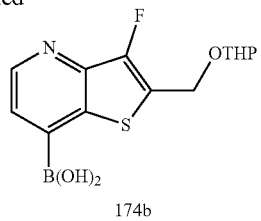

In a Schlenk flask was placed the compound 174a (52 mg; 0.172 mmol), potassium acetate (51 mg; 0.516 mmol), Pd(dppf)Cl₂×DCM (14 mg; 0.017 mmol), and anhydrous, degassed dioxane (1.5 mL). The flask was backfilled with an argon and stirred for 10 minutes. Then bis(pinacolo)diboron (87 mg; 0.344 mmol) was added and the resulting mixture was stirred at 90° C. overnight. Then Pd(PPh₃)₄ (10 mg; 0.009 mmol) was added and stirring was continued at 90° C. overnight. The reaction progress was monitored by LC-MS. When analysis indicated completion of the reaction, the mixture was cooled to room temperature and the product was not isolated. It was used to the next step without purification.

ESI-MS m/z for $C_{13}H_{16}BFNO_4S$ found 311.9 $[M+H]^+$, $R_t$=1.12 min

Step 3

Synthesis of tert-butyl ((3S)-1-(2-(3-fluoro-2-(((tetrahydro-2H-pyran-2-yl)oxy)methyl)thieno[3,2-b]pyridin-7-yl)-4-methyl-6-(trifluoromethyl)nicotinoyl)pyrrolidin-3-yl)(methyl)carbamate (174c)

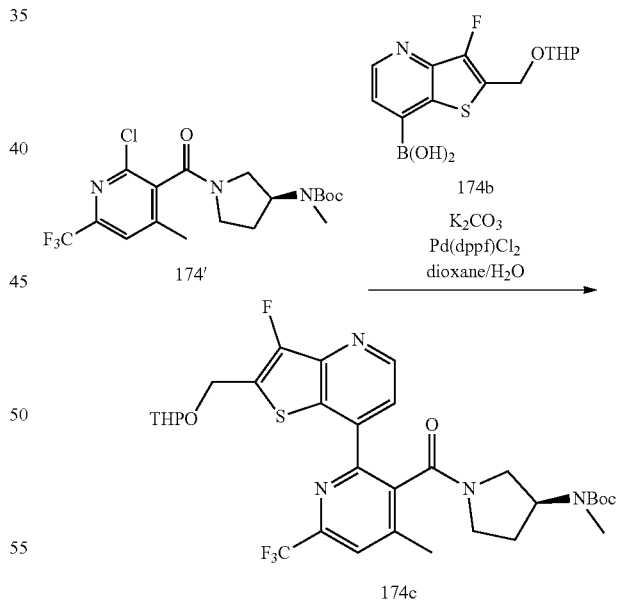

The title compound (174c) was obtained from 174b (the crude product) and from 174' (the synthesis of this compound was the same as for the compound 45a with the exception that, tert-butyl (S)-methyl(pyrrolidin-3-yl)carbamate was used instead of tert-butyl piperazine-1-carboxylate and acid II was used instead of 2-chloro-4-methylnicotinic acid)(72 mg; 0.172 mmol) according to the General Procedure Va as a yellow oil in 52% yield (per two steps)(60 mg; 0.09 mmol).

ESI-MS m/z for $C_{31}H_{37}F_4N_4O_5S$ found 653.2 $[M+H]^+$; $R_t$=1.81 min

Step 4

Synthesis of tert-butyl (S)-(1-(2-(3-fluoro-2-(hydroxymethyl)thieno[3,2-b]pyridin-7-yl)-4-methyl-6-(trifluoromethyl)nicotinoyl)pyrrolidin-3-yl)(methyl)carbamate (174d)

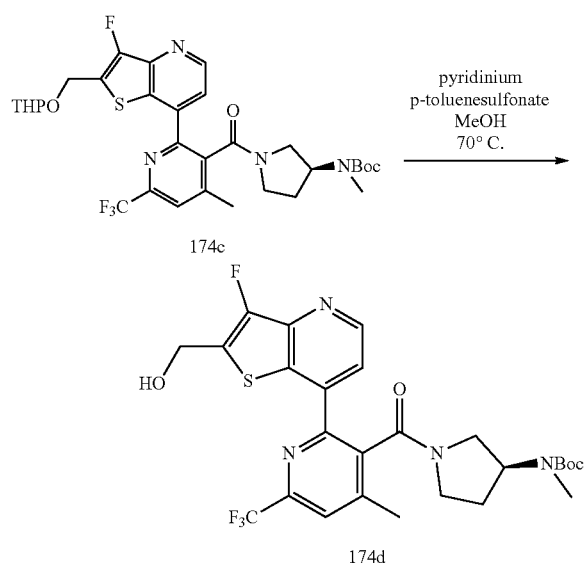

The solution of 174c (10 mg; 0.015 mmol) in MeOH (2 mL) and TFA (1 mL) pyridinium p-toluenesulfonate (7.7 mg; 0.030 mmol) was added and this mixture was stirred at 70° C. for 4 h. The reaction progress was monitored by LC-MS. When analysis indicated completion of the reaction, the mixture was concentrated in vacuo and the residue was purified by flash column chromatography on silica (hexane/AcOEt, 100:0 to 0:100, v/v, 30 min, 13 mL/min). The title compound (174d) was obtained in 60% yield (5 mg; 0.009 mmol).

ESI-MS m/z for $C_{26}H_{29}F_4N_4O_4S$ found 569.3 $[M+H]^+$; $R_t$=1.39 min

Step 5

Synthesis of (S)-(7-(3-(3-((tert-butoxycarbonyl)(methyl)amino)pyrrolidine-1-carbonyl)-4-methyl-6-(trifluoromethyl)pyridin-2-yl)-3-fluorothieno[3,2-b]pyridin-2-yl)methyl methanesulfonate (174e)

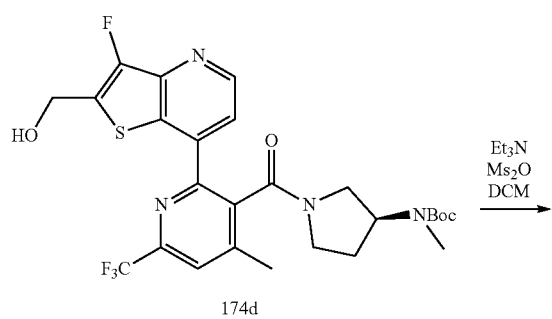

The title compound (174e) was obtained from 174d (8 mg; 0.014 mmol) according to the General Procedure VIII and after concentration the crude product was used to the next step without additional purification.

ESI-MS m/z for $C_{27}H_{31}F_4N_4O_6S_2$ found 647.2 $[M+H]^+$; $R_t$=1.51 min

Step 6

Synthesis of 3-((3-fluoro-7-(4-methyl-3-((S)-3-(methylamino)pyrrolidine-1-carbonyl)-6-(trifluoromethyl)pyridin-2-yl)thieno[3,2-b]pyridin-2-yl)methyl)-6,6-dimethyl-3-azabicyclo[3.1.0]hexane-2,4-dione hydrochloride (174)

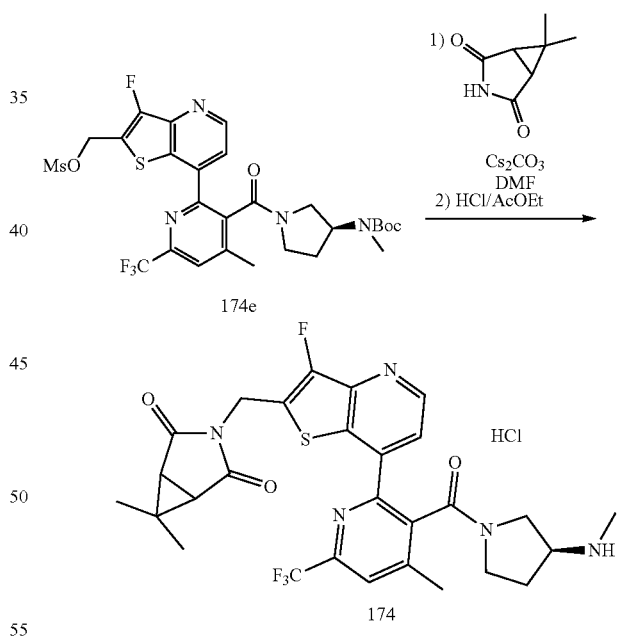

To a solution of 174e (the crude product) in anhydrous DMF (1 mL), 6,6-dimethy-3-aza-bicyclo[3.1.0]hexane 2,4-dione (2 mg; 0.014 mmol) and $Cs_2CO_3$ (9 mg; 0.028 mmol) were added. The resulting mixture was stirred at room temperature for 1 hour. The reaction progress was monitored by LC-MS. When analysis indicated completion of the reaction, DMF was removed in vacuo and the residue was dissolved in AcOEt (15 mL) and washed with water (10 mL). The organic phase was dried over anhydrous $Na_2SO_4$, filtered and concentrated in vacuo. The residue was then taken to the next step in which the title compound was obtained according to General Procedure IVa. The crude product was purified by preparative reversed-phase column chromatography (column: Cosmosil Cholester 20×250 mm, water+0.3‰ HCl (36%)/MeCN, 99:1 to 20:80, 30 min, 20 mL/min). The title compound (174) was obtained as a hydrochloride salt in 21% yield (per three steps)(2 mg; 0.003 mmol).

ESI-MS m/z for $C_{28}H_{25}F_4N_5O_3S$ found 590.5 $[M+H]^+$; $R_t$=1.12 min; $^1$H NMR (700 MHz, Methanol-$d_4$) δ 8.97-8.85 (m, 1H), 8.11-7.80 (m, 2H), 4.98-4.89 (m, 2H), 4.31-3.42 (m, 3H), 3.33-2.98 (m, 2H), 2.77-2.65 (m, 2H), 2.62-2.48 (m, 6H), 2.46-1.77 (m, 2H), 1.32-1.21 (m, 3H), 1.20-1.11 (m, 3H).

Example 175

Synthesis of 3-((7-(5-chloro-3-methyl-2-(pyrrolidin-3-ylamino)phenyl)thieno[3,2-b]pyridin-2-yl)methyl)-6,6-dimethyl-3-azabicyclo[3.1.0]hexane-2,4-dione hydrochloride (175)

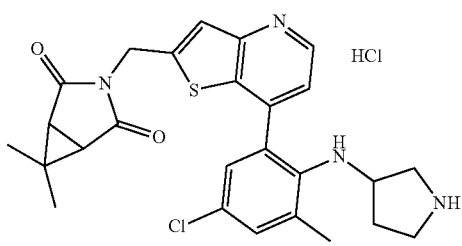

175

The title compound (175) was obtained as a hydrochloride salt in 12% overall yield in a similar way to Example 124 with the exception that, in the first step of the synthesis 2-bromo-4-chloro-6-methylaniline was used instead of 2-bromo-4,6-dimethylpyridin-3-amine and in the last step of the synthesis, the crude product was purified by preparative reversed-phase column chromatography (C-18, water+0.3‰ HCl (36%)/MeCN, 98:2 to 20:80, 30 min, 20 mL/min).

ESI-MS m/z for $C_{26}H_{28}ClN_4O_2S$ found 495.0/497.0 $[M+H]^+$; $R_t$=1.01 min; $^1$H NMR (700 MHz, Methanol-$d_4$) δ 8.84-8.78 (m, 1H), 7.71-7.67 (m, 1H), 7.62 (s, 1H), 7.40-7.36 (m, 1H), 7.24-7.21 (m, 1H), 4.90 (s, 2H), 3.30-3.27 (m, 1H), 3.23-3.19 (m, 1H), 3.04-2.99 (m, 1H), 2.90-2.75 (m, 2H), 2.51 (s, 2H), 2.41 (s, 3H), 1.86-1.74 (m, 1H), 1.68-1.64 (m, 1H), 1.25 (s, 3H), 1.12 (s, 3H).

Example 176

Synthesis of 3-((7-(4-amino-5-methyl-1-(((S)-morpholin-2-yl)methyl)-1H-pyrrol-2-yl)thieno[3,2-b]pyridin-2-yl))methyl)-6,6-dimethyl-3-azabicyclo[3.1.0]hexane-2,4-dione hydrochloride (176)

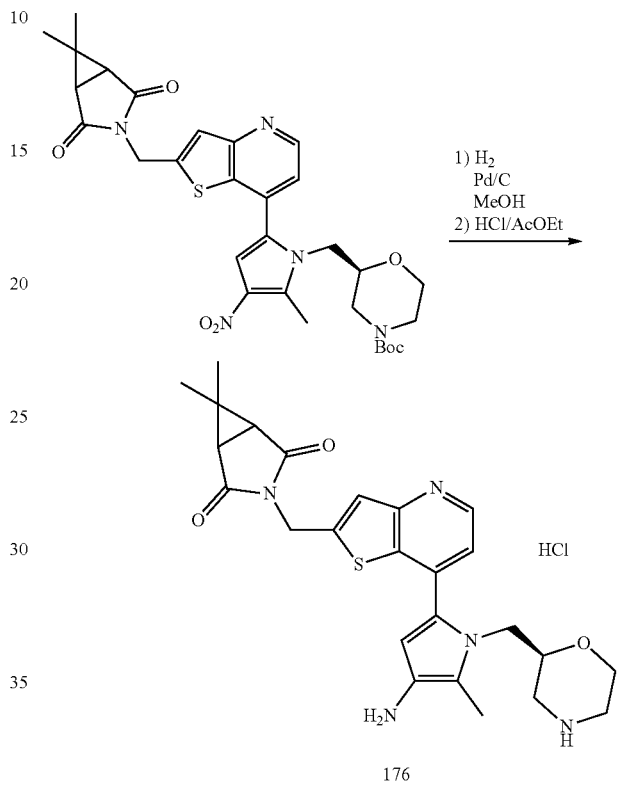

To the solution of tert-butyl (2R)-2-((5-(2-((6,6-dimethyl-2,4-dioxo-3-azabicyclo[3.1.0]hexan-3-yl)methyl)thieno[3,2-b]pyridin-7-yl)-2-methyl-3-nitro-1H-pyrrol-1-yl)methyl)morpholine-4-carboxylate (this compound was obtained during the synthesis of the compound 154)(19 mg; 0.031 mmol) in MeOH (2 mL) under an argon atmosphere Pd/C (10 mol %; cat.) was added. Then argon was replaced by hydrogen and the reaction mixture was conducted under hydrogen atmosphere at room temperature for 2 hours. The reaction progress was monitored by LC-MS. When analysis indicated completion of the reaction, Pd/C was filtered off through a Celite pad and the solvent was evaporated in vacuo. The residue was then taken to the next step in which the title compound was obtained according to General Procedure IVa. The crude product was purified by preparative reversed-phase column chromatography (C-18, water+ 0.3‰ HCl (36%)/MeCN, 99:1 to 70:30, 30 min, 20 mL/min). The title compound (176) was obtained as a hydrochloride salt in 9% yield (1.5 mg; 0.003 mmol).

ESI-MS m/z for $C_{25}H_{30}N_5O_3S$ found 480.0 $[M+H]^+$; $R_t$=0.94 min; $^1$H NMR (700 MHz, Methanol-$d_4$) δ 8.86 (s, 1H), 7.92 (s, 1H), 7.74 (s, 1H), 6.89 (s, 1H), 4.97 (s, 2H), 4.45-4.37 (m, 1H), 4.37-4.28 (m, 1H), 3.89-3.81 (m, 1H), 3.75-3.65 (m, 1H), 3.60-3.49 (m, 1H), 3.30-3.28 (m, 1H), 3.18-3.10 (m, 1H), 3.01-2.92 (m, 1H), 2.84-2.74 (m, 1H), 2.54 (s, 2H), 2.49 (s, 3H), 1.27 (s, 3H), 1.15 (s, 3H).

Example 177

Synthesis of 3-((7-(4-(dimethylamino)-5-methyl-1-(((S)-morpholin-2-yl)methyl)-1H-pyrrol-2-yl)thieno[3,2-b]pyridin-2-yl)methyl)-6,6-dimethyl-3-azabicyclo[3.1.0]hexane-2,4-dione hydrochloride (177)

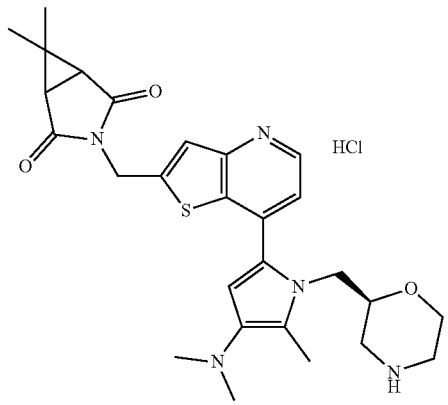

The title compound (177) was obtained as a hydrochloride salt during the synthesis of the compound 176 (as a by-product) in 5% yield (1 mg; 0.0015 mmol).

ESI-MS m/z for $C_7H$-4$N_5O_3S$ found 508.2 [M+H]$^+$; R$_t$=0.90 min; $^1$H NMR (700 MHz, Methanol-d$_4$) δ 8.90 (s, 1H), 7.95 (s, 1H), 7.76 (s, 1H), 7.16 (s, 1H), 4.99 (s, 2H), 4.41-4.35 (m, 1H), 4.33-4.26 (m, 1H), 3.90-3.83 (m, 1H), 3.70-3.65 (m, 1H), 3.62-3.56 (m, 1H), 3.34 (s, 6H), 3.30-3.28 (m, 1H), 3.17-3.12 (m, 1H), 2.99-2.92 (m, 1H), 2.82-2.76 (m, 1H), 2.60 (s, 3H), 2.55 (s, 2H), 1.27 (s, 3H), 1.17 (s, 3H).

Example 178

Synthesis of 3-((7-(5-chloro-3-methyl-2-(((S)-piperidin-3-yl)oxy)phenyl)thieno[3,2-b]pyridin-2-yl)methyl)piperazin-2-one hydrochloride (178)

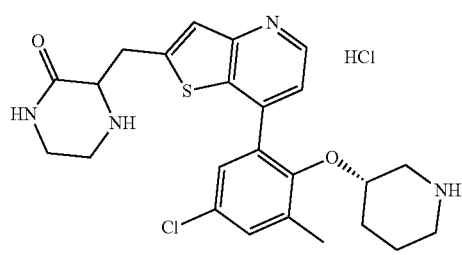

Step 1

Synthesis of 2-(bromomethyl)-7-chlorothieno[3,2-b]pyridine (178a)

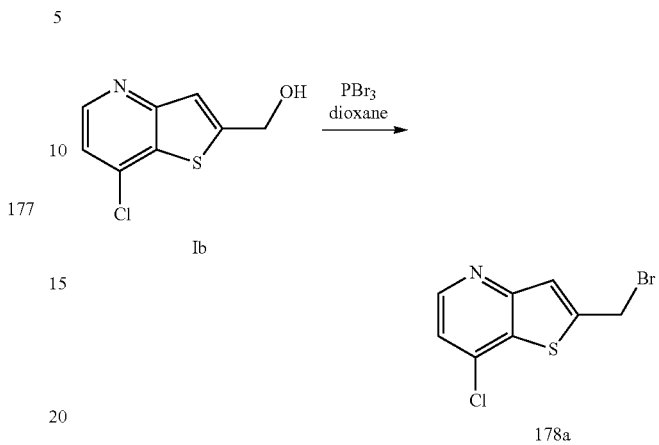

To a solution of Ib (1.00 g; 5.00 mmol) in dry dioxane (50 mL) PBr$_3$ (0.47 mL; 15.00 mmol) was added dropwise at room temperature and then the reaction mixture was stirred at 90° C. for 1 hour. The reaction progress was monitored by LC-MS. When analysis indicated completion of the reaction, the mixture was poured into crushed ice and the product was extracted with AcOEt. The organic layer was washed with 5% NaHCO$_3$ and then dried over anhydrous MgSO$_4$, filtered and concentrated in vacuo and the crude product was purified by flash column chromatography on silica (DCM, 100%, 20 minutes). Compound 178a was obtained as a white solid in 84% yield (1.10 g; 4.22 mmol).

ESI-MS m/z for $C_8H_6BrClNS$ found 261.8/263.8 [M+H]$^+$; R$_t$=1.39 min; $^1$H NMR (700 MHz, CDCl$_3$) δ 8.63-8.55 (m, 1H), 7.62-7.55 (m, 1H), 7.33-7.29 (m, 1H), 4.82-4.77 (m, 2H).

Step 2

Synthesis of di-tert-butyl 2-((7-chlorothieno[3,2-b]pyridin-2-yl)methyl)-3-oxopiperazine-1,4-dicarboxylate (178b)

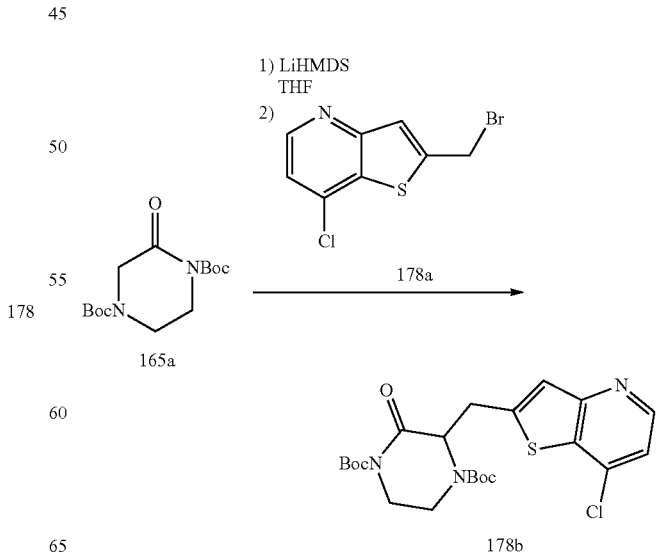

To a cooled to −78° C. solution of 165a (0.50 g; 1.66 mmol) in dry THF (20 mL) LiHMDS (1 M in THF; 1.66 mL; 1.66 mmol) was added dropwise and then the reaction mixture was stirred at this temperature for 1 hour. Then to this mixture a solution of 178a (438 mg; 1.66 mmol) in THF (5 mL) was added and the resulting mixture was stirred at −78° C. for 5 hours and then the mixture was slowly warmed up to room temperature and stirred overnight. The reaction progress was monitored by LC-MS. When analysis indicated completion of the reaction, the mixture was diluted with Et$_2$O and washed with NH$_4$Cl. An organic layer was dried over anhydrous MgSO$_4$, filtered and concentrated in vacuo and the crude product was purified by flash column chromatography on silica (hexane/AcOEt, 100:0 to 60:40, v/v, 25 minutes). The title compound 178b was obtained in 76% yield (610 mg; 1.27 mmol).

ESI-MS m/z for C$_{22}$H$_{29}$ClN$_3$O$_5$S found 482.2/483.9 [M+H]$^+$; R$_t$=1.69 min Step 3

Synthesis of 3-((7-chlorothieno[3,2-b]pyridin-2-yl)methyl)piperazin-2-one hydrochloride (178c)

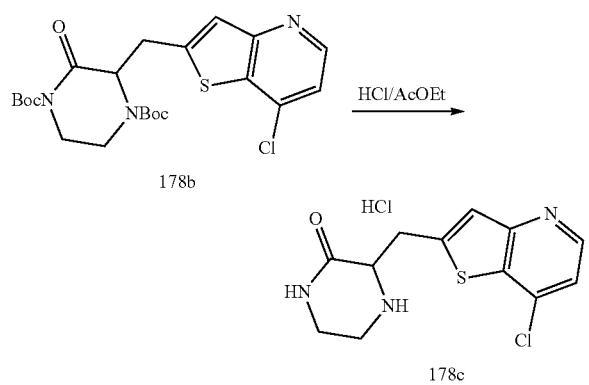

The title compound (178c) was obtained as a hydrochloride salt from 178b (610 mg; 1.27 mmol) according to the General Procedure IVa in 99% yield (400 mg; 1.26 mmol).

ESI-MS m/z for C$_{12}$H$_{13}$ClN$_3$OS found 281.9/283.7 [M+H]$^+$; R$_t$=0.28 min Step 4

Synthesis of tert-butyl (3S)-3-(4-chloro-2-methyl-6-(2-((3-oxopiperazin-2-yl)methyl)thieno[3,2-b]pyridin-7-yl)phenoxy)piperidine-1-carboxylate (178d)

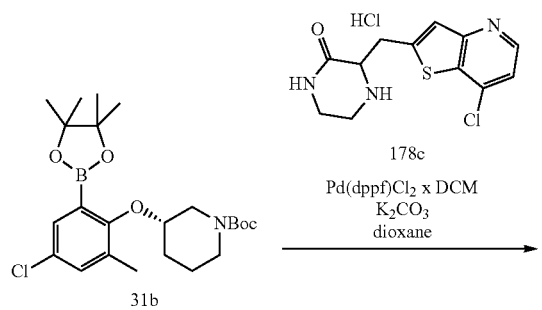

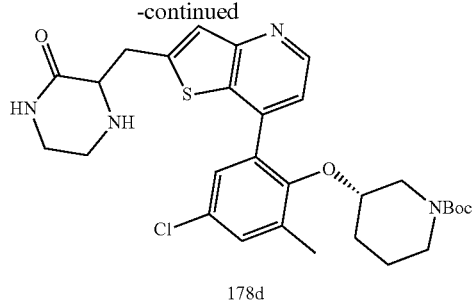

The title compound (178d) was obtained from 31b (50 mg; 0.111 mmol) and from 178c (35 mg; 0.111 mmol) according to the General Procedure Va in 67% yield (43 mg; 0.075 mmol). The crude product was purified by flash column chromatography on silica (DCM/MeOH, 100:0 to 0:15, v/v, 30 minutes).

ESI-MS m/z for C$_{29}$H$_{36}$ClN$_4$O$_4$S found 571.4/573.1 [M+H]$^+$; R$_t$=1.17

Step 5

Synthesis of 3-((7-(5-chloro-3-methyl-2-(((S)-piperidin-3-yl)oxy)phenyl)thieno[3,2-b]pyridin-2-yl)methyl)piperazin-2-one hydrochloride (178)

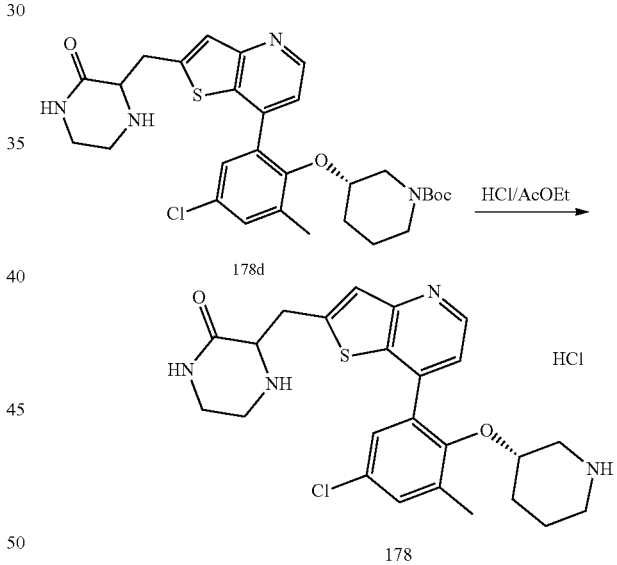

The title compound (178) was obtained as a hydrochloride salt from 178d (43 mg; 0.075 mmol) according to the General Procedure IVa in 55% yield (21 mg; 0.041 mmol). The crude product was purified by preparative reversed-phase column chromatography (column: Cosmosil Cholester 20×250 mm, water+0.3‰ HCl (36%)/MeCN, 99:1 to 40:60, 30 min, 20 mL/min, R$_t$=11.90 min).

ESI-MS m/z for C$_{24}$H$_{29}$ClN$_4$O$_2$S found 471.2/473.2 [M+H]$^+$; R$_t$=0.60 min; $^1$H NMR (700 MHz, DMSO-d$_6$+ D$_2$O, 348 K) δ 8.76-8.72 (m, 1H), 7.62-7.59 (m, 1H), 7.51-7.48 (m, 1H), 7.46-7.42 (m, 1H), 7.36-7.30 (m, 1H), 4.35-4.24 (m, 1H), 3.77-3.68 (m, 2H), 3.56-3.52 (m, 1H), 3.52-3.47 (m, 1H), 3.41-3.37 (m, 2H), 3.34-3.28 (m, 1H), 2.95-2.86 (m, 2H), 2.78-2.68 (m, 1H), 2.64-2.58 (m, 1H), 2.36 (s, 3H), 1.60-1.48 (m, 2H), 1.31-1.17 (m, 2H).

Example 179

Synthesis of 3-((7-(5-chloro-3-methyl-2-(((S)-piperidin-3-yl)oxy)phenyl)thieno[3,2-b]pyridin-2-yl)methyl)-4-hydroxypyrrolidin-2-one 2,2,2-trifluoroacetate (179)

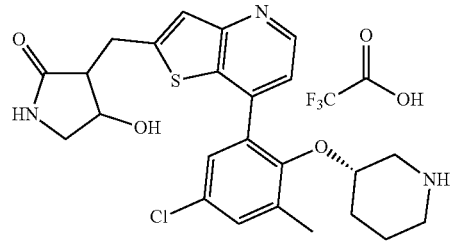

Step 1

Synthesis of 7-chloro-2-(chloromethyl)thieno[3,2-b]pyridine (179a)

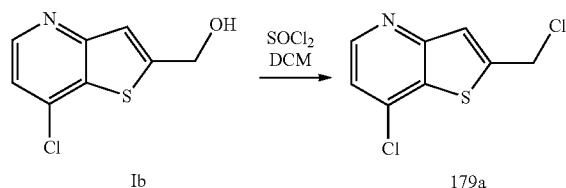 [SMILES: OCc1cc2nccc(Cl)c2s1 ; ClCc1cc2nccc(Cl)c2s1]

To the cooled to 0° C. solution of Ib (2.00 g; 10.01 mmol) in dry DCM (21 mL) SOCl$_2$ (2.2 mL; 30.03 mmol) was added dropwise and then the reaction mixture was stirred at room temperature overnight. The reaction progress was monitored by LC-MS. When analysis indicated completion of the reaction, DCM and SOCl$_2$ were removed in vacuo and the residue was suspended in DCM and the solvent was evaporated (2×). Then the product was suspended in toluene and evaporated (2×) to remove traces of SOCl$_2$. The obtained hydrochloride salt was dissolved in AcOEt and washed with 5% NaHCO$_3$. The title compound 179a was obtained in 99% yield (2.15 g; 9.91 mmol).

ESI-MS m/z for C$_8$H$_6$Cl$_2$NS found 217.8/219.8 [M+H]$^+$; R$_t$=1.34 min

Step 2

Synthesis of ethyl 4-((tert-butoxycarbonyl)amino)-2-((7-chlorothieno[3,2-b]pyridin-2-yl)methyl)-3-oxobutanoate (179b)

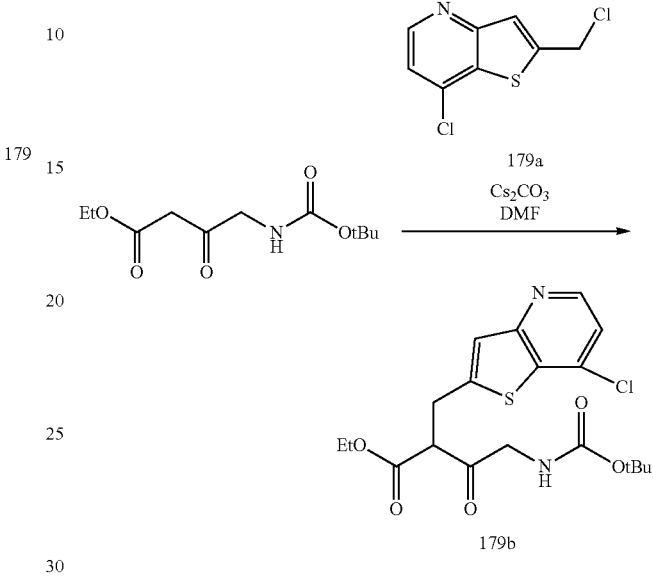

To the solution of ethyl 4-((tert-butoxycarbonyl)amino)-3-oxobutanoate (76 mg; 0.31 mmol) in DMF (6 mL) the compound 179a (45 mg; 0.21 mmol) and Cs$_2$CO$_3$ (135 mg; 0.41 mmol) were added and then the reaction mixture was stirred at room temperature overnight. The reaction progress was monitored by LC-MS. When analysis indicated completion of the reaction, DMF was removed in vacuo and the residue was dissolved in DCM and washed with water. An organic layer was washed with brine, dried over anhydrous MgSO$_4$, filtered and concentrated in vacuo and the crude product was purified by flash column chromatography on silica (hexane/AcOEt, 100:0 to 10:90, v/v, 25 minutes, 13 mL/min). Compound 179b was obtained in 35% yield (49 mg; 0.11 mmol).

ESI-MS m/z for C$_{19}$H$_{24}$ClN$_2$O$_5$S found 427.0/429.0 [M+H]$^+$; R$_t$=1.57 min

Step 3

Synthesis of ethyl 4-((tert-butoxycarbonyl)amino)-2-((7-chlorothieno[3,2-b]pyridin-2-yl)methyl)-3-hydroxybutanoate (179c)

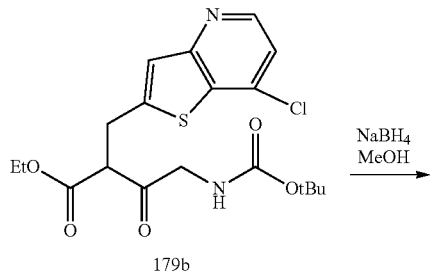

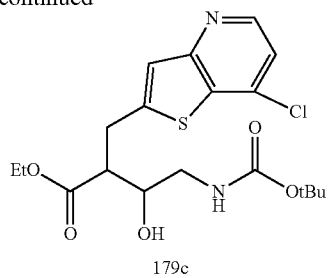

179c

To a cooled to −78° C. suspension of 179b (49 mg; 0.11 mmol) in MeOH (0.5 mL), NaBH$_4$ (6 mg; 0.16 mmol) was added. The resulting mixture was allowed to warm to −10° C. and stirred for 2 hours. Then, to the reaction mixture a saturated solution of NH$_4$C$_1$ was added at −10° C. and the product was extracted with AcOEt. The combined organic solutions were dried over anhydrous Na$_2$SO$_4$, filtered and concentrated in vacuo. The title compound 179c was obtained as a yellow glue in 98% yield (48 mg; 0.11 mmol).

ESI-MS m/z for C$_{19}$H$_{26}$ClN$_2$O$_5$S found 429.0/431.0 [M+H]$^+$; R$_t$=1.43 min Step 4

Synthesis of 3-((7-chlorothieno[3,2-b]pyridin-2-yl)methyl)-4-hydroxypyrrolidin-2-one (179d)

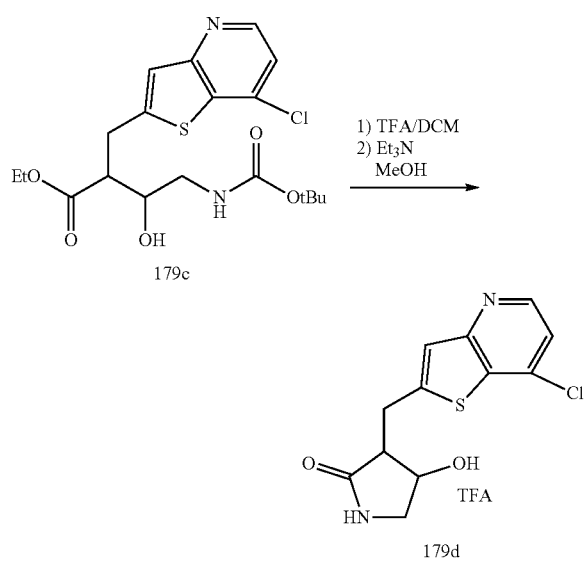

The title compound (179d) was obtained in two steps according to the General Procedure Vb, and then the crude product (contaminated with triethylamine trifluoroacetate, 113 mg) was dissolved in MeOH (1 mL) and to this solution Et$_3$N (235 μL) was added and then the reaction mixture was stirred at 50° C. overnight. The reaction progress was monitored by LC-MS. When analysis indicated completion of the reaction, the solvent was removed in vacuo and the crude product was purified by chromatography (Luna 5 μm Silica (2) 100 Å LC column 250×21.2 mm, hexane/iPrOH, 95:5-1 min, 95:5 to 50:50, 30 min, 20 mL/min). The title compound 179d was obtained as a two separated diastereoisomers in the ratio ca. 1:3, in 2% yield (per two steps)(1.5 mg; 0.0053 mmol).

For the first diastereoisomer: ESI-MS m/z for C$_{12}$H$_2$ClN$_2$O$_2$S found 283.0/285.0 [M+H]$^+$; R$_t$=0.72 min;

For the second diastereoisomer: ESI-MS m/z for C$_{12}$H$_{12}$ClN$_2$O$_2$S found 283.0/285.0 [M+H]$^+$; R$_t$=0.75 min.

Step 5

Synthesis of tert-butyl (3S)-3-(4-chloro-2-(2-((4-hydroxy-2-oxopyrrolidin-3-yl)methyl)thieno[3,2-b]pyridin-7-yl)-6-methylphenoxy)piperidine-1-carboxylate (179e)

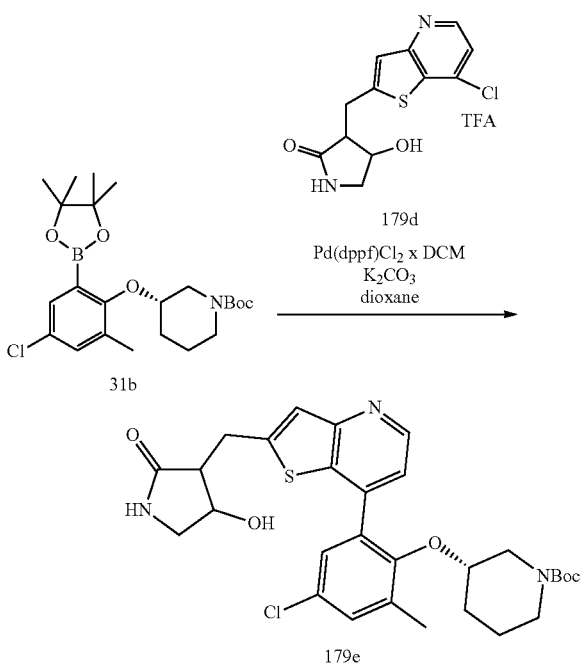

The title compound (179e) was obtained from 31b (31 mg; 0.068 mmol) and from 179d (the one diastereoisomer; 16 mg; 0.057 mmol) according to the General Procedure Va and after standard work-up the crude product was taken to the next step.

ESI-MS m/z for C$_{29}$H$_{35}$ClN$_3$O$_5$S found 572.0/574.0 [M+H]$^+$; R$_t$=1.48

Step 6

Synthesis of 3-((7-(5-chloro-3-methyl-2-(((S)-piperidin-3-yl)oxy)phenyl)thieno[3,2-b]pyridin-2-yl)methyl)-4-hydroxypyrrolidin-2-one 2,2,2-trifluoroacetate (179)

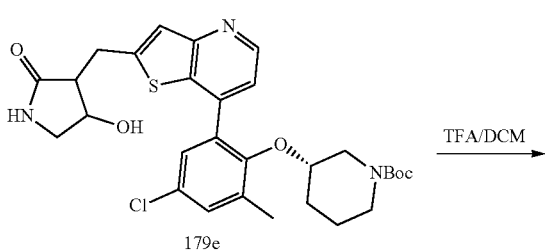

-continued

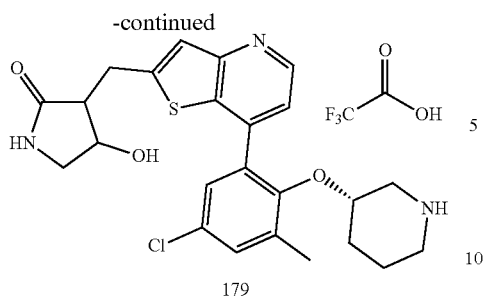

179

The title compound (179) was obtained as a single diastereoisomer as a TFA salt from 179e (the crude product) according to the General Procedure IVb in 5% yield (2 mg; 0.003 mmol). The crude product was purified by preparative reversed-phase column chromatography (column: Cosmosil Cholester 20×250 mm, water+0.4‰ TFA/MeCN, 99:1 to 40:60, 30 min, 20 mL/min, $R_t$=20.80 min).

ESI-MS m/z for $C_{24}H_{27}ClN_3O_3S$ found 472.0/474.0 $[M+H]^+$; $R_t$=0.85 min; $^1$H NMR (700 MHz, $D_2O$) δ 8.84-8.79 (m, 1H), 7.84-7.79 (m, 1H), 7.73-7.69 (m, 1H), 7.62-7.59 (m, 1H), 7.53-7.49 (m, 1H), 4.60-4.57 (m, 1H), 3.92-3.86 (m, 1H), 3.71-3.67 (m, 1H), 3.51-3.46 (m, 1H), 3.41-3.35 (m, 2H), 3.20-3.15 (m, 1H), 3.15-3.10 (m, 1H), 3.06-3.00 (m, 1H), 2.99-2.93 (m, 2H), 2.43 (s, 3H), 1.56 (d, J=10.8 Hz, 2H), 1.39-1.30 (m, 2H).

Example 180

Synthesis of 3-((7-(5-chloro-3-methyl-2-(((S)-piperidin-3-yl)oxy)phenyl)thieno[3,2-b]pyridin-2-yl)methyl)-4-hydroxypyrrolidin-2-one 2,2,2-trifluoroacetate (180)

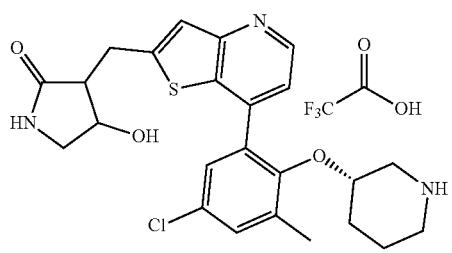

180

The title compound (180) was obtained as a second single diastereoisomer as a TFA salt in 1% overall yield in the same synthesis route as for the compound 179 with the exception that, in the fifth step of the synthesis the different diastereoisomer of the compound 179d was used, and in the last step of the synthesis, the crude product was purified by preparative reversed-phase column chromatography (column: Cosmosil Cholester 20×250 mm, water+0.4%0 TFA/MeCN, 99:1 to 40:60, 40 min, 20 mL/min, $R_t$=25.40 min).

ESI-MS m/z for $C_{24}H_{27}ClN_3O_3S$ found 472.1/474.1 $[M+H]^+$; $R_t$=0.85 min; $^1$H NMR (700 MHz, $D_2O$) δ 8.86-8.81 (m, 1H), 7.83-7.80 (m, 1H), 7.69 (s, 1H), 7.62-7.59 (m, 1H), 7.52-7.51 (m, 1H), 4.45-4.40 (m, 1H), 3.93-3.86 (m, 1H), 3.65-3.60 (m, 1H), 3.55-3.49 (m, 1H), 3.46-3.41 (m, 1H), 3.28-3.24 (m, 1H), 3.16-3.09 (m, 1H), 3.06-2.99 (m, 1H), 2.99-2.92 (m, 3H), 2.43 (s, 3H), 1.60-1.48 (m, 2H), 1.38-1.28 (m, 2H).

Example 181

Synthesis of 3-((7-(3-(3,3-difluoro-4-(methylamino)pyrrolidine-1-carbonyl)-4-methyl-6-(trifluoromethyl)pyridin-2-yl)thieno[3,2-b]pyridin-2-yl)methyl)-6,6-dimethyl-3-azabicyclo[3.1.0]hexane-2,4-dione hydrochloride (181)

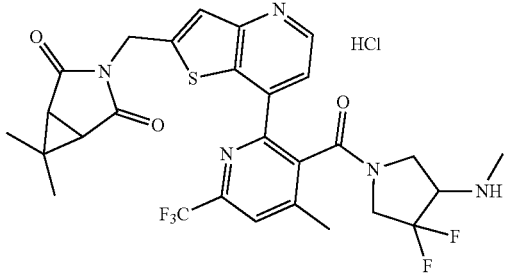

181

The title compound (181) was obtained as a hydrochloride salt in 13% overall yield in a similar way to Example 45 with the exception that, in the first step of the synthesis tert-butyl (4,4-difluoropyrrolidin-3-yl)(methyl)carbamate (this compound was synthesized according to the General Procedure C with the exception that, in the first step of the synthesis tert-butyl (4,4-difluoropyrrolidin-3-yl)carbamate was used instead of tert-butyl (S)-pyrrolidin-3-ylcarbamate and in the second step of the synthesis, MeI and DMF were used instead of EtI and THF and this reaction was carried out at 0° C. and slowly raised to room temperature and the whole was stirred overnight) was used instead of tert-butyl piperazine-1-carboxylate and acid II was used instead of 2-chloro-4-methylnicotinic acid and in the last step of the synthesis, the General Procedure IVb was used instead of the General Procedure IVa and the crude product was purified by preparative reversed-phase column chromatography (C-18, water+0.3‰ HCl (36%)/MeCN, 99:9 to 45:55, 35 min, 20 mL/min, $R_t$=24.3 min).

ESI-MS m/z for $C_{28}H_{27}F_5N_5O_3S$ found 608.3 $[M+H]^+$; $R_t$=1.18 min; $^1$H NMR (700 MHz, $D_2O$) δ 8.89-8.83 (m, 1H), 8.21-8.15 (m, 1H), 7.76-7.71 (m, 1H), 7.71-7.61 (m, 1H), 5.10-4.95 (m, 2H), 4.77-3.09 (m, 4H), 2.90-2.72 (m, 3H), 2.72-2.60 (m, 3H), 2.60-2.57 (m, 3H), 1.33-1.26 (m, 3H), 1.19-1.04 (m, 3H).

INCORPORATION BY REFERENCE

All U.S. patents, U.S. published patent applications, and PCT published patent applications designating the U.S. mentioned herein are hereby incorporated by reference in their entirety as if each individual publication or patent was specifically and individually indicated to be incorporated by reference. In case of conflict, the present application, including any definitions herein, will control.

EQUIVALENTS

The foregoing written specification is sufficient to enable one skilled in the art to practice the invention. The present invention is not to be limited in scope by the examples provided, since each of the examples is intended as a single illustration of one aspect of the invention—other functionally equivalent embodiments are within the scope of the

What is claimed is:
1. A compound of structural Formula (Ia):

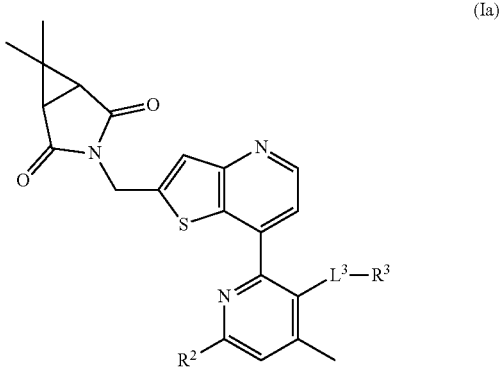

(Ia)

wherein:
R² is selected from hydrogen, methyl, ethyl, chloro, —C≡N, and —CF₃;
L³ represents a single bond, —CH₂—, —C(=O)—, —NH—, or —NH—C(=O)—; and
R³ is selected from (4-6) membered heterocycloalkyl containing 1 to 2 nitrogen heteroatoms or 1 nitrogen heteroatom and 1 oxygen heteroatom, and optionally substituted with 1 or 2 substituents selected from fluoro, methyl, ethyl, amino, methylamino, dimethylamino, ethylamino, isopropylamino, hydroxy, oxo, aminomethyl, 1-aminoethyl, (isopropylamino)methyl, ureido, alanylamino, valylamino, fluoromethyl, difluoromethyl, trifluoromethyl, and 2,2,2-trifluoroacetyl;
or a tautomer, stereoisomer, a racemic or scalemic mixture of stereoisomers, a pharmaceutically acceptable salt, ester, solvate, or polymorph thereof.

2. The compound according to claim 1, wherein the compound is:
 6,6-dimethyl-3-((7-(4-methyl-3-(pyrrolidin-3-ylamino)-6-(trifluoromethyl)pyridin-2-yl)thieno[3,2-b]pyridin-2-yl)methyl)-3-azabicyclo[3.1.0]hexane-2,4-dione;
 6-(2-((6,6-dimethyl-2,4-dioxo-3-azabicyclo[3.1.0]hexan-3-yl)methyl)thieno[3,2-b]pyridin-7-yl)-4-methyl-5-(pyrrolidin-3-ylamino)picolinonitrile;
 5-(azetidin-3-ylamino)-6-(2-((6,6-dimethyl-2,4-dioxo-3-azabicyclo[3.1.0]hexan-3-yl)methyl)thieno[3,2-b]pyridin-7-yl)-4-methylpicolinonitrile;
 N-(2-(2-((6,6-dimethyl-2,4-dioxo-3-azabicyclo[3.1.0]hexan-3-yl)methyl)thieno[3,2-b]pyridin-7-yl)-4-methyl-6-(trifluoromethyl)pyridin-3-yl)azetidine-3-carboxamide;
 6,6-dimethyl-3-((7-(4-methyl-3-(piperazin-2-ylmethyl)-6-(trifluoromethyl)pyridin-2-yl)thieno[3,2-b]pyridin-2-yl)methyl)-3-azabicyclo[3.1.0]hexane-2,4-dione;
 3-((7-(3-((1H-1,2,4-triazol-1-yl)methyl)-4-methyl-6-(trifluoromethyl)pyridin-2-yl)thieno[3,2-b]pyridin-2-yl)methyl)-6,6-dimethyl-3-azabicyclo[3.1.0]hexane-2,4-dione;
 3-((7-(3-((3,6-dioxopiperazin-2-yl)methyl)-4-methyl-6-(trifluoromethyl)pyridin-2-yl)thieno[3,2-b]pyridin-2-yl)methyl)-6,6-dimethyl-3-azabicyclo[3.1.0]hexane-2,4-dione;
 6,6-dimethyl-3-((7-(4-methyl-3-((3-oxomorpholino)methyl)-6-(trifluoromethyl)pyridin-2-yl)thieno[3,2-b]pyridin-2-yl)methyl)-3-azabicyclo[3.1.0]hexane-2,4-dione;
 6,6-dimethyl-3-((7-(4-methyl-3-((2-oxopyrrolidin-1-yl)methyl)-6-(trifluoromethyl)pyridin-2-yl)thieno[3,2-b]pyridin-2-yl)methyl)-3-azabicyclo[3.1.0]hexane-2,4-dione;
 6,6-dimethyl-3-((7-(4-methyl-3-((2-oxopiperazin-1-yl)methyl)-6-(trifluoromethyl)pyridin-2-yl)thieno[3,2-b]pyridin-2-yl)methyl)-3-azabicyclo[3.1.0]hexane-2,4-dione;
 6,6-dimethyl-3-((7-(4-methyl-3-((4-methyl-2-oxopiperazin-1-yl)methyl)-6-(trifluoromethyl)pyridin-2-yl)thieno[3,2-b]pyridin-2-yl)methyl)-3-azabicyclo[3.1.0]hexane-2,4-dione;
 6-(2-((6,6-dimethyl-2,4-dioxo-3-azabicyclo[3.1.0]hexan-3-yl)methyl)thieno[3,2-b]pyridin-7-yl)-5-(3-(dimethylamino)azetidine-1-carbonyl)-4-methylpicolinonitrile;
 6-(2-((6,6-dimethyl-2,4-dioxo-3-azabicyclo[3.1.0]hexan-3-yl)methyl)thieno[3,2-b]pyridin-7-yl)-5-((S)-3-(dimethylamino)pyrrolidine-1-carbonyl)-4-methylpicolinonitrile;
 6,6-dimethyl-3-((7-(4-methyl-3-(piperazine-1-carbonyl)pyridin-2-yl)thieno[3,2-b]pyridin-2-yl)methyl)-3-azabicyclo[3.1.0]hexane-2,4-dione;
 6,6-dimethyl-3-((7-(4-methyl-3-(piperazin-1-ylmethyl)pyridin-2-yl)thieno[3,2-b]pyridin-2-yl)methyl)-3-azabicyclo[3.1.0]hexane-2,4-dione;
 6-(2-((6,6-dimethyl-2,4-dioxo-3-azabicyclo[3.1.0]hexan-3-yl)methyl)thieno[3,2-b]pyridin-7-yl)-4-methyl-5-((S)-2-methylpiperazine-1-carbonyl)picolinonitrile;
 6,6-dimethyl-3-((7-(4-methyl-3-(morpholine-4-carbonyl)pyridin-2-yl)thieno[3,2-b]pyridin-2-yl)methyl)-3-azabicyclo[3.1.0]hexane-2,4-dione;
 3-((7-(3-(3,3-difluoropyrrolidine-1-carbonyl)-4-methylpyridin-2-yl)thieno[3,2-b]pyridin-2-yl)methyl)-6,6-dimethyl-3-azabicyclo[3.1.0]hexane-2,4-dione;
 3-((7-(3-(3,3-difluoroazetidine-1-carbonyl)-4-methylpyridin-2-yl)thieno[3,2-b]pyridin-2-yl)methyl)-6,6-dimethyl-3-azabicyclo[3.1.0]hexane-2,4-dione;
 5-(3,3-difluoroazetidine-1-carbonyl)-6-(2-((6,6-dimethyl-2,4-dioxo-3-azabicyclo[3.1.0]hexan-3-yl)methyl)thieno[3,2-b]pyridin-7-yl)-4-methylpicolinonitrile;
 6-(2-((6,6-dimethyl-2,4-dioxo-3-azabicyclo[3.1.0]hexan-3-yl)methyl)thieno[3,2-b]pyridin-7-yl)-5-((S)-2,4-dimethylpiperazine-1-carbonyl)-4-methylpicolinonitrile;
 6-(2-((6,6-dimethyl-2,4-dioxo-3-azabicyclo[3.1.0]hexan-3-yl)methyl)thieno[3,2-b]pyridin-7-yl)-5-(3,3-dimethylpiperazine-1-carbonyl)-4-methylpicolinonitrile;
 6-(2-((6,6-dimethyl-2,4-dioxo-3-azabicyclo[3.1.0]hexan-3-yl)methyl)thieno[3,2-b]pyridin-7-yl)-4-methyl-5-((R)-2-methylpiperazine-1-carbonyl)picolinonitrile;
 6-(2-((6,6-dimethyl-2,4-dioxo-3-azabicyclo[3.1.0]hexan-3-yl)methyl)thieno[3,2-b]pyridin-7-yl)-4-methyl-5-(piperazine-1-carbonyl)picolinonitrile;
 N-(azetidin-3-yl)-6-cyano-2-(2-((6,6-dimethyl-2,4-dioxo-3-azabicyclo[3.1.0]hexan-3-yl)methyl)thieno[3,2-b]pyridin-7-yl)-4-methylnicotinamide;

6-cyano-N-(3,3-difluorocyclobutyl)-2-(2-((6,6-dimethyl-2,4-dioxo-3-azabicyclo[3.1.0]hexan-3-yl)methyl)thieno[3,2-b]pyridin-7-yl)-4-methylnicotinamide;

6-(2-((6,6-dimethyl-2,4-dioxo-3-azabicyclo[3.1.0]hexan-3-yl)methyl)thieno[3,2-b]pyridin-7-yl)-4-methyl-5-(morpholine-4-carbonyl)picolinonitrile;

5-(3,3-difluoropyrrolidine-1-carbonyl)<sub>2</sub>-((6,6-dimethyl-2,4-dioxo-3-azabicyclo[3.1.0]hexan-3-yl)methyl)thieno[3,2-b]pyridin-7-yl)-4-methylpicolinonitrile;

3-((7-(3-((S)-3-(ethylamino)pyrrolidine-1-carbonyl)-4-methyl-6-(trifluoromethyl)pyridin-2-yl)thieno[3,2-b]pyridin-2-yl)methyl)-6,6-dimethyl-3-azabicyclo[3.1.0]hexane-2,4-dione;

3-((7-(3-((S)-3-(isopropylamino)pyrrolidine-1-carbonyl)-4-methyl-6-(trifluoromethyl)pyridin-2-yl)thieno[3,2-b]pyridin-2-yl)methyl)-6,6-dimethyl-3-azabicyclo[3.1.0]hexane-2,4-dione;

6,6-dimethyl-3-((7-(4-methyl-3-(piperazine-1-carbonyl)-6-(trifluoromethyl)pyridin-2-yl)thieno[3,2-b]pyridin-2-yl)methyl)-3-azabicyclo[3.1.0]hexane-2,4-dione;

6,6-dimethyl-3-((7-(4-methyl-3-((S)-3-(methylamino)pyrrolidine-1-carbonyl)-6-(trifluoromethyl)pyridin-2-yl)thieno[3,2-b]pyridin-2-yl)methyl)-3-azabicyclo[3.1.0]hexane-2,4-dione;

6,6-dimethyl-3-((7-(4-methyl-3-((S)-2-methylpiperazine-1-carbonyl)-6-(trifluoromethyl)pyridin-2-yl)thieno[3,2-b]pyridin-2-yl)methyl)-3-azabicyclo[3.1.0]hexane-2,4-dione;

3-((7-(3-((S)-2,4-dimethylpiperazine-1-carbonyl)-4-methyl-6-(trifluoromethyl)pyridin-2-yl)thieno[3,2-b]pyridin-2-yl)methyl)-6,6-dimethyl-3-azabicyclo[3.1.0]hexane-2,4-dione;

6,6-dimethyl-3-((7-(4-methyl-3-(4-methylpiperazine-1-carbonyl)-6-(trifluoromethyl)pyridin-2-yl)thieno[3,2-b]pyridin-2-yl)methyl)-3-azabicyclo[3.1.0]hexane-2,4-dione;

3-((7-(3-((S)-3-aminopyrrolidine-1-carbonyl)-4-methyl-6-(trifluoromethyl)pyridin-2-yl)thieno[3,2-b]pyridin-2-yl)methyl)-6,6-dimethyl-3-azabicyclo[3.1.0]hexane-2,4-dione;

3-((7-(3-((S)-3-(dimethylamino)pyrrolidine-1-carbonyl)-4-methyl-6-(trifluoromethyl)pyridin-2-yl)thieno[3,2-b]pyridin-2-yl)methyl)-6,6-dimethyl-3-azabicyclo[3.1.0]hexane-2,4-dione;

3-((7-(3-(3,3-difluoropyrrolidine-1-carbonyl)-4-methyl-6-(trifluoromethyl)pyridin-2-yl)thieno[3,2-b]pyridin-2-yl)methyl)-6,6-dimethyl-3-azabicyclo[3.1.0]hexane-2,4-dione;

6,6-dimethyl-3-((7-(4-methyl-3-(morpholine-4-carbonyl)-6-(trifluoromethyl)pyridin-2-yl)thieno[3,2-b]pyridin-2-yl)methyl)-3-azabicyclo[3.1.0]hexane-2,4-dione;

3-((7-(3-(3,3-difluoroazetidine-1-carbonyl)-4,6-dimethylpyridin-2-yl)thieno[3,2-b]pyridin-2-yl)methyl)-6,6-dimethyl-3-azabicyclo[3.1.0]hexane-2,4-dione;

6,6-dimethyl-3-((7-(2-methyl-3-(((R)-pyrrolidin-3-yl)methyl)-6-(trifluoromethyl)pyridin-4-yl)thieno[3,2-b]pyridin-2-yl)methyl)-3-azabicyclo[3.1.0]hexane-2,4-dione;

6,6-dimethyl-3-((7-(2-methyl-3-(((S)-pyrrolidin-3-yl)methyl)-6-(trifluoromethyl)pyridin-4-yl)thieno[3,2-b]pyridin-2-yl)methyl)-3-azabicyclo[3.1.0]hexane-2,4-dione;

6,6-dimethyl-3-((7-(4-methyl-3-(morpholin-2-ylmethyl)-6-(trifluoromethyl)pyridin-2-yl)thieno[3,2-b]pyridin-2-yl)methyl)-3-azabicyclo[3.1.0]hexane-2,4-dione;

6-(2-((6,6-dimethyl-2,4-dioxo-3-azabicyclo[3.1.0]hexan-3-yl)methyl)thieno[3,2-b]pyridin-7-yl)-4-methyl-5-(morpholin-2-ylmethyl)picolinonitrile;

6,6-dimethyl-3-((7-(4-methyl-3-(((S)-morpholin-2-yl)methyl)-6-(trifluoromethyl)pyridin-2-yl)thieno[3,2-b]pyridin-2-yl)methyl)-3-azabicyclo[3.1.0]hexane-2,4-dione;

6,6-dimethyl-3-((7-(4-methyl-3-(((R)-morpholin-2-yl)methyl)-6-(trifluoromethyl)pyridin-2-yl)thieno[3,2-b]pyridin-2-yl)methyl)-3-azabicyclo[3.1.0]hexane-2,4-dione;

6,6-dimethyl-3-((7-(4-methyl-3-(((S)-4-methylmorpholin-2-yl)methyl)-6-(trifluoromethyl)pyridin-2-yl)thieno[3,2-b]pyridin-2-yl)methyl)-3-azabicyclo[3.1.0]hexane-2,4-dione;

6,6-dimethyl-3-((7-(4-methyl-3-(((R)-4-methylmorpholin-2-yl)methyl)-6-(trifluoromethyl)pyridin-2-yl)thieno[3,2-b]pyridin-2-yl)methyl)-3-azabicyclo[3.1.0]hexane-2,4-dione;

3-((7-(3-((S)-3-(difluoromethyl)pyrrolidine-1-carbonyl)-4-methyl-6-(trifluoromethyl)pyridin-2-yl)thieno[3,2-b]pyridin-2-yl)methyl)-6,6-dimethyl-3-azabicyclo[3.1.0]hexane-2,4-dione;

3-((7-(3-((S)-3-(fluoromethyl)pyrrolidine-1-carbonyl)-4-methyl-6-(trifluoromethyl)pyridin-2-yl)thieno[3,2-b]pyridin-2-yl)methyl)-6,6-dimethyl-3-azabicyclo[3.1.0]hexane-2,4-dione;

3-((7-(3-((3S,4S)-3-amino-4-methylpyrrolidine-1-carbonyl)-4-methyl-6-(trifluoromethyl)pyridin-2-yl)thieno[3,2-b]pyridin-2-yl)methyl)-6,6-dimethyl-3-azabicyclo[3.1.0]hexane-2,4-dione;

3-((7-(3-((3S,4R)-3-amino-4-methylpyrrolidine-1-carbonyl)-4-methyl-6-(trifluoromethyl)pyridin-2-yl)thieno[3,2-b]pyridin-2-yl)methyl)-6,6-dimethyl-3-azabicyclo[3.1.0]hexane-2,4-dione;

(2S)-2-amino-N-((3S)-1-(2-(2-((6,6-dimethyl-2,4-dioxo-3-azabicyclo[3.1.0]hexan-3-yl)methyl)thieno[3,2-b]pyridin-7-yl)-4-methyl-6-(trifluoromethyl)nicotinoyl)pyrrolidin-3-yl)-3-methylbutanamide;

(2S)-2-amino-N-((3S)-1-(2-(2-((6,6-dimethyl-2,4-dioxo-3-azabicyclo[3.1.0]hexan-3-yl)methyl)thieno[3,2-b]pyridin-7-yl)-4-methyl-6-(trifluoromethyl)nicotinoyl)pyrrolidin-3-yl)propanamide;

3-((7-(3-(4-aminopiperidine-1-carbonyl)-4-methyl-6-(trifluoromethyl)pyridin-2-yl)thieno[3,2-b]pyridin-2-yl)methyl)-6,6-dimethyl-3-azabicyclo[3.1.0]hexane-2,4-dione;

3-((7-(3-((S)-3-hydroxypyrrolidine-1-carbonyl)-4-methyl-6-(trifluoromethyl)pyridin-2-yl)thieno[3,2-b]pyridin-2-yl)methyl)-6,6-dimethyl-3-azabicyclo[3.1.0]hexane-2,4-dione;

3-((7-(3-((S)-3-fluoropyrrolidine-1-carbonyl)-4-methyl-6-(trifluoromethyl)pyridin-2-yl)thieno[3,2-b]pyridin-2-yl)methyl)-6,6-dimethyl-3-azabicyclo[3.1.0]hexane-2,4-dione;

3-((7-(3-((R)-3-(aminomethyl)pyrrolidine-1-carbonyl)-4-methyl-6-(trifluoromethyl)pyridin-2-yl)thieno[3,2-b]pyridin-2-yl)methyl)-6,6-dimethyl-3-azabicyclo[3.1.0]hexane-2,4-dione;

3-((7-(3-((3R,4R)-3-amino-4-fluoropyrrolidine-1-carbonyl)-4-methyl-6-(trifluoromethyl)pyridin-2-yl)thieno[3,2-b]pyridin-2-yl)methyl)-6,6-dimethyl-3-azabicyclo[3.1.0]hexane-2,4-dione;

3-((7-(6-chloro-4-methyl-3-(2-oxotetrahydropyrimidin-1(2H)-yl)pyridin-2-yl)thieno[3,2-b]pyridin-2-yl)methyl)-6,6-dimethyl-3-azabicyclo[3.1.0]hexane-2,4-dione;

3-((7-(3-(azetidin-3-ylamino)-6-chloro-4-methylpyridin-2-yl)thieno[3,2-b]pyridin-2-yl)methyl)-6,6-dimethyl-3-azabicyclo[3.1.0]hexane-2,4-dione;

3-((7-(6-chloro-3-((3,3-difluorocyclobutyl)amino)-4-methylpyridin-2-yl)thieno[3,2-b]pyridin-2-yl)methyl)-6,6-dimethyl-3-azabicyclo[3.1.0]hexane-2,4-dione;

3-((7-(4,6-dimethyl-3-(pyrrolidin-3-ylamino)pyridin-2-yl)thieno[3,2-b]pyridin-2-yl)methyl)-6,6-dimethyl-3-azabicyclo[3.1.0]hexane-2,4-dione;

3-((7-(6-chloro-4-methyl-3-(pyrrolidin-3-ylamino)pyridin-2-yl)thieno[3,2-b]pyridin-2-yl)methyl)-6,6-dimethyl-3-azabicyclo[3.1.0]hexane-2,4-dione;

3-((7-(6-chloro-4-methyl-3-(piperidin-4-ylamino)pyridin-2-yl)thieno[3,2-b]pyridin-2-yl)methyl)-6,6-dimethyl-3-azabicyclo[3.1.0]hexane-2,4-dione;

6,6-dimethyl-3-((7-(4-methyl-3-(piperidin-4-ylamino)-6-(trifluoromethyl)pyridin-2-yl)thieno[3,2-b]pyridin-2-yl)methyl)-3-azabicyclo[3.1.0]hexane-2,4-dione;

3-((7-(6-chloro-4-methyl-3-(piperidin-3-ylamino)pyridin-2-yl)thieno[3,2-b]pyridin-2-yl)methyl)-6,6-dimethyl-3-azabicyclo[3.1.0]hexane-2,4-dione;

6,6-dimethyl-3-((7-(4-methyl-3-(piperidin-3-ylamino)-6-(trifluoromethyl)pyridin-2-yl)thieno[3,2-b]pyridin-2-yl)methyl)-3-azabicyclo[3.1.0]hexane-2,4-dione;

N-(2-(2-((6,6-dimethyl-2,4-dioxo-3-azabicyclo[3.1.0]hexan-3-yl)methyl)thieno[3,2-b]pyridin-7-yl)-4,6-dimethylpyridin-3-yl)azetidine-3-carboxamide;

N-(2-(2-((6,6-dimethyl-2,4-dioxo-3-azabicyclo[3.1.0]hexan-3-yl)methyl)thieno[3,2-b]pyridin-7-yl)-4,6-dimethylpyridin-3-yl)piperidine-4-carboxamide;

3-((7-(6-chloro-4-methyl-3-(piperazine-1-carbonyl)pyridin-2-yl)thieno[3,2-b]pyridin-2-yl)methyl)-6,6-dimethyl-3-azabicyclo[3.1.0]hexane-2,4-dione;

1-((3S)-1-(2-(2-((6,6-dimethyl-2,4-dioxo-3-azabicyclo[3.1.0]hexan-3-yl)methyl)thieno[3,2-b]pyridin-7-yl)-4-methyl-6-(trifluoromethyl)nicotinoyl)pyrrolidin-3-yl)urea;

3-((7-(3-(3-amino-3-methylpyrrolidine-1-carbonyl)-4-methyl-6-(trifluoromethyl)pyridin-2-yl)thieno[3,2-b]pyridin-2-yl)methyl)-6,6-dimethyl-3-azabicyclo[3.1.0]hexane-2,4-dione;

3-((7-(3-((3S)-3-(1-aminoethyl)pyrrolidine-1-carbonyl)-4-methyl-6-(trifluoromethyl)pyridin-2-yl)thieno[3,2-b]pyridin-2-yl)methyl)-6,6-dimethyl-3-azabicyclo[3.1.0]hexane-2,4-dione;

3-((7-(3-(3-(aminomethyl)pyrrolidine-1-carbonyl)-4-methyl-6-(trifluoromethyl)pyridin-2-yl)thieno[3,2-b]pyridin-2-yl)methyl)-6,6-dimethyl-3-azabicyclo[3.1.0]hexane-2,4-dione;

3-((7-(3-(3-((isopropylamino)methyl)pyrrolidine-1-carbonyl)-4-methyl-6-(trifluoromethyl)pyridin-2-yl)thieno[3,2-b]pyridin-2-yl)methyl)-6,6-dimethyl-3-azabicyclo[3.1.0]hexane-2,4-dione;

3-((7-(3-((2S,6S)-2,6-dimethylpiperazine-1-carbonyl)-4-methyl-6-(trifluoromethyl)pyridin-2-yl)thieno[3,2-b]pyridin-2-yl)methyl)-6,6-dimethyl-3-azabicyclo[3.1.0]hexane-2,4-dione;

3-((7-(3-((2R,6R)-2,6-dimethylpiperazine-1-carbonyl)-4-methyl-6-(trifluoromethyl)pyridin-2-yl)thieno[3,2-b]pyridin-2-yl)methyl)-6,6-dimethyl-3-azabicyclo[3.1.0]hexane-2,4-dione;

3-((7-(3-(4-ethylpiperazine-1-carbonyl)-4-methyl-6-(trifluoromethyl)pyridin-2-yl)thieno[3,2-b]pyridin-2-yl)methyl)-6,6-dimethyl-3-azabicyclo[3.1.0]hexane-2,4-dione;

6,6-dimethyl-3-((7-(4-methyl-3-((S)-3-(methylamino)piperidine-1-carbonyl)-6-(trifluoromethyl)pyridin-2-yl)thieno[3,2-b]pyridin-2-yl)methyl)-3-azabicyclo[3.1.0]hexane-2,4-dione;

or a tautomer, stereoisomer, a racemic or scalemic mixture of stereoisomers, a pharmaceutically acceptable salt, ester, solvate, or polymorph thereof.

3. The compound according to claim 2, wherein the compound is:

6,6-dimethyl-3-((7-(4-methyl-3-(pyrrolidin-3-ylamino)-6-(trifluoromethyl)pyridin-2-yl)thieno[3,2-b]pyridin-2-yl)methyl)-3-azabicyclo[3.1.0]hexane-2,4-dione;

6-(2-((6,6-dimethyl-2,4-dioxo-3-azabicyclo[3.1.0]hexan-3-yl)methyl)thieno[3,2-b]pyridin-7-yl)-4-methyl-5-(pyrrolidin-3-ylamino)picolinonitrile;

5-(azetidin-3-ylamino)-6-(2-((6,6-dimethyl-2,4-dioxo-3-azabicyclo[3.1.0]hexan-3-yl)methyl)thieno[3,2-b]pyridin-7-yl)-4-methylpicolinonitrile;

N-(2-(2-((6,6-dimethyl-2,4-dioxo-3-azabicyclo[3.1.0]hexan-3-yl)methyl)thieno[3,2-b]pyridin-7-yl)-4-methyl-6-(trifluoromethyl)pyridin-3-yl)azetidine-3-carboxamide;

6,6-dimethyl-3-((7-(4-methyl-3-(piperazin-2-ylmethyl)-6-(trifluoromethyl)pyridin-2-yl)thieno[3,2-b]pyridin-2-yl)methyl)-3-azabicyclo[3.1.0]hexane-2,4-dione;

6-(2-((6,6-dimethyl-2,4-dioxo-3-azabicyclo[3.1.0]hexan-3-yl)methyl)thieno[3,2-b]pyridin-7-yl)-4-methyl-5-((S)-2-methylpiperazine-1-carbonyl)picolinonitrile;

5-(3,3-difluoroazetidine-1-carbonyl)-6-(2-((6,6-dimethyl-2,4-dioxo-3-azabicyclo[3.1.0]hexan-3-yl)methyl)thieno[3,2-b]pyridin-7-yl)-4-methylpicolinonitrile;

6-(2-((6,6-dimethyl-2,4-dioxo-3-azabicyclo[3.1.0]hexan-3-yl)methyl)thieno[3,2-b]pyridin-7-yl)-5-((S)-2,4-dimethylpiperazine-1-carbonyl)-4-methylpicolinonitrile;

6-(2-((6,6-dimethyl-2,4-dioxo-3-azabicyclo[3.1.0]hexan-3-yl)methyl)thieno[3,2-b]pyridin-7-yl)-4-methyl-5-(piperazine-1-carbonyl)picolinonitrile;

5-(3,3-difluoropyrrolidine-1-carbonyl)$_2$-((6,6-dimethyl-2,4-dioxo-3-azabicyclo[3.1.0]hexan-3-yl)methyl)thieno[3,2-b]pyridin-7-yl)-4-methylpicolinonitrile;

3-((7-(3-((S)-3-(ethylamino)pyrrolidine-1-carbonyl)-4-methyl-6-(trifluoromethyl)pyridin-2-yl)thieno[3,2-b]pyridin-2-yl)methyl)-6,6-dimethyl-3-azabicyclo[3.1.0]hexane-2,4-dione;

3-((7-(3-((S)-3-(isopropylamino)pyrrolidine-1-carbonyl)-4-methyl-6-(trifluoromethyl)pyridin-2-yl)thieno[3,2-b]pyridin-2-yl)methyl)-6,6-dimethyl-3-azabicyclo[3.1.0]hexane-2,4-dione;

6,6-dimethyl-3-((7-(4-methyl-3-(piperazine-1-carbonyl)-6-(trifluoromethyl)pyridin-2-yl)thieno[3,2-b]pyridin-2-yl)methyl)-3-azabicyclo[3.1.0]hexane-2,4-dione;

6,6-dimethyl-3-((7-(4-methyl-3-((S)-3-(methylamino)pyrrolidine-1-carbonyl)-6-(trifluoromethyl)pyridin-2-yl)thieno[3,2-b]pyridin-2-yl)methyl)-3-azabicyclo[3.1.0]hexane-2,4-dione;

6,6-dimethyl-3-((7-(4-methyl-3-((S)-2-methylpiperazine-1-carbonyl)-6-(trifluoromethyl)pyridin-2-yl)thieno[3,2-b]pyridin-2-yl)methyl)-3-azabicyclo[3.1.0]hexane-2,4-dione;

3-((7-(3-((S)-2,4-dimethylpiperazine-1-carbonyl)-4-methyl-6-(trifluoromethyl)pyridin-2-yl)thieno[3,2-b]pyridin-2-yl)methyl)-6,6-dimethyl-3-azabicyclo[3.1.0]hexane-2,4-dione;

6,6-dimethyl-3-((7-(4-methyl-3-(4-methylpiperazine-1-carbonyl)-6-(trifluoromethyl)pyridin-2-yl)thieno[3,2-b]pyridin-2-yl)methyl)-3-azabicyclo[3.1.0]hexane-2,4-dione;

3-((7-(3-((S)-3-aminopyrrolidine-1-carbonyl)-4-methyl-6-(trifluoromethyl)pyridin-2-yl)thieno[3,2-b]pyridin-2-yl)methyl)-6,6-dimethyl-3-azabicyclo[3.1.0]hexane-2,4-dione;

3-((7-(3-((S)-3-(dimethylamino)pyrrolidine-1-carbonyl)-4-methyl-6-(trifluoromethyl)pyridin-2-yl)thieno[3,2-b]pyridin-2-yl)methyl)-6,6-dimethyl-3-azabicyclo[3.1.0]hexane-2,4-dione;

3-((7-(3-(3,3-difluoropyrrolidine-1-carbonyl)-4-methyl-6-(trifluoromethyl)pyridin-2-yl)thieno[3,2-b]pyridin-2-yl)methyl)-6,6-dimethyl-3-azabicyclo[3.1.0]hexane-2,4-dione;

6,6-dimethyl-3-((7-(2-methyl-3-(((R)-pyrrolidin-3-yl)methyl)-6-(trifluoromethyl)pyridin-4-yl)thieno[3,2-b]pyridin-2-yl)methyl)-3-azabicyclo[3.1.0]hexane-2,4-dione;

6,6-dimethyl-3-((7-(2-methyl-3-(((S)-pyrrolidin-3-yl)methyl)-6-(trifluoromethyl)pyridin-4-yl)thieno[3,2-b]pyridin-2-yl)methyl)-3-azabicyclo[3.1.0]hexane-2,4-dione;

6,6-dimethyl-3-((7-(4-methyl-3-(morpholin-2-ylmethyl)-6-(trifluoromethyl)pyridin-2-yl)thieno[3,2-b]pyridin-2-yl)methyl)-3-azabicyclo[3.1.0]hexane-2,4-dione;

6-(2-((6,6-dimethyl-2,4-dioxo-3-azabicyclo[3.1.0]hexan-3-yl)methyl)thieno[3,2-b]pyridin-7-yl)-4-methyl-5-(morpholin-2-ylmethyl)picolinonitrile;

6,6-dimethyl-3-((7-(4-methyl-3-(((S)-morpholin-2-yl)methyl)-6-(trifluoromethyl)pyridin-2-yl)thieno[3,2-b]pyridin-2-yl)methyl)-3-azabicyclo[3.1.0]hexane-2,4-dione;

6,6-dimethyl-3-((7-(4-methyl-3-(((R)-morpholin-2-yl)methyl)-6-(trifluoromethyl)pyridin-2-yl)thieno[3,2-b]pyridin-2-yl)methyl)-3-azabicyclo[3.1.0]hexane-2,4-dione;

6,6-dimethyl-3-((7-(4-methyl-3-(((R)-4-methylmorpholin-2-yl)methyl)-6-(trifluoromethyl)pyridin-2-yl)thieno[3,2-b]pyridin-2-yl)methyl)-3-azabicyclo[3.1.0]hexane-2,4-dione;

3-((7-(3-((S)-3-(difluoromethyl)pyrrolidine-1-carbonyl)-4-methyl-6-(trifluoromethyl)pyridin-2-yl)thieno[3,2-b]pyridin-2-yl)methyl)-6,6-dimethyl-3-azabicyclo[3.1.0]hexane-2,4-dione;

3-((7-(3-((S)-3-(fluoromethyl)pyrrolidine-1-carbonyl)-4-methyl-6-(trifluoromethyl)pyridin-2-yl)thieno[3,2-b]pyridin-2-yl)methyl)-6,6-dimethyl-3-azabicyclo[3.1.0]hexane-2,4-dione;

3-((7-(3-((3S,4S)-3-amino-4-methylpyrrolidine-1-carbonyl)-4-methyl-6-(trifluoromethyl)pyridin-2-yl)thieno[3,2-b]pyridin-2-yl)methyl)-6,6-dimethyl-3-azabicyclo[3.1.0]hexane-2,4-dione;

3-((7-(3-((3S,4R)-3-amino-4-methylpyrrolidine-1-carbonyl)-4-methyl-6-(trifluoromethyl)pyridin-2-yl)thieno[3,2-b]pyridin-2-yl)methyl)-6,6-dimethyl-3-azabicyclo[3.1.0]hexane-2,4-dione;

(2S)-2-amino-N-((3S)-1-(2-(2-((6,6-dimethyl-2,4-dioxo-3-azabicyclo[3.1.0]hexan-3-yl)methyl)thieno[3,2-b]pyridin-7-yl)-4-methyl-6-(trifluoromethyl)nicotinoyl)pyrrolidin-3-yl)-3-methylbutanamide;

3-((7-(3-(4-aminopiperidine-1-carbonyl)-4-methyl-6-(trifluoromethyl)pyridin-2-yl)thieno[3,2-b]pyridin-2-yl)methyl)-6,6-dimethyl-3-azabicyclo[3.1.0]hexane-2,4-dione;

3-((7-(3-((S)-3-hydroxypyrrolidine-1-carbonyl)-4-methyl-6-(trifluoromethyl)pyridin-2-yl)thieno[3,2-b]pyridin-2-yl)methyl)-6,6-dimethyl-3-azabicyclo[3.1.0]hexane-2,4-dione;

3-((7-(3-((S)-3-fluoropyrrolidine-1-carbonyl)-4-methyl-6-(trifluoromethyl)pyridin-2-yl)thieno[3,2-b]pyridin-2-yl)methyl)-6,6-dimethyl-3-azabicyclo[3.1.0]hexane-2,4-dione;

3-((7-(3-((3R,4R)-3-amino-4-fluoropyrrolidine-1-carbonyl)-4-methyl-6-(trifluoromethyl)pyridin-2-yl)thieno[3,2-b]pyridin-2-yl)methyl)-6,6-dimethyl-3-azabicyclo[3.1.0]hexane-2,4-dione;

3-((7-(3-(azetidin-3-ylamino)-6-chloro-4-methylpyridin-2-yl)thieno[3,2-b]pyridin-2-yl)methyl)-6,6-dimethyl-3-azabicyclo[3.1.0]hexane-2,4-dione;

3-((7-(4,6-dimethyl-3-(pyrrolidin-3-ylamino)pyridin-2-yl)thieno[3,2-b]pyridin-2-yl)methyl)-6,6-dimethyl-3-azabicyclo[3.1.0]hexane-2,4-dione;

3-((7-(6-chloro-4-methyl-3-(pyrrolidin-3-ylamino)pyridin-2-yl)thieno[3,2-b]pyridin-2-yl)methyl)-6,6-dimethyl-3-azabicyclo[3.1.0]hexane-2,4-dione;

3-((7-(6-chloro-4-methyl-3-(piperidin-4-ylamino)pyridin-2-yl)thieno[3,2-b]pyridin-2-yl)methyl)-6,6-dimethyl-3-azabicyclo[3.1.0]hexane-2,4-dione;

6,6-dimethyl-3-((7-(4-methyl-3-(piperidin-4-ylamino)-6-(trifluoromethyl)pyridin-2-yl)thieno[3,2-b]pyridin-2-yl)methyl)-3-azabicyclo[3.1.0]hexane-2,4-dione;

3-((7-(6-chloro-4-methyl-3-(piperidin-3-ylamino)pyridin-2-yl)thieno[3,2-b]pyridin-2-yl)methyl)-6,6-dimethyl-3-azabicyclo[3.1.0]hexane-2,4-dione;

6,6-dimethyl-3-((7-(4-methyl-3-(piperidin-3-ylamino)-6-(trifluoromethyl)pyridin-2-yl)thieno[3,2-b]pyridin-2-yl)methyl)-3-azabicyclo[3.1.0]hexane-2,4-dione;

3-((7-(3-(3-(aminomethyl)pyrrolidine-1-carbonyl)-4-methyl-6-(trifluoromethyl)pyridin-2-yl)thieno[3,2-b]pyridin-2-yl)methyl)-6,6-dimethyl-3-azabicyclo[3.1.0]hexane-2,4-dione;

3-((7-(3-(3-((isopropylamino)methyl)pyrrolidine-1-carbonyl)-4-methyl-6-(trifluoromethyl)pyridin-2-yl)thieno[3,2-b]pyridin-2-yl)methyl)-6,6-dimethyl-3-azabicyclo[3.1.0]hexane-2,4-dione;

3-((7-(3-((2S,6S)-2,6-dimethylpiperazine-1-carbonyl)-4-methyl-6-(trifluoromethyl)pyridin-2-yl)thieno[3,2-b]pyridin-2-yl)methyl)-6,6-dimethyl-3-azabicyclo[3.1.0]hexane-2,4-dione; or 3-((7-(3-(4-ethylpiperazine-1-carbonyl)-4-methyl-6-(trifluoromethyl)pyridin-2-yl)thieno[3,2-b]pyridin-2-yl)methyl)-6,6-dimethyl-3-azabicyclo[3.1.0]hexane-2,4-dione;

or a tautomer, stereoisomer, a racemic or scalemic mixture of stereoisomers, a pharmaceutically acceptable salt, ester, solvate, or polymorph thereof.

4. The compound according to claim 1, wherein the compound is:

6,6-dimethyl-3-((7-(4-methyl-3-(((S)-3-(methylamino)pyrrolidin-1-yl)methyl)-6-(trifluoromethyl)pyridin-2-yl)thieno[3,2-b]pyridin-2-yl)methyl)-3-azabicyclo[3.1.0]hexane-2,4-dione;

6,6-dimethyl-3-((7-(4-methyl-3-((3-oxopiperazin-2-yl)methyl)-6-(trifluoromethyl)pyridin-2-yl)thieno[3,2-b]pyridin-2-yl)methyl)-3-azabicyclo[3.1.0]hexane-2,4-dione;

6,6-dimethyl-3-((7-(4-methyl-3-((3R,4S)-3-methyl-4-(methylamino)pyrrolidine-1-carbonyl)-6-(trifluoromethyl)pyridin-2-yl)thieno[3,2-b]pyridin-2-yl)methyl)-3-azabicyclo[3.1.0]hexane-2,4-dione;

3-((7-(3-((3R,4S)-3-amino-4-fluoropyrrolidine-1-carbonyl)-4-methyl-6-(trifluoromethyl)pyridin-2-yl)thieno[3,2-b]pyridin-2-yl)methyl)-6,6-dimethyl-3-azabicyclo[3.1.0]hexane-2,4-dione;

3-((7-(3-((3S,4S)-3-amino-4-fluoropyrrolidine-1-carbonyl)-4-methyl-6-(trifluoromethyl)pyridin-2-yl)thieno[3,2-b]pyridin-2-yl)methyl)-6,6-dimethyl-3-azabicyclo[3.1.0]hexane-2,4-dione;

3-((7-(3-((3S,4R)-3-amino-4-fluoropyrrolidine-1-carbonyl)-4-methyl-6-(trifluoromethyl)pyridin-2-yl)thieno[3,2-b]pyridin-2-yl)methyl)-6,6-dimethyl-3-azabicyclo[3.1.0]hexane-2,4-dione; or 3-((7-(3-((3S,4R)-3-(dimethylamino)-4-methylpyrrolidine-1-carbonyl)-4-methyl-6-(trifluoromethyl)pyridin-2-yl)thieno[3,2-b]pyridin-2-yl)methyl)-6,6-dimethyl-3-azabicyclo[3.1.0]hexane-2,4-dione;

or a tautomer, stereoisomer, a racemic or scalemic mixture of stereoisomers, a pharmaceutically acceptable salt, ester, solvate, or polymorph thereof.

5. A pharmaceutical composition comprising (i) a therapeutically effective amount of at least one compound of claim 1, or a pharmaceutically acceptable salt, solvate, or polymorph thereof; and (ii) a pharmaceutically acceptable carrier, vehicle or excipient therefor.

* * * * *